(12) United States Patent
Johnson et al.

(10) Patent No.: US 11,466,016 B2
(45) Date of Patent: Oct. 11, 2022

(54) PHARMACEUTICAL COMPOUNDS

(71) Applicants: OTSUKA PHARMACEUTICAL CO., LTD., Tokyo (JP); TAIHO PHARMACEUTICAL CO., LTD., Tokyo (JP)

(72) Inventors: Christopher Norbert Johnson, Newport (GB); Ildiko Maria Buck, London (GB); Gianni Chessari, Cambridge (GB); James Edward Harvey Day, Foxton (GB); Hideto Fujiwara, Cambridge (GB); Christopher Charles Frederick Hamlett, Cambridge (GB); Steven Douglas Hiscock, Royston (GB); Rhian Sara Holvey, Cambridge (GB); Steven Howard, Cambridge (GB); John Walter Liebeschuetz, Cambridge (GB); Nicholas John Palmer, Cambridge (GB); Jeffrey David St Denis, Waterbeach (GB); David Geoffrey Twigg, Milton (GB); Andrew James Woodhead, Histon (GB)

(73) Assignees: OTSUKA PHARMACEUTICAL CO., LTD., Tokyo (JP); TAIHO PHARMACEUTICAL CO., LTD., Tokyo (JP)

( * ) Notice: Subject to any disclaimer, the term of this patent is extended or adjusted under 35 U.S.C. 154(b) by 0 days.

(21) Appl. No.: 16/976,631

(22) PCT Filed: Mar. 1, 2019

(86) PCT No.: PCT/IB2019/051641
§ 371 (c)(1),
(2) Date: Aug. 28, 2020

(87) PCT Pub. No.: WO2019/167000
PCT Pub. Date: Sep. 6, 2019

(65) Prior Publication Data
US 2021/0107908 A1   Apr. 15, 2021

(30) Foreign Application Priority Data

Mar. 2, 2018  (GB) ..................... 1803439
Aug. 30, 2018 (GB) ..................... 1814135

(51) Int. Cl.
| | | |
|---|---|---|
| C07D 487/04 | (2006.01) |
| A61K 31/4985 | (2006.01) |
| A61K 31/517 | (2006.01) |
| A61K 31/5377 | (2006.01) |
| A61K 45/06 | (2006.01) |
| C07D 519/00 | (2006.01) |

(52) U.S. Cl.
CPC ........ *C07D 487/04* (2013.01); *A61K 31/4985* (2013.01); *A61K 31/517* (2013.01); *A61K 31/5377* (2013.01); *A61K 45/06* (2013.01); *C07D 519/00* (2013.01); *C07B 2200/07* (2013.01)

(58) Field of Classification Search
None
See application file for complete search history.

(56) References Cited

FOREIGN PATENT DOCUMENTS

| | | |
|---|---|---|
| CN | 102311447 B | 11/2013 |
| JP | 2021/506776 A | 2/2021 |
| JP | 2021/514962 A | 6/2021 |
| WO | 2005099688 A2 | 10/2005 |
| WO | 2006058074 A1 | 6/2006 |
| WO | 2013/063214 A1 | 5/2013 |
| WO | 2015107493 A1 | 7/2015 |
| WO | 2015107494 A1 | 7/2015 |
| WO | 2015107495 A1 | 7/2015 |
| WO | 2016/208595 A1 | 12/2016 |
| WO | 2016203404 A1 | 12/2016 |

(Continued)

OTHER PUBLICATIONS

Di Bagdanoff, et al., "Optimization of Fused Bicyclic Allosteric SHP2 Inhibitors," J. Med. Chem. 2019, 62, 1781-1792.

(Continued)

*Primary Examiner* — Brian J Davis
(74) *Attorney, Agent, or Firm* — Heslin Rothenberg Farley & Mesiti P.C.

(57) ABSTRACT

The invention provides new pyrazine derivatives of formula (I):

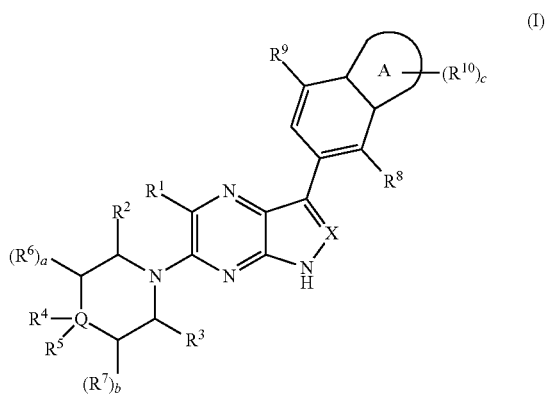

or a tautomer or a solvate or a pharmaceutically acceptable salt thereof, wherein the substituents are as defined herein. The invention also provides pharmaceutical compositions comprising said compounds and to the use of said compounds in the treatment of diseases, e.g. cancer.

27 Claims, No Drawings

(56) References Cited

FOREIGN PATENT DOCUMENTS

| | | |
|---|---|---|
| WO | 2016203405 A1 | 12/2016 |
| WO | 2016203406 A1 | 12/2016 |
| WO | 2017156397 A1 | 9/2017 |
| WO | 2017210134 A1 | 12/2017 |
| WO | 2017211303 A1 | 12/2017 |
| WO | 2017216706 A1 | 12/2017 |
| WO | 2018057884 A1 | 3/2018 |
| WO | 2018081091 A1 | 5/2018 |
| WO | 2018130928 A1 | 7/2018 |
| WO | 2018/193410 A1 | 10/2018 |
| WO | 2018218133 A1 | 11/2018 |
| WO | 2019051084 A1 | 3/2019 |
| WO | 2019118909 A1 | 6/2019 |
| WO | 2019165073 A1 | 8/2019 |
| WO | 2019182960 A1 | 9/2019 |
| WO | 2019183364 A1 | 9/2019 |
| WO | 2019213318 A1 | 11/2019 |
| WO | 2020/022323 A1 | 1/2020 |
| WO | 2020065452 A1 | 4/2020 |
| WO | 2020065453 A1 | 4/2020 |
| WO | 2021/033153 A1 | 2/2021 |
| WO | 2021/149817 A1 | 7/2021 |

OTHER PUBLICATIONS

Chen, et al., "Allosteric Inhibition of SHP2 Phosphatase Inhibits Cancers Driven by Receptor Tyrosine Kinases," Nature, vol. 535, Jul. 7, 2016, 148-164.

Yuan, et al., "Recent Advances of SHP2 Inhibitors in Cancer Therapy: Current Development and Clinical Application," J. Med. Chem. 2020, 63, 11368-11396.

Lamarche, et al., "Identification of TNO155, an Allosteric SHP2 Inhibitor for the Treatment of Cancer," J. Med. Chem. 2020, 63, 13578-13594.

Nichols, et al., "RAS Nucleotide Cycling Underlies the SHP2 Phosphatase Dependence of Mutant BRAF-NF1- and RAS-Driven Cancers," Nature Cell Biology Articles, 2018 pp. 1-16.

Search Report for GB 1803439.7 dated Oct. 26, 2018.

Search Report for GB 1814135.8 dated Mar. 27, 2019.

International SearchReport forPCT/IB2019/051641 dated Jun. 19, 2019.

Caira, Mino R., "Crystalline Polymorphism of Organic Compounds", Springer, Berlin, 198, 1998, 163-208.

J. R. Riggs et al., The Discovery of a Dual TTK Protein Kinase/CDC-2 Like Kinase (CLK2) Inhibitor for the Treatment of Triple Negative Breast Cancer Initiated from a Phenotypic Screen, Journal of Medicinal Chemistry, 2017, vol. 60, No. 21, pp. 8989-9002.

PHARMACEUTICAL COMPOUNDS

CROSS REFERENCE TO RELATED APPLICATIONS

This application is a national stage filing under section 371 of International Application No. PCT/IB2019/051641, filed on Mar. 1, 2019, and published on Sep. 6, 2019 as WO 2019/167000, which claims priority to Great Britain Application No. 1803439.7, filed on Mar. 2, 2018 and Great Britain Application No. 1814135.8, filed on Aug. 30, 2018. The entire contents of WO 2019/167000 are hereby incorporated herein by reference.

FIELD OF THE INVENTION

The invention relates to new pyrazine derivatives, to pharmaceutical compositions comprising said compounds and to the use of said compounds in the treatment of diseases, e.g. cancer.

RELATED APPLICATIONS

This application is related to United Kingdom patent application number 1803439.7 filed 2 Mar. 2018 and United Kingdom patent application number 1814135.8 filed 30 Aug. 2018, the contents of which are incorporated herein by reference in their entirety.

BACKGROUND OF THE INVENTION

Src homology region 2 (SH2)-containing protein tyrosine phosphatase 2 (SHP2) is a ubiquitously expressed protein tyrosine phosphatase encoded by the PTPN11 gene. SHP2 contains two N-terminal tandem SH2 domains (N—SH2, C—SH2), a catalytic phosphatase (PTP) domain and a C-terminal tail with 2 tyrosine phosphorylation sites.

SHP2 switches between "open" active and "closed" inactive forms due to autoinhibitory interactions between the N—SH2 and the PTP domain. This naturally occurring autoinhibition is released when bis-tyrosylphorphorylated peptides bind to the N—SH2 domains and SHP2 adopts an "open" conformation, resulting in activation of the enzyme and exposure of the PTP domain for substrate recognition and catalysis.

PTPN11 mutations have been linked to several human diseases including cancer. Germline PTPN11 mutations are associated with developmental disorders such as Noonan Syndrome and Leopard Syndrome, whilst somatic mutations occur in several types of hematologic malignancies, such as JMML and more rarely in solid tumours.

SHP2 is required for signalling downstream of receptor tyrosine kinases (e.g. EGFR, ALK, PDGFR) and plays a positive role in regulating many cellular processes such as proliferation in response to growth factor and cytokine stimulation. Previous studies have shown that SHP2 acts upstream of Ras and is required for full, sustained activation of the MAPK pathway. RTK deregulation often leads to a wide range of cancers, making SHP2 a valuable target in RTK-activated cancers. SHP2 is also reported to play a role in regulating immune responses by mediating immune checkpoint pathways (e.g. PD-1) as immunoreceptor tyrosine-based inhibitory motifs (ITIMs) bind to the SH2 domains of SHP2 to mediate a negative signal. It has been reported that some SHP2 inhibitor compounds show inhibitory effect on proliferation of in vitro cancer cells and on increase in tumour volume in a mouse xenograft model (Nature (2016) 535: 148-152).

The present invention describes a novel series of compounds which selectively inhibit SHP2 and which have anticancer activity.

SUMMARY OF THE INVENTION

In one aspect, the invention provides a compound of formula (I):

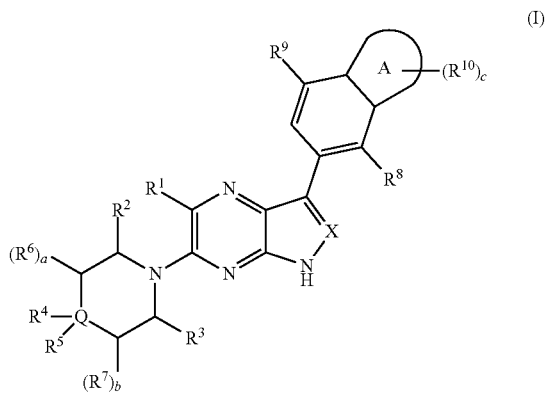

or a tautomer or a solvate or a pharmaceutically acceptable salt thereof, wherein:

X is CH or N;

$R^1$ is hydrogen, —$CH_3$ or —$CH_2OH$ but when X is N then $R^1$ is selected from —$CH_3$ and —$CH_2OH$;

$R^2$ and $R^3$ are either:
  (i) independently selected from hydrogen and $C_{1-4}$alkyl; or
  (ii) together form a one- to three-membered bridge group selected from $C_{1-3}$alkylene, $C_{2-3}$alkenylene, methylene-$NR^q$-methylene and methylene-O-methylene, wherein the bridge group is optionally substituted by a group selected from $C_{1-4}$alkyl, hydroxyl and halogen and $R^q$ is selected from hydrogen, $C_{1-4}$alkyl, hydroxyl and halogen;

Q is C or N;
  wherein when Q is C then either:
    (i) $R^4$ is hydrogen or $C_{1-4}$alkyl (e.g. methyl) optionally substituted by amino (e.g. —$CH_2NH_2$);
    $R^5$ is hydrogen, amino, hydroxyl or $C_{1-4}$alkyl (e.g. methyl) optionally substituted by 1 or 2 groups selected from halogen, hydroxyl (e.g. —$CH_2OH$) or amino;
    provided that $R^4$ and $R^5$ must not both be selected from amino and $C_{1-4}$alkyl substituted by amino; or
    (ii) $R^4$ and $R^5$ together with Q form a four- to six-membered nitrogen-containing heterocyclic ring; and
  wherein when Q is N then:
    $R^4$ is absent;
    $R^5$ is hydrogen; and
    $R^2$ and $R^3$ together form the one- to three-membered bridge group;

$R^6$ and $R^7$ are independently selected from halogen (e.g. fluorine), $C_{1-4}$alkyl (e.g. —$CH_3$) and hydroxyl provided that when Q is N then $R^6$ or $R^7$ are not halogen or hydroxyl;

a is selected from 0, 1 and 2;
b is selected from 0, 1 and 2;

Ring A is either:
(i) a five-membered nitrogen-containing heterocyclic ring (e.g. an aromatic ring or a non-aromatic ring) wherein the heterocyclic ring optionally contains one or two additional heteroatoms selected from N, O and S, or
(ii) a six-membered aromatic nitrogen-containing heterocyclic ring, wherein the heterocyclic ring optionally contains one or two additional heteroatoms selected from N, O and S; or
(iii) a six-membered non-aromatic nitrogen-containing heterocyclic ring, wherein the heterocyclic ring optionally contains one or two additional heteroatoms selected from N and S;

$R^8$ is selected from haloC$_{1-4}$alkyl (e.g. —CF$_3$), —CH$_3$ and halogen (e.g. chlorine or fluorine);

$R^9$ is selected from hydrogen, C$_{1-4}$alkyl (e.g. —CH$_3$), haloC$_{1-4}$alkyl (e.g. —CF$_3$) and halogen (e.g. chlorine);

$R^{10}$ are independently selected from halogen, cyano, cyanoC$_{1-4}$alkyl (e.g. —CH$_2$—CN), hydroxyl, =O (oxo), C$_{1-4}$alkyl (e.g. —CH$_3$, —CH$_2$CH$_3$, and —CH(CH$_3$)$_2$), haloC$_{1-4}$alkyl (e.g. —CHF$_2$), C$_{1-4}$alkoxy (e.g. —OCH$_3$, —OCH$_2$CH$_3$ and —OCH(CH$_3$)$_2$), hydroxylC$_{1-4}$alkyl (e.g. —CH$_2$C(CH$_3$)$_2$OH, —CH(CH$_3$)CH$_2$OH, —CH(CH$_3$)OH, —CH$_2$CH$_2$OH or —CH$_2$OH), C$_{1-4}$alkoxyC$_{1-4}$alkylene (e.g. —CH$_2$—O—CH$_3$ or —CH$_2$—CH$_2$—O—CH$_3$), C$_{1-4}$alkylsulfone (e.g. —SO$_2$CH$_3$), amino, monoC$_{1-4}$alkylamino, diC$_{1-4}$alkylamino (e.g. —N(CH$_3$)$_2$), aminoC$_{1-4}$alkylene (e.g. —CH$_2$NH$_2$), —C$_{0-4}$alkylene-C(=O)NH$_{(2-q)}$(C$_{1-6}$alkyl)$_q$), —C$_{1-4}$alkylene-NHC(=O)C$_{1-6}$ alkyl, sulfonamideC$_{0-4}$alkylene (e.g. —SO$_2$NR$^x_2$ or —CH$_2$SO$_2$NR$^x_2$, wherein R$^x$ is independently selected from H and C$_{1-6}$alkyl), 3 to 6 membered cycloalkyl, optionally substituted five- or six-membered unsaturated heterocyclic group containing 1, 2, 3 or 4 heteroatoms selected from O, N, or S where the optional substituent is selected from C$_{1-4}$alkyl, C$_{1-4}$alkyl substituted with 3 to 6 membered cycloalkyl, C$_{1-4}$alkyl substituted with optionally substituted five- or six-membered unsaturated heterocyclic group containing 1, 2, 3 or 4 heteroatoms selected from O, N, or S where the optional substituent is selected from C$_{1-4}$alkyl, C$_{1-4}$alkyl substituted with optionally substituted four- to six-membered saturated heterocyclic group containing 1 or 2 heteroatoms selected from O, N, or S where the optional substituent is selected from C$_{1-4}$alkyl and optionally substituted four- to six-membered saturated heterocyclic group containing 1 or 2 heteroatoms selected from O, N, or S where the optional substituent is selected from C$_{1-4}$alkyl;

q is selected from 0, 1 or 2; and
c is selected from 0, 1, 2 and 3.

In a second aspect, the invention provides a compound of formula (I), or a tautomer, N-oxide, pharmaceutically acceptable salt or solvate thereof, wherein:

X is CH or N;

$R^1$ is hydrogen, —CH$_3$ or —CH$_2$OH but when X is N then $R^1$ is selected from —CH$_3$ and —CH$_2$OH;

$R^2$ and $R^3$ are either:
(i) independently selected from hydrogen and C$_{1-4}$alkyl; or
(ii) together form a one- to three-membered bridge group selected from C$_{1-3}$alkylene, C$_{2-3}$alkenylene, methylene-NR$^q$-methylene and methylene-O-methylene, wherein the bridge group is optionally substituted by a group selected from C$_{1-4}$alkyl, hydroxyl and halogen and R$^q$ is selected from hydrogen, C$_{1-4}$alkyl, hydroxyl and halogen.

Q is C or N;

wherein when Q is C then either:
(i) $R^4$ is hydrogen or C$_{1-4}$alkyl (e.g. methyl) optionally substituted by amino (e.g. —CH$_2$NH$_2$);
$R^5$ is hydrogen, amino, or C$_{1-4}$alkyl (e.g. methyl) optionally substituted by 1 or 2 groups selected from halogen, hydroxyl (e.g. —CH$_2$OH) or amino;
provided that $R^4$ and $R^5$ must not both be selected from amino and C$_{1-4}$alkyl substituted by amino; or
(ii) $R^4$ and $R^5$ together with Q form a four- to six-membered nitrogen-containing heterocyclic ring; and wherein when Q is N then:
$R^4$ is absent;
$R^5$ is hydrogen; and
$R^2$ and $R^3$ together form the one- to three-membered bridge group;

$R^6$ and $R^7$ are independently selected from halogen (e.g. fluorine), C$_{1-4}$alkyl (e.g. —CH$_3$) and hydroxyl provided that when Q is N then $R^6$ or $R^7$ are not halogen or hydroxyl;

a is selected from 0, 1 and 2;
b is selected from 0, 1 and 2;

Ring A is either:
(i) a five-membered nitrogen-containing heterocyclic ring (e.g. an aromatic ring or a non-aromatic ring) wherein the heterocyclic ring optionally contains one or two additional heteroatoms selected from N, O and S, or
(ii) a six-membered aromatic nitrogen-containing heterocyclic ring, wherein the heterocyclic ring optionally contains one or two additional heteroatoms selected from N, O and S; or
(iii) a six-membered non-aromatic nitrogen-containing heterocyclic ring, wherein the heterocyclic ring optionally contains one or two additional heteroatoms selected from N and S;

$R^8$ is selected from haloC$_{1-4}$alkyl (e.g. —CF$_3$), —CH$_3$ and halogen (e.g. chlorine or fluorine);

$R^9$ is selected from hydrogen, C$_{1-4}$alkyl (e.g. —CH$_3$), haloC$_{1-4}$alkyl (e.g. —CF$_3$) and halogen (e.g. chlorine);

$R^{10}$ are independently selected from halogen, cyano, cyanoC$_{1-4}$alkyl (e.g. —CH$_2$—CN), hydroxyl, =O (oxo), C$_{1-4}$alkyl (e.g. —CH$_3$ or —CH$_2$CH$_3$), haloC$_{1-4}$alkyl, C$_{1-4}$alkoxy (e.g. —OCH$_3$), hydroxylC$_{1-4}$alkyl (e.g. —CH$_2$C(CH$_3$)$_2$OH, —CH(CH$_3$)CH$_2$OH, —CH(CH$_3$)OH, —CH$_2$CH$_2$OH or —CH$_2$OH), C$_{1-4}$alkoxyC$_{1-4}$alkylene (e.g. —CH$_2$—O—CH$_3$ or —CH$_2$—CH$_2$—O—CH$_3$), C$_{1-4}$alkylsulfone (e.g. —SO$_2$CH$_3$), amino, monoC$_{1-4}$alkylamino, diC$_{1-4}$alkylamino (e.g. —N(CH$_3$)$_2$), aminoC$_{1-4}$alkylene (e.g. —CH$_2$NH$_2$), —C$_{1-4}$alkylene-C(=O)NH$_{(2-q)}$(C$_{1-6}$alkyl)$_q$), —C$_{1-4}$alkylene-NHC(=O)C$_{1-6}$ alkyl, sulfonamideC$_{0-4}$alkylene (e.g. —SO$_2$NR$^x_2$ or —CH$_2$SO$_2$NR$^x_2$, wherein R$^x$ is independently selected from H and C$_{1-6}$alkyl), and optionally substituted four- to six-membered saturated heterocyclic group containing 1 or 2 heteroatoms selected from O, N, or S where the optional substituent is selected from C$_{1-4}$alkyl;

q is selected from 0, 1 or 2; and
c is selected from 0, 1 and 2.

In a third aspect, the invention provides a compound of formula (I):

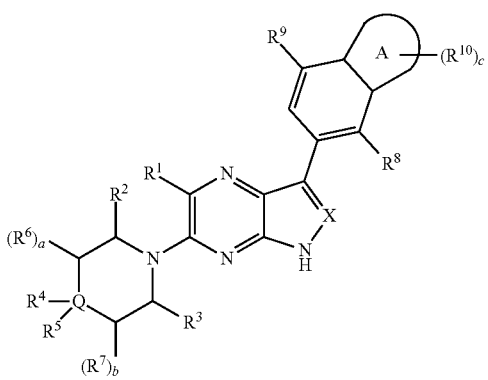

(I)

or a tautomer or a solvate or a pharmaceutically acceptable salt thereof, wherein:

X is CH or N;

$R^1$ is hydrogen, —$CH_3$ or —$CH_2OH$ but when X is N then $R^1$ is selected from —$CH_3$ and —$CH_2OH$;

$R^2$ and $R^3$ are either:
(i) independently selected from hydrogen and $C_{1-4}$alkyl; or
(ii) together form a one- to three-membered bridge group selected from $C_{1-3}$alkylene, $C_{2-3}$alkenylene, methylene-$NR^q$-methylene and methylene-O-methylene, wherein the bridge group is optionally substituted by a group selected from $C_{1-4}$alkyl, hydroxyl and halogen and $R^q$ is selected from hydrogen, $C_{1-4}$alkyl, hydroxyl and halogen;

Q is C or N;
wherein when Q is C then either:
(i) $R^4$ is hydrogen or $C_{1-4}$alkyl (e.g. methyl) optionally substituted by amino (e.g. —$CH_2NH_2$);
$R^5$ is hydrogen, amino, hydroxyl or $C_{1-4}$alkyl (e.g. methyl) optionally substituted by 1 or 2 groups selected from halogen, hydroxyl (e.g. —$CH_2OH$) or amino;
provided that $R^4$ and $R^5$ must not both be selected from amino and $C_{1-4}$alkyl substituted by amino; or
(ii) $R^4$ and $R^5$ together with Q form a four- to six-membered nitrogen-containing heterocyclic ring; and
wherein when Q is N then:
$R^4$ is absent;
$R^5$ is hydrogen; and
$R^2$ and $R^3$ together form the one- to three-membered bridge group;

$R^6$ and $R^7$ are independently selected from halogen (e.g. fluorine), $C_{1-4}$alkyl (e.g. —$CH_3$) and hydroxyl provided that when Q is N then $R^6$ or $R^7$ are not halogen or hydroxyl;

a is selected from 0, 1 and 2;
b is selected from 0, 1 and 2;

Ring A is either:
(i) a five-membered nitrogen-containing heterocyclic ring (e.g. an aromatic ring or a non-aromatic ring) wherein the heterocyclic ring optionally contains one or two additional heteroatoms selected from N, O and S, or
(ii) a six-membered aromatic nitrogen-containing heterocyclic ring, wherein the heterocyclic ring optionally contains one or two additional heteroatoms selected from N, O and S; or
(iii) a six-membered non-aromatic nitrogen-containing heterocyclic ring, wherein the heterocyclic ring optionally contains one or two additional heteroatoms selected from N and S;

$R^8$ is selected from halo$C_{1-4}$alkyl (e.g. —$CF_3$), —$CH_3$ and halogen (e.g. chlorine or fluorine);

$R^9$ is selected from hydrogen, $C_{1-4}$alkyl (e.g. —$CH_3$), halo$C_{1-4}$alkyl (e.g. —$CF_3$) and halogen (e.g. chlorine);

$R^{10}$ are independently selected from halogen, cyano, cyano$C_{1-4}$alkyl (e.g. —$CH_2$—CN), hydroxyl, =O (oxo), $C_{1-4}$alkyl (e.g. —$CH_3$ and —$CH_2CH_3$), halo$C_{1-4}$alkyl, $C_{1-4}$alkoxy (e.g. —$OCH_3$), hydroxyl$C_{1-4}$alkyl (e.g. —$CH_2C(CH_3)_2OH$, —$CH(CH_3)CH_2OH$, —$CH(CH_3)OH$, —$CH_2CH_2OH$ or —$CH_2OH$), $C_{1-4}$alkoxy$C_{1-4}$alkylene (e.g. —$CH_2$—O—$CH_3$ or —$CH_2$—$CH_2$—O—$CH_3$), $C_{1-4}$alkylsulfone (e.g. —$SO_2CH_3$), amino, mono$C_{1-4}$alkylamino, di$C_{1-4}$alkylamino (e.g. —$N(CH_3)_2$), amino$C_{1-4}$alkylene (e.g. —$CH_2NH_2$), —$C_{1-4}$alkylene-C(=O)$NH_{(2-q)}$($C_{1-6}$alkyl)$_q$), —$C_{1-4}$alkylene-NHC(=O)$C_{1-6}$ alkyl, sulfonamide$C_{0-4}$alkylene (e.g. —$SO_2NR^x_2$ or —$CH_2SO_2NR^x_2$, wherein $R^x$ is independently selected from H and $C_{1-6}$alkyl), 3 to 6 membered cycloalkyl, optionally substituted five- or six-membered unsaturated heterocyclic group containing 1, 2, 3 or 4 heteroatoms selected from O, N, or S where the optional substituent is selected from $C_{1-4}$alkyl, $C_{1-4}$alkyl substituted with 3 to 6 membered cycloalkyl, $C_{1-4}$alkyl substituted with optionally substituted five- or six-membered unsaturated heterocyclic group containing 1, 2, 3 or 4 heteroatoms selected from O, N, or S where the optional substituent is selected from $C_{1-4}$alkyl, $C_{1-4}$alkyl substituted with optionally substituted four- to six-membered saturated heterocyclic group containing 1 or 2 heteroatoms selected from O, N, or S where the optional substituent is selected from $C_{1-4}$alkyl and optionally substituted four- to six-membered saturated heterocyclic group containing 1 or 2 heteroatoms selected from O, N, or S where the optional substituent is selected from $C_{1-4}$alkyl;

q is selected from 0, 1 or 2; and
c is selected from 0, 1, 2 and 3.

In further aspects of the invention there is provided a compound of formula (I) for use in the prophylaxis or treatment of a disease or condition as described herein, methods for the prophylaxis or treatment of a disease or condition as described herein comprising administering to a patient a compound of formula (I), pharmaceutical compositions comprising a compound of formula (I) and processes for the synthesis of a compound of formula (I).

Definitions

Unless the context indicates otherwise, references to formula (I) in all sections of this document (including the uses, methods and other aspects of the invention) include references to all other sub-formula, sub-groups, embodiments and examples as defined herein.

"Potency" is a measure of drug activity expressed in terms of the amount required to produce an effect of given intensity. A highly potent drug evokes a larger response at low concentrations. Potency is proportional to affinity and efficacy. Affinity is the ability of the drug to bind to a receptor. Efficacy is the relationship between receptor occupancy and the ability to initiate a response at the molecular, cellular, tissue or system level.

The term "inhibitor" refers to an enzyme inhibitor that is a type of ligand or drug that blocks or dampens biological responses mediated by SHP2. Inhibitors mediate their effects by binding to the active site or to allosteric sites on enzymes, or they may interact at unique binding sites not normally involved in the biological regulation of the enzyme's activity. The inhibition may arise directly or indirectly, and may be mediated by any mechanism and at any physiological level. As a result, inhibition by ligands or drugs may under different circumstances manifest itself in functionally different ways. Inhibitory activity may be reversible or irreversible depending on the longevity of the inhibitor-enzyme complex, which, in turn, depends on the nature of inhibitor-enzyme binding.

As used herein, the term "mediated", as used e.g. in conjunction with SHP2 as described herein (and applied for example to various physiological processes, diseases, states, conditions, therapies, treatments or interventions) is intended to operate limitatively so that the various processes, diseases, states, conditions, treatments and interventions to which the term is applied are those in which the protein plays a biological role. In cases where the term is applied to a disease, state or condition, the biological role played by the protein may be direct or indirect and may be necessary and/or sufficient for the manifestation of the symptoms of the disease, state or condition (or its aetiology or progression). Thus, the protein function (and in particular aberrant levels of function, e.g. over- or under-expression) need not necessarily be the proximal cause of the disease, state or condition: rather, it is contemplated that the mediated diseases, states or conditions include those having multifactorial aetiologies and complex progressions in which the protein in question is only partially involved. In cases where the term is applied to treatment, prophylaxis or intervention, the role played by the protein may be direct or indirect and may be necessary and/or sufficient for the operation of the treatment, prophylaxis or outcome of the intervention. Thus, a disease state or condition mediated by a protein includes the development of resistance to any particular cancer drug or treatment.

The term "treatment" as used herein in the context of treating a condition i.e. state, disorder or disease, pertains generally to treatment and therapy, whether for a human or an animal (e.g. in veterinary applications), in which some desired therapeutic effect is achieved, for example, the inhibition of the progress of the condition, and includes a reduction in the rate of progress, a halt in the rate of progress, amelioration of the condition, diminishment or alleviation of at least one symptom associated or caused by the condition being treated and cure of the condition. For example, treatment can be diminishment of one or several symptoms of a disorder or complete eradication of a disorder.

The term "prophylaxis" (i.e. use of a compound as prophylactic measure) as used herein in the context of treating a condition i.e. state, disorder or disease, pertains generally to the prophylaxis or prevention, whether for a human or an animal (e.g. in veterinary applications), in which some desired preventative effect is achieved, for example, in preventing occurrence of a disease or guarding from a disease. Prophylaxis includes complete and total blocking of all symptoms of a disorder for an indefinite period of time, the mere slowing of the onset of one or several symptoms of the disease, or making the disease less likely to occur.

References to the prophylaxis or treatment of a disease state or condition such as cancer include within their scope alleviating or reducing the incidence e.g. of cancer.

The combinations of the invention may produce a therapeutically efficacious effect relative to the therapeutic effect of the individual compounds/agents when administered separately.

The term 'efficacious' includes advantageous effects such as additivity, synergism, reduced side effects, reduced toxicity, increased time to disease progression, increased time of survival, sensitization or resensitization of one agent to another, or improved response rate. Advantageously, an efficacious effect may allow for lower doses of each or either component to be administered to a patient, thereby decreasing the toxicity of chemotherapy, whilst producing and/or maintaining the same therapeutic effect. A "synergistic" effect in the present context refers to a therapeutic effect produced by the combination which is larger than the sum of the therapeutic effects of the agents of the combination when presented individually. An "additive" effect in the present context refers to a therapeutic effect produced by the combination which is larger than the therapeutic effect of any of the agents of the combination when presented individually. The term "response rate" as used herein refers, in the case of a solid tumour, to the extent of reduction in the size of the tumour at a given time point, for example 12 weeks. Thus, for example, a 50% response rate means a reduction in tumour size of 50%. References herein to a "clinical response" refer to response rates of 50% or greater. A "partial response" is defined herein as being a response rate of less than 50%.

As used herein, the term "combination", as applied to two or more compounds and/or agents, is intended to define material in which the two or more agents are associated. The terms "combined" and "combining" in this context are to be interpreted accordingly.

The association of the two or more compounds/agents in a combination may be physical or non-physical. Examples of physically associated combined compounds/agents include:

compositions (e.g. unitary formulations) comprising the two or more compounds/agents in admixture (for example within the same unit dose);

compositions comprising material in which the two or more compounds/agents are chemically/physicochemically linked (for example by crosslinking, molecular agglomeration or binding to a common vehicle moiety);

compositions comprising material in which the two or more compounds/agents are chemically/physicochemically co-packaged (for example, disposed on or within lipid vesicles, particles (e.g. micro- or nanoparticles) or emulsion droplets);

pharmaceutical kits, pharmaceutical packs or patient packs in which the two or more compounds/agents are co-packaged or co-presented (e.g. as part of an array of unit doses);

Examples of non-physically associated combined compounds/agents include:

material (e.g. a non-unitary formulation) comprising at least one of the two or more compounds/agents together with instructions for the extemporaneous association of the at least one compound to form a physical association of the two or more compounds/agents;

material (e.g. a non-unitary formulation) comprising at least one of the two or more compounds/agents together with instructions for combination therapy with the two or more compounds/agents;

material comprising at least one of the two or more compounds/agents together with instructions for administration to a patient population in which the other(s) of the two or more compounds/agents have been (or are being) administered;

material comprising at least one of the two or more compounds/agents in an amount or in a form which is specifically adapted for use in combination with the other(s) of the two or more compounds/agents.

As used herein, the term "combination therapy" is intended to define therapies which comprise the use of a combination of two or more compounds/agents (as defined above). Thus, references to "combination therapy", "combinations" and the use of compounds/agents "in combination" in this application may refer to compounds/agents that are administered as part of the same overall treatment regimen. As such, the posology of each of the two or more compounds/agents may differ: each may be administered at the same time or at different times. It will therefore be appreciated that the compounds/agents of the combination may be administered sequentially (e.g. before or after) or simultaneously, either in the same pharmaceutical formulation (i.e. together), or in different pharmaceutical formulations (i.e. separately). Simultaneously in the same formulation is as a unitary formulation whereas simultaneously in different pharmaceutical formulations is non-unitary. The posologies of each of the two or more compounds/agents in a combination therapy may also differ with respect to the route of administration.

As used herein, the term "pharmaceutical kit" defines an array of one or more unit doses of a pharmaceutical composition together with dosing means (e.g. measuring device) and/or delivery means (e.g. inhaler or syringe), optionally all contained within common outer packaging. In pharmaceutical kits comprising a combination of two or more compounds/agents, the individual compounds/agents may unitary or non-unitary formulations. The unit dose(s) may be contained within a blister pack. The pharmaceutical kit may optionally further comprise instructions for use.

As used herein, the term "pharmaceutical pack" defines an array of one or more unit doses of a pharmaceutical composition, optionally contained within common outer packaging. In pharmaceutical packs comprising a combination of two or more compounds/agents, the individual compounds/agents may unitary or non-unitary formulations. The unit dose(s) may be contained within a blister pack. The pharmaceutical pack may optionally further comprise instructions for use.

The term 'optionally substituted' as used herein refers to a group which may be unsubstituted or substituted by a substituent as herein defined.

The prefix "$C_{x-y}$" (where x and y are integers) as used herein refers to the number of carbon atoms in a given group. Thus, a $C_{1-6}$ alkyl group contains from 1 to 6 carbon atoms, a $C_{3-6}$ cycloalkyl group contains from 3 to 6 carbon atoms, a $C_{1-4}$ alkoxy group contains from 1 to 4 carbon atoms, and so on.

The term 'amino' as used herein refers to the group —$NH_2$.

The term 'halo' or 'halogen' as used herein refers to fluorine, chlorine, bromine or iodine, in particular fluorine or chlorine.

Each and every hydrogen in the compound (such as in an alkyl group or where referred to as hydrogen) includes all isotopes of hydrogen, in particular $^1H$ and $^2H$ (deuterium).

The term 'oxo' as used herein refers to the group =O.

The term '$C_{1-4}$ alkyl' as used herein as a group or part of a group refers to a linear or branched saturated hydrocarbon group containing from 1 to 4 carbon atoms respectively. Examples of such groups include methyl, ethyl, n-propyl, isopropyl, n-butyl, isobutyl, sec-butyl, tert butyl and the like.

The term '$C_{2-4}$ alkenyl' or '$C_{2-6}$ alkenyl' as used herein as a group or part of a group refers to a linear or branched hydrocarbon group containing from 2 to 4, or 2 to 6 carbon atoms, respectively, and containing a carbon carbon double bond. Examples of such groups include $C_{3-4}$ alkenyl or $C_{3-6}$ alkenyl groups, such as ethenyl (vinyl), 1-propenyl, 2-propenyl (allyl), isopropenyl, butenyl, buta-1,4-dienyl, pentenyl, and hexenyl.

The term '$C_{2-4}$ alkynyl' or '$C_{2-6}$ alkynyl' as used herein as a group or part of a group refers to a linear or branched hydrocarbon group having from 2 to 4 or 2 to 6 carbon atoms, respectively, and containing a carbon carbon triple bond. Examples of such groups include $C_{3-4}$ alkynyl or $C_{3-6}$ alkynyl groups such as ethynyl and 2 propynyl (propargyl) groups.

The term '$C_{1-4}$alkoxy' as used herein as a group or part of a group refers to an —O—$C_{1-4}$ alkyl group wherein $C_{1-4}$alkyl is as defined herein. Examples of such groups include methoxy, ethoxy, propoxy, butoxy, and the like.

The term '$C_{3-6}$cycloalkyl' as used herein refers to a saturated monocyclic hydrocarbon ring of 3 to 6 carbon atoms. Examples of such groups include cyclopropyl, cyclobutyl, cyclopentyl or cyclohexyl and the like.

The term '$C_{3-6}$cycloalkenyl' as used herein refers to a partially saturated monocyclic hydrocarbon ring of 3 to 6 carbon atoms having one or more (usually one) carbon carbon double bond(s). Examples of such groups include cyclopentenyl, cyclohexenyl, and cyclohexadienyl.

The term 'hydroxy$C_{1-4}$ alkyl' as used herein as a group or part of a group refers to a $C_{1-4}$alkyl group as defined herein wherein one or more (e.g. 1, 2 or 3) than one hydrogen atom is replaced with a hydroxyl group. The term 'hydroxy$C_{1-4}$ alkyl' therefore includes monohydroxy$C_{1-4}$ alkyl, and also polyhydroxy$C_{1-4}$ alkyl. There may be one, two, three or more hydrogen atoms replaced with a hydroxyl group, so the hydroxy$C_{1-4}$alkyl may have one, two, three or more hydroxyl groups. Examples of such groups include hydroxymethyl, hydroxyethyl, hydroxypropyl and the like.

The term 'halo$C_{1-4}$ alkyl' as used herein as a group or part of a group refers to a $C_{1-4}$alkyl group as defined herein wherein one or more (e.g. 1, 2 or 3) than one hydrogen atom is replaced with a halogen. The term 'halo$C_{1-4}$ alkyl' therefore includes monohalo$C_{1-4}$alkyl and also polyhalo$C_{1-4}$alkyl. There may be one, two, three or more hydrogen atoms replaced with a halogen, so the halo$C_{1-4}$alkyl may have one, two, three or more halogens. Examples of such groups include fluoroethyl, fluoromethyl, difluoromethyl, trifluoromethyl or trifluoroethyl and the like.

The term 'halo$C_{1-4}$alkoxy' as used herein as a group or part of a group refers to a —O—$C_{1-4}$alkyl group as defined herein wherein one or more (e.g. 1, 2 or 3) than one hydrogen atom is replaced with a halogen. The terms 'halo$C_{1-4}$alkoxy' therefore include monohalo$C_{1-4}$alkoxy, and also polyhalo$C_{1-4}$alkoxy. There may be one, two, three or more hydrogen atoms replaced with a halogen, so the halo$C_{1-4}$alkoxy may have one, two, three or more halogens. Examples of such groups include fluoroethyloxy, difluoromethoxy or trifluoromethoxy and the like.

The term "heterocyclyl group" as used herein shall, unless the context indicates otherwise, include both aromatic and non-aromatic ring systems. Thus, for example, the term "heterocyclyl group" include within their scope aromatic, non-aromatic, unsaturated, partially saturated and saturated heterocyclyl ring systems. In general, unless the context indicates otherwise, such groups may be monocyclic or bicyclic (including fused, spiro and bridged bicyclic groups) and may contain, for example, 3 to 12 ring members, more usually 5 to 10 ring members. Reference to 4 to 7 ring members includes 4, 5, 6 or 7 atoms in the ring and reference to 4 to 6 ring members include 4, 5, or 6 atoms in the ring. Examples of monocyclic groups are groups containing 3, 4, 5, 6, 7 and 8 ring members, more usually 3 to 7, or 4 to 7 and preferably 5, 6 or 7 ring members, more preferably 5 or 6 ring members. Examples of bicyclic groups are those containing 8, 9, 10, 11 and 12 ring members, and more usually 9 or 10 ring members. The heterocyclyl groups can be heteroaryl groups having from 5 to 12 ring members, more usually from 5 to 10 ring members. Where reference is made herein to a heterocyclyl group, the heterocyclyl ring can, unless the context indicates otherwise, be optionally substituted i.e. unsubstituted or substituted, by one or more (e.g. 1, 2, 3, or 4 in particular one or two) substituents as defined herein.

The heterocyclyl group can be, for example, a five membered or six membered monocyclic ring or a bicyclic structure formed from fused five and six membered rings or two fused six membered rings, or two fused five membered rings. Each ring may contain up to five heteroatoms particularly selected from nitrogen, sulfur and oxygen and oxidised forms of nitrogen or sulfur. Particularly the heterocyclyl ring will contain up to 4 heteroatoms, more particularly up to 3 heteroatoms, more usually up to 2, for example a single heteroatom. In one embodiment, the heterocyclyl ring will contain one or two heteroatoms selected from N, O, S and oxidised forms of N or S. In one embodiment, the heterocyclyl ring contains at least one ring nitrogen atom. The nitrogen atoms in the heterocyclyl rings can be basic, as in the case of an imidazole or pyridine, or essentially non-basic as in the case of an indole or pyrrole nitrogen. In general the number of basic nitrogen atoms present in the heterocyclyl group, including any amino group substituents of the ring, will be less than five.

The heterocyclyl groups can be attached via a carbon atom or a heteroatom (e.g. nitrogen). Equally the heterocyclyl groups can be substituted on a carbon atom or on a heteroatom (e.g. nitrogen).

Examples of five membered aromatic heterocyclyl groups include but are not limited to pyrrolyl, furanyl, thienyl, imidazolyl, furazanyl, oxazolyl, oxadiazolyl, oxatriazolyl, isoxazolyl, thiazolyl, thiadiazolyl, isothiazolyl, pyrazolyl, triazolyl and tetrazolyl groups.

Examples of six membered aromatic heterocyclic groups include but are not limited to pyridinyl, pyrazinyl, pyridazinyl, pyrimidinyl and triazinyl.

The term "heteroaryl" is used herein to denote a heterocyclyl group having aromatic character. The term "heteroaryl" embraces polycyclic (e.g. bicyclic) ring systems wherein one or more rings are non-aromatic, provided that at least one ring is aromatic. In such polycyclic systems, the group may be attached by the aromatic ring, or by a non-aromatic ring.

Examples of heteroaryl groups are monocyclic and bicyclic groups containing from five to twelve ring members, and more usually from five to ten ring members.

Examples of five membered heteroaryl groups include but are not limited to pyrrole, furan, thiophene, imidazole, furazan, oxazole, oxadiazole, oxatriazole, isoxazole, thiazole, thiadiazole, isothiazole, pyrazole, triazole and tetrazole groups.

Examples of six membered heteroaryl groups include but are not limited to pyridine, pyrazine, pyridazine, pyrimidine and triazine.

A bicyclic heteroaryl group may be, for example, a group selected from:
a) a benzene ring fused to a 5- or 6-membered ring containing 1, 2 or 3 ring heteroatoms;
b) a pyridine ring fused to a 5- or 6-membered ring containing 0, 1, 2 or 3 ring heteroatoms;
c) a pyrimidine ring fused to a 5- or 6-membered ring containing 0, 1 or 2 ring heteroatoms;
d) a pyrrole ring fused to a 5- or 6-membered ring containing 0, 1, 2 or 3 ring heteroatoms;
e) a pyrazole ring fused to a 5- or 6-membered ring containing 0, 1 or 2 ring heteroatoms;
f) an imidazole ring fused to a 5- or 6-membered ring containing 0, 1 or 2 ring heteroatoms;
g) an oxazole ring fused to a 5- or 6-membered ring containing 0, 1 or 2 ring heteroatoms;
h) an isoxazole ring fused to a 5- or 6-membered ring containing 0, 1 or 2 ring heteroatoms;
i) a thiazole ring fused to a 5- or 6-membered ring containing 0, 1 or 2 ring heteroatoms;
j) an isothiazole ring fused to a 5- or 6-membered ring containing 0, 1 or 2 ring heteroatoms;
k) a thiophene ring fused to a 5- or 6-membered ring containing 0, 1, 2 or 3 ring heteroatoms;
l) a furan ring fused to a 5- or 6-membered ring containing 0, 1, 2 or 3 ring heteroatoms;
m) a cyclohexyl ring fused to a 5- or 6-membered ring containing 1, 2 or 3 ring heteroatoms; and
n) a cyclopentyl ring fused to a 5- or 6-membered ring containing 1, 2 or 3 ring heteroatoms.

Particular examples of bicyclic heteroaryl groups containing a five membered ring fused to another five membered ring include but are not limited to imidazothiazole (e.g. imidazo[2,1-b]thiazole) and imidazoimidazole (e.g. imidazo[1,2-a]imidazole).

Particular examples of bicyclic heteroaryl groups containing a six membered ring fused to a five membered ring include but are not limited to benzofuran, benzothiophene, benzimidazole, benzoxazole, isobenzoxazole, benzisoxazole, benzothiazole, benzisothiazole, isobenzofuran, indole, isoindole, indolizine, indoline, isoindoline, purine (e.g., adenine, guanine), indazole, pyrazolopyrimidine (e.g. pyrazolo[1,5-a]pyrimidine), triazolopyrimidine (e.g. [1,2,4]triazolo[1,5-a]pyrimidine), benzodioxole, imidazopyridine and pyrazolopyridine (e.g. pyrazolo[1,5-a]pyridine) groups.

Particular examples of bicyclic heteroaryl groups containing two fused six membered rings include but are not limited to quinoline, isoquinoline, chroman, thiochroman, isochroman, chromene, isochromene, benzodioxan, quinolizine, benzoxazine, pyridopyridine, quinoxaline, quinazoline, cinnoline, phthalazine, naphthyridine and pteridine groups.

Examples of polycyclic heteroaryl groups containing an aromatic ring and a non-aromatic ring include, tetrahydroisoquinoline, tetrahydroquinoline, dihydrobenzthiophene, dihydrobenzofuran, 2,3-dihydro-benzo[1,4]dioxine, benzo[1,3]dioxole, 4,5,6,7-tetrahydrobenzofuran, tetrahydrotriazolopyrazine (e.g. 5,6,7,8-tetrahydro-[1,2,4]triazolo[4,3-a]pyrazine), chroman, thiochroman, isochroman, chromene, isochromene, benzodioxan, benzoxazine, benzodiazepine, and indoline groups.

A nitrogen-containing heteroaryl ring must contain at least one ring nitrogen atom. The nitrogen-containing heteroaryl ring can be N-linked or C-linked. Each ring may, in addition, contain up to about four other heteroatoms particularly selected from nitrogen, sulfur and oxygen. Particularly the heteroaryl ring will contain up to 3 heteroatoms, for example 1, 2 or 3, more usually up to 2 nitrogens, for example a single nitrogen. The nitrogen atoms in the heteroaryl rings can be basic, as in the case of an imidazole or pyridine, or essentially non-basic as in the case of an indole or pyrrole nitrogen. In general the number of basic nitrogen atoms present in the heteroaryl group, including any amino group substituents of the ring, will be less than five.

Examples of nitrogen-containing heteroaryl groups include, but are not limited to, monocyclic groups such as pyridyl, pyrrolyl, imidazolyl, oxazolyl, oxadiazolyl, thiadiazolyl, oxatriazolyl, isoxazolyl, thiazolyl, isothiazolyl, furazanyl, pyrazolyl, pyrazinyl, pyrimidinyl, pyridazinyl, triazinyl, triazolyl (e.g., 1,2,3-triazolyl, 1,2,4-triazolyl), tetrazolyl, and bicyclic groups such as quinolinyl, isoquinolinyl, benzimidazolyl, benzoxazolyl, benzisoxazole, benzothiazolyl and benzisothiazole, indolyl, 3H-indolyl, isoindolyl, indolizinyl, isoindolinyl, purinyl (e.g., adenine [6-aminopurine], guanine [2-amino-6-hydroxypurine]), indazolyl, quinolizinyl, benzoxazinyl, benzodiazepinyl, pyridopyridinyl, quinoxalinyl, quinazolinyl, cinnolinyl, phthalazinyl, naphthyridinyl and pteridinyl.

Examples of nitrogen-containing polycyclic heteroaryl groups containing an aromatic ring and a non-aromatic ring include tetrahydroisoquinolinyl, tetrahydroquinolinyl, and indolinyl.

The term "non-aromatic" embraces, unless the context indicates otherwise, unsaturated ring systems without aromatic character, partially saturated and saturated heterocyclyl ring systems. The terms "unsaturated" and "partially saturated" refer to rings wherein the ring structure(s) contains atoms sharing more than one valence bond i.e. the ring contains at least one multiple bond e.g. a C=C, C≡C or N=C bond. The term "saturated" refers to rings where there are no multiple bonds between ring atoms. Saturated heterocyclyl groups include piperidinyl, morpholinyl, and thiomorpholinyl. Partially saturated heterocyclyl groups include pyrazolinyl, for example pyrazolin-2-yl and pyrazolin-3-yl.

Examples of non-aromatic heterocyclyl groups are groups having from 3 to 12 ring members, more usually 5 to 10 ring members. Such groups can be monocyclic or bicyclic, for example, have 3 to 7 ring members in particular 4 to 6 ring members. Such groups particularly have from 1 to 5 or 1 to 4 heteroatom ring members (more usually 1, 2, or 3 heteroatom ring members), usually selected from nitrogen, oxygen and sulfur and oxidised forms thereof. The heterocyclyl groups can contain, for example, cyclic ether moieties (e.g. as in tetrahydrofuran and dioxane), cyclic thioether moieties (e.g. as in tetrahydrothiophene and dithiane), cyclic amine moieties (e.g. as in pyrrolidine), cyclic amide moieties (e.g. as in pyrrolidone), cyclic thioamides, cyclic thioesters, cyclic ureas (e.g. as in imidazolidin-2-one) cyclic ester moieties (e.g. as in butyrolactone), cyclic sulfones (e.g. as in sulfolane and sulfolene), cyclic sulfoxides, cyclic sulfonamides and combinations thereof (e.g. thiomorpholine).

Particular examples include morpholinyl, piperidinyl (e.g. piperidin-1-yl, piperidin-2-yl, piperidin-3-yl and piperidin-4-yl), piperidinonyl, pyrrolidinyl (e.g. pyrrolidin-1-yl, pyrrolidin-2-yl and pyrrolidin-3-yl), pyrrolidonyl, azetidinyl, pyranyl (2H-pyran or 4H-pyran), dihydrothienyl, dihydropyranyl, dihydrofuranyl, dihydrothiazolyl, tetrahydrofuranyl, tetrahydrothienyl, dioxanyl, oxanyl (also known as tetrahydropyranyl) (e.g. oxan-4-yl), imidazolinyl, imidazolidinonyl, oxazolinyl, thiazolinyl, pyrazolin-2-yl, pyrazolidinyl, piperazinonyl, piperazinyl, and N-alkyl piperazines such as N-methyl piperazinyl. In general, typical non-aromatic heterocyclyl groups include saturated groups such as piperidinyl, pyrrolidinyl, azetidinyl, morpholinyl, piperazinyl and N-alkyl piperazines such as N-methyl piperazinyl.

In a nitrogen-containing non-aromatic heterocyclyl ring the ring must contain at least one ring nitrogen atom. The nitrogen-containing heterocyclyl ring can be N-linked or C-linked. The heterocylic groups can contain, for example, cyclic amine moieties (e.g. as in pyrrolidinyl), cyclic amides (such as a pyrrolidinonyl, piperidinonyl or caprolactamyl), cyclic sulfonamides (such as an isothiazolidinyl 1,1-dioxide, [1,2]thiazinanyl 1,1-dioxide or [1,2]thiazepanyl 1,1-dioxide) and combinations thereof.

Particular examples of nitrogen-containing non-aromatic heterocyclyl groups include aziridinyl, morpholinyl, thiomorpholinyl, piperidinyl (e.g. piperidin-1-yl, piperidin-2yl, piperidin-3-yl and piperidin-4-yl), pyrrolidinyl; (e.g. pyrrolidin-1-yl, pyrrolidin-2-yl and pyrrolidin-3-yl), pyrrolidonyl, dihydrothiazolyl, imidazolinyl, imidazolidinonyl, oxazolinyl, thiazolinyl, 6H-1,2,5-thiadiazinyl, pyrazolin-2-yl, pyrazolin-3-yl, pyrazolidinyl, piperazinyl, and N-alkyl piperazines such as N-methyl piperazinyl.

The heterocyclyl groups can be polycyclic fused ring systems or bridged ring systems such as the oxa- and aza analogues of bicycloalkanes, tricycloalkanes (e.g. adamantane and oxa-adamantane). For an explanation of the distinction between fused and bridged ring systems, see Advanced Organic Chemistry, by Jerry March, 4th Edition, Wiley Interscience, pages 131-133, 1992.

Where, in a definition of a cyclic group or ring, it is stated that the cyclic group contains a certain number of heteroatom ring members, e.g. as in the phrase "a 5 or 6 membered ring containing 0, 1 or 2 nitrogen ring members", this is to be taken as meaning that apart from the certain number of heteroatom ring members specified, the remaining ring members are carbon atoms.

The compound of formula (I) may contain saturated cyclic groups that can be joined to the rest of the molecule by one or more bonds. When the cyclic group is joined to the rest of the molecule by two or more bonds, these bonds (or two of these bonds) can be made to the same atom (usually a carbon atom) of the ring or different atoms of the ring. Where the bonds are made to the same atom of the ring, this results in a cyclic group with a single atom (usually a quaternary carbon) bound to two groups. In other words, when the compound of formula (I) includes a cyclic group that group may either be linked to the rest of the molecule by a bond or the cyclic group and the rest of the molecule can have an atom in common e.g. a spiro compound.

The heterocyclyl group can each be unsubstituted or substituted by one or more (e.g. 1, 2 or 3) substituent groups. For example, heterocyclyl or carbocyclyl groups can be unsubstituted or substituted by 1, 2, 3 or 4 substituents and particularly it is unsubstituted or has 1, 2 or 3 substituents as defined herein. Where the cyclic group is saturated there may be 2 substituents joined to the same carbon (where the substituents are the same so called geminal or 'gem' disubstitution).

A combination of substituents is permissible only if such as combination results in a stable or chemically feasible compound (i.e. one that is not substantially altered when kept at 40° C. or less for at least a week).

The various functional groups and substituents making up the compounds of the invention are particularly chosen such that the molecular weight of the compound of the invention does not exceed 1000. More usually, the molecular weight of the compound will be less than 750, for example less than 700, or less than 650, or less than 600, or less than 550. More particularly, the molecular weight is less than 525 and, for example, is 500 or less.

DETAILED DESCRIPTION OF THE INVENTION

The invention provides a compound of formula (I):

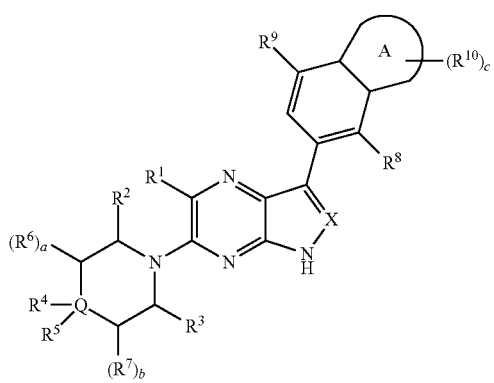

(I)

or a tautomer or a solvate or a pharmaceutically acceptable salt thereof, wherein X, Q, $R^1$, $R^2$, $R^3$, $R^4$, $R^5$, $R^6$, $R^7$, $R^8$, $R^9$, $R^{10}$, a, b, c and A are as defined herein.

X

X is CH or N.

Therefore, the bicyclic ring in the compound of formula (I) is either a pyrrolopyrazine or a pyrazolopyrazine:

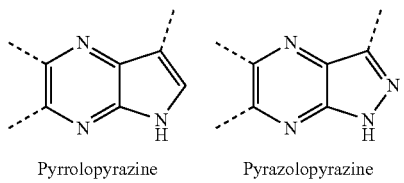

Pyrrolopyrazine     Pyrazolopyrazine

In one embodiment, X is CH and the compound is a pyrrolopyrazine. In one embodiment, X is N and the compound is a pyrazolopyrazine.

In particular, X is CH, and the compound of formula (I) is a compound of formula (II) or a tautomer or a solvate or a pharmaceutically acceptable salt thereof:

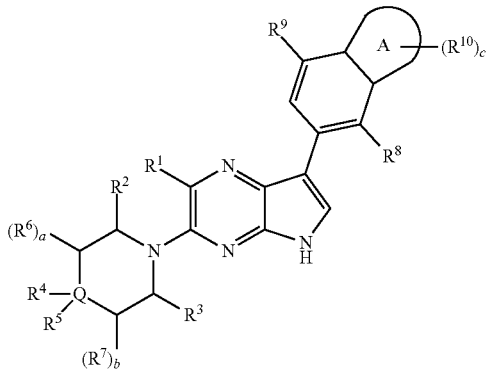

(II)

wherein Q, $R^1$, $R^2$, $R^3$, $R^4$, $R^5$, $R^6$, $R^7$, $R^8$, $R^9$, $R^{10}$, a, b, c and A are as defined herein.

In particular, X is N, and the compound of formula (I) is a compound of formula (IIa) or a tautomer or a solvate or a pharmaceutically acceptable salt thereof:

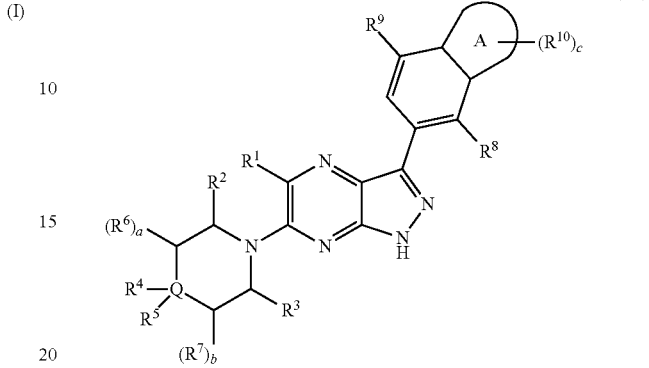

(IIa)

wherein Q, $R^2$, $R^3$, $R^4$, $R^5$, $R^6$, $R^7$, $R^8$, $R^9$, $R^{10}$, a, b, c and A are as defined herein and $R^1$ is —$CH_3$ or —$CH_2OH$.

$R^1$ $R^1$ is hydrogen, —$CH_3$ or —$CH_2OH$ but when X is N then $R^1$ is selected from —$CH_3$ and —$CH_2OH$.

In one embodiment, $R^1$ is hydrogen or —$CH_3$.

In one embodiment, $R^1$ is hydrogen or —$CH_2OH$.

In one embodiment, $R^1$ is —$CH_3$ or —$CH_2OH$.

In one embodiment, $R^1$ is —$CH_3$.

In one embodiment, $R^1$ is —$CH_2OH$.

In particular, $R^1$ is hydrogen and X is CH, and the compound of formula (I) is a compound of formula (III) or a tautomer or a solvate or a pharmaceutically acceptable salt thereof:

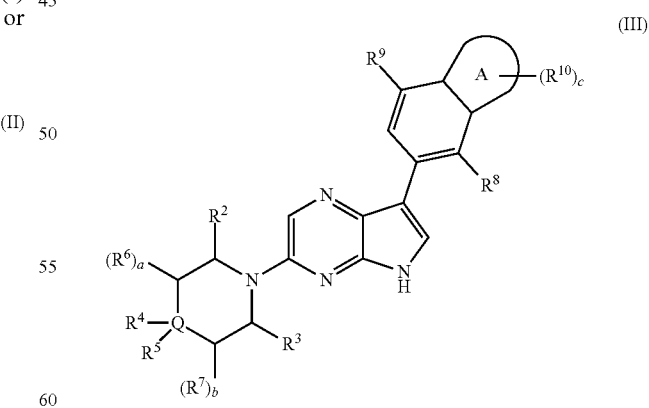

(III)

wherein $R^2$, $R^3$, $R^4$, $R^5$, $R^8$, $R^9$, $R^{10}$, a, b, c and A are as defined herein.

In particular, X is N, and the compound of formula (I) is a compound of formula (IIIa) or a tautomer or a solvate or a pharmaceutically acceptable salt thereof:

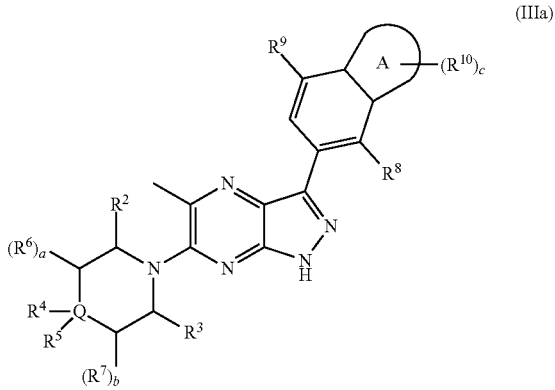

(IIIa)

wherein Q, $R^2$, $R^3$, $R^4$, $R^5$, $R^6$, $R^7$, $R^8$, $R^9$, $R^{10}$, a, b, c and A are as defined herein.

In particular, X is N, and the compound of formula (I) is a compound of formula (IIIb) or a tautomer or a solvate or a pharmaceutically acceptable salt thereof:

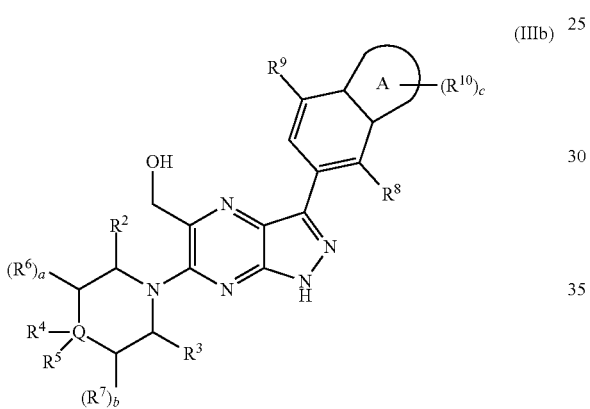

(IIIb)

wherein Q, $R^2$, $R^3$, $R^4$, $R^5$, $R^6$, $R^7$, $R^8$, $R^9$, $R^{10}$, a, b, c and A are as defined herein.

$R^2$ and $R^3$ $R^2$ and $R^3$ are either:

(i) independently selected from hydrogen and $C_{1-4}$alkyl; or (ii) together form a one- to three-membered bridge group selected from $C_{1-3}$alkylene, $C_{2-3}$alkenylene, methylene-NR$^q$-methylene and methylene-O-methylene, wherein the bridge group is optionally substituted by a group selected from $C_{1-4}$alkyl, hydroxyl and halogen and R$^q$ is selected from hydrogen, $C_{1-4}$alkyl, hydroxyl and halogen (for example hydrogen and $C_{1-4}$alkyl).

In one embodiment, the bridge group is optionally substituted by a group selected from $C_{1-4}$alkyl, hydroxyl and halogen. In particular the bridge group is optionally substituted by a group selected from $C_{1-4}$alkyl, hydroxyl and halogen, but excluding compounds wherein a hydroxyl or halogen is at a position α to an N or O atom and excluding compounds wherein a hydroxyl group is bonded to an alkene carbon.

In one embodiment, $R^2$ and $R^3$ together form a one- to three-membered bridge group selected from $C_{1-3}$alkylene (e.g. —$CH_2$—, —$CH_2$—$CH_2$— or —$CH_2CH_2CH_2$—), $C_{2-3}$alkenylene (e.g. —CH═CH—), methylene-NH-methylene (e.g. —$CH_2$—NH—$CH_2$—) and methylene-O-methylene (e.g. —$CH_2$—O—$CH_2$—), wherein the bridge group is optionally substituted by a group selected from $C_{1-4}$alkyl, hydroxyl and halogen but excluding compounds wherein a hydroxyl or halogen is at a position α to an N or O atom and excluding compounds wherein a hydroxyl group is bonded to an alkene carbon.

In one embodiment, $R^2$ and $R^3$ together form a one- to three-membered bridge group selected from $C_{1-3}$alkylene (e.g. —$CH_2$—, —$CH_2$—$CH_2$— or —$CH_2CH_2CH_2$—), $C_{2-3}$alkenylene (e.g. —CH═CH—), methylene-NH-methylene (e.g. —$CH_2$—NH—$CH_2$—) and methylene-O-methylene (e.g. —$CH_2$—O—$CH_2$—), wherein the $C_{1-3}$alkylene (e.g. —$CH_2$—, —$CH_2$—$CH_2$— or —$CH_2CH_2CH_2$—) or $C_{2-3}$alkenylene (e.g. —CH═CH—) bridge group is optionally substituted by a group selected from $C_{1-4}$alkyl and halogen. In one embodiment the halogen substituent is not alpha to the O or N present in the bridge group.

Therefore, the moiety

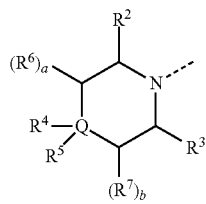

is a moiety as follows, wherein the one- to three-membered bridge group is represented by a curved line:

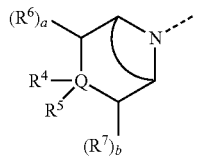

The bridge group may include one, two or three ring members. Therefore, together with the two carbon atoms to which the bridge group is attached and the nitrogen atom between those two carbon atoms on the heterocylic ring, the bridge group forms part of a four-membered ring (when the bridge group includes one ring member), a five-membered ring (when the bridge group includes two ring members), or a six-membered ring (when the bridge group includes three ring members).

In one embodiment, the bridge group is $C_{1-3}$alkylene, for example —$CH_2$—, —$CH_2$—$CH_2$— or —$CH_2CH_2CH_2$— wherein the bridge group is optionally substituted by a group selected from $C_{1-4}$alkyl, hydroxyl and halogen.

In one embodiment, the bridge group is $C_{1-3}$alkylene, for example —$CH_2$—, —$CH_2$—$CH_2$— or —$CH_2CH_2CH_2$— and the compound of formula (I) is a compound of formula (IV) or a tautomer or a solvate or a pharmaceutically acceptable salt thereof:

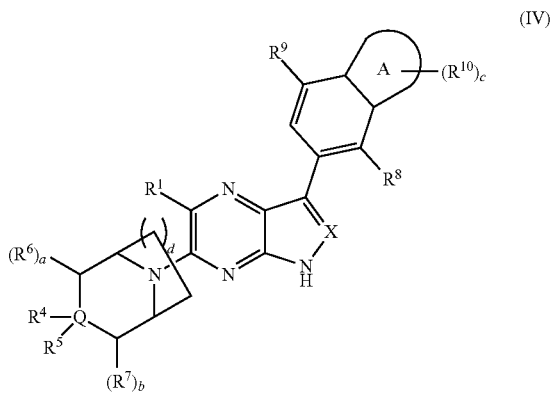

(IV)

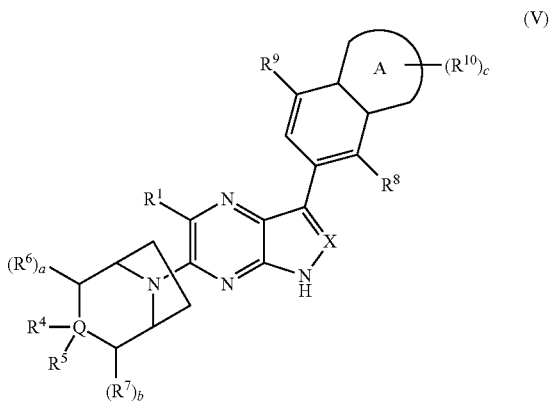

(V)

wherein Q, $R^1$, $R^4$, $R^5$, $R^6$, $R^7$, $R^8$, $R^9$, $R^{10}$, a, b, c and A are as defined herein, and d is 0, 1 or 2.

In one embodiment, the bridge group is $C_{2-3}$alkenylene, for example —CH=CH— or —CH$_2$—CH=CH—, wherein the bridge group is optionally substituted by a group selected from $C_{1-4}$alkyl, hydroxyl and halogen but excluding compounds wherein a hydroxyl group is bonded to an alkene carbon (i.e. excluding enols). In one embodiment, the bridge group is $C_{2-3}$alkenylene, for example —CH=CH— or —CH$_2$—CH=CH—, wherein the bridge group is optionally substituted by a group selected from $C_{1-4}$alkyl, and halogen.

In one embodiment, the bridge group is $C_{2-3}$alkenylene, for example —CH=CH— or —CH$_2$—CH=CH—.

In one embodiment, the bridge group is methylene-NR$^q$-methylene, for example —CH$_2$—NH—CH$_2$—, wherein the bridge group is optionally substituted by a group selected from $C_{1-4}$alkyl and $R^q$ is selected from hydrogen and $C_{1-4}$alkyl.

In one embodiment, the bridge group is methylene-NR$^q$-methylene, for example —CH$_2$—NH—CH$_2$—, optionally substituted by a group selected from $C_{1-4}$alkyl and $R^q$ is selected from hydrogen and $C_{1-4}$alkyl.

In one embodiment, the bridge group is methylene-NR$^q$-methylene, for example —CH$_2$—NH—CH$_2$—, and $R^q$ is selected from hydrogen and $C_{1-4}$alkyl.

In one embodiment, the bridge group is methylene-NH-methylene, for example —CH$_2$—NH—CH$_2$—.

In one embodiment, the bridge group is methylene-O-methylene, for example —CH$_2$—O—CH$_2$—, wherein the bridge group is optionally substituted by a group selected from $C_{1-4}$alkyl.

In one embodiment, the bridge group is methylene-O-methylene, for example —CH$_2$—O—CH$_2$—.

The bridge group is optionally substituted by a group selected from $C_{1-4}$alkyl, hydroxyl and halogen, for example —CH$_3$, in particular excluding compounds wherein a hydroxyl or halogen is at a position α to an N or O atom and excluding compounds wherein a hydroxyl group is bonded to an alkene carbon.

In particular, the bridge group is unsubstituted.

In particular, the bridge group is alkylene, for example —CH$_2$—, —CH$_2$—CH$_2$— or —CH$_2$CH$_2$CH$_2$—, e.g. —CH$_2$—CH$_2$— or —CH$_2$CH$_2$CH$_2$—. In particular, the bridge group is unsubstituted alkylene, for example —CH$_2$—, —CH$_2$—CH$_2$— or —CH$_2$CH$_2$CH$_2$—, e.g. —CH$_2$—CH$_2$— or —CH$_2$CH$_2$CH$_2$—.

In particular, the bridge group is —CH$_2$—CH$_2$—, and the compound of formula (I) is a compound of formula (V) or a tautomer or a solvate or a pharmaceutically acceptable salt thereof:

wherein X, Q, $R^1$, $R^4$, $R^5$, $R^6$, $R^7$, $R^8$, $R^9$, $R^{10}$, a, b, c and A are as defined herein.

In another embodiment, $R^2$ and $R^3$ are independently selected from hydrogen and $C_{1-4}$alkyl.

In one embodiment, $R^2$ and $R^3$ are independently selected from hydrogen and —CH$_3$.

In one embodiment, $R^2$ and $R^3$ are hydrogen.

In one embodiment, $R^2$ and $R^3$ are either:
(i) hydrogen; or
(ii) together form a one- to three-membered alkylene bridge group (e.g. —CH$_2$— or —CH$_2$—CH$_2$—).

Q, $R^4$ and $R^5$

Q is C or N;
  wherein when Q is C then either:
    (i) $R^4$ is hydrogen or $C_{1-4}$alkyl (e.g. methyl) optionally substituted by amino (e.g. —CH$_2$NH$_2$);
    $R^5$ is hydrogen, amino, hydroxyl or $C_{1-4}$alkyl (e.g. methyl) optionally substituted by 1 or 2 groups selected from halogen, hydroxyl (e.g. —CH$_2$OH) or amino;
    provided that $R^4$ and $R^5$ must not both be selected from amino and $C_{1-4}$alkyl substituted by amino; or
    (ii) $R^4$ and $R^5$ together with Q form a four- to six-membered nitrogen-containing heterocyclic ring; and
  wherein when Q is N then:
    $R^4$ is absent;
    $R^5$ is hydrogen; and
    $R^2$ and $R^3$ together form the one- to three-membered bridge group.

In the embodiment when Q is C, then $R^2$ and $R^3$ are either:
(i) independently selected from hydrogen and $C_{1-4}$alkyl; or
(ii) together form a one- to three-membered bridge group selected from $C_{1-3}$alkylene, $C_{2-3}$alkenylene, methylene-NR$^q$-methylene and methylene-O-methylene, wherein the bridge group is optionally substituted by a group selected from $C_{1-4}$alkyl, hydroxyl and halogen and $R^q$ is selected from hydrogen, $C_{1-4}$alkyl, hydroxyl and halogen.

In the embodiment when Q is N then:
$R^4$ is absent;
$R^5$ is hydrogen; and
$R^2$ and $R^3$ together form the one- to three-membered bridge group as defined herein i.e. a one- to three-membered bridge group selected from $C_{1-3}$alkylene, $C_{2-3}$alkenylene, methylene-NR$^q$-methylene and methylene-O-methylene, wherein the bridge group is optionally substituted by a group selected from $C_{1-4}$alkyl, hydroxyl and halogen and R$^q$ is selected from hydrogen, C$_{1-4}$alkyl, hydroxyl and halogen.

In one embodiment, Q is C or N;
wherein when Q is C then either:
(i) R$^4$ is hydrogen or C$_{1-4}$alkyl (e.g. methyl) optionally substituted by amino (e.g. —CH$_2$NH$_2$);
R$^5$ is hydrogen, amino or C$_{1-4}$alkyl (e.g. methyl) optionally substituted by 1 or 2 groups selected from halogen, hydroxyl (e.g. —CH$_2$OH) or amino;
provided that R$^4$ and R$^5$ must not both be selected from amino and C$_{1-4}$alkyl substituted by amino; or
(ii) R$^4$ and R$^5$ together with Q form a four- to six-membered nitrogen-containing heterocyclic ring; and
wherein when Q is N then:
R$^4$ is absent;
R$^5$ is hydrogen; and
R$^2$ and R$^3$ together form the one- to three-membered bridge group.

In one embodiment, Q is C and the compound of formula (I) is a compound of formula (VI) or a tautomer or a solvate or a pharmaceutically acceptable salt thereof:

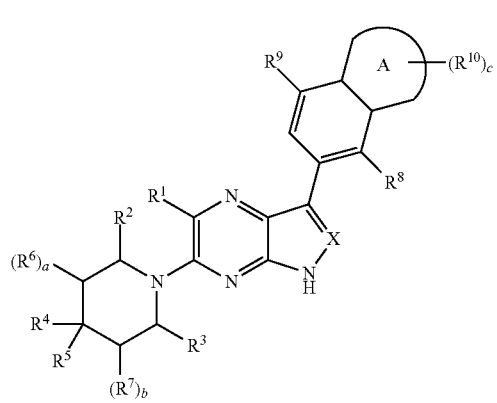

(VI)

wherein X, R$^1$, R$^2$, R$^3$, R$^4$, R$^5$, R$^6$, R$^7$, R$^8$, R$^9$, R$^{10}$, a, b, c and A are as defined herein.

In one embodiment Q is C and either:
(i) R$^4$ is hydrogen or C$_{1-4}$alkyl (e.g. methyl) optionally substituted by amino (e.g. —CH$_2$NH$_2$);
R$^5$ is hydrogen, amino, or C$_{1-4}$alkyl (e.g. methyl) optionally substituted by 1 or 2 groups selected from halogen, hydroxyl (e.g. —CH$_2$OH) or amino;
provided that R$^4$ and R$^5$ must not both be selected from amino and C$_{1-4}$alkyl substituted by amino or
(ii) R$^4$ and R$^5$ together with Q form a four- to six-membered nitrogen-containing heterocyclic ring.

When Q is C, in one embodiment R$^4$ is hydrogen or C$_{1-4}$alkyl (e.g. methyl).

When Q is C, in particular R$^4$ is hydrogen or —CH$_3$, for example hydrogen.

When Q is C, in one embodiment R$^5$ is hydrogen, amino, or C$_{1-4}$alkyl (e.g. —CH$_3$) optionally substituted by 1 or 2 groups selected from halogen, hydroxyl (e.g. —CH$_2$OH) or amino.

When Q is C, in one embodiment R$^5$ is C$_{1-4}$alkyl (e.g. —CH$_3$) optionally substituted by hydroxyl (e.g. —CH$_2$OH) or amino (e.g. CH$_2$N).

When Q is C, in one embodiment R$^5$ is amino, hydroxyl or C$_{1-4}$alkyl (e.g. —CH$_3$) substituted by amino or hydroxyl.

When Q is C, in one embodiment R$^5$ is amino or C$_{1-4}$alkyl (e.g. —CH$_3$) substituted by amino.

When Q is C, in particular R$^5$ is amino or —CH$_3$.

R$^4$ and R$^5$ must not both be selected from amino and C$_{1-4}$alkyl substituted by amino. In one embodiment when Q is C, only one of R$^4$ and R$^5$ is amino or C$_{1-4}$alkyl substituted by amino i.e. one of R$^4$ and R$^5$ is amino or C$_{1-4}$alkyl substituted by amino and one of R$^4$ and R$^5$ is other than amino and C$_{1-4}$alkyl substituted by amino.

In one embodiment when Q is C, one of R$^4$ is C$_{1-4}$alkyl (e.g. —CH$_3$) substituted by amino or R$^5$ is amino or C$_{1-4}$alkyl (e.g. —CH$_3$) substituted by amino.

In one embodiment when Q is C, R$^4$ is hydrogen and R$^5$ is amino or C$_{1-4}$alkyl (e.g. —CH$_3$) substituted by amino.

When Q is C, in particular R$^5$ is amino and the compound of formula (I) is a compound of formula (VII) or a tautomer or a solvate or a pharmaceutically acceptable salt thereof:

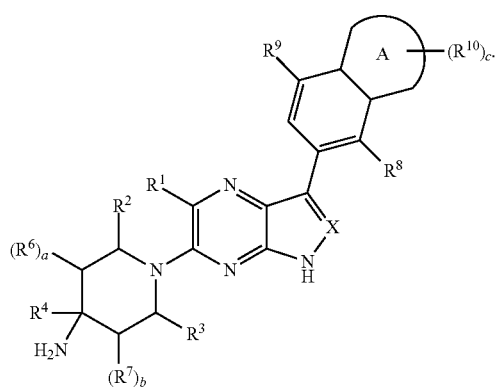

(VII)

wherein X, R$^1$, R$^2$, R$^3$, R$^4$, R$^6$, R$^7$, R$^8$, R$^9$, R$^{10}$, a, b, c and A are as defined herein.

When Q is C, in one embodiment R$^4$ is hydrogen or —CH$_3$ and R$^5$ is amino or —CH$_3$.

When Q is C, in particular R$^4$ is hydrogen and R$^5$ is amino.

When Q is C, in one embodiment R$^4$ is —CH$_3$ and R$^5$ is amino.

When Q is C and at least one of R$^2$ and R$^3$ is other than hydrogen, then the compounds of formula (I) may exist in more than one stereoisomeric form, for example (R$^4$, R$^6$ and R$^7$ not shown for simplicity):

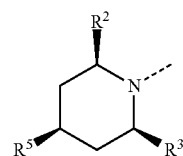

(a)

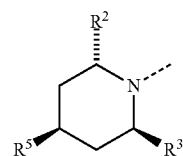

(b)

(c) 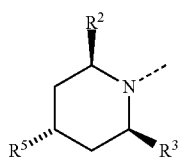

(d) 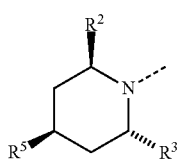

(e) 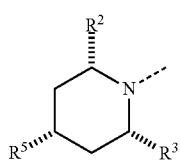

(f) 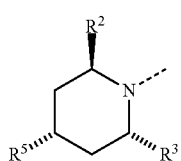

(g) 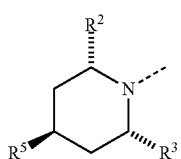

(h) 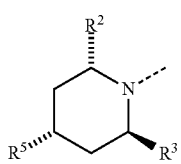

Certain of these stereoisomers are pairs of enantiomers:
(a) and (e) (if $R^2$ and $R^3$ are different, otherwise a meso form);
(b) and (f);
(c) and (g) (if $R^2$ and $R^3$ are different, otherwise a meso form); and
(d) and (h).

In one embodiment the compounds of formula (I) are racemic mixtures. In particular the compounds of formula (I) non-racemic. Typically, at least 55% (e.g. at least 60%, 65%, 70%, 75%, 80%, 85%, 90% or 95%) of the compound of the formula (I) is present as one stereoisomer. In particular, 97% (e.g. 99%) or more (e.g. substantially all) of the total amount of the compound of the formula (I) may be present as a single stereoisomer.

In one embodiment, $R^5$ is amino.

When Q is C, $R^5$ is other than hydrogen, and $R^2$ and $R^3$ together form a bridge group, then $R^5$ may either be orientated towards the bridge group or away from the bridge group.

In one embodiment, $R^5$ is orientated towards the bridge group ($R^4$, $R^6$ and $R^7$ not shown for clarity):

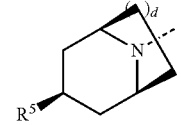

wherein d is 0, 1 or 2, in particular d is 1.

In one embodiment, $R^5$ is orientated away from the bridge group ($R^4$, $R^6$ and $R^7$ not shown for clarity):

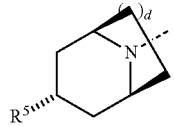

wherein d is 0, 1 or 2, in particular d is 1.

In one embodiment when Q is C, $R^5$ is amino. In one embodiment when Q is C, $R^5$ is amino and $R^4$ is hydrogen.

In particular, $R^5$ is orientated towards the bridge group, and the compound of formula (I) is a compound of formula (VIII) or a tautomer or a solvate or a pharmaceutically acceptable salt thereof:

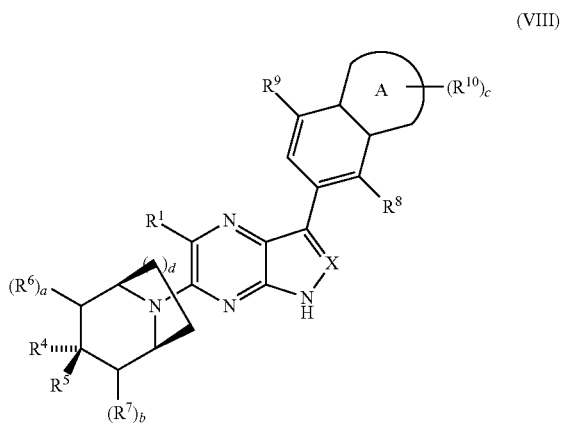

(VIII)

wherein X, $R^1$, $R^4$, $R^5$, $R^6$, $R^7$, $R^8$, $R^9$, $R^{10}$, a, b, c and A are as defined herein, and d is 0, 1 or 2.

In particular, $R^5$ is orientated towards the bridge group, d is 1, and the compound of formula (VIII) is a compound of formula (VIIIa) or a tautomer or a solvate or a pharmaceutically acceptable salt thereof:

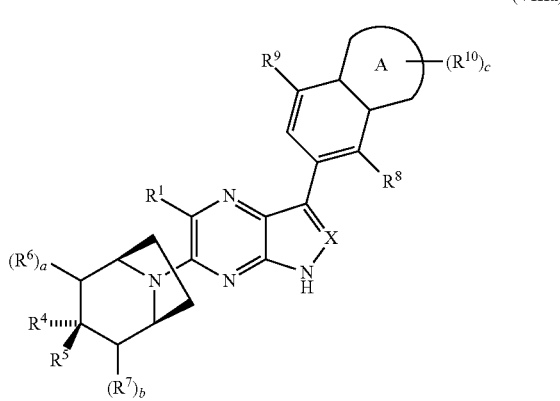

(VIIIa)

wherein X, $R^1$, $R^4$, $R^5$, $R^6$, $R^7$, $R^8$, $R^9$, $R^{10}$, a, b, c and A are as defined herein.

When Q is C, in one embodiment $R^4$ and $R^5$ together with Q form a four- to six-membered nitrogen-containing heterocyclic ring, for example azetidinyl, pyrrolidinyl or piperidinyl, such as azetidinyl or pyrrolidinyl, and in particular azetidinyl.

In one embodiment, Q is N and $R^4$ is absent, $R^5$ is hydrogen, and $R^2$ and $R^3$ together form the one- to three-membered bridge group.

In one embodiment, Q is C or N;
wherein when Q is C then either:
(i) $R^4$ is hydrogen or $C_{1-4}$alkyl (e.g. methyl) optionally substituted by amino (e.g. —$CH_2NH_2$);
$R^5$ is hydrogen, amino, or $C_{1-4}$alkyl (e.g. methyl) optionally substituted by amino; provided that $R^4$ and $R^5$ must not both be selected from amino and $C_{1-4}$alkyl substituted by amino; or
(ii) $R^4$ and $R^5$ together with Q form a four- to six-membered nitrogen-containing heterocyclic ring (e.g. azetidine); and
wherein when Q is N then:
$R^4$ is absent, $R^5$ is hydrogen and $R^2$ and $R^3$ together form the one- to three-membered alkylene bridge group (e.g. —$CH_2$— or —$CH_2$—$CH_2$—).

$R^6$, $R^7$, a and b $R^6$ and $R^7$ are independently selected from halogen (e.g. fluorine), $C_{1-4}$alkyl (e.g. —$CH_3$) and hydroxyl provided that when Q is N then $R^6$ or $R^7$ are not halogen or hydroxyl;
a is selected from 0, 1 and 2; and
b is selected from 0, 1 and 2.

a is 0, 1 or 2. When a is 0, a $CH_2$ group is present between Q and $CHR^2$. When a is 1, a $CHR^6$ group is present between Q and $CHR^2$. When a is 2, a $C(R^6)_2$ group is present between Q and $CHR^2$.

In one embodiment, a is 0 or 1. In particular, a is 0. In an alternative embodiment, a is 1.

b is 0, 1 or 2. When b is 0, a $CH_2$ group is present between Q and $CHR^3$. When b is 1, a $CHR^7$ group is present between Q and $CHR^3$. When b is 2, a $C(R^7)_2$ group is present between Q and $CHR^3$.

In one embodiment, b is 0 or 1. In particular, b is 0. In an alternative embodiment, b is 1.

In one embodiment, a is 1 and b is 0. In an alternative embodiment, a is 0 and b is 1.

In one embodiment, Q is C and $R^7$ is halogen (e.g. fluorine) or hydroxyl.

In particular, a is 0 and b is 0 i.e. a $CH_2$ group is present between Q and $CHR^2$ and a $CH_2$ group is present between Q and $CHR^3$, and the compound of formula (I) is a compound of formula (IX) or a tautomer or a solvate or a pharmaceutically acceptable salt thereof:

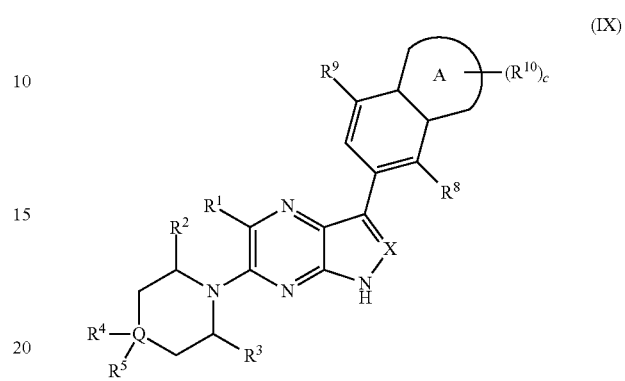

(IX)

wherein X, Q, $R^1$, $R^2$, $R^3$, $R^4$, $R^5$, $R^8$, $R^9$, $R^{10}$, a, b, c and A are as defined herein.

In one embodiment, $R^6$ and $R^7$ are independently selected from halogen (e.g. fluorine), and hydroxyl;
a is selected from 0, 1 and 2; and
b is selected from 0 and 1;
provided that when Q is N then a and b are 0.

In one embodiment, when present $R^6$ and $R^7$ are halogen (e.g. fluorine);
a is selected from 0, 1 and 2; and
b is selected from 0 and 1;
provided that when Q is N then a and b are 0.

In one embodiment, a is 1 and $R^6$ is halogen (e.g. fluorine) or hydroxyl. In particular, a is 1 and $R^6$ is fluorine.

In one embodiment, a is 1 and $R^7$ is halogen (e.g. fluorine) or hydroxyl. In particular, b is 1 and $R^6$ is fluorine.

In one embodiment, a is 1 and b is 1 and $R^6$ and $R^7$ are independently selected from halogen (e.g. fluorine) and hydroxyl.

When Q is C, $R^4$ and/or $R^5$ are other than hydrogen, and a and/or b is other than zero, then the compounds of formula (I) may exist in more than one stereoisomeric form.

For example in the case where $R^5$ is other than hydrogen, a is 1 and b is 0 ($R^2$ and $R^3$ not shown for simplicity):

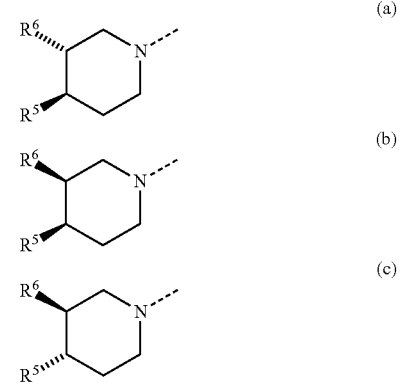

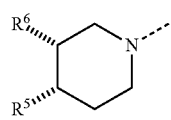
(d)

In particular, in one embodiment the compound is stereoisomer (a).

For example in the case where $R^5$ is other than hydrogen, a is 1 and b is 0 ($R^2$ and $R^3$ not shown for simplicity):

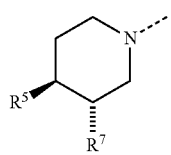
(a')

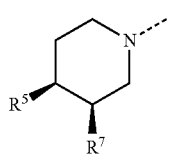
(b')

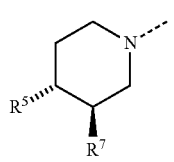
(c')

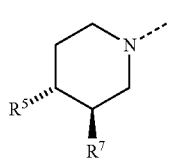
(d')

In the case that $R^2$ and $R^3$ are other than hydrogen, further stereosiomers are possible. In particular, the following stereoisomers are possible, for example wherein $R^2$ and $R^3$ together form the one- to three-membered bridge group defined herein e.g. $C_{1-3}$alkylene and in particular —$CH_2CH_2$—:

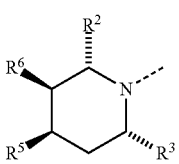
(e)

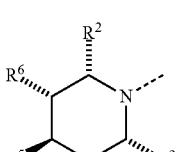
(f)

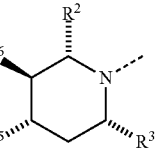
(g)

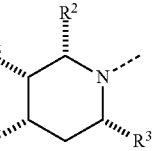
(h)

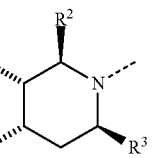
(e¢)

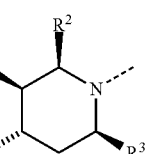
(f¢)

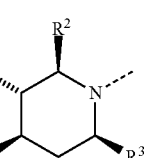
(g¢)

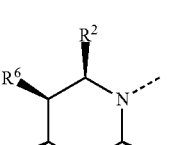
(h¢)

In particular, in one embodiment the compound is stereoisomer (h) or stereoisomer (e').

In particular, in one embodiment the compound is stereoisomer (h) or stereoisomer (e') and $R^6$ is fluorine and $R^5$ is amino.

In particular, in one embodiment the compound is stereoisomer (h) or stereoisomer (e') and $R^2$ and $R^3$ together form a —$CH_2CH_2$— group.

In particular, in one embodiment the compound is stereoisomer (h) or stereoisomer (e') and $R^6$ is fluorine and $R^5$ is amino and $R^2$ and $R^3$ together form a —$CH_2CH_2$— group.

In particular, in one embodiment the compound is stereoisomer (h) or stereoisomer (e'), for example wherein $R^6$ is fluorine.

In particular, in one embodiment the compound is stereoisomer (h) or stereoisomer (e') and $R^6$ is fluorine.

In particular, in one embodiment the compound is stereoisomer (h) or stereoisomer (e') and $R^6$ is fluorine and $R^2$ and $R^3$ together form a —$CH_2CH_2$— group.

In particular, in one embodiment the compound is stereoisomer (e'), for example wherein $R^6$ is fluorine and $R^5$ is amino.

In particular, in one embodiment the compound is stereoisomer (e') and $R^6$ is fluorine and $R^5$ is amino and $R^2$ and $R^3$ together form a —$CH_2CH_2$— group.

In particular, in one embodiment the compound is stereoisomer (e'), for example wherein $R^6$ is fluorine.

In particular, in one embodiment the compound is stereoisomer (e') and $R^6$ is fluorine.

In particular, in one embodiment the compound is stereoisomer (e') and $R^6$ is fluorine and $R^2$ and $R^3$ together form a —CH$_2$CH$_2$— group.

In particular, the following stereoisomers are possible:

(e)
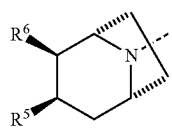

(f)
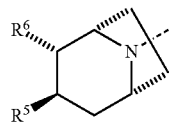

(g)
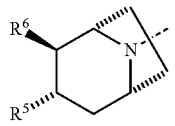

(h)
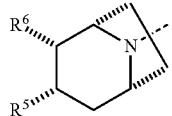

(e')
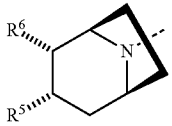

(f')
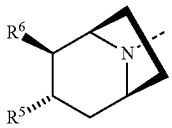

(g')
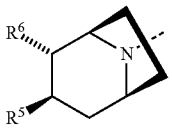

(h')
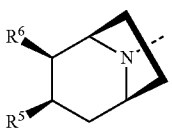

In one embodiment $R^5$ is amino and $R^4$ is halogen (e.g. fluorine).

$R^8$ $R^8$ is selected from haloC$_{1-4}$alkyl (e.g. —CF$_3$), —CH$_3$ and halogen (e.g. chlorine or fluorine).

In one embodiment, $R^8$ is selected from —CH$_3$, chlorine and fluorine.

In one embodiment, $R^8$ is halogen, and the compound of formula (I) is a compound of formula (X) or a tautomer or a solvate or a pharmaceutically acceptable salt thereof:

(X)
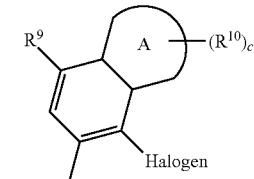
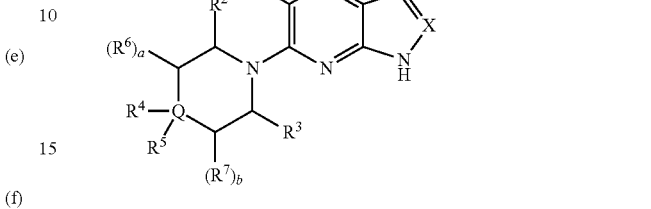

wherein X, Q, $R^1$, $R^2$, $R^3$, $R^4$, $R^5$, $R^6$, $R^7$, $R^9$, $R^{10}$, a, b, c and A are as defined herein, in particular wherein halogen is chlorine.

In one embodiment, $R^8$ is selected from methyl, chlorine and fluorine.

In one embodiment, $R^8$ is selected from chlorine and fluorine.

In particular, $R^8$ is methyl.

In particular, $R^8$ is chlorine.

$R^9$ $R^9$ is selected from hydrogen, C$_{1-4}$alkyl (e.g. —CH$_3$), haloC$_{1-4}$alkyl (e.g. —CF$_3$) and halogen (e.g. chlorine).

In one embodiment, $R^9$ is selected from hydrogen, —CH$_3$, —CF$_3$ and chlorine.

In one embodiment, $R^9$ is selected from hydrogen, —CH$_3$, —CF$_3$, chlorine and fluorine.

In particular, $R^9$ is hydrogen and the compound of formula (I) is a compound of formula (XI) or a tautomer or a solvate or a pharmaceutically acceptable salt thereof:

(XI)

wherein X, Q, $R^1$, $R^2$, $R^3$, $R^4$, $R^5$, $R^6$, $R^7$, $R^8$, $R^{10}$, a, b, c and A are as defined herein.

Ring A, $R^{10}$ and c

Ring A is either:
(i) a five-membered nitrogen-containing heterocyclic ring (e.g. an aromatic ring or a non-aromatic ring) wherein the heterocyclic ring optionally contains one or two additional heteroatoms selected from N, O and S, or
(ii) a six-membered aromatic nitrogen-containing heterocyclic ring, wherein the heterocyclic ring optionally contains one or two additional heteroatoms selected from N, O and S; or (iii) a six-membered non-aromatic nitrogen-containing heterocyclic ring, wherein the heterocyclic ring optionally contains one or two additional heteroatoms selected from N and S.

In one embodiment, ring A is a five-membered nitrogen-containing heterocyclic ring (e.g. an aromatic ring or a non-aromatic ring), or a six-membered aromatic nitrogen-containing heterocyclic ring, wherein the heterocyclic ring optionally contains one or two additional heteroatoms selected from N, O and S.

In one embodiment, ring A is pyrazolyl, thiazolyl, pyrazinyl, and pyridyl. This then with the fused benzo moiety forms indazolyl, benzothiazolyl, quinoxalinyl or quinolinyl respectively.

In one embodiment, ring A is a five-membered nitrogen-containing heterocyclic ring (e.g. an aromatic ring or a non-aromatic ring), wherein the heterocyclic ring optionally contains one or two additional heteroatoms selected from N, O and S.

In one embodiment, ring A is a five-membered nitrogen-containing heterocyclic ring (e.g. an aromatic ring or a non-aromatic ring), or a six-membered aromatic nitrogen-containing heterocyclic ring, wherein the heterocyclic ring optionally contains one or two additional heteroatoms selected from N, O and S.

In one embodiment, ring A is a five-membered nitrogen-containing heterocyclic ring wherein the heterocyclic ring optionally contains one or two additional heteroatoms selected from N, O and S.

In one embodiment, ring A is a five-membered nitrogen-containing heterocyclic ring wherein the heterocyclic ring optionally contains one additional heteroatom selected from N, O and S.

In one embodiment, ring A is a five-membered nitrogen-containing heterocyclic ring wherein the heterocyclic ring optionally contains one additional heteroatom which is N or S.

In one embodiment, ring A is a five-membered aromatic nitrogen-containing heterocyclic ring, wherein the heterocyclic ring optionally contains one or two additional heteroatoms selected from N and S.

In one embodiment, ring A is a five-membered nitrogen-containing heterocyclic ring wherein the heterocyclic ring contains one additional heteroatom which is N.

In one embodiment, ring A is a five-membered aromatic nitrogen-containing heterocyclic ring wherein the heterocyclic ring contains one additional heteroatom which is N.

In one embodiment, ring A is a five-membered nitrogen-containing heterocyclic ring wherein the heterocyclic ring contains one additional heteroatom which is S.

In one embodiment, ring A is a five-membered aromatic nitrogen-containing heterocyclic ring wherein the heterocyclic ring contains one additional heteroatom which is S.

In one embodiment, ring A is pyrrolyl, imidazolyl, oxazolyl, oxadiazolyl, isoxazolyl, thiazolyl, thiadiazolyl, isothiazolyl, pyrazolyl and triazolyl, for example wherein Ring A is thiazolyl or pyrazolyl.

In one embodiment, ring A is a five-membered nitrogen-containing heterocyclic ring (e.g. an aromatic ring or a non-aromatic ring), wherein the heterocyclic ring optionally contains one or two additional heteroatoms selected from N, O and S, and the compound of formula (I) is a compound of formula (XII) or a tautomer or a solvate or a pharmaceutically acceptable salt thereof:

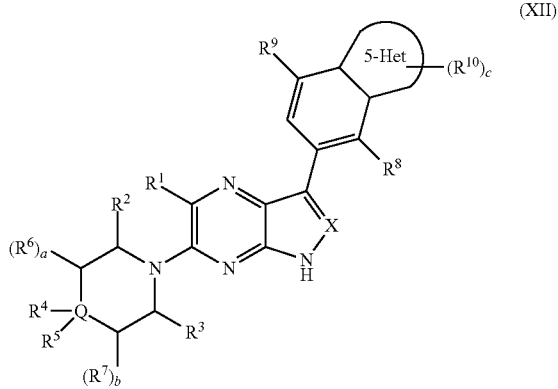

(XII)

wherein X, Q, $R^1$, $R^2$, $R^3$, $R^4$, $R^5$, $R^6$, $R^7$, $R^8$, $R^9$, $R^{10}$, a, b, and c are as defined herein, and 5-Het is a five-membered nitrogen-containing heterocyclic ring (e.g. an aromatic ring or a non-aromatic ring), wherein the heterocyclic ring optionally contains one or two additional heteroatoms selected from N, O and S.

In one embodiment, the moiety

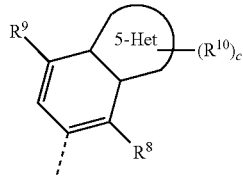

is selected from the following options in Table I:

TABLE I

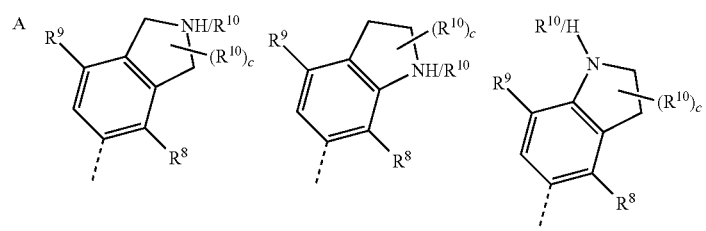

TABLE I-continued
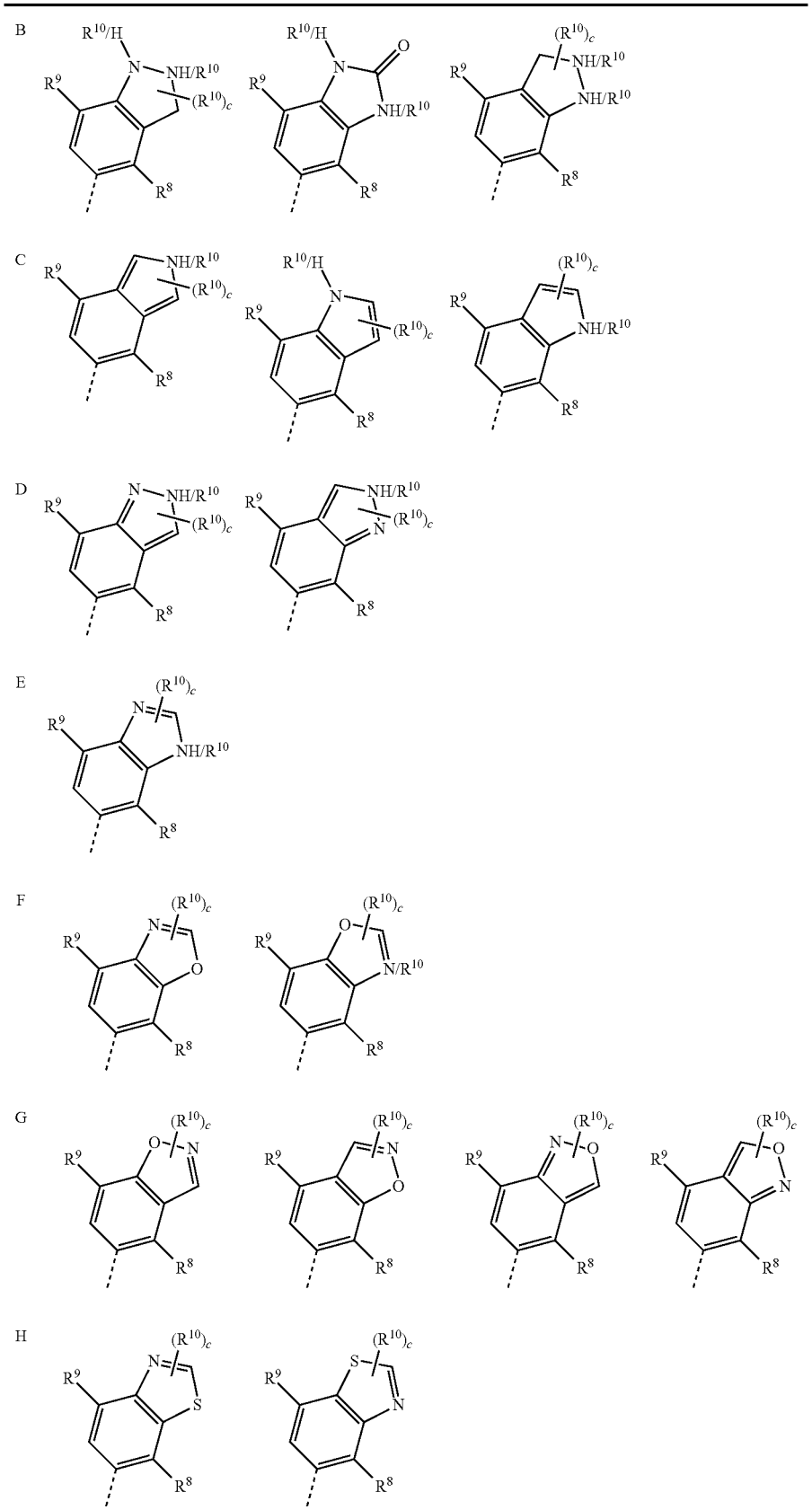

TABLE I-continued
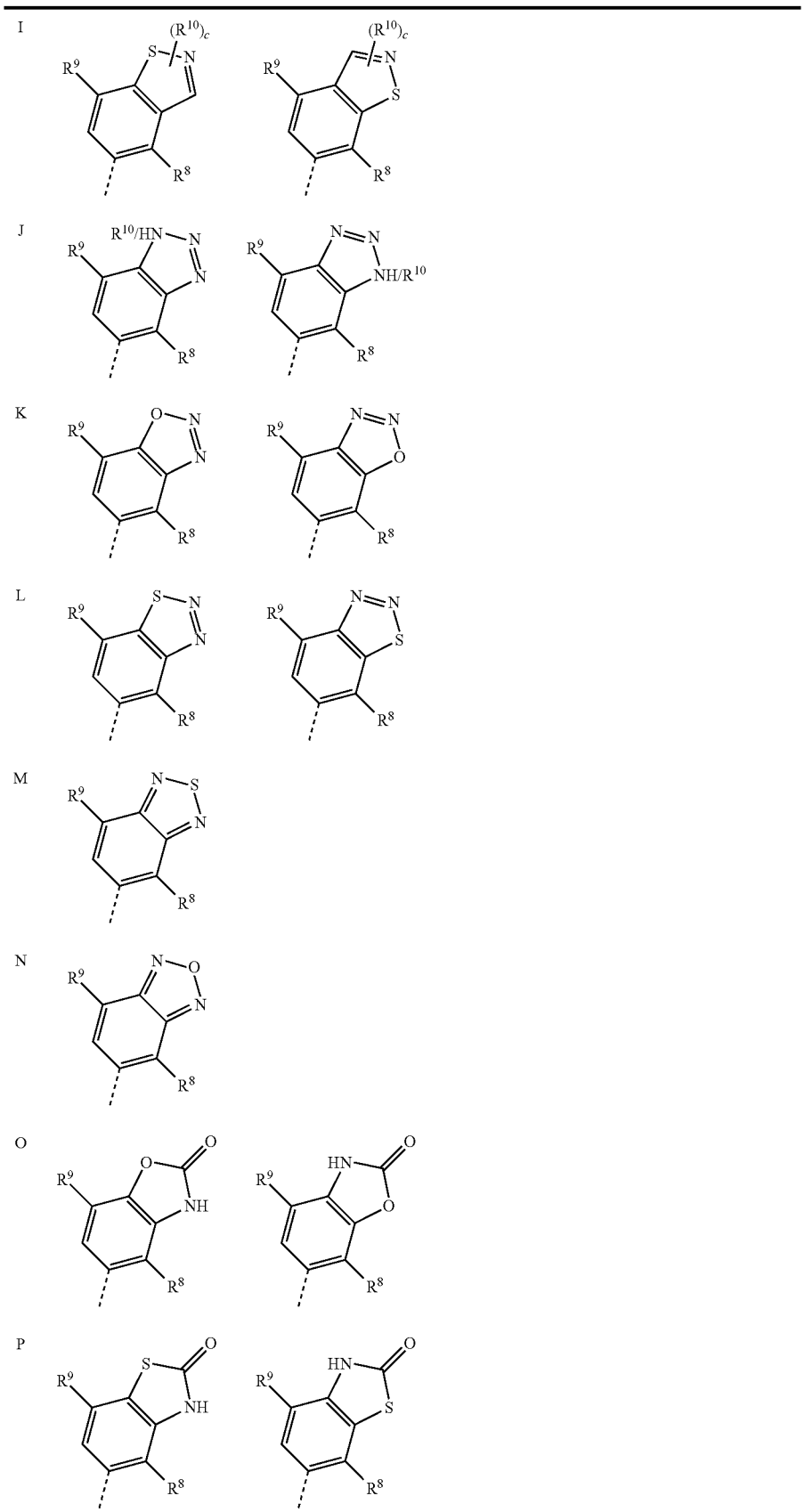

TABLE I-continued
Q 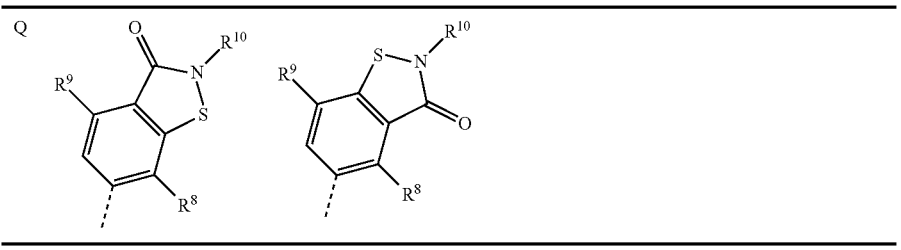
In one embodiment, the moiety
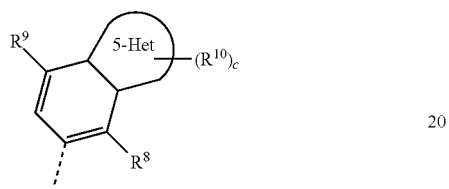
(15)
(20)
is selected from the following options in Table I':
TABLE I'
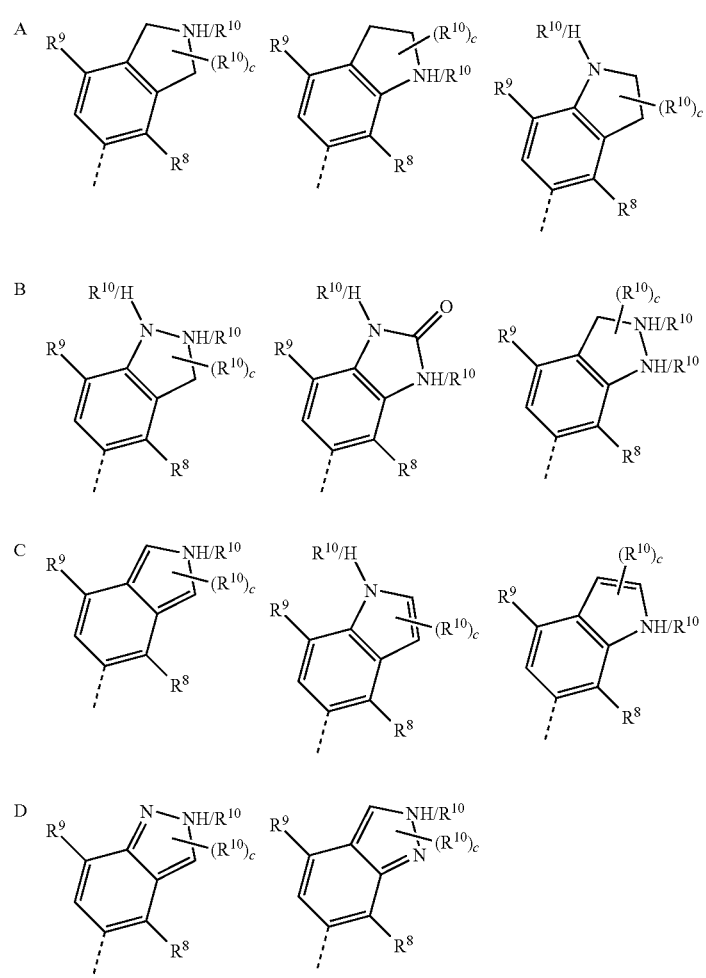

TABLE I'-continued
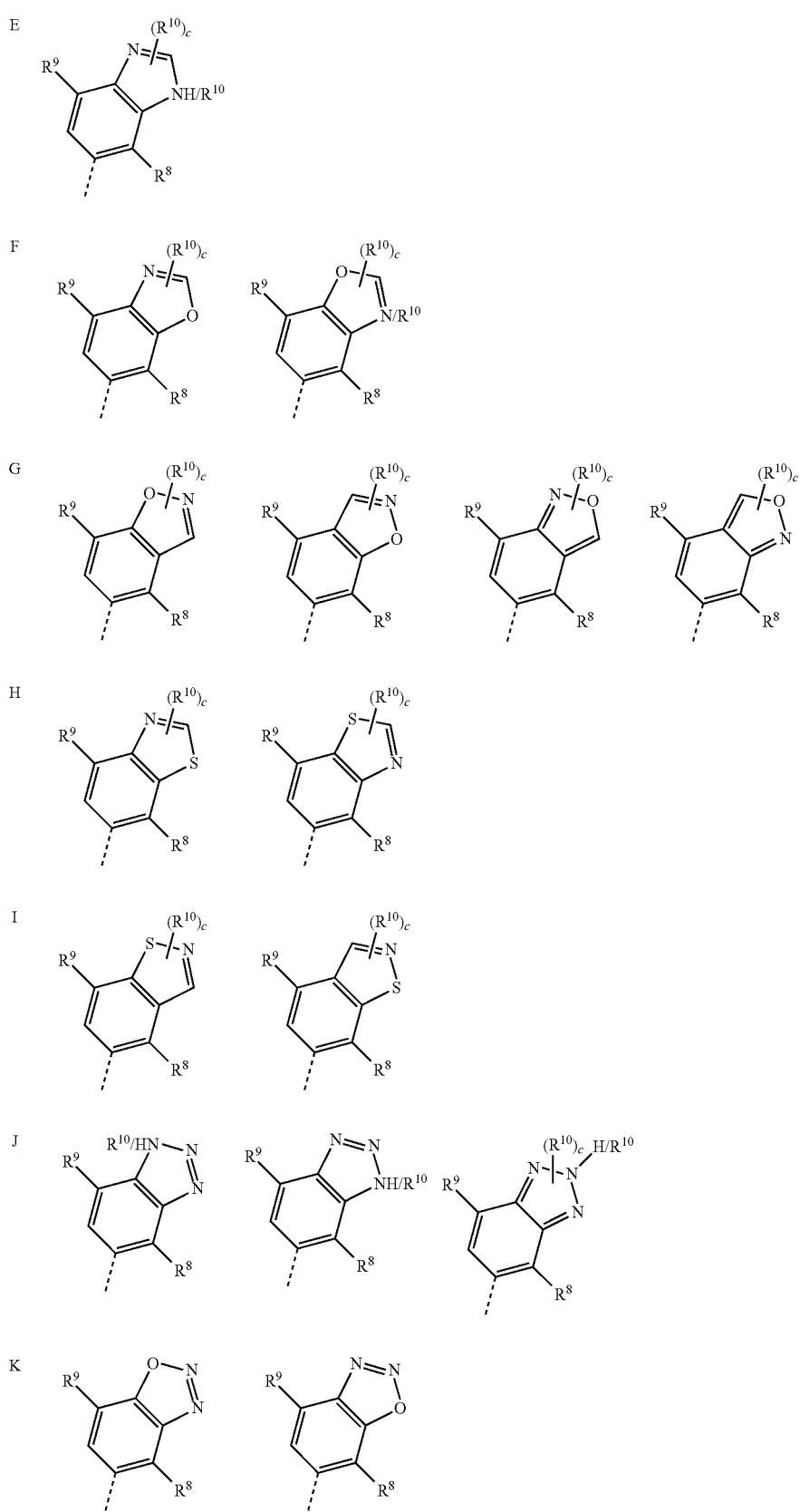

TABLE I'-continued
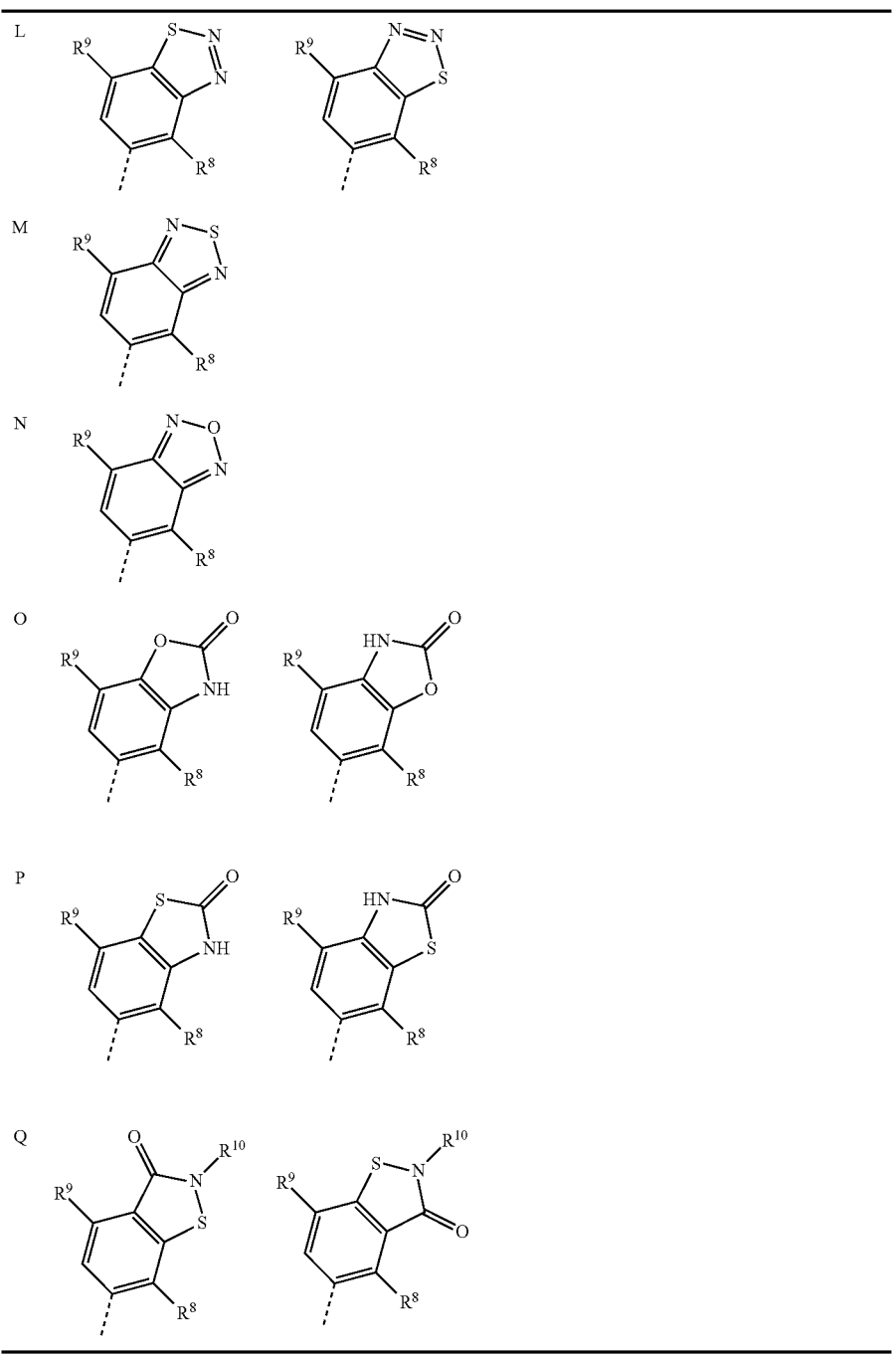
In one embodiment, the moiety
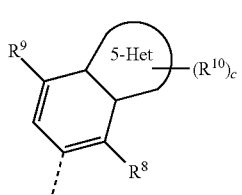

is selected from the following options in Table I":
TABLE I"
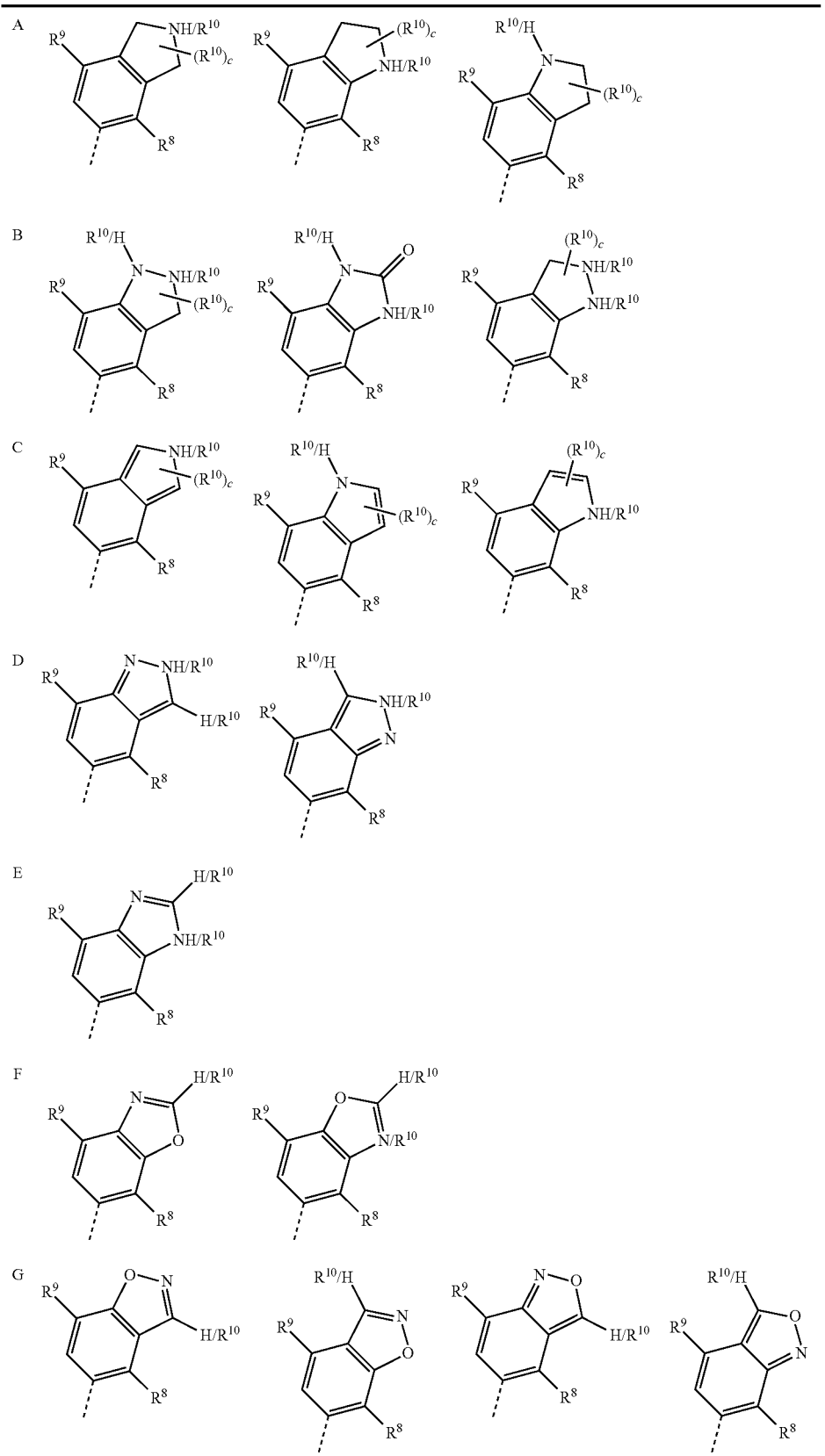

TABLE I''-continued
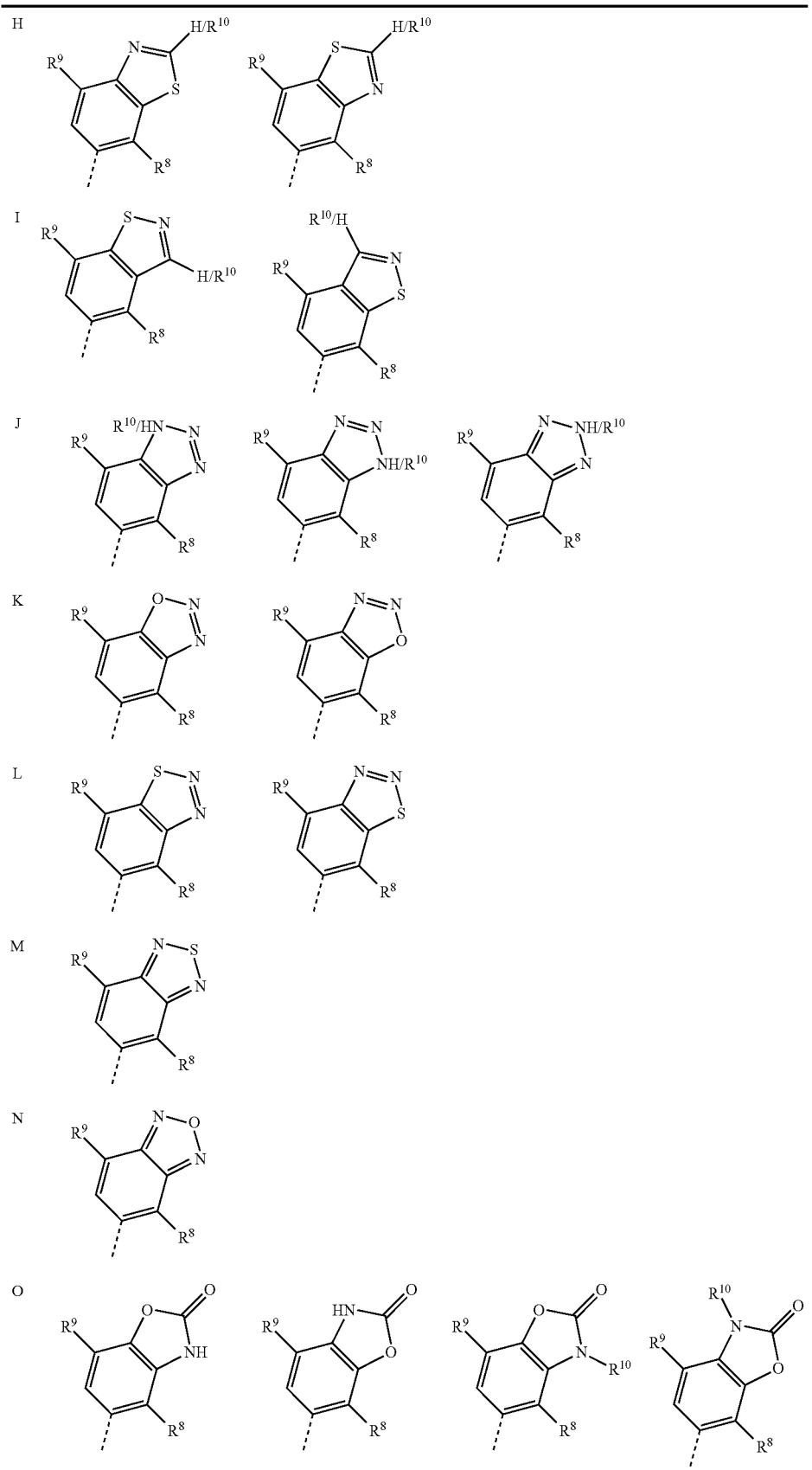

TABLE I''-continued
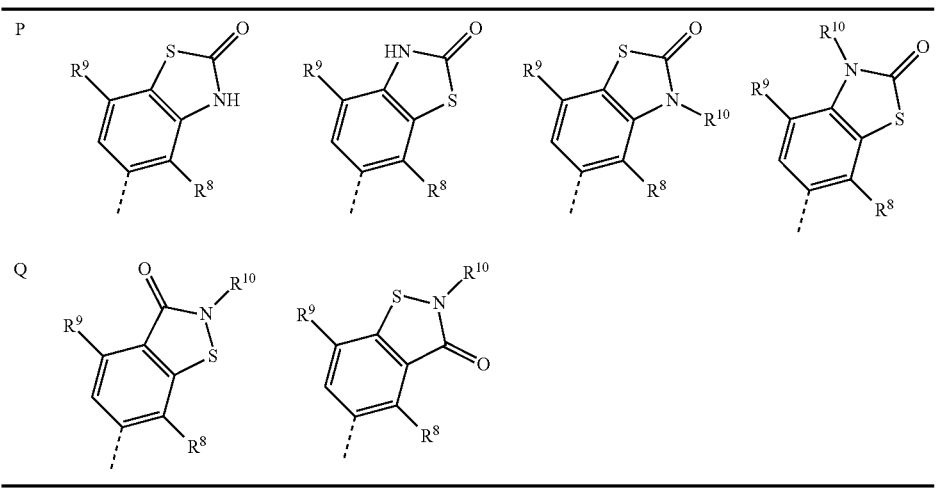
For example, the moiety
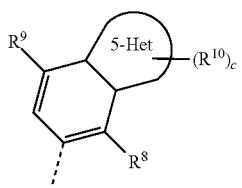
is selected from options A, B, C, D, E, F, G, H, I, O, P and Q in Table I.
In particular, the moiety
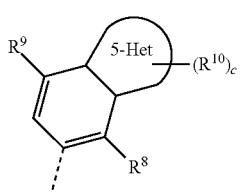
is selected from options C, D, E, F, G, H, I, O, P and Q in Table I.
In particular, the moiety
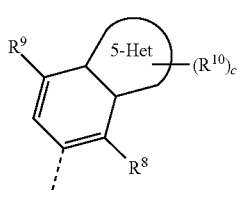
is selected from options D, H, P and Q in Table I. In one embodiment the moiety is selected from D and H.
In particular, the moiety
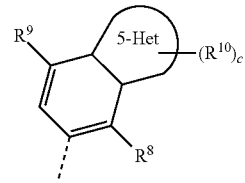
is selected from:
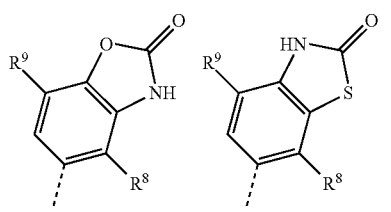
for example
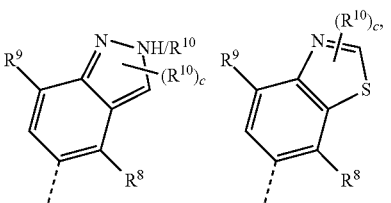
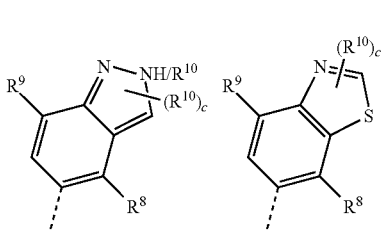

In particular, the moiety

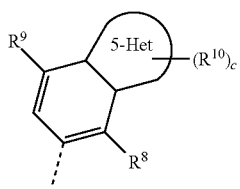

is selected from

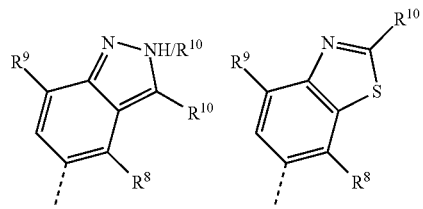

In particular, the compound of formula (XII) is a compound of formula (XIIa) or a tautomer or a solvate or a pharmaceutically acceptable salt thereof:

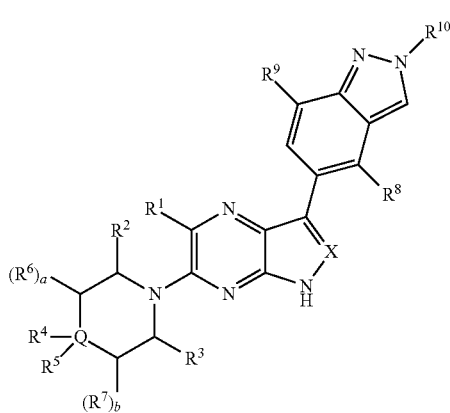

(XIIa)

wherein X, Q, $R^1$, $R^2$, $R^3$, $R^4$, $R^5$, $R^6$, $R^7$, $R^8$, $R^9$, $R^{10}$, a and b are as defined herein, for example wherein $R^{10}$ is $C_{1-4}$ alkyl.

In particular, the compound of formula (XIIa) is a compound of formula (XIIb) or a tautomer or a solvate or a pharmaceutically acceptable salt thereof:

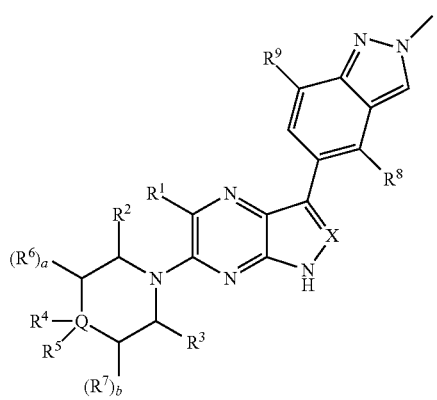

(XIIb)

wherein X, Q, $R^1$, $R^2$, $R^3$, $R^4$, $R^5$, $R^6$, $R^7$, $R^8$, $R^9$, a and b are as defined herein.

In particular, the compound of formula (XII) is a compound of formula (XIIc) or a tautomer or a solvate or a pharmaceutically acceptable salt thereof:

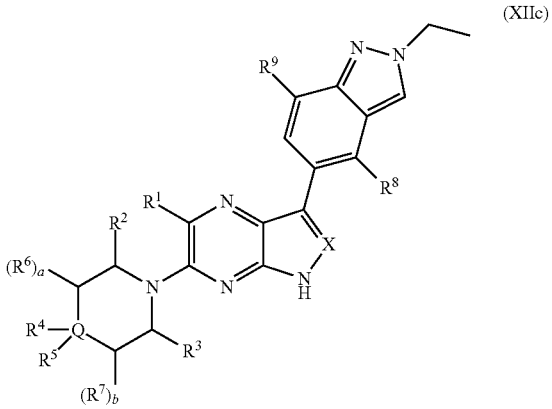

(XIIc)

wherein X, Q, $R^1$, $R^2$, $R^3$, $R^4$, $R^5$, $R^6$, $R^7$, $R^8$, $R^9$, a and b are as defined herein.

In particular, the compound of formula (XII) is a compound of formula (XIId) or a tautomer or a solvate or a pharmaceutically acceptable salt thereof:

(XIId)

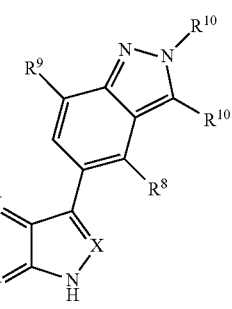

wherein X, Q, $R^1$, $R^2$, $R^3$, $R^4$, $R^5$, $R^6$, $R^7$, $R^8$, $R^9$, $R^{10}$, a and b are as defined herein, for example wherein one $R^{10}$ is $C_{1-4}$ alkyl and the other is halogen (for example chlorine).

In particular, the compound of formula (XII) is a compound of formula (XIIe) or a tautomer or a solvate or a pharmaceutically acceptable salt thereof:

(XIIe)

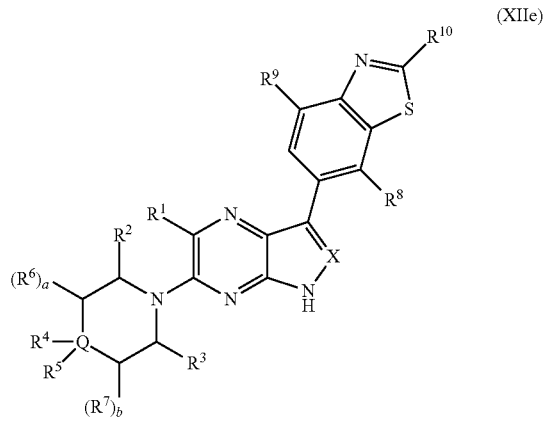

wherein X, Q, $R^1$, $R^2$, $R^3$, $R^4$, $R^5$, $R^6$, $R^7$, $R^8$, $R^9$, $R^{10}$, a and b are as defined herein.

In one embodiment, ring A is either:
(i) a six-membered aromatic nitrogen-containing heterocyclic ring, wherein the heterocyclic ring optionally contains one or two additional heteroatoms selected from N, O and S; or
(ii) a six-membered non-aromatic nitrogen-containing heterocyclic ring, wherein the heterocyclic ring optionally contains one or two additional heteroatoms selected from N and S.

In one embodiment, ring A is a six-membered aromatic nitrogen-containing heterocyclic ring, and the compound of formula (I) is a compound of formula (XIII) or a tautomer or a solvate or a pharmaceutically acceptable salt thereof:

(XIII)

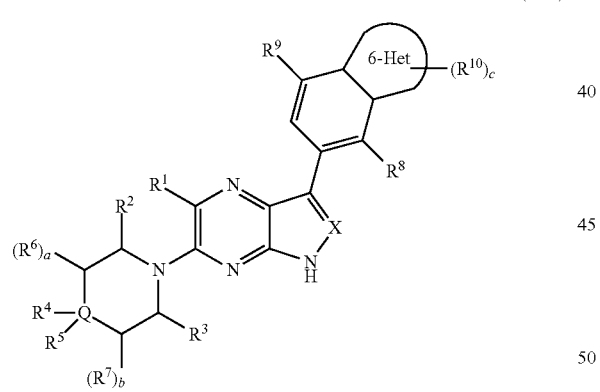

wherein X, Q, $R^1$, $R^2$, $R^3$, $R^4$, $R^5$, $R^6$, $R^7$, $R^8$, $R^9$, $R^{10}$, a, b, and c are as defined herein, and 6-Het is either:
(i) a six-membered aromatic nitrogen-containing heterocyclic ring, wherein the heterocyclic ring optionally contains one or two additional heteroatoms selected from N, O and S; or
(iii) a six-membered non-aromatic nitrogen-containing heterocyclic ring, wherein the heterocyclic ring optionally contains one or two additional heteroatoms selected from N and S.

When ring A is a six-membered nitrogen-containing ring, if the ring is aromatic then the ring may optionally contain one or two additional heteroatoms selected from N, O and S. However, if the six-membered nitrogen-containing ring is non-aromatic then the ring may optionally contain one or two additional heteroatoms selected from N and S i.e. the ring cannot include a further heteroatom which is O.

In one embodiment, 6-Het is a six-membered nitrogen-containing heterocyclic ring, wherein the heterocyclic ring optionally contains one or two additional heteroatoms selected from N and S.

In particular, 6-Het is a six-membered nitrogen-containing heterocyclic ring, wherein the heterocyclic ring optionally contains one or two additional heteroatoms selected from N.

In particular, 6-Het is a six-membered nitrogen-containing heterocyclic ring, wherein the heterocyclic ring optionally contains one additional heteroatom selected from N.

In particular, 6-Het is a six-membered nitrogen-containing heterocyclic ring, wherein the heterocyclic ring contains one additional heteroatom which is N.

In one embodiment, the moiety

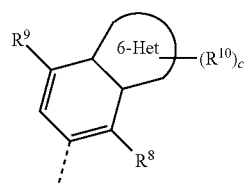

is selected from the following options in Table II:

TABLE II

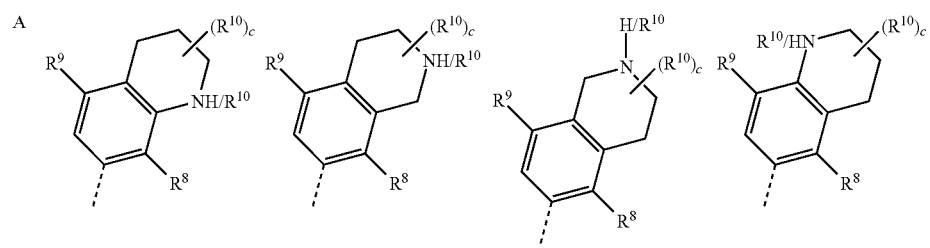

TABLE II-continued
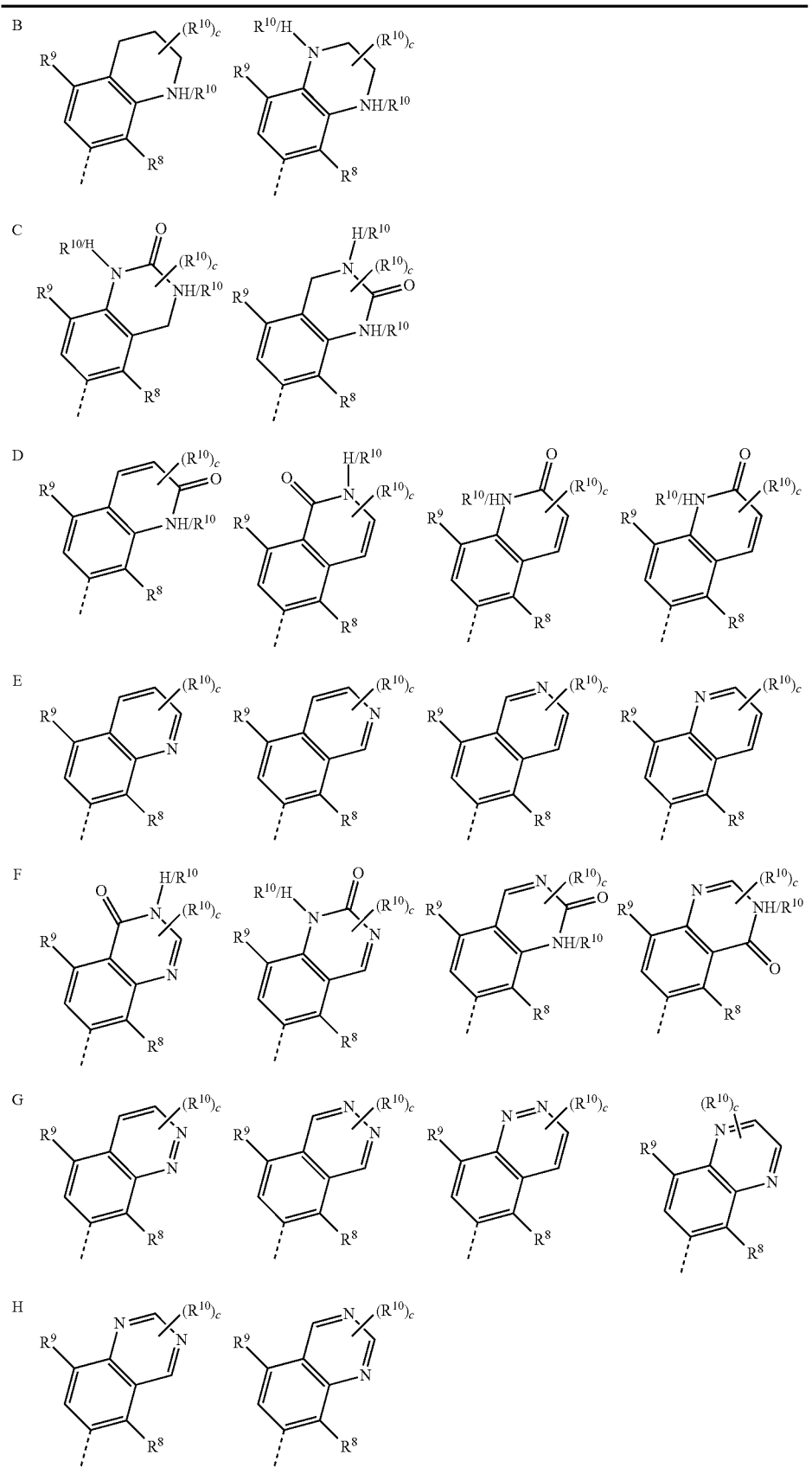

In particular, the moiety

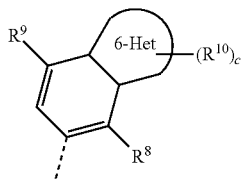

is selected from options D, E and H in Table II, for example D.

In particular, the moiety

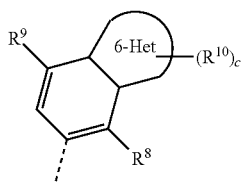

is selected from:

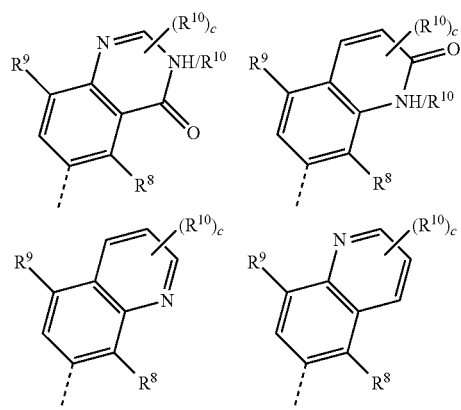

In particular, the moiety

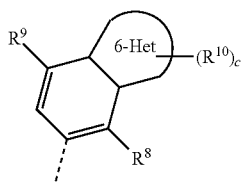

is:

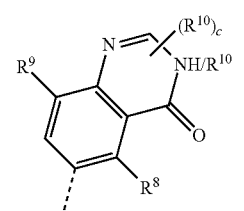

In particular, the moiety

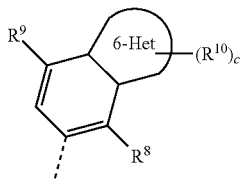

is selected from options E and G in Table II, in particular option G.

In particular, the moiety

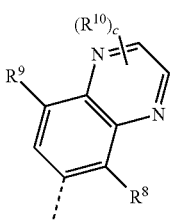

is selected from:

(structures shown)

In particular the moiety

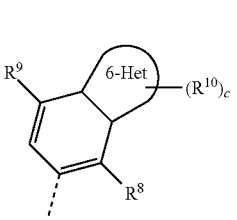 is: 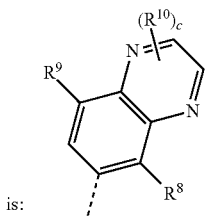.

In one embodiment, the compound of formula (I) is a compound of formula (XIIIa) or a tautomer or a solvate or a pharmaceutically acceptable salt thereof:

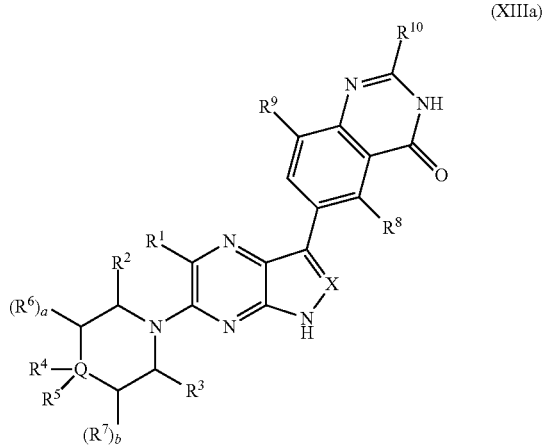

(XIIIa)

wherein X, Q, $R^1$, $R^2$, $R^3$, $R^4$, $R^5$, $R^6$, $R^7$, $R^8$, $R^9$, $R^{10}$, a and b are as defined herein.

In one embodiment, the compound of formula (XIIIa) is a compound of formula (XIIIb) or a tautomer or a solvate or a pharmaceutically acceptable salt thereof:

(XIIIb)

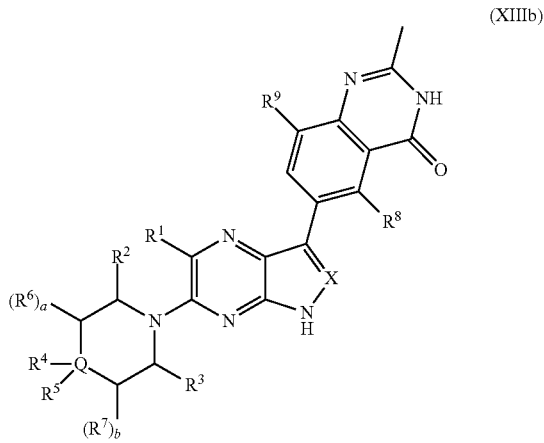

wherein X, Q, $R^1$, $R^2$, $R^3$, $R^4$, $R^5$, $R^6$, $R^7$, $R^8$, $R^9$, a and b are as defined herein.

In one embodiment, the compound of formula (XIII) is a compound of formula (XIIIc) or a tautomer or a solvate or a pharmaceutically acceptable salt thereof:

(XIIIc)

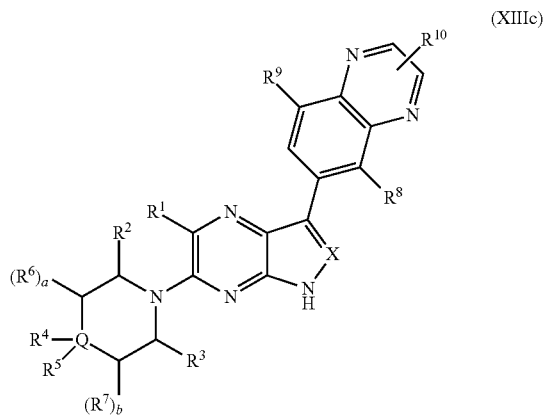

wherein X, Q, $R^1$, $R^2$, $R^3$, $R^4$, $R^5$, $R^6$, $R^7$, $R^8$, $R^9$, a and b are as defined herein.

In one embodiment, ring A includes a nitrogen atom adjacent to (i.e. bonded directly to) the benzene ring and the compound of formula (I) is a compound of formula (XIVa) or (XIVb) or a tautomer or a solvate or a pharmaceutically acceptable salt thereof, i.e.:

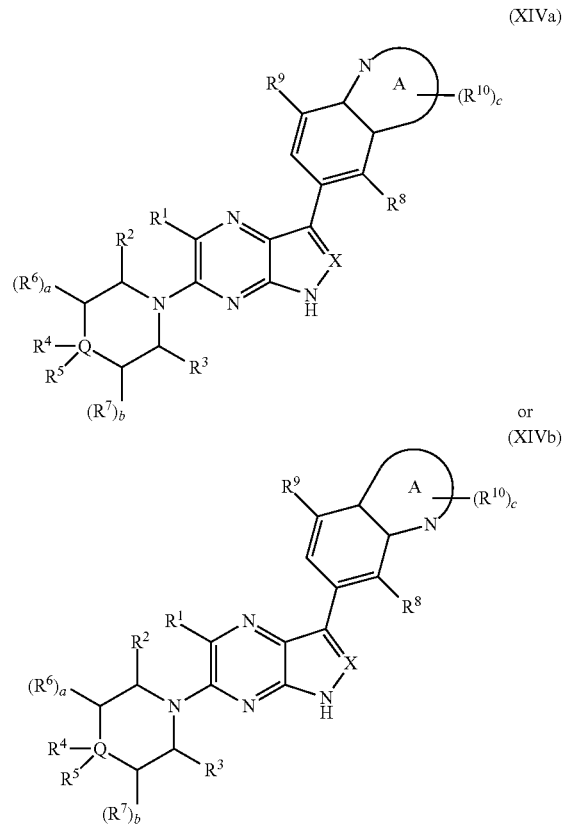

(XIVa)

or (XIVb)

wherein X, Q, $R^1$, $R^2$, $R^3$, $R^4$, $R^5$, $R^6$, $R^7$, $R^8$, $R^9$, $R^{10}$, a, b, c and A are as defined herein.

$R^{10}$ are independently selected from halogen, cyano, cyano$C_{1-4}$alkyl (e.g. —$CH_2$—CN), hydroxyl, =O (oxo), $C_{1-4}$alkyl (e.g. —$CH_3$ or —$CH_2CH_3$), halo$C_{1-4}$alkyl, $C_{1-4}$alkoxy (e.g. —$OCH_3$), hydroxyl$C_{1-4}$alkyl (e.g. —$CH_2C(CH_3)_2OH$, —$CH(CH_3)CH_2OH$, —$CH(CH_3)OH$, —$CH_2CH_2OH$ or —$CH_2OH$), $C_{1-4}$alkoxy$C_{1-4}$alkylene (e.g. —$CH_2$—O—$CH_3$ or —$CH_2$—$CH_2$—O—$CH_3$), $C_{1-4}$alkylsulfone (e.g. —$SO_2CH_3$), amino, mono$C_{1-4}$alkylamino, di$C_{1-4}$alkylamino (e.g. —$N(CH_3)_2$), amino$C_{1-4}$alkylene (e.g. —$CH_2NH_2$), —$C_{1-4}$alkylene-C(=O)$NH_{(2-q)}(C_{1-6}$alkyl)$_q$), —$C_{1-4}$alkylene-NHC(=O)$C_{1-6}$ alkyl, sulfonamide$C_{0-4}$alkylene (e.g. —$SO_2NR^x_2$ or —$CH_2SO_2NR^x_2$, wherein $R^x$ is independently selected from H and $C_{1-6}$alkyl), 3 to 6 membered cycloalkyl, optionally substituted five- or six-membered unsaturated heterocyclic group containing 1, 2, 3 or 4 heteroatoms selected from O, N, or S where the optional substituent is selected from $C_{1-4}$alkyl, $C_{1-4}$alkyl substituted with 3 to 6 membered cycloalkyl, $C_{1-4}$alkyl substituted with optionally substituted five- or six-membered unsaturated heterocyclic group containing 1, 2, 3 or 4 heteroatoms selected from O, N, or S where the optional substituent is selected from $C_{1-4}$alkyl, $C_{1-4}$alkyl substituted with optionally substituted four- to six-membered saturated heterocyclic group containing 1 or 2 heteroatoms selected from O, N, or S where the optional substituent is selected from $C_{1-4}$alkyl and optionally substituted four- to six-membered saturated heterocyclic group containing 1 or 2 heteroatoms selected from O, N, or S where the optional substituent is selected from $C_{1-4}$alkyl;
q is selected from 0, 1 or 2; and
c is selected from 0, 1, 2 and 3.

In one embodiment, $R^{10}$ are independently selected from halogen, cyano, cyano$C_{1-4}$alkyl (e.g. —$CH_2$—CN), hydroxyl, =O (oxo), $C_{1-4}$alkyl (e.g. —$CH_3$ or —$CH_2CH_3$), halo$C_{1-4}$alkyl, $C_{1-4}$alkoxy (e.g. —$OCH_3$), hydroxyl$C_{1-4}$alkyl (e.g. —$CH_2C(CH_3)_2OH$, —$CH(CH_3)CH_2OH$, —CH($CH_3$)OH, —$CH_2CH_2OH$ or —$CH_2OH$), $C_{1-4}$alkoxy$C_{1-4}$alkylene (e.g. —$CH_2$—O—$CH_3$ or —$CH_2$—$CH_2$—O—$CH_3$), $C_{1-4}$alkylsulfone (e.g. —$SO_2CH_3$), amino, mono$C_{1-4}$alkylamino, di$C_{1-4}$alkylamino (e.g. —N($CH_3$)$_2$), amino$C_{1-4}$alkylene (e.g. —$CH_2NH_2$), —$C_{1-4}$alkylene-C(=O)NH$_{(2-q)}$($C_{1-6}$ alkyl)$_q$), —$C_{1-4}$alkylene-NHC(=O)$C_{1-6}$ alkyl, sulfonamide$C_{0-4}$alkylene (e.g. —$SO_2NR^x_2$ or —$CH_2SO_2NR^x_2$, wherein $R^x$ is independently selected from H and $C_{1-6}$alkyl), and optionally substituted four- to six-membered saturated heterocyclic group containing 1 or 2 heteroatoms selected from O, N, or S where the optional substituent is selected from $C_{1-4}$alkyl;
q is selected from 0, 1 or 2; and
c is selected from 0, 1, and 2.

In one embodiment, $R^{10}$ are independently selected from halogen, cyano, cyano$C_{1-4}$alkyl (e.g. —$CH_2$—CN), hydroxyl, =O (oxo), $C_{1-4}$alkyl (e.g. —$CH_3$ or —$CH_2CH_3$), halo$C_{1-4}$alkyl, $C_{1-4}$alkoxy (e.g. —$OCH_3$), hydroxyl$C_{1-4}$alkyl (e.g. —$CH_2C(CH_3)_2OH$, —$CH(CH_3)CH_2OH$, —CH($CH_3$)OH, —$CH_2CH_2OH$ or —$CH_2OH$), —$C_{1-4}$alkylene $C_{1-4}$alkoxy (e.g. —$CH_2$—O—$CH_3$ or —$CH_2$—$CH_2$—O—$CH_3$), $C_{1-4}$alkylsulfone (e.g. —$SO_2CH_3$), amino, mono$C_{1-4}$alkylamino, di$C_{1-4}$alkylamino (e.g. —N($CH_3$)$_2$), —$C_{1-4}$alkyleneamino (e.g. —$CH_2NH_2$), —$C_{1-4}$alkylene-C(=O)NH$_{(2-q)}$($C_{1-6}$ alkyl)$_q$), —$C_{1-4}$alkylene-NHC(=O)$C_{1-6}$ alkyl, —$C_{0-4}$alkylenesulfonamide (e.g. —$SO_2NR^x_2$ or —$CH_2SO_2NR^x_2$, wherein $R^x$ is independently selected from H and $C_{1-6}$alkyl), and optionally substituted four- to six-membered saturated heterocyclic group containing 1 or 2 heteroatoms selected from O, N, or S where the optional substituent is selected from $C_{1-4}$alkyl.

In one embodiment c is 2; one $R^{10}$ is =O (oxo) and one $R^{10}$ is independently selected from halogen, cyano, cyano$C_{1-4}$alkyl (e.g. —$CH_2$—CN), hydroxyl, $C_{1-4}$alkyl (e.g. —$CH_3$ or —$CH_2CH_3$), halo$C_{1-4}$alkyl, $C_{1-4}$alkoxy (e.g. —$OCH_3$), hydroxyl$C_{1-4}$alkyl (e.g. —$CH_2C(CH_3)_2OH$, —$CH(CH_3)CH_2OH$, —CH($CH_3$)OH, —$CH_2CH_2OH$ or —$CH_2OH$), $C_{1-4}$alkoxy$C_{1-4}$alkylene (e.g. —$CH_2$—O—$CH_3$ or —$CH_2$—$CH_2$—O—$CH_3$), $C_{1-4}$alkylsulfone (e.g. —$SO_2CH_3$), amino, mono$C_{1-4}$alkylamino, di$C_{1-4}$alkylamino (e.g. —N($CH_3$)$_2$), amino$C_{1-4}$alkylene (e.g. —$CH_2NH_2$), —$C_{1-4}$alkylene-C(=O)NH$_{(2-q)}$($C_{1-6}$ alkyl)$_q$), —$C_{1-4}$alkylene-NHC(=O)$C_{1-6}$ alkyl, sulfonamide$C_{0-4}$alkylene (e.g. —$SO_2NR^x_2$ or —$CH_2SO_2NR^x_2$, wherein $R^x$ is independently selected from H and $C_{1-6}$alkyl), and optionally substituted four- to six-membered saturated heterocyclic group containing 1 or 2 heteroatoms selected from O, N, or S where the optional substituent is selected from $C_{1-4}$alkyl.

In one embodiment, q is 0 or 1. In particular, q is 1. In particular, q is 2.

In one embodiment, c is 0 or 1. In particular, c is 1. In particular, c is 2. In particular, c is 0.

In one embodiment, $R^{10}$ are independently selected from halogen, cyano, cyano$C_{1-4}$alkyl (e.g. —$CH_2$—CN), hydroxyl, =O (oxo), $C_{1-4}$alkyl (e.g. —$CH_3$ or —$CH_2CH_3$), halo$C_{1-4}$alkyl, $C_{1-4}$alkoxy (e.g. —$OCH_3$), hydroxyl$C_{1-4}$alkyl (e.g. —$CH(CH_3)CH_2OH$, —CH($CH_3$)OH, —$CH_2CH_2OH$ or —$CH_2OH$), di$C_{1-4}$alkylamino (e.g. —N($CH_3$)$_2$), and $C_{1-4}$alkoxy$C_{1-4}$alkylene (e.g. —$CH_2$—O—$CH_3$), for example wherein $R^{10}$ are independently selected from halogen, cyano, hydroxyl, =O (oxo), and $C_{1-4}$alkyl (e.g. —$CH_3$ or —$CH_2CH_3$).

In one embodiment, $R^{10}$ are independently selected from halogen, cyano, cyano$C_{1-4}$alkyl (e.g. —$CH_2$—CN), hydroxyl, =O (oxo), $C_{1-4}$alkyl (e.g. —$CH_3$ or —$CH_2CH_3$), halo$C_{1-4}$alkyl, $C_{1-4}$alkoxy (e.g. —$OCH_3$), hydroxyl$C_{1-4}$alkyl (e.g. —$CH(CH_3)CH_2OH$, —CH($CH_3$)OH, —$CH_2CH_2OH$ or —$CH_2OH$) and $C_{1-4}$alkoxy$C_{1-4}$alkylene (e.g. —$CH_2$—O—$CH_3$), for example wherein $R^{10}$ are independently selected from halogen, cyano, hydroxyl, =O (oxo), and $C_{1-4}$alkyl (e.g. —$CH_3$ or —$CH_2CH_3$).

In one embodiment, $R^{10}$ are independently selected from halogen, cyano, cyano$C_{1-4}$alkyl (e.g. —$CH_2$—CN), hydroxyl, =O (oxo), $C_{1-4}$alkyl (e.g. —$CH_3$ or —$CH_2CH_3$), halo$C_{1-4}$alkyl, $C_{1-4}$alkoxy (e.g. —$OCH_3$), hydroxyl$C_{1-4}$alkyl (e.g. —$CH(CH_3)CH_2OH$, —CH($CH_3$)OH, —$CH_2CH_2OH$ or —$CH_2OH$) and $C_{1-4}$alkoxy$C_{1-4}$alkylene (e.g. —$CH_2$—O—$CH_3$), for example wherein $R^{10}$ are independently selected from halogen, cyano, hydroxyl, =O (oxo), and $C_{1-4}$alkyl (e.g. —$CH_3$ or —$CH_2CH_3$).

In one embodiment, $R^{10}$ are independently selected from halogen, cyano, hydroxyl, =O (oxo), and $C_{1-4}$alkyl (e.g. —$CH_3$ or —$CH_2CH_3$), for example wherein $R^{10}$ are independently selected from hydroxyl, =O (oxo) and $C_{1-4}$alkyl (e.g. —$CH_3$).

In one embodiment, $R^{10}$ are independently selected from halogen (e.g. chlorine or fluorine), =O (oxo), $C_{1-4}$alkyl (e.g. —$CH_3$, —$CH_2CH_3$, —CH($CH_3$)$_2$), $C_{1-4}$alkoxy (e.g. —$OCH_3$), and di$C_{1-4}$alkylamino (e.g. —N($CH_3$)$_2$, for example wherein $R^{10}$ are independently selected from halogen, =O (oxo), and $C_{1-4}$alkyl (e.g. —$CH_3$ or —$CH_2CH_3$).

In one embodiment, $R^{10}$ are independently selected from halogen (e.g. chlorine), cyano, cyano$C_{1-4}$alkyl (e.g. —$CH_2$—CN), $C_{1-4}$alkoxy (e.g. —$OCH_3$, —$OCH_2CH_3$ and —OCH($CH_3$)$_2$), =O (oxo), $C_{1-4}$alkyl (e.g. —$CH_3$, —$CH_2CH_3$ and —CH($CH_3$)$_2$), hydroxyl$C_{1-4}$alkyl (e.g. —$CH_2OH$, —$CH_2CH_2OH$ or —$CH_2C(CH_3)_2OH$), halo$C_{1-4}$alkyl (e.g. —$CHF_2$), di$C_{1-4}$alkylamino (e.g. —N($CH_3$)$_2$), $C_{1-4}$alkoxy$C_{1-4}$alkylene (e.g. —$CH_2$—O—$CH_3$ or —$CH_2$—$CH_2$—O—$CH_3$), —$C_{0-4}$alkylene-C(=O)NH$_{(2-q)}$($C_{1-6}$alkyl)$_q$) (e.g. —CO—N($CH_3$)$_2$, —$CH_2$—$CH_2$—CO—N($CH_3$)$_2$, —$CH_2$—CO—N($CH_3$)$_2$, —$CH_2$—CO—NH(C($CH_3$)$_3$) or —$CH_2$—CO—NH($CH_3$), four- to six-membered saturated heterocyclic group containing O or N (e.g. tetrahydrofuranyl, morpholino, azetidinyl or oxetanyl), and $C_{1-4}$alkyl (e.g $C_1$ alkyl) substituted with optionally substituted five- or six-membered unsaturated heterocyclic group (e.g. five-membered unsaturated heterocyclic group) containing 1, 2, 3 or 4 heteroatoms selected from O, N, and S (e.g. N or O) where the optional substituent is selected from $C_{1-4}$alkyl (e.g. —$CH_3$).

In one embodiment, $R^{10}$ is halogen (e.g. chlorine), cyano, $C_{1-4}$alkyl (e.g. —$CH_3$, —CH($CH_3$)$_2$ or —$CH_2CH_3$), halo$C_{1-4}$alkyl (e.g. —$CHF_2$), $C_{1-4}$alkoxyl (e.g. —$OCH_3$, —$OCH_2CH_3$ or —OCH($CH_3$)$_2$), $C_{1-4}$alkoxy$C_{1-4}$alkene (e.g. —$CH_2OCH_3$). di$C_{1-4}$alkylamino (e.g. —N($CH_3$)$_2$) or optionally substituted (e.g. unsubstituted) four- to six-membered saturated heterocyclic group containing 1 or 2 heteroatoms selected from O or N where the optional substituent is selected from $C_{1-4}$alkyl (e.g. morpholinyl or azetidinyl).

In one embodiment, R$^{10}$ is —C$_{0-4}$alkylene-C(=O)NH$_{(2-q)}$(C$_{1-6}$ alkyl)$_q$) which is selected from —C$_{1-4}$alkylene-C(=O)NH$_{(2-q)}$(C$_{1-6}$ alkyl)$_q$) (e.g. —CH$_2$—CH$_2$—CO—N(CH$_3$)$_2$, —CH$_2$—CO—N(CH$_3$)$_2$, —CH$_2$—CO—NH(C(CH$_3$)$_3$) or —CH$_2$—CO—NH(CH$_3$) and —CO—N(CH$_3$)$_2$).

In one embodiment, R$^{10}$ are independently selected from halogen, cyano, hydroxyl, =O (oxo), and C$_{1-4}$alkyl (e.g. —CH$_3$ or —CH$_2$CH$_3$), for example wherein R$^{10}$ are independently selected from C$_{1-4}$alkyl (e.g. —CH$_3$), halogen or oxo.

In one embodiment, R$^{10}$ are independently selected from =O (oxo), hydroxyl and C$_{1-4}$alkyl (e.g. —CH$_3$ or —CH$_2$CH$_3$). In particular, R$^{10}$ are independently selected from =O (oxo), hydroxyl and —CH$_3$.

In particular, c is 1 and R$^{10}$ are independently selected from =O (oxo), hydroxyl and —CH$_3$.

In particular, c is 1 and R$^{10}$ is —CH$_3$.

In one embodiment, c is 2 and one R$^{10}$ is =O (oxo) and one R$^{10}$ is C$_{1-4}$alkyl (e.g. —CH$_3$ or —CH$_2$CH$_3$).

In one embodiment, R$^{10}$ is C$_{1-4}$alkyl (e.g. —CH$_3$, —CH$_2$CH$_3$, or —CH(CH$_3$)$_2$)

In one embodiment, R$^{10}$ are independently selected from halogen (e.g. chlorine), C$_{1-4}$alkoxy (e.g. —OCH$_3$), =O (oxo), C$_{1-4}$alkyl (e.g. —CH$_3$ or —CH$_2$CH$_3$), hydroxylC$_{1-4}$alkyl (e.g. —CH$_2$CH$_2$OH or —CH$_2$OH), diC$_{1-4}$alkylamino (e.g. —N(CH$_3$)$_2$), C$_{1-4}$alkoxyC$_{1-4}$alkylene (e.g. —CH$_2$—O—CH$_3$ or —CH$_2$—CH$_2$—O—CH$_3$), and four- to six-membered saturated heterocyclic group containing O (e.g. tetrahydrofuran); and c is selected from 0, 1 and 2.

It is to be understood that the above definitions of heterocycles and substituents R$^{10}$ cover all possible tautomeric forms of the rings. Thus, for example, the following compound can exist in the following tautomeric forms and both fall within the scope of formula (I):

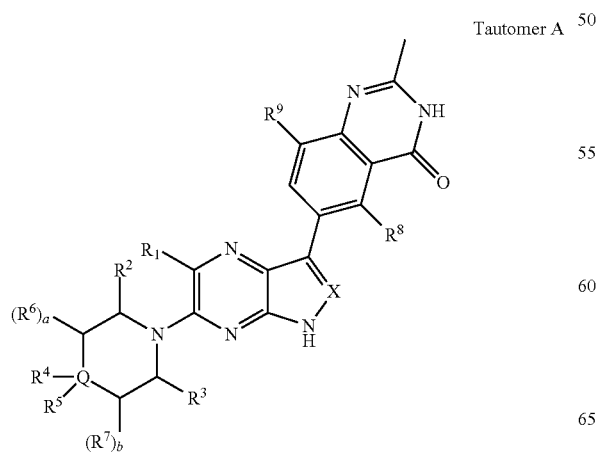

Tautomer A

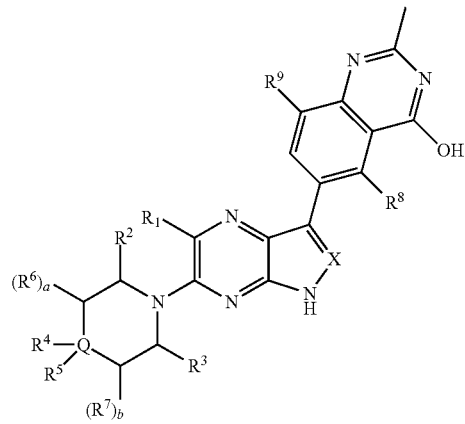

Tautomer B

Also, for example, the following compound can exist in the following tautomeric forms and both fall within the scope of formula (I):

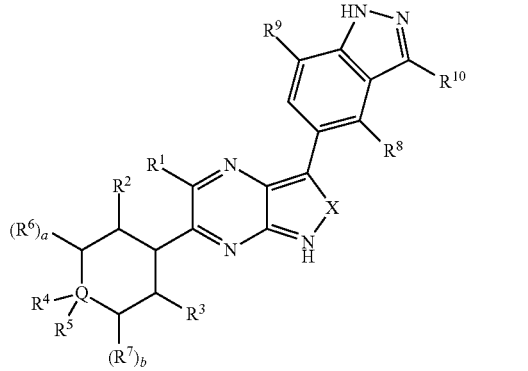

Tautomer A

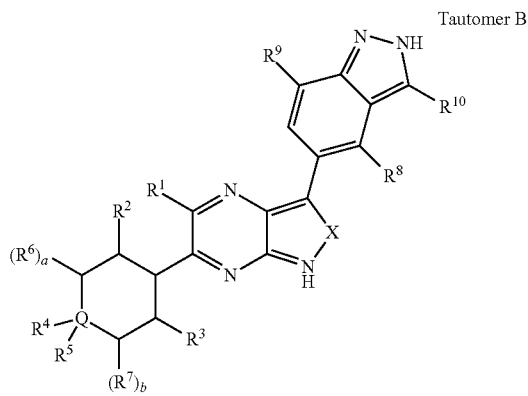

Tautomer B

In one embodiment, the moiety
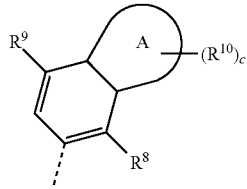
is selected from:
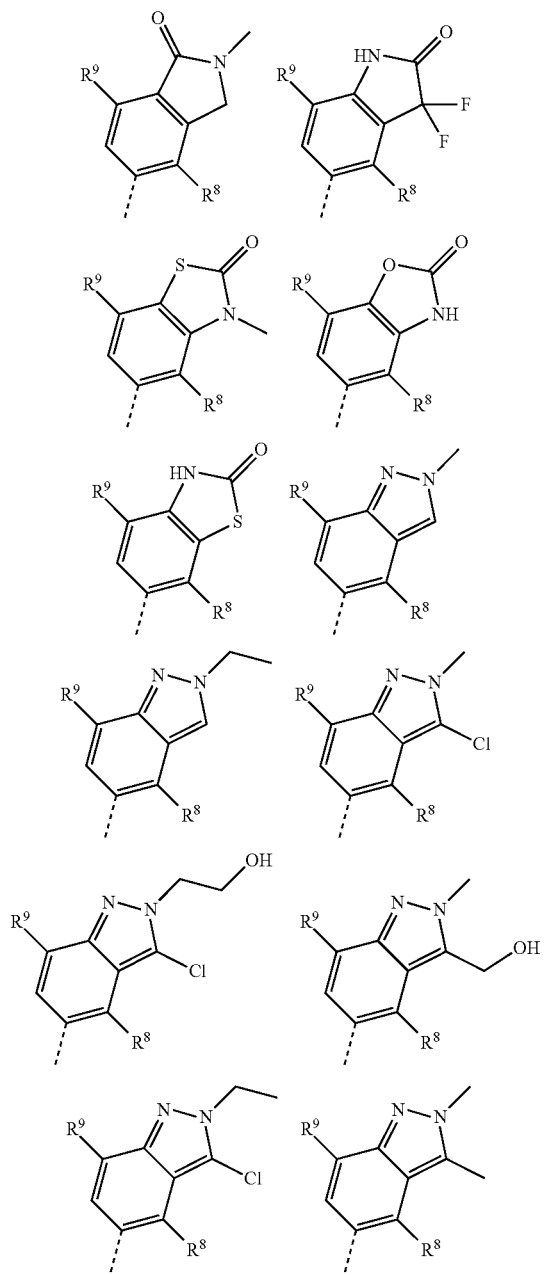
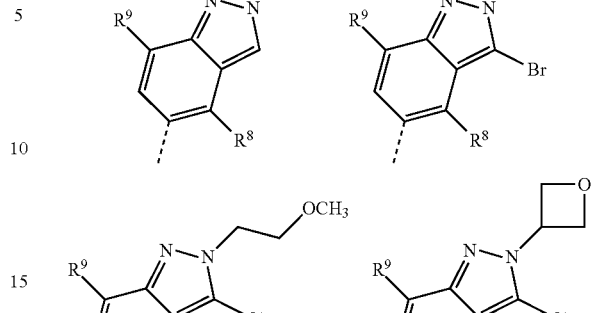

-continued
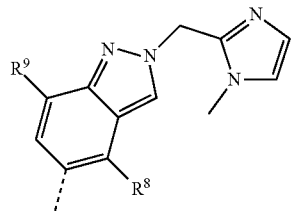
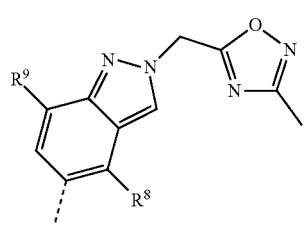
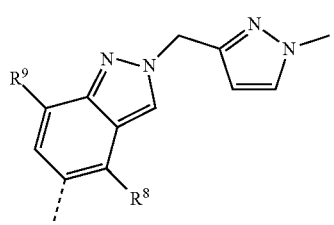
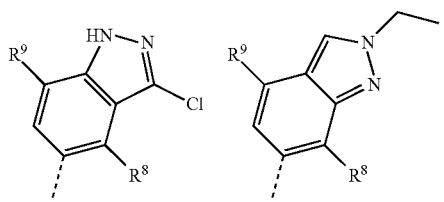
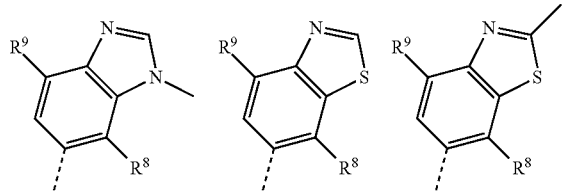
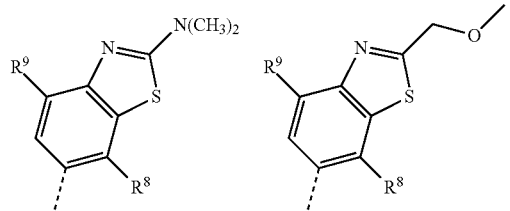
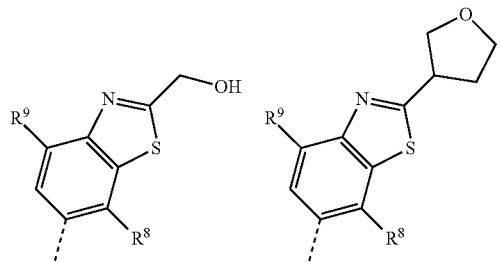
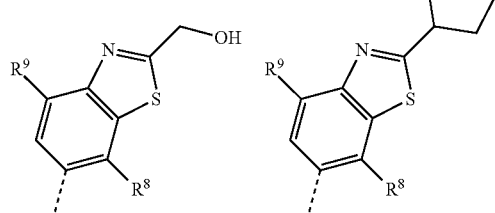
-continued
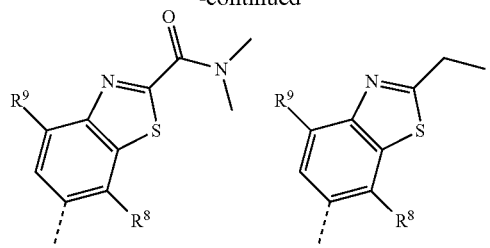
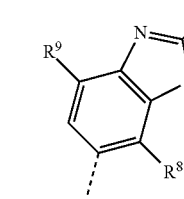
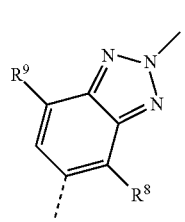
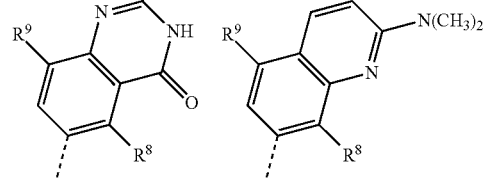
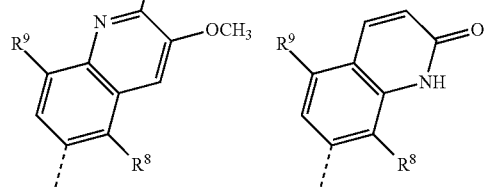
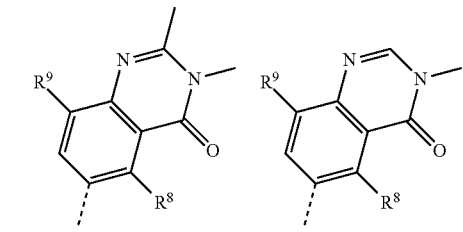
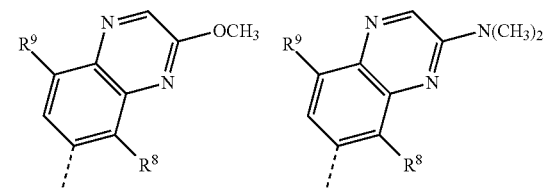
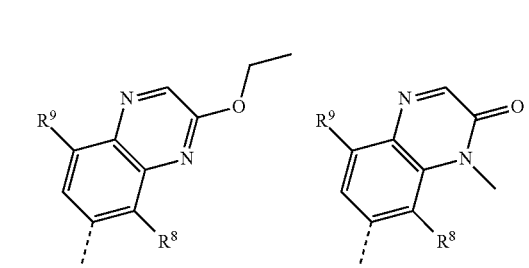

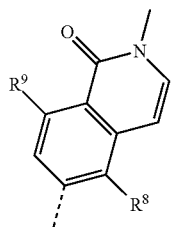
In one embodiment, the moiety
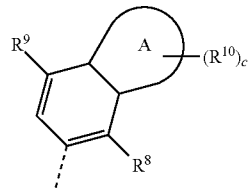
is selected from:
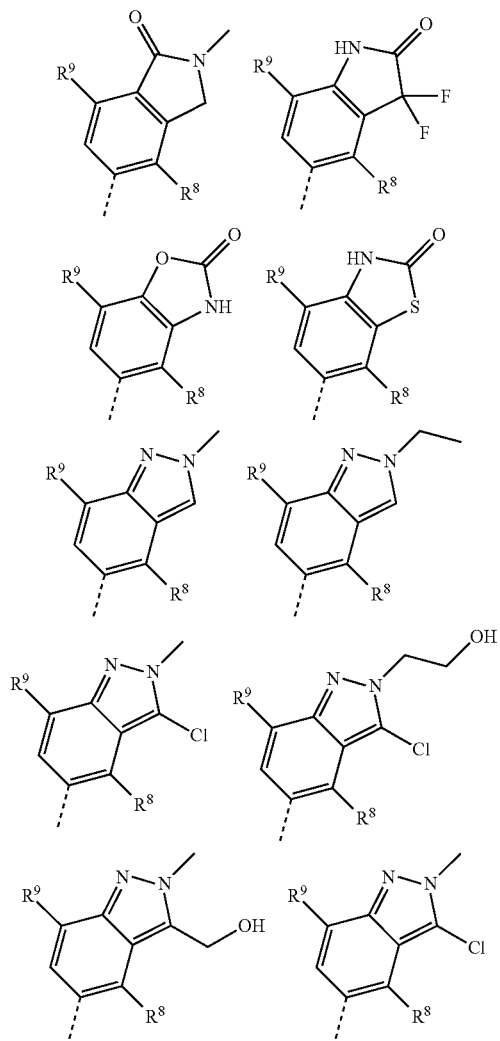
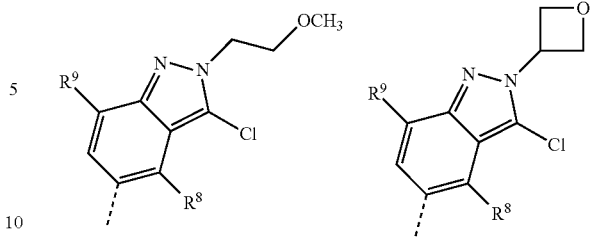
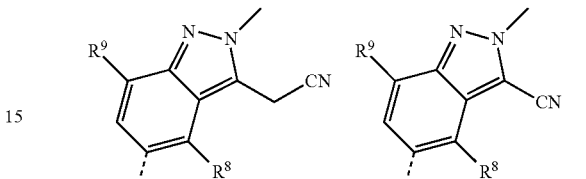
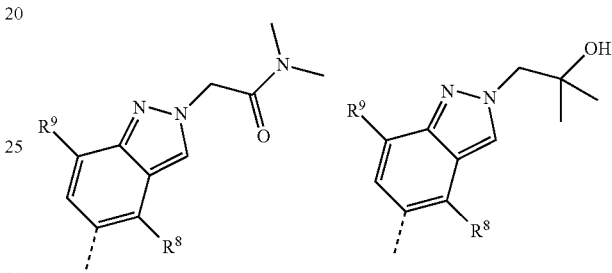
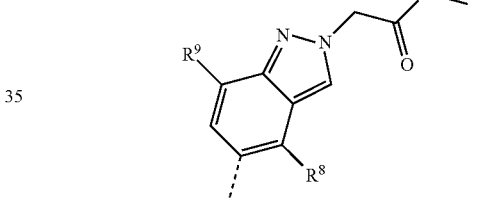
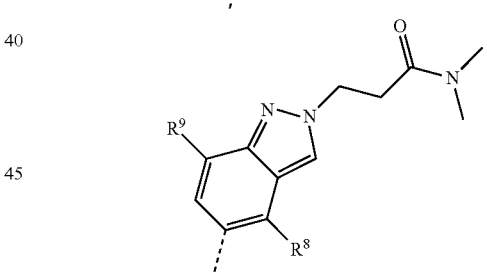
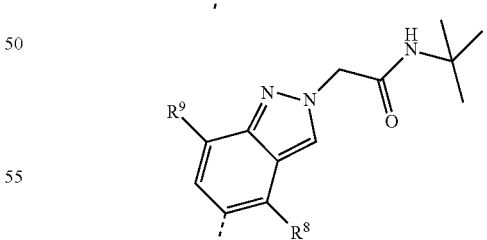
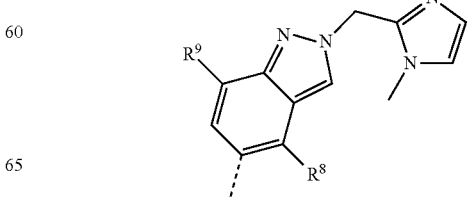

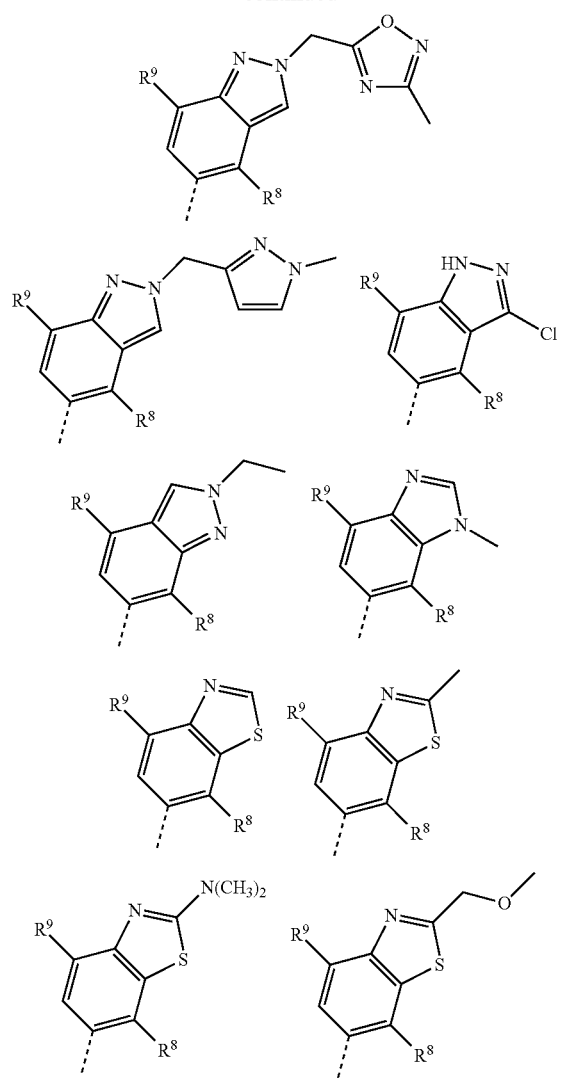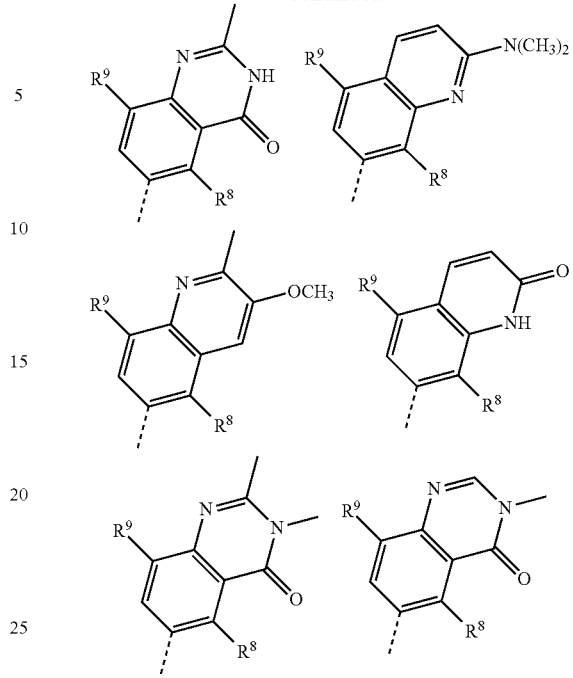
In one embodiment, the moiety
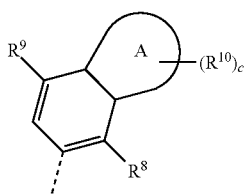
is selected from:
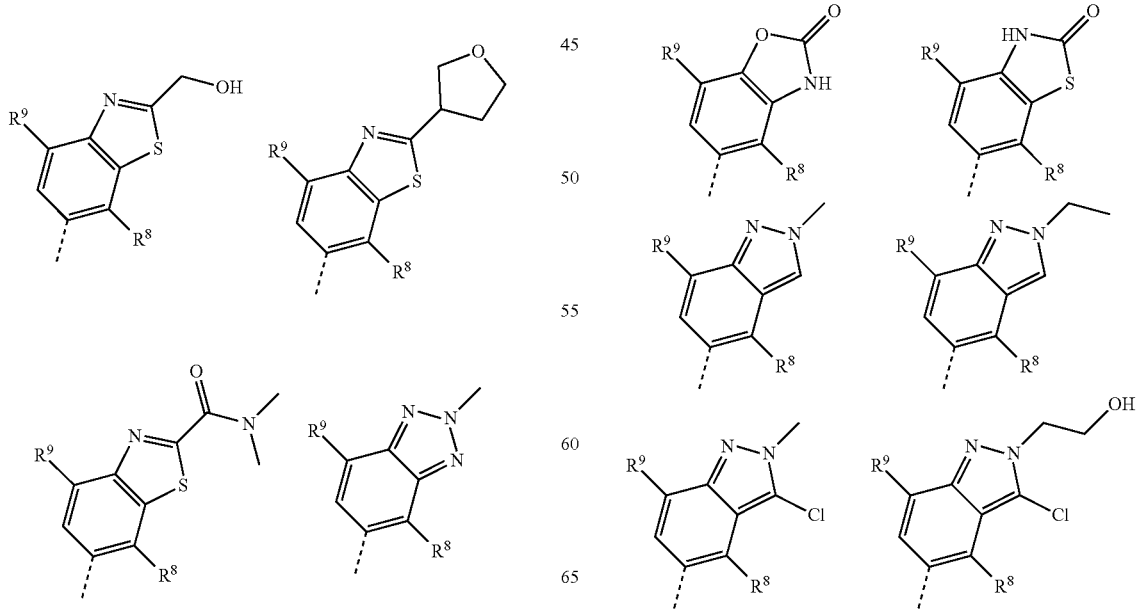

71
-continued
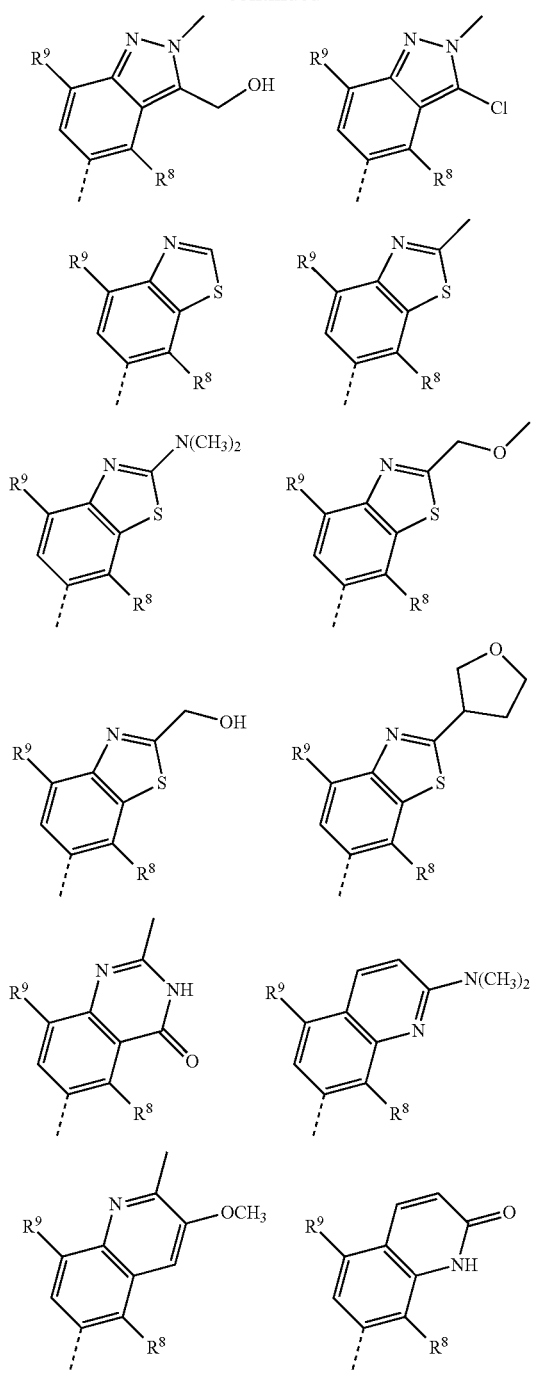
In one embodiment, the moiety
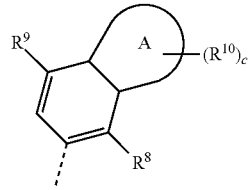
72
is selected from:
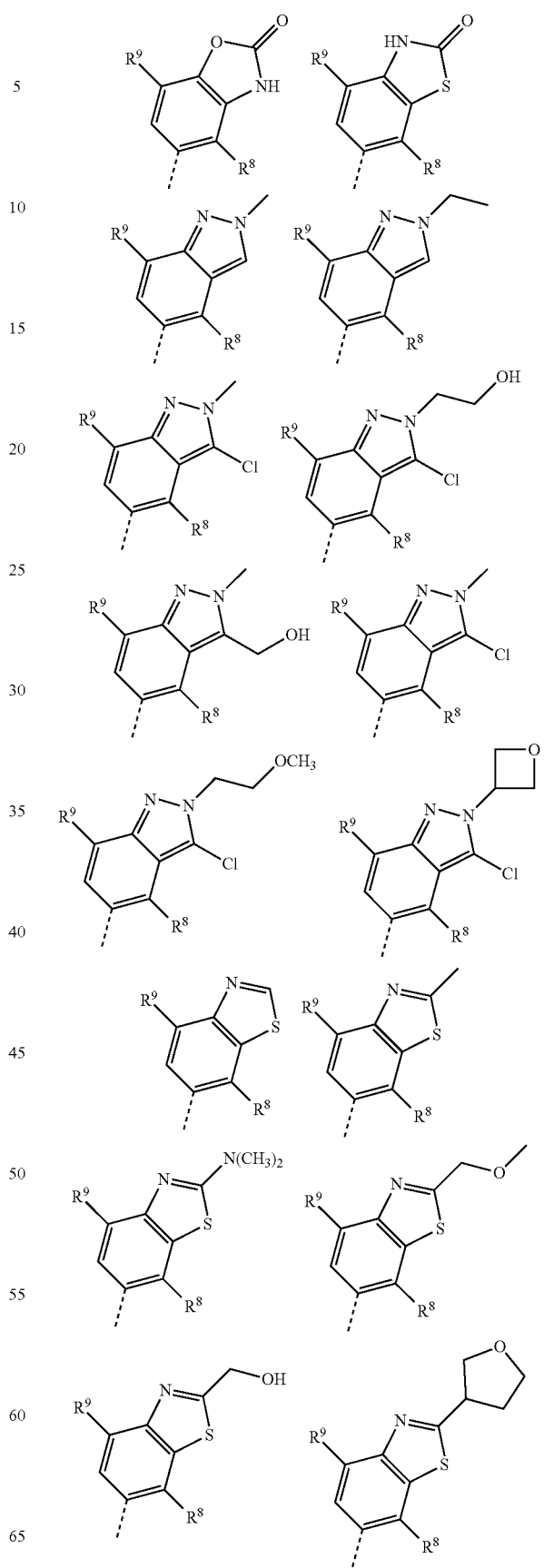

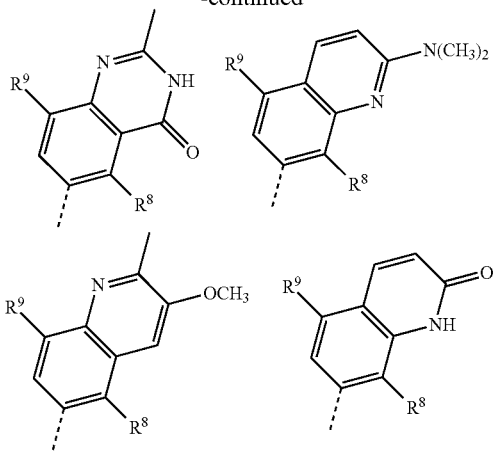
In one embodiment, the moiety
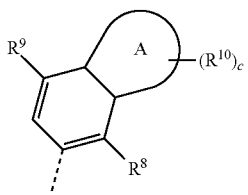
is selected from:
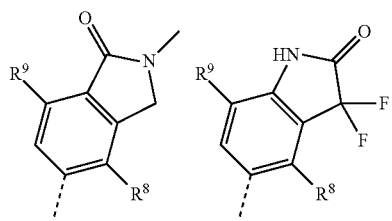
In one embodiment, the moiety
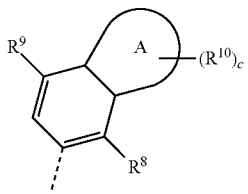
is selected from:
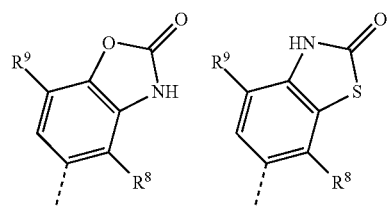
In one embodiment, the moiety
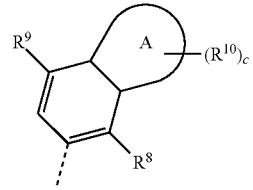
is selected from:
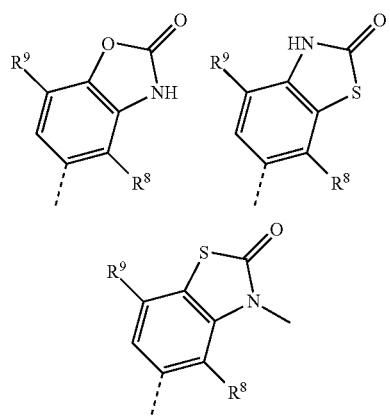
In one embodiment, the moiety
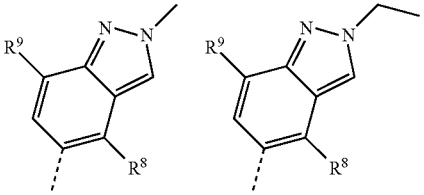
is selected from:
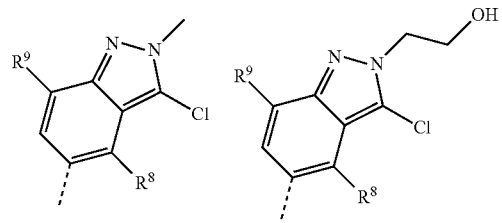

75
-continued
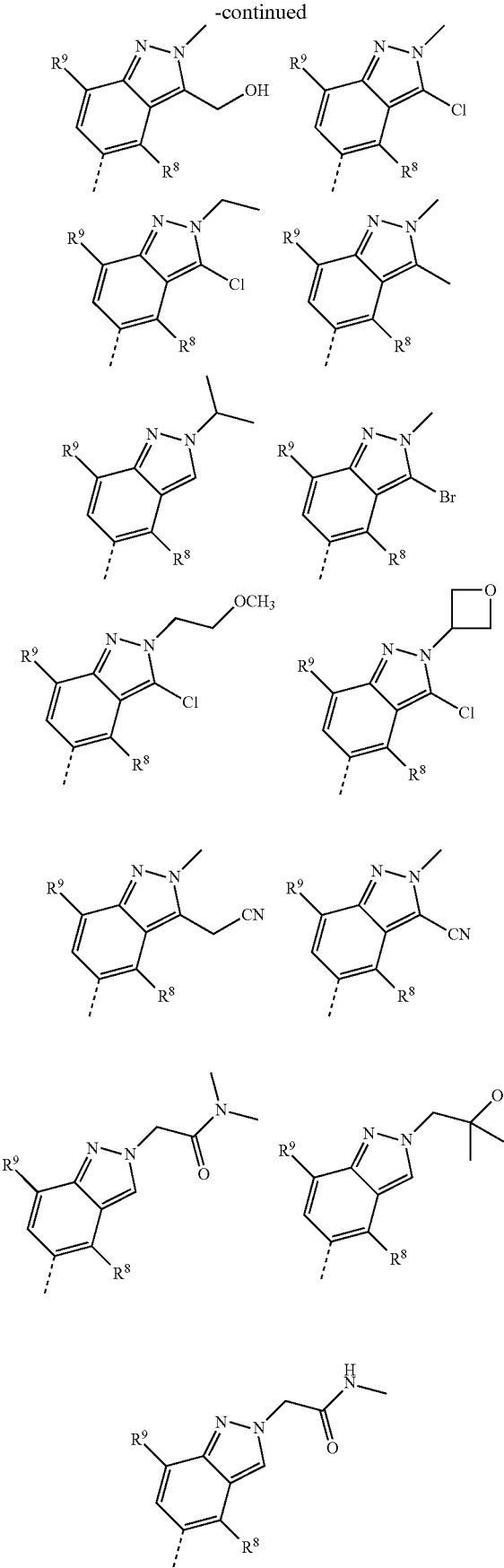
76
-continued
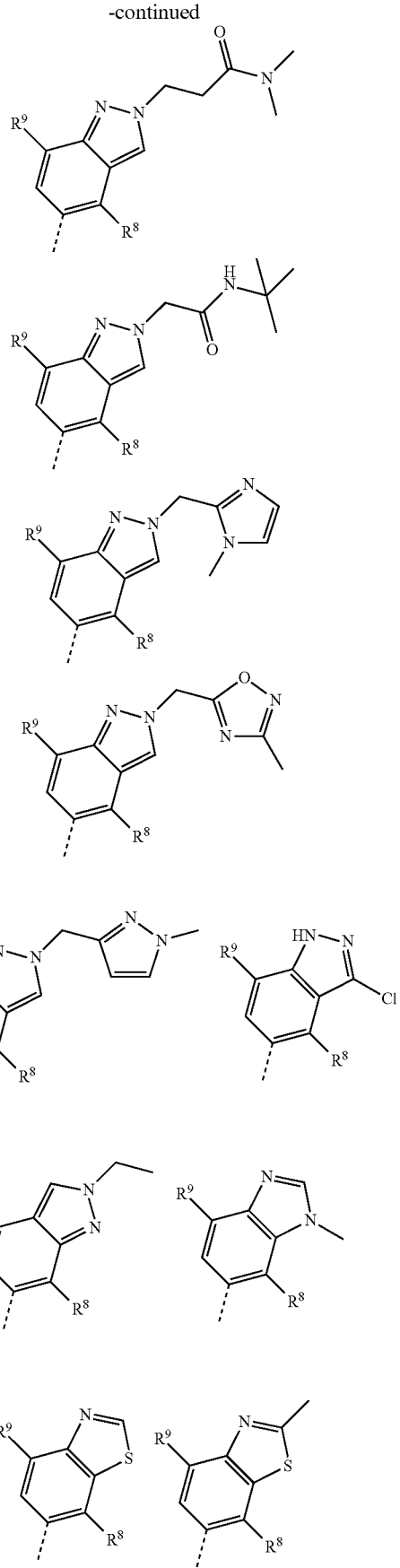

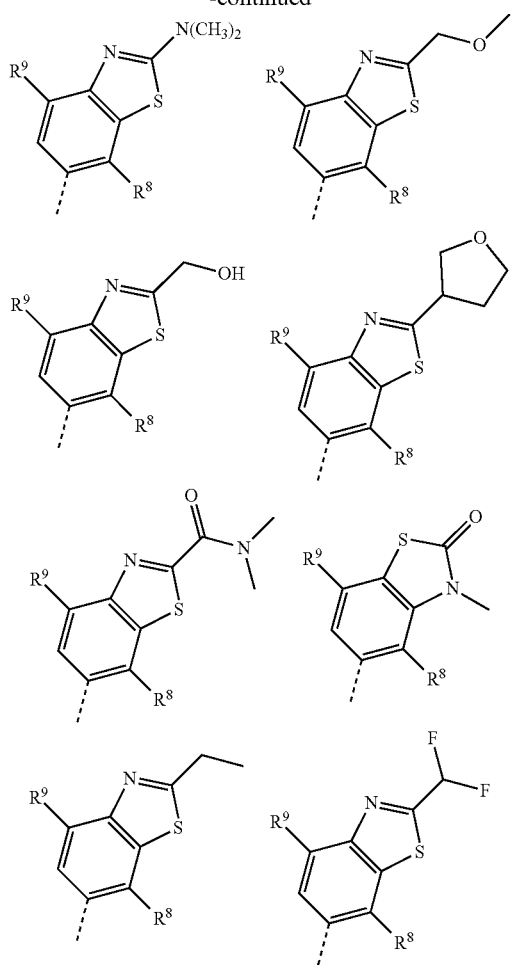
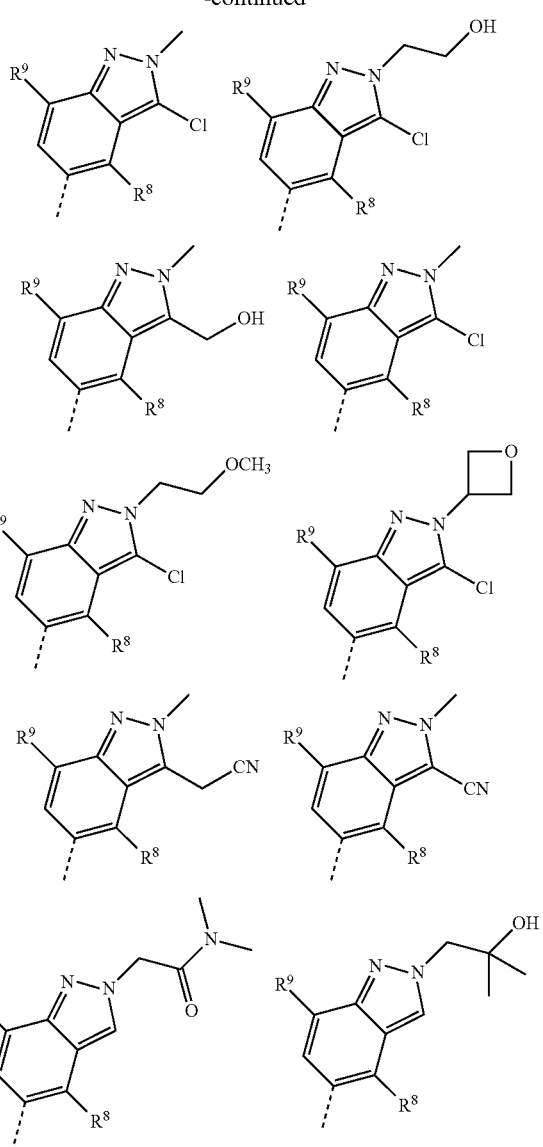
In one embodiment, the moiety
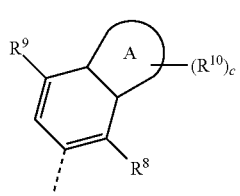
is selected from:
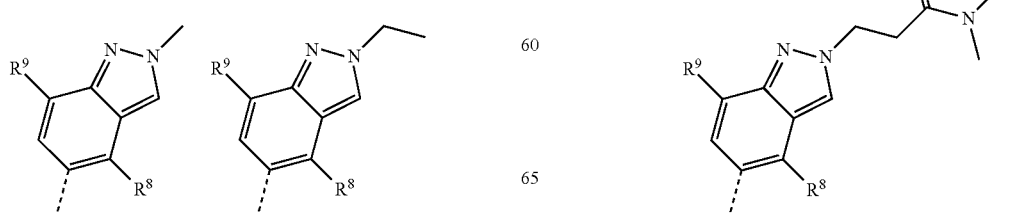

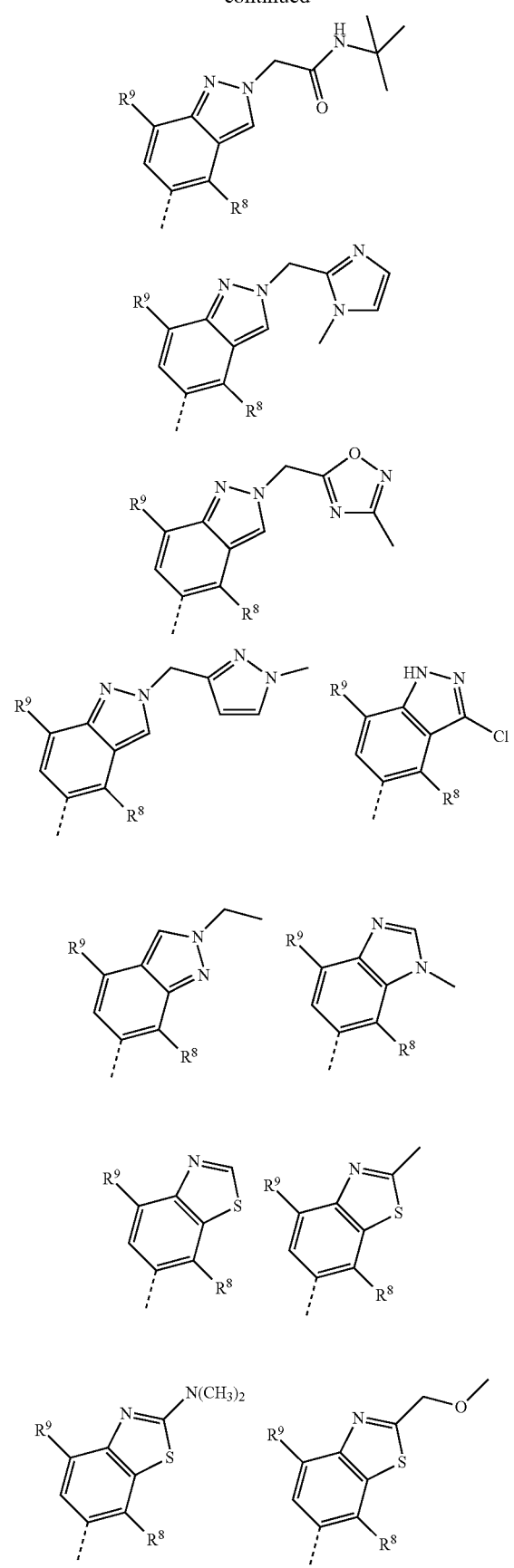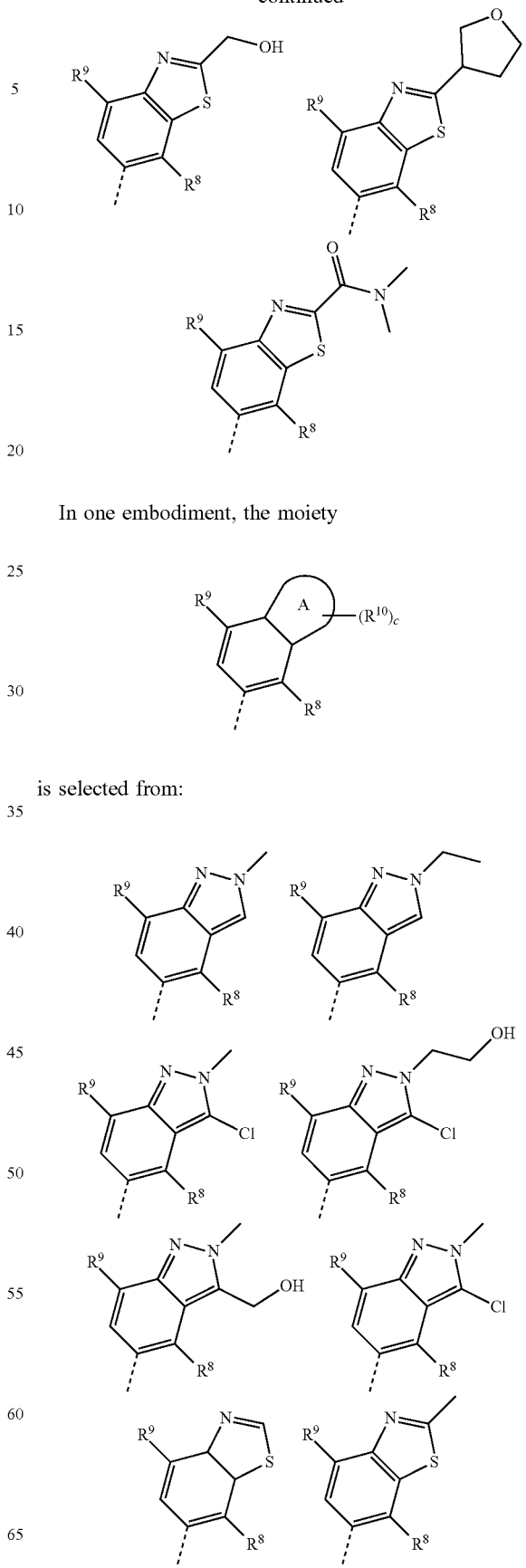
In one embodiment, the moiety
is selected from:

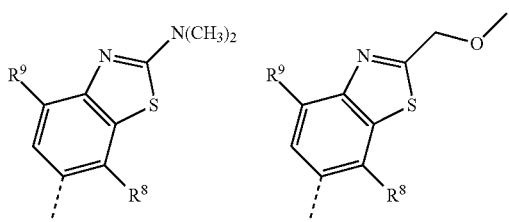
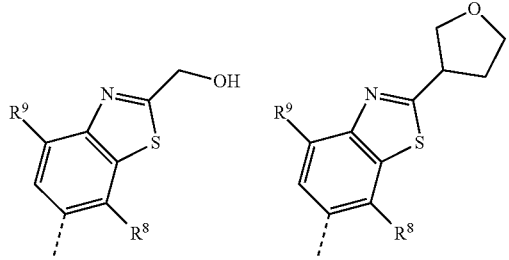
In one embodiment, the moiety
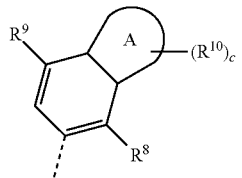
is selected from:
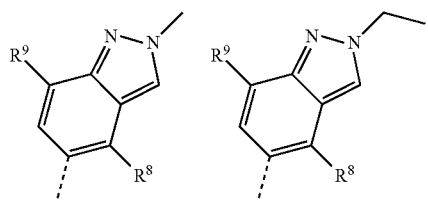
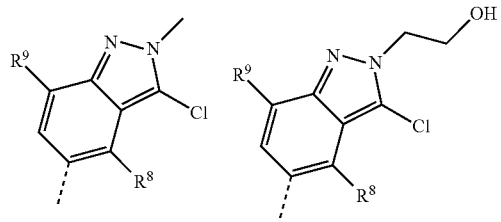
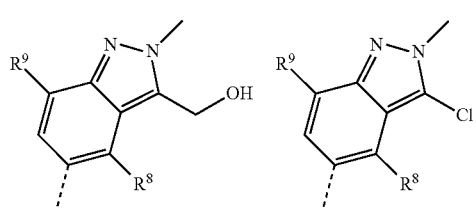
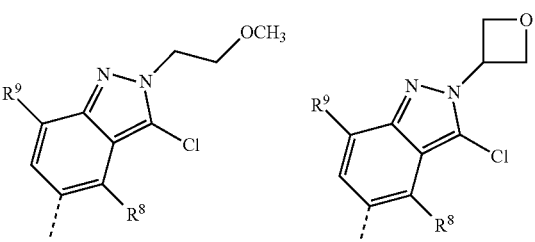
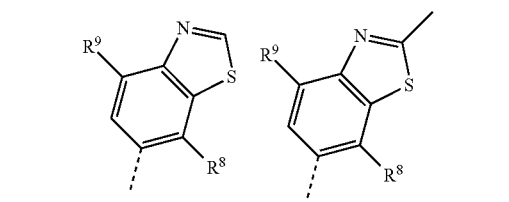
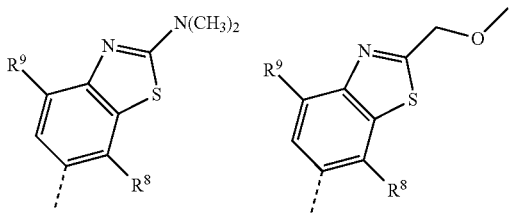
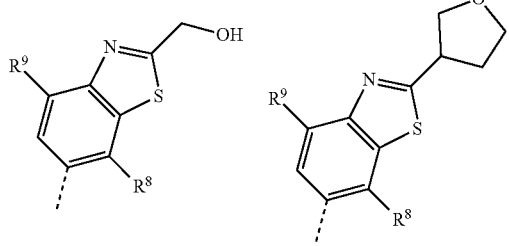
In one embodiment, the moiety
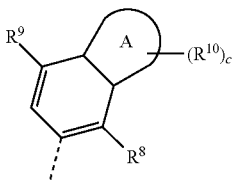
is selected from:
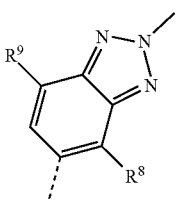

83
In one embodiment, the moiety
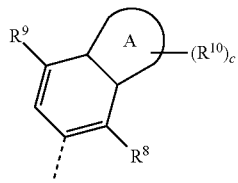
is selected from:
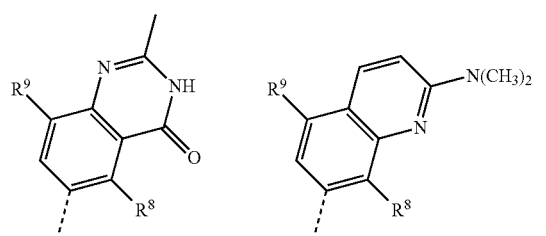
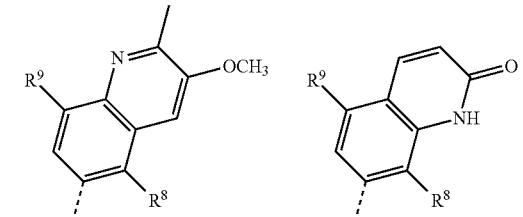
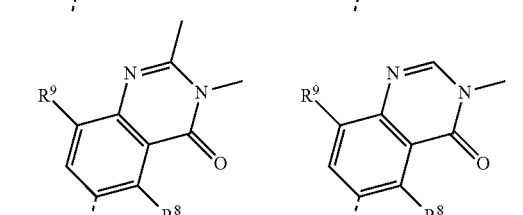
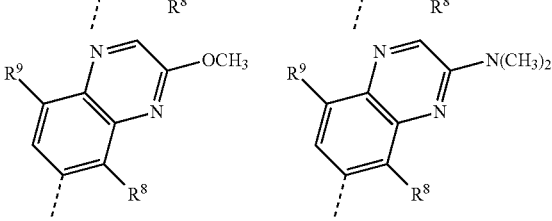
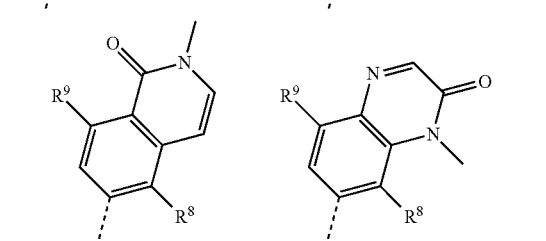
84
In one embodiment, the moiety
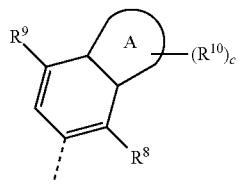
is selected from:
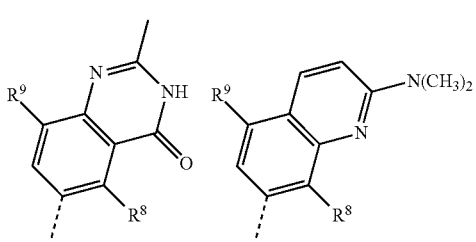
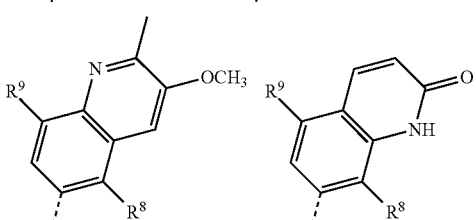
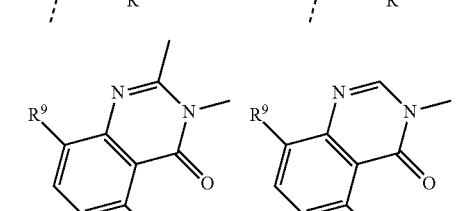
In one embodiment, the moiety
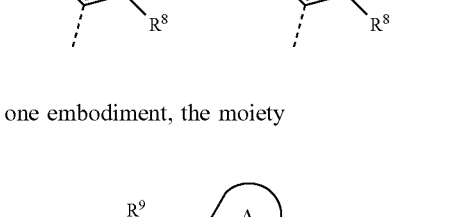
is selected from:
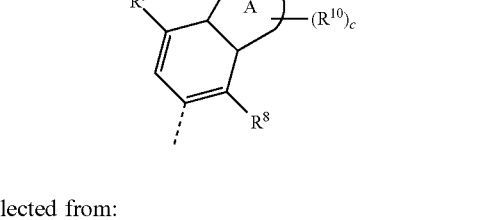

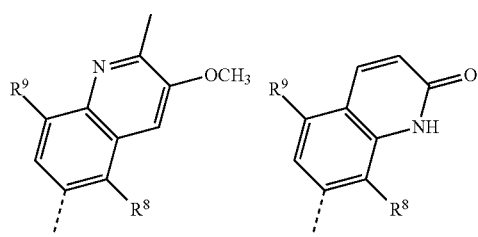
In particular, the moiety
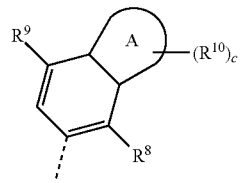
is selected from:
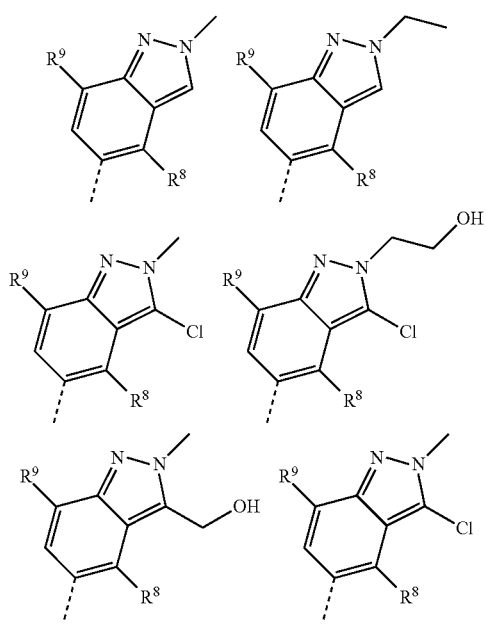
In one embodiment the moiety
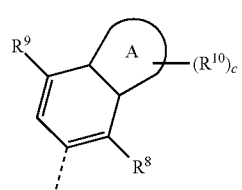
is selected from:
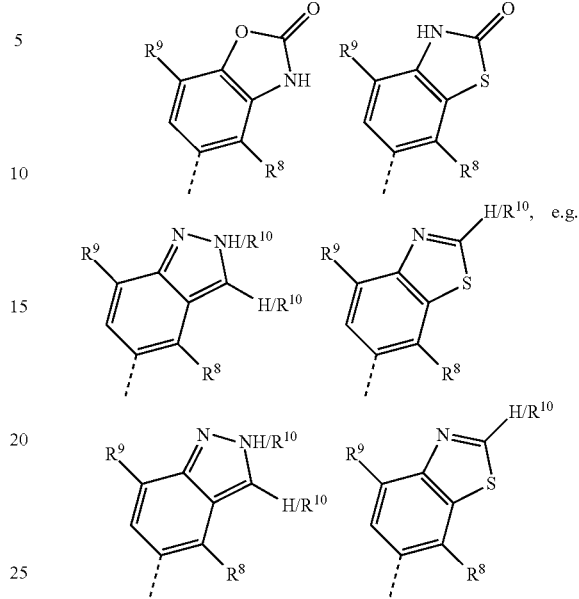
or is selected from:
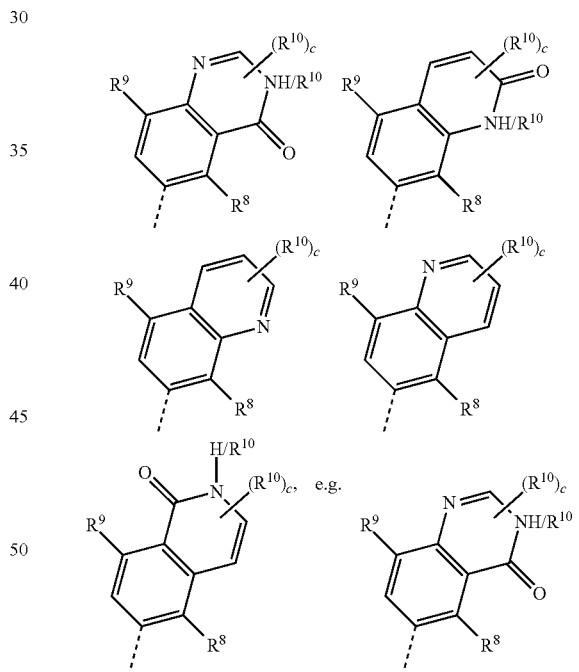
In another embodiment the moiety
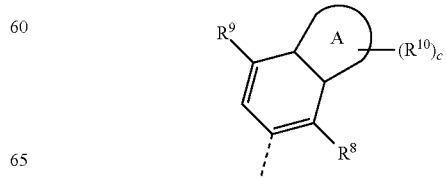

is selected from:

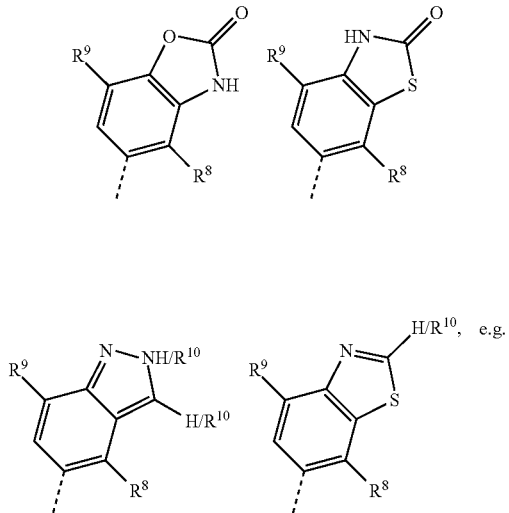

or is selected from:

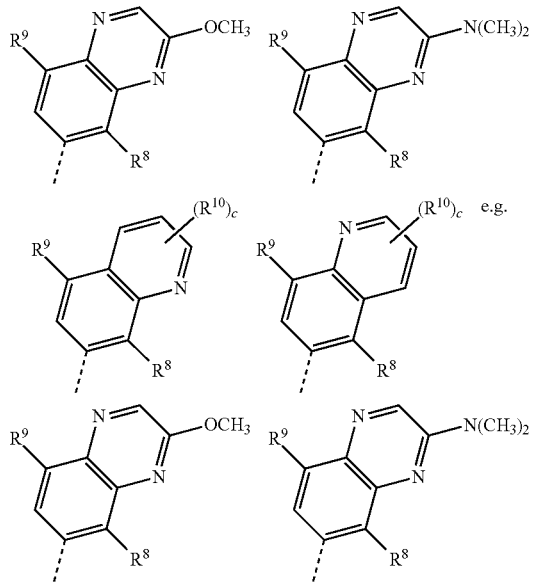

Combinations of Substituents

In one embodiment, the compound of formula (I) is a compound of formula (XV) or a tautomer or a solvate or a pharmaceutically acceptable salt thereof:

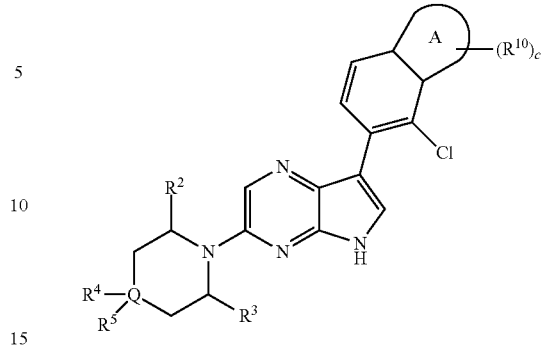

wherein Q, $R^2$, $R^3$, $R^4$, $R^5$, $R^{10}$, c and A are as defined herein.

In one embodiment, the compound of formula (XV) is a compound of formula (XVI) or a tautomer or a solvate or a pharmaceutically acceptable salt thereof:

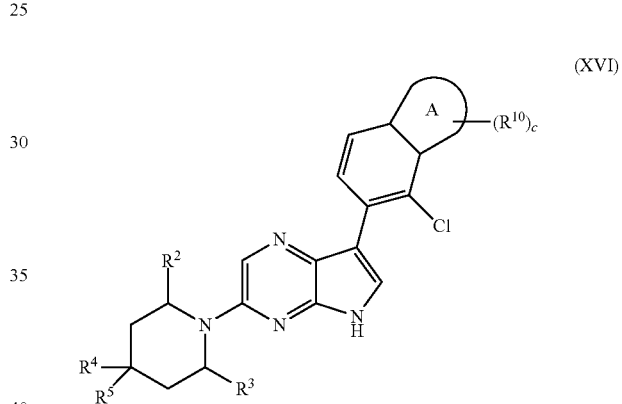

wherein $R^2$, $R^3$, $R^4$, $R^5$, $R^{10}$, c and A are as defined herein.

In one embodiment, the compound of formula (XVI) is a compound of formula (XVII) or a tautomer or a solvate or a pharmaceutically acceptable salt thereof:

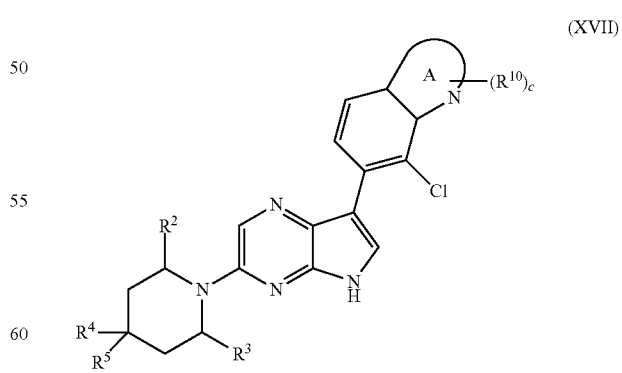

wherein $R^2$, $R^3$, $R^4$, $R^5$, $R^{10}$, c and A are as defined herein.

In one embodiment, the compound of formula (XVI) is a compound of formula (XVII') or a tautomer or a solvate or a pharmaceutically acceptable salt thereof:

(XVII')

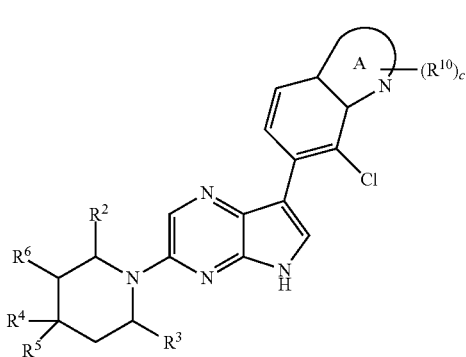

wherein $R^2$, $R^3$, $R^4$, $R^5$, $R^6$, $R^{10}$, c and A are as defined herein.

In one embodiment, the compound of formula (XVII) is a compound of formula (XVIII) or a tautomer or a solvate or a pharmaceutically acceptable salt thereof:

(XVIII)

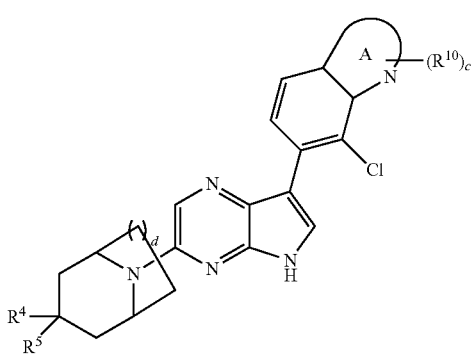

wherein $R^4$, $R^5$, $R^{10}$, c and A are as defined herein, and d is 0, 1 or 2 (e.g. 1).

In one embodiment, the compound of formula (XVII) is a compound of formula (XVIII') or a tautomer or a solvate or a pharmaceutically acceptable salt thereof:

(XVIII')

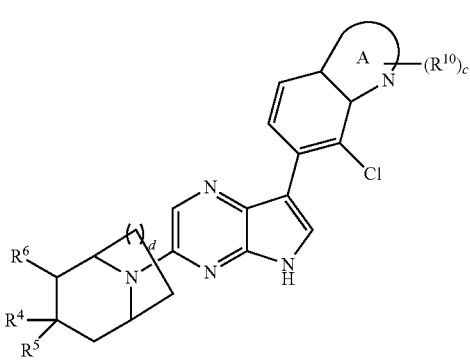

wherein $R^4$, $R^5$, $R^6$, $R^{10}$, c and A are as defined herein, and d is 0, 1 or 2 (e.g. 1).

In one embodiment, the compound of formula (XVIII) is a compound of formula (XVIIIa) or a tautomer or a solvate or a pharmaceutically acceptable salt thereof:

(XVIIIa)

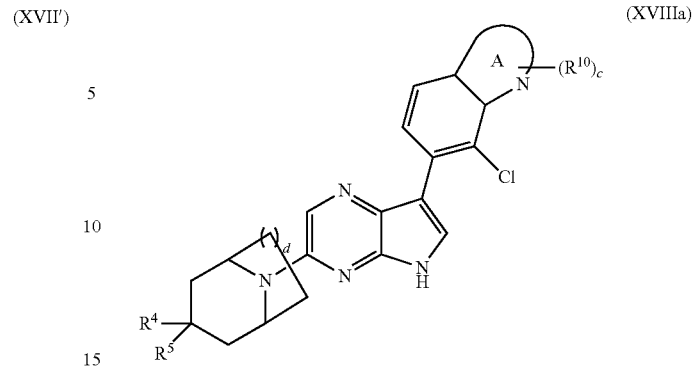

wherein
$R^4$ is hydrogen or $C_{1-4}$alkyl;
$R^5$ is amino, or $C_{1-4}$alkyl (e.g. methyl) optionally substituted by amino;
$R^{10}$ is =O (oxo), $C_{1-4}$alkyl (e.g. —CH$_3$ or —CH$_2$CH$_3$), hydroxyl$C_{1-4}$alkyl (e.g. —CH$_2$CH$_2$OH or —CH$_2$OH) or di$C_{1-4}$alkylamino (e.g. —N(CH$_3$)$_2$);
c is 0 or 1,
d is 0, 1 or 2 (e.g. 1),
and the moiety

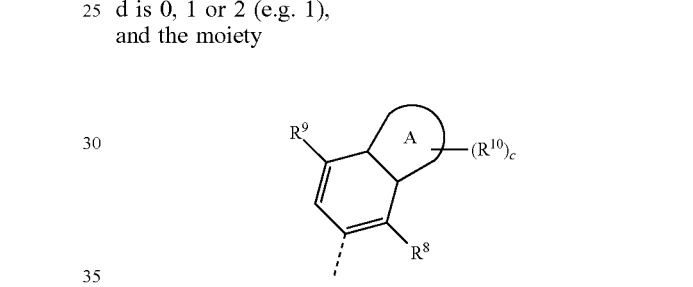

is selected from:
(i) options A, B, C, D, E, F, G, H, I, J, O, P and Q in Table I, and in particular is selected from:

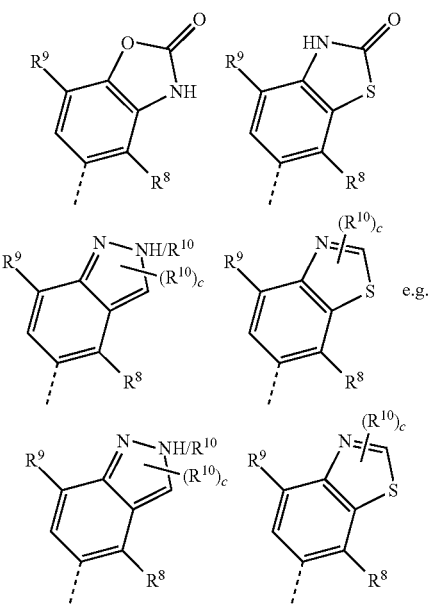

or (ii) options D, E and H in Table II, and in particular is selected from:

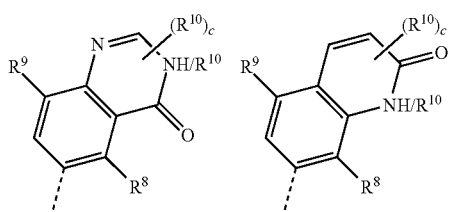 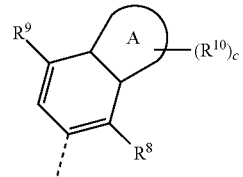

and the moiety

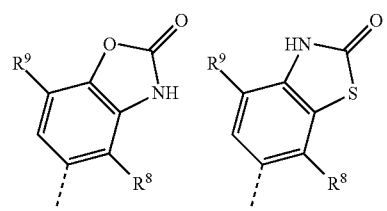

is selected from:
(i) options A, B, C, D, E, F, G, H, I, J, O, P and Q in Table I, and in particular is selected from:

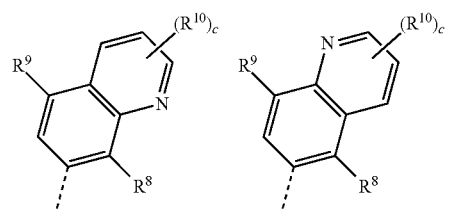

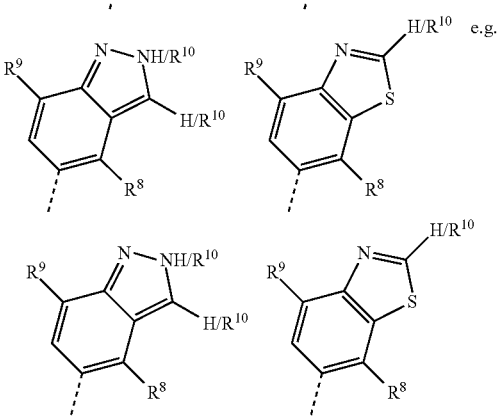

In one embodiment, the compound of formula (XVIII') is a compound of formula (XVIIIa') or a tautomer or a solvate or a pharmaceutically acceptable salt thereof:

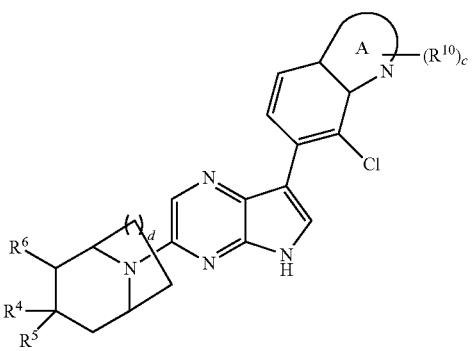

(XVIIIa')

wherein
$R^4$ is hydrogen or $C_{1-4}$alkyl;
$R^5$ is amino, or $C_{1-4}$alkyl (e.g. methyl) optionally substituted by amino;
$R^6$ is halogen (e.g. fluorine) or hydroxyl;
$R^{10}$ is =O (oxo), $C_{1-4}$alkyl (e.g. —CH$_3$ or —CH$_2$CH$_3$), hydroxyl$C_{1-4}$alkyl (e.g. —CH$_2$CH$_2$OH or —CH$_2$OH) or di$C_{1-4}$alkylamino (e.g. —N(CH$_3$)$_2$);
c is 0 or 1,
d is 0, 1 or 2 (e.g. 1), or (ii) options D, E and H in Table II, and in particular is selected from:

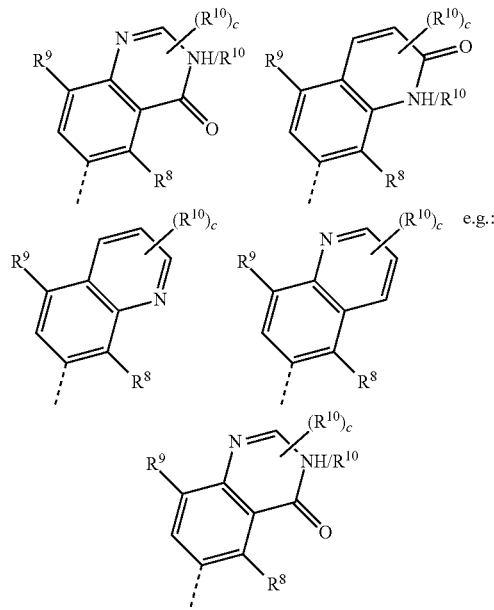

In one embodiment, the compound of formula (I) is a compound of formula (XV*) or a tautomer or a solvate or a pharmaceutically acceptable salt thereof:

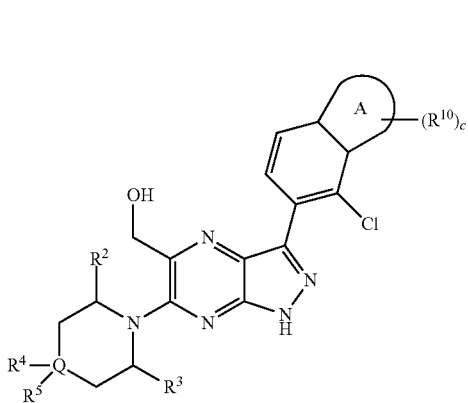

(XV*)

wherein Q, $R^2$, $R^3$, $R^4$, $R^5$, $R^{10}$, c and A are as defined herein.

In one embodiment, the compound of formula (XV*) is a compound of formula (XVI*) or a tautomer or a solvate or a pharmaceutically acceptable salt thereof:

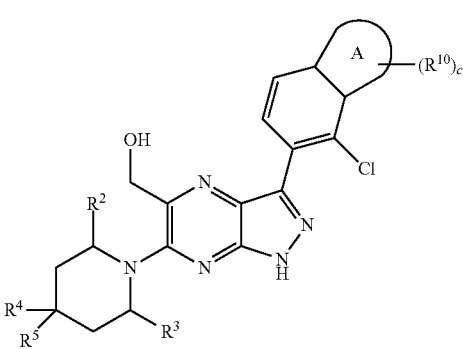

(XVI*)

wherein $R^2$, $R^3$, $R^4$, $R^5$, $R^{10}$, c and A are as defined herein.

In one embodiment, the compound of formula (XVI*) is a compound of formula (XVII*) or a tautomer or a solvate or a pharmaceutically acceptable salt thereof:

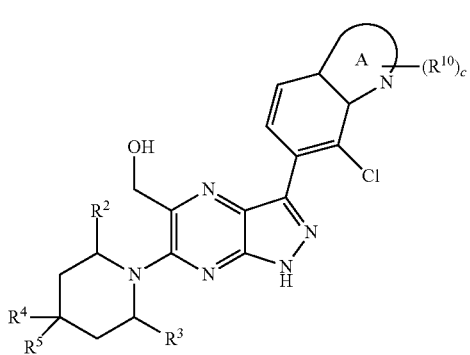

(XVII*)

wherein $R^2$, $R^3$, $R^4$, $R^5$, $R^{10}$, c and A are as defined herein.

In one embodiment, the compound of formula (XVI*) is a compound of formula (XVIII or a tautomer or a solvate or a pharmaceutically acceptable salt thereof:

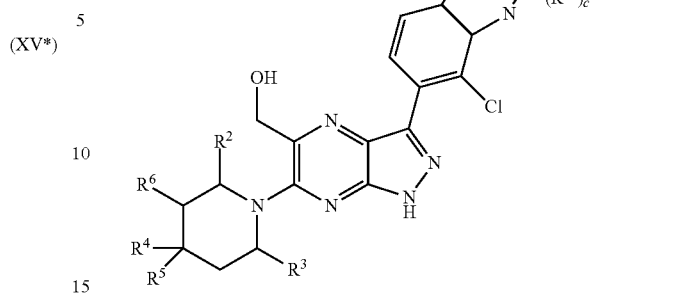

(XVII'*)

wherein $R^2$, $R^3$, $R^4$, $R^5$, $R^6$, $R^{10}$, c and A are as defined herein.

In one embodiment, the compound of formula (XVII*) is a compound of formula (XVIII*) or a tautomer or a solvate or a pharmaceutically acceptable salt thereof:

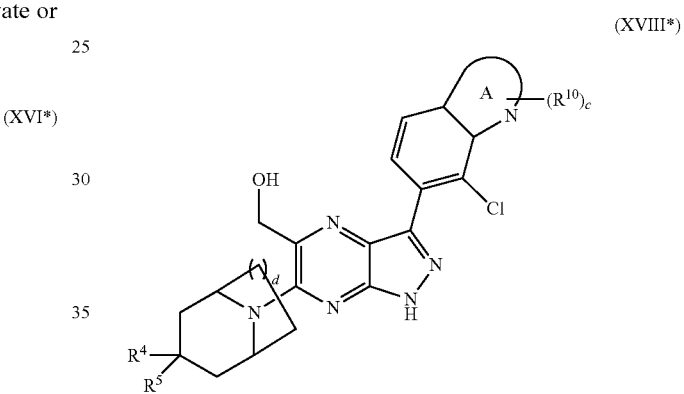

(XVIII*)

wherein $R^4$, $R^5$, $R^{10}$, c and A are as defined herein, and d is 0, 1 or 2 (e.g. 1).

In one embodiment, the compound of formula (XVII*) is a compound of formula (XVIII'*) or a tautomer or a solvate or a pharmaceutically acceptable salt thereof:

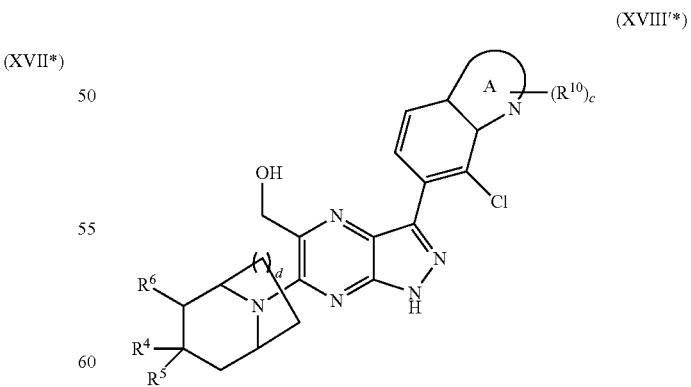

(XVIII'*)

wherein $R^4$, $R^5$, $R^6$, $R^{10}$, c and A are as defined herein, and d is 0, 1 or 2 (e.g. 1).

In one embodiment, the compound of formula (XVIII'*) is a compound of formula (XVIIIa'*) or a tautomer or a solvate or a pharmaceutically acceptable salt thereof:

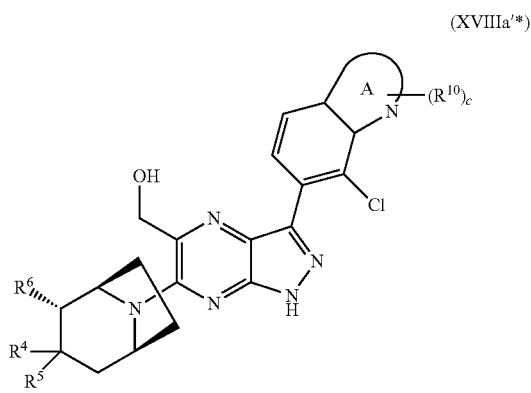

(XVIIIa'*)

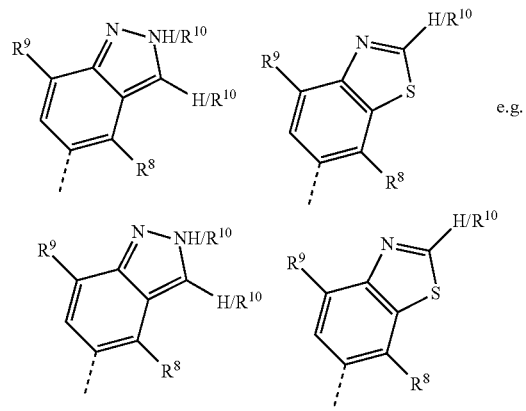

e.g.

or (ii) options E and G in Table II, and in particular is selected from:

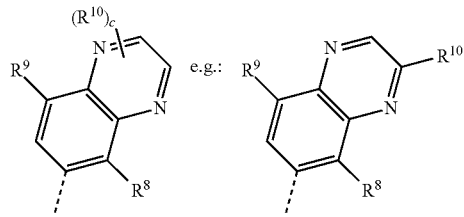

e.g.:

In one embodiment, the compound of formula (I) is a compound of formula (IIa) or a tautomer or a solvate or a pharmaceutically acceptable salt thereof:

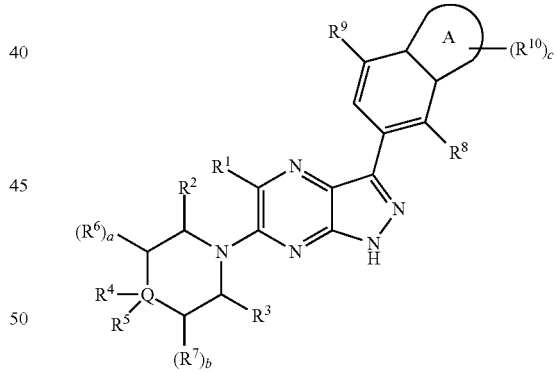

(IIa)

wherein
$R^4$ is hydrogen or $C_{1-4}$alkyl;
$R^5$ is amino, hydroxyl or $C_{1-4}$alkyl (e.g. methyl) optionally substituted by amino;
$R^6$ is halogen (e.g. fluorine);
$R^{10}$ is halogen (e.g. chlorine), cyano, $C_{1-4}$alkyl (e.g. —CHs, —CH(CH$_3$)$_2$ or —CH$_2$CH$_3$), oxo, halo$C_{1-4}$alkyl (e.g. —CHF$_2$), $C_{1-4}$alkoxyl (e.g. —OCH$_3$, —OCH$_2$CH$_3$ or —OCH(CH$_3$)$_2$), hydroxyl$C_{1-4}$alkyl (e.g. —CH$_2$CH$_2$OH), $C_{1-4}$alkoxy$C_{1-4}$alkene (e.g. —CH$_2$OCH$_3$). di$C_{1-4}$alkylamino (e.g. —N(CH$_3$)$_2$) or optionally substituted (e.g. unsubstituted) four- to six-membered saturated heterocyclic group containing 1 or 2 heteroatoms selected from O or N where the optional substituent is selected from $C_{1-4}$alkyl (e.g. morpholinyl or azetidinyl);
c is 0 or 1; and
the moiety

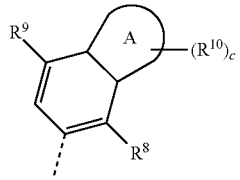

is as defined herein.
In one embodiment of formula (XVIIIa'*) the moiety

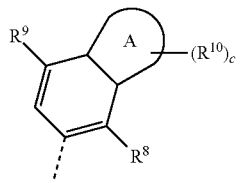

is selected from:
(i) options A, B, C, D, E, F, G, H, I, J, O, P and Q in Table I, and in particular is selected from:

wherein
Q is C or N;
$R^1$ is CH$_3$ or —CH$_2$OH;
$R^2$ and $R^3$ are either:
(i) hydrogen; or
(ii) together form a two- to three-membered $C_{1-3}$alkylene bridge group;
$R^4$ is hydrogen or $C_{1-4}$alkyl (e.g. methyl);
$R^5$ is amino;
or $R^4$ and $R^5$ together with Q (when Q=C), form a four-membered nitrogen-containing heterocyclic ring;
either: (i) a is 1 and b is 0 and $R^6$ is halogen (e.g. fluorine) or hydroxyl; or (ii) a is 0 and b is 1 and $R^7$ is halogen (e.g. fluorine) or hydroxyl;

$R^8$ is halogen (e.g. chlorine or fluorine)

$R^{10}$ is halogen (e.g. chlorine), cyano, $C_{1-4}$alkyl (e.g. —CHs, —CH(CH$_3$)$_2$ or —CH$_2$CH$_3$), halo$C_{1-4}$alkyl (e.g. —CHF$_2$), $C_{1-4}$alkoxyl (e.g. —OCH$_3$, —OCH$_2$CH$_3$ or —OCH(CH$_3$)$_2$), $C_{1-4}$alkoxy$C_{1-4}$alkene (e.g. —CH$_2$OCH$_3$) di$C_{1-4}$alkylamino (e.g. —N(CH$_3$)$_2$) or optionally substituted (e.g. unsubstituted) four- to six-membered saturated heterocyclic group containing 1 or 2 heteroatoms selected from O or N where the optional substituent is selected from $C_{1-4}$alkyl (e.g. morpholinyl or azetidinyl);

c is 0 or 1, d is 0, 1 or 2 (e.g. 1), and the moiety

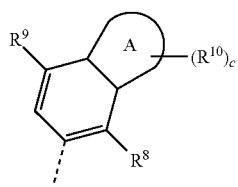

is selected from:

(i) options A, B, C, D, E, F, G, H, I, J, O, P and Q in Table I, and in particular is selected from:

or (ii) options E and G in Table II, and in particular is selected from:

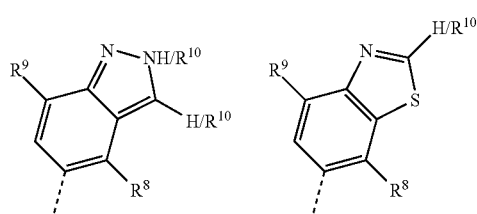

In one embodiment of the compound of formula (IIa), $R^1$ is CH$_3$.

In one embodiment, the compound of formula (IIa) is a compound of formula (XVIIIa*) or a tautomer or a solvate or a pharmaceutically acceptable salt thereof:

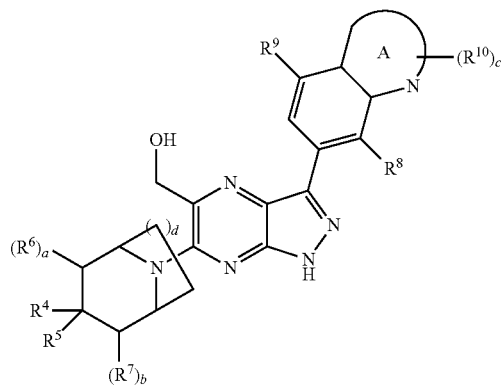

(XVIIIa*)

wherein $R^4$ is hydrogen or $C_{1-4}$alkyl (e.g. methyl);

$R^5$ is amino;

$R^6$ or $R^7$ is halogen (e.g. fluorine);

$R^8$ is halogen (e.g. chlorine or fluorine)

$R^{10}$ is halogen (e.g. chlorine), cyano, $C_{1-4}$alkyl (e.g. —CHs, —CH(CH$_3$)$_2$ or —CH$_2$CH$_3$), halo$C_{1-4}$alkyl (e.g. —CHF$_2$), $C_{1-4}$alkoxyl (e.g. —OCH$_3$, —OCH$_2$CH$_3$ or —OCH(CH$_3$)$_2$), $C_{1-4}$alkoxy$C_{1-4}$alkene (e.g. —CH$_2$OCH$_3$). di$C_{1-4}$alkylamino (e.g. —N(CH$_3$)$_2$) or optionally substituted (e.g. unsubstituted) four- to six-membered saturated heterocyclic group containing 1 or 2 heteroatoms selected from O or N where the optional substituent is selected from $C_{1-4}$alkyl (e.g. morpholinyl or azetidinyl);

a is 0 or 1;

b is 0 or 1;

c is 0 or 1, d is 0, 1 or 2 (e.g. 1), and the moiety

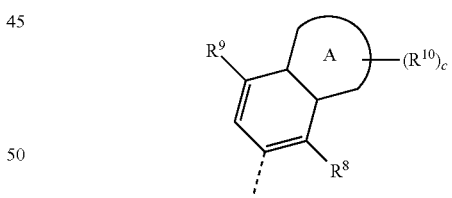

is selected from:

(i) options A, B, C, D, E, F, G, H, I, J, O, P and Q in Table I, and in particular is selected from:

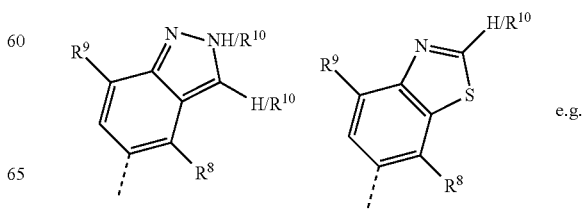

e.g.

-continued

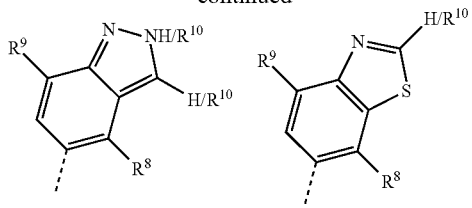

or (ii) options E and G in Table II, and in particular is selected from:

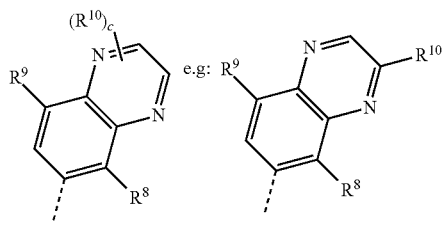

A Particular Group of Compounds

In one embodiment, the invention provides a compound of formula (I):

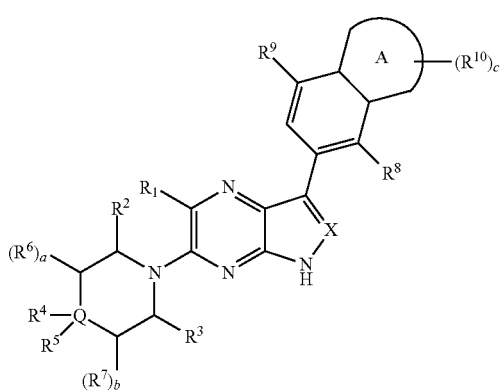

or a tautomer or a solvate or a pharmaceutically acceptable salt thereof, wherein:
X is CH or N;
$R^1$ is hydrogen, —$CH_3$ or —$CH_2OH$ but when X is N then $R^1$ is selected from —$CH_3$ and —$CH_2OH$;
$R^2$ and $R^3$ are either:
  (i) hydrogen; or
  (ii) together form a one- to three-membered alkylene bridge group (e.g. —$CH_2$— or —$CH_2$—$CH_2$—);
Q is C or N;
  wherein when Q is C then either:
    (i) $R^4$ is hydrogen, amino, or $C_{1-4}$alkyl (e.g. methyl) optionally substituted by amino (e.g. —$CH_2NH_2$); $R^5$ is hydrogen, amino, or $C_{1-4}$alkyl (e.g. methyl) optionally substituted by amino or hydroxyl;
    provided that $R^4$ and $R^5$ must not both be selected from amino and $C_{1-4}$alkyl substituted by amino; or
    (ii) $R^4$ and $R^5$ together with Q form a four- to six-membered nitrogen-containing heterocyclic ring (e.g. azetidine); and wherein when Q is N then:
  $R^4$ is absent, $R^5$ is hydrogen and $R^2$ and $R^3$ together form the one- to three-membered alkylene bridge group (e.g. —$CH_2$— or —$CH_2$—$CH_2$—);
$R^6$ and $R^7$ are independently selected from halogen (e.g. fluorine), and hydroxyl;
a is selected from 0, 1 and 2;
b is selected from 0 and 1;
provided that when Q is N then a and b are 0;
Ring A is either:
  (i) a five-membered nitrogen-containing heterocyclic ring (e.g. an aromatic ring or a non-aromatic ring) wherein the heterocyclic ring optionally contains one additional heteroatoms selected from N, O and S;
  (ii) a six-membered aromatic or non-aromatic nitrogen-containing heterocyclic ring, wherein the heterocyclic ring optionally contains one additional heteroatom which is N; or
$R^8$ is selected from halogen (for example chlorine or fluorine, e.g. chlorine);
$R^9$ is hydrogen;
$R^{10}$ are independently selected from halogen (e.g. chlorine), cyano, cyano$C_{1-4}$alkyl (e.g. —$CH_2$—CN), $C_{1-4}$alkoxy (e.g. —$OCH_3$), =O (oxo), hydroxyl, $C_{1-4}$alkyl (e.g. —$CH_3$ or —$CH_2CH_3$), hydroxyl$C_{1-4}$alkyl (e.g. —$CH_2CH_2OH$ or —$CH_2OH$), di$C_{1-4}$alkylamino (e.g. —$N(CH_3)_2$), $C_{1-4}$alkoxy$C_{1-4}$alkylene (e.g. —$CH_2$—O—$CH_3$), —$C_{1-4}$alkylene-C(=O)$N_{(2-q)}(C_{1-6}$ alkyl$)_q$), —$C_{1-4}$alkylene-NHC(=O)$C_{1-6}$alkyl, $C_{1-4}$alkyl (e.g $C_1$ alkyl) substituted with optionally substituted five- or six-membered unsaturated heterocyclic group (e.g. five-membered unsaturated heterocyclic group) containing 2 or 3 heteroatoms selected from O, N, or S where the optional substituent is selected from $C_{1-4}$alkyl, and four- to six-membered saturated heterocyclic group containing O (e.g. tetrahydrofuranyl or oxetanyl);
q is selected from 0, 1 and 2; and
c is selected from 0, 1, 2 and 3.

In one embodiment, the invention provides a compound of formula (I):

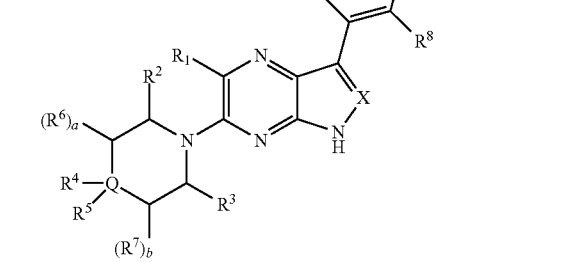

or a tautomer or a solvate or a pharmaceutically acceptable salt thereof, wherein:
X is CH or N;
$R^1$ is hydrogen, —$CH_3$ or —$CH_2OH$ but when X is N then $R^1$ is selected from —$CH_3$ and —$CH_2OH$;
$R^2$ and $R^3$ are either:
  (i) hydrogen; or
  (ii) together form a one- to three-membered alkylene bridge group (e.g. —$CH_2$— or —$CH_2$—$CH_2$—);
Q is C or N;

wherein when Q is C then either:
(i) $R^4$ is hydrogen, amino, or $C_{1-4}$alkyl (e.g. methyl) optionally substituted by amino (e.g. —$CH_2NH_2$);
$R^5$ is hydrogen, amino, or $C_{1-4}$alkyl (e.g. methyl) optionally substituted by amino or hydroxyl;
provided that $R^4$ and $R^5$ must not both be selected from amino and $C_{1-4}$alkyl substituted by amino; or
(ii) $R^4$ and $R^5$ together with Q form a four- to six-membered nitrogen-containing heterocyclic ring (e.g. azetidine); and
wherein when Q is N then:
$R^4$ is absent, $R^5$ is hydrogen and $R^2$ and $R^3$ together form the one- to three-membered alkylene bridge group (e.g. —$CH_2$— or —$CH_2$—$CH_2$—);
$R^6$ and $R^7$ are independently selected from halogen (e.g. fluorine), and hydroxyl;
a is selected from 0, 1 and 2;
b is selected from 0 and 1;
provided that when Q is N then a and b are 0;
Ring A is either:
(i) a five-membered nitrogen-containing heterocyclic ring (e.g. an aromatic ring or a non-aromatic ring) wherein the heterocyclic ring optionally contains one additional heteroatoms selected from N, O and S;
(ii) a six-membered aromatic or non-aromatic nitrogen-containing heterocyclic ring, wherein the heterocyclic ring optionally contains one additional heteroatom which is N; or
$R^8$ is selected from halogen (for example chlorine or fluorine, e.g. chlorine);
$R^9$ is hydrogen;
$R^{10}$ are independently selected from halogen (e.g. chlorine), $C_{1-4}$alkoxy (e.g. —$OCH_3$), =O (oxo), hydroxyl, $C_{1-4}$alkyl (e.g. —$CH_3$ or —$CH_2CH_3$), hydroxyl$C_{1-4}$alkyl (e.g. —$CH_2CH_2OH$ or —$CH_2OH$), di$C_{1-4}$alkylamino (e.g. —$N(CH_3)_2$), $C_{1-4}$alkoxy$C_{1-4}$alkylene (e.g. —$CH_2$—O—$CH_3$) and four- to six-membered saturated heterocyclic group containing O (e.g. tetrahydrofuranyl or oxetanyl); and
c is selected from 0, 1 and 2.

In one embodiment, the invention provides a compound of formula (I):

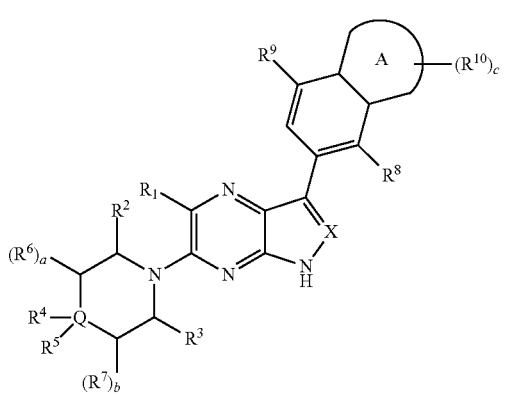

(I)

or a tautomer or a solvate or a pharmaceutically acceptable salt thereof, wherein:
X is CH or N;
$R^1$ is hydrogen, —$CH_3$ or —$CH_2OH$ but when X is N then $R^1$ is selected from —$CH_3$ and —$CH_2OH$;
$R^2$ and $R^3$ are either:
(i) hydrogen; or
(ii) together form a one- to three-membered alkylene bridge group (e.g. —$CH_2$—, —$CH_2$—$CH_2$— or —$CH_2$—$CH_2$—$CH_2$—);
Q is C or N;
wherein when Q is C then either:
(i) $R^4$ is hydrogen, amino, or $C_{1-4}$alkyl (e.g. methyl) optionally substituted by amino (e.g. —$CH_2NH_2$);
$R^5$ is hydrogen, amino, hydroxyl, or $C_{1-4}$alkyl (e.g. methyl) optionally substituted by either amino (e.g. —$CH_2NH_2$) or hydroxyl (e.g. —$CH_2OH$);
provided that $R^4$ and $R^5$ must not both be selected from amino and $C_{1-4}$alkyl substituted by amino; or
(ii) $R^4$ and $R^5$ together with Q form a four- to five-membered nitrogen-containing heterocyclic ring (e.g. azetidinyl or pyrrolidinyl); and
wherein when Q is N then:
$R^4$ is absent, $R^5$ is hydrogen and $R^2$ and $R^3$ together form the one- to three-membered alkylene bridge group (e.g. —$CH_2$— or —$CH_2$—$CH_2$—);
$R^6$ and $R^7$ are independently selected from halogen (e.g. fluorine), and hydroxyl;
a is selected from 0, 1 and 2;
b is selected from 0 and 1;
provided that when Q is N then a and b are 0;
Ring A is either:
(i) a five-membered nitrogen-containing heterocyclic ring (e.g. an aromatic ring or a non-aromatic ring) wherein the heterocyclic ring optionally contains one additional heteroatoms selected from N, O and S;
(ii) a six-membered aromatic or non-aromatic nitrogen-containing heterocyclic ring, wherein the heterocyclic ring optionally contains one additional heteroatom which is N; or
$R^8$ is selected from halogen (for example chlorine or fluorine, e.g. chlorine) and $C_{1-4}$alkyl (e.g. —$CH_3$);
$R^9$ is selected from hydrogen, halogen (for example fluorine) and $C_{1-4}$alkyl (e.g. —$CH_3$);
$R^{10}$ are independently selected from halogen (e.g. chlorine or bromine), cyano, cyano$C_{1-4}$alkyl (e.g. —$CH_2$—CN), $C_{1-4}$alkoxy (e.g. —$OCH_3$, —$OCH_2CH_3$ and —$OCH(CH_3)_2$), =O (oxo), $C_{1-4}$alkyl (e.g. —$CH_3$, —$CH_2CH_3$ and —$CH(CH_3)_2$), hydroxyl$C_{1-4}$alkyl (e.g. —$CH_2OH$, —$CH_2CH_2OH$ or —$CH_2C(CH_3)_2OH$), halo$C_{1-4}$alkyl (e.g. —$CHF_2$), di$C_{1-4}$alkylamino (e.g. —$N(CH_3)_2$), $C_{1-4}$alkoxy$C_{1-4}$alkylene (e.g. —$CH_2$—O—$CH_3$ or —$CH_2$—$CH_2$—O—$CH_3$), —$C_{0-4}$alkylene-C(=O)NH$_{(2-q)}$($C_{1-6}$alkyl)$_q$ (e.g. —CO—N(CH$_3$)$_2$, —CH$_2$—CH$_2$—CO—N(CH$_3$)$_2$, —CH$_2$—CO—N(CH$_3$)$_2$, —CH$_2$—CO—NH(C(CH$_3$)$_3$) or —CH$_2$—CO—NH(CH$_3$), four- to six-membered saturated heterocyclic group containing O or N (e.g. tetrahydrofuranyl, morpholinyl, azetidinyl or oxetanyl), and $C_{1-4}$alkyl (e.g $C_1$ alkyl) substituted with optionally substituted five- or six-membered unsaturated heterocyclic group (e.g. five-membered unsaturated heterocyclic group) containing 1, 2, 3 or 4 heteroatoms selected from O, N, and S (e.g. N or O) where the optional substituent is selected from $C_{1-4}$alkyl (e.g. —$CH_3$); and
q is selected from 0, 1 and 2; and
c is selected from 0, 1 and 2.

In one embodiment, the moiety
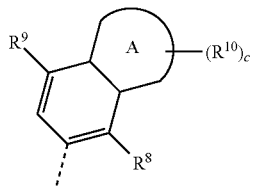
is selected from:
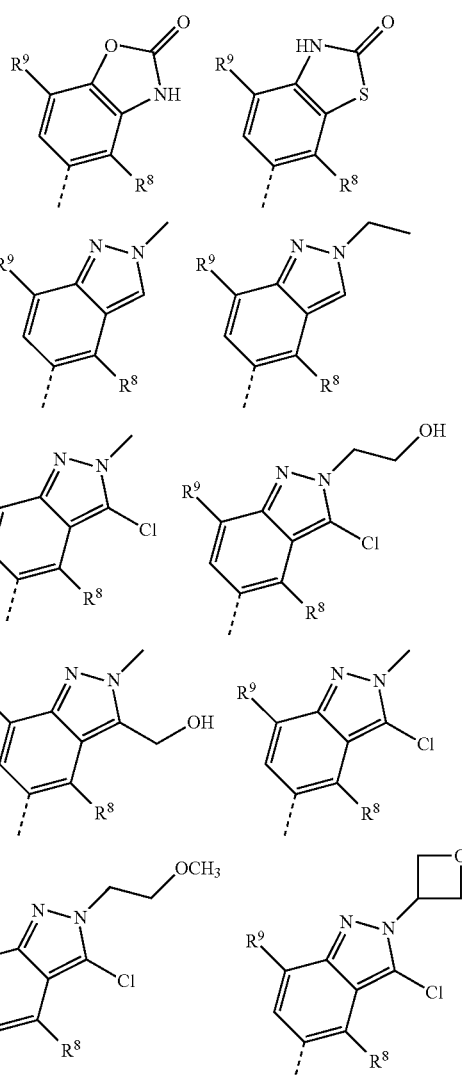
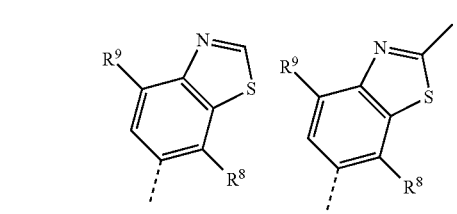
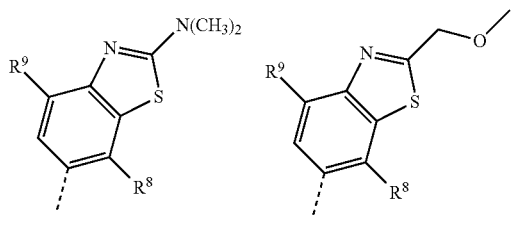
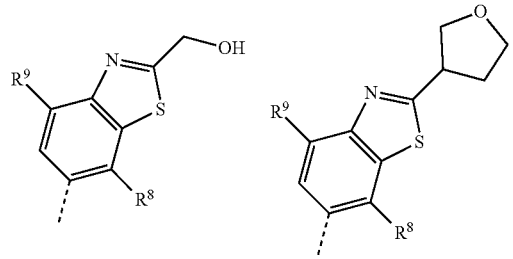
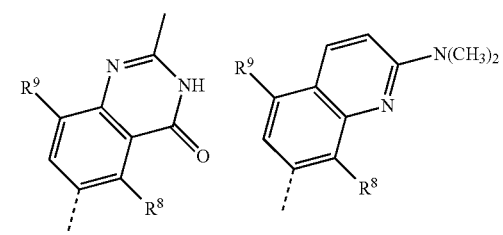
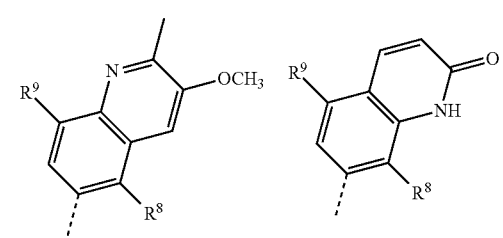
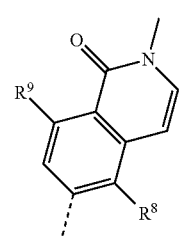
In one embodiment, the moiety
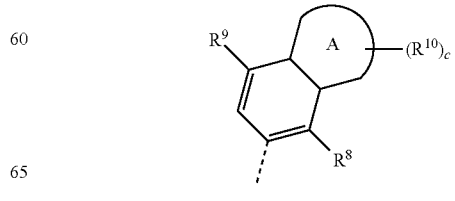

is selected from:
-continued
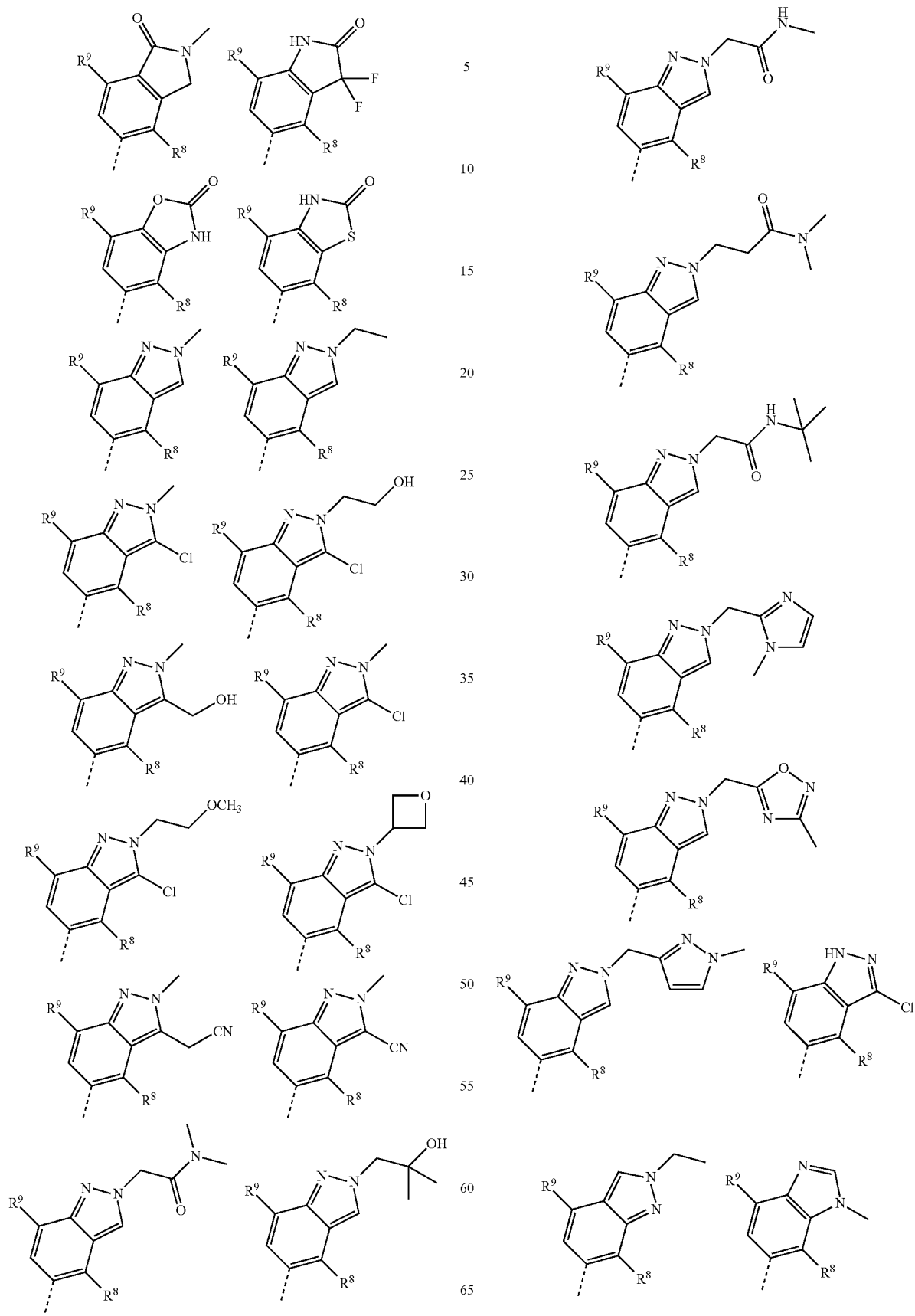

-continued
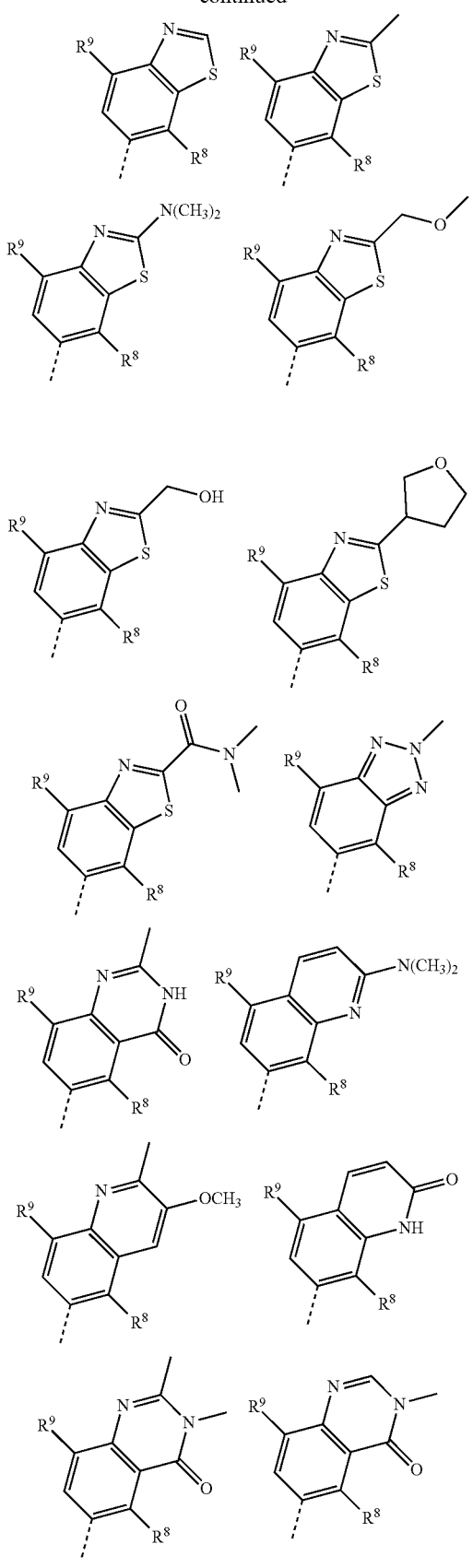
In one embodiment, the moiety
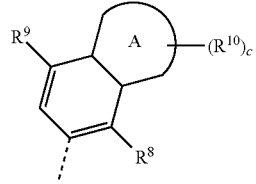
is selected from:
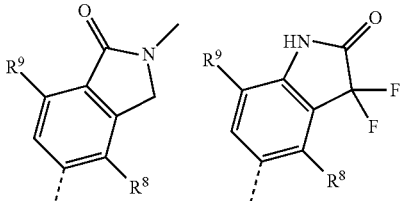
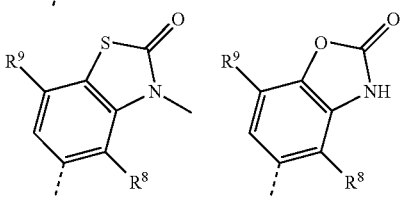
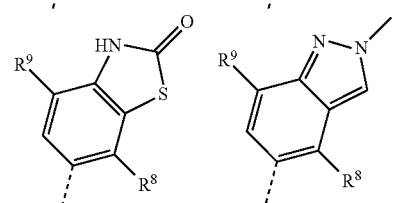
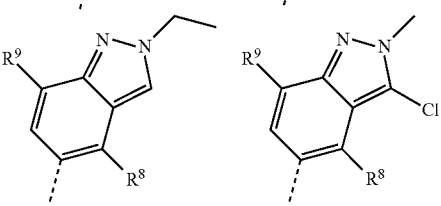
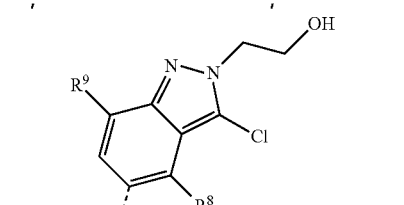
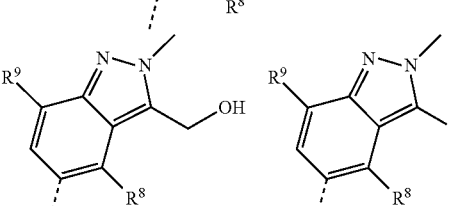
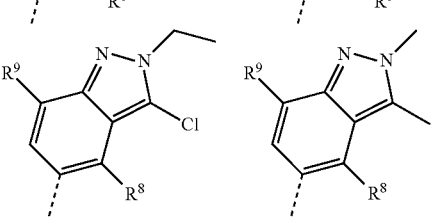

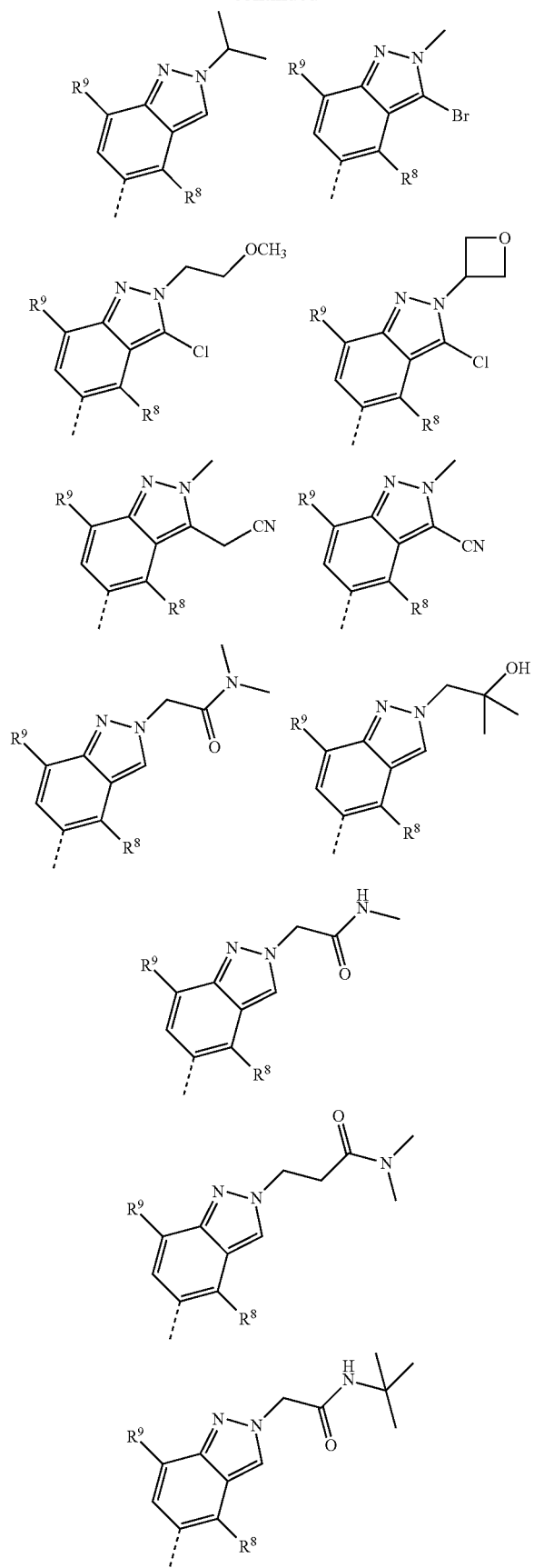
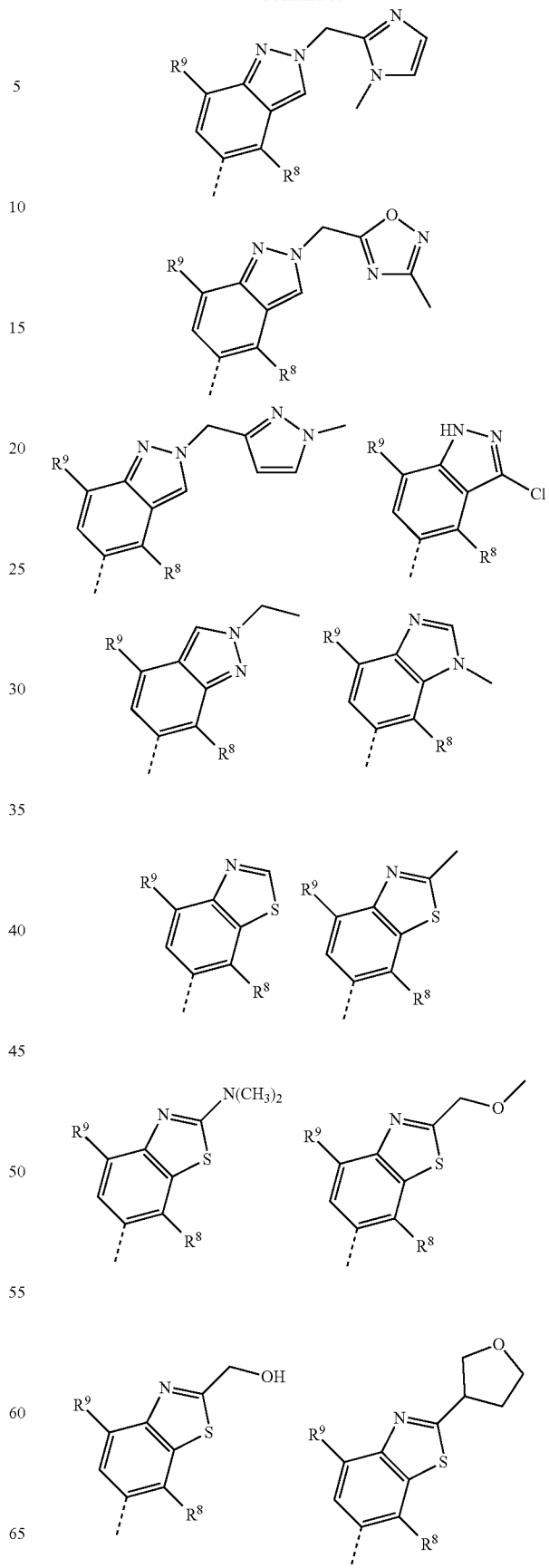

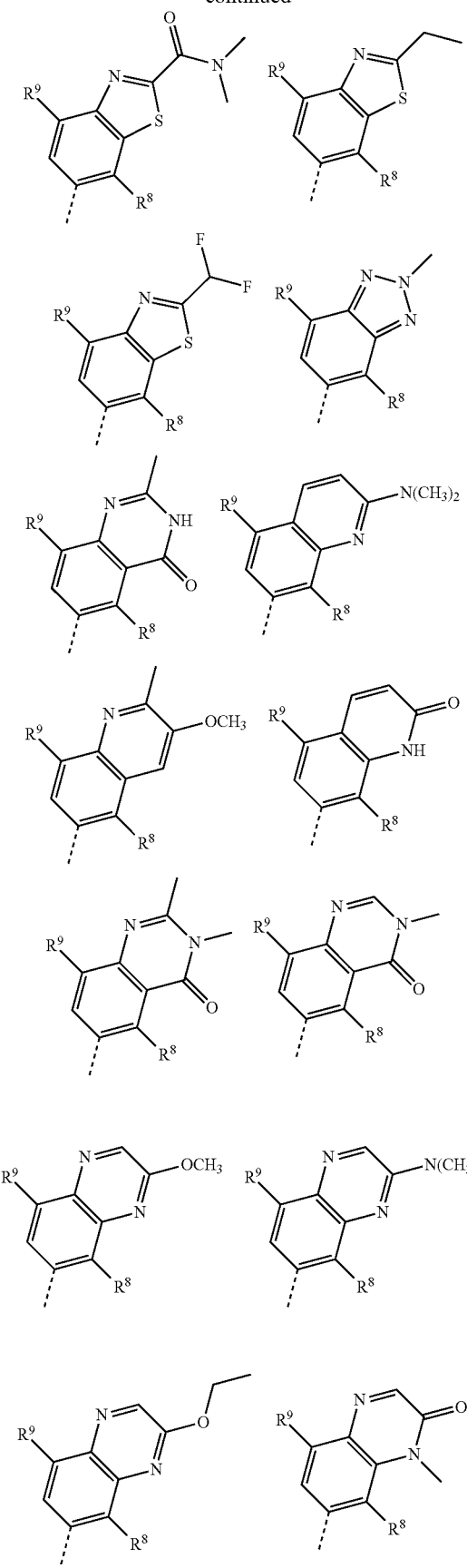

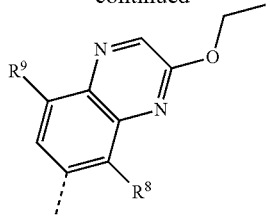

Particular Compounds

In one embodiment, the invention provides a compound of formula (I) which is one of the Examples 1-48 or is a tautomer, N-oxide, pharmaceutically acceptable salt or solvate thereof.

In one embodiment, the invention provides a compound of formula (I) which is one of the Examples 1-46 or is a tautomer, N-oxide, pharmaceutically acceptable salt or solvate thereof.

In one embodiment, the invention provides a compound of formula (I) which is one of the Examples 47-48 or is a tautomer, N-oxide, pharmaceutically acceptable salt or solvate thereof.

In one embodiment, the invention provides a compound of formula (I) which is one of the Examples 1-74 or is a tautomer, N-oxide, pharmaceutically acceptable salt or solvate thereof.

In one embodiment, the invention provides a compound of formula (I) which is one of the Examples 1-74 or is a tautomer, N-oxide, pharmaceutically acceptable salt or solvate thereof.

In one embodiment, the invention provides a compound of formula (I) which is one of the Examples 47-74 or is a tautomer, N-oxide, pharmaceutically acceptable salt or solvate thereof.

In one embodiment, the invention provides a compound of formula (I) which is one of the Examples 1-150 or is a tautomer, N-oxide, pharmaceutically acceptable salt or solvate thereof.

In one embodiment, the invention provides a compound of formula (I) which is one of the Examples 74-150 or is a tautomer, N-oxide, pharmaceutically acceptable salt or solvate thereof.

In one embodiment, the invention provides a compound of formula (I) which is selected from the following compounds, or a tautomer, N-oxide, pharmaceutically acceptable salt or solvate thereof:

endo-8-[7-(4-chloro-2-methyl-2H-indazol-5-yl)-5H-pyrrolo[2,3-b]pyrazin-3-yl]-8-azabicyclo[3.2.1]octan-3-amine;

endo-8-[7-(4-chloro-2-methyl-2H-indazol-5-yl)-5H-pyrrolo[2,3-b]pyrazin-3-yl]-3-methyl-8-azabicyclo[3.2.1]octan-3-amine; and 6-{3-[endo-3-amino-8-azabicyclo[3.2.1]octan-8-yl]-5H-pyrrolo[2,3-b]pyrazin-7-yl}-5-chloro-2-methyl-3,4-dihydroquinazolin-4-one.

In one embodiment, the invention provides a compound of formula (I) which is selected from the following compounds, or a tautomer, N-oxide, pharmaceutically acceptable salt or solvate thereof:

endo-8-[7-(4-chloro-2-methyl-2H-indazol-5-yl)-5H-pyrrolo[2,3-b]pyrazin-3-yl]-8-azabicyclo[3.2.1]octan-3-amine;

endo-8-[7-(4-chloro-2-methyl-2H-indazol-5-yl)-5H-pyrrolo[2,3-b]pyrazin-3-yl]-3-methyl-8-azabicyclo[3.2.1]octan-3-amine;

6-{3-[endo-3-amino-8-azabicyclo[3.2.1]octan-8-yl]-5H-pyrrolo[2,3-b]pyrazin-7-yl}-5-chloro-2-methyl-3,4-dihydroquinazolin-4-one; and
(1R,2S,3S,5S)-8-[7-(4-chloro-2-methyl-2H-indazol-5-yl)-5H-pyrrolo[2,3-b]pyrazin-3-yl]-2-fluoro-8-azabicyclo[3.2.1]octan-3-amine.

In one embodiment, the invention provides a compound of formula (I) which is selected from the following compounds, or a tautomer, N-oxide, pharmaceutically acceptable salt or solvate thereof:
endo-8-[7-(4-chloro-2-methyl-2H-indazol-5-yl)-5H-pyrrolo[2,3-b]pyrazin-3-yl]-8-azabicyclo[3.2.1]octan-3-amine;
endo-8-[7-(4-chloro-2-methyl-2H-indazol-5-yl)-5H-pyrrolo[2,3-b]pyrazin-3-yl]-3-methyl-8-azabicyclo[3.2.1]octan-3-amine;
6-{3-[endo-3-amino-8-azabicyclo[3.2.1]octan-8-yl]-5H-pyrrolo[2,3-b]pyrazin-7-yl}-5-chloro-2-methyl-3,4-dihydroquinazolin-4-one;
(1R,2S,3S,5S)-8-[7-(4-chloro-2-methyl-2H-indazol-5-yl)-5H-pyrrolo[2,3-b]pyrazin-3-yl]-2-fluoro-8-azabicyclo[3.2.1]octan-3-amine;
{6-[(1R,2S,3S,5S)-3-amino-2-fluoro-8-azabicyclo[3.2.1]octan-8-yl]-3-(3,4-dichloro-2-methyl-2H-indazol-5-yl)-1H-pyrazolo[3,4-b]pyrazin-5-yl}methanol;
{6-[(1S,2S,3S,5R)-3-amino-2-fluoro-8-azabicyclo[3.2.1]octan-8-yl]-3-(3,4-dichloro-2-methyl-2H-indazol-5-yl)-1H-pyrazolo[3,4-b]pyrazin-5-yl}methanol;
(1R,2S,3S,5S)-8-[3-(5-chloro-3-methoxyquinoxalin-6-yl)-5-methyl-1H-pyrazolo[3,4-b]pyrazin-6-yl]-2-fluoro-8-azabicyclo[3.2.1]octan-3-amine;
(6-{6-[(1R,2S,3S,5S)-3-amino-2-fluoro-8-azabicyclo[3.2.1]octan-8-yl]-5-methyl-1H-pyrazolo[3,4-b]pyrazin-3-yl}-7-chloro-1,3-benzothiazol-2-yl)methanol;
{6-[(1R,2S,3S,5S)-3-amino-2-fluoro-8-azabicyclo[3.2.1]octan-8-yl]-3-[3-(azetidin-1-yl)-5-chloroquinoxalin-6-yl]-1H-pyrazolo[3,4-b]pyrazin-5-yl}methanol;
{6-[(1R,2S,3S,5S)-3-amino-2-fluoro-8-azabicyclo[3.2.1]octan-8-yl]-3-[7-chloro-2-(methoxymethyl)-1,3-benzothiazol-6-yl]-1H-pyrazolo[3,4-b]pyrazin-5-yl}methanol; and
(1S,2S,3S,5R)-8-[3-(7-chloro-2-methyl-1,3-benzothiazol-6-yl)-5-methyl-1H-pyrazolo[3,4-b]pyrazin-6-yl]-2-fluoro-8-azabicyclo[3.2.1]octan-3-amine.

In one embodiment, the invention provides a compound of formula (I) which is the following compound, or a tautomer, N-oxide, pharmaceutically acceptable salt or solvate thereof:
endo-8-[7-(4-chloro-2-methyl-2H-indazol-5-yl)-5H-pyrrolo[2,3-b]pyrazin-3-yl]-8-azabicyclo[3.2.1]octan-3-amine.

In one embodiment, the invention provides a compound of formula (I) which is the following compound, or a tautomer, N-oxide, pharmaceutically acceptable salt or solvate thereof:
endo-8-[7-(4-chloro-2-methyl-2H-indazol-5-yl)-5H-pyrrolo[2,3-b]pyrazin-3-yl]-3-methyl-8-azabicyclo[3.2.1]octan-3-amine.

In one embodiment, the invention provides a compound of formula (I) which is the following compound, or a tautomer, N-oxide, pharmaceutically acceptable salt or solvate thereof:
6-{3-[endo-3-amino-8-azabicyclo[3.2.1]octan-8-yl]-5H-pyrrolo[2,3-b]pyrazin-7-yl}-5-chloro-2-methyl-3,4-dihydroquinazolin-4-one.

In one embodiment, the invention provides a compound of formula (I) which is the following compound, or a tautomer, N-oxide, pharmaceutically acceptable salt or solvate thereof:
(1R,2S,3S,5S)-8-[7-(4-chloro-2-methyl-2H-indazol-5-yl)-5H-pyrrolo[2,3-b]pyrazin-3-yl]-2-fluoro-8-azabicyclo[3.2.1]octan-3-amine.

In one embodiment, the invention provides a compound of formula (I) which is the following compound, or a tautomer, N-oxide, pharmaceutically acceptable salt or solvate thereof:
{6-[(1R,2S,3S,5S)-3-amino-2-fluoro-8-azabicyclo[3.2.1]octan-8-yl]-3-(3,4-dichloro-2-methyl-2H-indazol-5-yl)-1H-pyrazolo[3,4-b]pyrazin-5-yl}methanol.

In one embodiment, the invention provides a compound of formula (I) which is the following compound, or a tautomer, N-oxide, pharmaceutically acceptable salt or solvate thereof:
{6-[(1S,2S,3S,5R)-3-amino-2-fluoro-8-azabicyclo[3.2.1]octan-8-yl]-3-(3,4-dichloro-2-methyl-2H-indazol-5-yl)-1H-pyrazolo[3,4-b]pyrazin-5-yl}methanol.

In one embodiment, the invention provides a compound of formula (I) which is the following compound, or a tautomer, N-oxide, pharmaceutically acceptable salt or solvate thereof:
(1R,2S,3S,5S)-8-[3-(5-chloro-3-methoxyquinoxalin-6-yl)-5-methyl-1H-pyrazolo[3,4-b]pyrazin-6-yl]-2-fluoro-8-azabicyclo[3.2.1]octan-3-amine.

In one embodiment, the invention provides a compound of formula (I) which is the following compound, or a tautomer, N-oxide, pharmaceutically acceptable salt or solvate thereof:
(6-{6-[(1R,2S,3S,5S)-3-amino-2-fluoro-8-azabicyclo[3.2.1]octan-8-yl]-5-methyl-1H-pyrazolo[3,4-b]pyrazin-3-yl}-7-chloro-1,3-benzothiazol-2-yl)methanol.

In one embodiment, the invention provides a compound of formula (I) which is the following compound, or a tautomer, N-oxide, pharmaceutically acceptable salt or solvate thereof:
{6-[(1R,2S,3S,5S)-3-amino-2-fluoro-8-azabicyclo[3.2.1]octan-8-yl]-3-[3-(azetidin-1-yl)-5-chloroquinoxalin-6-yl]-1H-pyrazolo[3,4-b]pyrazin-5-yl}methanol.

In one embodiment, the invention provides a compound of formula (I) which is the following compound, or a tautomer, N-oxide, pharmaceutically acceptable salt or solvate thereof:
{6-[(1R,2S,3S,5S)-3-amino-2-fluoro-8-azabicyclo[3.2.1]octan-8-yl]-3-[7-chloro-2-(methoxymethyl)-1,3-benzothiazol-6-yl]-1H-pyrazolo[3,4-b]pyrazin-5-yl}methanol.

In one embodiment, the invention provides a compound of formula (I) which is the following compound, or a tautomer, N-oxide, pharmaceutically acceptable salt or solvate thereof:
(1S,2S,3S,5R)-8-[3-(7-chloro-2-methyl-1,3-benzothiazol-6-yl)-5-methyl-1H-pyrazolo[3,4-b]pyrazin-6-yl]-2-fluoro-8-azabicyclo[3.2.1]octan-3-amine.

For the avoidance of doubt, it is to be understood that each general and specific embodiment and example for one substituent may be combined with each general and specific embodiment and example for one or more, in particular all, other substituents as defined herein and that all such embodiments are embraced by this application.

Salts, Solvates, Tautomers, Isomers, N-Oxides, Esters, Prodrugs and Isotopes

A reference to a compound of the formula (I), sub-groups thereof (e.g. formulae (I), (II), (IIa), (III), (IIIa), (IIIb), (IV), (V), (VI), (VII), (VIII), (VIIIa), (IX), (X), (XI), (XII), (XIIa), (XIIb), (XIIc), (XIId), (XIIe), (XIII), (XIIIa), (XIIIb), (XIIIc), (XIV), (XIVa), (XIVb), (XV), (XV*), (XVI), (XVI*), (XVII), (XVII*), (XVII'), (XVII'*), (XVIII), (XVIII'), (XVIIIa), (XVIIIa'), (XVIII*), (XVIII'*), (XVIIIa*) and (XVIIIa'*)) and any example also includes ionic forms, salts, solvates, isomers (including geometric and stereochemical isomers unless specified), tautomers, N-oxides, esters, prodrugs, isotopes and protected forms thereof, for example, as discussed below; in particular, the salts or tautomers or isomers or N-oxides or solvates thereof; and more particularly the salts or tautomers or N-oxides or solvates thereof. In one embodiment reference to a compound of the formula (I), sub-groups thereof (e.g. formulae (I), (II), (IIa), (III), (IIIa), (IIIb), (IV), (V), (VI), (VII), (VIII), (VIIIa), (IX), (X), (XI), (XII), (XIIa), (XIIb), (XIIc), (XIId), (XIIe), (XIII), (XIIIa), (XIIIb), (XIIIc), (XIV), (XIVa), (XIVb), (XV), (XV*), (XVI), (XVI*), (XVII), (XVII*), (XVII'), (XVII'*), (XVIII), (XVIII'), (XVIIIa), (XVIIIa'), (XVIII*), (XVIII'*), (XVIIIa*) and (XVIIIa'*)) and any example also includes the salts or tautomers or solvates thereof.

Salts

Many compounds of the formula (I) can exist in the form of salts, for example acid addition salts or, in certain cases salts of organic and inorganic bases such as carboxylate, sulfonate and phosphate salts. All such salts are within the scope of this invention, and references to compounds of the formula (I) include the salt forms of the compounds.

The salts of the present invention can be synthesized from the parent compound that contains a basic or acidic moiety by conventional chemical methods such as methods described in *Pharmaceutical Salts: Properties, Selection, and Use*, P. Heinrich Stahl (Editor), Camille G. Wermuth (Editor), ISBN: 3-90639-026-8, Hardcover, 388 pages, August 2002. Generally, such salts can be prepared by reacting the free acid or base forms of these compounds with the appropriate base or acid in water or in an organic solvent, or in a mixture of the two; generally, nonaqueous media such as ether, ethyl acetate, ethanol, isopropanol, or acetonitrile are used.

Acid addition salts (mono- or di-salts) may be formed with a wide variety of acids, both inorganic and organic. Examples of acid addition salts include mono- or di-salts formed with an acid selected from acetic, 2,2-dichloroacetic, adipic, alginic, ascorbic (e.g. L-ascorbic), L-aspartic, benzenesulfonic, benzoic, 4-acetamidobenzoic, butanoic, (+) camphoric, camphor-sulfonic, (+)-(1S)-camphor-10-sulfonic, capric, caproic, caprylic, cinnamic, citric, cyclamic, dodecylsulfuric, ethane-1,2-disulfonic, ethanesulfonic, 2-hydroxyethanesulfonic, formic, fumaric, galactaric, gentisic, glucoheptonic, D-gluconic, glucuronic (e.g. D-glucuronic), glutamic (e.g. L-glutamic), α-oxoglutaric, glycolic, hippuric, hydrohalic acids (e.g. hydrobromic, hydrochloric, hydriodic), isethionic, lactic (e.g. (+)-L-lactic, (±)-DL-lactic), lactobionic, maleic, malic, (−)-L-malic, malonic, (±)-DL-mandelic, methanesulfonic, naphthalene-2-sulfonic, naphthalene-1,5-disulfonic, 1-hydroxy-2-naphthoic, nicotinic, nitric, oleic, orotic, oxalic, palmitic, pamoic, phosphoric, propionic, pyruvic, L-pyroglutamic, salicylic, 4-amino-salicylic, sebacic, stearic, succinic, sulfuric, tannic, (+)-L-tartaric, thiocyanic, p-toluenesulfonic, undecylenic and valeric acids, as well as acylated amino acids and cation exchange resins.

One particular group of salts consists of salts formed from acetic, hydrochloric, hydriodic, phosphoric, nitric, sulfuric, citric, lactic, succinic, maleic, malic, isethionic, fumaric, benzenesulfonic, toluenesulfonic, methanesulfonic (mesylate), ethanesulfonic, naphthalenesulfonic, valeric, acetic, propanoic, butanoic, malonic, glucuronic and lactobionic acids. One particular salt is the hydrochloride salt.

In one embodiment the compound is the sodium or mesylate salt.

If the compound is anionic, or has a functional group which may be anionic (e.g., —COOH may be —COO⁻), then a salt may be formed with an organic or inorganic base, generating a suitable cation. Examples of suitable inorganic cations include, but are not limited to, alkali metal ions such as $Li^+$, $Na^+$ and $K^+$, alkaline earth metal cations such as $Ca^{2+}$ and $Mg^{2+}$, and other cations such as $Al^{3+}$ or $Zn^+$. Examples of suitable organic cations include, but are not limited to, ammonium ion (i.e., $NH_4^+$) and substituted ammonium ions (e.g., $NH_3R^+$, $NH_2R^{2+}$, $NHR_3^+$, $NR_4^+$). Examples of some suitable substituted ammonium ions are those derived from: methylamine, ethylamine, diethylamine, propylamine, dicyclohexylamine, triethylamine, butylamine, ethylenediamine, ethanolamine, diethanolamine, piperazine, benzylamine, phenylbenzylamine, choline, meglumine, and tromethamine, as well as amino acids, such as lysine and arginine. An example of a common quaternary ammonium ion is $N(CH_3)_4^+$.

Where the compounds of the formula (I) contain an amine function, these may form quaternary ammonium salts, for example by reaction with an alkylating agent according to methods well known to the skilled person. Such quaternary ammonium compounds are within the scope of formula (I).

The compounds of the invention may exist as mono- or di-salts depending upon the pKa of the acid from which the salt is formed.

The salt forms of the compounds of the invention are typically pharmaceutically acceptable salts, and examples of pharmaceutically acceptable salts are discussed in Berge et al., 1977, "Pharmaceutically Acceptable Salts," *J. Pharm. Sci.*, Vol. 66, pp. 1-19. However, salts that are not pharmaceutically acceptable may also be prepared as intermediate forms which may then be converted into pharmaceutically acceptable salts. Such non-pharmaceutically acceptable salt forms, which may be useful, for example, in the purification or separation of the compounds of the invention, also form part of the invention.

In one embodiment of the invention, there is provided a pharmaceutical composition comprising a solution (e.g. an aqueous solution) containing a compound of the formula (I) and sub-groups and examples thereof as described herein in the form of a salt in a concentration of greater than 10 mg/ml, typically greater than 15 mg/ml and typically greater than 20 mg/ml.

N-Oxides

Compounds of the formula (I) containing an amine function may also form N-oxides. A reference herein to a compound of the formula (I) that contains an amine function also includes the N-oxide.

Where a compound contains several amine functions one, or more than one, nitrogen atom may be oxidised to form an N-oxide. Particular examples of N-oxides are the N-oxides of a tertiary amine or a nitrogen atom of a nitrogen-containing heterocyclylic group.

N-Oxides can be formed by treatment of the corresponding amine with an oxidizing agent such as hydrogen peroxide or a per-acid (e.g. a peroxycarboxylic acid), see for example *Advanced Organic Chemistry*, by Jerry March, 4th Edition, Wiley Interscience, pages. More particularly, N-oxides can be made by the procedure of L. W. Deady (*Syn. Comm.* 1977, 7, 509-514) in which the amine compound is reacted with m-chloroperoxybenzoic acid (MCPBA), for example, in an inert solvent such as dichloromethane.

In one embodiment of the invention, the compound is an N-oxide, e.g. from a nitrogen atom on the $R^6$ or $R^7$ group, for example a pyridine N-oxide.

Geometric Isomers and Tautomers

Compounds of the formula (I) may exist in a number of different geometric isomeric, and tautomeric forms and references to compounds of the formula (I) include all such forms. For the avoidance of doubt, where a compound can exist in one of several geometric isomeric or tautomeric forms and only one is specifically described or shown, all others are nevertheless embraced by formula (I).

For example, certain heteroaryl rings can exist in the two tautomeric forms such as A and B shown below. For simplicity, a formula may illustrate one form but the formula is to be taken as embracing both tautomeric forms.

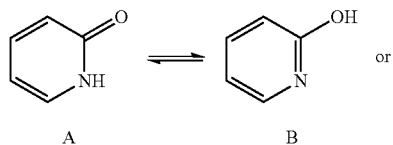

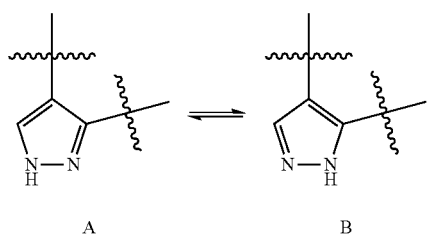

Other examples of tautomeric forms include, for example, keto-, enol-, and enolate-forms, as in, for example, the following tautomeric pairs: keto/enol (illustrated below), imine/enamine, amide/imino alcohol, amidine/enediamines, nitroso/oxime, thioketone/enethiol, and nitro/aci-nitro.

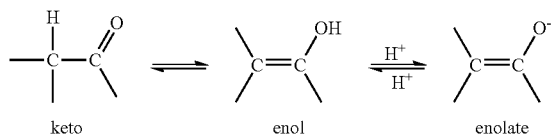

Stereoisomers

Unless otherwise mentioned or indicated, the chemical designation of compounds denotes the mixture of all possible stereochemically isomeric forms.

Stereocentres are illustrated in the usual fashion, using 'hashed' or 'solid' wedged lines. e.g.

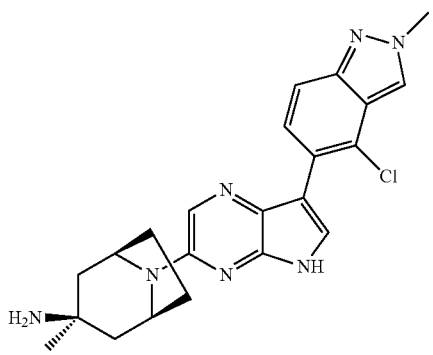 [SMILES: Cn1cc2c(Cl)c(-c3c[nH]c4nc(N5[C@@H]6CC[C@H]5C[C@@](C)(N)C6)cnc34)ccc2n1]

Where a compound is described as a mixture of two diastereoisomers/epimers, the configuration of the stereocentre is not specified and is represented by straight lines.

Where compounds of the formula (I) contain one or more chiral centres, and can exist in the form of two or more optical isomers, references to compounds of the formula (I) include all optical isomeric forms thereof (e.g. enantiomers, epimers and diastereoisomers), either as individual optical isomers, or mixtures (e.g. racemic or scalemic mixtures) or two or more optical isomers, unless the context requires otherwise.

The optical isomers may be characterised and identified by their optical activity (i.e. as + and − isomers, or d and l isomers) or they may be characterised in terms of their absolute stereochemistry using the "R and S" nomenclature developed by Cahn, Ingold and Prelog, see *Advanced Organic Chemistry* by Jerry March, 4$^{th}$ Edition, John Wiley & Sons, New York, 1992, pages 109-114, and see also Cahn, Ingold & Prelog, *Angew. Chem. Int. Ed. Engl.,* 1966, 5, 385-415.

Optical isomers can be separated by a number of techniques including chiral chromatography (chromatography on a chiral support) and such techniques are well known to the person skilled in the art.

As an alternative to chiral chromatography, optical isomers can be separated by forming diastereoisomeric salts with chiral acids such as (+)-tartaric acid, (−)-pyroglutamic acid, (−)-di-toluoyl-L-tartaric acid, (+)-mandelic acid, (−)-malic acid, and (−)-camphorsulfonic acid, separating the diastereoisomers by preferential crystallisation, and then dissociating the salts to give the individual enantiomer of the free base.

Additionally, enantiomeric separation can be achieved by covalently linking a enantiomerically pure chiral auxiliary onto the compound and then performing diastereisomer separation using conventional methods such as chromatography. This is then followed by cleavage of the aforementioned covalent linkage to generate the appropriate enantiomerically pure product.

Where compounds of the formula (I) exist as two or more optical isomeric forms, one enantiomer in a pair of enantiomers may exhibit advantages over the other enantiomer, for example, in terms of biological activity. Thus, in certain circumstances, it may be desirable to use as a therapeutic agent only one of a pair of enantiomers, or only one of a plurality of diastereoisomers.

Accordingly, the invention provides compositions containing a compound of the formula (I) having one or more chiral centres, wherein at least 55% (e.g. at least 60%, 65%, 70%, 75%, 80%, 85%, 90% or 95%) of the compound of the formula (I) is present as a single optical isomer (e.g. enantiomer or diastereoisomer). In one general embodiment, 99% or more (e.g. substantially all) of the total amount of the compound of the formula (I) may be present as a single optical isomer (e.g. enantiomer or diastereoisomer).

Compounds encompassing double bonds can have an E (entgegen) or Z (zusammen) stereochemistry at said double bond. Substituents on bivalent cyclic or (partially) saturated radicals may have either the cis- or trans-configuration. The terms cis and trans when used herein are in accordance with Chemical Abstracts nomenclature (J. Org. Chem. 1970, 35 (9), 2849-2867), and refer to the position of the substituents on a ring moiety.

Of special interest are those compounds of formula (I) which are stereochemically pure. When a compound of formula (I) is for instance specified as R, this means that the compound is substantially free of the S isomer. If a compound of formula (I) is for instance specified as E, this means that the compound is substantially free of the Z isomer. The terms cis, trans, R, S, E and Z are well known to a person skilled in the art.

Isotopic Variations

The present invention includes all pharmaceutically acceptable isotopically-labeled compounds of the invention, i.e. compounds of formula (I), wherein one or more atoms are replaced by atoms having the same atomic number, but an atomic mass or mass number different from the atomic mass or mass number usually found in nature.

Examples of isotopes suitable for inclusion in the compounds of the invention comprise isotopes of hydrogen, such as $^2$H (D) and $^3$H (T), carbon, such as $^{11}$C, $^{13}$C and $^{14}$C, chlorine, such as $^{36}$Cl, fluorine, such as $^{18}$F, iodine, such as $^{123}$I, $^{125}$I and $^{131}$I, nitrogen, such as $^{13}$N and $^{15}$N, oxygen, such as $^{15}$O, $^{17}$O and $^{18}$O, phosphorus, such as $^{32}$P, and sulfur, such as $^{35}$S.

Certain isotopically-labelled compounds of formula (I), for example, those incorporating a radioactive isotope, are useful in drug and/or substrate tissue distribution studies. The compounds of formula (I) can also have valuable diagnostic properties in that they can be used for detecting or identifying the formation of a complex between a labelled compound and other molecules, peptides, proteins, enzymes or receptors. The detecting or identifying methods can use compounds that are labelled with labelling agents such as radioisotopes, enzymes, fluorescent substances, luminous substances (for example, luminol, luminol derivatives, luciferin, aequorin and luciferase), etc. The radioactive isotopes tritium, i.e. $^3$H (T), and carbon-14, i.e. $^{14}$C, are particularly useful for this purpose in view of their ease of incorporation and ready means of detection.

Substitution with heavier isotopes such as deuterium, i.e. $^2$H (D), may afford certain therapeutic advantages resulting from greater metabolic stability, for example, increased in vivo half-life or reduced dosage requirements, and hence may be used in some circumstances.

In particular, every reference to hydrogen in the application should be constructed to cover $^1$H and $^2$H, whether hydrogen is defined explicitly, or hydrogen is present implicitly to satisfy the relevant atom's (in particular carbon's) valency.

Substitution with positron emitting isotopes, such as $^{11}$C, $^{18}$F, $^{15}$O and $^{13}$N, can be useful in Positron Emission Topography (PET) studies for examining target occupancy.

Isotopically-labeled compounds of formula (I) can generally be prepared by conventional techniques known to those skilled in the art or by processes analogous to those described in the accompanying Examples and Preparations using an appropriate isotopically-labeled reagents in place of the non-labeled reagent previously employed.

Esters

Esters such as carboxylic acid esters, acyloxy esters and phosphate esters of the compounds of formula (I) bearing a carboxylic acid group or a hydroxyl group are also embraced by Formula (I). Examples of esters are compounds containing the group —C(=O)OR, wherein R is an ester substituent, for example, a $C_{1-7}$ alkyl group, a $C_{3-12}$ heterocyclyl group, or a $C_{5-12}$ aryl group, typically a $C_{1-6}$ alkyl group. Particular examples of ester groups include, but are not limited to, —C(=O)OCH$_3$, —C(=O)OCH$_2$CH$_3$, —C(=O)OC(CH$_3$)$_3$, and —C(=O)OPh. Examples of acyloxy (reverse ester) groups are represented by —OC(=O)R, wherein R is an acyloxy substituent, for example, a $C_{1-6}$alkyl group, a $C_{3-12}$ heterocyclyl group, or a $C_{5-12}$ aryl group, typically a $C_{1-6}$alkyl group. Particular examples of acyloxy groups include, but are not limited to, —OC(=O)CH$_3$ (acetoxy), —OC(=O)CH$_2$CH$_3$, —OC(=O)C(CH$_3$)$_3$, —OC(=O)Ph, and —OC(=O)CH$_2$Ph. Examples of phosphate esters are those derived from phosphoric acid.

In one embodiment of the invention, formula (I) includes within its scope esters of compounds of the formula (I) bearing a carboxylic acid group or a hydroxyl group. In another embodiment of the invention, formula (I) does not include within its scope esters of compounds of the formula (I) bearing a carboxylic acid group or a hydroxyl group.

Solvates and Crystalline Forms

Also encompassed by formula (I) are any polymorphic forms of the compounds, and solvates such as hydrates, alcoholates and the like.

The compounds of the invention may form solvates, for example with water (i.e., hydrates) or common organic solvents. As used herein, the term "solvate" means a physical association of the compounds of the present invention with one or more solvent molecules. This physical association involves varying degrees of ionic and covalent bonding, including hydrogen bonding. In certain instances the solvate will be capable of isolation, for example when one or more solvent molecules are incorporated in the crystal lattice of the crystalline solid. The term "solvate" is intended to encompass both solution-phase and isolatable solvates. Non-limiting examples of suitable solvates include compounds of the invention in combination with water, isopropanol, ethanol, methanol, DMSO, ethyl acetate, acetic acid or ethanolamine and the like. The compounds of the invention may exert their biological effects whilst they are in solution.

Solvates are well known in pharmaceutical chemistry. They can be important to the processes for the preparation of a substance (e.g. in relation to their purification, the storage of the substance (e.g. its stability) and the ease of handling of the substance and are often formed as part of the isolation or purification stages of a chemical synthesis. A person skilled in the art can determine by means of standard and long used techniques whether a hydrate or other solvate has formed by the isolation conditions or purification conditions used to prepare a given compound. Examples of such techniques include thermogravimetric analysis (TGA), differential scanning calorimetry (DSC), X-ray crystallography (e.g. single crystal X-ray crystallography or X-ray powder diffraction) and Solid State NMR (SS-NMR, also known as Magic Angle Spinning NMR or MAS-NMR). Such techniques are as much a part of the standard analytical toolkit of the skilled chemist as NMR, IR, HPLC and MS.

Alternatively, the skilled person can deliberately form a solvate using crystallisation conditions that include an amount of the solvent required for the particular solvate.

Thereafter the standard methods described herein, can be used to establish whether solvates had formed.

Furthermore, the compounds of the present invention may have one or more polymorph or amorphous crystalline forms and as such are intended to be included in the scope of the invention.

Complexes

Formula (I) also includes within its scope complexes (e.g. inclusion complexes or clathrates with compounds such as cyclodextrins, or complexes with metals) of the compounds. Inclusion complexes, clathrates and metal complexes can be formed by means of methods well known to the skilled person.

Prodrugs

Also encompassed by formula (I) are any pro-drugs of the compounds of the formula (I). By "prodrugs" is meant for example any compound that is converted in vivo into a biologically active compound of the formula (I).

For example, some prodrugs are esters of the active compound (e.g., a physiologically acceptable metabolically labile ester). During metabolism, the ester group (—C(=O) OR) is cleaved to yield the active drug. Such esters may be formed by esterification, for example, of any of the carboxylic acid groups (—C(=O)OH) in the parent compound, with, where appropriate, prior protection of any other reactive groups present in the parent compound, followed by deprotection if required.

Examples of such metabolically labile esters include those of the formula —C(=O)OR wherein R is:

$C_{1-7}$alkyl (e.g., -Me, -Et, -nPr, -iPr, -nBu, -sBu, -iBu, -tBu);

$C_{1-7}$aminoalkyl (e.g., aminoethyl; 2-(N,N-diethylamino) ethyl; 2-(4-morpholino)ethyl); and acyloxy-$C_{1-7}$ alkyl (e.g., acyloxymethyl; acyloxyethyl; pivaloyloxymethyl; acetoxymethyl; 1-acetoxyethyl; 1-(1-methoxy-1-methyl)ethyl-carbonxyloxyethyl; 1-(benzoyloxy)ethyl; isopropoxy-carbonyloxymethyl; 1-isopropoxy-carbonyloxyethyl; cyclohexylcarbonyloxymethyl; 1-cyclohexyl-carbonyloxyethyl; cyclohexyloxy-carbonyloxymethyl; 1-cyclohexyloxy-carbonyloxyethyl; (4-oxanyloxy) carbonyloxymethyl; 1-(4-oxanyloxy)carbonyloxyethyl; (4-oxanyl)carbonyloxymethyl; and 1-(4-tetrahydropyranyl)carbonyloxyethyl).

Also, some prodrugs are activated enzymatically to yield the active compound, or a compound which, upon further chemical reaction, yields the active compound (for example, as in antigen-directed enzyme pro-drug therapy (ADEPT), gene-directed enzyme pro-drug therapy (GDEPT), and ligand-directed enzyme pro-drug therapy (LIDEPT), etc.). For example, the prodrug may be a sugar derivative or other glycoside conjugate, or may be an amino acid ester derivative. In one embodiment formula (I) does not include pro-drugs of the compounds of the formula (I) within its scope.

Methods for the Preparation of Compounds of Formula (I)

In this section, as in all other sections of this application unless the context indicates otherwise, references to formula (I) also include all other subformulae (e.g. formulae (I), (II), (IIa), (III), (IIIa), (IIIb), (IV), (V), (VI), (VII), (VIII), (VIIIa), (IX), (X), (XI), (XII), (XIIa), (XIIb), (XIIc), (XIId), (XIIe), (XIII), (XIIIa), (XIIIb), (XIIIc), (XIV), (XIVa), (XIVb), (XV), (XV*), (XVI), (XVI*), (XVII), (XVII*), (XVII'), (XVII'*), (XVIII), (XVIII'), (XVIIIa), (XVIIIa'), (XVIII*), (XVIII'*), (XVIIIa*) and (XVIIIa'*)) and examples thereof as defined herein, unless the context indicates otherwise.

Compounds of the formula (I) can be prepared in accordance with synthetic methods well known to the skilled person.

According to a further aspect of the invention there is provided a process for preparing a compound of formula (I), or a tautomer, stereoisomer, N-oxide, pharmaceutically acceptable salt, or solvate thereof, which comprises:
(a) coupling a compound of formula (A) or a protected derivative thereof:

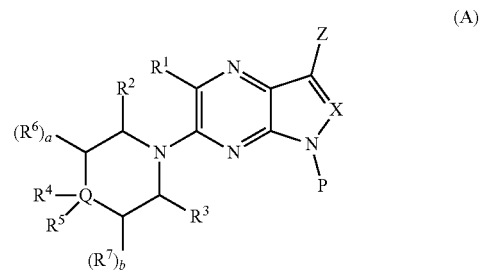

(A)

wherein $R^1$, $R^2$, $R^3$, $R^4$, $R^5$, $R^6$, $R^7$, Q, X, a, b, are as defined hereinbefore for the compounds of formula (I), and P represents a protecting group (such as 2-(trimethylsilyl) ethoxymethyl; SEM) or is hydrogen, and Z is a metal residue (such as zinc halide e.g. zinc chloride) or a leaving group (such as a halogen e.g. iodine or bromine)
with a compound of the formula (B) or a protected version thereof

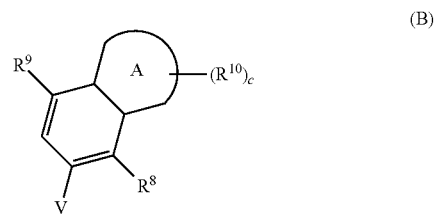

(B)

wherein $R^8$, $R^9$, $R^{10}$, A, c, are as defined hereinbefore for the compounds of formula (I) and V represents a metal or metaloid residue (such as boronic acid, pinacol boronate, magnesium halide or zinc halide e.g. boronic acid, pinacol boronate) or a leaving group such as halogen,
followed by a deprotection reaction suitable to remove the protecting groups;
(b) coupling a compound of formula (C) or a protected derivative thereof:

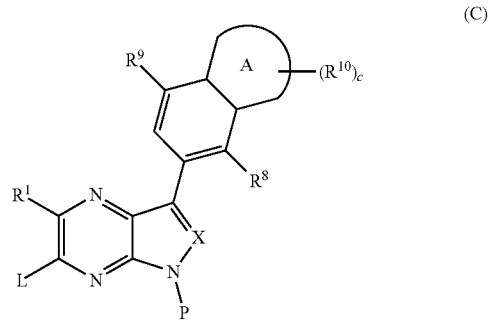

(C)

wherein $R^8$, $R^9$, $R^{10}$, A, c, are as defined hereinbefore for the compounds of formula (I), X is CH, P represents protecting group (such as 2-(trimethylsilyl)ethoxymethyl; SEM) or is hydrogen, L is leaving group (such as chloride), with a compound of formula (D) or a protected derivative thereof, wherein $R^2$, $R^3$, $R^4$, $R^5$, $R^6$, $R^7$, Q, a, b, are as defined hereinbefore for the compounds of formula (I).

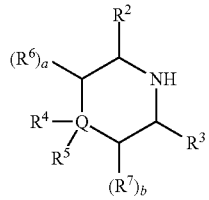

(D)

(c) reacting a compound of formula (K) or a protected derivative thereof,

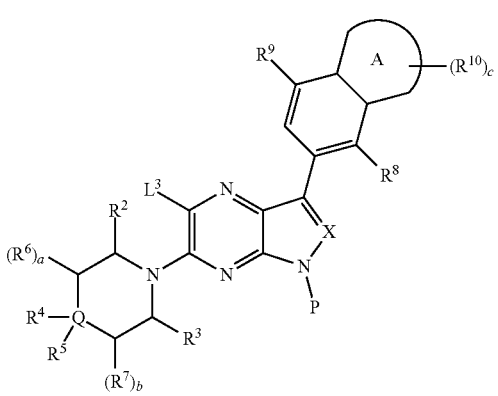

(K)

wherein $R^2$, $R^3$, $R^4$, $R^5$, $R^6$, $R^7$, $R^8$, $R^9$, $R^{10}$, Q, a, b and c are as defined herein for the compound of formula (I), P represents an amine protecting group (such as 2-(trimethylsilyl)ethoxymethyl; SEM), N,N-dimethylsulfamoyl or hydrogen, $L^3$ is leaving group (such as halogen e.g. bromine) either:

(i) with a organometallic species of the formula $CH_3M$, where M is a metal (for example $CH_3$—Zn-Hal, where Hal is halogen e.g. chloride, bromide or iodide) in the presence of a metal catalyst (such as (1,3-diisopropylimidazol-2-ylidene)(3-chloropyridyl)palladium(II) dichloride) to give a compound of formula (I) wherein $R^1$ is —$CH_3$; or (ii) with an alkyl boronate (such as potassium (2-trimethylsilyl)-ethoxymethyl trifluoroborate) in the presence of a photoredox catalyst (such as $[Ir\{dFCF_3ppy\}_2(bpy)]PF_6$), a metal catalyst (such as nickel(II) chloride ethylene glycol dimethyl ether complex), a ligand (such as 4,4'-di-tert-butyl-2,2'-dipyridyl), a base (such as dipotassium phosphate), and a source of light (such as a blue LED), to give a compound of formula (I) wherein $R^1$ is —$CH_2OH$;

(d) cyclisation of a compound of formula (R), or a protected derivatives thereof;

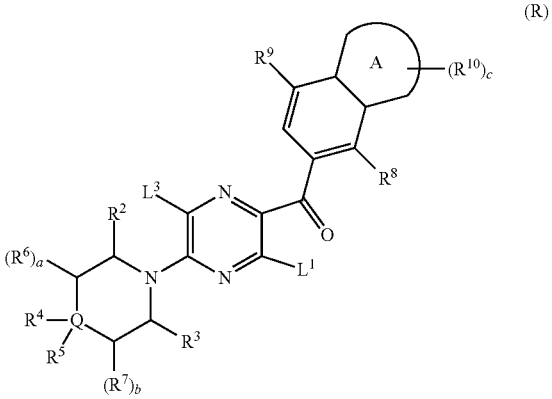

(R)

wherein $R^1$, $R^2$, $R^3$, $R^4$, $R^5$, $R^6$, $R^7$, $R^8$, $R^9$, $R^{10}$, Q, a, b, c, A, are as defined hereinbefore for the compounds of formula (I) and $L^1$ represents a suitable leaving group, such as a halogen, using hydrazine or a protected hydrazine derivative;

in each case optionally followed by a deprotection step; or (e) deprotection of a protected derivative of a compound of formula (I); or (f) interconversion of a compound of formula (I) or protected derivative thereof to a further compound of formula (I) or protected derivative thereof; or (g) optionally formation of a pharmaceutically acceptable salt of a compound of formula (I).

Preparative Methods (a), (b), (c) and (d)

Compounds of formula (B) were either commercially available, or are prepared using methods analogous to those described in the examples e.g. compounds of formula (B) where V is a boronate residue are either used directly in a one pot procedure as in general procedure 3 or isolated in a manner analogous to boronates listed in table 2 and used directly in the reaction as in general procedure 2 (Table 2).

Process (a) typically comprises, reacting a compound of formula (A) with a compound of formula (B) in a suitable solvent, a suitable base and a suitable catalyst at a suitable temperature. Examples of suitable bases are potassium carbonate or potassium phosphate. Example of suitable catalysts are [1,1'-bis(diphenylphosphino)ferrocene]palladium (II) dichloride. Examples of suitable solvents are 1,2-dimethoxyethane or tetrahydrofuran.

Where Z is a metal residue such as zinc halide, the process typically comprises reacting a compound of formula (A) with a compound of formula (B) where V is a leaving group such as a halogen. Typically compounds of formula (A) where Z is a leaving group such as a halogen dissolved in a suitable solvent such as tetrahydrofuran are treated with a reagent such as isopropylmagnesium chloride lithium chloride complex solution, for a suitable time such as 35 min to completely effect metalation. The newly formed organomagnesium species is treated with a suitable metal salt such as zinc chloride to effect transmetalation and optionally stirred for a suitable time such as 10 min then allowed to warm to a suitable temperature such as room temperature fora period of time such as 40 min. The resulting heteroaryl zinc reagent is used directly in the cross coupling reaction with formula (B) using a suitable catalyst such as methanesulfonato(2-dicyclohexylphosphino-2',6'-dimethoxy-1,1'-biphenyl)(2'-methylamino-1,1'-biphenyl-2-yl)palladium(II) (SPhos G4 palladacycle) at a suitable temperature such as room temperature for a suitable time such as 18 h.

Compounds of formula (D) or protected derivatives thereof are obtained from commercially available starting materials, prepared from literature procedures or using methods indicated within the examples outlined in this application or analogous methods thereto.

Compounds of formula (C) or a protected derivative thereof, in particular where R¹ is hydrogen and X is CH, may be obtained by reacting a compound of formula (E):

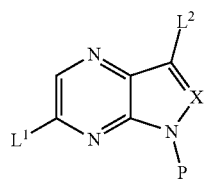

(E)

Wherein X is as defined hereinbefore for the compounds of formula (I) and P represents a suitable amine protecting group (such as 2-(trimethylsilyl)ethoxymethyl; SEM) or is hydrogen, and L¹ and L² independently represent leaving groups (such as a halide e.g. chlorine, bromine or iodine) with a compound of formula (B) or protected derivative thereof, using a method analogous to process (a).

Compounds of formula (E) are obtained from commercially available starting materials, prepared from literature procedures or using methods indicated within the examples outlined in this patent or analogous methods, thereto.

Compounds of formula (A) or protected derivatives thereof may be obtained by reacting compound of formula (E), where R¹ is H, with a compound of formula (D) or protected derivative thereof, using a suitable base such as diisopropylethylamine, in a suitable solvent such as dimethylsulfoxide or N-methyl-2-pyrrolidinone, at a suitable temperature such as 150° C.

Compounds of formula (A) or protected derivatives thereof may be obtained from compounds of formula (F) wherein X is CH or protected derivatives thereof

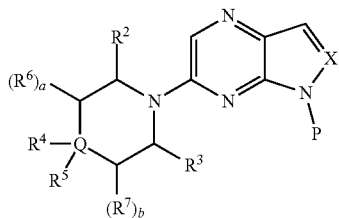

(F)

wherein R², R³, R⁴, R⁵, R⁶, R⁷, Q, X, a, b, are as defined hereinbefore for the compounds of formula (I) and P represents a suitable amine protecting group (such as 2-(trimethylsilyl)ethoxymethyl; SEM) or is hydrogen,
by introducing a suitable leaving group Z such as a halogen, for example using a suitable halogenating reagent (such as N-iodosuccinimide) followed by an optional protection step to introduce the amine protecting group P (such as 2-(trimethylsilyl)ethoxymethyl; SEM).

Compounds of formula (A), or protected derivatives thereof in particular where R¹ is methyl or CH₂OH, may be be obtained by reacting a compound of formula (X') or protected derivative thereof:

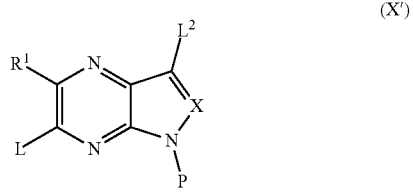

(X')

Wherein R¹ is either methyl or CH₂OH, P represents a protecting group (such as 2-tetrahydropyran; THP or 2-(trimethylsilyl)ethoxymethyl; SEM) or is hydrogen, and L¹ and L² independently represent leaving groups (such as a halide e.g. chlorine, bromine or iodine), with a compound of formula (D) or protected derivative thereof.

Compounds of formula (X'), in particular where R¹ is CH₂OH or protected derivatives thereof, may be obtained by reacting a compound of formula (Y) or protected derivative thereof:

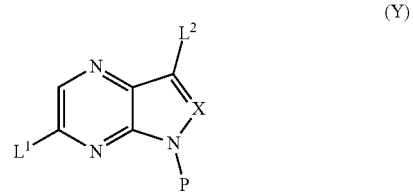

(Y)

wherein P represents a protecting group (such as 2-tetrahydropyran; THP or 2-(trimethylsilyl)ethoxymethyl; SEM) or is hydrogen, and L¹ and L² independently represent leaving groups (such as a halide e.g. chlorine, bromine or iodine), with methanol in the presence of a photoredox catalyst (such as 2,4,5,6-tetra(9H-carbazol-9-yl)isophthalonitrile), a peroxide reagent such as tert-butyl peracetate solution, an acid (such as TFA), and a source of light (such as a blue LED), in a solvent such as DMSO. Alternatively, the reaction can be performed with an excess of an alcohol, such as methanol in the presence of a metal salt such as silver (II) nitrate, a peroxide reagent such as ammonium persulfate, an acid (such as TFA), in a solvent such as DMSO or water and a source of heat (30-150° C.).

Alternatively, compounds of formula (X'), or protected derivatives thereof, may be obtained by reacting a compound of formula (W') or protected derivative thereof:

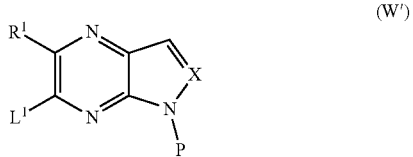

(W')

wherein P represents a protecting group (such as 2-tetrahydropyran; THP or 2-(trimethylsilyl)ethoxymethyl; SEM) or is hydrogen, and L¹ is a leaving group (such as a halogen e.g. iodine or bromine), with a suitable halogenating agent (such as N-bromosuccinimide or N-iodosuccinimide) to introduce a leaving group such as a halogen (e.g. bromine or iodine).

Compounds of formula (W'), or protected derivatives thereof in particular where R¹ is methyl, may be obtained by reacting a compound of formula (Y') or protected derivative thereof:

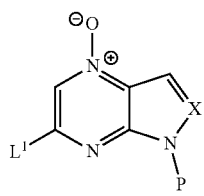

(Y')

wherein P represents a protecting group (such as 2-tetrahydropyran; THP or 2-(trimethylsilyl)ethoxymethyl; SEM) or is hydrogen, and $L^1$ is a leaving group (such as a halogen e.g. iodine or bromine), with an organometallic residue (such as an organomagnesium species e.g. methyl magnesium chloride).

Compounds of formula (Y'), or protected derivatives thereof, may be obtained by reacting a compound of formula (Z) or protected derivative thereof:

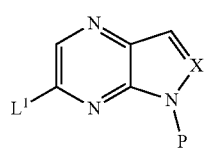

(Z)

wherein X is N, P represents a protecting group (such as 2-tetrahydropyran; THP or 2-(trimethylsilyl)ethoxymethyl; SEM) or is hydrogen, and $L^1$ is a leaving group (such as a halogen e.g. iodine or bromine), with an oxidising agent (such as a peroxide reagent e.g. trifluoroperacetic acid).

Compounds of formula (F), where X=CH, or protected derivatives thereof, may be obtained by reacting a compound of formula (G) or protected derivatives thereof

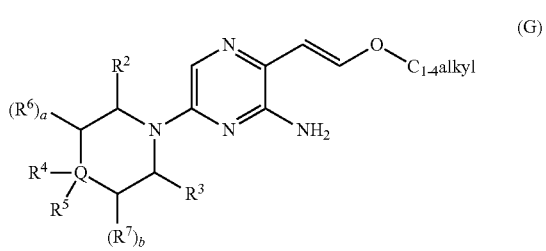

(G)

wherein $R^2$, $R^3$, $R^4$, $R^5$, $R^6$, $R^7$, Q, a, b, are as defined hereinbefore for the compounds of formula (I), by intramolecular cyclisation of the alkoxy vinyl ether and the amine using a suitable acid (such as TFA). Under such conditions, one or more protecting groups may also be removed, and therefore the cyclisation step may optionally be followed by a re-protection step, for example with di-tert-butyl dicarbonate to give an N-Boc derivative.

Compounds of formula (G) or protected derivatives thereof may be obtained by reacting a compound of formula (H) or protected derivative thereof,

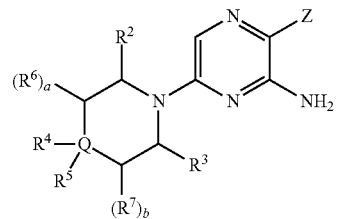

(H)

wherein $R^2$, $R^3$, $R^4$, $R^5$, $R^6$, $R^7$, Q, a and b are as defined hereinbefore for the compounds of formula (I), where Z is a leaving group (such as a halogen)
with an alkoxy vinyl derivative such as (E)-1-ethoxyethene-2-boronic acid pinacol ester via metal catalysis (for example using palladium acetate and a suitable ligand such as 2-dicyclohexylphosphino-2',6'-dimethoxybiphenyl i.e. Sphos and a base such as potassium phosphate). The reaction may take place in a suitable solvent or solvent combination such as acetonitrile and water and at a suitable temperature such as 70° C.

Compounds of formula (H) or protected derivatives thereof may be obtained by reacting a compound of formula (J):

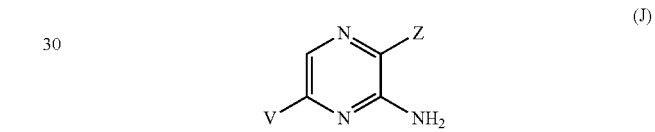

(J)

with a compound of formula (D) or protected derivative thereof, wherein, Z is a leaving group (such as a halogen) and V is leaving group (such as a halogen), with a suitable base (such as N,N-diisopropylethylamine), in a suitable solvent (such as N-methyl-2-pyrrolidone) at a suitable temperature (such as 120° C.).

Compounds of formula (K), or protected derivatives thereof, may be obtained by reacting a compound of formula (L) or protected derivative thereof:

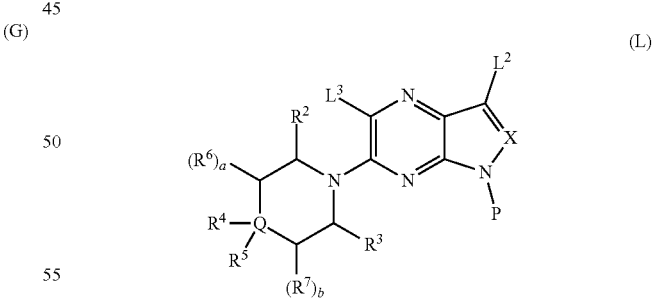

(L)

wherein $R^4$, $R^5$, $R^6$, $R^7$, Q, X, a, b, are as defined hereinbefore for the compounds of formula (I), P represents an amine protecting group (such as 2-(trimethylsilyl)ethoxymethyl; SEM), N,N-dimethylsulfamoyl or is hydrogen, $L^2$ is a leaving group (such as halogen e.g. iodide), $L^3$ is a leaving group (such as halogen e.g. bromide), with a compound of formula (B), using procedures such as those outlined for (a).

Compounds of formula (L), or protected derivative thereof, may be obtained by reacting a compound of formula (M):

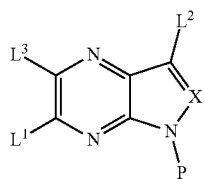

(M)

wherein X is as defined hereinbefore for the compounds of formula (I), P represents a suitable protecting group such as 2-(trimethylsilyl)ethoxymethyl (SEM) or N,N-dimethylsulfamoyl, L¹ is a leaving group such as chloride, L² is a leaving group such as iodide and L³ is leaving group such as bromide, with a compound of formula (D) using procedures such as those outlined for (b).

Compounds of formula (M) or protected derivatives thereof, may be obtained from commercially available starting materials, prepared from literature procedures or using methods indicated within the examples outlined in this patent or analogous methods.

Alternatively, compounds of formula (L) or protected derivatives thereof may be obtained by reacting a compound of formula (N) or a protected derivative thereof:

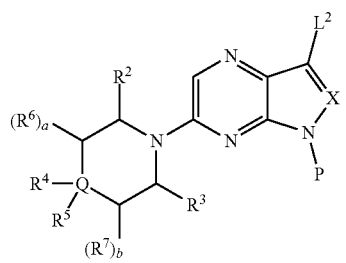

(N)

wherein R², R³, R⁴, R⁵, R⁶, R⁷, Q, X, a, b, are as defined hereinbefore for the compounds of formula (I), P represents an amine protecting group (such as 2-(trimethylsilyl)ethoxymethyl; SEM) or is hydrogen, with a suitable halogenating agent (such as N-bromosuccinimide or N-iodosuccinimide) to introduce a leaving group such as a halogen (e.g. bromine or iodine).

Compounds of formula (N) or protected derivatives thereof can be obtained by reacting a compound of formula (O) or protected derivatives thereof:

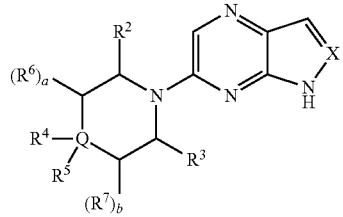

(O)

wherein R², R³, R⁴, R⁵, R⁶, R⁷, Q, X, a, b, are as defined hereinbefore for the compounds of formula (I), with a suitable halogenating agent such as N-iodosuccinimide to introduce a leaving group such as a halogen and suitable conditions to introduce the protecting group.

Compounds of formula (O) or protected derivatives thereof, where X is a nitrogen may be obtained by reacting a compound of formula (P):

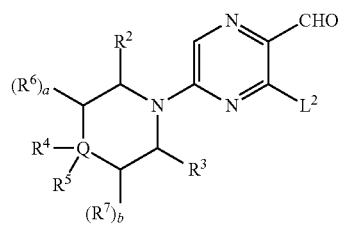

(P)

wherein R², R³, R⁴, R⁵, R⁶, R⁷, Q, a, b, are as defined hereinbefore for the compounds of formula (I), L² is a leaving group such as chloride, with a suitable hydrazine derivative such as hydrazine hydrate.

Compounds of formula (P) or protected derivatives thereof may be obtained by reacting a compound of formula (Q):

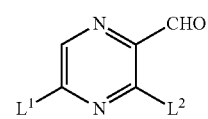

(Q)

with a compound of formula (D) or protected derivative thereof, where L¹ and L² are leaving groups such as chloride.

Compounds of formula (Q) or protected derivatives thereof, are obtained from commercially available starting materials or prepared from literature procedures or using methods indicated within the examples outlined in this patent or analogous methods.

Compounds of formula (R), or protected derivatives thereof, may be obtained by reacting a compound of formula (S) or protected derivative thereof:

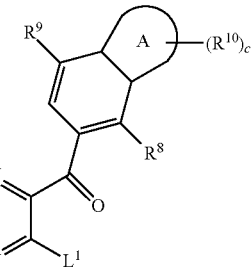

(S)

wherein R¹, R⁸, R⁹, R¹⁰, A, c, are as defined hereinbefore for the compounds of formula (I) and both L¹ and L² represent a suitable leaving group, such as a halogen, with a compound of formula (D).

Compounds of formula (S), or protected derivatives thereof, may be obtained by reacting a compound of formula (T) or protected derivative thereof:

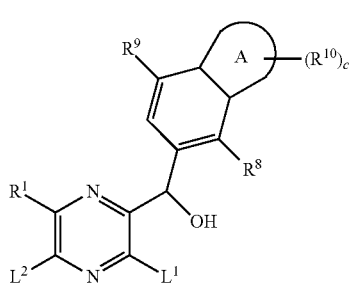

(T)

wherein $R^1$, $R^8$, $R^9$, $R^{10}$, A, c, are as defined hereinbefore for the compounds of formula (I) and both $L^1$ and $L^2$ represent a suitable leaving group, such as a halogen, with a suitable oxidising reagent such as manganese (IV) oxide.

Compounds of formula (T), or protected derivatives thereof, may be obtained by reacting a compound of formula (U) or protected derivative thereof:

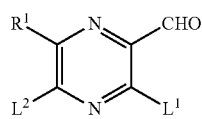

(U)

wherein $R^1$ are as defined hereinbefore for the compounds of formula (I) and both $L^1$ and $L^2$ represent a suitable leaving groups, such as a halogen, with a compound of formula (B), wherein V is a metal or metaloid residue (such as a magnesium halide).

Compounds of formula (U), or protected derivatives thereof, may be obtained by reacting a compound of formula (V') or protected derivative thereof:

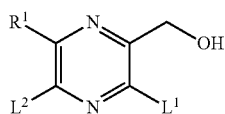

(V')

wherein $R^1$, are as defined hereinbefore for the compounds of formula (I) and both $L^1$ and $L^2$ represent a suitable leaving groups, such as a halogen, with a suitable oxidising reagent such as Dess-Martin periodinane.

Compounds of formula (V), or protected derivatives thereof, may be obtained by reacting a compound of formula (N) or protected derivative thereof:

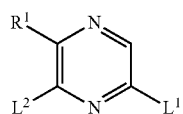

(W)

wherein $R^1$, is as defined hereinbefore for the compounds of formula (I) and both $L^1$ and $L^2$ represent a suitable leaving group, such as a halogen, with an alcohol, such as methanol in the presence of a photoredox catalyst (such as 2,4,5,6-tetra(9H-carbazol-9-yl)isophthalonitrile), a peroxide reagent such as tert-butyl peracetate solution, an acid (such as TFA), and a source of light (such as a blue LED), in a solvent such as DMSO.

Compounds of formula (W) or protected derivatives thereof, are obtained from commercially available starting materials or prepared from literature procedures or using methods indicated within the examples outlined in this patent or analogous methods.

Compounds of formula (T), or protected derivatives thereof, may also be obtained by reacting a compound of formula (Z') or protected derivative thereof:

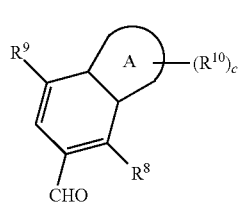

(Z')

wherein $R^8$, $R^9$, $R^{10}$, A, c are as defined hereinbefore for the compounds of formula (I) with a compound of formula (N). The process typically comprises reacting a compound of formula (N) with a reagent such as 2,2,6,6-tetramethylpiperidinylmagnesium chloride lithium chloride complex solution, for a suitable time such as 2.5 h to completely effect metalation. The newly formed organomagnesium species is treated with a compound of formula (Z') and allowed to warm up e.g. to room temperature and stirred for a suitable time, such as 18 h.

Compounds of formula (Z') or protected derivatives thereof, are prepared using methods indicated within the examples outlined in this patent or analogous methods.

Deprotection of a Protected Derivative of a Compound of Formula (I)

Process (e) typically comprises any suitable deprotection reaction, the conditions of which will depend upon the nature of the protecting group. When the protecting group P represents SEM, such a deprotection reaction will typically comprise the use of a suitable acid in a suitable solvent, followed by removal of the hydroxymethyl adduct formed during the acid deprotection of the SEM protecting group with ethylenediamine. For example, the acid may suitably comprise of trifluoroacetic acid or hydrogen chloride and the solvent may suitably comprise dichloromethane, DMF or methanol. Optionally a mixture of solvents may be used, for example water and methanol. The second step involves concentration in vacuo, followed by dissolving the crude material in a suitable solvent such as methanol and treatment with a suitable scavenging reagent such as ethylenediamine in a suitable solvent such as methanol.

Where the protecting group is a N,N-dimethylsulfamoyl group ($SO_2NMe_2$), a stronger acid such as trifluoromethanesulfonic acid may be used at a suitable temperature.

The deprotection may be carried out in accordance with the procedures described herein as general procedures for preparation of compounds of formula (I), Methods 1-12.

Formation of a Pharmaceutically Acceptable Salt of a Compound of Formula (I)

The salt formation may be carried out by treatment of a compound of formula (I) in the free base form, dissolved in a suitable solvent, with a stoichiometric amount or an excess of a pharmaceutically acceptable organic or inorganic acid, then isolation of the resulting salt by methods well known in the art, e.g. evaporation of solvent or crystallisation.

General

If appropriate, the reactions previously described in processes (a), (b) and (c) are followed or preceded by one or more reactions known to the skilled of the art and are performed in an appropriate order to achieve the requisite substitutions defined above to afford other compounds of formula (I). Non-limiting examples of such reactions whose conditions can be found in the literature include:
protection of reactive functions,
deprotection of reactive functions,
halogenation,
dehalogenation,
dealkylation,
alkylation and arylation of amine, aniline, alcohol and phenol,
Mitsunobu reaction on hydroxyl groups,
cycloaddition reactions on appropriate groups,
reduction of nitro, esters, cyano, aldehydes,
transition metal-catalyzed coupling reactions,
acylation,
sulfonylation/introduction of sulfonyl groups,
saponification/hydrolysis of esters groups,
amidification or transesterification of ester groups,
esterification or amidification of carboxylic groups,
halogen exchange,
nucleophilic substitution with amine, thiol or alcohol,
reductive amination,
oxime formation on carbonyl and hydroxylamine groups,
S-oxidation,
N-oxidation, and
salification.

A wide range of well known functional group interconversions are know by a person skilled in the art for converting a precursor compound to a compound of formula I and are described in *Advanced Organic Chemistry* by Jerry March, 4th Edition, John Wiley & Sons, 1992. For example, possible metal catalysed functionalisations such as using organo-tin reagents (the Stille reaction), Grignard reagents and reactions with nitrogen nucleophiles are described in 'Palladium Reagents and Catalysts' [Jiro Tsuji, Wiley, ISBN 0-470-85032-9] and Handbook of OrganoPalladium Chemistry for Organic Synthesis [Volume 1, Edited by Ei-ichi Negishi, Wiley, ISBN 0-471-31506-0].

Protecting Groups

In many of the reactions described above, it may be necessary to protect one or more groups to prevent reaction from taking place at an undesirable location on the molecule. Examples of protecting groups, and methods of protecting and deprotecting functional groups, can be found in *Protective Groups in Organic Synthesis* (T. Green and P. Wuts; 3rd Edition; John Wiley and Sons, 1999).

A hydroxy group may be protected, for example, as an ether (—OR) or an ester (—OC(=O)R), for example, as: a t-butyl ether; a tetrahydropyranyl (THP) ether; a benzyl, benzhydryl (diphenylmethyl), or trityl (triphenylmethyl) ether; a trimethylsilyl or t-butyldimethylsilyl ether; or an acetyl ester (—OC(=O)CH$_3$).

An aldehyde or ketone group may be protected, for example, as an acetal (R—CH(OR)$_2$) or ketal (R$_2$C(OR)$_2$), respectively, in which the carbonyl group (>C=O) is treated with, for example, a primary alcohol. The aldehyde or ketone group is readily regenerated by hydrolysis using a large excess of water in the presence of acid.

An amine group may be protected, for example, as an amide (—NRCO—R) or a carbamate (—NRCO—OR), for example, as: a methyl amide (—NHCO—CH$_3$); a benzyl carbamate (—NHCO—OCH$_2$C$_6$H$_5$, —NH—Cbz or —NH—Z); as a t-butyl carbamate (—NHCO—OC(CH$_3$)$_3$, —NH—Boc); a 2-biphenyl-2-propyl carbamate (—NHCO—OC(CH$_3$)$_2$C$_6$H$_4$C$_6$H$_5$, —NH—Bpoc), as a 9-fluorenylmethyl carbamate (—NH—Fmoc), as a 6-nitroveratryl carbamate (—NH—Nvoc), as a 2-trimethylsilylethyl carbamate (—NH-Teoc), as a 2,2,2-trichloroethyl carbamate (—NH-Troc), as an allyl carbamate (—NH-Alloc), or as a 2(-phenylsulfonyl)ethyl carbamate (—NH—Psec).

For example, in compounds of formula I contains an amino group, the amino group can be protected by means of a protecting group as hereinbefore defined, one preferred group being the ted-butyloxycarbonyl (Boc) group while the additional funactionalisation is introduced. Where no subsequent modification of the amino group is required, the protecting group can be carried through the reaction sequence to give an N-protected form of a compound of the formula (I) which can then be de-protected by standard methods (e.g. treatment with acid in the case of the Boc group) to give the compound of formula (I).

Other protecting groups for amines, such as cyclic amines and heterocyclic N—H groups, include toluenesulfonyl (tosyl) and methanesulfonyl (mesyl) groups, benzyl groups such as a para-methoxybenzyl (PMB) group and tetrahydropyranyl (THP) groups.

A carboxylic acid group may be protected as an ester for example, as: an C$_{1-7}$ alkyl ester (e.g., a methyl ester; a t-butyl ester); a C$_{1-7}$ haloalkyl ester (e.g., a C$_{1-7}$ trihaloalkyl ester); a triC$_{1-7}$ alkylsilyl-C$_{1-7}$ alkyl ester; or a C$_{5-20}$ aryl-C$_{1-7}$ alkyl ester (e.g., a benzyl ester; a nitrobenzyl ester; para-methoxybenzyl ester. A thiol group may be protected, for example, as a thioether (—SR), for example, as: a benzyl thioether; an acetamidomethyl ether (—S—CH$_2$NHC(=O)CH$_3$).

Isolation and Purification of the Compounds of the Invention

The compounds of the invention can be isolated and purified according to standard techniques well known to the person skilled in the art and examples of such methods include chromatographic techniques such as column chromatography (e.g. flash chromatography) and HPLC. One technique of particular usefulness in purifying the compounds is preparative liquid chromatography using mass spectrometry as a means of detecting the purified compounds emerging from the chromatography column.

Preparative LC-MS is a standard and effective method used for the purification of small organic molecules such as the compounds described herein. The methods for the liquid chromatography (LC) and mass spectrometry (MS) can be varied to provide better separation of the crude materials and improved detection of the samples by MS. Optimisation of the preparative gradient LC method will involve varying columns, volatile eluents and modifiers, and gradients. Methods are well known in the art for optimising preparative LC-MS methods and then using them to purify compounds. Such methods are described in Rosentreter U, Huber U.; Optimal fraction collecting in preparative LC/MS; *J Comb Chem.;* 2004; 6(2), 159-64 and Leister W, Strauss K, Wisnoski D, Zhao Z, Lindsley C., Development of a custom high-throughput preparative liquid chromatography/mass spectrometer platform for the preparative purification and analytical analysis of compound libraries; *J Comb Chem.;* 2003; 5(3); 322-9. An example of such a system for purifying compounds via preparative LC-MS is described below in the Examples section of this application (under the heading "Mass Directed Purification LC-MS System").

Methods of recrystallisation of compounds of formula (I) and salt thereof can be carried out by methods well known to the skilled person—see for example (P. Heinrich Stahl (Editor), Camille G. Wermuth (Editor), ISBN: 3-90639-026-

8, Handbook of Pharmaceutical Salts: Properties, Selection, and Use, Chapter 8, Publisher Wiley-VCH). Products obtained from an organic reaction are seldom pure when isolated directly from the reaction mixture. If the compound (or a salt thereof) is solid, it may be purified and/or crystallized by recrystallisation from a suitable solvent. A good recrystallisation solvent should dissolve a moderate quantity of the substance to be purified at elevated temperatures but only a small quantity of the substance at lower temperature. It should dissolve impurities readily at low temperatures or not at all. Finally, the solvent should be readily removed from the purified product. This usually means that it has a relatively low boiling point and a person skilled in the art will know recrystallising solvents for a particular substance, or if that information is not available, test several solvents. To get a good yield of purified material, the minimum amount of hot solvent to dissolve all the impure material is used. In practice, 3-5% more solvent than necessary is used so the solution is not saturated. If the impure compound contains an impurity which is insoluble in the solvent it may then be removed by filtration and then allowing the solution to crystallize. In addition, if the impure compound contains traces of coloured material that are not native to the compound, it may be removed by adding a small amount of decolorizing agent e.g. activating charcoal to the hot solution, filtering it and then allowing it to crystallize. Usually crystallization spontaneously occurs upon cooling the solution. If it is not, crystallization may be induced by cooling the solution below room temperature or by adding a single crystal of pure material (a seed crystal). Recrystallisation can also be carried out and/or the yield optimized by the use of an anti-solvent or co-solvent. In this case, the compound is dissolved in a suitable solvent at elevated temperature, filtered and then an additional solvent in which the required compound has low solubility is added to aid crystallization. The crystals are then typically isolated using vacuum filtration, washed and then dried, for example, in an oven or via desiccation.

Other examples of methods for purification include sublimation, which includes a heating step under vacuum for example using a cold finger, and crystallization from melt (Crystallization Technology Handbook 2nd Edition, edited by A. Mersmann, 2001).

Biological Effects

It is envisaged that the compound of the invention will be useful in medicine or therapy. The compounds of the invention, subgroups and examples thereof, have been shown to inhibit SHP2. Such inhibition leads to inhibition of tumor cell proliferation and activation of T cell immune responses toward cancer cells, which may be useful in preventing or treating disease states or conditions described herein, for example the diseases and conditions discussed below and the diseases and conditions described in the "Background of the Invention" section above in which SHP2 plays a role. Thus, for example, it is envisaged that the compounds of the invention will be useful in alleviating or reducing the incidence of cancer, preventing or treating diseases or conditions mediated by SHP2, for example diseases or conditions such as cancers in which there are activating mutations within upstream components (such as RAS, KRAS and NRAS) of the MAPK pathway or Receptor Tyrosine Kinase (RTK) activated cancers. The compounds of the present invention may be useful for the treatment of the adult population. The compounds of the present invention may be useful for the treatment of the pediatric population.

The compounds of the present invention have been shown to be good inhibitors of SHP2. The compounds of formula (I) are capable of binding to SHP2 and exhibiting potency for SHP2. The efficacies of the compounds of the present invention have been determined against SHP2 using the assay protocol described herein and other methods known in the art. More particularly, the compounds of the formula (I) and sub-groups thereof have potency for SHP2.

Certain compounds of the invention are those having $IC_{50}$ values of less than 0.1 µM in particular less than 0.01 or 0.001 µM.

SHP2 function has been implicated in many diseases due to its role in cell survival and proliferation, primarily through activation of the RAS-ERK signalling pathway, as well as in oncogenesis. As a consequence of their affinity for SHP2 it is anticipated that the compounds may prove useful in treating or preventing a range of diseases or conditions including disorders associated with cell accumulation (e.g. cancer, autoimmune disorders, inflammation and restenosis), disorders where excessive apoptosis results in cell loss (e.g. stroke, heart failure, neurodegeneration such as Alzheimers' disease, Parkinson's disease, Huntington's disease, amyotrophic lateral sclerosis, AIDS, ischemia (stroke, myocardial infarction) and osteoporosis or treating autoimmune diseases such as multiple sclerosis (MS).

Therefore, it is also envisaged that the compounds of the invention as defined herein may be useful in treating other conditions such as inflammation, hepatitis, ulcerative colitis, gastritis, autoimmunity, inflammation, restenosis, stroke, heart failure, neurodegenerative conditions such as Alzheimers' disease, Parkinson's disease, Huntington's disease, myotonic dystrophy, and amyotrophic lateral sclerosis, AIDS, ischemia such as traumatic brain injury, spinal cord injury, cerebral ischemia, cerebral ischemia/reperfusion (I/R) injury, acute and chronic CNS injury ischemia, stroke or myocardial infarction, degenerative diseases of the musculoskeletal system such as osteoporosis, autoimmune diseases such as multiple sclerosis (MS) and Type I diabetes, and eye diseases such as retinal degeneration which result from loss of control of programmed cell death.

As a consequence of their activity against SHP2 it is anticipated that the compounds may prove useful in treating or preventing proliferative disorders such as cancers.

Examples of cancers (and their benign counterparts) which may be treated (or inhibited) include, but are not limited to tumours of epithelial origin (adenomas and carcinomas of various types including adenocarcinomas, squamous carcinomas, transitional cell carcinomas and other carcinomas) such as carcinomas of the bladder and urinary tract, breast, gastrointestinal tract (including the esophagus, stomach (gastric), small intestine, colon, bowel, colorectal, rectum and anus), liver (hepatocellular carcinoma), gall bladder and biliary system, exocrine pancreas, kidney (for example renal cell carcinoma), lung (for example adenocarcinomas, small cell lung carcinomas, non-small cell lung carcinomas, bronchioalveolar carcinomas and mesotheliomas), head and neck (for example cancers of the tongue, buccal cavity, larynx, pharynx, nasopharynx, tonsil, salivary glands, nasal cavity and paranasal sinuses), ovary, fallopian tubes, peritoneum, vagina, vulva, penis, testes, cervix, myometrium, endometrium, thyroid (for example thyroid follicular carcinoma), brain, adrenal, prostate, skin and adnexae (for example melanoma, basal cell carcinoma, squamous cell carcinoma, keratoacanthoma, dysplastic naevus); haematological malignancies (i.e. leukemias, lymphomas) and premalignant haematological disorders and disorders of borderline malignancy including haematological malignancies and related conditions of lymphoid lineage (for example acute lymphocytic leukemia [ALL], chronic lymphocytic leukemia [CLL], B-cell lymphomas such as diffuse large B-cell lymphoma [DLBCL], follicular lymphoma, Burkitt's lymphoma, mantle cell lymphoma, T-cell lymphomas and leukaemias, natural killer [NK] cell lymphomas, Hodgkin's lymphomas, hairy cell leukaemia, monoclonal gammopathy of uncertain significance, plasmacytoma, multiple myeloma, and post-transplant lymphoproliferative disorders), and haematological malignancies and related conditions of myeloid lineage (for example acute myelogenous leukemia [AML], chronic myelogenous leukemia [CML], chronic myelomonocytic leukemia [CMML], hypereosinophilic syndrome, myeloproliferative disorders such as polycythaemia vera, essential thrombocythaemia and primary myelofibrosis, myeloproliferative syndrome, myelodysplastic syndrome, and promyelocytic leukemia); tumours of mesenchymal origin, for example sarcomas of soft tissue, bone or cartilage such as osteosarcomas, fibrosarcomas, chondrosarcomas, rhabdomyosarcomas, leiomyosarcomas, liposarcomas, angiosarcomas, Kaposi's sarcoma, Ewing's sarcoma, synovial sarcomas, epithelioid sarcomas, gastrointestinal stromal tumours, benign and malignant histiocytomas, and dermatofibrosarcoma protuberans; tumours of the central or peripheral nervous system (for example astrocytomas (e.g. gliomas), neuromas and glioblastomas, meningiomas, ependymomas, pineal tumours and schwannomas); endocrine tumours (for example pituitary tumours, adrenal tumours, islet cell tumours, parathyroid tumours, carcinoid tumours and medullary carcinoma of the thyroid); ocular and adnexal tumours (for example retinoblastoma); germ cell and trophoblastic tumours (for example teratomas, seminomas, dysgerminomas, hydatidiform moles and choriocarcinomas); and paediatric and embryonal tumours (for example medulloblastoma, neuroblastoma, Wilms tumour, and primitive neuroectodermal tumours); or syndromes, congenital or otherwise, which leave the patient susceptible to malignancy (for example Xeroderma Pigmentosum).

Growth of cells is a closely controlled function. Cancer, a condition of abnormal cell growth, results when cells replicate in an uncontrolled manner (increasing in number), uncontrollably grow (getting larger) and/or experience reduced cell death by apoptosis (programmed cell death), necrosis, or annoikis. In one embodiment abnormal cell growth is selected from uncontrolled cell proliferation, excessive cell growth or reduced programmed cell death. In particular, the condition or disease of abnormal cell growth is a cancer.

Thus, in the pharmaceutical compositions, uses or methods of this invention for treating a disease or condition comprising abnormal cell growth (i.e. uncontrolled and/or rapid cell growth), the disease or condition comprising abnormal cell growth in one embodiment is a cancer.

The compounds of the invention may be useful in the treatment of metastasis and metastatic cancers. Metastasis or metastatic disease is the spread of a disease from one organ or part to another non-adjacent organ or part. The cancers which can be treated by the compounds of the invention include primary tumours (i.e. cancer cells at the originating site), local invasion (cancer cells which penetrate and infiltrate surrounding normal tissues in the local area), and metastatic (or secondary) tumours ie. tumours that have formed from malignant cells which have circulated through the bloodstream (haematogenous spread) or via lymphatics or across body cavities (trans-coelomic) to other sites and tissues in the body. In particular, the compounds of the invention may be useful in the treatment of metastasis and metastatic cancers.

In one embodiment the haematological malignancies is a leukaemia. In another embodiment the haematological malignancies is a lymphoma. In one embodiment the cancer is AML. In another embodiment the cancer is CLL.

In one embodiment the compound of the invention is for use in the prophylaxis or treatment of leukemia, such as acute or chronic leukaemia, in particular acute myeloid leukaemia (AML), acute lymphocytic leukaemia (ALL), chronic lymphocytic leukaemia (CLL), or chronic myeloid leukemia (CML). In one embodiment the compound of the invention is for use in the prophylaxis or treatment of lymphoma, such as acute or chronic lymphoma, in particular Burkitt lymphoma, Hodgkin lymphoma, non-Hodgkin lymphoma or difuse large B-cell lymphoma.

In one embodiment the compound of the invention is for use in the prophylaxis or treatment of acute myeloid leukaemia (AML) or acute lymphocytic leukaemia (ALL).

The cancers may be cancers which are sensitive to treatment with SHP2 inhibitors. The cancers may be cancers which overexpress SHP2. The cancer may be cancers which are SHP2 wild-type. The cancer may be cancers which are mutant SHP2. In one embodiment the cancer has activating mutations in SHP2.

Particular cancers include hepatocellular carcinoma, melanoma, oesophageal, renal, colon, colorectal, lung e.g. NSCLC, mesothelioma or lung adenocarcinoma, breast, bladder, gastrointestinal, ovarian and prostate cancers.

Particular cancers include those with activated SHP2 (activating mutations, amplified and/or SHP2 wild-type overexpression), for example, hepatocellular carcinoma, breast, lung, colorectal and neuroblastoma.

Particular cancers include those with oncogenic alterations in the RAS-RAF-MEK-ERK pathway, including mutant forms of KRAS.

Particular cancers include those where RTK activity drives disease or resistance to cancer therapies.

The compounds of the invention will be particularly useful in the treatment or prevention of cancers of a type associated with or characterised by the presence of elevated Ras, BRAF and/or MEK signalling.

Elevated levels of Ras, BRAF or MEK signalling are found in many cancers and are associated with a poor prognosis. In addition, cancers with activating Ras mutations may also be sensitive to an SHP2 inhibitor. The elevated levels of Ras signalling and mutations in Ras can be identified by the techniques outlined herein.

A further subset of cancers consists of NRas melanoma and NRas AML.

Another subset of cancers consists of KRas lung cancer, KRas pancreatic cancer and KRas colorectal cancer (CRC).

In one embodiment, the cancer is colorectal, breast, lung and brain

In one embodiment, the cancer is a paediatric cancer.

In one embodiment, the cancer is breast cancer, leukaemia, lung cancer, liver cancer, gastric cancer, laryngeal cancer or oral cancer.

Whether a particular cancer is one which is sensitive to SHP2 inhibitors, may be determined by a method as set out in the section headed "Methods of Diagnosis".

A further aspect provides the use of a compound for the manufacture of a medicament for the treatment of a disease or condition as described herein, in particular cancer.

Certain cancers are resistant to treatment with particular drugs. This can be due to the type of the tumour (most common epithelial malignancies are inherently chemoresistant and prostate is relatively resistant to currently available regimens of chemotherapy or radiation therapy) or resistance can arise spontaneously as the disease progresses or as a result of treatment. In this regard, references to prostate includes prostate with resistance towards anti-androgen therapy, in particular abiraterone or enzalutamide, or castrate-resistant prostate. Similarly references to multiple myeloma includes bortezomib-insensitive multiple myeloma or refractory multiple myeloma and references to chronic myelogenous leukemia includes imitanib-insensitive chronic myelogenous leukemia and refractory chronic myelogenous leukemia. In this regard, references to mesothelioma includes mesothelioma with resistance towards topoisomerase poisons, alkylating agents, antitubulines, antifolates, platinum compounds and radiation therapy, in particular cisplatin-resistant mesothelioma. References to melanoma include melanomas that are resistant to treatment with BRAF and/or MEK inhibitors.

The compounds may also be useful in the treatment of tumour growth, pathogenesis, resistance to chemo- and radio-therapy by sensitising cells to chemotherapy and as an anti-metastatic agent.

Therapeutic anticancer interventions of all types necessarily increase the stresses imposed on the target tumour cells. Inhibitors of SHP2 represent a class of chemotherapeutics with the potential for: (i) sensitizing malignant cells to anticancer drugs and/or treatments; (ii) alleviating or reducing the incidence of resistance to anticancer drugs and/or treatments; (iii) reversing resistance to anticancer drugs and/or treatments; (iv) potentiating the activity of anticancer drugs and/or treatments; (v) delaying or preventing the onset of resistance to anticancer drugs and/or treatments.

In one embodiment the invention provides a compound for use in the treatment of a disease or condition which is mediated by SHP2. In a further embodiment the disease or condition which is mediated by SHP2 is a cancer which is characterised by overexpression and/or increased activity of SHP2.

A further aspect provides the use of a compound for the manufacture of a medicament for the treatment of a disease or condition as described herein, in particular cancer.

In one embodiment there is provided a compound for use in the prophylaxis or treatment of a disease or condition mediated by SHP2.

In one embodiment there is provided a pharmaceutical composition comprising an effective amount of at least one compound as defined. In a further aspect of the present invention, there is provided a compound as defined in the present In one embodiment there is provided a method for the prophylaxis or treatment of cancer comprising the steps of administering to a mammal a medicament comprising at least one compound as defined.

Methods of Diagnosis

Prior to administration of a compound of the formula (I), a patient may be screened to determine whether a disease or condition from which the patient is or may be suffering is one which would be susceptible to treatment with a compound which inhibits SHP2. The term 'patient' includes human and veterinary subjects such as primates, in particular human patients.

For example, a biological sample taken from a patient may be analysed to determine whether a condition or disease, such as cancer, that the patient is or may be suffering from is one which is characterised by a genetic abnormality or abnormal protein expression which leads to up-regulation of the levels of SHP2 or to upregulation of a biochemical pathway downstream of SHP2.

Examples of such abnormalities that result in activation or sensitisation of SHP2, loss of, or inhibition of regulatory pathways impacting on SHP2 expression, up-regulation of receptors or their ligands, cytogenetic aberrations or presence of mutant variants of the receptors or ligands. Tumours with up-regulation of SHP2, in particular over-expression or activating mutants of SHP2, or include activating mutations in a Ras isoform such as KRAS may be particularly sensitive to inhibitors of SHP2.

Mutations of Ras have been detected in cell lines and primary tumours including but not limited to melanoma, colorectal cancer, non-small cell lung cancer, and cancers of the pancreas, prostate, thyroid, urinary tract and upper respiratory tract (Cancer Res. 2012; 72: 2457-2467).

The term up-regulation includes elevated expression or over-expression, including gene amplification (i.e. multiple gene copies), cytogenetic aberration and increased expression by a transcriptional or post-translational effect. Thus, the patient may be subjected to a diagnostic test to detect a marker characteristic of up-regulation of SHP2. The term diagnosis includes screening. By marker we include genetic markers including, for example, the measurement of DNA composition to identify amplification SHP2 or presence of mutations of SHP2, or to identify presence of mutations of Ras (e.g. KRAS). The term marker also includes markers which are characteristic of up regulation of SHP2, including protein levels, protein state and mRNA levels of the aforementioned proteins. Gene amplification includes greater than 7 copies, as well as gains of between 2 and 7 copies.

Diagnostic assays for detecting KRAS mutations are described in de Castro et al. *Br. J. Cancer.* 2012 Jul. 10; 107(2):345-51. doi: 10.1038/bjc.2012.259. Epub 2012 Jun. 19, "A comparison of three methods for detecting KRAS mutations in formalin-fixed colorectal cancer specimens." and references cited therein.

The diagnostic tests and screens are typically conducted on a biological sample (i.e. body tissue or body fluids) selected from tumour biopsy samples, blood samples (isolation and enrichment of shed tumour cells), cerebrospinal fluid, plasma, serum, saliva, stool biopsies, sputum, chromosome analysis, pleural fluid, peritoneal fluid, buccal smears, skin biopsy or urine.

Methods of identification and analysis of cytogenetic aberration, genetic amplification, mutations and up-regulation of proteins are known to a person skilled in the art. Screening methods could include, but are not limited to, standard methods such as DNA sequence analysis by conventional Sanger or next-generation sequencing methods, reverse-transcriptase polymerase chain reaction (RT-PCR), RNA sequencing (RNAseq), nanostring hybridisation proximity RNA nCounter assays, or in-situ hybridization such as fluorescence in situ hybridization (FISH) or allele-specific polymerase chain reaction (PCR). Newer, next-generation sequencing (NGS) technologies, such as massively parallel sequencing allow for whole exome sequencing or whole genome sequencing.

In screening by RT-PCR, the level of mRNA in the tumour is assessed by creating a cDNA copy of the mRNA followed by amplification of the cDNA by PCR. Methods of PCR amplification, the selection of primers, and conditions for amplification, are known to a person skilled in the art. Nucleic acid manipulations and PCR are carried out by standard methods, as described for example in Ausubel, F. M. et al., eds. (2004) Current Protocols in Molecular Biology, John Wiley & Sons Inc., or Innis, M. A. et al., eds. (1990) PCR Protocols: a guide to methods and applications, Academic Press, San Diego. Reactions and manipulations involving nucleic acid techniques are also described in Sambrook et al., (2001), 3$^{rd}$ Ed, Molecular Cloning: A Laboratory Manual, Cold Spring Harbor Laboratory Press. Alternatively a commercially available kit for RT-PCR (for example Roche Molecular Biochemicals) may be used, or methodology as set forth in U.S. Pat. Nos. 4,666,828; 4,683,202; 4,801,531; 5,192,659, 5,272,057, 5,882,864, and 6,218,529 and incorporated herein by reference. An example of an in-situ hybridisation technique for assessing mRNA expression would be fluorescence in-situ hybridisation (FISH) (see Angerer (1987) Meth. Enzymol., 152: 649).

Generally, in situ hybridization comprises the following major steps: (1) fixation of tissue to be analyzed; (2) prehybridization treatment of the sample to increase accessibility of target nucleic acid, and to reduce nonspecific binding; (3) hybridization of the mixture of nucleic acids to the nucleic acid in the biological structure or tissue; (4) post-hybridization washes to remove nucleic acid fragments not bound in the hybridization, and (5) detection of the hybridized nucleic acid fragments. The probes used in such applications are typically labelled, for example, with radio-isotopes or fluorescent reporters. Certain probes are sufficiently long, for example, from about 50, 100, or 200 nucleotides to about 1000 or more nucleotides, to enable specific hybridization with the target nucleic acid(s) under stringent conditions. Standard methods for carrying out FISH are described in Ausubel, F. M. et al., eds. (2004) Current Protocols in Molecular Biology, John Wiley & Sons Inc and Fluorescence In Situ Hybridization: Technical Overview by John M. S. Bartlett in Molecular Diagnosis of Cancer, Methods and Protocols, 2nd ed.; ISBN: 1-59259-760-2; March 2004, pps. 077-088; Series: Methods in Molecular Medicine.

Methods for gene expression profiling are described by (DePrimo et al. (2003), *BMC Cancer*, 3:3). Briefly, the protocol is as follows: double-stranded cDNA is synthesized from total RNA using a (dT)24 oligomer for priming first-strand cDNA synthesis from polyadenylated mRNA, followed by second strand cDNA synthesis with random hexamer primers. The double-stranded cDNA is used as a template for in vitro transcription of cRNA using biotinylated ribonucleotides. cRNA is chemically fragmented according to protocols described by Affymetrix (Santa Clara, Calif., USA), and then hybridized overnight to gene-specific oligonucleotide probes on Human Genome Arrays. Alternatively, single nucleotide polymorphism (SNP) arrays, a type of DNA microarray, can be used to detect polymorphisms within a population.

Alternatively, the protein products expressed from the mRNAs may be assayed by immunohistochemistry of tumour samples, solid phase immunoassay with microtitre plates, Western blotting, 2-dimensional SDS-polyacrylamide gel electrophoresis, ELISA, flow cytometry and other methods known in the art for detection of specific proteins e.g. capillary electrophoresis. Detection methods would include the use of site specific antibodies. The skilled person will recognize that all such well-known techniques can be used for detection of upregulation of SHP2, detection of SHP2 or SHP2 variants or mutants, or loss of negative regulators of SHP2 in the present case.

Abnormal levels of proteins such as SHP2 can be measured using standard protein assays, for example, those assays described herein. Elevated levels or overexpression could also be detected in a tissue sample, for example, a tumour tissue by measuring the protein levels with an assay such as that from Chemicon International. The protein of interest would be immunoprecipitated from the sample lysate and its levels measured. Assay methods also include the use of markers.

In other words, SHP2 overexpression or mutant SHP2 can be measured by tumour biopsy.

Methods for assessing gene copy changes include techniques commoly used in cytogenetic laboratories such as MLPA (Multiplex Ligation-dependent Probe Amplification) a multiplex PCR method detecting abnormal copy numbers, or other PCR techniques which can detect gene amplification, gain and deletion.

Ex-functional assays could also be utilised where appropriate, for example measurement of circulating leukemia cells in a cancer patient, to assess the response to challenge with a SHP2 inhibitor.

Therefore all of these techniques could also be used to identify tumours particularly suitable for treatment with the compounds of the invention.

Therefore in a further aspect of the invention includes use of a compound according to the invention for the manufacture of a medicament for the treatment or prophylaxis of a disease state or condition in a patient who has been screened and has been determined as suffering from, or being at risk of suffering from, a disease or condition which would be susceptible to treatment with an SHP2 inhibitor.

Another aspect of the invention includes a compound of the invention for use in the prophylaxis or treatment of cancer in a patient selected from a sub-population possessing amplification of SHP2.

Another aspect of the invention includes a compound of the invention for use in the prophylaxis or treatment of cancer in a patient possessing loss of a SHP2 negative regulator.

Another aspect of the invention includes a compound of the invention for use in the prophylaxis or treatment of cancer in a patient selected from a sub-population possessing RTK-driven activation of the MAPK signalling pathway.

MRI determination of vessel normalization (e.g. using MRI gradient echo, spin echo, and contrast enhancement to measure blood volume, relative vessel size, and vascular permeability) in combination with circulating biomarkers may also be used to identify patients suitable for treatment with a compound of the invention.

Thus a further aspect of the invention is a method for the diagnosis and treatment of a disease state or condition mediated by SHP2, which method comprises (i) screening a patient to determine whether a disease or condition from which the patient is or may be suffering is one which would be susceptible to treatment with SHP2 inhibitor; and (ii) where it is indicated that the disease or condition from which the patient is thus susceptible, thereafter administering to the patient a compound of formula (I) and sub-groups or examples thereof as defined herein.

Advantages of Compounds of the Invention

The compounds of the formula (I) have a number of advantages over prior art compounds. Compounds of the invention may have particular advantage in one or more of the following aspects:

(i) Superior potency;
    (ii) Superior in vivo efficacy
    (iii) Superior PK;
    (iv) Superior metabolic stability;
    (v) Superior oral bioavailabilty;
    (vi) Superior physiochemical properties; and/or
    (vii) Superior safety profile or therapeutic index (TI).

Superior Potency and In Vivo Efficacy

The compounds of the formula (I) have increased affinity for SHP2 and in particular increased cell potency against cell lines known to be sensitive to SHP2 antagonists.

Enhanced target engagement is a highly desirable property in a pharmaceutical compound as it allows for a reduced dosage of drug and a good separation ('therapeutic window') between SHP2 activity and toxic effects.

The compounds of the formula (I) have improved cell potency and/or improved selectivity for SHP2 cell lines. As a result of increased potency against SHP2, compounds of the invention may have increased in vivo efficacy in cancer cell lines and in vivo models.

Superior PK and Metabolic Stability

The compounds of the formula (I) may have advantageous ADMET properties for example better metabolic stability (for example as determined with mouse liver microsomes), a better P450 profile, short half-life and/or beneficial clearance (e.g. low or high clearance). It has also been found that many compounds of the formula (I) have an improved PK profile.

These features could confer the advantage of having more drug available in the systemic circulation to reach the appropriate site of action to exert its therapeutic effect. Increased drug concentrations to exert pharmacological action in tumours potentially leads to improved efficacy which thereby allows reduced dosages to be administered. Thus, the compounds of formula (I) should exhibit reduced dosage requirements and should be more readily formulated and administered.

This results in a good separation ('therapeutic window') between SHP2 activity and toxic effects. Many compounds of the formula (I) have a reduction in Cmax required for efficacy (due to better SHP2 potency and/or PK).

Superior Oral Bioavailability

Potentially the compounds of the invention have physiochemical properties suitable for oral exposure (oral exposure or AUC). In particular, compounds of the formula (I) may exhibit improved oral bioavailability or improved reproducibility of oral absorption. Oral bioavailability can be defined as the ratio (F) of the plasma exposure of a compound when dosed by the oral route to the plasma exposure of the compound when dosed by the intravenous (i.v.) route, expressed as a percentage.

Compounds having an oral bioavailability (F value) of greater than 10%, 20% or 30%, more particularly greater than 40%, are particularly advantageous in that they may be administered orally rather than, or as well as, by parenteral administration.

Superior Physiochemical Properties

The compounds of the formula (I) may have advantageous physiochemical properties in particular chemical stability in acidic conditions and reduced lipophilicity.

Lipophilicity can be measured using a partition-coefficient (log P) or a distribution-coefficient (log D). The partition coefficient is a ratio of concentrations of un-ionized compound between two immiscible phases (n-octanol and water) at equilibrium whereas the distribution coefficient is the ratio of the sum of the concentrations of all forms of the compound (ionized plus un-ionized) in each of the two phases. High lipophilicity is associated with poor drug like properties such us low aqueous solubility, poor pharmacokinetics properties (low oral bioavailability), undesired drug metabolism and high promiscuity. Compounds with optimal lipophilicity might have greater chances of success in drug development. However reduced log P (or calculated log P, clog P) can be challenging to achieve whilst retaining an acceptable level of potency for inhibition of protein-protein interactions (PPIs) due to the lipophilic nature of the targets involved.

Superior Safety Profile or Therapeutic Index (TI)

In the late 1990s a number of drugs, approved by the US FDA, had to be withdrawn from sale in the US when it was discovered they were implicated in deaths caused by heart malfunction. It was subsequently found that a side effect of these drugs was the development of arrhythmias caused by the blocking of hERG channels in heart cells. The hERG channel is one of a family of potassium ion channels the first member of which was identified in the late 1980s in a mutant *Drosophila melanogaster* fruitfly (see Jan, L. Y. and Jan, Y. N. (1990). A Superfamily of Ion Channels. Nature, 345 (6277):672). The biophysical properties of the hERG potassium ion channel are described in Sanguinetti, M. C., Jiang, C., Curran, M. E., and Keating, M. T. (1995). A Mechanistic Link Between an Inherited and an Acquired Cardiac Arrhythmia: HERG encodes the Ikr potassium channel. Cell, 81:299-307, and Trudeau, M. C., Warmke, J. W., Ganetzky, B., and Robertson, G. A. (1995). HERG, a Human Inward Rectifier in the Voltage-Gated Potassium Channel Family. Science, 269:92-95. Therefore, elimination of hERG blocking activity remains an important consideration in the development of any new drug.

Compounds that have reduced hERG activity and/or a good separation between activity and hERG activity have a greater 'therapeutic window' or 'therapeutic index'. One method for measurement of hERG activity is the patch clamp electrophysiology method. Alternative methods for measurement of functional hERG activity include hERG binding assays, which can use commercially available membranes isolated from cells stably expressing the hERG channel or commercially available cell lines expressing the hERG channel.

Compounds can also have an improved Cardiac Safety Index (CSI) [CSI=hERG IC50/Cmax(unbound)] (Shultz et al, J. Med. Chem., 2011; Redfern et al, Cardiovasc. Res., 2003). This can be due to an increase in hERG IC50 or a reduction in Cmax required for efficacy (due to better potency and/or PK). Particular compounds may show CV advantage in vivo.

Particular compounds have reduced hERG ion channel blocking activity. Compounds can have mean $IC_{50}$ values against hERG that are greater than 30 times, or greater than 40 times, or greater than 50 times the $IC_{50}$ values of the compounds in cellular proliferation assays.

Pharmaceutical Formulations

While it is possible for the active compound to be administered alone, it is generally presented as a pharmaceutical composition (e.g. formulation).

Thus, the present invention further provides pharmaceutical compositions, as defined above, and methods of making a pharmaceutical composition comprising (e.g admixing) at least one compound of formula (I) (and sub-groups thereof as defined herein), together with one or more pharmaceutically acceptable excipients and optionally other therapeutic or prophylactic agents as described herein.

The pharmaceutically acceptable excipient(s) can be selected from, for example, carriers (e.g. a solid, liquid or semi-solid carrier), adjuvants, diluents, fillers or bulking agents, granulating agents, coating agents, release-controlling agents, binding agents, disintegrants, lubricating agents, preservatives, antioxidants, buffering agents, suspending agents, thickening agents, flavouring agents, sweeteners, taste masking agents, stabilisers or any other excipients conventionally used in pharmaceutical compositions.

Examples of excipients for various types of pharmaceutical compositions are set out in more detail below.

The term "pharmaceutically acceptable" as used herein pertains to compounds, materials, compositions, and/or dosage forms which are, within the scope of sound medical judgment, suitable for use in contact with the tissues of a subject (e.g. a human subject) without excessive toxicity, irritation, allergic response, or other problem or complication, commensurate with a reasonable benefit/risk ratio. Each excipient must also be "acceptable" in the sense of being compatible with the other ingredients of the formulation.

Pharmaceutical compositions containing compounds of the formula (I) can be formulated in accordance with known techniques, see for example, Remington's Pharmaceutical Sciences, Mack Publishing Company, Easton, Pa., USA.

The pharmaceutical compositions can be in any form suitable for oral, parenteral, topical, intranasal, intrabronchial, sublingual, ophthalmic, otic, rectal, intra-vaginal, or transdermal administration. Where the compositions are intended for parenteral administration, they can be formulated for intravenous, intramuscular, intraperitoneal, subcutaneous administration or for direct delivery into a target organ or tissue by injection, infusion or other means of delivery. The delivery can be by bolus injection, short-term infusion or longer term infusion and can be via passive delivery or through the utilisation of a suitable infusion pump or syringe driver.

Pharmaceutical formulations adapted for parenteral administration include aqueous and non-aqueous sterile injection solutions which may contain anti-oxidants, buffers, bacteriostats, co-solvents, surface active agents, organic solvent mixtures, cyclodextrin complexation agents, emulsifying agents (for forming and stabilizing emulsion formulations), liposome components for forming liposomes, gellable polymers for forming polymeric gels, lyophilisation protectants and combinations of agents for, inter alia, stabilising the active ingredient in a soluble form and rendering the formulation isotonic with the blood of the intended recipient. Pharmaceutical formulations for parenteral administration may also take the form of aqueous and non-aqueous sterile suspensions which may include suspending agents and thickening agents (R. G. Strickly, Solubilizing Excipients in oral and injectable formulations, Pharmaceutical Research, Vol 21 (2) 2004, p 201-230).

The formulations may be presented in unit-dose or multi-dose containers, for example sealed ampoules, vials and prefilled syringes, and may be stored in a freeze-dried (lyophilised) condition requiring only the addition of the sterile liquid carrier, for example water for injections, immediately prior to use. In one embodiment, the formulation is provided as an active pharmaceutical ingredient in a bottle for subsequent reconstitution using an appropriate diluent.

The pharmaceutical formulation can be prepared by lyophilising a compound of formula (I), or sub-groups thereof. Lyophilisation refers to the procedure of freeze-drying a composition. Freeze-drying and lyophilisation are therefore used herein as synonyms.

Extemporaneous injection solutions and suspensions may be prepared from sterile powders, granules and tablets.

Pharmaceutical compositions of the present invention for parenteral injection can also comprise pharmaceutically acceptable sterile aqueous or non-aqueous solutions, dispersions, suspensions or emulsions as well as sterile powders for reconstitution into sterile injectable solutions or dispersions just prior to use. Examples of suitable aqueous and nonaqueous carriers, diluents, solvents or vehicles include water, ethanol, polyols (such as glycerol, propylene glycol, polyethylene glycol, and the like), carboxymethylcellulose and suitable mixtures thereof, vegetable oils (such as sunflower oil, safflower oil, corn oil or olive oil), and injectable organic esters such as ethyl oleate. Proper fluidity can be maintained, for example, by the use of thickening materials such as lecithin, by the maintenance of the required particle size in the case of dispersions, and by the use of surfactants.

The compositions of the present invention may also contain adjuvants such as preservatives, wetting agents, emulsifying agents, and dispersing agents. Prevention of the action of microorganisms may be ensured by the inclusion of various antibacterial and antifungal agents, for example, paraben, chlorobutanol, phenol, sorbic acid, and the like. It may also be desirable to include agents to adjust tonicity such as sugars, sodium chloride, and the like. Prolonged absorption of the injectable pharmaceutical form may be brought about by the inclusion of agents which delay absorption such as aluminum monostearate and gelatin.

In one typical embodiment of the invention, the pharmaceutical composition is in a form suitable for i.v. administration, for example by injection or infusion. For intravenous administration, the solution can be dosed as is, or can be injected into an infusion bag (containing a pharmaceutically acceptable excipient, such as 0.9% saline or 5% dextrose), before administration.

In another typical embodiment, the pharmaceutical composition is in a form suitable for sub-cutaneous (s.c.) administration.

Pharmaceutical dosage forms suitable for oral administration include tablets (coated or uncoated), capsules (hard or soft shell), caplets, pills, lozenges, syrups, solutions, powders, granules, elixirs and suspensions, sublingual tablets, wafers or patches such as buccal patches.

Thus, tablet compositions can contain a unit dosage of active compound together with an inert diluent or carrier such as a sugar or sugar alcohol, e.g.; lactose, sucrose, sorbitol or mannitol; and/or a non-sugar derived diluent such as sodium carbonate, calcium phosphate, calcium carbonate, or a cellulose or derivative thereof such as microcrystalline cellulose (MCC), methyl cellulose, ethyl cellulose, hydroxypropyl methyl cellulose, and starches such as corn starch. Tablets may also contain such standard ingredients as binding and granulating agents such as polyvinylpyrrolidone, disintegrants (e.g. swellable crosslinked polymers such as crosslinked carboxymethylcellulose), lubricating agents (e.g. stearates), preservatives (e.g. parabens), antioxidants (e.g. BHT), buffering agents (for example phosphate or citrate buffers), and effervescent agents such as citrate/bicarbonate mixtures. Such excipients are well known and do not need to be discussed in detail here.

Tablets may be designed to release the drug either upon contact with stomach fluids (immediate release tablets) or to release in a controlled manner (controlled release tablets) over a prolonged period of time or with a specific region of the GI tract.

Capsule formulations may be of the hard gelatin or soft gelatin variety and can contain the active component in solid, semi-solid, or liquid form. Gelatin capsules can be formed from animal gelatin or synthetic or plant derived equivalents thereof.

The solid dosage forms (eg; tablets, capsules etc.) can be coated or un-coated. Coatings may act either as a protective film (e.g. a polymer, wax or varnish) or as a mechanism for controlling drug release or for aesthetic or identification purposes. The coating (e.g. a Eudragit™ type polymer) can be designed to release the active component at a desired location within the gastro-intestinal tract. Thus, the coating can be selected so as to degrade under certain pH conditions within the gastrointestinal tract, thereby selectively release the compound in the stomach or in the ileum, duodenum, jejenum or colon.

Instead of, or in addition to, a coating, the drug can be presented in a solid matrix comprising a release controlling agent, for example a release delaying agent which may be adapted to release the compound in a controlled manner in the gastrointestinal tract. Alternatively the drug can be presented in a polymer coating e.g. a polymethacrylate polymer coating, which may be adapted to selectively release the compound under conditions of varying acidity or alkalinity in the gastrointestinal tract. Alternatively, the matrix material or release retarding coating can take the form of an erodible polymer (e.g. a maleic anhydride polymer) which is substantially continuously eroded as the dosage form passes through the gastrointestinal tract. In another alternative, the coating can be designed to disintegrate under microbial action in the gut. As a further alternative, the active compound can be formulated in a delivery system that provides osmotic control of the release of the compound. Osmotic release and other delayed release or sustained release formulations (for example formulations based on ion exchange resins) may be prepared in accordance with methods well known to those skilled in the art.

The compound of formula (I) may be formulated with a carrier and administered in the form of nanoparticles, the increased surface area of the nanoparticles assisting their absorption. In addition, nanoparticles offer the possibility of direct penetration into the cell. Nanoparticle drug delivery systems are described in "Nanoparticle Technology for Drug Delivery", edited by Ram B Gupta and Uday B. Kompella, Informa Healthcare, ISBN 9781574448573, published 13th March 2006. Nanoparticles for drug delivery are also described in J. Control. Release, 2003, 91 (1-2), 167-172, and in Sinha et al., Mol. Cancer Ther. August 1, (2006) 5, 1909.

The pharmaceutical compositions typically comprise from approximately 1% (w/w) to approximately 95% active ingredient and from 99% (w/w) to 5% (w/w) of a pharmaceutically acceptable excipient or combination of excipients. Typically, the compositions comprise from approximately 20% (w/w) to approximately 90%,% (w/w) active ingredient and from 80% (w/w) to 10% of a pharmaceutically acceptable excipient or combination of excipients. The pharmaceutical compositions comprise from approximately 1% to approximately 95%, typically from approximately 20% to approximately 90%, active ingredient. Pharmaceutical compositions according to the invention may be, for example, in unit dose form, such as in the form of ampoules, vials, suppositories, pre-filled syringes, dragées, tablets or capsules.

The pharmaceutically acceptable excipient(s) can be selected according to the desired physical form of the formulation and can, for example, be selected from diluents (e.g solid diluents such as fillers or bulking agents; and liquid diluents such as solvents and co-solvents), disintegrants, buffering agents, lubricants, flow aids, release controlling (e.g. release retarding or delaying polymers or waxes) agents, binders, granulating agents, pigments, plasticizers, antioxidants, preservatives, flavouring agents, taste masking agents, tonicity adjusting agents and coating agents.

The skilled person will have the expertise to select the appropriate amounts of ingredients for use in the formulations. For example tablets and capsules typically contain 0-20% disintegrants, 0-5% lubricants, 0-5% flow aids and/or 0-99% (w/w) fillers/or bulking agents (depending on drug dose). They may also contain 0-10% (w/w) polymer binders, 0-5% (w/w) antioxidants, 0-5% (w/w) pigments. Slow release tablets would in addition contain 0-99% (w/w) polymers (depending on dose). The film coats of the tablet or capsule typically contain 0-10% (w/w) release-controlling (e.g. delaying) polymers, 0-3% (w/w) pigments, and/or 0-2% (w/w) plasticizers.

Parenteral formulations typically contain 0-20% (w/w) buffers, 0-50% (w/w) cosolvents, and/or 0-99% (w/w) Water for Injection (WFI) (depending on dose and if freeze dried). Formulations for intramuscular depots may also contain 0-99% (w/w) oils.

Pharmaceutical compositions for oral administration can be obtained by combining the active ingredient with solid carriers, if desired granulating a resulting mixture, and processing the mixture, if desired or necessary, after the addition of appropriate excipients, into tablets, dragee cores or capsules. It is also possible for them to be incorporated into a polymer or waxy matrix that allow the active ingredients to diffuse or be released in measured amounts.

The compounds of the invention can also be formulated as solid dispersions. Solid dispersions are homogeneous extremely fine disperse phases of two or more solids. Solid solutions (molecularly disperse systems), one type of solid dispersion, are well known for use in pharmaceutical technology (see (Chiou and Riegelman, J. Pharm. Sci., 60, 1281-1300 (1971)) and are useful in increasing dissolution rates and increasing the bioavailability of poorly water-soluble drugs.

This invention also provides solid dosage forms comprising the solid solution described herein. Solid dosage forms include tablets, capsules, chewable tablets and dispersible or effervescent tablets. Known excipients can be blended with the solid solution to provide the desired dosage form. For example, a capsule can contain the solid solution blended with (a) a disintegrant and a lubricant, or (b) a disintegrant, a lubricant and a surfactant. In addition a capsule can contain a bulking agent, such as lactose or microcrystalline cellulose. A tablet can contain the solid solution blended with at least one disintegrant, a lubricant, a surfactant, a bulking agent and a glidant. A chewable tablet can contain the solid solution blended with a bulking agent, a lubricant, and if desired an additional sweetening agent (such as an artificial sweetener), and suitable flavours. Solid solutions may also be formed by spraying solutions of drug and a suitable polymer onto the surface of inert carriers such as sugar beads ('non-pareils'). These beads can subsequently be filled into capsules or compressed into tablets.

The pharmaceutical formulations may be presented to a patient in "patient packs" containing an entire course of treatment in a single package, usually a blister pack. Patient packs have an advantage over traditional prescriptions, where a pharmacist divides a patient's supply of a pharmaceutical from a bulk supply, in that the patient always has access to the package insert contained in the patient pack, normally missing in patient prescriptions. The inclusion of a package insert has been shown to improve patient compliance with the physician's instructions.

Compositions for topical use and nasal delivery include ointments, creams, sprays, patches, gels, liquid drops and inserts (for example intraocular inserts). Such compositions can be formulated in accordance with known methods.

Examples of formulations for rectal or intra-vaginal administration include pessaries and suppositories which may be, for example, formed from a shaped moldable or waxy material containing the active compound. Solutions of the active compound may also be used for rectal administration.

Compositions for administration by inhalation may take the form of inhalable powder compositions or liquid or powder sprays, and can be administrated in standard form using powder inhaler devices or aerosol dispensing devices. Such devices are well known. For administration by inhalation, the powdered formulations typically comprise the active compound together with an inert solid powdered diluent such as lactose.

The compounds of the formula (I) will generally be presented in unit dosage form and, as such, will typically contain sufficient compound to provide a desired level of biological activity. For example, a formulation may contain from 1 nanogram to 2 grams of active ingredient, e.g. from 1 nanogram to 2 milligrams of active ingredient. Within these ranges, particular sub-ranges of compound are 0.1 milligrams to 2 grams of active ingredient (more usually from 10 milligrams to 1 gram, e.g. 50 milligrams to 500 milligrams), or 1 microgram to 20 milligrams (for example 1 microgram to 10 milligrams, e.g. 0.1 milligrams to 2 milligrams of active ingredient).

For oral compositions, a unit dosage form may contain from 1 milligram to 2 grams, more typically 10 milligrams to 1 gram, for example 50 milligrams to 1 gram, e.g. 100 miligrams to 1 gram, of active compound.

The active compound will be administered to a patient in need thereof (for example a human or animal patient) in an amount sufficient to achieve the desired therapeutic effect.

Methods of Treatment

The compounds of the formula (I) and sub-groups as defined herein may be useful in the prophylaxis or treatment of a range of disease states or conditions mediated by SHP2. Examples of such disease states and conditions are set out above.

The compounds are generally administered to a subject in need of such administration, for example a human or animal patient, typically a human.

The compounds will typically be administered in amounts that are therapeutically or prophylactically useful and which generally are non-toxic. However, in certain situations (for example in the case of life threatening diseases), the benefits of administering a compound of the formula (I) may outweigh the disadvantages of any toxic effects or side effects, in which case it may be considered desirable to administer compounds in amounts that are associated with a degree of toxicity.

The compounds may be administered over a prolonged term to maintain beneficial therapeutic effects or may be administered for a short period only. Alternatively they may be administered in a continuous manner or in a manner that provides intermittent dosing (e.g. a pulsatile manner).

A typical daily dose of the compound of formula (I) can be in the range from 100 picograms to 100 milligrams per kilogram of body weight. The compounds of the invention can also be administered by bolus or continuous infusion.

The quantity of compound administered and the type of composition used will be commensurate with the nature of the disease or physiological condition being treated and will be at the discretion of the physician.

It may be beneficial to use a compound of the invention as a single agent or to combine the compound of the invention with another agent which acts via a different mechanism to regulate cell growth thus treating two of the characteristic features of cancer development. Combination experiments can be performed, for example, as described in Chou T C, Talalay P. Quantitative analysis of dose-effect relationships: the combined effects of multiple drugs or enzyme inhibitors. Adv Enzyme Regulat 1984; 22: 27-55.

The compounds as defined herein can be administered as the sole therapeutic agent or they can be administered in combination therapy with one of more other compounds (or therapies) for treatment of a particular disease state, for example a neoplastic disease such as a cancer as hereinbefore defined. For the treatment of the above conditions, the compounds of the invention may be advantageously employed in combination with one or more other medicinal agents, more particularly, with other anti-cancer agents or adjuvants (supporting agents in the therapy) in cancer therapy.

Where the compound of the formula (I) is administered in combination therapy with one, two, three, four or more other therapeutic agents (typically one or two, more typically one), the compounds can be administered simultaneously or sequentially. In the latter case, the two or more compounds will be administered within a period and in an amount and manner that is sufficient to ensure that an advantageous or synergistic effect is achieved.

It will be appreciated that the typical method and order of administration and the respective dosage amounts and regimes for each component of the combination will depend on the particular other medicinal agent and compound of the present invention being administered, their route of administration, the particular tumour being treated and the particular host being treated.

The weight ratio of the compound according to the present invention and the one or more other anticancer agent(s) when given as a combination may be determined by the person skilled in the art. Said ratio and the exact dosage and frequency of administration depends on the particular compound according to the invention and the other anticancer agent(s) used, the particular condition being treated, the severity of the condition being treated, the age, weight, gender, diet, time of administration and general physical condition of the particular patient, the mode of administration as well as other medication the individual may be taking, as is well known to those skilled in the art. Furthermore, it is evident that the effective daily amount may be lowered or increased depending on the response of the treated subject and/or depending on the evaluation of the physician prescribing the compounds of the instant invention.

The compounds of the invention may also be administered in conjunction with non-chemotherapeutic treatments such as radiotherapy, photodynamic therapy, gene therapy; surgery and controlled diets. Radiotherapy may be for radical, palliative, adjuvant, neoadjuvant or prophylactic purposes.

For use in combination therapy with another chemotherapeutic agent, the compound of the formula (I) and one, two, three, four or more other therapeutic agents can be, for example, formulated together in a dosage form containing two, three, four or more therapeutic agents i.e. in a unitary pharmaceutical composition containing all components. In an alternative, the individual therapeutic agents may be formulated separately and presented together in the form of a kit, optionally with instructions for their use.

In a further embodiment, the invention provides a combination of a compound as defined herein and another therapeutic agent.

In another embodiment, the invention provides a pharmaceutical composition comprising a compound as defined herein together with a pharmaceutically acceptable carrier and one or more therapeutic agent(s) as defined above.

In one embodiment the pharmaceutical composition comprises a compound of formula I together with a pharmaceutically acceptable carrier and optionally one or more therapeutic agent(s)

In another embodiment the invention relates to the use of a combination according to the invention in the manufacture of a pharmaceutical composition for inhibiting the growth of tumour cells.

In a further embodiment the invention relates to a product containing a compound of formula I and one or more anticancer agent, as a combined preparation for simultaneous, separate or sequential use in the treatment of patients suffering from cancer.

EXAMPLES

Synthetic Methods

By following methods similar and/or analogous to general procedures below, the compounds set out below were prepared.

The following synthetic procedures are provided for illustration of the methods used; for a given preparation or step the precursor used may not necessarily derive from the individual batch synthesised according to the step in the description given.

Where a compound is described as a mixture of two diastereoisomers/epimers, the configuration of the stereocentre is not specified and is represented by straight lines.

As understood by a person skilled in the art, compounds synthesised using the protocols as indicated may exist as a solvate e.g. hydrate, and/or contain residual solvent or minor impurities. Compounds isolated as a salt form, may be integer stoichiometric i.e. mono- or di-salts, or of intermediate stoichiometry.

Some of the compounds below are isolated as the salt, for example depending on the acid used in the purification method. Some compounds are isolated as the free base.

Compounds containing a single stereocentre are typically isolated as a single isomer using preparative chiral HPLC (as described in general methods); at (or towards) the final stage of the synthetic sequence. In these cases the stereochemistry is designated in accordance with IUPAC, using 'hashed' or 'solid' wedged lines. Unless stated otherwise, a straight line at a stereocentre indicates the compound exists as a mixture of both isomers.

Compounds containing a second stereocentre are typically isolated as a single isomer by preparative achiral and/or chiral HPLC.

The optical isomers may be characterised by their optical activity (i.e. as + and − isomers, or d and l isomers). The stereocentre can also assigned as "R or S" according to the nomenclature developed by Cahn, Ingold and Prelog, see *Advanced Organic Chemistry* by Jerry March, 4th Edition, John Wiley & Sons, New York, 1992, pages 109-114, and see also Cahn, Ingold & Prelog, *Angew. Chem. Int. Ed. Engl.*, 1966, 5, 385-415.

Optical isomers can be separated by a number of techniques including chiral chromatography (chromatography on a chiral support) and such techniques are well known to the person skilled in the art.

As an alternative to chiral chromatography, optical isomers of basic compounds can be separated by forming diastereoisomeric salts with chiral acids such as (+)-tartaric acid, (−)-pyroglutamic acid, (−)-di-toluoyl-L-tartaric acid, (+)-mandelic acid, (−)-malic acid, and (−)-camphorsulfonic acid, separating the diastereoisomeric salts by preferential crystallisation, and then dissociating the salts to give the individual enantiomer of the free base. Likewise, optical iomers of acidic compounds can be separated by forming diastereoisomeric salts with chiral amines such as Brucine, Cinchonidine, quinine etc.

Additionally enantiomeric separation can be achieved by covalently linking a enantiomerically pure chiral auxiliary onto the compound and then performing diastereisomer separation using conventional methods such as chromatography. This is then followed by cleavage of the aforementioned covalent linkage to generate the appropriate enantiomerically pure product. Examples could include making menthol esters of an acidic compound.

Where compounds of the formula (I) exist as two or more optical isomeric forms, one enantiomer in a pair of enantiomers may exhibit advantages over the other enantiomer, for example, in terms of biological activity. Thus, in certain circumstances, it may be desirable to use as a therapeutic agent only one of a pair of enantiomers, or only one of a plurality of diastereoisomers.

Accordingly, the invention provides compositions containing a compound of the formula (I) having one or more chiral centres, wherein at least 55% (e.g. at least 60%, 65%, 70%, 75%, 80%, 85%, 90% or 95%) of the compound of the formula (I) is present as a single optical isomer (e.g. enantiomer or diastereoisomer). In one general embodiment, 99% or more (e.g. substantially all) of the total amount of the compound of the formula (I) may be present as a single optical isomer (e.g. enantiomer or diastereoisomer).

Compounds encompassing double bonds can have an E (entgegen) or Z (zusammen) stereochemistry at said double bond. Substituents on bivalent cyclic or (partially) saturated radicals may have either the cis- or trans-configuration. The terms cis and trans when used herein are in accordance with Chemical Abstracts nomenclature (J. Org. Chem. 1970, 35 (9), 2849-2867), and refer to the position of the substituents on a ring moiety.

Of special interest are those compounds of formula (I) which are stereochemically pure. When a compound of formula (I) is for instance specified as R, this means that the compound is substantially free of the S isomer. If a compound of formula (I) is for instance specified as E, this means that the compound is substantially free of the Z isomer. The terms cis, trans, R, S, E and Z are well known to a person skilled in the art.

The terms exo and endo refer to the stereochemistry of a bridged bicycloalkane, such as a substituted tropane, described in PAC, 1996, 68, 2193, basic terminology of stereochemistry (IUPAC Recommendations 1996). If a substituent, e.g. the amino group, is orientated towards the highest numbered bridge it is given the description exo; if it is orientated away from the highest numbered bridge it is given the description endo. Where there are two substituents on the same carbon atom, the terms exo and endo refer to the higher priority substituent. The FIGURE below illustrates the pictorial representation of how the amino tropane is defined in this patent.

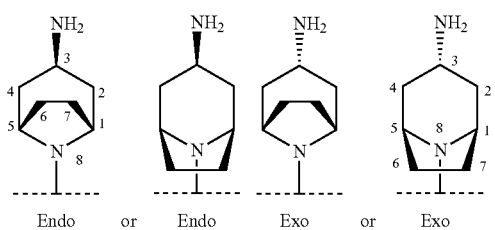

Endo or Endo     Exo or Exo

EXAMPLES

The invention will now be illustrated, but not limited, by reference to the specific embodiments described in the following examples. Compounds are named, for example, using an automated naming package such as AutoNom (MDL), using IUPAC rules or are as named by the chemical supplier. In the examples, the following abbreviations are used.

AcOH acetic acid
Aq. Aqueous
Boc tert-butyloxycarbonyl
BuLi butyllithium
Cbz Carboxybenzyl
DCE 1,2-dichloroethane
DCM dichloromethane
DIPEA N,N-Diisopropylethylamine
DMF N,N-dimethylformamide
DMSO dimethyl sulfoxide
$Et_3N$ triethylamine
EtOAc ethyl acetate
EtOH ethanol
$Et_2O$ diethyl ether
$Et_3SiH$ Triethylsilane
HOAt 1-hydroxyazabenzotriazole
HPLC high pressure liquid chromatography
IPA isopropyl alcohol
KO$^t$Bu Potassium tert-butoxide
LED Light emitting diode
MeCN acetonitrile
MeOH methanol
min minutes
MS mass spectrometry
$NaBH(OAc)_3$ sodium triacetoxyborohydride
NaOEt Sodium ethoxide
NaOtBu Sodium tert-butoxide
NMP N-methyl-2-pyrrolidinone
NMR nuclear magnetic resonance spectroscopy
Pd/C Palladium on carbon
$Pd_2(dba)_3$ tris(dibenzylideneacetone)dipalladium(0)
$Pd(OAc)_2$ palladium(II) acetate
$Pd(PPh_3)_4$ tetrakis(triphenylphosphine)palladium(0)
petrol petroleum ether fraction with boiling point range 40-60° C.
RT Room temperature
sat Saturated
SEM 2-(trimethylsilyl)ethoxymethyl
$SiO_2$ silica
TBAF tetrabutylammonium fluoride
TFA trifluoroacetic acid
THF tetrahydrofuran
TLC Thin Layer chromatography
TMSOTf Trimethylsilyl trifluoromethanesulfonate Synthetic Methods All starting materials and solvents were obtained either from commercial sources or prepared according to the literature citation. Unless otherwise stated all reactions were stirred. Organic solutions were routinely dried over anhydrous magnesium sulfate. Hydrogenations were performed on a Parr hydrogenator, a Thales H-cube flow reactor under the conditions stated or under a balloon of hydrogen. Microwave reactions were performed in a CEM Discover and Smithcreator microwave reactor, heating to a constant temperature using variable power microwave irradiation. Normal phase column chromatography was routinely carried out on an automated flash chromatography system such as CombiFlash Companion or CombiFlash RF system using pre-packed silica (230-400 mesh, 40-63 μm) cartridges. SCX was purchased from Supelco and treated with 1M hydrochloric acid prior to use. Unless stated otherwise the reaction mixture to be purified was first diluted with MeOH and made acidic with a few drops of AcOH. This solution was loaded directly onto the SCX and washed with MeOH. The desired material was then eluted by washing with a solvent such as 1% $NH_3$ in MeOH. $NH_2$ ion exchange silica gel purification was done with Strata $NH_2$ (55 μm, 70 Å) columns, loaded directly onto the $NH_2$ column and eluting with a solvent such as methanol. Biotage® KP-NH SNAP silica gel columns were purchased from Biotage®. Reverse phase purification was done using Biotage® SNAP Ultra C18 silica gel columns and were purchased from Biotage®.

NMR Data $^1$H NMR spectra were acquired on a Bruker Avance III spectrometer at 400 MHz, an AL400 (400 MHz; produced by JEOL), a Mercury 400 (400 MHz; produced by Agilent Technologies, Inc.), or a 500 MHz Bruker Avance III HD NMR Spectrometer. Either the central peaks of chloroform-d, dimethylsulfoxide-$d_6$ or an internal standard of tetramethylsilane were used as references. For NMR data, where the number of protons assigned is less than the theoretical number of protons in the molecule, it is assumed that the apparently missing signal(s) is/are obscured by solvent and/or water peaks. In addition, where spectra were obtained in protic NMR solvents, exchange of NH and/or OH protons with solvent occurs and hence such signals are normally not observed.

Analytical and Preparative LC-MS Systems
Analytical LC-MS System and Method Description In the following examples, compounds were characterised by mass spectroscopy using the systems and operating conditions set out below. Where atoms with different isotopes are present and a single mass quoted, the mass quoted for the compound is the monoisotopic mass (i.e. $^{35}Cl$; $^{79}Br$ etc.).

Shimadzu Nexera
HPLC System: Shimadzu SIL-30AC autosampler/2× Shimadzu LC-30AD pumps
Mass Spec Detector: Shimadzu LCMS-2020 single quadrupole MS
Second Detector: Shimadzu SPD-M20A diode array detector
MS Operating Conditions
Qarray DC voltage: 20V on ES Pos (−20V on ES Neg)
Drying gas flow: 20.0 L/min
DL Temperature: 300° C.
Heat Block Temperature: 350° C.
Nebulising Gas Flow: 1.5 L/min
Scan Range:
Ionisation Mode: ElectroSpray Positive-Negative switching
Agilent 1290 Infinity II—6130 LC-MS System HPLC System: Agilent 1290 Infinity II
Mass Spec Detector: Agilent 6130 single quadrupole
Second Detector: Agilent 1290 Infinity II Diode Array Detector
MS Operating Conditions
Capillary voltage: 3000V
Fragmentor/Gain: 70
Gain: 1
Drying gas flow: 13.0 L/min
Gas Temperature: 350° C.
Nebuliser Pressure: 40 psig
Scan Range: 150-1000 amu
Sheath Gas Temperature: 360° C.
Sheath Gas Flow: 10.0 L/min
Nozzle Voltage: 300 (+ve mode)/1750 (−ve mode)
Ionisation Mode: Agilent Jet Stream Electrospray Positive-Negative switching
LCMS spectra were alternatively measured with an SQD manufactured by Waters Corporation under the following two conditions, and the $[M+H]^+$ values were shown.
MS detection: ESI positive
UV detection: 254 nm
Column flow rate: 0.5 mL/min
Mobile phase: water/acetonitrile (0.1% formic acid)
Injection volume: 1 µL
Method
Column: Acguity BEH, 2.1×50 mm, 1.7 µm
Gradient:

| Time (min) | water/acetonitrile (0.1% formic acid) |
|---|---|
| 0 | 95/5 |
| 0.1 | 95/5 |
| 2.1 | 5/95 |
| 3.0 | STOP |

Preparative LC-MS System and Method Description

Preparative LC-MS is a standard and effective method used for the purification of small organic molecules such as the compounds described herein. The methods for the liquid chromatography (LC) and mass spectrometry (MS) can be varied to provide better separation of the crude materials and improved detection of the samples by MS. Optimisation of the preparative gradient LC method will involve varying columns, volatile eluents and modifiers, and gradients. Methods are well known in the art for optimising preparative LC-MS methods and then using them to purify compounds. Such methods are described in Rosentreter U, Huber U.; Optimal fraction collecting in preparative LC/MS; *J Comb Chem.*; 2004; 6(2), 159-64 and Leister W, Strauss K, Wisnoski D, Zhao Z, Lindsley C., Development of a custom high-throughput preparative liquid chromatography/mass spectrometer platform for the preparative purification and analytical analysis of compound libraries; *J Comb Chem.*; 2003; 5(3); 322-9.

Several systems for purifying compounds via preparative LC-MS are described below although a person skilled in the art will appreciate that alternative systems and methods to those described could be used. From the information provided herein, or employing alternative chromatographic systems, a person skilled in the art could purify the compounds described herein by preparative LC-MS.

Mass Directed Purification LC-MS System

Preparative LC-MS is a standard and effective method used for the purification of small organic molecules such as the compounds described herein. The methods for the liquid chromatography (LC) and mass spectrometry (MS) can be varied to provide better separation of the crude materials and improved detection of the samples by MS. Optimisation of the preparative gradient LC method will involve varying columns, volatile eluents and modifiers, and gradients. Methods are well known in the art for optimising preparative LC-MS methods and then using them to purify compounds. Such methods are described in Rosentreter U, Huber U.; Optimal fraction collecting in preparative LC/MS; *J Comb Chem.*; 2004; 6(2), 159-64 and Leister W, Strauss K, Wisnoski D, Zhao Z, Lindsley C., Development of a custom high-throughput preparative liquid chromatography/mass spectrometer platform for the preparative purification and analytical analysis of compound libraries; *J Comb Chem.*; 2003; 5(3); 322-9.

One such system for purifying compounds via preparative LC-MS is described below although a person skilled in the art will appreciate that alternative systems and methods to those described could be used. In particular, normal phase preparative LC based methods might be used in place of the reverse phase methods described here. Most preparative LC-MS systems utilise reverse phase LC and volatile acidic modifiers, since the approach is very effective for the purification of small molecules and because the eluents are compatible with positive ion electrospray mass spectrometry. Employing other chromatographic solutions e.g. normal phase LC, alternatively buffered mobile phase, basic modifiers etc as outlined in the analytical methods described above could alternatively be used to purify the compounds.

Agilent 1260 LC-MS Preparative System
Hardware:
Autosampler: G2260A Prep ALS
Pumps: 2×G1361A Prep Pumps for preparative flow gradient, G1311C Quat Pump VL for pumping modifier in prep flow and G1310B Iso Pump for make-up pump flow
UV detector: G1365C 1260 MWD
MS detector: G6120B Quadrupole LC-MS
Fraction Collector: 2×G1364B 1260 FC-PS
G1968D Active Splitter
Software:
Agilent OpenLab C01.06
Agilent MS operating conditions:
Capillary voltage: 3000 V
Fragmentor/Gain: 70/1
Drying gas flow: 12.0 L/min
Drying Gas Temperature: 275° C.
Nebuliser Pressure: 40 psig
Vaporizer Temperature: 200° C.
Scan Range: 125-800 amu
Ionisation Mode: ElectroSpray Positive
Columns:
1. Waters XBridge Prep C18 5 m OBD 100×19 mm
Typically used for ammonium bicarbonate-based methods
2. Waters SunFire Prep C18 OBD 5 m 100×19 mm
Typically used for TFA-based methods
3. Waters XBridge Prep Phenyl 5 m OBD 100×19 mm
Typically used for neutral pH ammonium acetate-based methods
4. Supelco Ascentis RP-Amide 5 m 100×21.2 mm
Typically used for formic acid-based methods
5. Phenomenex Synergi Fusion-RP 4 m 100×21.2 mm
Typically used for formic acid-based methods
Eluents:
Solvent A: Water
Solvent B: Acetonitrile
Solvent C: Choice of available modifiers:
2.5% Trifluoroacetic acid in water 2.5% Formic acid in water
250 mM ammonium bicarbonate in water pH 9.4
250 mM ammonium acetate
Make Up Solvent:
90:10 Methanol:Water+0.2% Formic Acid (for all chromatography types)

Methods:

According to the analytical trace the most appropriate preparative chromatography type was chosen. A typical routine was to run an analytical LC-MS using the type of chromatography (low or high pH) most suited for compound structure. Once the analytical trace showed good chromatography a suitable preparative method of the same type was chosen. Typical running conditions for both low and high pH chromatography methods were:

Flow rate: 25 mL/min

Gradient: Generally all gradients had an initial 0.4 min step with 95% A+5% B (with additional modifier C). Then according to analytical trace a 6.6 min gradient was chosen in order to achieve good separation (e.g. from 5% to 50% B for early retaining compounds; from 35% to 80% B for middle retaining compounds and so on)

Wash: 1.6 minute wash step was performed at the end of the gradient

Make Up flow rate: 0.8 mL/min

Solvent:

All compounds were usually dissolved in 100% MeOH or 100% DMSO

From the information provided someone skilled in the art could purify the compounds described herein by preparative LC-MS.

Waters Fractionlynx System
Hardware:
2767 Dual Loop Autosampler/Fraction Collector
2525 preparative pump
CFO (column fluidic organiser) for column selection
RMA (Waters reagent manager) as make up pump
Waters ZQ Mass Spectrometer
Waters 2996 Photo Diode Array detector
Waters ZQ Mass Spectrometer
Software:
Masslynx 4.1
Waters MS running conditions:
Capillary voltage: 3.5 kV (3.2 kV on ES Negative)
Cone voltage: 25 V
Source Temperature: 120° C.
Multiplier: 500 V
Scan Range: 125-800 amu
Ionisation Mode: ElectroSpray Positive or ElectroSpray Negative Alternatively Reverse phase preparative HPLC column chromatography was performed at the following conditions.
Column: CAPCELL PAK C18 AQ manufactured by SHISEIDO, 30×50 mm, 5 µm
UV detection: 254 nm
Column flow rate: 40 mL/min
Mobile phase: water/acetonitrile (0.1% formic acid)
Injection volume: 1.0 mL
Basic gradient method: water/acetonitrile 0%-50% (8 minutes)

Achiral Preparative Chromatography

The compound examples described have undergone HPLC purification, where indicated, using methods developed following recommendations as described in Snyder L. R., Dolan J. W., High-Performance Gradient Elution The Practical Application of the Linear-Solvent-Strength Model, Wiley, Hoboken, 2007.

Chiral Preparative Chromatography

Preparative separations using Chiral Stationary Phases (CSPs) are the natural technique to apply to the resolution of enantiomeric mixtures. Equally, it can be applied to the separation of diastereomers and achiral molecules. Methods are well known in the art for optimising preparative chiral separations on CSPs and then using them to purify compounds. Such methods are described in Beesley T. E., Scott R. P. W.; Chiral Chromatography; Wiley, Chichester, 1998.

Preparation 1: 7-Bromo-3-chloro-5H-pyrrolo[2,3-b]pyrazine

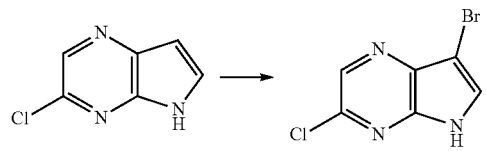 [SMILES: Clc1cnc2cc[nH]c2n1 ; Clc1cnc2c(Br)c[nH]c2n1]

N-Bromosuccinimide (25.5 g, 0.143 mol) was added gradually to an ice bath cooled, stirred mixture of 3-chloro-5H-pyrrolo[2,3-b]pyrazine (20 g, 0.13 mol) in DMF (200 mL) under nitrogen. The mixture was aged overnight, warming to ambient temperature. Water (200 mL) was added and the resulting slurry was stirred at RT for 1 h. The solid was isolated by filtration, and washed with water (100 mL), then petrol (100 mL) and dried overnight in vacuo at 40° C., to give the title compound (27.7 g). $^1$H NMR (400 MHz, DMSO-d$_6$): 12.73 (1H, s), 8.56 (1H, s), 8.18 (1H, d).

Preparation 2: 3-Chloro-7-iodo-5H-pyrrolo[2,3-b]pyrazine

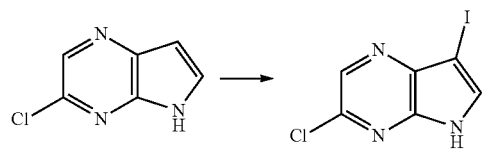 [SMILES: Clc1cnc2cc[nH]c2n1 ; Clc1cnc2c(I)c[nH]c2n1]

N-Iodosuccinimide (7.88 g, 35 mmol) was added to a solution of 3-chloro-5H-pyrrolo[2,3-b]pyrazine (5.36 g, 35 mmol) in DMF (175 mL) at RT. The reaction was stirred for 1 h at RT. Water was added until precipitation occurred. The solid was collected by vacuum filtration, washing with water and dried in a vacuum oven for 24 h, to give the title compound (9.06 g). MS: [M+H]$^+$=279.

Preparation 3: 3-Chloro-7-iodo-5-{[2-(trimethylsilyl)ethoxy]methyl}-5H-pyrrolo[2,3-b]pyrazine

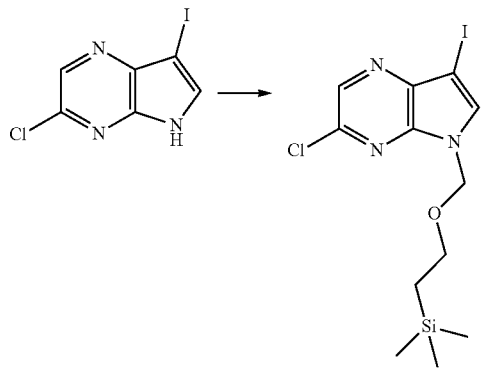 [SMILES: Clc1cnc2c(I)c[nH]c2n1 ; C[Si](C)(C)CCOCn1cc(I)c2ncc(Cl)nc21]

3-Chloro-7-iodo-5H-pyrrolo[2,3-b]pyrazine (9.06 g, 32.6 mmol) was dissolved in THF (163 mL) and sodium hydride (60% in min. oil, 1.70 g, 42.4 mmol) was added portionwise over 1 h at 0-4° C. (ice bath). The reaction was warmed to 11° C. and then cooled to 0-4° C. (ice bath). 2-(Trimethylsilyl)ethoxymethyl chloride (7.07 g, 42.4 mmol) was added dropwise keeping the temperature below 7° C. and the deep red/orange solution stirred for 1 h and warmed to RT for 2 h. Sat. NH$_4$Cl was added and the mixture extracted with EtOAc (3×). The combined organics were passed through a phase separator and concentrated in vacuo. The residue was purified by column chromatography on silica gel (gradient elution, 0-50%, EtOAc/petrol), to give the title compound (13 g), MS: [M+H]$^+$=410.

Preparation 4: 7-Bromo-3-chloro-5-{[2-(trimethylsilyl)ethoxy]methyl}-5H-pyrrolo[2,3-b]pyrazine

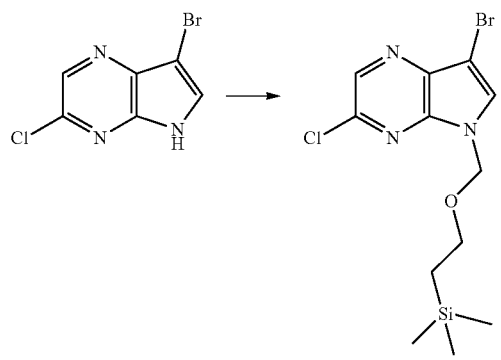 [SMILES: Clc1cnc2c(Br)c[nH]c2n1 ; C[Si](C)(C)CCOCn1cc(Br)c2ncc(Cl)nc21]

Prepared in an analogous way to 3-chloro-7-iodo-5-{[2-(trimethylsilyl)ethoxy]methyl}-5H-pyrrolo[2,3-b]pyrazine except using 7-bromo-3-chloro-5H-pyrrolo[2,3-b]pyrazine, to give the title compound, $^1$H NMR (400 MHz, DMSO-d$_6$): 8.64 (1H, s), 8.38 (1H, s), 5.60 (2H, s), 3.54 (2H, t), 0.92-0.77 (2H, m), −0.08-0.10 (9H, m).

Preparation 5: 3-Chloro-7-iodo-N,N-dimethyl-5H-pyrrolo[2,3-b]pyrazine-5-sulfonamide

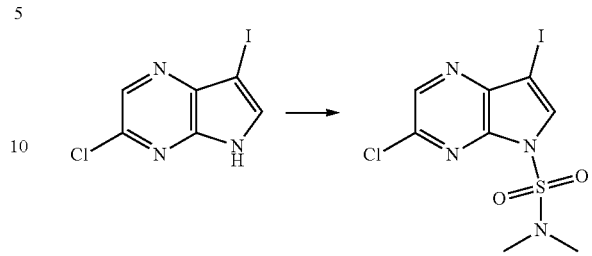

3-Chloro-7-iodo-5H-pyrrolo[2,3-b]pyrazine (5.0 g, 17.93 mmol) was dissolved in THF (89.6 mL) and sodium hydride (60% in mineral oil, 0.932 g, 23.31 mmol) was added portionwise over 1 h at 0-4° C. (ice bath). Dimethylsulfamoyl chloride (2.5 mL, 23.31 mL) was added dropwise and the solution stirred for 18 h. Sat. NH$_4$Cl was added and the mixture extracted with EtOAc (3×). The combined organics were passed through a phase separator and concentrated in vacuo. The residue was purified by column chromatography on silica gel (DCM), to give the title compound (3.12 g), $^1$H NMR (400 MHz, DMSO-d$_6$): 8.76 (1H, s), 8.34 (1H, s), 2.97 (6H, s).

Preparation 6: 8-Benzyl-3-methyl-8-azabicyclo[3.2.1]octan-3-ol

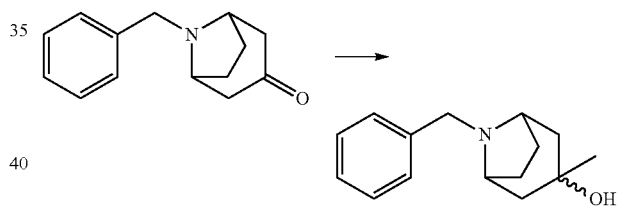

To a solution of 8-benzyl-8-azabicyclo[3.2.1]octan-3-one (4.28 g, 19.9 mmol) in THF (47.0 mL) was added 3.0 mol/L methylmagnesium chloride in THF solution (29.4 mL, 88.4 mmol) under MeCN-dry ice bath, and the reaction stirred for 30 min at this temperature and then 20 h at RT. Sat. NH$_4$Cl solution was added at 0° C. and the mixture was extracted with EtOAc. The combined organic layers were washed with water and sat. sodium chloride solution, and dried over anhydrous sodium sulfate. After the desiccant was filtered off, the solvent was removed at reduced pressure. The residue was purified by column chromatography on silica gel (NH silica gel, gradient elution, 20-50%, CH$_2$Cl$_2$:petrol), to give the title compound (4.50 g) MS: [M+H]$^+$=232.

Preparation 7: N-{endo-8-Benzyl-3-methyl-8-azabicyclo[3.2.1]octan-3-yl}acetamide

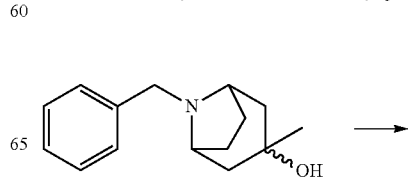

-continued

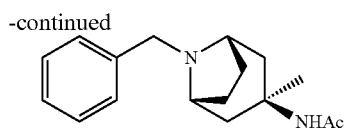

To a solution of 8-benzyl-3-methyl-8-azabicyclo[3.2.1]octan-3-ol (4.28 g, 18.48 mmol) in acetonitrile (26 mL) was added conc. sulfuric acid (18 mL) dropwise over 15 min. at 0° C., and stirred for 18 h at RT. The reaction mixture was poured into ice (ca. 200 g), and basified (ca pH 10) with 5 mol/L sodium hydroxide solution (ca. 100 mL). The reaction mixture was extracted with EtOAc. The combined organic layers were washed with water and sat. sodium chloride solution, and dried over anhydrous sodium sulfate. After the desiccant was filtered off, the solvent was removed at reduced pressure. The residue was washed with diethylether and petrol, to give the title compound (2.45 g) MS: [M+H]$^+$=273.

Preparation 8: tert-Butyl N-{endo-8-benzyl-3-methyl-8-azabicyclo[3.2.1]octan-3-yl}carbamate

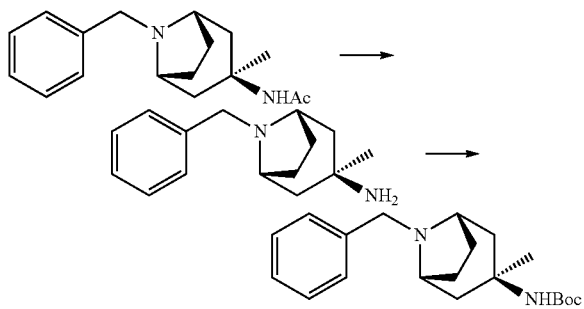

To N-{endo-8-benzyl-3-methyl-8-azabicyclo[3.2.1]octan-3-yl}acetamide was added 6 mol/L hydrochloric acid (80 mL) and the mixture stirred for 11 days at 140° C. The reaction mixture was basified with 4 mol/L sodium hydroxide solution at 0° C., and 1,4-dioxane (20 mL), and di-tert-butyl dicarbonate (3.93 g, 18.0 mmol) was added. The reaction was stirred for 1 h at 0° C., and 18 h at RT. The reaction mixture was extracted with EtOAc. The combined organic layers were washed with water and sat. sodium chloride solution, and dried over anhydrous sodium sulfate. After the desiccant was filtered off, the solvent was removed at reduced pressure. The residue was purified by column chromatography on silica gel (gradient elution, 0-10% MeOH-DCM) to give the title compound (3.05 g). MS: [M+H]$^+$=331.

Preparation 9: tert-Butyl N-{endo-3-methyl-8-azabicyclo[3.2.1]octan-3-yl}carbamate

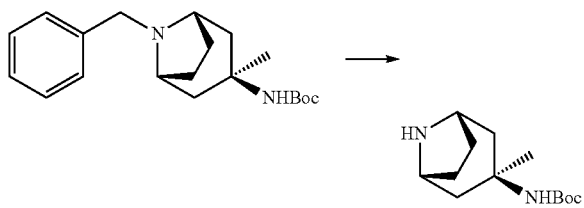

Pd(OH)$_2$/C (10 wt % Pd, 637 mg, 0.454 mmol) was added to a solution of tert-butyl N-{endo-8-benzyl-3-methyl-8-azabicyclo[3.2.1]octan-3-yl}carbamate (3.0 g, 9.08 mmol) in MeOH (20 mL) and the reaction subjected to hydrogenation at ambient pressure and RT for 24 h. The reaction was filtered through Celite and the filtrate evaporated. The residue was triturated with diethyl ether to give the title compound (1.86 g). MS: [M+H]$^+$=241.

Preparation 10: rac-tert-Butyl (1S,2R,3R,5R)-3-(benzylamino)-2-fluoro-8-azabicyclo[3.2.1]octane-8-carboxylate

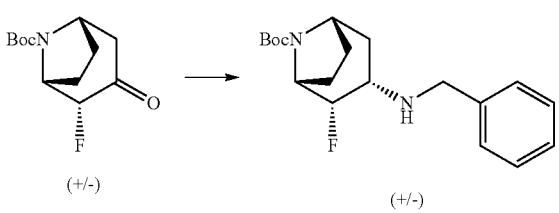 [SMILES: CC(C)(C)OC(=O)N1[C@H]2CC[C@@H]1[C@@H](F)C(=O)C2 ; CC(C)(C)OC(=O)N1[C@H]2CC[C@@H]1[C@@H](F)[C@@H](NCc1ccccc1)C2]

To a solution of rac-tert-butyl (1S,2S,5R)-2-fluoro-3-oxo-8-azabicyclo[3.2.1]octane-8-carboxylate (10 g, 41.1 mmol) in DCE (97.93 mL), were added benzylamine (4.94 mL, 45.24 mmol) and sodium triacetoxyborohydride (13.08 g, 61.70 mmol). After stirring for 18 h at RT, the reaction was partitioned between DCM (100 mL) and sat. sodium carbonate (200 mL). The organic layer was separated, passed through a phase separator and concentrated in vacuo. The residue was partitioned between diethyl ether (100 mL) and extracted into 0.1M HCl (3×100 mL). The combined aq. extracts were washed with diethyl ether (300 mL). After basifying with 5M NaOH until pH 9, the aq. phase was extracted with EtOAc (3×300 mL), and the combined organics were dried over sodium sulfate, filtered and concentrated in vacuo. The crude was purified by column chromatography on silica gel (gradient elution, 0-50%, EtOAc/petrol), to give the title compound (1.83 g), $^1$H NMR (400 MHz, Me-d$_3$-OD): 7.41-7.30 (4H, m), 7.30-7.23 (1H, m), 4.69 (1H, d), 4.50 (1H, s), 4.25 (1H, s), 3.85 (1H, d), 3.80 (1H, d), 3.05-2.82 (1H, m), 1.93 (2H, s), 1.87-1.79 (1H, m), 1.72 (1H, d), 1.65-1.51 (2H, m), 1.47 (9H, s).

Preparation 11: rac-tert-Butyl (1S,2R,3R,5R)-3-amino-2-fluoro-8-azabicyclo[3.2.1]octane-8-carboxylate

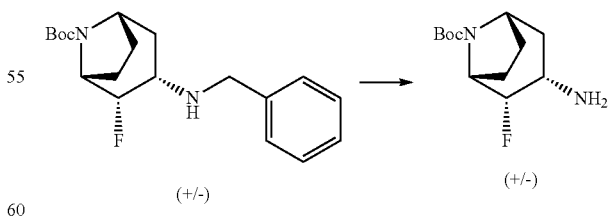

rac-tert-Butyl (1S,2R,3R,5R)-3-(benzylamino)-2-fluoro-8-azabicyclo[3.2.1]octane-8-carboxylate (0.419 g, 1.25 mmol) and Pd/C (10%, 0.133 g, 0.13 mmol) were dissolved in glacial acetic acid/ethanol (1:3, 6.27 mL) and stirred under a hydrogen atmosphere at 1 bar for 2 h. The mixture was filtered using a GF/A glass microfiber filter and concentrated in vacuo. The residue was partitioned between chloroform/IPA (9:1) (5.0 mL) and sat. sodium bicarbonate (5.0 mL). The aq. phase was extracted with chloroform/IPA (9:1) (3×), and the combined organics were passed through a phase separator and concentrated in vacuo, to give the title compound (305 mg), $^1$H NMR (400 MHz, DMSO-$d_6$): 4.46-4.37 (1H, m), 4.31 (2H, s), 4.07 (1H, s), 3.00-2.81 (1H, m), 1.79 (2H, d), 1.64-1.43 (5H, m), 1.43-1.34 (9H, m).

Preparation 12: rac-tert-Butyl (1S,2R,3R,5R)-3-{[(benzyloxy)carbonyl]amino}-2-fluoro-8-azabicyclo[3.2.1]octane-8-carboxylate

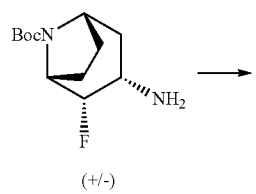

(+/-)

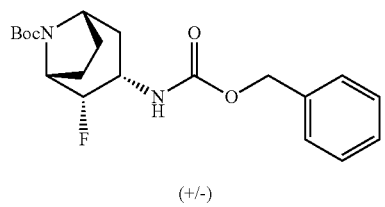

(+/-)

To rac-tert-butyl (1S,2R,3R,5R)-3-amino-2-fluoro-8-azabicyclo[3.2.1]octane-8-carboxylate (305 mg, 1.25 mmol) dissolved in DCM/THF (8:1, 6.25 mL), was added DIPEA (0.653 mL, 3.75 mmol) and benzyl chloroformate (0.213 mL, 1.50 mmol) under ice-cooling. The resulting mixture was stirred at RT for 18 h. Sat. sodium bicarbonate solution was added to the reaction mixture, which was extracted with dichloromethane three times. The combined organics were passed through a phase separator and concentrated in vacuo. The residue was purified by column chromatography on silica gel (gradient elution, 0-40%, EtOAc/petrol), to give the title compound (487 mg), $^1$H NMR (400 MHz, DMSO-$d_6$): 7.37 (5H, s), 5.77 (1H, s), 5.05 (2H, s), 4.56 (1H, d), 4.35 (1H, s), 4.13 (1H, s), 4.01-3.73 (1H, m), 1.91-1.49 (6H, m), 1.40 (9H, s).

Preparation 13: rac-Benzyl N-[(1S,2S,3R,5R)-2-fluoro-8-azabicyclo[3.2.1]octan-3-yl]carbamate hydrochloride

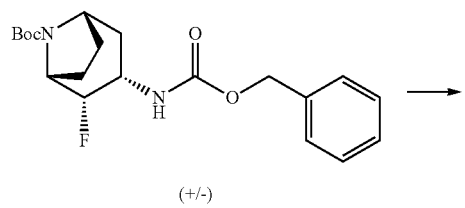

(+/-)

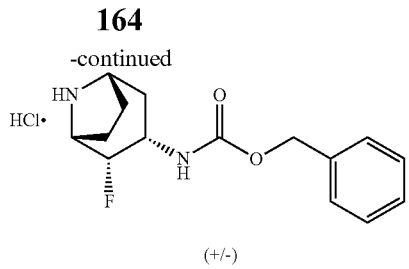

(+/-)

To rac-tert-butyl (1S,2R,3R,5R)-3-{[(benzyloxy)carbonyl]amino}-2-fluoro-8-azabicyclo[3.2.1]octane-8-carboxylate (0.487 g, 1.29 mmol) in DCM (2.15 mL) was added 4M HCl in 1,4-dioxane (2.15 mL) at RT and stirred for 1.5 h. The reaction was concentrated in vacuo, to give the title compound (404 mg) $^1$H NMR (400 MHz, Me-$d_3$-OD): 7.49-7.28 (5H, m), 5.14 (2H, s), 4.38-4.24 (1H, m), 4.17-3.98 (2H, m), 2.32-2.06 (4H, m), 2.03 (2H, dd).

General Procedure 1: tert-Butyl N-[endo-8-(7-iodo-5-{[2-(trimethylsilyl)ethoxy]methyl}-5H-pyrrolo[2,3-b]pyrazin-3-yl)-8-azabicyclo[3.2.1]octan-3-yl]carbamate

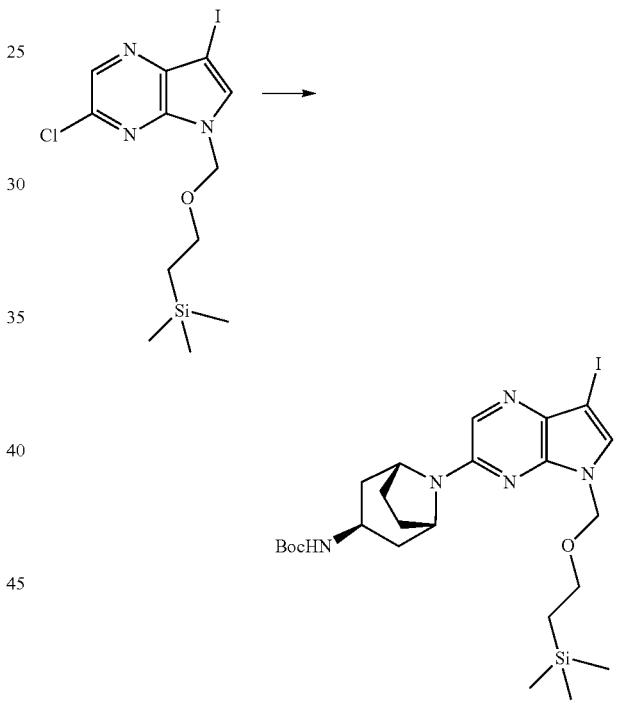

A 30 mL microwave tube was charged with 3-chloro-7-iodo-5-{[2-(trimethylsilyl)ethoxy]methyl}-5H-pyrrolo[2,3-b]pyrazine (2.90 g, 7.08 mmol), tert-butyl N-(endo-8-azabicyclo[3.2.1]octan-3-yl)carbamate (3.20 g, 14.2 mmol) and NMP (6.0 mL). The vessel was de-gassed and back-filled with $N_2$ (3×). Di-iso-propylethylamine (2.47 mL, 14.2 mmol) was added and the tube was capped, sealed and heated to 150° C. for 3 days in a sand bath. After cooling, the reaction was diluted with EtOAc, then washed with brine/sat. aq. $NH_4Cl$ (3×). The organic phase was dried ($MgSO_4$) and evaporated. The residue was purified by column chromatography on silica gel (gradient elution, 5-35% EtOAc/petrol) to give the title compound (2.59 g). MS: $[M+H]^+=600.2$.

Compounds of Table 1 below were prepared using procedures analogous to that described in general procedure 1, starting from the appropriate substituted protected pyrrolopyrazine and varying the amine (synthesised as described above with any significant variations indicated below).

TABLE 1

| Compound | Compound Name | NMR or MS: [M + H]+ m/z | Procedure |
|---|---|---|---|
| | tert-Butyl N-[exo-8-(7-bromo-5-{[2-(trimethylsilyl)ethoxy]methyl}-5H-pyrrolo[2,3-b]pyrazin-3-yl)-8-azabicyclo[3.2.1]octan-3-yl]carbamate | 552 | Prepared as general procedure 1 using 7-bromo-3-chloro-5-{[2-(trimethylsilyl)ethoxy]methyl}-5H-pyrrolo[2,3-b]pyrazine, tert-butyl N-(exo-8-azabicyclo[3.2.1]octan-3-yl)carbamate and DMSO instead of NMP as solvent, heating for 18 h. |
| | tert-Butyl N-[exo-8-(7-iodo-5-{[2-(trimethylsilyl)ethoxy]methyl}-5H-pyrrolo[2,3-b]pyrazin-3-yl)-8-azabicyclo[3.2.1]octan-3-yl]carbamate | 600 | Prepared as general procedure 1 using 3-chloro-7-iodo-5-{[2-(trimethylsilyl)ethoxy]methyl}-5H-pyrrolo[2,3-b]pyrazine and tert-butyl N-(exo-8-azabicyclo[3.2.1]octan-3-yl)carbamate, heating for 96 h. |
| | tert-Butyl N-[endo-8-(7-bromo-5-{[2-(trimethylsilyl)ethoxy]methyl}-5H-pyrrolo[2,3-b]pyrazin-3-yl)-8-azabicyclo[3.2.1]octan-3-yl]carbamate | 552 | Prepared as general procedure 1 using 7-bromo-3-chloro-5-{[2-(trimethylsilyl)ethoxy]methyl}-5H-pyrrolo[2,3-b]pyrazine and DMSO instead of NMP as solvent, heating for 12 h. |
| | exo-8-(7-Bromo-5-{[2-(trimethylsilyl)ethoxy]methyl}-5H-pyrrolo[2,3-b]pyrazin-3-yl)-8-azabicyclo[3.2.1]octane-3-carbonitrile | 462 | Prepared as general procedure 1 using 7-bromo-3-chloro-5-{[2-(trimethylsilyl)ethoxy]methyl}-5H-pyrrolo[2,3-b]pyrazine, exo-8-azabicyclo[3.2.1]octane-3-carbonitrile and DMSO instead of NMP as solvent, heating for 18 h. |
| | tert-Butyl N-[9-(7-bromo-5-{[2-(trimethylsilyl)ethoxy]methyl}-5H-pyrrolo[2,3-b]pyrazin-3-yl)-9-azabicyclo[3.3.1]nonan-3-yl]carbamate | 566 | Prepared as general procedure 1 using 7-bromo-3-chloro-5-{[2-(trimethylsilyl)ethoxy]methyl}-5H-pyrrolo[2,3-b]pyrazine, tert-butyl N-{9-azabicyclo[3.3.1]nonan-3-yl}carbamate and DMSO instead of NMP as solvent, heating for 18 h. |

TABLE 1-continued

| Compound | Compound Name | NMR or MS: [M + H]+ m/z | Procedure |
|---|---|---|---|
| (structure with BocHN-piperidine, pyrrolopyrazine-Br, SEM group) | tert-Butyl N-[1-(7-bromo-5-{[2-(trimethylsilyl)ethoxy]methyl}-5H-pyrrolo[2,3-b]pyrazin-3-yl)piperidin-4-yl]carbamate | 526 | Prepared as general procedure 1 using 7-bromo-3-chloro-5-{[2-(trimethylsilyl)ethoxy]methyl}-5H-pyrrolo[2,3-b]pyrazine, tert-butyl N-(piperidin-4-yl)carbamate and DMSO instead of NMP as solvent, heating for 18 h. |
| (structure with BocHN-4-methylpiperidine, pyrrolopyrazine-Br, SEM group) | tert-Butyl N-[1-(7-bromo-5-{[2-(trimethylsilyl)ethoxy]methyl}-5H-pyrrolo[2,3-b]pyrazin-3-yl)-4-methylpiperidin-4-yl]carbamate | 540 | Prepared as general procedure 1 using 7-bromo-3-chloro-5-{[2-(trimethylsilyl)ethoxy]methyl}-5H-pyrrolo[2,3-b]pyrazine, tert-butyl N-(4-methylpiperidin-4-yl)-carbamate and DMSO instead of NMP as solvent, heating for 18 h. |
| (structure with BocHN-methyl-azabicyclo, pyrrolopyrazine-Br, SEM group) | tert-Butyl N-[endo-8-(7-bromo-5-{[2-(trimethylsilyl)ethoxy]methyl}-5H-pyrrolo[2,3-b]pyrazin-3-yl)-3-methyl-8-azabicyclo[3.2.1]octan-3-yl]carbamate | 566 | Prepared as general procedure 1 using 7-bromo-3-chloro-5-{[2-(trimethylsilyl)ethoxy]methyl}-5H-pyrrolo[2,3-b]pyrazine, and tert-butyl N-{endo-3-methyl-8-azabicyclo[3.2.1]octan-3-yl}carbamate using DMSO instead of NMP as solvent, heating for 18 h. |
| (structure with BocN-diazaspiro, pyrrolopyrazine-Br, SEM group) | tert-Butyl 7-(7-bromo-5-{[2-(trimethylsilyl)ethoxy]methyl}-5H-pyrrolo[2,3-b]pyrazin-3-yl)-2,7-diazaspiro[3.5]nonane-2-carboxylate | 552 | Prepared as general procedure 1 using 7-bromo-3-chloro-5-{[2-(trimethylsilyl)ethoxy]methyl}-5H-pyrrolo[2,3-b]pyrazine and tert-butyl 2,7-diazaspiro[3.5]nonane-2-carboxylate |
| (structure with BocN-diazaspiro, pyrrolopyrazine-I, SEM group) | tert-Butyl 7-(7-iodo-5-{[2-(trimethylsilyl)ethoxy]methyl}-5H-pyrrolo[2,3-b]pyrazin-3-yl)-1,7-diazaspiro[3.5]nonane-1-carboxylate | 600 | Prepared as general procedure 1 using 3-chloro-7-iodo-5-{[2-(trimethylsilyl)ethoxy]methyl}-5H-pyrrolo[2,3-b]pyrazine and tert-butyl 1,7-diazaspiro[3.5]nonane-1-carboxylate |

TABLE 1-continued

| Compound | Compound Name | NMR or MS: [M + H]+ m/z | Procedure |
|---|---|---|---|
| (structure with Boc-diazabicyclooctane, bromo-pyrrolopyrazine, SEM) | tert-Butyl 8-(7-bromo-5-{[2-(trimethylsilyl)ethoxy]methyl}-5H-pyrrolo[2,3-b]pyrazin-3-yl)-3,8-diazabicyclo[3.2.1]octane-3-carboxylate | 538 | Prepared as general procedure 1 using 7-bromo-3-chloro-5-{[2-(trimethylsilyl)ethoxy]methyl}-5H-pyrrolo[2,3-b]pyrazine and tert-butyl 3,8-diazabicyclo[3.2.1]octane-3-carboxylate, heating for 4 days. |
| (structure with BocHN, F, iodo-pyrrolopyrazine, SEM) | tert-Butyl N-[(3S,4S)-3-fluoro-1-(7-iodo-5-{[2-(trimethylsilyl)ethoxy]methyl}-5H-pyrrolo[2,3-b]pyrazin-3-yl)piperidin-4-yl]carbamate | $^1$H NMR (400 MHz DMSO-$d_6$): 8.33 (1H, s), 7.74 (1H, s), 7.06 (1H, d), 5.47 (2H, s), 4.58-4.31 (2H, m), 4.15 (1H, d), 3.72 (1H, s), 3.53 (2H, t), 3.26-3.12 (2H, m), 1.97-1.78 (1H, m), 1.58-1.45 (1H, m), 1.40 (9H, s), 0.85 (2H, t), -0.07--0.10 (9H, m). | Prepared as general procedure 1 using 3-chloro-7-iodo-5-{[2-(trimethylsilyl)ethoxy]methyl}-5H-pyrrolo[2,3-b]pyrazine and tert-butyl N-[(3S,4S)-3-fluoropiperidin-4-yl]carbamate, heating for 48 h. |
| (structure with BocHN, F, iodo-pyrrolopyrazine, SEM) | tert-Butyl N-[(3R,4R)-3-fluoro-1-(7-iodo-5-{[2-(trimethylsilyl)ethoxy]methyl}-5H-pyrrolo[2,3-b]pyrazin-3-yl)piperidin-4-yl]carbamate | 592 | Prepared as general procedure 1 using 3-chloro-7-iodo-5-{[2-(trimethylsilyl)ethoxy]methyl}-5H-pyrrolo[2,3-b]pyrazine, tert-butyl N-[(3R,4R)-3-fluoropiperidin-4-yl]carbamate, and tetraethylethylenediamine, heating for 72 h. |
| (structure with BocHN, HO, bromo-pyrrolopyrazine, SEM) | tert-Butyl N-[1-(7-bromo-5-{[2-(trimethylsilyl)ethoxy]methyl}-5H-pyrrolo[2,3-b]pyrazin-3-yl)-4-(hydroxymethyl)piperidin-4-yl]carbamate | 556 | Prepared as general procedure 1 using 7-bromo-3-chloro-5-{[2-(trimethylsilyl)ethoxy]methyl}-5H-pyrrolo[2,3-b]pyrazine, tert-butyl N-[4-(hydroxymethyl)piperidin-4-yl]carbamate, and DMSO instead of NMP as solvent, heating for 3 h in microwave at 150° C. |
| (structure with BocN, F,F, iodo-pyrrolopyrazine, dimethylsulfamoyl) | tert-Butyl 7-[5-(dimethylsulfamoyl)-7-iodo-5H-pyrrolo[2,3-b]pyrazin-3-yl]-5,5-difluoro-2,7-diazaspiro[3.5]nonane-2-carboxylate | 613 | Prepared as general procedure 1 using 3-chloro-7-iodo-N,N-dimethyl-5H-pyrrolo[2,3-b]pyrazine-5-sulfonamide and tert-butyl 5,5-difluoro-2,7-diazaspiro[3.5]nonane-2-carboxylate, heating for 18 h. |

TABLE 1-continued

| Compound | Compound Name | NMR or MS: [M + H]+ m/z | Procedure |
|---|---|---|---|
| (structure with HO, BocHN, piperidine, iodo-pyrrolopyrazine, SEM) | rac-tert-Butyl N-[(3S,4S)-3-hydroxy-1-(7-iodo-5-{[2-(trimethylsilyl)ethoxy]methyl}-5H-pyrrolo[2,3-b]pyrazin-3-yl)piperidin-4-yl]carbamate | 590 | Prepared as general procedure 1, using 3-chloro-7-iodo-5-{[2-(trimethylsilyl)ethoxy]methyl}-5H-pyrrolo[2,3-b]pyrazine and rac-tert-butyl N-[(3S,4S)-3-hydroxypiperidin-4-yl]carbamate |
| (structure with BocHN, F, piperidine, iodo-pyrrolopyrazine, SEM) | tert-Butyl N-[(3S,4R)-3-fluoro-1-(7-iodo-5-{[2-(trimethylsilyl)ethoxy]methyl}-5H-pyrrolo[2,3-b]pyrazin-3-yl)piperidin-4-yl]carbamate | 592 | Prepared as general procedure 1 using 3-chloro-7-iodo-5-{[2-(trimethylsilyl)ethoxy]methyl}-5H-pyrrolo[2,3-b]pyrazine, tert-butyl N-[(3S,4R)-3-fluoropiperidin-4-yl]carbamate and tetraethylethylenediamine, heating for 72 h. |
| (structure with BocHN, F, piperidine, iodo-pyrrolopyrazine, SEM) | tert-Butyl N-[(3R,4S)-3-fluoro-1-(7-iodo-5-{[2-(trimethylsilyl)ethoxy]methyl}-5H-pyrrolo[2,3-b]pyrazin-3-yl)piperidin-4-yl]carbamate | 592 | Prepared as general procedure 1 using 3-chloro-7-iodo-5-{[2-(trimethylsilyl)ethoxy]methyl}-5H-pyrrolo[2,3-b]pyrazine, tert-butyl N-[(3R,4S)-3-fluoropiperidin-4-yl]carbamate and tetraethylethylenediamine, heating for 72 h. |

Preparation 14: 6-Bromo-7-chloro-2,3-dihydro-1,3-benzothiazole-2-thione

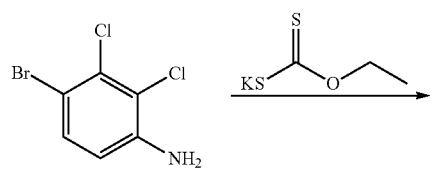

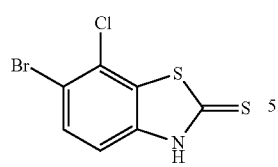

A mixture of 4-bromo-2,3-dichloroaniline (10.0 g, 41.5 mmol) and potassium ethyl xanthate (15.0 g, 93.4 mmol) in DMF (100 mL) was stirred at 120° C. for 18 h. The mixture was quenched with 2M aq. HCl (80 ml) and water (400 mL). The mixture was filtered and washed with water to give the title compound (1.13 g). $^1$H NMR (400 MHz, DMSO-$d_6$): 14.10 (1H, s), 7.78 (1H, d), 7.19 (1H, d).

Preparation 15: 6-Bromo-7-chloro-1,3-benzothiazole

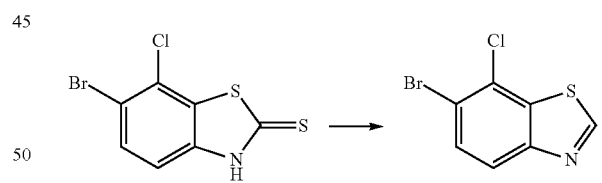

A round bottomed flask charged with 6-bromo-7-chloro-2,3-dihydro-1,3-benzothiazole-2-thione (1.13 g, 40.3 mmol), iron powder (12.4 g, 221.5 mmol) and acetic acid (200 mL) at RT was stirred (with mechanical stirrer) at 120° C. for 2 h. Further iron powder (24.8 g, 443.0 mmol) was added and the mixture was stirred at 120° C. for 2 h. Additional iron powder (12.4 g, 221.5 mmol) was added and the reaction stirred at 120° C. for 15 h. The mixture was filtered and the filtrate concentrated under reduced pressure. The residue was purified by recrystallization from EtOAc and then by column chromatography on silica gel (10% EtOAc:petrol) to give the title compound (2.7 g) MS: [M+H]+=248.

Preparation 16:
N-(4-Bromo-3-chloro-2-fluorophenyl)acetamide

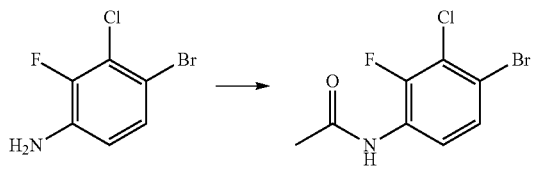

To a solution of 4-bromo-3-chloro-2-fluoroaniline (25 g, 111 mmol) and di-iso-propylethylamine (48.5 ml, 278 mmol) in DCM (250 mL) cooled in an ice bath was added acetic anhydride (11.05 ml, 117 mmol) over 1.5 h. The reaction was warmed to RT and stirred for 24 h. The reaction was washed with HCl (1 M, 250 mL), NaHCO₃ (150 mL) and water (100 mL). The organic phase was dried (MgSO₄) and concentrated under reduced pressure. The residue was purified by column chromatography on silica gel (gradient elution, 0-40% EtOAc/petrol) to give the title compound (23.8 g). $^1$H NMR (500 MHz, DMSO-$d_6$) 9.97 (s, 1H), 7.95-7.77 (m, 1H), 7.56 (dd, 1H), 2.10 (s, 3H).

Preparation 17:
6-Bromo-7-chloro-2-methyl-1,3-benzothiazole

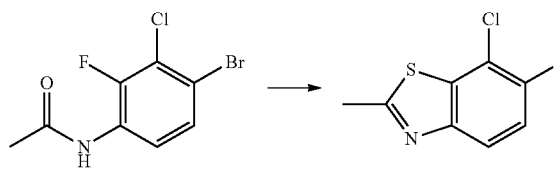

To a solution of N-(4-bromo-3-chloro-2-fluorophenyl) acetamide (1.0 g, 3.77 mmol) in xylene (9.86 mL) was added Lawesson's Reagent (1.53 g, 2.26 mmol). The reaction was heated to 110° C. for 18 h. Cesium carbonate (4.11 g, 7.55 mmol) was added and the mixture was stirred at 110° C. for 18 h. The reaction was cooled to RT and the reaction was diluted with water (500 mL) and ethyl acetate. The organic layer was separated and washed with sat. brine solution, then dried over anhydrous Na₂SO₄, filtered and concentrated under reduced pressure. The residue was purified by column chromatography on silica (gradient elution, 0-20% EtOAc/petrol), to give the title compound (0.97 g). $^1$H NMR (400 MHz, DMSO-$d_6$): 7.85 (2H, d), 2.83 (3H, s).

Preparation 18:
7-Bromo-8-chloro-2-methoxyquinoline

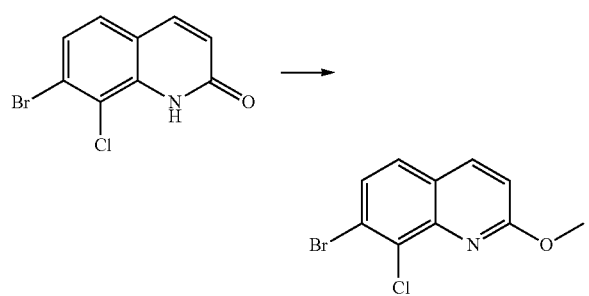

To a solution of 7-bromo-8-chloro-1,2-dihydroquinolin-2-one (520 mg, 2.0 mmol) in anhydrous DMF (10 mL) was added sodium hydride (60% in mineral oil, 120 mg, 3.0 mmol) and the reaction mixture was stirred for 30 min. Iodomethane (0.38 mL, 6.0 mmol) was added and the reaction mixture was stirred for 1 h. Water (20 mL) was added and the product was extracted with EtOAc (2×20 mL). The combined organic layer was washed with brine (2×20 mL), dried (MgSO₄), filtered and the solvent evaporated. The residue was purified by column chromatography on silica gel (gradient elution, 0-50%, EtOAc/petrol), to give the title compound (414 mg), MS: [M+H]⁺=273

Preparation 19:
7-Bromo-8-chloro-N,N-dimethylquinolin-2-amine

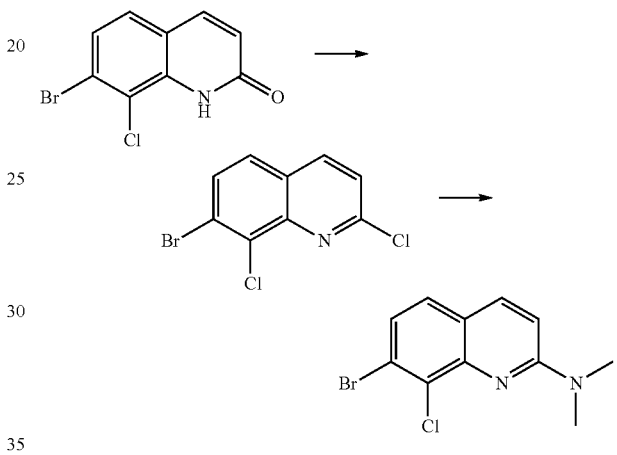

A solution of 7-bromo-8-chloro-1,2-dihydroquinolin-2-one (1.0 g, 3.87 mmol) in POCl₃ was heated at reflux for 1 h. After cooling, most of the POCl₃ was evaporated, ice and NH₄OH were added and the product extracted with EtOAc. The organic phase was dried (MgSO₄), filtered and evaporated to afford 7-bromo-2,8-dichloroquinoline (0.79 g), MS: [M+H]⁺=278. 7-Bromo-2,8-dichloroquinoline (250 mg, 0.9 mmol) was dissolved in pyridine (1.5 mL), dimethylamine (40% solution in water, 1.5 mL) was added and the reaction mixture was heated in a sealed tube for 3 h. After cooling, water (10 ml) was added and the product extracted with EtOAc (2×15 mL). The organic phase was dried (MgSO₄), filtered and evaporated. The residue was purified by column chromatography on silica gel (gradient elution, 0-50%, EtOAc/petrol), to give the title compound (220 mg), MS: [M+H]⁺=287.

Preparation 20: 6-Bromo-7-chloro-N,N-dimethyl-1,3-benzothiazol-2-amine

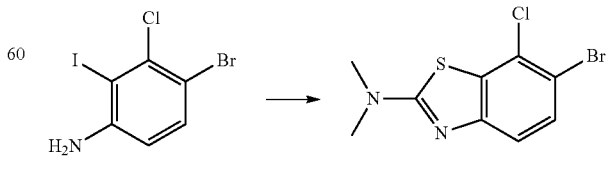

Carbon disulfide (0.11 mL, 1.81 mmol) and dimethylamine solution (40 wt % in water, 0.29 mL, 2.26 mmol) were added to a suspension of 4-bromo-3-chloro-2-iodoaniline (500 mg, 1.50 mmol), CuCl$_2$ (202 mg, 1.50 mmol) and K$_2$CO$_3$ (624 mg, 4.51 mmol) in DMF (5.0 mL) and the reaction heated to 110° C. for 6 h under N$_2$. After cooling, the reaction was diluted with EtOAc and washed with water (4×) and brine, then dried (MgSO$_4$) and evaporated. The residue was purified by column chromatography on silica gel (gradient elution, 0-25%, EtOAc/petrol), to give the title compound (362 mg). MS: [M+H]$^+$=291.

Preparation 21: 6-Bromo-5-chloro-2-methyl-3,4-dihydroquinazolin-4-one

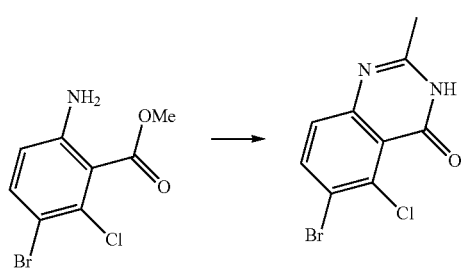

Methyl 6-amino-3-bromo-2-chlorobenzoate (3.0 g, 13.16 mmol) was dissolved in 4 M HCl/1,4-dioxane (50 ml). Acetonitrile (2.01 mL, 39.54 mmol) was added and the reaction was heated to reflux overnight. The reaction was allowed to cool, resulting in a thick white precipitate which was collected by filtration and dried in a vacuum oven overnight, to give the title compound (2.5 g). MS: [M+H]$^+$=273.

Preparation 22: 6-Bromo-5-chloro-2-methyl-3-{[2-(trimethylsilyl)ethoxy]methyl}-3,4-dihydroquinazolin-4-one

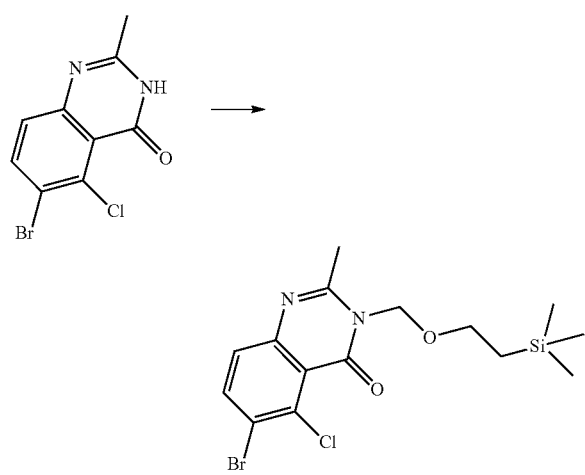

6-Bromo-5-chloro-2-methyl-3,4-dihydroquinazolin-4-one (0.5 g, 1.83 mmol) and K$_2$CO$_3$ (0.76 g, 5.49 mmol) were dissolved in DMF (7 mL). 2-(Trimethylsilyl)ethoxymethyl chloride (0.388 mL, 2.196 mmol) was added dropwise and the reaction was stirred at RT overnight. The reaction was diluted with diethyl ether, washed with water and brine. The organic phase was was passed through a phase separator and concentrated in vacuo. The residue was purified by column chromatography on silica gel (gradient elution, 0-20%, EtOAc/petrol), to give the title compound (0.361 g) as a white solid. MS: [M+H]$^+$=403.

Preparation 23: 2-Ethylhexyl 3-[(6-amino-3-bromo-2-chlorophenyl)sulfanyl]propanoate

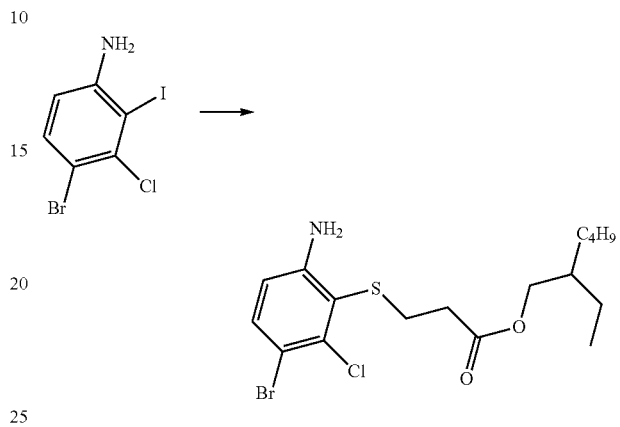

4-Bromo-3-chloro-2-iodoaniline (4.80 g, 14.4 mmol), 2-ethylhexyl 3-sulfanylpropanoate (3.61 mL, 15.9 mmol), tris(dibenzylideneacetone)dipalladium(0) (661 mg, 0.72 mmol), [5-(diphenylphosphanyl)-9,9-dimethyl-9H-xanthen-4-yl]diphenylphosphane (836 mg, 1.44 mmol), DIPEA (6.3 mL, 36 mmol) and 1,4-dioxane (100 mL) were combined, degassed and backfilled with nitrogen (×2) before heating to 100° C. for 2 h. The reaction was cooled and partitioned between EtOAc and water, the layers were separated and the aq. extracted with EtOAc (3×). Combined organics were dried over anhydrous sodium sulfate, filtered and evaporated. The residue was purified by column chromatography on silica gel (gradient elution, 0-20%, EtOAc/petrol) to give the title compound (5.95 g). MS: [M+H]$^+$=422.

Preparation 24: 6-Bromo-7-chloro-2,3-dihydro-1,3-benzothiazol-2-one

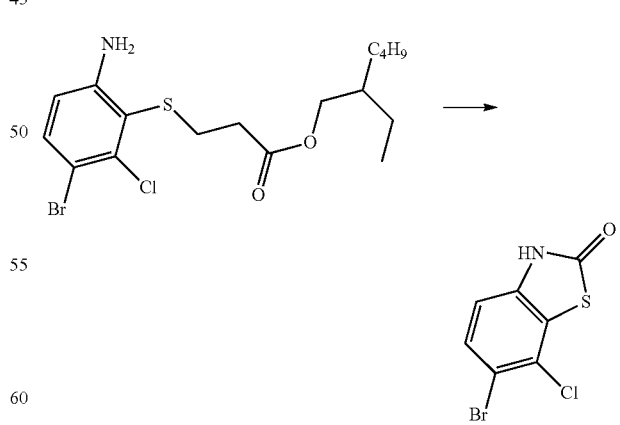

2-Ethylhexyl 3-[(6-amino-3-bromo-2-chlorophenyl)sulfanyl]propanoate (1.0 g, 2.4 mmol) was dissolved in THF (20 mL) and treated with 20% sodium ethoxide in ethanol, stirring for 2 h. Acetic acid (2.24 mL, 39.2 mmol) and N,N'-carbonyldiimidazole (3.18 g, 19.6 mmol) were added and stirred for 2 h. The reaction was diluted with EtOAc (20 mL) and washed with sat. aq. sodium bicarbonate (2×20 mL) and brine (20 mL), then dried over anhydrous sodium sulfate, filtered and evaporated. The residue purified by column chromatography on silica gel (gradient elution, 0-50%, EtOAc/petrol), to give the title compound (294 mg), MS: [M−H]⁻=262.

Preparation 25: 6-Bromo-7-chloro-3-{[2-(trimethylsilyl)ethoxy]methyl}-2,3-dihydro-1,3-benzothiazol-2-one

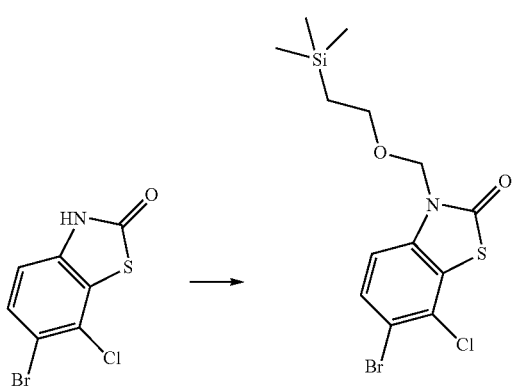 [SMILES: O=c1[nH]c2ccc(Br)c(Cl)c2s1 ; C[Si](C)(C)CCOCn1c(=O)sc2c(Cl)c(Br)ccc21]

To a suspension of 6-bromo-7-chloro-2,3-dihydro-1,3-benzothiazol-2-one (294 mg, 1.11 mmol) and potassium carbonate (306 mg, 2.22 mmol) in DMF (4 mL) was added 2-(trimethylsilyl)ethoxymethyl chloride (297 μL, 1.67 mmol) and stirred for 2 h. The reaction was diluted with EtOAc (10 mL) and washed with water (3×10 mL) and brine (10 mL). The combined organics were dried over anhydrous sodium sulfate, filtered and evaporated, to give the title compound (448 mg), ¹H NMR (400 MHz, DMSO-d₆): 7.81 (1H, d), 7.34 (1H, d), 5.37 (2H, s), 3.58 (2H, t), 0.88-0.84 (2H, m), −0.04-0.08 (9H, m).

Preparation 26: 6-Bromo-7-chloro-2-(oxolan-3-yl)-1,3-benzothiazole

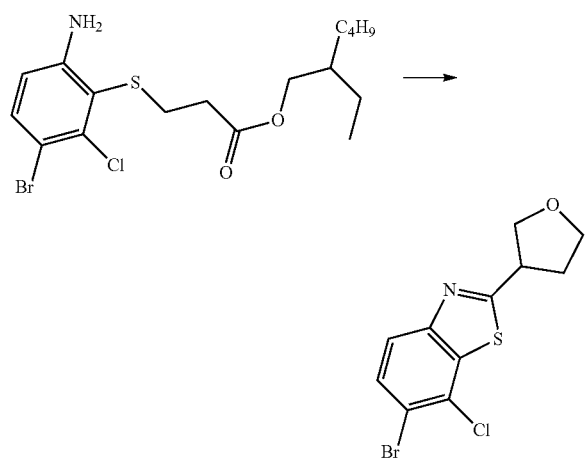

DIPEA (0.62 mL, 3.55 mmol) and tetrahydrofuran-3-carbonyl chloride (0.26 mL, 2.37 mmol) were added to a solution of 2-ethylhexyl 3-[(6-amino-3-bromo-2-chlorophenyl)sulfanyl]propanoate (500 mg, 1.18 mmol) in DCM (6 mL) at 0° C. and the reaction then allowed to warm to RT and stirred for 16 h. The reaction was partitioned between DCM and sat. aq. NaHCO₃ and the separated aq. layer extracted with DCM (2×). Combined organics were dried (MgSO₄) and evaporated. The residue was purified by column chromatography on silica gel (gradient elution, 0-25%, EtOAc/petrol) to provide the intermediate amide. This residue was re-dissolved in THF (6 mL), NaOEt solution (20 wt % in EtOH, 1.4 mL, 3.55 mmol) was added and the reaction stirred for 30 min. After cooling to 0° C., TFA (2.7 mL, 35.5 mmol) was carefully added and the reaction then heated to 60° C. for 4 h. After cooling to 0° C., sat. aq. NaHCO₃ was added carefully and the mixture extracted with EtOAc (3×). Combined organics were washed with brine, dried (MgSO₄) and evaporated. The residue was purified by column chromatography on silica gel (gradient elution, 0-25%, EtOAc/petrol) then filtered through NH₂ ion exchange silica gel to give the title compound (271 mg). MS: [M+H]⁺=318.

Preparation 27: 6-Bromo-7-chloro-2-(methoxymethyl)-1,3-benzothiazole

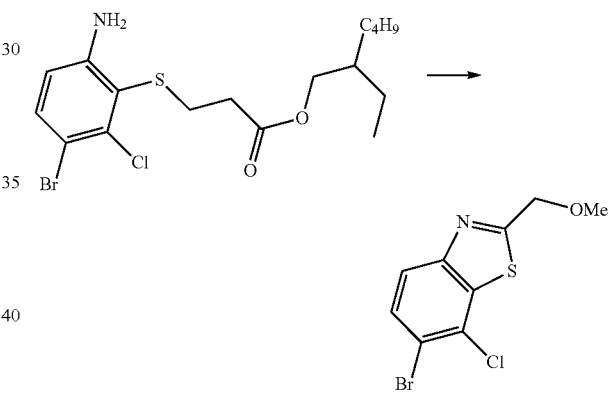

DIPEA (0.82 mL, 4.73 mmol) and methoxyacetyl chloride (0.32 mL, 3.55 mmol) were added to a solution of 2-ethylhexyl 3-[(6-amino-3-bromo-2-chlorophenyl)sulfanyl]propanoate (1.0 g, 2.37 mmol) in DCM (12 mL) at 0° C. and the reaction then allowed to warm to RT and stirred for 1 h. The reaction was partitioned between DCM and sat. aq. NaHCO₃ and the separated aq. layer extracted with DCM (2×). Combined organics were dried (MgSO₄) and evaporated. The residue was purified by column chromatography on silica gel (gradient elution, 0-25%, EtOAc/petrol) to provide the intermediate amide as an orange oil. This residue was re-dissolved in THF (12 mL), NaOEt solution (20 wt % in EtOH, 2.8 mL, 7.10 mmol) was added and the reaction stirred for 30 min. After cooling to 0° C., TFA (5.5 mL, 71.0 mmol) was carefully added and the reaction then heated to 60° C. for 2 h. After cooling to 0° C., sat. aq. NaHCO₃ was added carefully and the mixture extracted with EtOAc (3×). Combined organics were washed with brine, dried (MgSO₄) and evaporated. The residue was purified by column chromatography on NH₂ ion exchange silica gel (gradient elution, 0-30%, acetone/petrol) to give the title compound (567 mg). MS: [M+H]⁺=292.

Preparation 28: 2-Amino-4-bromo-3-chlorophenol

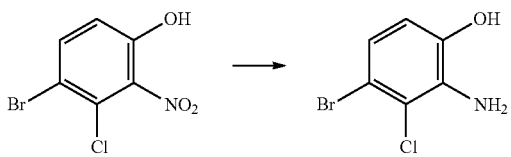 [SMILES: O=[N+]([O-])c1c(O)ccc(Br)c1Cl ; Nc1c(O)ccc(Br)c1Cl]

Iron powder (2.43 g, 43.6 mmol) was added to a solution of 4-bromo-3-chloro-2-nitrophenol (1.10 g, 4.36 mmol) in EtOH (20 mL) and AcOH (10 mL) and the suspension heated to 90° C. for 4 h. After cooling, the reaction was filtered, rinsing with EtOAc (~100 mL), and the filtrate washed with water (3×) and brine, then dried (MgSO$_4$) and evaporated to give the title compound (950 mg). MS: [M+H]$^+$=222

Preparation 29: 5-bromo-4-chloro-2,3-dihydro-1,3-benzoxazol-2-one

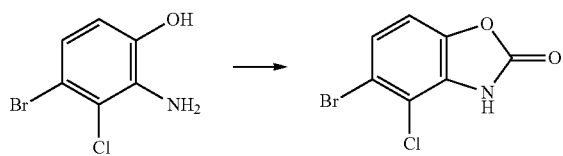 [SMILES: Nc1c(O)ccc(Br)c1Cl ; O=c1[nH]c2c(Cl)c(Br)ccc2o1]

1,1'-Carbonyldiimidazole (2.08 g, 12.8 mmol) was added to a solution of 2-amino-4-bromo-3-chlorophenol (950 mg, 4.27 mmol) in THF (22 mL) and the reaction heated to reflux for 2 h. After cooling, the solvent was evaporated and the residue re-dissolved in EtOAc, then washed sequentially with 2M HCl (3×), water and brine. The organic fraction was dried (MgSO$_4$) and evaporated to give the title compound (1.04 g). MS: [M–H]$^-$=246

Preparation 30: 5-Bromo-4-chloro-3-{[2-(trimethylsilyl)ethoxy]methyl}-2,3-dihydro-1,3-benzoxazol-2-one

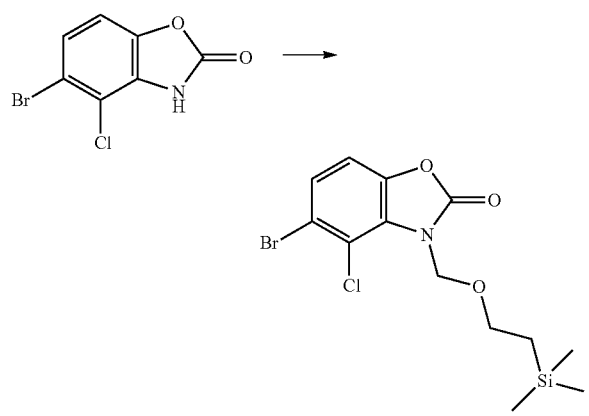

2-(Trimethylsilyl)ethoxymethyl chloride (0.53 mL, 3.02 mmol) was added to a suspension of 5-bromo-4-chloro-2,3-dihydro-1,3-benzoxazol-2-one (500 mg, 2.01 mmol) and K$_2$CO$_3$ (556 mg, 4.03 mmol) in DMF (7.5 mL) and the reaction stirred at RT under N$_2$ for 3 h. The reaction was diluted with EtOAc and washed with water (3×) and brine, then dried (MgSO$_4$) and evaporated to give the title compound (752 mg). MS: [M+H]$^+$=378

Preparation 31: 5-Bromo-4-chloro-2-methyl-2H-indazole

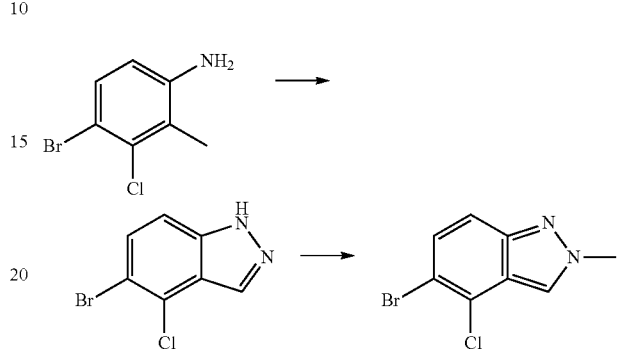

A solution of sodium nitrite (58.6 g, 0.85 mol) in water (98 ml) was added to an ice bath cooled solution of 4-bromo-3-chloro-2-methylaniline (150 g, 0.68 mol) in acetic acid (3 L) with mechanical stirring and the mixture was aged for 1 h at ambient temperature. Most of the solvent was evaporated and the residue suspended in water (500 mL) and filtered, washing with water (250 ml×4), petrol (250 ml×4) and drying in vacuo at 40° C., to give 5-bromo-4-chloro-1H-indazole (130 g), $^1$H NMR (400 MHz, DMSO-d$_6$): 13.61 (1H, s), 8.16 (1H, s), 7.62 (1H, d), 7.53 (1H, dd).

Solid trimethyloxonium tetrafluoroborate (258 g, 1.74 mol) was charged to a solution of ice bath cooled 5-bromo-4-chloro-1H-indazole (367 g, 1.59 mol) in EtOAc (1.9 L) and the resulting mixture was stirred at ambient temperature for 4 h. The reaction mixture was diluted with petrol (1.9 L) and aged for 10 min before filtration, washing with petrol (400 mL×2). The filter cake was combined with sat. sodium bicarbonate (1.5 L), EtOAc (2 L) and the phases were separated. The organic phase was washed with sat. sodium bicarbonate, dried (MgSO$_4$) and concentrated in vacuo, to give the title compound (236 g).

$^1$H NMR (400 MHz, DMSO-d$_6$): 8.53 (1H, s), 7.56 (1H, dd), 7.48 (1H, d), 4.20 (3H, s).

Preparation 32: 5-Bromo-4-chloro-2-ethyl-2H-indazole

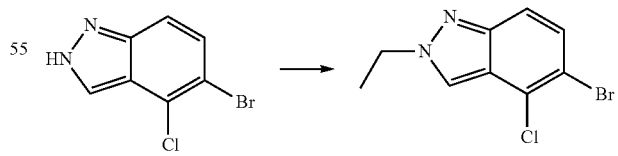

Triethyloxonium hexafluorophosphate (20 g, 80.6 mmol) was added to 5-bromo-4-chloro-1H-indazole (12.4 g, 53.7 mmol) in EtOAc (186 mL) and the resulting mixture was stirred at ambient temperature overnight. The reaction mixture was quenched with sat. sodium bicarbonate (125 ml), and the phases were separated. The aq. was extracted with EtOAc (70 mL) and the combined organics were washed with brine (70 mL), dried (MgSO$_4$) and concentrated in vacuo. The red/brown residue was treated with activated charcoal (12.5 g) in ethanol (125 ml) and EtOAc (125 mL). After stirring at ambient temperature, the mixture was filtered and concentrated in vacuo, to give the title compound (9.88 g). $^1$H NMR (400 MHz, DMSO-d$_6$): 8.58 (1H, s), 7.58 (1H, dd), 7.48 (1H, d), 4.49 (2H, q), 1.52 (3H, t).

Preparation 33:
5-Bromo-4-fluoro-2-methyl-2H-indazole

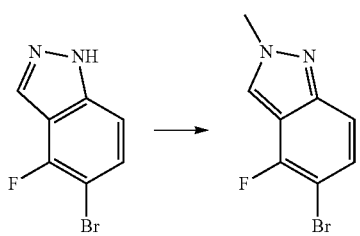

To a suspension of 5-bromo-4-fluoro-1H-indazole (1.0 g, 4.7 mmol) in EtOAc (20 mL) was added trimethyloxonium tetrafluoroborate (1.0 g, 7.0 mmol) at room temperature. After stirring at the same temperature for 14.5 h, the mixture was quenched with sat. NaHCO$_3$ aq. and extracted with EtOAc. The organic phase was washed with brine, dried over Na$_2$SO$_4$, filtered, and concentrated in vacuo. The residue was purified by column chromatography on silica gel (gradient elution, 0-60% EtOAc/hexane) to give the title compound (0.91 g), MS: [M+H]$^+$=230.

Preparation 34:
(4-Chloro-2-ethyl-2H-indazol-5-yl)boronic acid

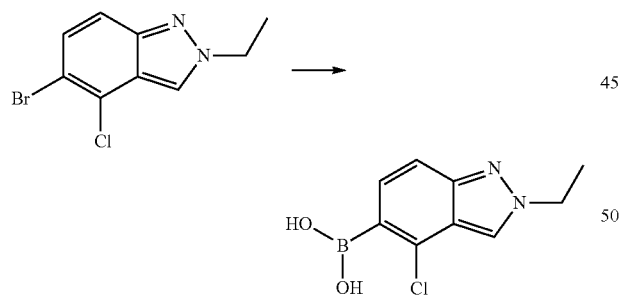

Triisopropylborate (10 ml, 43.2 mmol) was added to a solution of 5-bromo-4-chloro-2-ethyl-2H-indazole (9.1 g, 39.3 mmol) in THF (45 mL) and toluene (136 mL), stirring at ambient temperature under nitrogen. The reaction mixture was cooled to −70° C. and n-butyllithium (2.5M, 17.3 mL, 43.2 mmol) was added over 50 min. The reaction was warmed to ambient temperature, before quenching with 2M hydrochloric acid (65 mL) and stirring overnight. The mixture was filtered, washing with petrol (50 mL) and the solid was dried in vacuo, to give the title compound (1.4 g)$^1$H NMR (400 MHz, DMSO-d$_6$): 8.45 (1H, s), 7.50 (1H, dd), 7.28 (1H, d), 4.52-4.38 (2H, m), 1.52 (3H, t).

Preparation 35:
5-Bromo-3,4-dichloro-2-methyl-2H-indazole

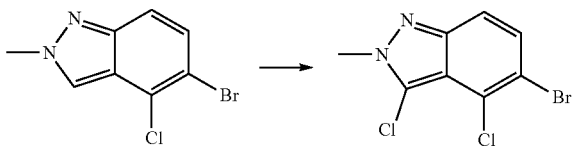

N-Chlorosuccinimide (550 mg, 4.12 mmol) was added to 5-bromo-4-chloro-2-methyl-2H-indazole (1.0 g, 4.12 mmol) in DMF (20.6 mL) at RT. After stirring for 18 h, water was added to effect precipitation. The precipitate was filtered, washed with water and dried in a vacuum oven. The solid was taken up in EtOAc/petrol, filtered and washed with petrol. Dried in a vacuum oven, to give the title compound (440 mg). MS: [M+H]$^+$=280.

Preparation 36:
6-Amino-3-bromo-2-chlorobenzaldehyde

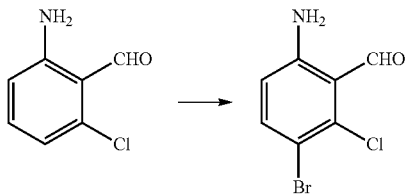 [SMILES: Nc1cccc(Cl)c1C=O ; Nc1ccc(Br)c(Cl)c1C=O]

2-Amino-6-chlorobenzaldehyde (500 mg, 3.22 mmol) was dissolved in DMF (16 mL) at RT and N-bromosuccinimide (573 mg, 3.22 mmol) added in one portion. The reaction was stirred for 66 h. Water was added and the precipitate by vacuum filtration, washing with water and petrol. The solid was dried in a vacuum oven, to give the title compound (438 mg). MS: [M+H]$^+$=233.

Preparation 37:
6-Bromo-5-chloro-3-methoxy-2-methylquinoline

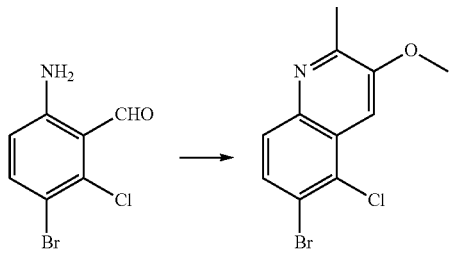

A solution of 6-amino-3-bromo-2-chlorobenzaldehyde (582 mg, 2.50 mmol), methoxyacetone (308 mg, 3.50 mmol), and ethanolic KOH in ethanol (10%, w/v, 0.70 mL) was stirred at RT for 20 min. The precipitate which formed was filtered and dried in a vacuum oven, to give the title compound (440 mg). MS: [M+H]$^+$=285.

Preparation 38: 5-Bromo-2-{2-[(tert-butyldimethyl-silyl)oxy]ethyl}-4-chloro-2H-indazole

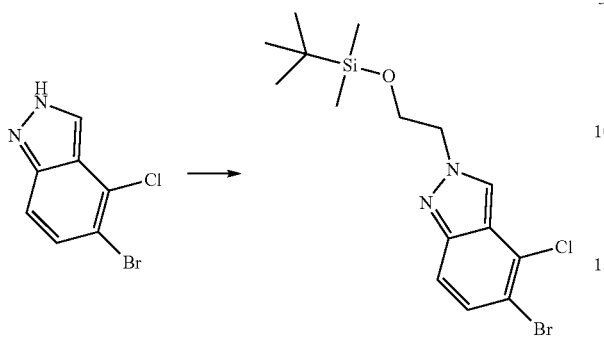

5-Bromo-4-chloro-2H-indazole (2.0 g, 8.70 mmol) and cesium carbonate (5.67 g, 10.44 mmol) were combined in NMP (43.39 mL) and heated to 60° C. After stirring for 30 min (2-bromoethoxy)-tert-butyldimethylsilane (2.05 mL, 2.29 g, 9.57 mmol) was added. The reaction was stirred for 1 h and cooled to RT. Sat. NH$_4$Cl was added and the aq. phase extracted with EtOAc (3×). The combined organics were passed through a phase separator and concentrated in vacuo. The residue was purified by column chromatography on silica gel (gradient elution, 0-50%, EtOAc/petrol), to give the title compound (631 mg), $^1$H NMR (400 MHz, CDCl$_3$): 8.08 (1H, s), 7.49 (1H, d), 7.44 (1H, d), 4.58-4.46 (2H, m), 4.13-3.98 (2H, m), 0.85 (9H, s), −0.09 (6H, s).

Preparation 39: 5-Bromo-2-{2-[(tert-butyldimethyl-silyl)oxy]ethyl}-3,4-dichloro-2H-indazole

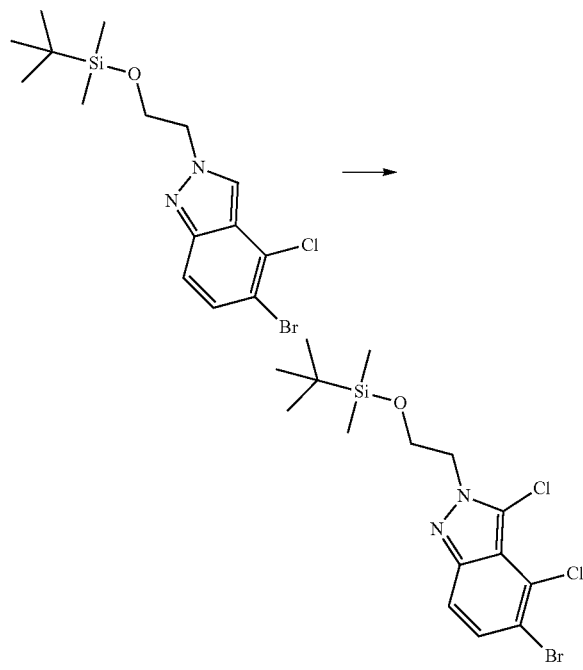

Prepared from 5-bromo-2-{2-[(tert-butyldimethylsilyl)oxy]ethyl}-4-chloro-2H-indazole using similar procedure for the preparation of 5-bromo-3,4-dichloro-2-methyl-2H-indazole, to give the title compound, MS: [M+H]$^+$=423.

Preparation 40: 5-Bromo-4-chloro-2-methyl-2H-indazole-3-carbaldehyde

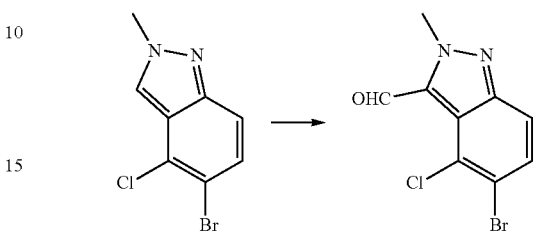

To 5-bromo-4-chloro-2-methyl-2H-indazole (1.0 g, 4.10 mmol) in THF (8.0 mL), cooled to −78° C. was added lithium diisopropylamide (1.0 M, in THF, 7.38 mL, 7.38 mmol) and the reaction stirred for 90 min. The temperature was raised to 0° C. (ice bath) and stirred for 25 min. DMF (1.0 mL) was added and the reaction stirred for 30 min. Sat. NH$_4$Cl was added and the reaction extracted with EtOAc (3×). The combined organics were washed with sat. brine solution (3×), passed through a phase separator and concentrated in vacuo. The residue was purified by column chromatography on silica gel (gradient elution, 0-50%, EtOAc/petrol), to give the title compound (865 mg), $^1$H NMR (400 MHz, DMSO-d$_6$): 10.63 (1H, s), 7.80 (1H, d), 7.71 (1H, d), 4.43 (3H, s).

Preparation 41: (5-Bromo-4-chloro-2-methyl-2H-indazol-3-yl)methanol

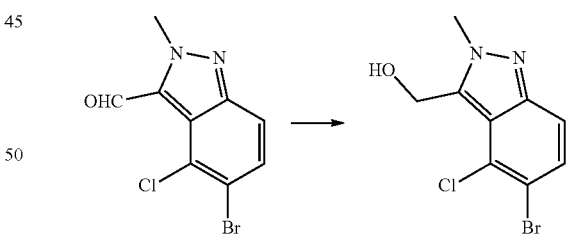

5-Bromo-4-chloro-2-methyl-2H-indazole-3-carbaldehyde (0.707 g, 2.60 mmol) was suspended in methanol/THF (1:1, 13 mL) at 0° C. and solid sodium borohydride (0.108 g, 2.86 mmol) was added portionwise over 10 min. The resulting mixture was stirred at 0° C. for 30 min then at RT for another 10 min. The reaction was quenched by the addition of ice. The residue was partitioned between EtOAc and water. The aq. layer was twice extracted with EtOAc and the combined organic layers were dried (MgSO$_4$), filtered and concentrated in vacuo, to give the title compound (543 mg), $^1$H NMR (400 MHz, DMSO-d$_6$): 7.54 (1H, d), 7.48 (1H, d), 5.44 (1H, t), 5.05 (2H, d), 4.19 (3H, s).

Preparation 42: 5-Bromo-3-{[(tert-butyldimethylsilyl)oxy]methyl}-4-chloro-2-methyl-2H-indazole

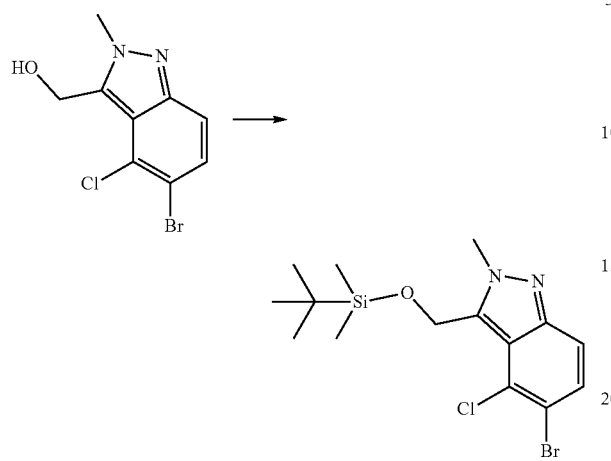

tert-Butylchlorodimethylsilane (0.377 g, 2.50 mmol) was added to an ice-cooled solution of (5-bromo-4-chloro-2-methyl-2H-indazol-3-yl)methanol (0.653 g, 2.38 mmol) and imidazole (0.178 g, 2.62 mmol) in DMF (5.96 mL) under an argon atmosphere. After stirring at ambient temperature for 2 h, the mixture was quenched with ice water and extracted with EtOAc (2×). The combined extracts were washed with sat. brine solution, dried over sodium sulfate and concentrated in vacuo. The crude material was purified by column chromatography on silica gel (gradient elution, 0-50%, EtOAc/petrol), to give the title compound (783 mg), MS: [M+H]$^+$=389.

Preparation 43: 4-Chloro-2-methyl-5-(4,4,5,5-tetramethyl-1,3,2-dioxaborolan-2-yl)-2H-indazole

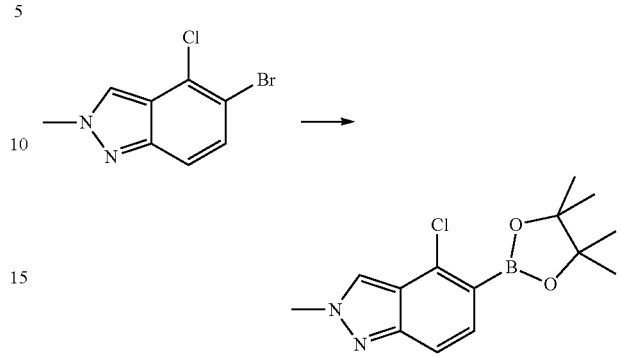

5-Bromo-4-chloro-2-methyl-2H-indazole (5.0 g, 20.50 mmol), bis(pinacolato)diboron (6.25 g, 24.60 mmol), [1,1'-bis(diphenylphosphino)ferrocene]dichloropalladium(II) (0.750 g, 1.02 mmol) and potassium acetate (6.04 g, 61.50 mmol) were slurried in 1,4-dioxane (103 mL) and heated to 95-100° C. for 18 h. The reaction was cooled to RT, filtered and washed with EtOAc. The filtrate was concentrated in vacuo and the residue dissolved in toluene and petrol added until precipitation occurred. The suspension was filtered under vacuum suction and the filtrate concentrated in vacuo, to give the title compound (11.8 g), MS: [M+H]$^+$=293.

Compounds of Table 2 below were prepared using procedures analogous to that described in preparation 43, starting from the appropriate substituted aryl halide (synthesised as described above with any significant variations indicated)

TABLE 2

| Compound | Compound Name | MS: [M + H]$^+$ m/z | Procedure |
| --- | --- | --- | --- |
|  | 7-Chloro-2-methyl-6-(4,4,5,5-tetramethyl-1,3,2-dioxaborolan-2-yl)-1,3-benzothiazole | 310 | Prepared as preparation 43 above using 6-bromo-7-chloro-2-methyl-1,3-benzothiazole, heating to 125° C. for 1.5 h |
|  | 3,4-Dichloro-2-methyl-5-(4,4,5,5-tetramethyl-1,3,2-dioxaborolan-2-yl)-2H-indazole | 327 | Prepared as preparation 43 above using 5-bromo-3,4-dichloro-2-methyl-2H-indazole |
|  | 4-Fluoro-2-methyl-5-(4,4,5,5-tetramethyl-1,3,2-dioxaborolan-2-yl)-2H-indazole | 276 | Prepared as preparation 43 above using 5-bromo-4-fluoro-2-methyl-2H-indazole, except heating to 120° C., the filtrate was concentrated in vacuo. Column chromatography (SNAP Ultra 25 g, 0-60% EtOAc in hexane) |

TABLE 2-continued

| Compound | Compound Name | MS: [M + H]+ m/z | Procedure |
|---|---|---|---|
| (structure: 5-chloro-3-methoxy-2-methylquinoline with pinacol boronate) | 5-Chloro-3-methoxy-2-methyl-6-(4,4,5,5-tetramethyl-1,3,2-dioxaborolan-2-yl)quinoline | 334 | Prepared as preparation 43 above, using 6-bromo-5-chloro-3-methoxy-2-methylquinoline |
| (structure: 3,4-dichloroindazole with TBS-oxyethyl and pinacol boronate) | 2-{2-[(tert-Butyldimethylsilyl)oxy]ethyl}-3,4-dichloro-5-(4,4,5,5-tetramethyl-1,3,2-dioxaborolan-2-yl)-2H-indazole | 471 | Prepared as preparation 43 above, using 5-bromo-2-{2-[(tert-butyldimethylsilyl)oxy]ethyl}-3,4-dichloro-2H-indazole |
| (structure: 4-chloro-2-methylindazole with TBS-oxymethyl and pinacol boronate) | 3-{[(tert-Butyldimethylsilyl)oxy]methyl}-4-chloro-2-methyl-5-(4,4,5,5-tetramethyl-1,3,2-dioxaborolan-2-yl)-2H-indazole | 437 | Prepared as preparation 43 above, using 5-bromo-3-{[(tert-butyldimethylsilyl)oxy]methyl}-4-chloro-2-methyl-2H-indazole |

General Procedure 2: tert-Butyl N-[endo-8-[7-(4-chloro-2-methyl-2H-indazol-5-yl)-5-{[2-(trimethylsilyl)ethoxy]methyl}-5H-pyrrolo[2,3-b]pyrazin-3-yl]-8-azabicyclo[3.2.1]octan-3-yl]carbamate

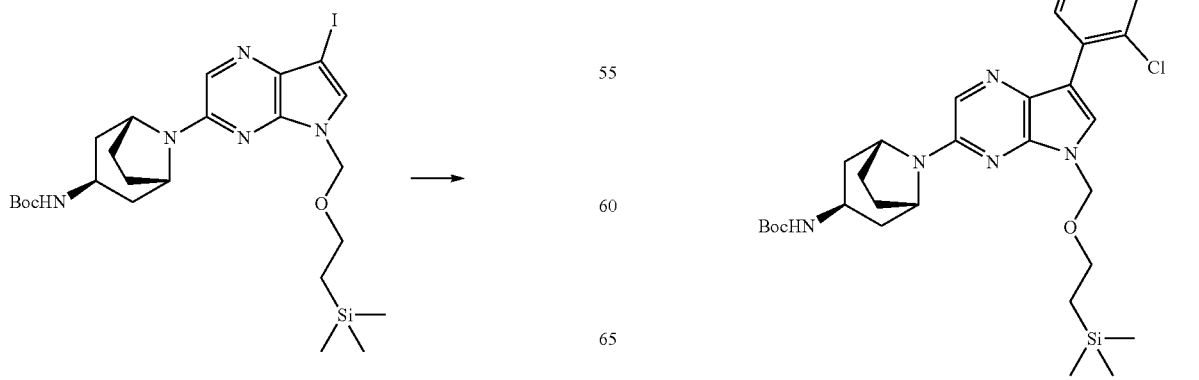

tert-Butyl N-[endo-8-(7-iodo-5-{[2-(trimethylsilyl)ethoxy]methyl}-5H-pyrrolo[2,3-b]pyrazin-3-yl)-8-azabicyclo[3.2.1]octan-3-yl]carbamate (0.500 g, 0.83 mmol), 4-chloro-2-methyl-5-(4,4,5,5-tetramethyl-1,3,2-dioxaborolan-2-yl)-2H-indazole (0.255 g, 1.34 mmol), [1,1'-bis(diphenylphosphino)ferrocene]dichloropalladium(II) (0.061 g, 0.08 mmol) and potassium carbonate (0.231 g, 1.67 mmol) were dissolved in water (2.78 mL) and 1,2-dimethoxyethane (4.17 mL). The reaction mixture was heated to 95-100° C. and stirred for 3 h. After cooling to RT, water was added and the aq. layer extracted with EtOAc (3×). The combined organics were passed through a phase separator and concentrated in vacuo. The residue was purified by column chromatography on silica gel (gradient elution, 0-50%, EtOAc/petrol), to give the title compound (261 mg), MS: [M+H]$^+$=638.

Compounds of Table 3 set out below were prepared in an analogous manner to general procedure 2, using the corresponding aryl halide and boronate or boronic acid, with any significant variations indicated.

TABLE 3

| Compound | Compound Name | NMR or MS: [M + H]$^+$ m/z | Procedure |
| --- | --- | --- | --- |
| (structure) | tert-Butyl N-{1-[7-(4-chloro-2-methyl-2H-indazol-5-yl)-5-{[2-(trimethylsilyl)ethoxy]methyl}-5H-pyrrolo[2,3-b]pyrazin-3-yl]piperidin-4-yl}carbamate | 612 | Prepared as general procedure 2 using tert-butyl N-[1-(7-bromo-5-{[2-(trimethylsilyl)ethoxy]methyl}-5H-pyrrolo[2,3-b]pyrazin-3-yl)piperidin-4-yl]carbamate and THF as solvent instead of 1,2-dimethoxyethane |
| (structure) | tert-Butyl N-{1-[7-(4-chloro-2-methyl-2H-indazol-5-yl)-5-{[2-(trimethylsilyl)ethoxy]methyl}-5H-pyrrolo[2,3-b]pyrazin-3-yl]-4-methylpiperidin-4-yl}carbamate | 626 | Prepared as general procedure 2 using tert-butyl N-[1-(7-bromo-5-{[2-(trimethylsilyl)ethoxy]methyl}-5H-pyrrolo[2,3-b]pyrazin-3-yl)-4-methylpiperidin-4-yl]carbamate and THF as solvent instead of 1,2-dimethoxyethane |
| (structure) | exo-8-[7-(4-chloro-2-methyl-2H-indazol-5-yl)-5-{[2-(trimethylsilyl)ethoxy]methyl}-5H-pyrrolo[2,3-b]pyrazin-3-yl]-8-azabicyclo[3.2.1]octane-3-carbonitrile | 548 | Prepared as general procedure 2 using exo-8-(7-bromo-5-{[2-(trimethylsilyl)ethoxy]methyl}-5H-pyrrolo[2,3-b]pyrazin-3-yl)-8-azabicyclo[3.2.1]octane-3-carbonitrile and THF as solvent instead of 1,2-dimethoxyethane |

TABLE 3-continued

| Compound | Compound Name | NMR or MS: [M + H]+ m/z | Procedure |
|---|---|---|---|
| (structure with BocHN-azabicyclic-pyrrolopyrazine-chloroethylindazole-SEM) | tert-Butyl N-[(endo)-8-[7-(4-chloro-2-ethyl-2H-indazol-5-yl)-5-{[2-(trimethylsilyl)ethoxy]methyl}-5H-pyrrolo[2,3-b]pyrazin-3-yl]-8-azabicyclo[3.2.1]octan-3-yl]carbamate | 652 | Prepared as general procedure 2 using (4-chloro-2-ethyl-2H-indazol-5-yl)boronic acid |
| (structure with BocHN-exo-azabicyclic-pyrrolopyrazine-chloromethylindazole-SEM) | tert-Butyl N-[exo-8-[7-(4-chloro-2-methyl-2H-indazol-5-yl)-5-{[2-(trimethylsilyl)ethoxy]methyl}-5H-pyrrolo[2,3-b]pyrazin-3-yl]-8-azabicyclo[3.2.1]octan-3-yl]carbamate | 638 | Prepared as general procedure 2 using tert-butyl N-[exo-8-(7-bromo-5-{[2-(trimethylsilyl)ethoxy]methyl}-5H-pyrrolo[2,3-b]pyrazin-3-yl)-8-azabicyclo[3.2.1]octan-3-yl]carbamate and THF as solvent instead of 1,2-dimethoxyethane |
| (structure with BocHN-9-azabicyclo[3.3.1]nonane-pyrrolopyrazine-chloromethylindazole-SEM) | tert-Butyl N-{9-[7-(4-chloro-2-methyl-2H-indazol-5-yl)-5-{[2-(trimethylsilyl)ethoxy]methyl}-5H-pyrrolo[2,3-b]pyrazin-3-yl]-9-azabicyclo[3.3.1]nonan-3-yl}carbamate | 652 | Prepared as general procedure 2, tert-butyl N-[9-(7-bromo-5-{[2-(trimethylsilyl)ethoxy]methyl}-5H-pyrrolo[2,3-b]pyrazin-3-yl)-9-azabicyclo[3.3.1]nonan-3-yl]carbamate and THF as solvent instead of 1,2-dimethoxyethane |
| (structure with BocHN-endo-azabicyclic-pyrrolopyrazine-chloromethylbenzothiazole-SEM) | tert-Butyl N-[endo-8-[7-(7-chloro-2-methyl-1,3-benzothiazol-6-yl)-5-{[2-(trimethylsilyl)ethoxy]methyl}-5H-pyrrolo[2,3-b]pyrazin-3-yl]-8-azabicyclo[3.2.1]octan-3-yl]carbamate | 655 | Prepared as general procedure 2 using tert-butyl N-[endo-8-(7-iodo-5-{[2-(trimethylsilyl)ethoxy]methyl}-5H-pyrrolo[2,3-b]pyrazin-3-yl)-8-azabicyclo[3.2.1]octan-3-yl]carbamate and 7-chloro-2-methyl-6-(4,4,5,5-tetramethyl-1,3,2-dioxaborolan-2-yl)-1,3-benzothiazole |

TABLE 3-continued

| Compound | Compound Name | NMR or MS: [M + H]+ m/z | Procedure |
| --- | --- | --- | --- |
| | tert-Butyl N-{endo-8-[7-(4-chloro-2-methyl-2H-indazol-5-yl)-5-{[2-(trimethylsilyl)ethoxy]methyl}-5H-pyrrolo[2,3-b]pyrazin-3-yl]-3-methyl-8-azabicyclo[3.2.1]octan-3-yl}carbamate | 652 | Prepared as general procedure 2 using tert-butyl N-[endo-8-(7-bromo-5-{[2-(trimethylsilyl)ethoxy]methyl}-5H-pyrrolo[2,3-b]pyrazin-3-yl)-3-methyl-8-azabicyclo[3.2.1]octan-3-yl]carbamate |
| | tert-Butyl 8-[7-(4-chloro-2-methyl-2H-indazol-5-yl)-5-{[2-(trimethylsilyl)ethoxy]methyl}-5H-pyrrolo[2,3-b]pyrazin-3-yl]-3,8-diazabicyclo[3.2.1]octane-3-carboxylate | 624 | Prepared as general procedure 2 using tert-butyl 8-(7-bromo-5-{[2-(trimethylsilyl)ethoxy]methyl}-5H-pyrrolo[2,3-b]pyrazin-3-yl)-3,8-diazabicyclo[3.2.1]octane-3-carboxylate and a mixture of 1,4-dioxane and water as solvent heated at 90° C. for 1.5 h. |
| | tert-Butyl N-[(3S,4S)-1[7-(4-chloro-2-methyl-2H-indazol-5-yl)-5-[2-(trimethylsilyl)ethoxy]-5H-pyrrolo[2,3-b]pyrazin-3-yl]-3-fluoropiperidin-4-yl]carbamate | $^1$H NMR (400 MHz, DMSO-d$_6$): 8.48 (1H, s), 8.37 (1H, s), 7.99-7.94 (1H, m), 7.89 (1H, d), 7.64 (1H, dd), 7.12-7.01 (1H, m), 5.60 (2H, s), 4.62-4.33 (2H, m), 4.23-4.14 (4H, m), 3.74 (1H, s), 3.62 (2H, t), 3.19 (2H, d), 1.97-1.89 (1H, m), 1.59-1.47 (1H, m), 1.41 (9H, s), 0.89 (2H, t), -0.06--0.08 (9H, m). | Prepared as general procedure 2 using using tert-butyl N-[(3S,4S)-3-fluoro-1-(7-iodo-5-{[2-(trimethylsilyl)ethoxy]methyl}-5H-pyrrolo[2,3-b]pyrazin-3-yl)piperidin-4-yl]carbamate |
| | tert-Butyl N-[(3R,4R)-1-[7-(4-chloro-2-methyl-2H-indazol-5-yl)-5-{[2-(trimethylsilyl)ethoxy]methyl}-5H-pyrrolo[2,3-b]pyrazin-3-yl]-3-fluoropiperidin-4-yl]carbamate | 631 | Prepared as general procedure 2 using tert-butyl N-[(3R,4R)-3-fluoro-1-(7-iodo-5-{[2-(trimethylsilyl)ethoxy]methyl}-5H-pyrrolo[2,3-b]pyrazin-3-yl)piperidin-4-yl]carbamate |

TABLE 3-continued

| Compound | Compound Name | NMR or MS: [M + H]+ m/z | Procedure |
|---|---|---|---|
| (structure with BocHN-azabicyclo[3.2.1]octane, pyrrolopyrazine, dichloro-methyl-indazole, SEM group) | tert-Butyl N-[(endo-8-[7-(3,4-dichloro-2-methyl-2H-indazol-5-yl)-5-{[2-(trimethylsilyl)ethoxy]methyl}-5H-pyrrolo[2,3-b]pyrazin-3-yl]-8-azabicyclo[3.2.1]oct-an-3-yl]carbamate | 672 | Prepared as general procedure 2 using 3,4-dichloro-2-methyl-5-(4,4,5,5-tetramethyl-1,3,2-dioxaborolan-2-yl)-2H-indazole |
| (structure with BocHN-, HO-piperidine, pyrrolopyrazine, chloro-methyl-indazole, SEM group) | tert-Butyl N-{1-[7-(4-chloro-2-methyl-2H-indazol-5-yl)-5-{[2-(trimethylsilyl)ethoxy]methyl}-5H-pyrrolo[2,3-b]pyrazin-3-yl]-4-(hydroxymethyl)piperidin-4-yl}carbamate | 643 | Prepared as general procedure 2 using tert-butyl N-[1-(7-bromo-5-{[2-(trimethylsilyl)ethoxy]methyl}-5H-pyrrolo[2,3-b]pyrazin-3-yl)-4-(hydroxymethyl)piperidin-4-yl]carbamate |
| (structure with BocN-difluoro-diazaspiro[3.5]nonane, pyrrolopyrazine with dimethylsulfamoyl, chloro-methyl-indazole) | tert-Butyl 7-[7-(4-chloro-2-methyl-2H-indazol-5-yl)-5-(dimethylsulfamoyl)-5H-pyrrolo[2,3-b]pyrazin-3-yl]-5,5-difluoro-2,7-diazaspiro[3.5]nonane-2-carboxylate | 651 | Prepared as general procedure 2 using tert-butyl 7-[5-(dimethylsulfamoyl)-7-iodo-5H-pyrrolo[2,3-b]pyrazin-3-yl]-5,5-difluoro-2,7-diazaspiro[3.5]nonane-2-carboxylate, heating to 70° C. |
| (structure with BocN-diazaspiro[3.5]nonane, pyrrolopyrazine, chloro-methyl-indazole, SEM group) | tert-Butyl 7-[7-(4-chloro-2-methyl-2H-indazol-5-yl)-5-{[2-(trimethylsilyl)ethoxy]methyl}-5H-pyrrolo[2,3-b]pyrazin-3-yl]-2,7-diazaspiro[3.5]nonane-2-carboxylate | 638 | Prepared as general procedure 2 using tert-butyl 7-(7-bromo-5-{[2-(trimethylsilyl)ethoxy]methyl}-5H-pyrrolo[2,3-b]pyrazin-3-yl)-2,7-diazaspiro[3.5]nonane-2-carboxylate |

TABLE 3-continued

| Compound | Compound Name | NMR or MS: [M + H]+ m/z | Procedure |
|---|---|---|---|
| | tert-Butyl 7-[7-(4-chloro-2-methyl-2H-indazol-5-yl)-5-{[2-(trimethylsilyl)ethoxy]methyl}-5H-pyrrolo[2,3-b]pyrazin-3-yl]-1,7-diazaspiro[3.5]nonane-1-carboxylate | 638 | Prepared as general procedure 2 using tert-butyl 7-(7-iodo-5-{[2-(trimethylsilyl)ethoxy]methyl}-5H-pyrrolo[2,3-b]pyrazin-3-yl)-1,7-diazaspiro[3.5]nonane-1-carboxylate |
| | tert-Butyl N-[endo-8-[7-(4-fluoro-2-methyl-2H-indazol-5-yl)-5-{[2-(trimethylsilyl)ethoxy]methyl}-5H-pyrrolo[2,3-b]pyrazin-3-yl]-8-azabicyclo[3.2.1]octan-3-yl]carbamate | 622 | Prepared as general procedure 2, using tert-butyl N-[endo-8-(7-bromo-5-{[2-(trimethylsilyl)ethoxy]methyl}-5H-pyrrolo[2,3-b]pyrazin-3-yl)-8-azabicyclo[3.2.1]octan-3-yl]carbamate and 4-fluoro-2-methyl-5-(4,4,5,5-tetramethyl-1,3,2-dioxaborolan-2-yl)-2H-indazole, heating at 80° C. for 13 h |
| | tert-Butyl N-[endo-8-[7-(5-chloro-3-methoxy-2-methylquinolin-6-yl)-5-{[2-(trimethylsilyl)ethoxy]methyl}-5H-pyrrolo[2,3-b]pyrazin-3-yl]-8-azabicyclo[3.2.1]octan-3-yl]carbamate | 679 | Prepared as general procedure 2, using, 5-chloro-3-methoxy-2-methyl-6-(4,4,5,5-tetramethyl-1,3,2-dioxaborolan-2-yl)quinoline |
| | tert-Butyl N-[endo-8-[7-(3-{[(tert-butyldimethylsilyl)oxy]methyl}-4-chloro-2-methyl-2H-indazol-5-yl)-5-{[2-(trimethylsilyl)ethoxy]methyl}-5H-pyrrolo[2,3-b]pyrazin-3-yl]-8-azabicyclo[3.2.1]octan-3-yl]carbamate | 726 (-tBu ion) | Prepared as general procedure 2, using, 3-{[(tert-butyldimethylsilyl)oxy]methyl}-4-chloro-2-methyl-5-(4,4,5,5-tetramethyl-1,3,2-dioxaborolan-2-yl)-2H-indazole |

TABLE 3-continued

| Compound | Compound Name | NMR or MS: [M + H]+ m/z | Procedure |
|---|---|---|---|
|  | tert-Butyl N-[endo-8-[7-(2-{2-[(tert-butyldimethylsilyl)oxy] ethyl}-3,4-dichloro-2H-indazol-5-yl)-5-{[2-(trimethylsilyl)ethoxy] methyl}-5H-pyrrolo[2,3-b] pyrazin-3-yl]-8-azabicyclo [3.2.1]octan-3-yl]carbamate | 1H NMR (400 MHz, DMSO-d6): 8.20-8.13 (1H, m), 7.92 (2H, d), 7.66 (1H, d), 6.92-6.78 (1H, m), 5.57 (2H, s), 4.61-4.54 (4H, m), 4.10 (2H, t), 3.62 (2H, t), 2.17-2.08 (5H, m), 1.98-1.94 (2H, m), 1.77 (2H, d), 1.40 (9H, s), 0.93-0.85 (2H, m), 0.79-0.74 (9H, m), -0.07--0.09 (9H, m), -0.13--0.14 (6H, m). | Prepared as general procedure 2, using, 2-{2-[(tert-butyldimethylsilyl)oxy] ethyl}-3,4-dichloro-5-(4,4,5,5-tetramethyl-1,3,2-dioxaborolan-2-yl)-2H-indazole |
|  | tert-Butyl N-[exo-8-[7-(3, 4-dichloro-2-methyl-2H-indazol-5-yl)-5-{[2-(trimethylsilyl)ethoxy] methyl}-5H-pyrrolo[2,3-b] pyrazin-3-yl]-8-azabicyclo [3.2.1]octan-3-yl]carbamate | 672 | Prepared as general procedure 2 using tert-butyl N-[exo-8-(7-iodo-5-{[2-(trimethylsilyl) ethoxy]methyl}-5H-pyrrolo[2,3-b]pyrazin-3-yl)-8-azabicyclo[3.2.1] octan-3-yl]carbamate and 3,4-dichloro-2-methyl-5-(4,4,5,5-tetramethyl-1,3,2-dioxaborolan-2-yl)-2H-indazole. |
|  | rac-tert-Butyl N-[(3S, 4S)-1-[7-(4-chloro-2-methyl-2H-indazol-5-yl)-5-{[2-(trimethylsilyl) ethoxy]methyl}-5H-pyrrolo[2,3-b]pyrazin-3-yl]-3-hydroxypiperidin-4-yl]carbamate | 628 | Prepared as general procedure 2 using rac-(3S,4S)-4-amino-1-{7-iodo-5H-pyrrolo [2,3-b]pyrazin-3-yl} piperidin-3-ol |

TABLE 3-continued

| Compound | Compound Name | NMR or MS: [M + H]+ m/z | Procedure |
|---|---|---|---|
| (structure) | tert-Butyl N-[(3S,4R)-1-[7-(4-chloro-2-methyl-2H-indazol-5-yl)-5-{[2-(trimethylsilyl)ethoxy]methyl}-5H-pyrrolo[2,3-b]pyrazin-3-yl]-3-fluoropiperidin-4-yl]carbamate | 631 | Prepared as general procedure 2 using tert-butyl N-[(3S,4R)-3-fluoro-1-(7-iodo-5-{[2-(trimethylsilyl)ethoxy]methyl}-5H-pyrrolo[2,3-b]pyrazin-3-yl)piperidin-4-yl]carbamate |
| (structure) | tert-Butyl N-[(3R,4S)-1-[7-(4-chloro-2-methyl-2H-indazol-5-yl)-5-{[2-(trimethylsilyl)ethoxy]methyl}-5H-pyrrolo[2,3-b]pyrazin-3-yl]-3-fluoropiperidin-4-yl]carbamate | 631 | Prepared as general procedure 2 using tert-butyl N-[(3R,4S)-3-fluoro-1-(7-iodo-5-{[2-(trimethylsilyl)ethoxy]methyl}-5H-pyrrolo[2,3-b]pyrazin-3-yl)piperidin-4-yl]carbamate |

General Procedure 3 (One-pot Suzuki reaction): tert-Butyl N-[endo-8-{7-[7-chloro-2-(methoxymethyl)-1,3-benzothiazol-6-yl]-5-{[2-(trimethylsilyl)ethoxy]methyl}-5H-pyrrolo[2,3-b]pyrazin-3-yl}-8-azabicyclo[3.2.1]octan-3-yl]carbamate

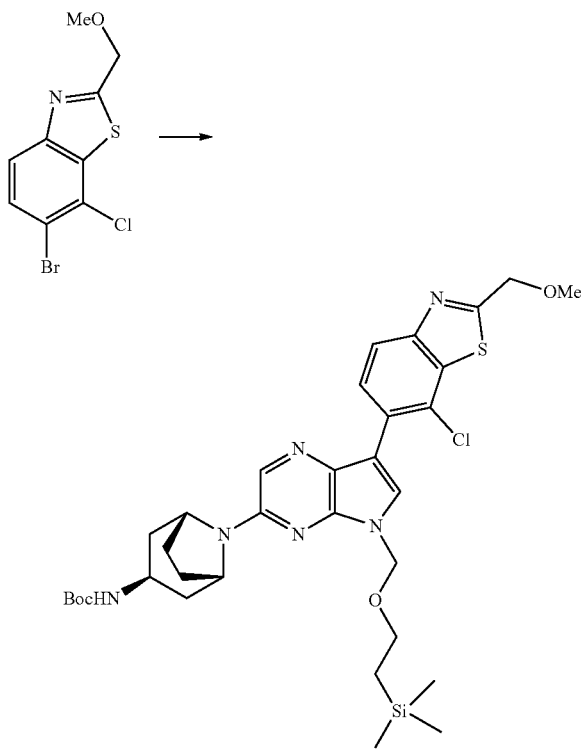

6-Bromo-7-chloro-2-(methoxymethyl)-1,3-benzothiazole (350 mg, 1.2 mmol), bis(pinacolato)diboron (456 mg, 1.8 mmol), [1,1'-bis(diphenylphosphino)ferrocene]dichloropalladium(II) (175 mg, 0.24 mmol) and potassium acetate (587 mg, 6.0 mmol) were combined in a 30 mL microwave tube, sealed, evacuated and backfilled with nitrogen (×2). 1,4-Dioxane (6 mL) was added and the tube backfilled again (×2) before heating to 90° C. for 2 h. After cooling, tert-butyl N-[endo-8-(7-iodo-5-{[2-(trimethylsilyl)ethoxy]methyl}-5H-pyrrolo[2,3-b]pyrazin-3-yl)-8-azabicyclo[3.2.1]octan-3-yl]carbamate (717 mg, 1.2 mmol), bis(diphenylphosphino)ferrocene]dichloropalladium(II) (175 mg, 0.24 mmol), potassium carbonate (992 mg, 7.2 mmol) and water (3 mL) were added. The reaction was resealed, backfilled with nitrogen (×2) and heated to 70° C. for 2 h. After cooling, the reaction was diluted with water and extracted with EtOAc (3×). Combined organics were dried over anhydrous MgSO₄, filtered and evaporated. The residue was purified by column chromatography on silica gel (gradient elution, 0-100%, EtOAc/petrol), to give the title compound (412 mg). MS: [M+H]+=685.

Compounds of Table 4 set out below were prepared in an analogous manner to general procedure 3, using the corresponding aryl halides, with any significant variations indicated.

TABLE 4

| Compound | Compound Name | NMR or MS: [M + H]+ m/z | Procedure |
|---|---|---|---|
| (structure) | tert-Butyl N-[endo-8-[7-(7-chloro-1,3-benzothiazol-6-yl)-5-{[2-(trimethylsilyl)ethoxy]methyl}-5H-pyrrolo[2,3-b]pyrazin-3-yl]-8-azabicyclo[3.2.1]octan-3-yl]carbamate | 641 | Prepared as general procedure 3 using 6-bromo-7-chloro-1,3-benzothiazole |
| (structure) | tert-Butyl N-[endo-8-{7-[7-chloro-2-(dimethylamino)-1,3-benzothiazol-6-yl]-5-{[2-(trimethylsilyl)ethoxy]methyl}-5H-pyrrolo[2,3-b]pyrazin-3-yl}-8-azabicyclo[3.2.1]octan-3-yl]carbamate | 684 | Prepared as general procedure 3 using 6-bromo-7-chloro-N,N-dimethyl-1,3-benzothiazol-2-amine, except replacing K$_2$CO$_3$ with K$_3$PO$_4$ (3.0 eq) |
| (structure) | tert-Butyl N-[endo-8-[7-(4-chloro-2-oxo-3-{[2-(trimethylsilyl)ethoxy]methyl}-2,3-dihydro-1,3-benzoxazol-5-yl)-5-{[2-(trimethylsilyl)ethoxy]methyl}-5H-pyrrolo[2,3-b]pyrazin-3-yl]-8-azabicyclo[3.2.1]octan-3-yl]carbamate | 771 | Prepared as general procedure 3 using 5-bromo-4-chloro-3-{[2-(trimethylsilyl)ethoxy]methyl}-2,3-dihydro-1,3-benzoxazol-2-one, except replacing K$_2$CO$_3$ with K$_3$PO$_4$ (3.0 eq) |
| (structure) | tert-Butyl N-[endo-8-{7-[8-chloro-2-(dimethylamino)quinolin-7-yl]-5-{[2-(trimethylsilyl)ethoxy]methyl}-5H-pyrrolo[2,3-b]pyrazin-3-yl}-8-azabicyclo[3.2.1]octan-3-yl]carbamate | 678 | Prepared as general procedure 3 using 7-bromo-8-chloro-N,N-dimethylquinolin-2-amine. |

TABLE 4-continued

| Compound | Compound Name | NMR or MS: [M + H]+ m/z | Procedure |
|---|---|---|---|
|  | tert-Butyl N-[endo-8-[7-(8-chloro-2-methoxyquinolin-7-yl)-5-{[2-(trimethylsilyl)ethoxy]methyl}-5H-pyrrolo[2,3-b]pyrazin-3-yl]-8-azabicyclo[3.2.1]octan-3-yl]carbamate | 665 | Prepared as general procedure 3 using 7-bromo-8-chloro-2-methoxyquinoline. |
|  | tert-butyl N-[endo-8-[7-(5-chloro-2-methyl-4-oxo-3-{[2-(trimethylsilyl)ethoxy]methyl}-3,4-dihydroquinazolin-6-yl)-5-{[2-(trimethylsilyl)ethoxy]methyl}-5H-pyrrolo[2,3-b]pyrazin-3-yl]-8-azabicyclo[3.2.1]octan-3-yl]carbamate | 796 | Prepared as general procedure 3 using 6-bromo-5-chloro-2-methyl-3-{[2-(trimethylsilyl)ethoxy]methyl}-3,4-dihydroquinazolin-4-one. |
|  | tert-Butyl N-[endo-8-{7-[7-chloro-2-(oxolan-3-yl)-1,3-benzothiazol-6-yl]-5-{[2-(trimethylsilyl)ethoxy]methyl}-5H-pyrrolo[2,3-b]pyrazin-3-yl}-8-azabicyclo[3.2.1]octan-3-yl]carbamate | 711 | Prepared as general procedure 3 using 6-bromo-7-chloro-2-(oxolan-3-yl)-1,3-benzothiazole. |
|  | tert-Butyl N-[endo-8-[7-(8-chloro-2-oxo-1,2-dihydroquinolin-7-yl)-5-{[2-(trimethylsilyl)ethoxy]methyl}-5H-pyrrolo[2,3-b]pyrazin-3-yl]-8-azabicyclo[3.2.1]octan-3-yl]carbamate | 651 | Prepared as general procedure 3, using 7-bromo-8-chloro-1,2-dihydroquinolin-2-one. |

TABLE 4-continued

| Compound | Compound Name | NMR or MS: [M + H]+ m/z | Procedure |
|---|---|---|---|
| (structure shown) | tert-Butyl N-[endo-8-[7-(7-chloro-2-oxo-3-{[2-(trimethylsilyl)ethoxy]methyl}-2,3-dihydro-1,3-benzothiazol-6-yl)-5H-pyrrolo[2,3-b]pyrazin-3-yl]-8-azabicyclo[3.2.1]octan-3-yl]carbamate | $^1$H NMR (400 MHz, DMSO-$d_6$): 8.17 (1H, s), 8.09 (1H, d), 7.91 (1H, s), 7.47 (1H, d), 6.96-6.74 (1H, m), 5.57 (2H, s), 5.40 (2H, s), 4.59 (2H, s), 3.66-3.58 (4H, m), 3.43 (1H, d), 2.17-2.09 (4H, m), 1.96 (3H, d), 1.77 (2H, d), 1.40 (9H, s), 0.88 (4H, q), -0.04 (9H, s), -0.08 (9H, s). | Prepared as general procedure 3, using 6-bromo-7-chloro-3-{[2-(trimethylsilyl)ethoxy]methyl}-2,3-dihydro-1,3-benzothiazol-2-one |

Preparation 44: 1-[exo-8-[7-(4-Chloro-2-methyl-2H-indazol-5-yl)-5-{[2-(trimethylsilyl)ethoxy]methyl}-5H-pyrrolo[2,3-b]pyrazin-3-yl]-8-azabicyclo[3.2.1]octan-3-yl]methanamine exo-8-[7-(4-Chloro-2-methyl-2H-indazol-5-yl)-5-{[2-(trimethylsilyl)ethoxy]methyl}-5H-pyrrolo[2,3-b]pyrazin-3-yl]-8-azabicyclo[3.2.1]octane-3-carbonitrile (69 mg, 0.13 mmol) dissolved in THF (1.26 mL) and LiAlH$_4$ (1.0M in THF, 0.151 mL) added at RT over 10 min. After stirring for 30 min, 1M sodium hydroxide (3.0 mL) was added. The aq. layer was extracted with EtOAc (3×). The combined organics were passed through a phase separator and concentrated in vacuo, to give the title compound which was used directly in the next step. MS: [M+H]$^+$=552.

Preparation 45: tert-Butyl 7-[7-(4-chloro-2-methyl-2H-indazol-5-yl)-5H-pyrrolo[2,3-b]pyrazin-3-yl]-1,7-diazaspiro[3.5]nonane-1-carboxylate

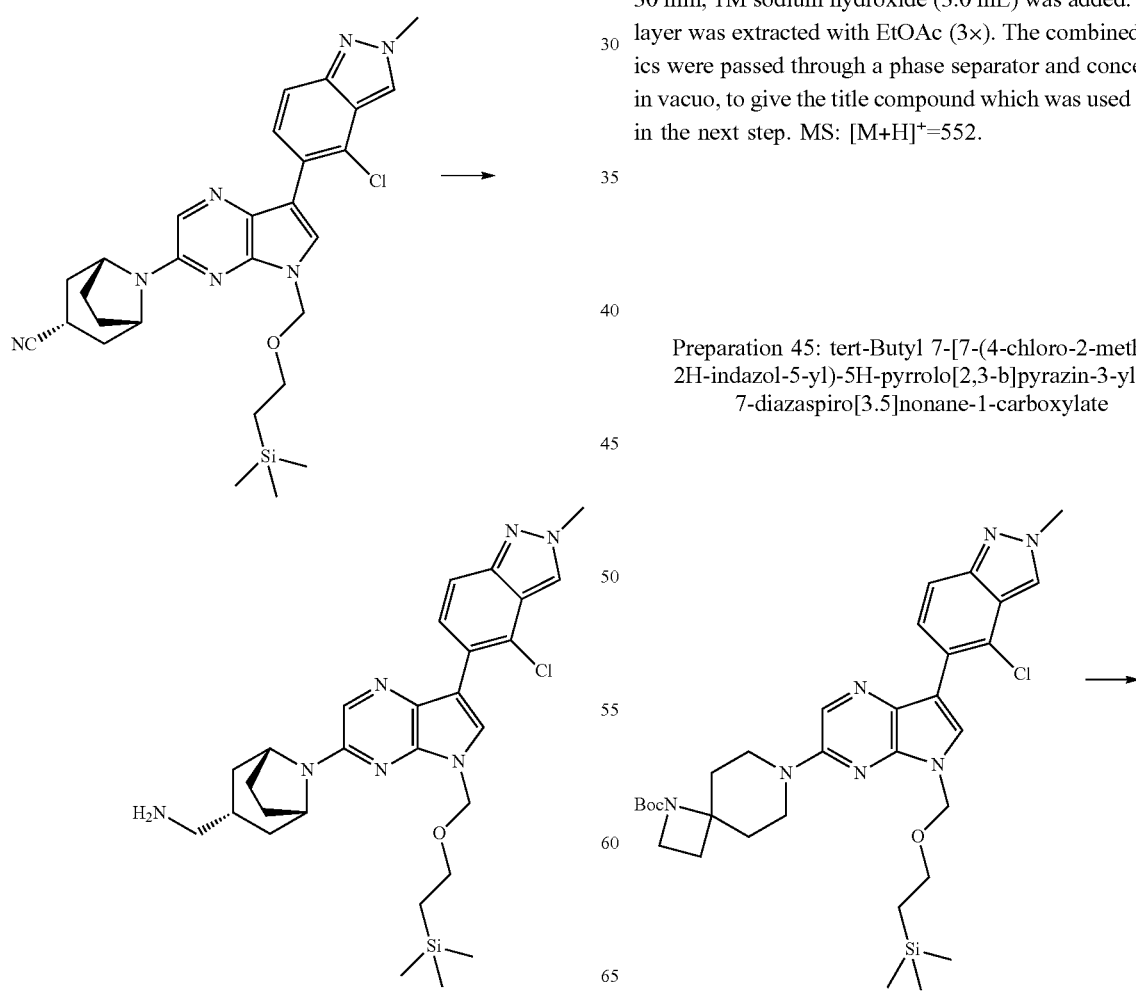

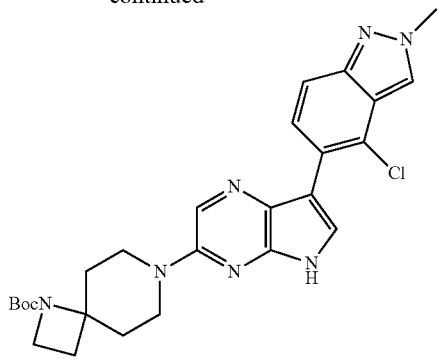

A stirred mixture of tert-butyl 7-[7-(4-chloro-2-methyl-2H-indazol-5-yl)-5-{[2-(trimethylsilyl)ethoxy]methyl}-5H-pyrrolo[2,3-b]pyrazin-3-yl]-1,7-diazaspiro[3.5]nonane-1-carboxylate (285 mg, 0.45 mmol), 1 M TBAF in THF (0.89 mL, 0.89 mmol), and THF (1.0 mL) was heated to reflux for 18 h. The reaction was partitioned between EtOAc and brine, and the separated aq. layer extracted with EtOAc (2×). Combined organics were dried (Na$_2$SO$_4$) and evaporated. The crude was purified by recrystallization from small amount of MeOH and ether to give the title compound (180 mg, 79%). MS: [M+H]=508.

Preparation 46: 4-Chloro-5-(3-chloro-5-{[2-(trimethylsilyl)ethoxy]methyl}-5H-pyrrolo[2,3-b]pyrazin-7-yl)-2-methyl-2H-indazole

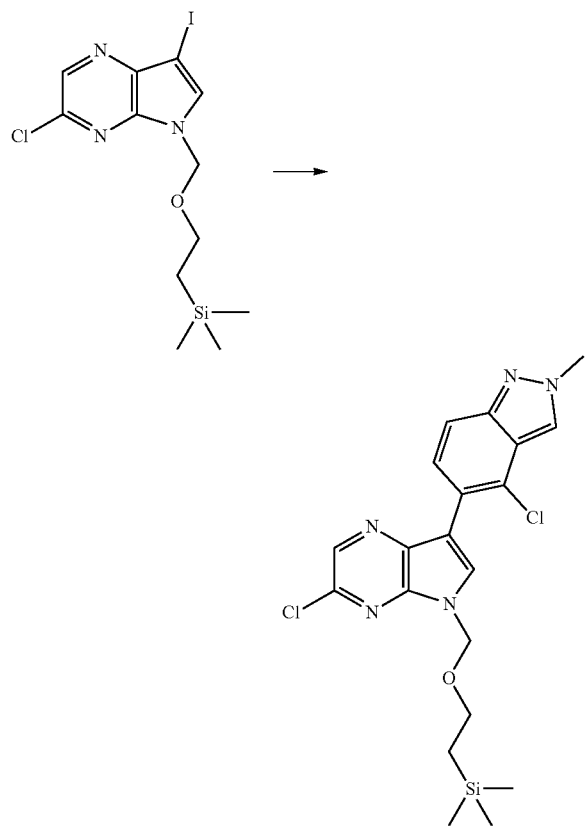

Prepared by general suzuki procedure 2, using 3-chloro-7-iodo-5-{[2-(trimethylsilyl)ethoxy]methyl}-5H-pyrrolo[2,3-b]pyrazine (1 eq) and 4-chloro-2-methyl-5-(4,4,5,5-tetramethyl-1,3,2-dioxaborolan-2-yl)-2H-indazole (1 eq), to give the title compound MS: [M+H]$^+$=448

Preparation 47: rac-Benzyl N-[(1S,2R,3R,5R)-8-[7-(4-chloro-2-methyl-2H-indazol-5-yl)-5-{[2-(trimethylsilyl)ethoxy]methyl}-5H-pyrrolo[2,3-b]pyrazin-3-yl]-2-fluoro-8-azabicyclo[3.2.1]octan-3-yl]carbamate

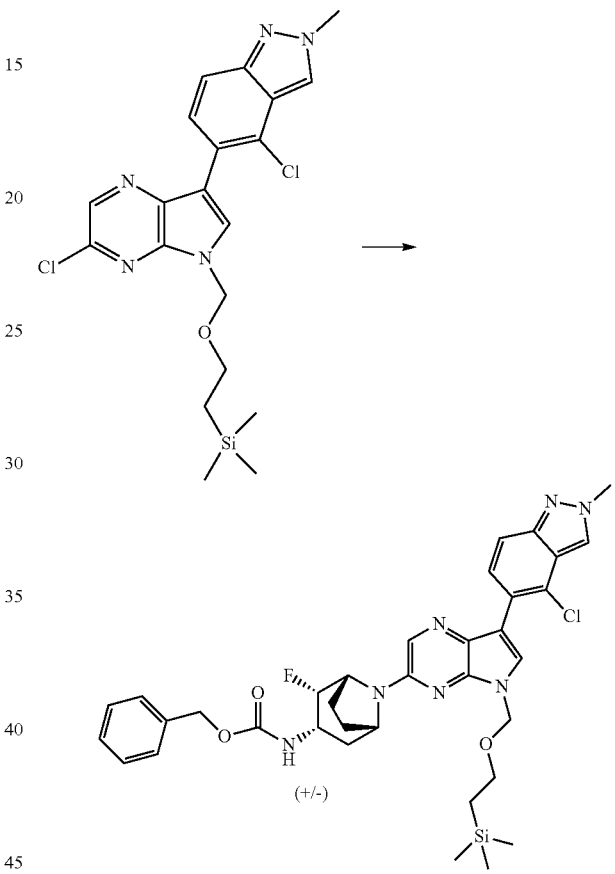

A solution of 4-chloro-5-(3-chloro-5-{[2-(trimethylsilyl)ethoxy]methyl}-5H-pyrrolo[2,3-b]pyrazin-7-yl)-2-methyl-2H-indazole (0.188 g, 0.42 mmol), rac-benzyl N-[(1S,2S,3R,5R)-2-fluoro-8-azabicyclo[3.2.1]octan-3-yl]carbamate hydrochloride (0.158 g, 0.5 mmol), tris(dibenzylideneacetone)dipalladium(0)-chloroform adduct (22 mg, 0.02 mmol), dicyclohexyl[2',4',6'-tris(propan-2-yl)-[1,1'-biphenyl]-2-yl]phosphane (20 mg, 0.04 mmol), and cesium carbonate (0.507 g, 1.56 mmol) in toluene (4.21 mL) was degassed under nitrogen for 5 min. The reaction was heated to 110° C. for 18 h. The reaction was diluted with DCM and purified by column chromatography on silica gel (gradient elution, 0-50%, EtOAc/petrol), to give the title compound (72 mg), MS: [M+H]$^+$=690.

Compounds of the Table 5 below were prepared in an analogous manner to the synthesis of rac-benzyl N-[(1S,2R,3R,5R)-8-[7-(4-chloro-2-methyl-2H-indazol-5-yl)-5-{[2-(trimethylsilyl)ethoxy]methyl}-5H-pyrrolo[2,3-b]pyrazin-3-yl]-2-fluoro-8-azabicyclo[3.2.1]octan-3-yl]carbamate of preparation 47, using the corresponding aryl halide and amine.

TABLE 5

| Compound | Compound Name | MS: [M + H]+ m/z | Procedure |
|---|---|---|---|
| 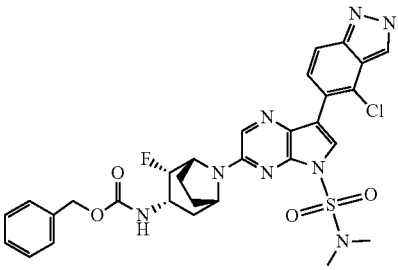 | Benzyl N-[(1R,2S,3S,5S)-8-[7-(4-chloro-2-methyl-2H-indazol-5-yl)-5-(dimethylsulfamoyl)-5H-pyrrolo[2,3-b]pyrazin-3-yl]-2-fluoro-8-azabicyclo[3.2.1]octan-3-yl]carbamate | 667 | Using 3-chloro-7-(4-chloro-2-methyl-2H-indazol-5-yl)-N,N-dimethyl-5H-pyrrolo[2,3-b]pyrazine-5-sulfonamide and benzyl N-[(1R,2R,3S,5S)-2-fluoro-8-azabicyclo[3.2.1]octan-3-yl]carbamate, hydrochloride salt |
| 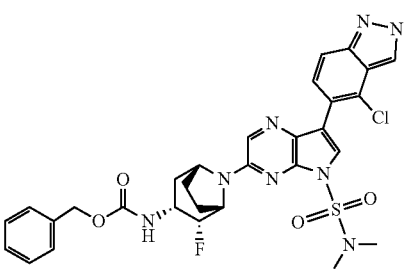 | Benzyl N-[(1S,2R,3R,5R)-8-[7-(4-chloro-2-methyl-2H-indazol-5-yl)-5-(dimethylsulfamoyl)-5H-pyrrolo[2,3-b]pyrazin-3-yl]-2-fluoro-8-azabicyclo[3.2.1]octan-3-yl]carbamate | 667 | Using 3-chloro-7-(4-chloro-2-methyl-2H-indazol-5-yl)-N,N-dimethyl-5H-pyrrolo[2,3-b]pyrazine-5-sulfonamide and benzyl N-[(1S,2S,3R,5R)-2-fluoro-8-azabicyclo[3.2.1]octan-3-yl]carbamate, hydrochloride salt, to give the title compound |
| 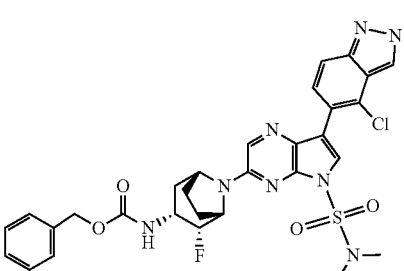 | Benzyl N-[(1S,2R,3S,5R)-8-[7-(4-chloro-2-methyl-2H-indazol-5-yl)-5-(dimethylsulfamoyl)-5H-pyrrolo[2,3-b]pyrazin-3-yl]-2-fluoro-8-azabicyclo[3.2.1]octan-3-yl]carbamate | 667 | Using 3-chloro-7-(4-chloro-2-methyl-2H-indazol-5-yl)-N,N-dimethyl-5H-pyrrolo[2,3-b]pyrazine-5-sulfonamide and benzyl N-[(1S,2S,3S,5R)-2-fluoro-8-azabicyclo[3.2.1]octan-3-yl]carbamate hydrochloride, to give the title compound |
| 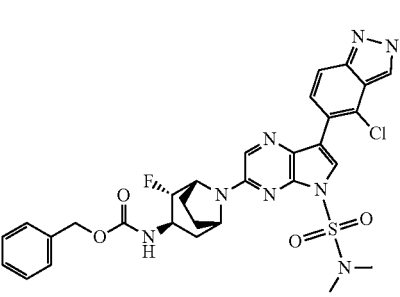 | Benzyl N-[(1R,2S,3R,5S)-8-[7-(4-chloro-2-methyl-2H-indazol-5-yl)-5-(dimethylsulfamoyl)-5H-pyrrolo[2,3-b]pyrazin-3-yl]-2-fluoro-8-azabicyclo[3.2.1]octan-3-yl]carbamate | 667 | Using 3-chloro-7-(4-chloro-2-methyl-2H-indazol-5-yl)-N,N-dimethyl-5H-pyrrolo[2,3-b]pyrazine-5-sulfonamide and benzyl N-[(1R,2R,3R,5S)-2-fluoro-8-azabicyclo[3.2.1]octan-3-yl]carbamate hydrochloride, to give the title compound |

Preparation 48: rac-Benzyl N-[(1S,2R,3R,5R)-8-[7-(4-chloro-2-methyl-2H-indazol-5-yl)-5H-pyrrolo[2,3-b]pyrazin-3-yl]-2-fluoro-8-azabicyclo[3.2.1]octan-3-yl]carbamate

Preparation 49: tert-Butyl N-[exo-8-[7-(4-chloro-2-ethyl-2H-indazol-5-yl)-5-{[2-(trimethylsilyl)ethoxy]methyl}-5H-pyrrolo[2,3-b]pyrazin-3-yl]-8-azabicyclo[3.2.1]octan-3-yl]carbamate

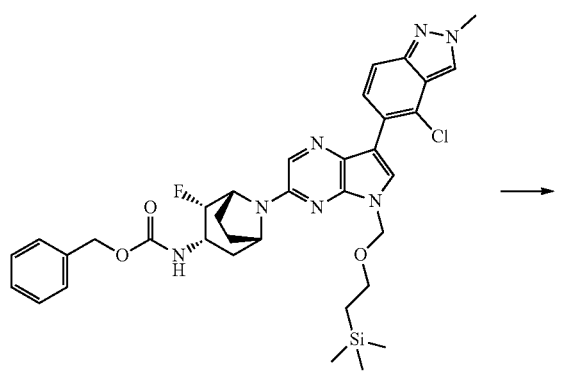

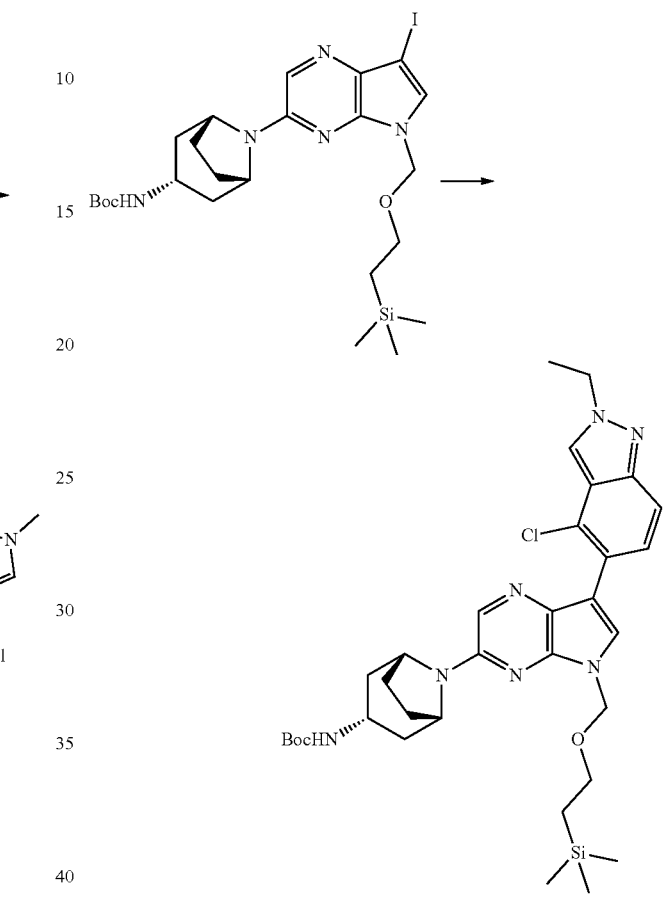

Trifluoroacetic acid (0.7 mL) was added to rac-benzyl N-[(1S,2R,3R,5R)-8-[7-(4-chloro-2-methyl-2H-indazol-5-yl)-5-{[2-(trimethylsilyl)ethoxy]methyl}-5H-pyrrolo[2,3-b]pyrazin-3-yl]-2-fluoro-8-azabicyclo[3.2.1]octan-3-yl]carbamate (72 mg, 0.10 mmol) dissolved in DCM (0.7 mL and the mixture was stirred for 1.5 h. Additional trifluoroacetic acid (0.5 mL) was added and the reaction stirred for 2 h. The reaction was concentrated in vacuo and the residue was dissolved in methanol (1.0 mL). Ethylene diamine was added (1.0 mL) to the reaction and stirred for 2 h. The reaction was concentrated in vacuo and water was added to the residue. The aq. was extracted with ethyl acetate (3×) and the combined organics washed with brine solution and concentrated in vacuo. The residue was purified by column chromatography on silica gel (gradient elution, 0-100%, ethyl acetate/petrol 40-60° C.), to give the title compound (37 mg), MS: [M+H]$^+$=560.

To a stirred solution of tert-butyl N-[exo-8-(7-iodo-5-{[2-(trimethylsilyl)ethoxy]methyl}-5H-pyrrolo[2,3-b]pyrazin-3-yl)-8-azabicyclo[3.2.1]octan-3-yl]carbamate (0.5 g, 0.834 mmol) (azeotropically dried with dry toluene, ×2) in THF (6.68 mL) at 0° C. was added isopropylmagnesium chloride lithium chloride complex solution (1.3 M in THF) (1.41 mL, 1.84 mmol) dropwise. The yellow-orange solution was stirred at 0° C. for 35 min. Zinc chloride solution (0.5 M in THF) (3.67 mL, 1.84 mmol) was added dropwise, the mixture stirred for 10 min then allowed to warm to RT for 40 min. A solid mixture of 5-bromo-4-chloro-2-ethyl-2H-indazole (0.217 g, 0.834 mmol) and SPhos Pd G4 (0.0331 g, 0.0417 mmol) was added, the vessel was evacuated and back-filled with N$_2$ (×4) and the mixture was stirred at RT overnight. The reaction was diluted with EtOAc/30% brine solution/sat. NH$_4$Cl solution, the phases separated and the organic phase was washed with 30% brine solution (×2). The organic extract was dried (Na$_2$SO$_4$), filtered and concentrated. The residue was purified by column chromatography on silica gel, (gradient elution, 5-40% acetone/petrol) to give the title compound (140 mg), MS: [M+H]$^+$=652.

Preparation 50: 5-Bromo-6-chloro-3-[2-(trimethylsilyl)ethynyl]pyrazin-2-amine

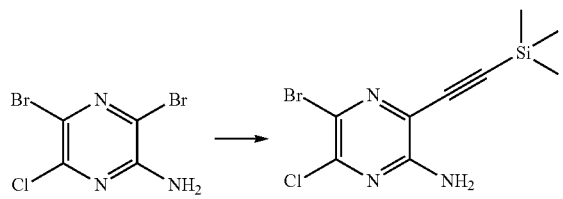

To a solution of 3,5-dibromo-6-chloropyrazin-2-amine (5.0 g, 17.42 mmol) in anhydrous EtOAc (40 mL) was added triethylamine (2.54 ml, 18.29 mmol) and CuI (0.165 g, 0.87 mmol). The mixture was degassed with bubbling $N_2$ for 20 min then Pd(PPh$_3$)$_4$ (0.10 g, 0.87 mmol) was added. The reaction mixture was cooled to 0° C., ethynyltrimethylsilane (2.52 ml, 18.29 mmol) was added slowly and the temperature was allowed to gradually increase to 15° C. over 3 h. The reaction mixture was diluted with water (30 mL) and extracted with EtOAc (3×). The combined organic layers were dried using a phase separator cartridge then concentrated. The residue was purified by column chromatography on silica gel (gradient elution, 0-10%, EtOAc/petrol), to give the title compound (4.77 g). MS: [M+H]$^+$=304.

Preparation 51: 2-Bromo-3-chloro-5H-pyrrolo[2,3-b]pyrazine

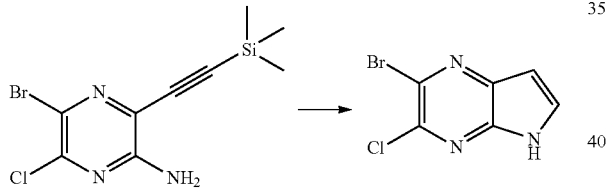

5-Bromo-6-chloro-3-[2-(trimethylsilyl)ethynyl]pyrazin-2-amine (5.29 g, 17.42 mmol) was dissolved in anhydrous DMF (20 mL) under a nitrogen atmosphere and cooled to 0° C. KOtBu (2.34 g, 20.90 mmol) was added portion wise over 5 min and the reaction mixture was stirred at 0° C. for a further 10 min. The reaction was allowed to warm to RT and stirred for 2 h. The reaction was quenched with sat. aq. NR$_4$Cl (20 mL) and more water was added resulting in a precipitate. The precipitate was filtered and washed with water then dried in a vacuum oven overnight, to give the title product (3.03 g). MS: [M+H]$^+$=232.

Preparation 52: 2-Bromo-3-chloro-7-iodo-5H-pyrrolo[2,3-b]pyrazine

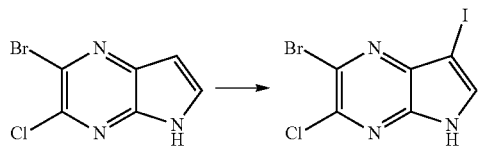 [SMILES: Clc1nc2[nH]ccc2nc1Br ; Clc1nc2[nH]cc(I)c2nc1Br]

2-Bromo-3-chloro-5H-pyrrolo[2,3-b]pyrazine (2.49 g, 10.53 mmol) was dissolved in DMF (20 mL) and N-iodosuccinimide (2.607 g, 11.58 mmol) added at RT. The reaction was stirred for 1 h at RT. Water was added until precipitation occurred. The solid was collected by vacuum filtration, washed with water and dried in a vacuum oven for 24 h, to give the title compound (3.39 g). MS: [M−H]$^+$=357.

Preparation 53: tert-Butyl N-{[1-(2-bromo-7-iodo-5-{[2-(trimethylsilyl)ethoxy]methyl}-5H-pyrrolo[2,3-b]pyrazin-3-yl)-4-methylpiperidin-4-yl]methyl}carbamate

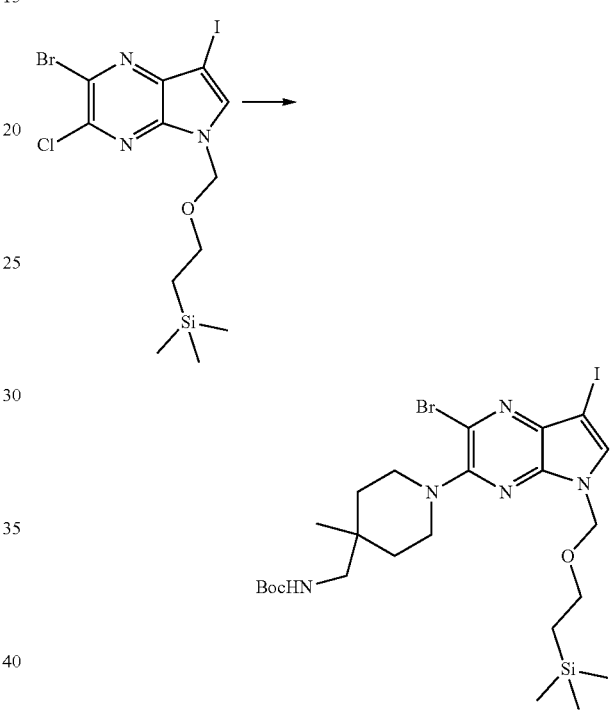

2-Bromo-3-chloro-7-iodo-5H-pyrrolo[2,3-b]pyrazine (1.0 g, 2.8 mmol) was dissolved in DMF (10 mL) and sodium hydride (60% in mineral oil, 0.134 g, 3.37 mmol) was added portionwise over 5 min at 0-4° C. (ice bath). The reaction was warmed to RT for 30 min then cooled to 0-4° C. (ice bath). 2-(Trimethylsilyl)ethoxymethyl chloride (0.596 mL, 3.37 mmol) was added dropwise and the deep red/orange solution stirred for 1 h then warmed to RT and stirred for 2 h. Sat. NH$_4$Cl was added and the reaction was diluted with diethyl ether. The organic phase was washed with water then brine, dried by passing through a phase separator and concentrated in vacuo. The residue was purified by column chromatography on silica gel (gradient elution, 0-30%, EtOAc/petrol), to give 2-bromo-3-chloro-7-iodo-5-{[2-(trimethylsilyl)ethoxy]methyl}-5H-pyrrolo[2,3-b]pyrazine (0.99 g), which was used directly in the next step.

2-Bromo-3-chloro-7-iodo-5-{[2-(trimethylsilyl)ethoxy]methyl}-5H-pyrrolo[2,3-b]pyrazine (0.20 g, 0.40 mmol) and tert-butyl N-[(4-methylpiperidin-4-yl)methyl]carbamate (0.112 g, 0.488 mmol) were dissolved in NMP (3 mL). Et$_3$N (0.3 mL, 2.1 mmol) was added and the reaction was heated to 70° C. in a microwave for 2 h. After cooling the reaction was diluted with diethyl ether and washed with water then brine. The organic layer was dried using a phase separator

217 cartridge then concentrated under reduced pressure. The residue was purified by column chromatography on silica gel (gradient elution, 0-50%, EtOAc/petrol), to give the title compound (0.15 g). MS: [M+H]⁺=681.

Preparation 54: tert-Butyl N-({1-[2-bromo-7-(4-chloro-2-methyl-2H-indazol-5-yl)-5-{[2-(trimethylsilyl)ethoxy]methyl}-5H-pyrrolo[2,3-b]pyrazin-3-yl]-4-methylpiperidin-4-yl}methyl)carbamate

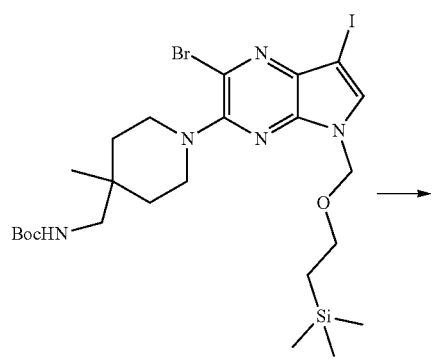

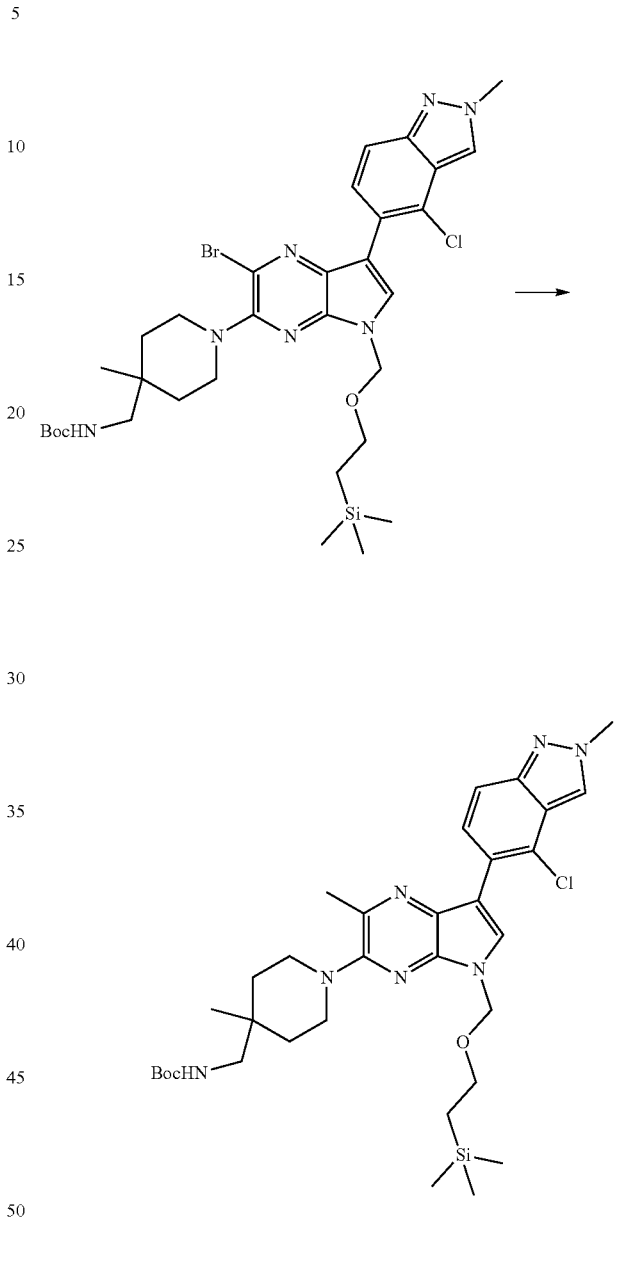

Prepared following general procedure 2. Starting with tert-butyl N-{[1-(2-bromo-7-iodo-5-{[2-(trimethylsilyl)ethoxy]methyl}-5H-pyrrolo[2,3-b]pyrazin-3-yl)-4-methylpiperidin-4-yl]methyl}carbamate (0.148 g, 0.217 mmol), to give the title compound (0.056 g). MS: [M+H]⁺=720.

218

Preparation 55: tert-Butyl N-({1-[7-(4-chloro-2-methyl-2H-indazol-5-yl)-2-methyl-5-{[2-(trimethylsilyl)ethoxy]methyl}-5H-pyrrolo[2,3-b]pyrazin-3-yl]-4-methylpiperidin-4-yl}methyl)carbamate tert-Butyl N-({1-[2-bromo-7-(4-chloro-2-methyl-2H-indazol-5-yl)-5-{[2-(trimethylsilyl)ethoxy]methyl}-5H-pyrrolo[2,3-b]pyrazin-3-yl]-4-methylpiperidin-4-yl}methyl)carbamate (0.056 g, 0.077 mmol), lithium bromide (0.021 g, 0.2 mmol) and (1,3-diisopropylimidazol-2-ylidene)(3-chloropyridyl)palladium(II) dichloride (PEPPSI) (0.003 g, 0.003 mmol) were dissolved in THF (1.5 mL) and NMP (1.5 mL). Methylzinc chloride solution in THF (2M, 0.117 mL, 0.231 mmol) was added and the reaction was stirred at RT for 30 min. Sat. NH₄Cl was added and the reaction was diluted with diethyl ether and washed with water then brine. The organic layer was dried using a phase separator cartridge then concentrated under reduced pressure to give the title compound. MS: [M+H]⁺=654.

Preparation 56: 2-Bromo-3-chloro-7-iodo-N,N-dimethyl-5H-pyrrolo[2,3-b]pyrazine-5-sulfonamide

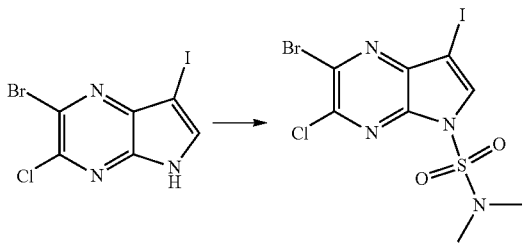 [SMILES: Clc1nc2[nH]cc(I)c2nc1Br ; CN(C)S(=O)(=O)n1cc(I)c2nc(Br)c(Cl)nc21]

2-Bromo-3-chloro-7-iodo-5H-pyrrolo[2,3-b]pyrazine (2.0 g, 5.61 mmol) was dissolved in anhydrous DMF (10 mL) under a nitrogen atmosphere and cooled to 0° C. NaH (60% in mineral oil, 0.247 g, 6.17 mmol) was added in small portions then the reaction was allowed to warm to RT and stirred for 30 min by which time all hydrogen evolution had stopped. The reaction was cooled to 0° C. and dimethylsulfamoyl chloride (0.662 mL, 6.17 mmol) was added dropwise. The reaction was allowed to warm to RT, stirred for 1 h then quenched with Sat. aq. NH$_4$Cl (10 mL). The reaction mixture was diluted with EtOAc and washed with water then brine. The organic layer was dried using a phase separator cartridge then concentrated under reduced pressure. The residue was purified by column chromatography on silica gel (gradient elution, 0-50%, EtOAc/petrol), to give the title compound (2.11 g). MS: [M+H]$^+$=466.

Preparation 57: tert-Butyl N-[endo-8-[2-bromo-5-(dimethylsulfamoyl)-7-iodo-5H-pyrrolo[2,3-b]pyrazin-3-yl]-8-azabicyclo[3.2.1]octan-3-yl]carbamate

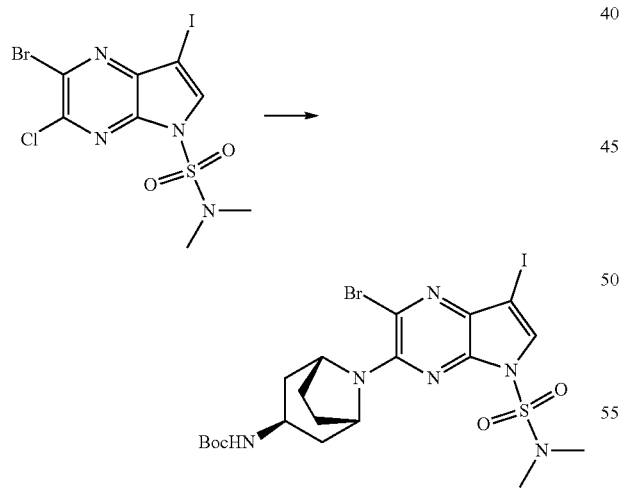

2-Bromo-3-chloro-7-iodo-N,N-dimethyl-5H-pyrrolo[2,3-b]pyrazine-5-sulfonamide (0.84 g, 1.82 mmol) and tert-butyl N-[endo-8-azabicyclo[3.2.1]octan-3-yl]carbamate (0.82 g, 3.64 mmol) were dissolved in NMP (7 mL). Et$_3$N (0.716 mL, 5.46 mmol) was added and the reaction was heated to 60° C. overnight. After cooling, the reaction diluted with diethyl ether and washed with water then brine. The organic layer was dried using a phase separator cartridge then concentrated under reduced pressure. The residue was purified by column chromatography on silica gel (gradient elution, 0-70%, EtOAc/petrol) to give the title compound (0.908 g). MS: [M+H]$^+$=655.

Preparation 58: tert-Butyl N-[endo-8-[2-bromo-7-(4-chloro-2-methyl-2H-indazol-5-yl)-5-(dimethylsulfamoyl)-5H-pyrrolo[2,3-b]pyrazin-3-yl]-8-azabicyclo[3.2.1]octan-3-yl]carbamate

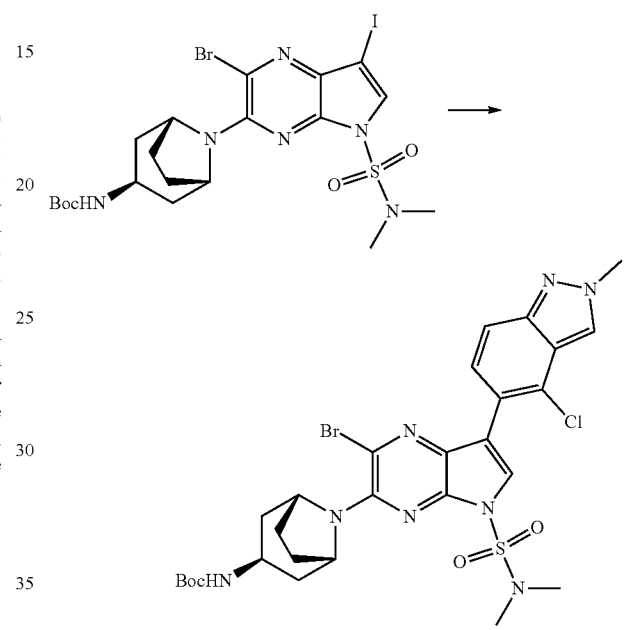

Prepared by general Suzuki procedure 2, using tert-butyl N-[endo-8-[2-bromo-5-(dimethylsulfamoyl)-7-iodo-5H-pyrrolo[2,3-b]pyrazin-3-yl]-8-azabicyclo[3.2.1]octan-3-yl]carbamate (0.908 g, 1.488 mmol), to give the title compound (0.536 g). MS: [M+H]$^+$=695.

Preparation 59: tert-Butyl N-[endo-8-[7-(4-chloro-2-methyl-2H-indazol-5-yl)-5-(dimethylsulfamoyl)-2-methyl-5H-pyrrolo[2,3-b]pyrazin-3-yl]-8-azabicyclo[3.2.1]octan-3-yl]carbamate

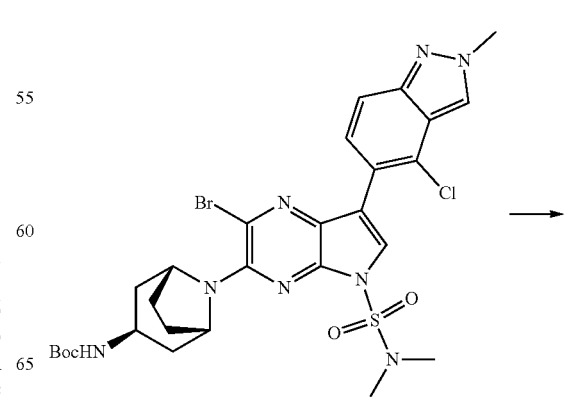

221
-continued

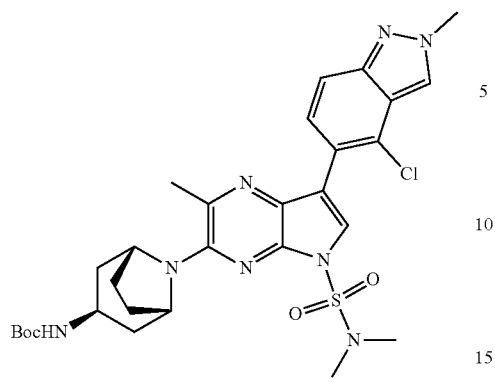

tert-Butyl N-[endo-8-[2-bromo-7-(4-chloro-2-methyl-2H-indazol-5-yl)-5-(dimethylsulfamoyl)-5H-pyrrolo[2,3-b]pyrazin-3-yl]-8-azabicyclo[3.2.1]octan-3-yl]carbamate (0.20 g, 0.287 mmol), lithium bromide (0.074 g, 0.863 mmol) and (1,3-diisopropylimidazol-2-ylidene)(3-chloropyridyl)palladium(II) dichloride (PEPPSI) (0.014 g, 0.02 mmol) were dissolved in THF (2 mL) and NMP (2 mL). Methylzinc chloride solution in THF (2M, 0.344 mL, 0.689 mmol) was added and the reaction was stirred at RT for 30 min. Sat. NH₄Cl was added and the reaction was diluted with diethyl ether and washed with water then brine. The organic layer was dried using a phase separator cartridge then concentrated under reduced pressure. The residue was used directly in the next step. MS: [M+H]⁺=629.

Preparation 60: tert-Butyl N-[exo-8-[7-(4-chloro-2-methyl-2H-indazol-5-yl)-5-(dimethylsulfamoyl)-2-methyl-5H-pyrrolo[2,3-b]pyrazin-3-yl]-8-azabicyclo[3.2.1]octan-3-yl]carbamate

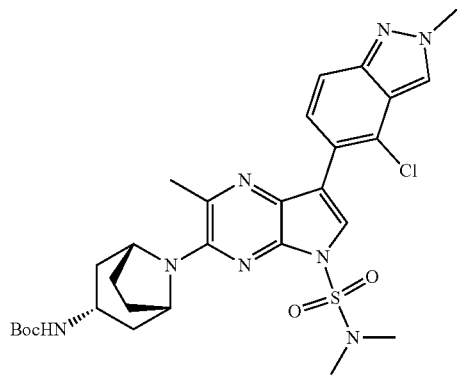 [SMILES: Cc1nc2c(-c3ccc4nn(C)cc4c3Cl)cn(S(=O)(=O)N(C)C)c2nc1N1[C@@H]2CC[C@H]1C[C@H](NC(=O)OC(C)(C)C)C2]

Prepared similar to tert-butyl N-[endo-8-[7-(4-chloro-2-methyl-2H-indazol-5-yl)-5-(dimethylsulfamoyl)-2-methyl-5H-pyrrolo[2,3-b]pyrazin-3-yl]-8-azabicyclo[3.2.1]octan-3-yl]carbamate i.e. preparations; 57, 58 and 59, to give the title compound, MS: [M+H]⁺=629

222
Preparation 61: tert-Butyl N-{1-[7-(4-chloro-2-methyl-2H-indazol-5-yl)-5-(dimethylsulfamoyl)-2-methyl-5H-pyrrolo[2,3-b]pyrazin-3-yl]-4-methylpiperidin-4-yl}carbamate

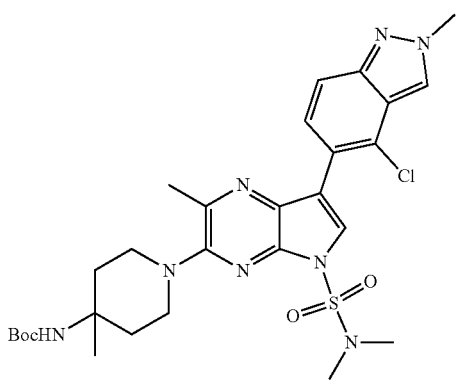 [SMILES: Cc1nc2c(-c3ccc4nn(C)cc4c3Cl)cn(S(=O)(=O)N(C)C)c2nc1N1CCC(C)(NC(=O)OC(C)(C)C)CC1]

Prepared similar to tert-butyl N-[endo-8-[7-(4-chloro-2-methyl-2H-indazol-5-yl)-5-(dimethylsulfamoyl)-2-methyl-5H-pyrrolo[2,3-b]pyrazin-3-yl]-8-azabicyclo[3.2.1]octan-3-yl]carbamate, i.e. preparations; 57, 58 and 59, to give the title compound, MS: [M+H]⁺=617

Preparation 62: tert-Butyl N-[exo-8-(6-chloro-5-formylpyrazin-2-yl)-8-azabicyclo[3.2.1]octan-3-yl]carbamate

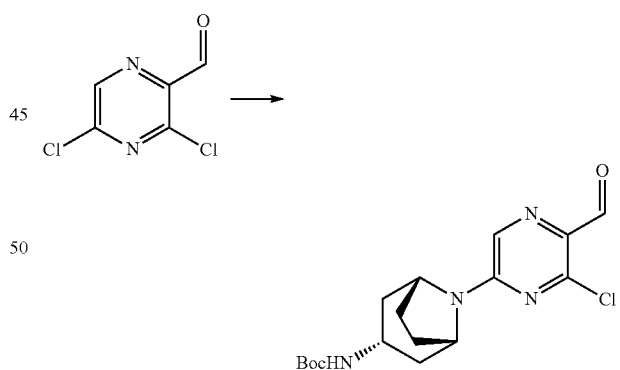

3,5-Dichloropyrazine-2-carbaldehyde (2.0 g, 11.29 mmol) was dissolved in DMF (20 mL) and cooled to 0° C. Triethylamine (3.14 mL, 22.58 mmol) was added followed by tert-butyl N-[exo-8-azabicyclo[3.2.1]octan-3-yl]carbamate (2.55 g, 11.29 mmol). The reaction was allowed to warm to room temperature overnight then diluted with diethyl ether and washed with water then brine. The organic layer was dried by passing through a phase separator cartridge then concentrated under reduced pressure, to give the title compound (3.94 g) was used in the next step without further purification. MS: [M+H]⁺=367.

Preparation 63: tert-Butyl N-[exo-8-{1H-pyrazolo[3,4-b]pyrazin-6-yl}-8-azabicyclo[3.2.1]octan-3-yl]carbamate

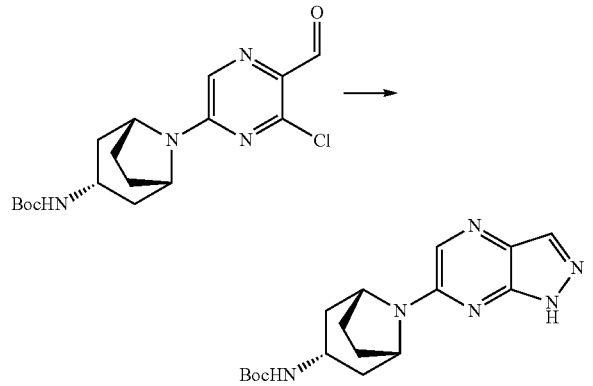

Hydrazine hydrate (2.61 mL, 53.72 mmol) was added to a solution of tert-butyl N-[exo-8-(6-chloro-5-formylpyrazin-2-yl)-8-azabicyclo[3.2.1]octan-3-yl]carbamate (3.943 g, 10.74 mmol) in 1,4-dioxane (40 mL). The reaction was heated to 100° C. over night. After cooling, water was added until precipitation occurred. The solid was collected by vacuum filtration, washing with water and dried in a vacuum oven at 40° C. overnight, to give the title compound (3.40 g). LC-MS: $[M+H]^+=345$.

Preparation 64: tert-Butyl N-[exo-8-{3-iodo-1H-pyrazolo[3,4-b]pyrazin-6-yl}-8-azabicyclo[3.2.1]octan-3-yl]carbamate

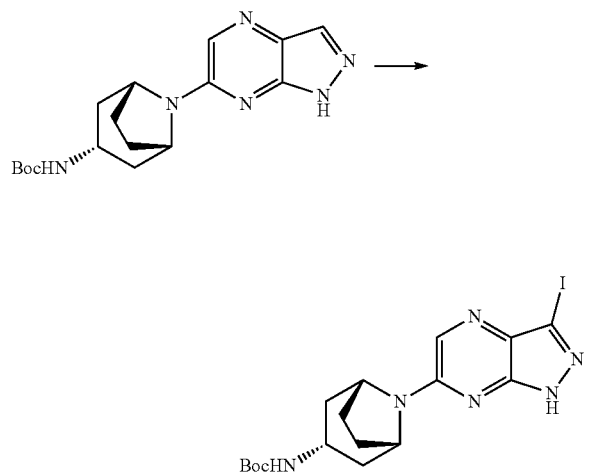

N-Iodosuccinimide (5.927 g, 23.24 mmol) was added to a solution of tert-butyl N-[exo-8-{1H-pyrazolo[3,4-b]pyrazin-6-yl}-8-azabicyclo[3.2.1]octan-3-yl]carbamate (3.998 g, 11.62 mmol) in DMF (40 mL). The reaction was heated to 60° C. for 2 h then allowed to cool to room temperature. Water was added until precipitation occurred. The solid was collected by vacuum filtration, washed with water and dried in a vacuum oven at 40° C. overnight, to give the title compound (4.1 g). MS: $[M+H]^+=471$.

Preparation 65: tert-Butyl N-[exo-8-{5-bromo-3-iodo-1H-pyrazolo[3,4-b]pyrazin-6-yl}-8-azabicyclo[3.2.1]octan-3-yl]carbamate

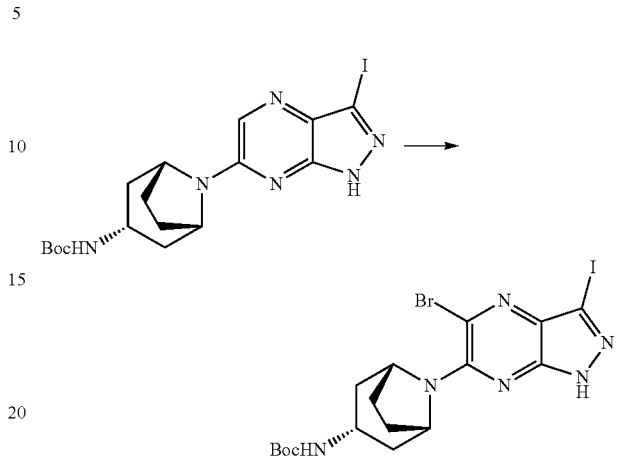

N-Bromosuccinimide (0.9 g, 5.06 mmol) was added to a solution of tert-butyl N-[exo-8-{3-iodo-1H-pyrazolo[3,4-b]pyrazin-6-yl}-8-azabicyclo[3.2.1]octan-3-yl]carbamate (1.586 g, 3.37 mmol) in DMF (15 mL). The reaction was stirred at room temperature overnight then diluted with diethyl ether, washed with sodium thiosulfate and brine. The organic layer was dried by passing through a phase separator cartridge then concentrated under reduced pressure. The residue was purified by column chromatography on silica gel (gradient elution, 0-25%, EtOAc/petrol) to give the title compound (1.64 g). MS: $[M+H]^+=549$.

Preparation 66: tert-Butyl N-[exo-8-(5-bromo-3-iodo-1-{[2-(trimethylsilyl)ethoxy]methyl}-1H-pyrazolo[3,4-b]pyrazin-6-yl)-8-azabicyclo[3.2.1]octan-3-yl]carbamate and tert-butyl N-[exo-8-(5-bromo-3-iodo-2-{[2-(trimethylsilyl)ethoxy]methyl}-2H-pyrazolo[3,4-b]pyrazin-6-yl)-8-azabicyclo[3.2.1]octan-3-yl]carbamate

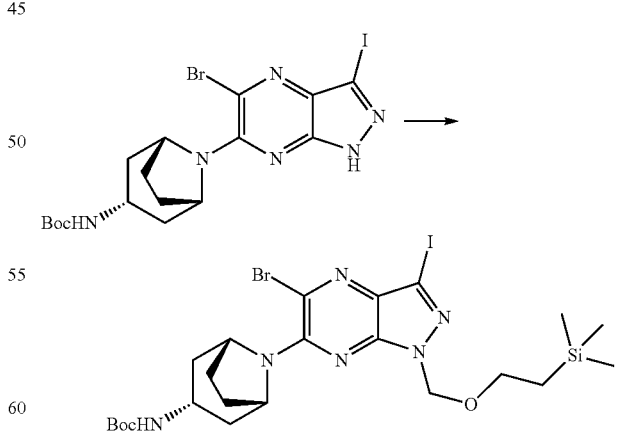

tert-Butyl N-[exo-8-{5-bromo-3-iodo-1H-pyrazolo[3,4-b]pyrazin-6-yl}-8-azabicyclo[3.2.1]octan-3-yl]carbamate (1.64 g, 2.99 mmol) was dissolved in DMF (10 mL) and sodium hydride (60% in mineral oil, 0.229 g, 3.29 mmol) was added portionwise over 5 minutes at 0-4° C. (ice bath).

The reaction was warmed to room temperature for 30 minutes then cooled to 0-4° C. (ice bath). 2-(Trimethylsilyl)ethoxymethyl chloride (0.582 mL, 3.29 mmol) was added dropwise and the deep red/orange solution stirred for 1 h then warmed to room temperature and stirred for 2 h. Saturated ammonium chloride was added and the reaction was diluted with diethyl ether. The organic phase was washed with water then brine, dried by passing through a phase separator and concentrated in vacuo. The residue was purified by column chromatography on silica gel (gradient elution, 0-30%, EtOAc/petrol), to give the title compound (1.20 g). MS: No molecular ion seen under MS conditions used.

Preparation 67: tert-Butyl N-[exo-8-[5-bromo-3-(4-chloro-2-methyl-2H-indazol-5-yl)-1-{[2-(trimethylsilyl)ethoxy]methyl}-1H-pyrazolo[3,4-b]pyrazin-6-yl]-8-azabicyclo[3.2.1]octan-3-yl]carbamate

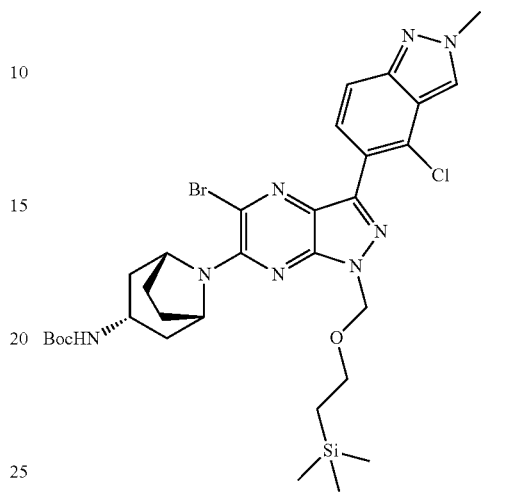

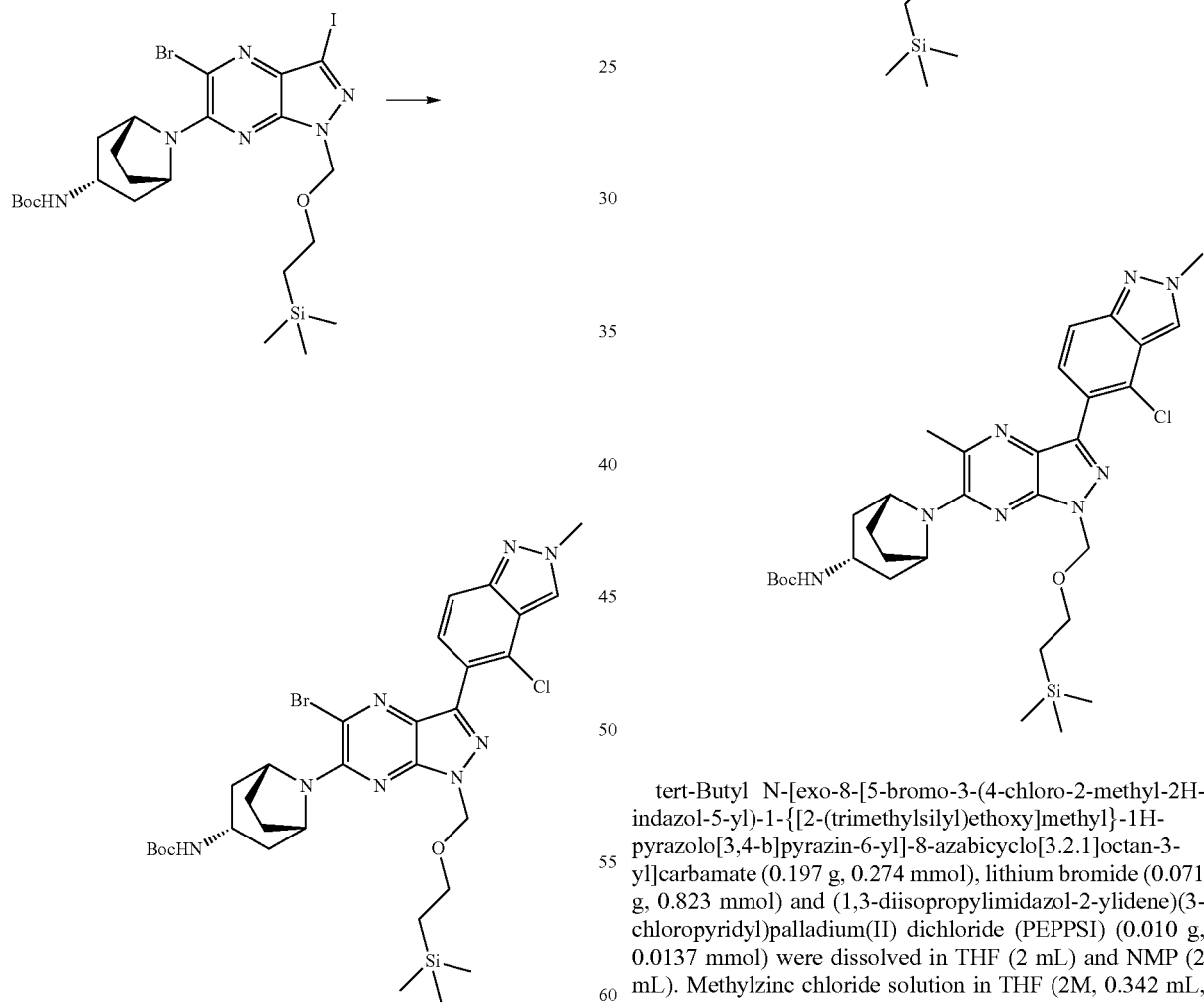

Prepared following general procedure 2, starting with tert-butyl N-[exo-8-(5-bromo-3-iodo-1-{[2-(trimethylsilyl)ethoxy]methyl}-1H-pyrazolo[3,4-b]pyrazin-6-yl)-8-azabicyclo[3.2.1]octan-3-yl]carbamate (1.198 g, 1.76 mmol), to give the title compound (0.197 g). MS: [M+H]⁺=719.

Preparation 68: tert-Butyl N-[exo-8-[3-(4-chloro-2-methyl-2H-indazol-5-yl)-5-methyl-1-{[2-(trimethylsilyl)ethoxy]methyl}-1H-pyrazolo[3,4-b]pyrazin-6-yl]-8-azabicyclo[3.2.1]octan-3-yl]carbamate tert-Butyl N-[exo-8-[5-bromo-3-(4-chloro-2-methyl-2H-indazol-5-yl)-1-{[2-(trimethylsilyl)ethoxy]methyl}-1H-pyrazolo[3,4-b]pyrazin-6-yl]-8-azabicyclo[3.2.1]octan-3-yl]carbamate (0.197 g, 0.274 mmol), lithium bromide (0.071 g, 0.823 mmol) and (1,3-diisopropylimidazol-2-ylidene)(3-chloropyridyl)palladium(II) dichloride (PEPPSI) (0.010 g, 0.0137 mmol) were dissolved in THF (2 mL) and NMP (2 mL). Methylzinc chloride solution in THF (2M, 0.342 mL, 0.685 mmol) was added and the reaction was stirred at room temperature for 30 minutes. Saturated ammonium chloride was added and the reaction was diluted with diethyl ether and washed with water then brine. The organic layer was dried using a phase separator cartridge then concentrated under reduced pressure, to give the title compound that was used directly in the next step. MS: [M+H]⁺=654.

227

Preparation 69: tert-Butyl N-[endo-8-[7-(4-chloro-2-methyl-2H-indazol-5-yl)-2-{[2-(trimethylsilyl)ethoxy]methyl}-5H-pyrrolo[2,3-b]pyrazin-3-yl]-8-azabicyclo[3.2.1]octan-3-yl]carbamate

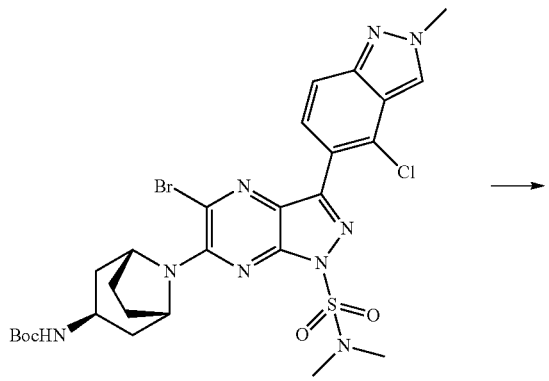

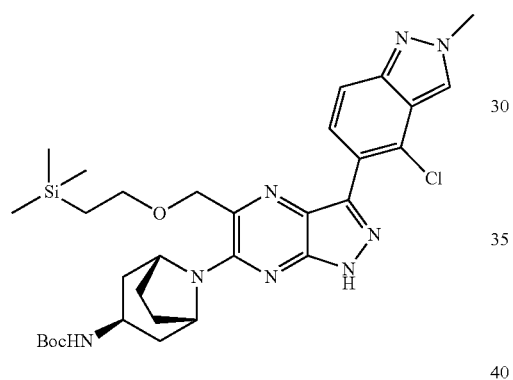

To an oven-dried microwave vial equipped with a magnetic stir bar was charged tert-butyl N-[endo-8-[2-bromo-7-(4-chloro-2-methyl-2H-indazol-5-yl)-5-(dimethylsulfamoyl)-5H-pyrrolo[2,3-b]pyrazin-3-yl]-8-azabicyclo[3.2.1]octan-3-yl]carbamate (120 mg, 0.17 mmol), [Ir{dFCF$_3$ppy}$_2$)(bpy)](PF$_6$) (3.0 mg, 0.003 mmol), NiCl$_2$.diglyme (1.1 mg, 0.0045 mmol), potassium (2-trimethylsilyl)-ethoxymethyl trifluoroborate (45.3 mg, 0.19 mmol), K$_2$HPO$_4$ (45.2 mg, 0.26 mmol) and 4,4-ditert-butyl bipyridine (1.7 mg, 0.0045 mmol). The vial was evacuated and backfilled with nitrogen gas (3×), then to the vial was added nitrogen-sparged 1,4-dioxane (3.5 mL) and nitrogen-sparged NMP (0.6 mL). The vial was then irradiated with a blue LED Kessel lamp (34 W) overnight. The reaction was concentrated under reduced pressure. To the residue was added 4% aq. LiCl and EtOAc. The organic phase was separated and the aq. was extracted with EtOAc (3×). The combined organics were dried over anhydrous sodium sulfate, filtered and concentrated in vacuo. The residue was purified by column chromatography on silica gel (gradient elution, 0-25% petrol/acetone), to give the title compound. MS: [M+H]$^+$=638.

228

Preparation 70: 5-Bromo-4-chloro-2-methyl-2H-1,2,3-benzotriazole

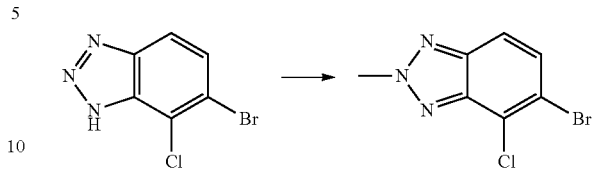

To a solution of 6-bromo-7-chloro-1H-1,2,3-benzotriazole (400 mg, 1.72 mmol) in THF (8 mL) was added triphenylphosphine (542 mg, 2.06 mmol), MeOH (0.084 mL, 2.06 mmol) and bis(2-methoxyethyl) azodicarboxylate (484 mg, 2.06 mmol) at RT. The mixture was stirred at RT for 2 h. The reaction solution was then concentrated in vacuo, and the residue was purified by column chromatography on silica gel (gradient elution, 10-40%, EtOAc/hexane). The fractions containing target product were collected and concentrated in vacuo. The residue was purified by column chromatography on NH silica gel (gradient elution, 0-20%, EtOAc/hexane), to give the title compound (160 mg). MS: [M+H]$^+$=246, 248.

Preparation 71: 4-Chloro-2-methyl-5-(4,4,5,5-tetramethyl-1,3,2-dioxaborolan-2-yl)-2H-1,2,3-benzotriazole

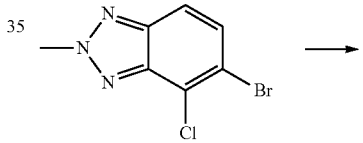

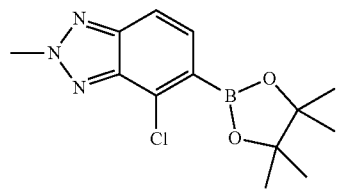

The mixture of 5-bromo-4-chloro-2-methyl-2H-1,2,3-benzotriazole (150 mg, 0.609 mmol), bis(pinacolato)diboron (232 mg, 0.913 mmol), [1,1'-bis(diphenylphosphino)ferrocene]dichloropalladium(II) complex with dichloromethane (39.8 mg, 0.0487 mmol) and potassium acetate (119 mg, 1.22 mmol) in 1,4-dioxane (1.5 mL) was degassed, purged with nitrogen, and stirred at 100° C. for 3 h. The reaction was cooled to RT, filtered through a pad of Celite, and washed with EtOAc. The filtrate was concentrated in vacuo. The residue was purified by column chromatography on NH silica gel (gradient elution, 0-70%, EtOAc/hexane), to give the title compound (155 mg). MS: [M+H]$^+$=294, 296.

Preparation 72: tert-Butyl N-[endo-8-[7-(4-chloro-2-methyl-2H-1,2,3-benzotriazol-5-yl)-5-{[2-(trimethylsilyl)ethoxy]methyl}-5H-pyrrolo[2,3-b]pyrazin-3-yl]-8-azabicyclo[3.2.1]octan-3-yl]carbamate

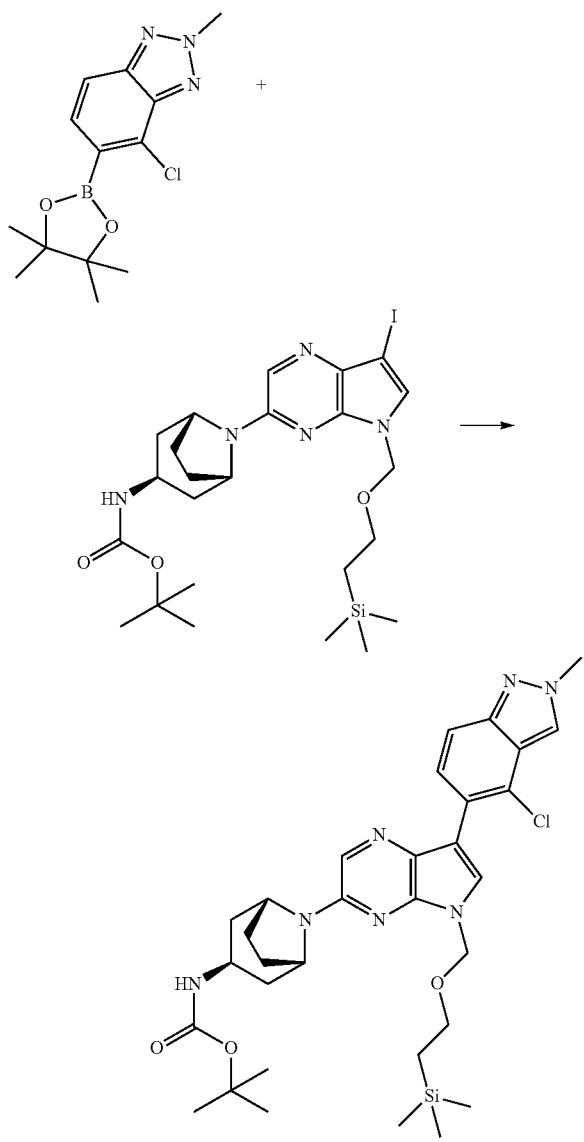

To a suspension of tert-butyl N-(endo-8-(7-iodo-5-((2-(trimethylsilyl)ethoxy)methyl)-5H-pyrrolo[2,3-b]pyrazin-3-yl)-8-azabicyclo[3.2.1]octan-3-yl)carbamate (50 mg, 0.0834 mmol) and 4-chloro-2-methyl-5-(4,4,5,5-tetramethyl-1,3,2-dioxaborolan-2-yl)-2H-1,2,3-benzotriazole (29.4 mg, 0.100 mmol) in 1,4-dioxane (0.50 mL) and water (0.05 mL) was added potassium phosphate (35.4 mg, 0.167 mmol) and 1,1'-bis(diphenylphosphino)ferrocene-palladium(II) dichloride dichloromethane complex (6.81 mg, 0.00834 mmol) at RT. The mixture was stirred at 100° C. for 1 h. The reaction was cooled to RT, filtered through a pad of Celite, and washed with EtOAc. The filtrate was concentrated in vacuo. The residue was diluted with EtOAc and added water. The organic layer was washed with water and brine, dried over anhydrous $Na_2SO_4$, filtered, and concentrated in vacuo. The residue was purified by column chromatography on silica gel (gradient elution, 50-100%, EtOAc/hexane), to give the title compound (38 mg). MS: $[M+H]^+=639, 641$.

Preparation 73: tert-Butyl 2-(5-bromo-4-chloro-2H-indazol-2-yl)acetate

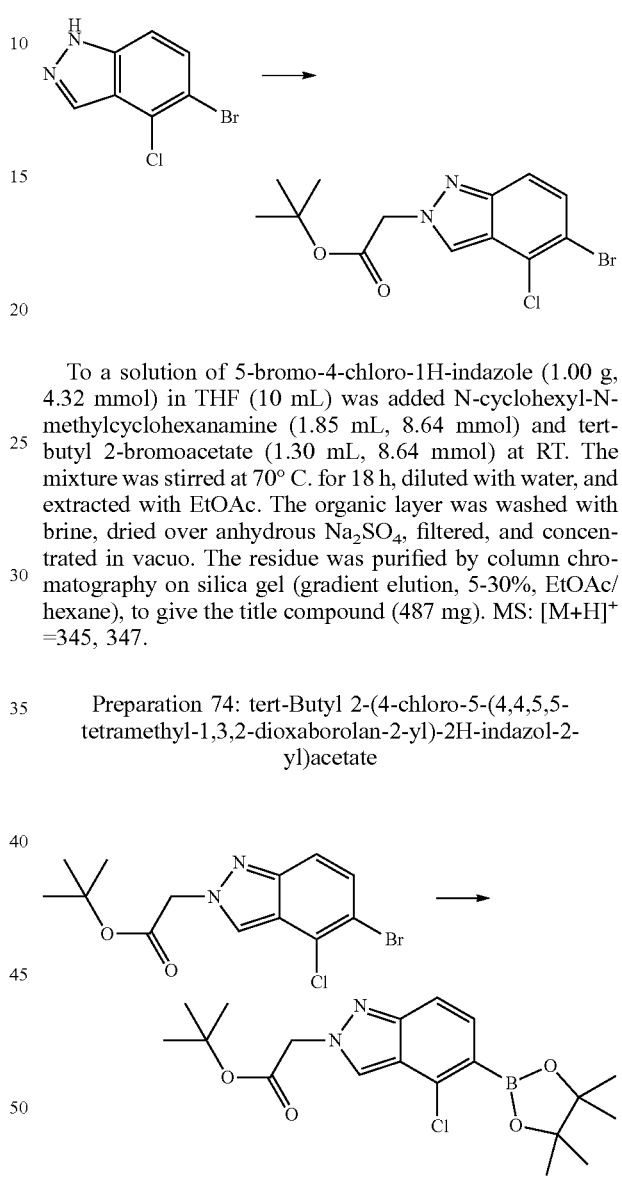

To a solution of 5-bromo-4-chloro-1H-indazole (1.00 g, 4.32 mmol) in THF (10 mL) was added N-cyclohexyl-N-methylcyclohexanamine (1.85 mL, 8.64 mmol) and tert-butyl 2-bromoacetate (1.30 mL, 8.64 mmol) at RT. The mixture was stirred at 70° C. for 18 h, diluted with water, and extracted with EtOAc. The organic layer was washed with brine, dried over anhydrous $Na_2SO_4$, filtered, and concentrated in vacuo. The residue was purified by column chromatography on silica gel (gradient elution, 5-30%, EtOAc/hexane), to give the title compound (487 mg). MS: $[M+H]^+=345, 347$.

Preparation 74: tert-Butyl 2-(4-chloro-5-(4,4,5,5-tetramethyl-1,3,2-dioxaborolan-2-yl)-2H-indazol-2-yl)acetate The mixture of tert-butyl 2-(5-bromo-4-chloro-2H-indazol-2-yl)acetate (480 mg, 1.39 mmol), bis(pinacolato)diboron (529 mg, 2.08 mmol), [1,1'-bis(diphenylphosphino)ferrocene]dichloropalladium(II) complex with dichloromethane (90.7 mg, 0.111 mmol) and potassium acetate (273 mg, 2.78 mmol) in 1,4-dioxane (4.8 mL) was degassed, purged with nitrogen, and stirred at 100° C. for 18 h. The reaction was cooled to RT, filtered through a pad of Celite, and washed with EtOAc. The filtrate was concentrated in vacuo. The residue was purified by column chromatography on NH silica gel (gradient elution, 10-30%, EtOAc/hexane), to give the title compound (423 mg). MS: $[M+H]^+=393, 395$.

231

Preparation 75: 2-(4-Chloro-5-(4,4,5,5-tetramethyl-1,3,2-dioxaborolan-2-yl)-2H-indazol-2-yl)acetic acid

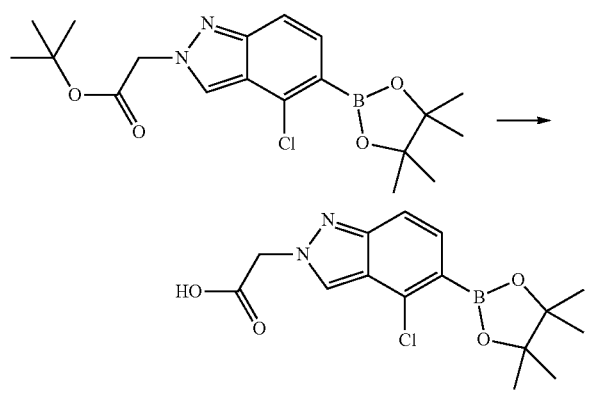

To a solution of tert-butyl 2-(4-chloro-5-(4,4,5,5-tetramethyl-1,3,2-dioxaborolan-2-yl)-2H-indazol-2-yl)acetate (423 mg, 1.08 mmol) in CHCl$_3$ (4.00 mL) was added TFA (2.00 mL, 26.0 mmol) at RT. The mixture was stirred at 60° C. for 1 h. The reaction solution was then vacuum-concentrated, the residue was diluted with water, and extracted with CHCl$_3$. The organic layer was washed with brine, dried over anhydrous Na$_2$SO$_4$, filtered, and concentrated in vacuo, to give the title compound (323 mg). MS: [M+H]$^+$=337, 339.

Preparation 76: 2-(4-Chloro-5-(4,4,5,5-tetramethyl-1,3,2-dioxaborolan-2-yl)-2H-indazol-2-yl)-N-methylacetamide

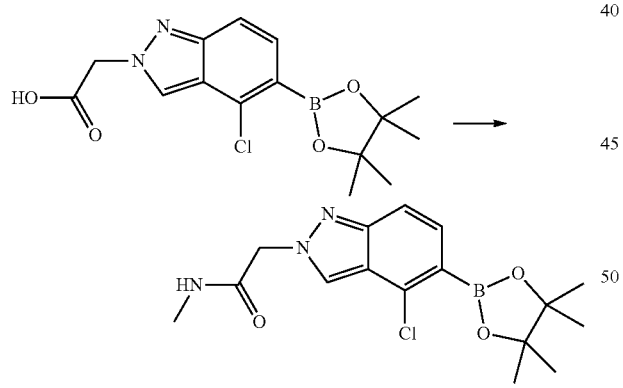

To a solution of 2-(4-chloro-5-(4,4,5,5-tetramethyl-1,3,2-dioxaborolan-2-yl)-2H-indazol-2-yl)acetic acid (100 mg, 0.297 mmol) in THF (2.00 mL) was added Et$_3$N (0.414 mL, 2.97 mmol), 2,4,6-tripropyl-1,3,5,2,4,6-trioxatriphosphorinane-2,4,6-trioxide (1.6 M in THF, 0.56 mL, 0.891 mmol), and methylamine (2.0 M in THF, 0.594 mL, 1.19 mmol) at RT. The mixture was stirred at RT for 1 h. The reaction solution was then vacuum-concentrated, and the residue was purified by column chromatography on silica gel (gradient elution, 80-100%, EtOAc/hexane), to give the title compound (50 mg). MS: [M+H]$^+$=350, 352.

232

Preparation 77: tert-Butyl N-[(endo-8-(7-{4-chloro-2-[(methylcarbamoyl)methyl]-2H-indazol-5-yl}-5-{[2-(trimethylsilyl)ethoxy]methyl}-5H-pyrrolo[2,3-b]pyrazin-3-yl)-8-azabicyclo[3.2.1]octan-3-yl]carbamate

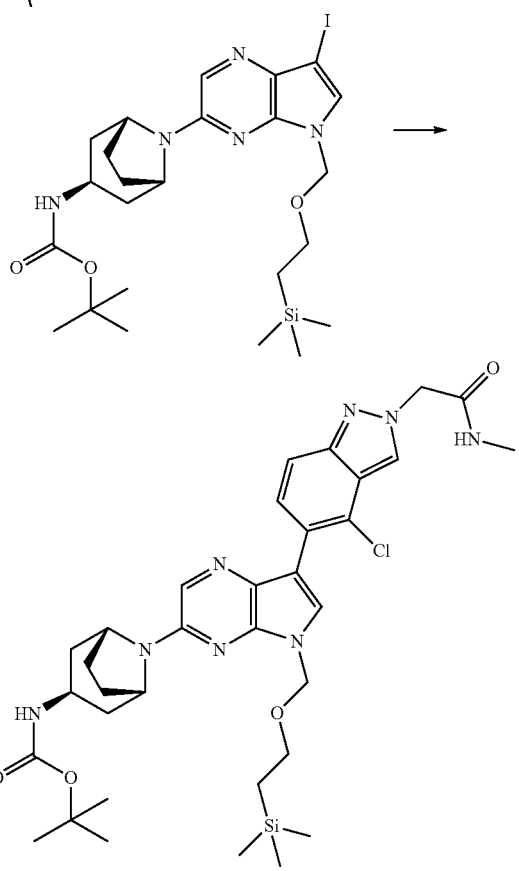

To a suspension of tert-butyl N-(endo-8-(7-iodo-5-((2-(trimethylsilyl)ethoxy)methyl)-5H-pyrrolo[2,3-b]pyrazin-3-yl)-8-azabicyclo[3.2.1]octan-3-yl)carbamate (50 mg, 0.0834 mmol) and 2-(4-chloro-5-(4,4,5,5-tetramethyl-1,3,2-dioxaborolan-2-yl)-2H-indazol-2-yl)-N-methylacetamide (35.0 mg, 0.100 mmol) in 1,4-dioxane (0.50 mL) and water (0.05 mL) was added potassium phosphate (35.4 mg, 0.167 mmol) and 1,1'-bis(diphenylphosphino)ferrocene-palladium(II) dichloride dichloromethane complex (6.81 mg, 0.00834 mmol) at RT. The mixture was stirred at 100° C. for 1 h. The reaction was cooled to RT, filtered through a pad of Celite, and washed with EtOAc. The filtrate was concentrated in vacuo. The residue was diluted with EtOAc and added water.

The organic layer was washed with water and brine, dried over anhydrous Na$_2$SO$_4$, filtered, and concentrated in vacuo. The residue was purified by column chromatography on silica gel (gradient elution, 50-100%, EtOAc/hexane), to give the title compound (25 mg). MS: [M+H]$^+$=695, 697.

Preparation 78: tert-Butyl 3-(5-bromo-4-chloro-2H-indazol-2-yl)propanoate

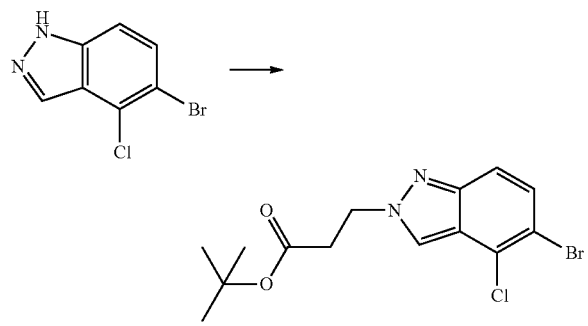

To a solution of 5-bromo-4-chloro-1H-indazole (1 g, 4.32 mmol) in DMF (10 mL) was added K$_2$CO$_3$ (1.19 g, 8.64 mmol) and tert-butyl 3-bromopropanoate (1.44 mL, 8.64 mmol) at RT. The mixture was stirred at 100° C. for 2 h, diluted with water, and extracted with EtOAc. The organic layer was washed with brine, dried over anhydrous Na$_2$SO$_4$, filtered, and concentrated in vacuo. The residue was purified by column chromatography on silica gel (gradient elution, 5-30%, EtOAc/hexane), to give the title compound (599 mg). MS: [M+H]+=359, 361.

Preparation 79: tert-Butyl 3-[4-chloro-5-(4,4,5,5-tetramethyl-1,3,2-dioxaborolan-2-yl)-2H-indazol-2-yl]propanoate

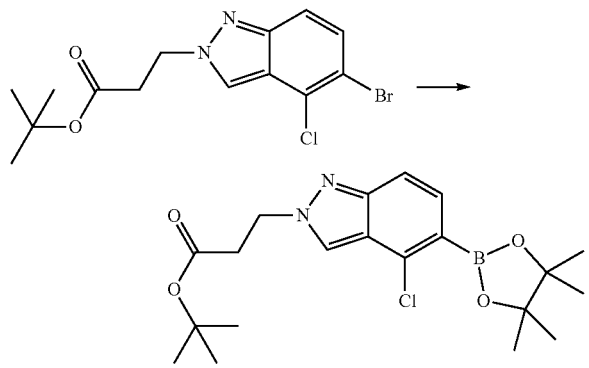

The mixture of tert-butyl 3-(5-bromo-4-chloro-2H-indazol-2-yl)propanoate (599 mg, 1.67 mmol), bis(pinacolato)diboron (634 mg, 2.50 mmol), [1,1'-bis(diphenylphosphino)ferrocene]dichloropalladium(II) complex with dichloromethane (109 mg, 0.133 mmol) and potassium acetate (327 mg, 3.33 mmol) in 1,4-dioxane (6 mL) was degassed, purged with nitrogen, and stirred at 120° C. for 5 h. The reaction was cooled to RT, filtered through a pad of Celite, and washed with EtOAc. The filtrate was concentrated in vacuo. The residue was purified by column chromatography on NH silica gel (gradient elution, 10-30%, EtOAc/hexane), to give the title compound (553 mg). MS: [M+H]$^+$=407.

Preparation 80: tert-Butyl 3-(5-{3-[endo-3-{[(tert-butoxy)carbonyl]amino}-8-azabicyclo[3.2.1]octan-8-yl]-5-{[2-(trimethylsilyl)ethoxy]methyl}-5H-pyrrolo[2,3-b]pyrazin-7-yl}-4-chloro-2H-indazol-2-yl)propanoate

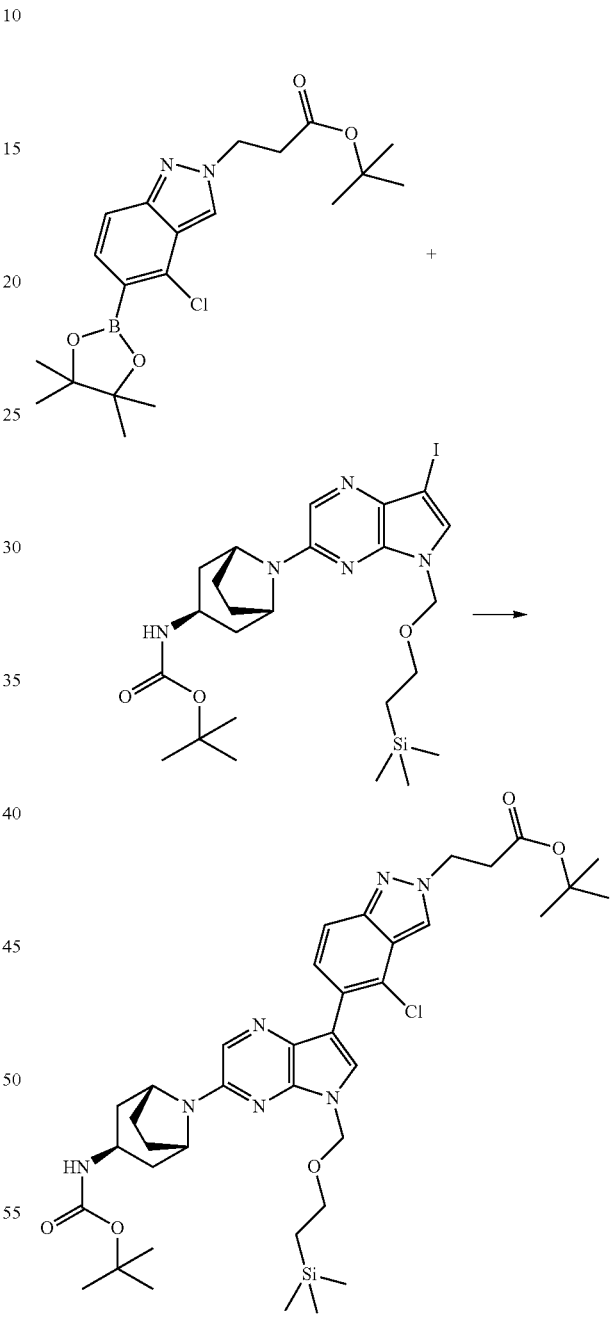

To a suspension of tert-butyl N-(endo-8-(7-iodo-5-((2-(trimethylsilyl)ethoxy)methyl)-5H-pyrrolo[2,3-b]pyrazin-3-yl)-8-azabicyclo[3.2.1]octan-3-yl)carbamate (100 mg, 0.167 mmol) and tert-butyl 3-[4-chloro-5-(4,4,5,5-tetramethyl-1,3,2-dioxaborolan-2-yl)-2H-indazol-2-yl]propanoate (81.4 mg, 0.200 mmol) in 1,4-dioxane (1.00 mL) and water (0.10 mL) was added potassium phosphate (70.8 mg, 0.334 mmol) and 1,1'-bis(diphenylphosphino)ferrocene-palladium(II) dichloride dichloromethane complex (13.6 mg, 0.0167 mmol) at RT. The mixture was stirred at 100° C. for 1 h. The reaction was cooled to RT, filtered through a pad of Celite, and washed with EtOAc. The filtrate was concentrated in vacuo. The residue was diluted with EtOAc and added water. The organic layer was washed with water and brine, dried over anhydrous $Na_2SO_4$, filtered, and concentrated in vacuo. The residue was purified by column chromatography on silica gel (gradient elution, 50-100%, EtOAc/hexane), to give the title compound (77 mg). MS: $[M+H]^+$=752, 754.

Preparation 81: 3-(5-{3-[endo-3-Amino-8-azabicyclo[3.2.1]octan-8-yl]-5H-pyrrolo[2,3-b]pyrazin-7-yl}-4-chloro-2H-indazol-2-yl)propanoic acid methanol twice and dried in a vacuum oven, to give the title compound (18 mg). MS: $[M+H]^+$=466, 468.

Preparation 82: 5-Bromo-3,4-dichloro-1H-indazole

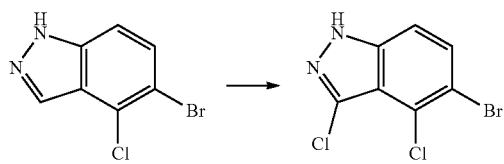 [SMILES: Clc1c(Br)ccc2[nH]ncc12 ; Clc1n[nH]c2ccc(Br)c(Cl)c12]

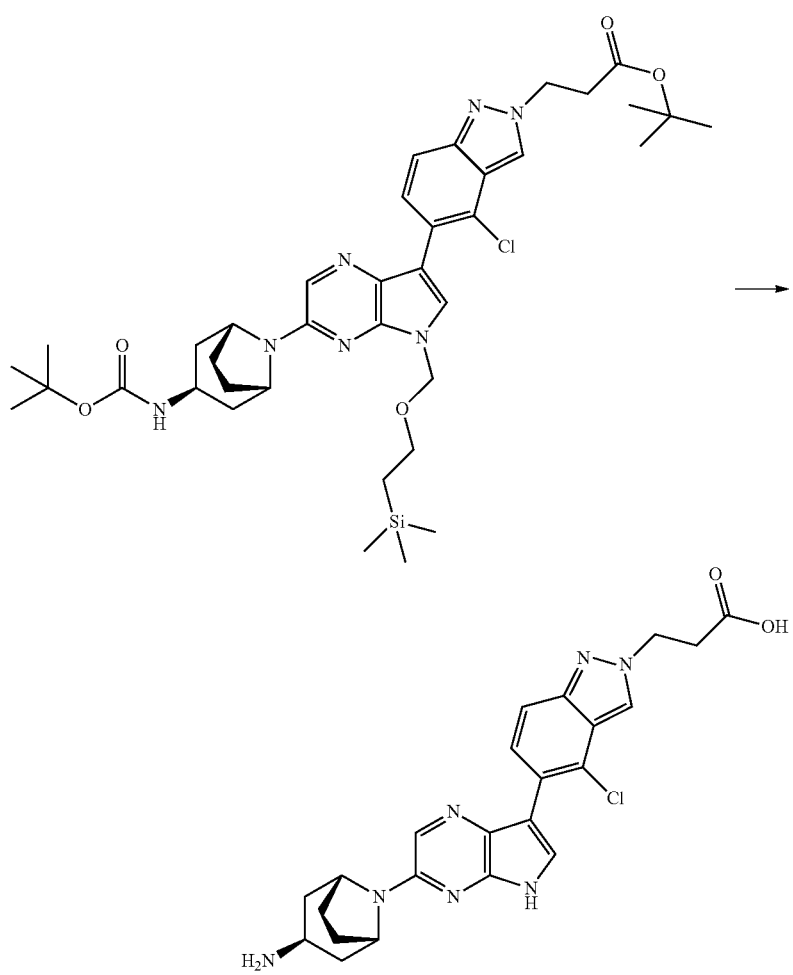

To a solution of tert-butyl 3-(5-{3-[endo-3-{[(tert-butoxy)carbonyl]amino}-8-azabicyclo[3.2.1]octan-8-yl]-5-{[2-(trimethylsilyl)ethoxy]methyl}-5H-pyrrolo[2,3-b]pyrazin-7-yl}-4-chloro-2H-indazol-2-yl)propanoate (50.0 mg, 0.0665 mmol) in $CHCl_3$ (1.00 mL) was added TFA (0.500 mL, 6 mmol) at RT. The mixture was stirred at 60° C. for 1 h. The reaction was concentrated in vacuo and to the residue dissolved in methanol (1.00 mL), ethylenediamine (0.200 mL, 3 mmol) was added. The reaction was stirred at RT for 18 h, and the solid which formed was filtered, washed with A mixture of 5-bromo-4-chloro-1H-indazole (1.7 g, 7.34 mmol) and 1-chloropyrrolidine-2,5-dione (1.079 g, 8.08 mmol) in $CH_3CN$ (50 mL) was stirred at rt for 1 h and warmed to 60° C. for 18 h. The solvent was removed under reduced pressure and the residue was taken into DCM (100 mL) and washed with $NaHCO_3$ (50 mL), water (50 mL) and brine. The organic phase was dried ($MgSO_4$) and concentrated under reduced pressure to give the title compound (1.53 g). 1H NMR (500 MHz, DMSO-$d_6$) δ 13.80 (1H, s), 7.69 (1H, d), 7.51 (1H, d).

Preparation 83:
5-Bromo-4-chloro-7-methyl-1H-indazole

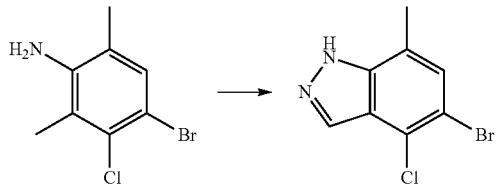

To a mixture of 4-bromo-3-chloro-2,6-dimethylaniline (4.8 g, 20 mmol), potassium acetate (3.1 g, 31 mmol), acetic acid (1.8 g, 29 mmol) and toluene (61 mL) was added tert-butyl nitrite (2.5 g, 25 mmol) at RT. The mixture was stirred at 45° C. overnight. To the mixture was added EtOAc (40 mL) and 1 M NaOH (40 mL). The separated organic layer was washed with brine and concentrated in vacuo. The residue was suspended in toluene and heptane. The precipitate was collected and dried at 50° C. under reduced pressure, to give a mixture of 5-bromo-4-chloro-7-methyl-1H-indazole and 5-bromo-6-chloro-7-methyl-1H-indazole (3.4 g). MS: [M+H]$^+$=245.

Preparation 84:
5-Bromo-4-chloro-2,7-dimethyl-2H-indazole

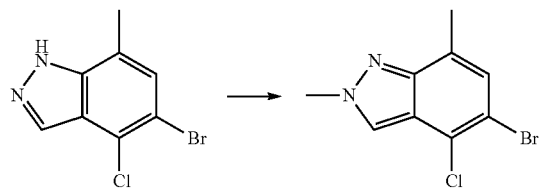

To a solution of a mixture of 5-bromo-4-chloro-7-methyl-1H-indazole and 5-bromo-6-chloro-7-methyl-1H-indazole (0.99 g, 4.0 mmol) in EtOAc (20 mL) was added trimethyloxonium tetrafluoroborate (1.2 g, 8.4 mmol) and the resulting mixture was stirred at RT for 24 h. The reaction mixture was diluted with EtOAc, quenched with sat. aq. NaHCO$_3$ and the phases were separated. The organic phase was washed with brine and concentrated in vacuo. The residue was purified by column chromatography on silica gel (gradient elution, 0-40%, EtOAc/hexane), to give the title compound (0.57 g), MS: [M+H]$^+$=259.

Preparation 85:
3-Bromo-2-chloro-5,6-difluorobenzaldehyde

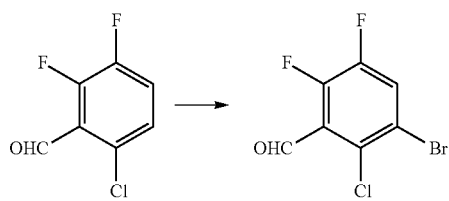 [SMILES: O=Cc1c(Cl)ccc(F)c1F ; O=Cc1c(F)c(F)cc(Br)c1Cl]

To a mixture of 2-chloro-5,6-difluorobenzaldehyde (5.3 g, 30 mmol) and sulfuric acid (15 mL) was added N-bromo-succinimide (6.6 g, 37 mmol) at 60° C. The resulting mixture was stirred at the same temperature for 5 h. The mixture was poured onto crushed ice, and then extracted with EtOAc. The organic phase was washed with brine and concentrated in vacuo. The residue was purified by column chromatography on silica gel (gradient elution, 0-20%, EtOAc/hexane), to give the title compound (6.5 g), $^1$H-NMR (400 MHz, CDCl$_3$): 10.37 (1H, s), 7.72 (1H, dd).

Preparation 86:
3-Bromo-2-chloro-5,6-difluorobenzaldehyde O-methyl oxime

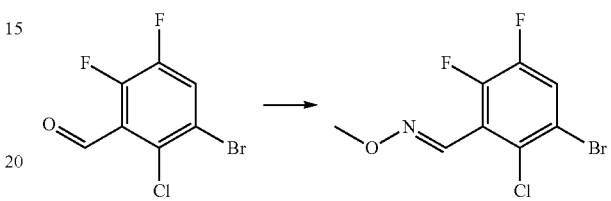

A mixture of 3-bromo-2-chloro-5,6-difluorobenzaldehyde (6.5 g, 26 mmol), O-methylhydroxylamine hydrochloride (2.4 g, 29 mmol), potassium carbonate (4.6 g, 33 mmol) and 1,2-dimethoxyethane (26 mL) was stirred at 60° C. overnight. The mixture was filtered and concentrated in vacuo. The residue was purified by column chromatography on silica gel (gradient elution, 0-20%, EtOAc/hexane), to give the title compound (7.2 g), MS: [M+H]$^+$=284.

Preparation 87:
5-Bromo-4-chloro-7-fluoro-1H-indazole

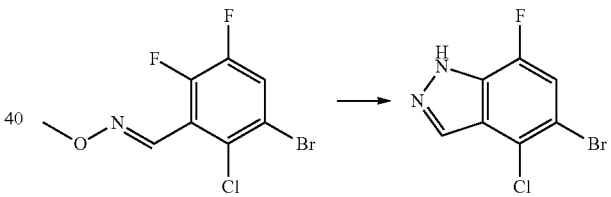

A mixture of 3-bromo-2-chloro-5,6-difluorobenzaldehyde O-methyl oxime (7.1 g, 25 mmol), tetrahydrofuran (25 mL) and hydrazine monohydrate (25 mL) was stirred under reflux for 30 h. To the mixture was added EtOAc (120 mL) and water (50 mL). The separated organic layer was concentrated in vacuo. The residue was suspended in EtOAc and hexane. The precipitate was collected and dried at 50° C. under reduced pressure, to give the title compound (4.4 g), MS: [M+H]$^+$=249.

Preparation 88:
5-Bromo-4-chloro-7-fluoro-2-methyl-2H-indazole

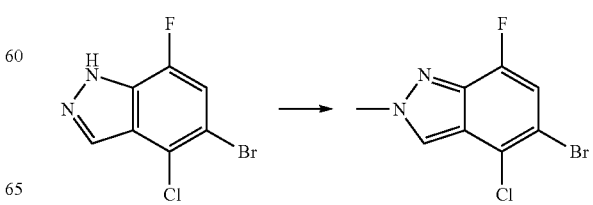

To a solution of 5-bromo-4-chloro-7-fluoro-1H-indazole (1.8 g, 7.4 mmol) in EtOAc (40 mL) was added trimethyloxonium tetrafluoroborate (1.7 g, 12 mmol) and the resulting mixture was stirred at RT overnight. The reaction mixture was diluted with EtOAc, quenched with sat. aq. NaHCO$_3$ and the phases were separated. The organic phase was washed with brine and concentrated in vacuo. The residue was purified by column chromatography on silica gel (gradient elution, 0-60%, EtOAc/hexane), to give the title compound (0.76 g), MS: [M+H]$^+$=263.

Preparation 89: 4-Chloro-2,7-dimethyl-5-(4,4,5,5-tetramethyl-1,3,2-dioxaborolan-2-yl)-2H-indazole

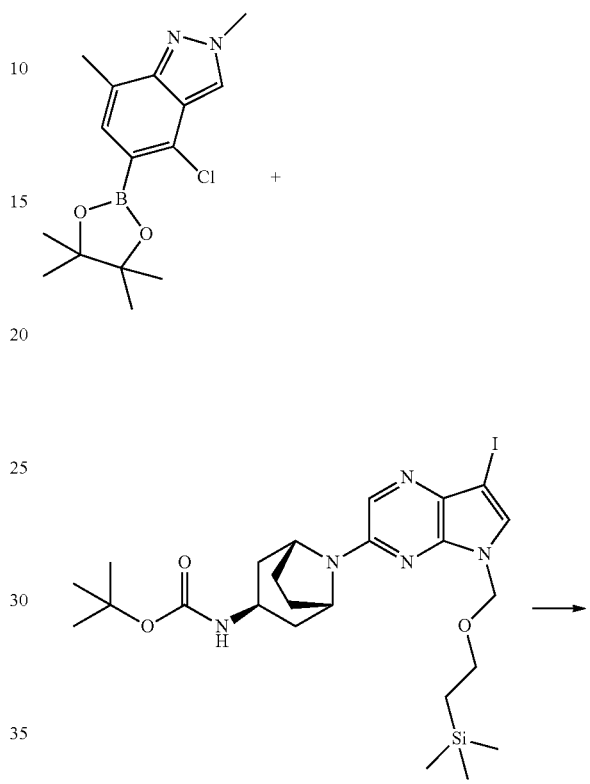

Prepared as preparation 43, except using 5-bromo-4-chloro-2,7-dimethyl-2H-indazole, to give the title compound. MS: [M+H]$^+$=307.

Preparation 90: 4-Chloro-7-fluoro-2-methyl-5-(4,4,5,5-tetramethyl-1,3,2-dioxaborolan-2-yl)-2H-indazole Prepared as preparation 43, except using 5-bromo-4-chloro-7-fluoro-2-methyl-2H-indazole, to give the title compound. MS: [M+H]$^+$=311.

Preparation 91: tert-Butyl N-[endo-8-[7-(4-chloro-2,7-dimethyl-2H-indazol-5-yl)-5-{[2-(trimethylsilyl)ethoxy]methyl}-5H-pyrrolo[2,3-b]pyrazin-3-yl]-8-azabicyclo[3.2.1]octan-3-yl]carbamate

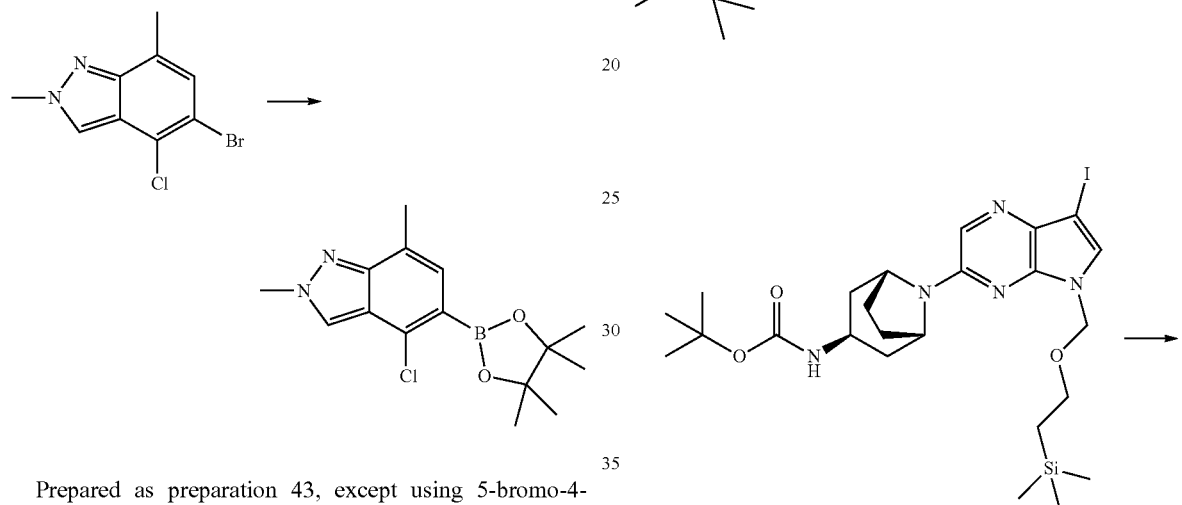

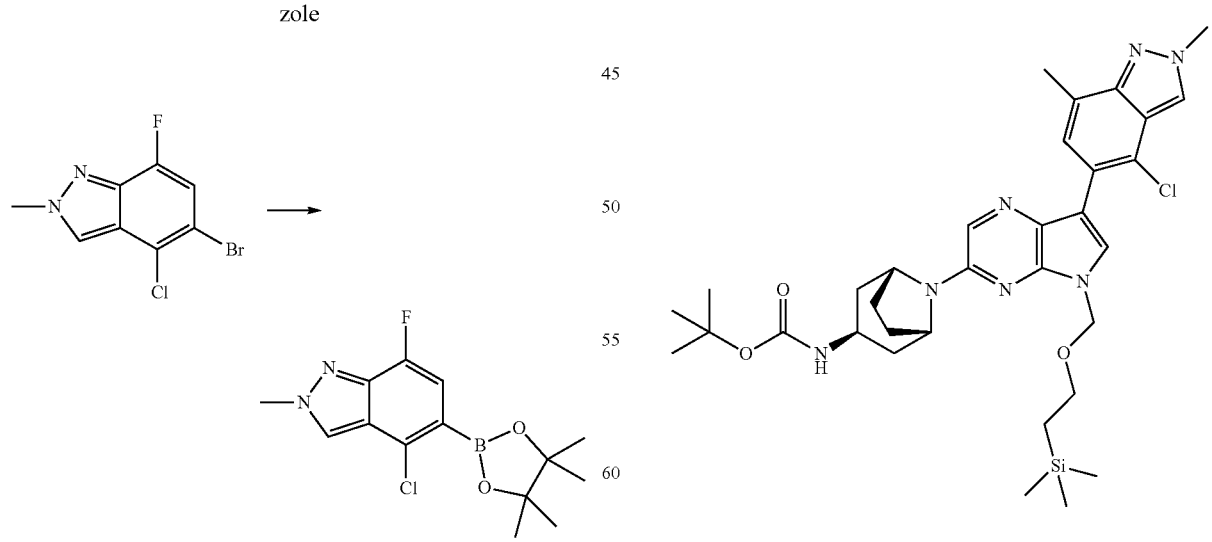

Prepared as General Procedure 2, except using 4-chloro-2,7-dimethyl-5-(4,4,5,5-tetramethyl-1,3,2-dioxaborolan-2-yl)-2H-indazole, to give the title compound. MS: [M+H]$^+$=652.

Preparation 92: tert-Butyl N-[endo-8-[7-(4-chloro-7-fluoro-2-methyl-2H-indazol-5-yl)-5-{[2-(trimethylsilyl)ethoxy]methyl}-5H-pyrrolo[2,3-b]pyrazin-3-yl]-8-azabicyclo[3.2.1]octan-3-yl]carbamate

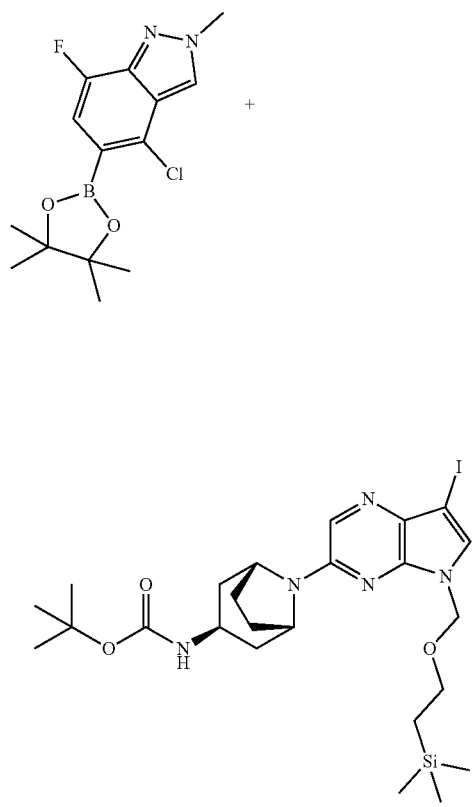

Prepared as general procedure 2, except using 4-chloro-7-fluoro-2-methyl-5-(4,4,5,5-tetramethyl-1,3,2-dioxaborolan-2-yl)-2H-indazole, to give the title compound. MS: [M+H]⁺=656.

Preparation 93: rac-tert-Butyl (1S,2R,3S,5R)-3-(benzylamino)-2-fluoro-8-azabicyclo[3.2.1]octane-8-carboxylate and rac-tert-Butyl (1S,2R,3R,5R)-3-(benzylamino)-2-fluoro-8-azabicyclo[3.2.1]octane-8-carboxylate

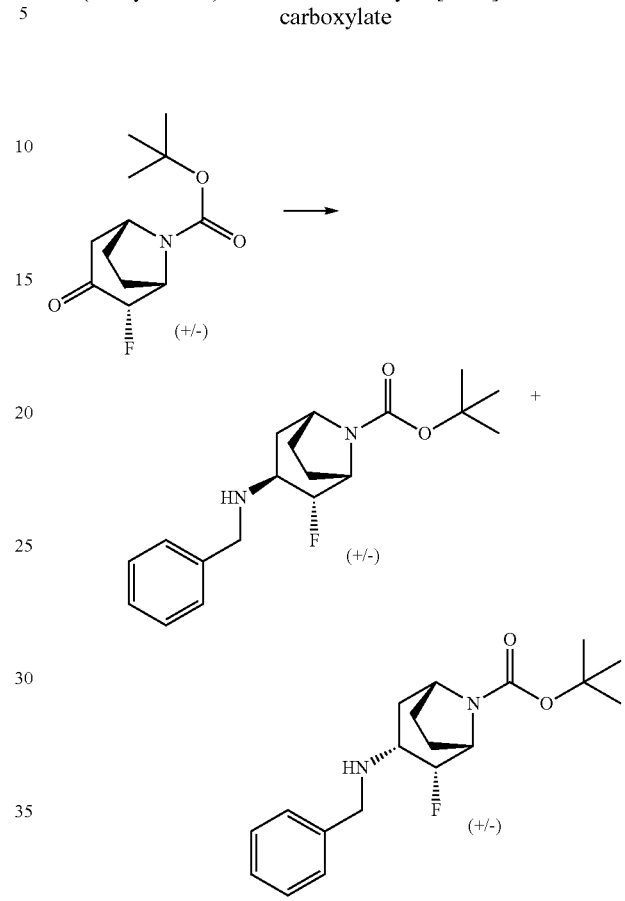

Sodium triacetoxyborohydride (41 g, 193 mmol) was added portion wise to a solution of (±)-tert-butyl 2-fluoro-3-oxo-8-azabicyclo[3.2.1]octane-8-carboxylate (34.8 g, 129 mmol), acetic acid (11.0 ml, 192 mmol) and benzylamine (20 ml, 183 mmol) in dichloromethane (500 mL) then stirred at RT overnight. The mixture was diluted with 10% sodium hydrogen carbonate (500 mL) then extracted with dichloromethane (3×500 mL). The combined organic phases were dried (MgSO₄), filtered and concentrated under reduced pressure to give the crude mixture of products. Recrystallisation from EtOAc:isohexane (800 mL, 1:3), gave:

Preparation 94: rac-tert-Butyl (1S,2R,3S,5R)-3-(benzylamino)-2-fluoro-8-azabicyclo[3.2.1]octane-8-carboxylate

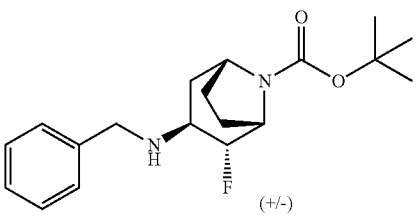 [SMILES: CC(C)(C)OC(=O)N1[C@@H]2CC[C@H]1[C@H](F)[C@@H](NCc1ccccc1)C2]

(11.6 g). ¹H NMR (500 MHz, DMSO-d₆) δ: 7.39-7.27 (m, 4H), 7.27-7.19 (m, 1H), 4.51 (br d, 1H), 4.38-4.21 (m, 1H), 4.13-4.04 (m, 1H), 3.83-3.65 (m, 2H), 2.80 (dd, 1H), 2.48-2.33 (m, 1H), 2.09 (s, 1H), 2.03-1.88 (m, 2H), 1.86-1.69 (m, 2H), 1.56 (d, 1H), 1.37 (s, 9H).

The filtrate, from the crystalisation above, was concentrated under reduced pressure to give a residue (~14 g) which was then purified by column chromatography on silica gel (gradient elution, 0-50% EtOAc/isohexane), to give:

Preparation 95: rac-tert-Butyl (1S,2R,3R,5R)-3-(benzylamino)-2-fluoro-8-azabicyclo[3.2.1]octane-8-carboxylate

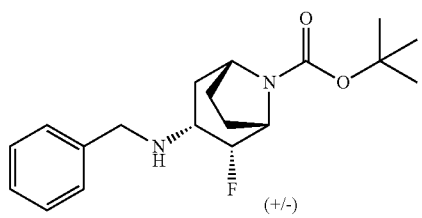 [SMILES: CC(C)(C)OC(=O)N1[C@@H]2CC[C@H]1[C@H](F)[C@H](NCc1ccccc1)C2]

(+/-)

(11.9 g). ¹H NMR (500 MHz, DMSO-d₆) δ: 7.38-7.26 (m, 4H), 7.26-7.15 (m, 1H), 4.66 (dt, 1H), 4.48-4.24 (m, 1H), 4.19-4.06 (m, 1H), 3.77 (d, 1H), 3.72 (d, 1H), 2.96-2.72 (m, 1H), 1.95-1.64 (m, 4H), 1.61-1.43 (m, 3H), 1.38 (s, 9H).

Preparation 96: rac-tert-Butyl (1S,2R,3S,5R)-3-amino-2-fluoro-8-azabicyclo[3.2.1]octane-8-carboxylate

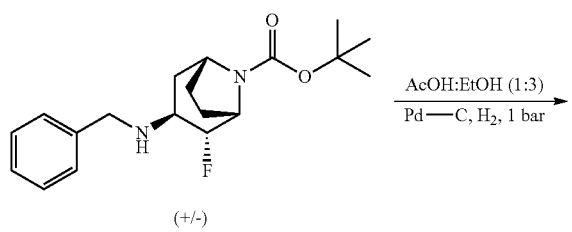

(+/-)

rac-tert-Butyl (1S,2R,3S,5R)-3-(benzylamino)-2-fluoro-8-azabicyclo[3.2.1]octane-8-carboxylate (18.5 g, 55.3 mmol) and 10% palladium on carbon (JM Type 39, 57.3% moisture) (4.0 g, 1.605 mmol) were dissolved in acetic acid/ethanol (1:3, 200 mL) and stirred under hydrogen at 1 bar for 2 h. The catalyst was removed by filtration and the filtrate was concentrated under reduced pressure. The residue was treated with sodium bicarbonate slurry (10 g in 100 mL) then extracted with chloroform/IPA (9:1, 3×100 mL). The combined organic phases were concentrated under reduced pressure, to give the title compound (13.5 g). ¹H NMR (500 MHz, DMSO-d₆) δ: 4.39-4.15 (m, 2H), 4.07 (m, 1H), 3.11 (dd, 1H), 2.12-1.88 (m, 4H), 1.83-1.65 (m, 4H), 1.37 (s, 9H).

Preparation 97: rac-tert-Butyl (1S,2R,3R,5R)-3-amino-2-fluoro-8-azabicyclo[3.2.1]octane-8-carboxylate

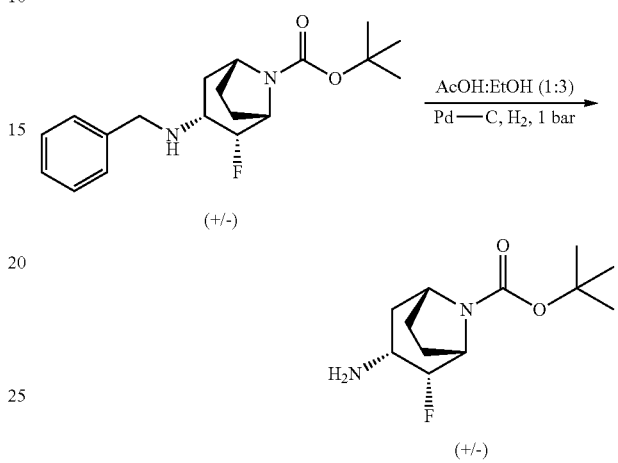

(+/-)

The title compound was prepared similar fashion to rac-tert-butyl (1S,2R,3S,5R)-3-amino-2-fluoro-8-azabicyclo[3.2.1]octane-8-carboxylate using rac-tert-butyl (1S,2R,3R,5R)-3-(benzylamino)-2-fluoro-8-azabicyclo[3.2.1]octane-8-carboxylate (11 g, 32.9 mmol), to give the title compound (8.25 g). ¹H NMR (500 MHz, DMSO-d₆) δ: 4.37 (dt, 2H), 4.38-4.33 (m, 1H), 4.16-4.09 (m, 1H), 2.95 (dddd, 1H), 1.88-1.76 (m, 3H), 1.66-1.46 (m, 4H), 1.41 (d, J=0.5 Hz, 9H).

Preparation 98: rac-tert-Butyl (1S,2R,3S,5R)-3-{[(benzyloxy)carbonyl]amino}-2-fluoro-8-azabicyclo[3.2.1]octane-8-carboxylate

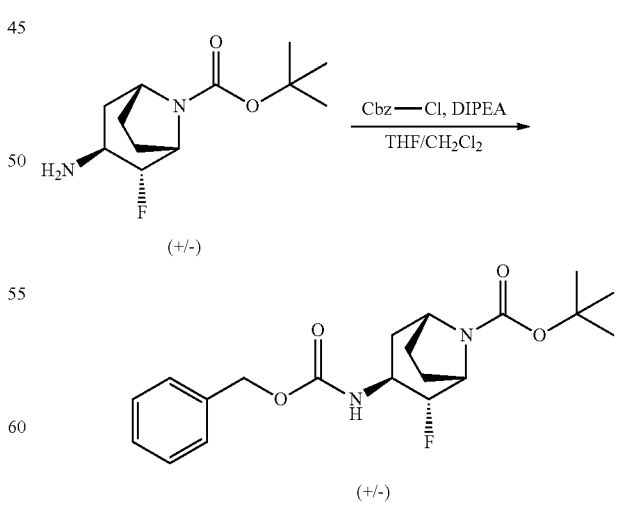

(+/-)

Benzyl chloroformate (10 mL, 70.0 mmol) was added to a cooled (0° C.) solution of rac-tert-butyl (1S,2R,3S,5R)-3-amino-2-fluoro-8-azabicyclo[3.2.1]octane-8-carboxylate (13.5 g, 52.5 mmol) and DIPEA (27 mL, 155 mmol) in THF/DCM (375 mL: 1:4) then stirred at RT overnight. Water (400 mL) was added then the mixture was extracted with dichloromethane (3×400 mL) and combined organic phases were concentrated under reduced pressure. The crude product was purified by chromatography on silica gel (0-30% EtOAc/isohexane). The purified oil was purified again by column chromatography on silica gel (gradient elution, 0-10% EtOAc/DCM), to give the title compound (19.5 g). $^1$H NMR (500 MHz, DMSO-$d_6$) δ: 7.46-7.39 (m, 1H), 7.39-7.34 (m, 4H), 7.34-7.29 (m, 1H), 5.07 (d, 1H), 5.02 (d, 1H), 4.51 (br d, 1H), 4.38-4.20 (m, 1H), 4.16-4.06 (m, 1H), 3.64-3.49 (m, 1H), 2.23-2.11 (m, 1H), 1.94-1.79 (m, 2H), 1.78-1.66 (m, 2H), 1.49-1.43 (m, 1H), 1.38 (s, 9H).

Preparation 99: rac-tert-Butyl (1S,2R,3R,5R)-3-{[(benzyloxy)carbonyl]amino}-2-fluoro-8-azabicyclo[3.2.1]octane-8-carboxylate

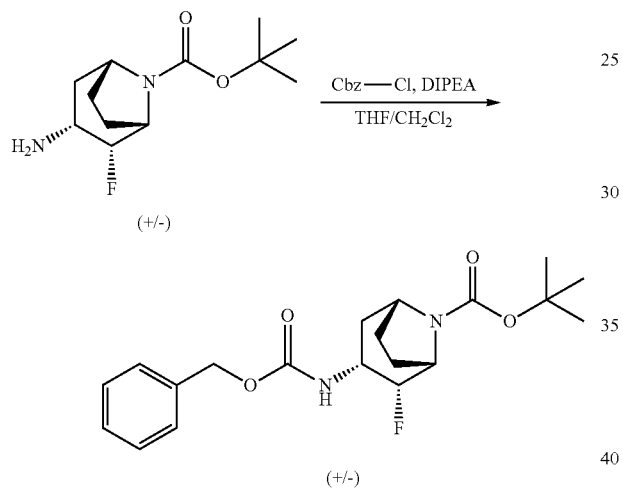

The title compound was prepared similar fashion to rac-tert-butyl (1S,2R,3S,5R)-3-{[(benzyloxy)carbonyl] amino}-2-fluoro-8-azabicyclo[3.2.1]octane-8-carboxylate using rac-tert-butyl (1S,2R,3R,5R)-3-amino-2-fluoro-8-azabicyclo[3.2.1]octane-8-carboxylate (8.25 g, 32.1 mmol), to give the title compound (10.9 g). $^1$H NMR (500 MHz, DMSO-$d_6$) δ: 7.46-7.26 (m, 6H), 5.11-4.94 (m, 2H), 4.54 (dt, 1H), 4.43-4.26 (m, 1H), 4.20-4.06 (m, 1H), 3.92-3.72 (m, 1H), 1.99-1.69 (m, 3H), 1.70-1.48 (m, 3H), 1.38 (s, 9H).

Preparation 100: rac-Benzyl N-[(1S,2S,3S,5R)-2-fluoro-8-azabicyclo[3.2.1]octan-3-yl]carbamate

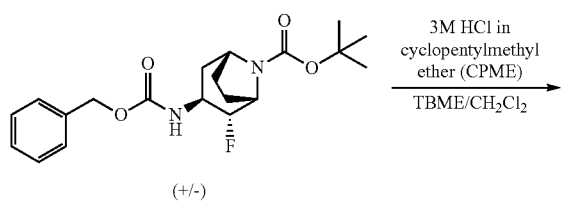

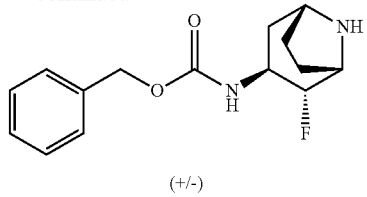

3.0 M hydrogen chloride in cyclopentyl methyl ether (130 mL, 390 mmol) was added to a solution of rac-tert-butyl (1S,2R,3S,5R)-3-{[(benzyloxy)carbonyl]amino}-2-fluoro-8-azabicyclo[3.2.1]octane-8-carboxylate (14.5 g, 36.4 mmol) in tert-butyl methyl ether (15 mL) then stirred at RT for 18 h. The mixture was concentrated under reduced pressure then partitioned between dichloromethane (200 mL) and saturated sodium hydrogen carbonate solution (200 mL). The organic layer was concentrated under reduced pressure then purified by column chromatography on silica gel (gradient elution, 0-10% (0.7 M Ammonia/MeOH)/DCM), to give the title compound (6.0 g). $^1$H NMR (500 MHz, DMSO-$d_6$) δ: 7.41-7.28 (m, 5H), 7.28-7.20 (m, 1H), 5.10-4.97 (m, 2H), 4.29 (ddd, 1H), 3.69-3.51 (m, 1H), 3.41 (dd, 1H), 3.37-3.29 (m, 1H), 2.30-2.09 (m, 1H), 2.10-1.97 (m, 1H), 1.77-1.63 (m, 2H), 1.64-1.47 (m, 2H), 1.30-1.14 (m, 1H).

Preparation 101: rac-Benzyl N-[(1S,2S,3R,5R)-2-fluoro-8-azabicyclo[3.2.1]octan-3-yl]carbamate hydrochloride

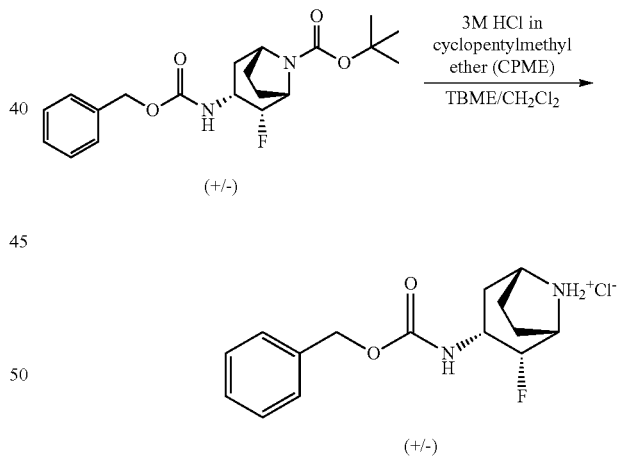

3.0 M hydrogen chloride in cyclopentyl methyl ether (100 mL, 300 mmol) was added to a suspension of (±)-tert-butyl (1S,2R,3R,5R)-3-(((benzyloxy)carbonyl)amino)-2-fluoro-8-azabicyclo[3.2.1]octane-8-carboxylate (10.9 g, 27.4 mmol) in tert-butyl methyl ether (15 mL) and dichloromethane (10 mL) then stirred at RT for 18 h. The resulting precipitate was collected by filtration, to give the title compound (8.8 g). $^1$H NMR (500 MHz, DMSO-$d_6$) δ: 10.28-9.22 (m, 1H), 9.22-8.29 (m, 1H), 7.74-7.59 (m, 1H), 7.42-7.35 (m, 4H), 7.35-7.29 (m, 1H), 5.07 (d, 1H), 5.04 (d, 1H), 4.83 (dt, 1H), 4.22-4.12 (m, 1H), 3.99-3.92 (m, 1H), 3.92-3.75 (m, 1H), 2.08-1.86 (m, 4H), 1.86-1.68 (m, 2H).

Preparation 102: Benzyl N-[(1S,2S,3S,5R)-2-fluoro-8-azabicyclo[3.2.1]octan-3-yl]carbamate (Fast Eluting Isomer)

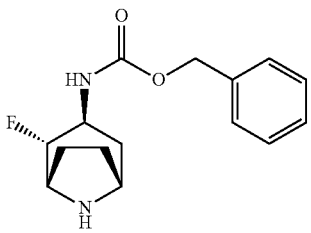 [SMILES: O=C(N[C@H]1C[C@H]2CC[C@H](N2)[C@@H]1F)OCc1ccccc1]

rac-Benzyl N-[(1S,2S,3S,5R)-2-fluoro-8-azabicyclo[3.2.1]octan-3-yl]carbamate (5.82 g) was dissolved in methanol (150 mL) then purified by chiral preparative supercritical fluid chromatography (Lux A1 column, (21.2 mm×250 mm, 5 um); 40° C., Flow Rate 50 mL/min, BPR 100 BarG, Detection at 210 nm, Injection Volume 200 uL (30 mg), 35:65 MeOH:$CO_2$ (0.2% v/v $NH_3$)). Pure fractions were combined then evaporated, to give the title compound (2.58 g) as the faster eluting enantiomer. $^1$H NMR (500 MHz, DMSO-$d_6$) δ: 7.41-7.28 (m, 5H), 7.28-7.20 (m, 1H), 5.10-4.97 (m, 2H), 4.29 (ddd, 1H), 3.69-3.51 (m, 1H), 3.41 (dd, 1H), 3.37-3.29 (m, 1H), 2.30-2.09 (m, 1H), 2.10-1.97 (m, 1H), 1.77-1.63 (m, 2H), 1.64-1.47 (m, 2H), 1.30-1.14 (m, 1H).

Preparation 103: Benzyl N-[(1R,2R,3R,5S)-2-fluoro-8-azabicyclo[3.2.1]octan-3-yl]carbamate (Slow Eluting Isomer)

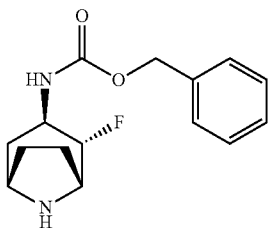 [SMILES: O=C(N[C@@H]1C[C@@H]2CC[C@@H](N2)[C@H]1F)OCc1ccccc1]

From the same chromatography experiment described in preparation 102, the title compound was obtained as the slow eluting isomer (2.99 g). $^1$H NMR (500 MHz, DMSO-$d_6$) δ: 7.41-7.28 (m, 5H), 7.28-7.20 (m, 1H), 5.10-4.97 (m, 2H), 4.29 (ddd, 1H), 3.69-3.51 (m, 1H), 3.41 (dd, 1H), 3.37-3.29 (m, 1H), 2.30-2.09 (m, 1H), 2.10-1.97 (m, 1H), 1.77-1.63 (m, 2H), 1.64-1.47 (m, 2H), 1.30-1.14 (m, 1H).

Preparation 104: Benzyl N-[(1S,2S,3S,5R)-2-fluoro-8-azabicyclo[3.2.1]octan-3-yl]carbamate hydrochloride

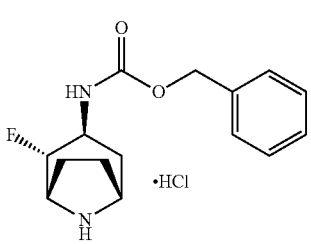 [SMILES: O=C(N[C@H]1C[C@H]2CC[C@H](N2)[C@@H]1F)OCc1ccccc1 ; Cl]

Fast eluting isomer benzyl N-[(1S,2S,3S,5R)-2-fluoro-8-azabicyclo[3.2.1]octan-3-yl]carbamate (3.8 g) was dissolved in dichloromethane (10 mL) then treated with 3.0 M hydrogen chloride in cyclopentyl methyl ether (10 ml, 30.0 mmol), to give a white solid which was recrystallised in acetonitrile (50 mL), to give the title compound (2.2 g). $^1$H NMR (500 MHz, DMSO-$d_6$) δ: 9.34 (br s, 2H), 7.76-7.56 (m, 1H), 7.45-7.27 (m, 5H), 5.09 (d, 1H), 5.04 (d, 1H), 4.95-4.77 (m, 1H), 4.17-4.06 (m, 1H), 3.98-3.87 (m, 1H), 3.77-3.60 (m, 1H), 2.33 (ddd, 1H), 2.18 (q, 1H), 2.03-1.89 (m, 3H), 1.79 (d, 1H).

Preparation 105: Benzyl N-[(1R,2R,3R,5S)-2-fluoro-8-azabicyclo[3.2.1]octan-3-yl]carbamate hydrochloride

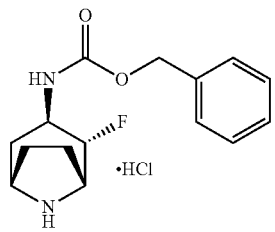 [SMILES: O=C(N[C@@H]1C[C@@H]2CC[C@@H](N2)[C@H]1F)OCc1ccccc1 ; Cl]

Slow eluting isomer benzyl N-[(1R,2R,3R,5S)-2-fluoro-8-azabicyclo[3.2.1]octan-3-yl]carbamate (3.8 g) was dissolved in dichloromethane (10 mL) then treated with 3.0 M hydrogen chloride in cyclopentyl methyl ether (10 ml, 30.0 mmol), to give a white solid which was recrystallised in acetonitrile (50 mL), to give the title compound (3.2 g). $^1$H NMR (500 MHz, DMSO-$d_6$) δ: 9.34 (br s, 2H), 7.76-7.56 (m, 1H), 7.45-7.27 (m, 5H), 5.09 (d, 1H), 5.04 (d, 1H), 4.95-4.77 (m, 1H), 4.17-4.06 (m, 1H), 3.98-3.87 (m, 1H), 3.77-3.60 (m, 1H), 2.33 (ddd, 1H), 2.18 (q, 1H), 2.03-1.89 (m, 3H), 1.79 (d, 1H).

Preparation 106: Benzyl N-[(1S,2S,3R,5R)-2-fluoro-8-azabicyclo[3.2.1]octan-3-yl]carbamate (Fast Eluting Isomer)

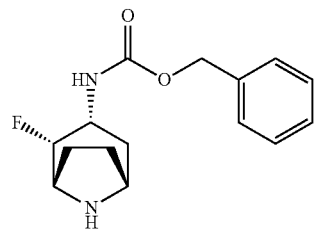 [SMILES: O=C(N[C@@H]1C[C@H]2CC[C@H](N2)[C@@H]1F)OCc1ccccc1]

rac-Benzyl N-[(1S,2S,3R,5R)-2-fluoro-8-azabicyclo[3.2.1]octan-3-yl]carbamate (8.8 g) was dissolved in methanol (50 mg m$L^{-1}$) then purified by chiral preparative supercritical fluid chromatography (Lux C2 (4.6 mm×250 mm, 5 um); 40° C., Flow Rate 50 mL/min, BPR 100 BarG, Detection at 210 nm, Injection Volume 500 uL (25 mg), 35:65 EtOH:$CO_2$ (0.2% v/v $NH_3$)). Pure fractions were combined then evaporated, to give the title compound (4.04 g) as the faster eluting enantiomer. $^1$H NMR (500 MHz, DMSO-$d_6$) δ: 8.08-7.57 (m, 2), 7.53 (d, 1H), 7.41-7.28 (m, 5H), 5.04 (d, 1H), 5.02 (d, 1H), 4.67 (dt, 1H), 3.99-3.89 (m, 1H), 3.85-3.67 (m, 2H), 1.97-1.59 (m, 6H). (compound isolated as a partial hydrochloride salt)

Preparation 107: Benzyl N-[(1R,2R,3S,5S)-2-fluoro-8-azabicyclo[3.2.1]octan-3-yl]carbamate (Slow Eluting Isomer)

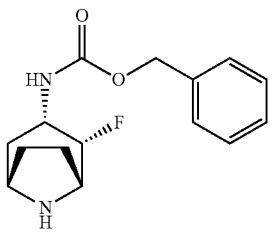 [SMILES: O=C(N[C@H]1C[C@@H]2CC[C@@H](N2)[C@H]1F)OCc1ccccc1]

From the same chromatography experiment described in preparation 106, the title compound was obtained as the slow eluting isomer (4.01 g). $^1$H NMR (500 MHz, DMSO-d$_6$) δ: 7.47-7.28 (m, 6H), 5.97-4.75 (m, 2H), 5.08-4.99 (m, 2H), 4.52 (dt, 1H), 3.82-3.72 (m, 1H), 3.73-3.65 (m, 2H), 3.59-3.51 (m, 1H), 1.85-1.72 (m, 2H), 1.72-1.50 (m, 3H). (compound isolated as a partial hydrochloride salt)

Preparation 108: Benzyl N-[(1S,2S,3R,5R)-2-fluoro-8-azabicyclo[3.2.1]octan-3-yl]carbamate, hydrochloride Salt

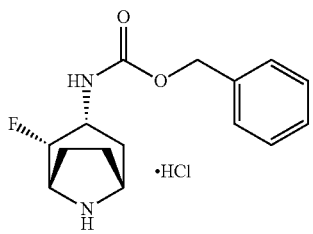

Partial HCl salt of benzyl ((1S,2S,3R,5R)-2-fluoro-8-azabicyclo[3.2.1]octan-3-yl)carbamate (faster eluting enantiomer) (4.0 g, 13.65 mmol) was slurried in a minimal amount of dichloromethane (10 mL) and tert-butyl methyl ether (50 mL) then treated with 3M hydrogen chloride solution in cyclopentyl methyl ether (7 ml, 21.00 mmol). The mixture was slurried overnight then collected by filtration, to give the title compound (4.19 g). $^1$H NMR (500 MHz, DMSO-d$_6$) δ: 10.3-8.10 (br m, 2H), 7.65 (d, 1H), 7.46-7.24 (m, 5H), 5.18-4.94 (m, 2H), 4.82 (d, J=47.7 Hz, 1H), 4.25-4.09 (m, 1H), 3.99-3.90 (m, 1H), 3.90-3.75 (m, 1H), 2.08-1.73 (m, 6H). $[α]^{20}_D$=15.47° (c 1.00, MeOH).

Preparation 109: Benzyl N-[(1R,2R,3S,5S)-2-fluoro-8-azabicyclo[3.2.1]octan-3-yl]carbamate, hydrochloride Salt

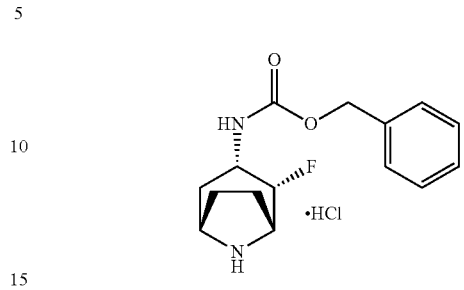

Benzyl N-[(1R,2R,3S,5S)-2-fluoro-8-azabicyclo[3.2.1]octan-3-yl]carbamate (slow eluting isomer) (4.0 g, 13.65 mmol) was slurried in a minimal amount of dichloromethane (10 mL) and tert-butyl methyl ether (50 mL) then treated with 3M hydrogen chloride solution in cyclopentyl methyl ether (7 mL, 21.00 mmol). The mixture was slurried overnight then collected by filtration, to give the title compound (4.23 g). $^1$H NMR (500 MHz, DMSO-d$_6$) δ: 10.3-8.10 (br m, 2H), 7.65 (d, 1H), 7.46-7.24 (m, 5H), 5.18-4.94 (m, 2H), 4.82 (d, J=47.7 Hz, 1H), 4.25-4.09 (m, 1H), 3.99-3.90 (m, 1H), 3.90-3.75 (m, 1H), 2.08-1.73 (m, 6H). $[α]^{20}_D$=-11.88° (c 1.05, MeOH).

Preparation 110: 6-Bromo-5-chloro-3-methyl-3,4-dihydroquinazolin-4-one

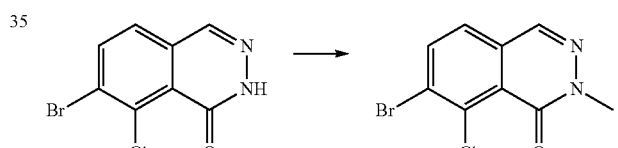

Methyl iodide (0.132 mL, 2.12 mmol) was added to a suspension of 6-bromo-5-chloro-3,4-dihydroquinazolin-4-one (500 mg, 1.93 mmol) and K$_2$CO$_3$ (799 mg, 5.78 mmol) in DMF (10 mL) and the reaction stirred at RT under N$_2$ for 1.5 h. Water was added and the resultant precipitate collected by vacuum filtration, washing with water, then dried in a vacuum oven, to give the title compound (470 mg). MS: [M+H]$^+$=273.

Preparation 111: 6-Bromo-5-chloro-2,3-dimethyl-3,4-dihydroquinazolin-4-one

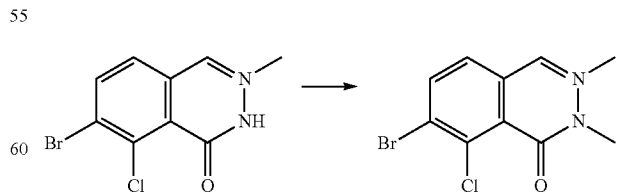

Prepared in a similar fashion to 6-bromo-5-chloro-3-methyl-3,4-dihydroquinazolin-4-one, except using 6-bromo-5-chloro-2-methyl-3,4-dihydroquinazolin-4-one to give the title compound. MS: [M+H]$^+$=286.

Preparation 112: 6-Bromo-7-chloro-N,N-dimethyl-1,3-benzothiazole-2-carboxamide

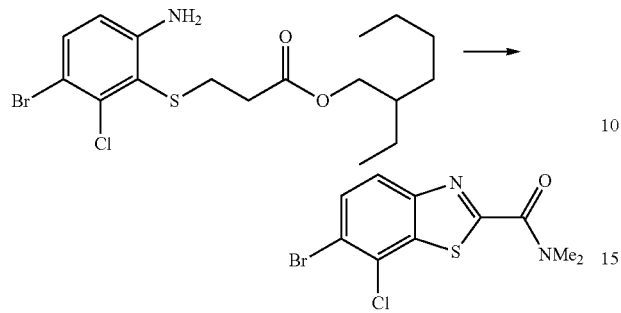

DIPEA (0.41 mL, 2.37 mmol) was added to a solution of 2-ethylhexyl 3-[(6-amino-3-bromo-2-chlorophenyl)sulfanyl]propanoate (500 mg, 1.18 mmol), N,N-dimethyloxamic acid (139 mg, 1.18 mmol) and 1-[bis(dimethylamino)methylene]-1H-1,2,3-triazolo[4,5-b]pyridinium 3-oxide hexafluorophosphate (495 mg, 1.30 mmol) in DMF (6 mL) and the reaction stirred at RT for 16 h. The reaction was diluted with EtOAc and washed sequentially with sat. aq. $NH_4Cl$ (2×), $H_2O$ (3×) and brine, then dried ($MgSO_4$) and evaporated. The residue was purified by column chromatography on silica gel (gradient elution, 0-25%, EtOAc/petrol) to provide the intermediate amide. This residue was re-dissolved in THF (12 mL), NaOEt solution (20 wt % in EtOH, 1.4 mL, 3.55 mmol) was added and the reaction stirred for 30 min. After cooling to 0° C., TFA (2.7 mL, 35.5 mmol) was carefully added and the reaction then heated to 60° C. for 2 h. After cooling to 0° C., sat. aq. $NaHCO_3$ was added carefully and the mixture extracted with EtOAc (3×). Combined organics were washed with brine, dried ($MgSO_4$) and evaporated. To the residue in a mixture of 1,4-dioxane/MeOH (6 mL, 1:1) was added $Et_3N$ (1.65 mL, 11.8 mmol) and dimethylamine hydrochloride (482 mg, 5.91 mmol). The reaction sealed and heated to 100° C. for 1 h. After cooling, the reaction was evaporated and the residue purified by column chromatography on silica gel (gradient elution, 0-25%, EtOAc/petrol), to give the title compound (145 mg). MS: $[M+H]^+=319$.

Preparation 113: 5-Bromo-4-chloro-3,3-difluoro-2,3-dihydro-1H-indol-2-one

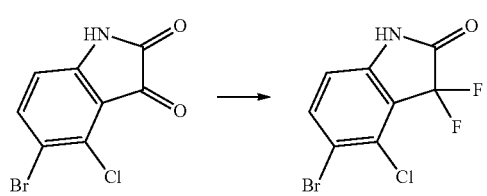 [SMILES: O=C1Nc2ccc(Br)c(Cl)c2C1=O ; O=C1Nc2ccc(Br)c(Cl)c2C1(F)F]

5-Bromo-4-chloro-2,3-dihydro-1H-indole-2,3-dione (0.685 g, 2.65 mmol) was dissolved in DCM (7 mL) and cooled to 0° C. Diethylaminosulfur trifluoride (1.05 mL, 7.96 mmol) was added dropwise and the reaction was allowed to warm to RT and stirred overnight. The reaction was diluted with DCM, washed with sat. aq. $NaHCO_3$ then brine. The organic phase was dried by passing through a phase separator and concentrated in vacuo. The residue was purified by column chromatography on silica gel (gradient elution, 0-20%, EtOAc/petrol), to give the title compound (0.30 g). MS: $[M-H]^-=281$.

Preparation 114: 5-Bromo-4-chloro-3,3-difluoro-1-{[2-(trimethylsilyl)ethoxy]methyl}-2,3-dihydro-1H-indol-2-one

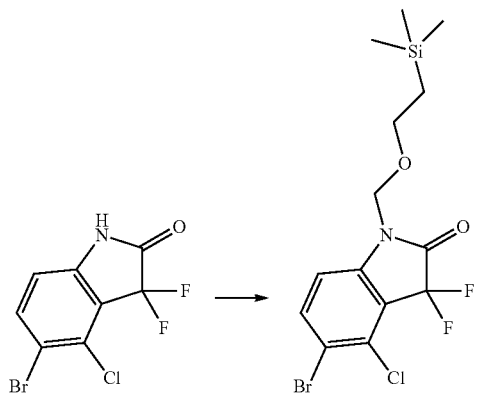 [SMILES: O=C1Nc2ccc(Br)c(Cl)c2C1(F)F ; C[Si](C)(C)CCOCN1C(=O)C(F)(F)c2c1ccc(Br)c2Cl]

5-Bromo-4-chloro-3,3-difluoro-2,3-dihydro-1H-indol-2-one (0.3 g, 1.06 mmol) was dissolved in DMF (5 mL) and cooled to 0° C. Sodium hydride (60 wt % in mineral oil, 0.055 g, 1.38 mmol) was added and the reaction stirred until homogeneous. 2-(Trimethylsilyl)ethoxymethyl chloride (0.243 mL, 1.38 mmol) was added dropwise and the reaction was stirred at RT overnight. The reaction was diluted with $Et_2O$, washed with water then brine. The organic phase was dried by passing through a phase separator and concentrated in vacuo. The residue was purified by column chromatography on silica gel (gradient elution, 0-20%, EtOAc/petrol), to give the title compound (0.392 g). $^1$H NMR (400 MHz, DMSO-$d_6$): 8.07 (1H, d), 7.27 (1H, d), 5.15 (2H, s), 3.56 (2H, t), 0.95-0.85 (2H, m), −0.01-0.16 (9H, m).

Preparation 115: 5-Chloro-2,3-dimethyl-6-(4,4,5,5-tetramethyl-1,3,2-dioxaborolan-2-yl)-3,4-dihydroquinazolin-4-one

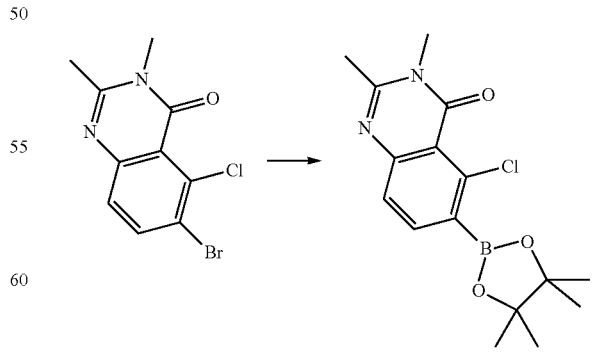

Prepared as preparation 43, except using 6-bromo-5-chloro-2,3-dimethyl-3,4-dihydroquinazolin-4-one, to give the title compound. MS: $[M+H]^+=335$

Preparation 116: 3-Chloro-7-(4-chloro-2-methyl-2H-indazol-5-yl)-N,N-dimethyl-5H-pyrrolo[2,3-b]pyrazine-5-sulfonamide

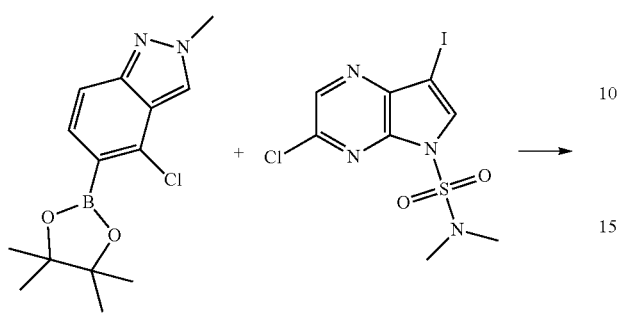

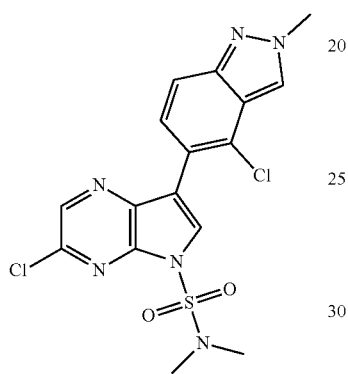

Prepared as general procedure 2, except using 3-chloro-7-iodo-N,N-dimethyl-5H-pyrrolo[2,3-b]pyrazine-5-sulfonamide (5.5 g, 14.4 mmol), 4-chloro-2-methyl-5-(4,4,5,5-tetramethyl-1,3,2-dioxaborolan-2-yl)-2H-indazole (70% pure, 7.22 g, 17.3 mmol), [1,1'-bis(diphenylphosphino)ferrocene]dichloropalladium(II) (0.105 g, 0.14 mmol), potassium carbonate (3.98 g, 28.83 mmol), water (48 mL) and 1,2-dimethoxyethane (72 mL) at 70° C., MS: [M+H]$^+$=425

Preparation 117: tert-Butyl N-[endo-8-[7-(5-chloro-2,3-dimethyl-4-oxo-3,4-dihydroquinazolin-6-yl)-5-{[2-(trimethylsilyl)ethoxy]methyl}-5H-pyrrolo[2,3-b]pyrazin-3-yl]-8-azabicyclo[3.2.1]octan-3-yl]carbamate

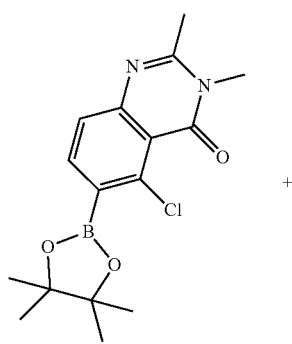

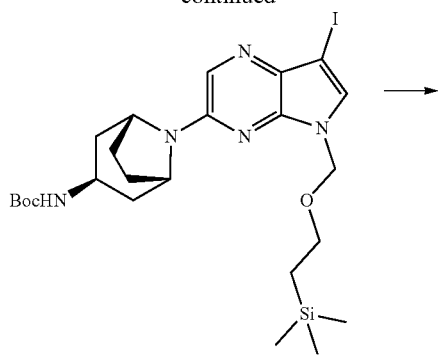

-continued

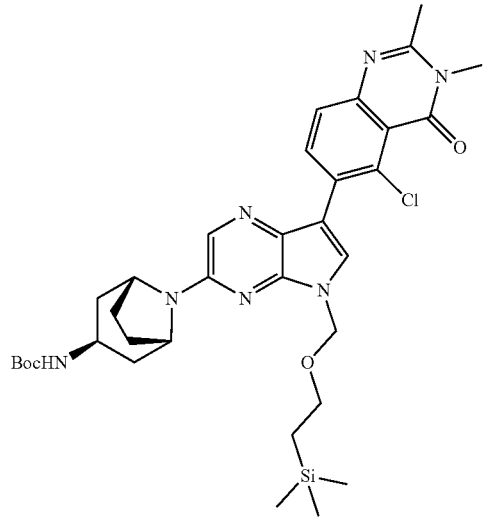

Prepared as general procedure 2, except using 5-chloro-2,3-dimethyl-6-(4,4,5,5-tetramethyl-1,3,2-dioxaborolan-2-yl)-3,4-dihydroquinazolin-4-one, MS: [M+H]$^+$=680

Preparation 118: tert-Butyl N-[endo-8-[7-(5-chloro-3-methyl-4-oxo-3,4-dihydroquinazolin-6-yl)-5-{[2-(trimethylsilyl)ethoxy]methyl}-5H-pyrrolo[2,3-b]pyrazin-3-yl]-8-azabicyclo[3.2.1]octan-3-yl]carbamate

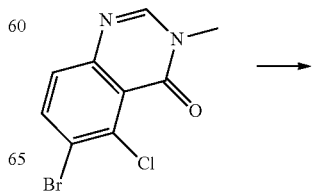

-continued

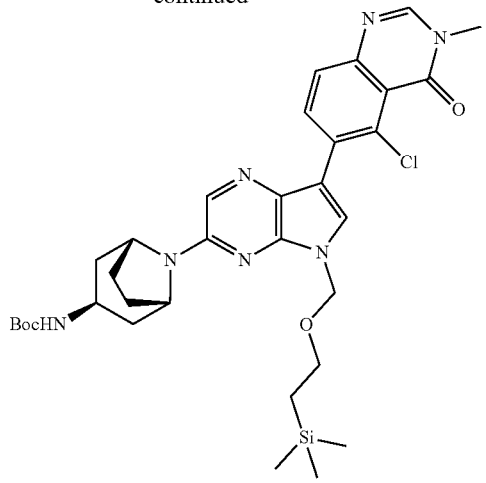

Prepared as general procedure 3 except using 6-bromo-5-chloro-3-methyl-3,4-dihydroquinazolin-4-one, MS: [M+H]+=666

Preparation 119: tert-Butyl N-[endo-8-{7-[7-chloro-2-(dimethylcarbamoyl)-1,3-benzothiazol-6-yl]-5-{[2-(trimethylsilyl)ethoxy]methyl}-5H-pyrrolo[2,3-b]pyrazin-3-yl}-8-azabicyclo[3.2.1]octan-3-yl]carbamate

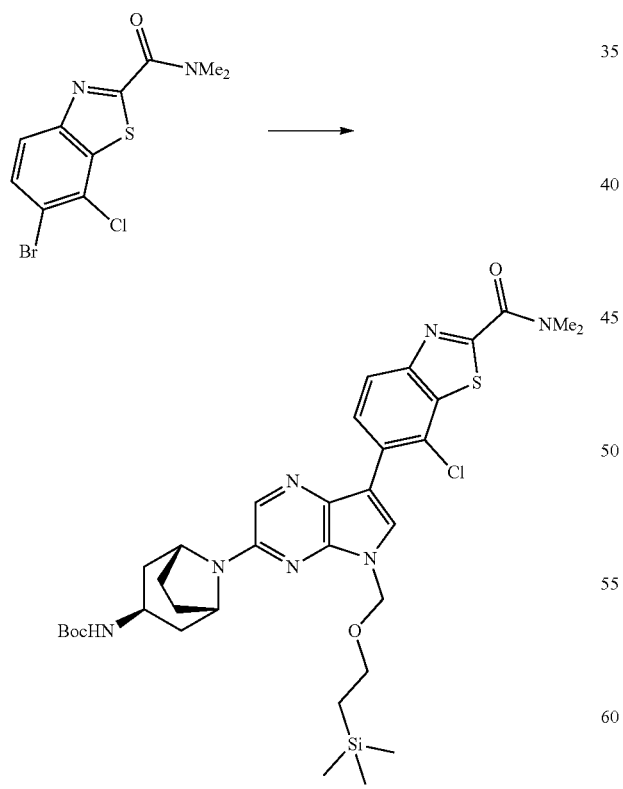

Prepared as general procedure 3 except using 6-bromo-7-chloro-N,N-dimethyl-1,3-benzothiazole-2-carboxamide, MS: [M+H]+=712

Preparation 120: tert-Butyl N-[endo-8-[7-(4-chloro-3,3-difluoro-2-oxo-1-{[2-(trimethylsilyl)ethoxy]methyl}-2,3-dihydro-1H-indol-5-yl)-5-{[2-(trimethylsilyl)ethoxy]methyl}-5H-pyrrolo[2,3-b]pyrazin-3-yl]-8-azabicyclo[3.2.1]octan-3-yl]carbamate

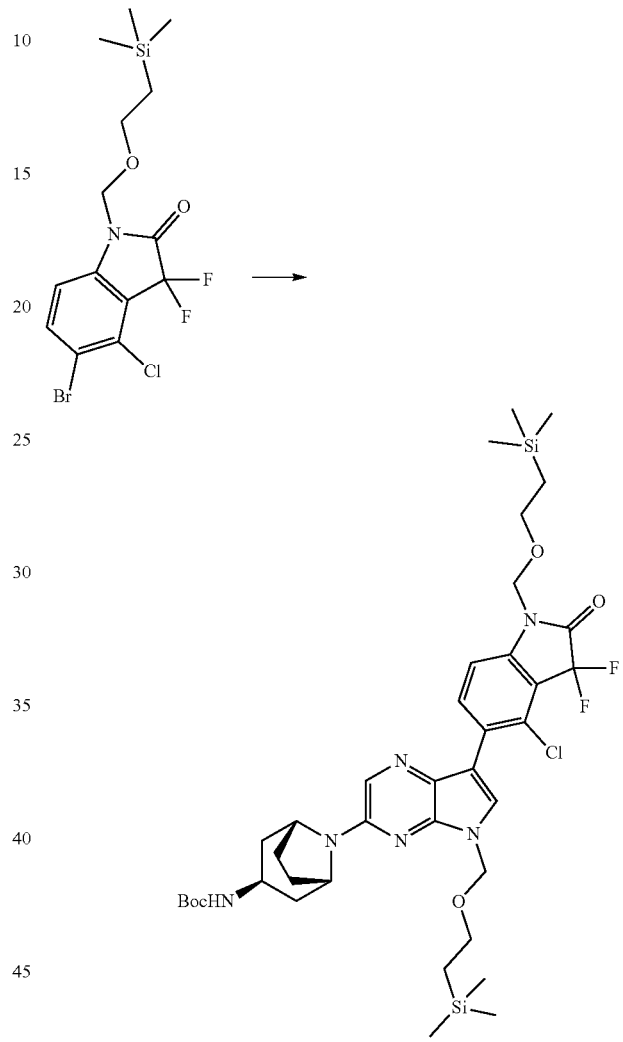

Prepared as general procedure 3 except using 5-bromo-4-chloro-3,3-difluoro-1-{[2-(trimethylsilyl)ethoxy]methyl}-2,3-dihydro-1H-indol-2-one, MS: [M+H]+=805

Preparation 121: (3,5-Dichloro-6-methylpyrazin-2-yl)methanol

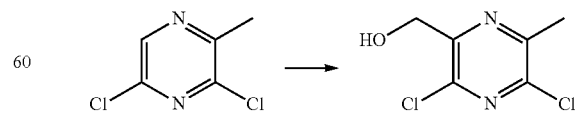

To each of 12 reaction tubes was added TFA (0.40 mL, 5.21 mmol), 3,5-dichloro-2-methylpyrazine (85 mg, 0.52 mmol), 2,4,5,6-tetra(9H-carbazol-9-yl)isophthalonitrile (4 mg, 0.0052 mmol), ted-butyl peracetate solution (50 wt % in odourless mineral spirits, 0.75 mL, 2.87 mmol) and degassed MeOH/DMSO (9:1, 5 mL). Each vial was briefly flushed with $N_2$ then sealed and stirred under blue LED illumination (Kessel lamp, 34 W) for 18 h. The contents of the 12 tubes were combined and most of the solvent was evaporated. The residue was partitioned between EtOAc and sat. aq. NaHCO$_3$, the separated aq. layer was extracted with EtOAc (2×) and combined organics were washed with brine (3×), dried (MgSO$_4$) and evaporated. The residue was purified by column chromatography on silica gel (gradient elution, 0-30%, EtOAc/petrol), to give the title compound (480 mg). MS: $[M+H]^+=193$.

Preparation 122: 3,5-Dichloro-6-methylpyrazine-2-carbaldehyde

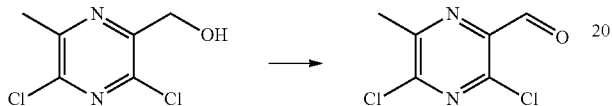

To a stirred mixture of (3,5-dichloro-6-methylpyrazin-2-yl)methanol (0.32 g, 1.66 mmol) in DCM (16.6 mL) was added Dess-Martin periodinane (1.05 g, 2.49 mmol) and the mixture was stirred at RT for 2 h. The reaction was quenched with sat. aq. NaHCO$_3$ and sat. aq. Na$_2$S$_2$O$_3$. EtOAc was added, the phases were separated and the EtOAc layer was washed with sat. aq. NaHCO$_3$ (2×). The organic layer was dried (Na$_2$SO$_4$), filtered and concentrated, to give the title compound which was used without further purification.

Preparation 123: (4-Chloro-2-methyl-2H-indazol-5-yl)(3,5-dichloro-6-methylpyrazin-2-yl)methanol

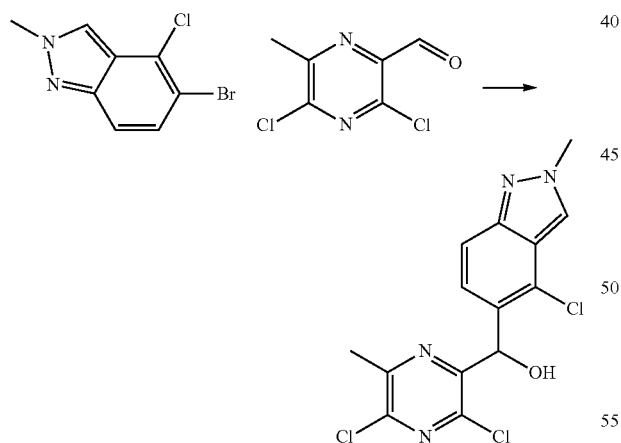

To a solution of isopropylmagnesium chloride lithium chloride complex solution (1.3 M in THF, 2.58 mL, 3.36 mmol) in THF (4.48 mL) at 30° C. was added a solution of 5-bromo-4-chloro-2-methyl-2H-indazole (0.55 g, 2.24 mmol, azeotropically dried from toluene 3×) in THF (4.48 mL) at 30° C. dropwise over 10 min. The mixture was stirred at this temperature for 25 min before it was cooled to 0° C. and a solution of 3,5-dichloro-6-methylpyrazine-2-carbaldehyde (0.319 g, 1.68 mmol, azeotropically dried from THF 3×) in THF (4.48 mL) was added dropwise over 10 min. 30% brine solution, sat. aq. NH$_4$Cl and EtOAc were added, the phases separated, and the aqueous phase was further extracted with EtOAc (2×). The combined organic extracts were dried (Na$_2$SO$_4$), filtered and concentrated. The residue was purified by column chromatography on silica gel (gradient elution, 20-35%, acetone/petrol), to give the title compound (0.32 g), MS: $[M+H]^+=357$.

Preparation 124: 4-Chloro-5-(3,5-dichloro-6-methylpyrazine-2-carbonyl)-2-methyl-2H-indazole

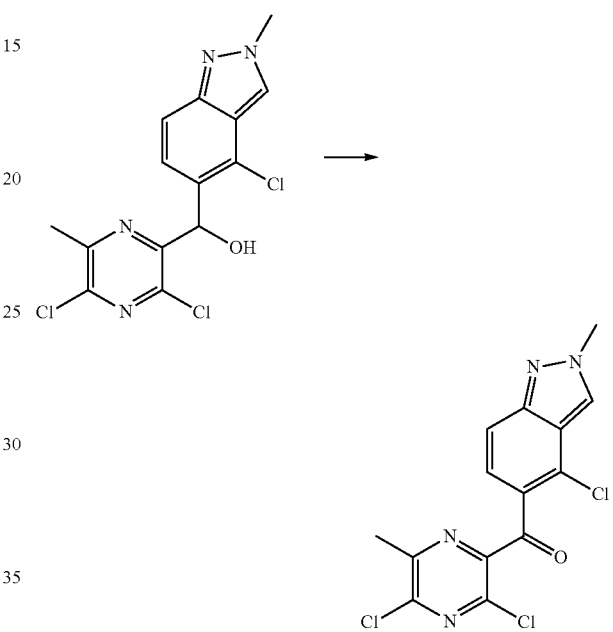

To a stirred solution of (4-chloro-2-methyl-2H-indazol-5-yl)(3,5-dichloro-6-methylpyrazin-2-yl)methanol (0.32 g, 0.895 mmol) in DCM (8.95 mL) at RT was added manganese(IV) oxide (1.56 g, 17.9 mmol). The suspension was stirred overnight before it was filtered, washing with DCM (3×) and concentrated, to give the title compound (0.231 g) which was used without further purification, MS: $[M+H]^+=355$.

Preparation 125: Benzyl N-[(1R,2S,3S,5S)-8-[6-chloro-5-(4-chloro-2-methyl-2H-indazole-5-carbonyl)-3-methylpyrazin-2-yl]-2-fluoro-8-azabicyclo[3.2.1]octan-3-yl]carbamate

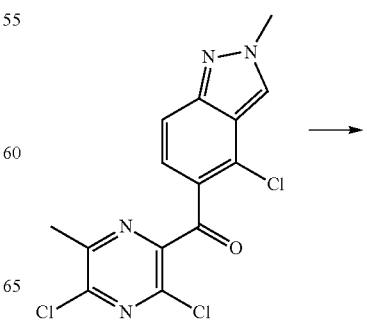

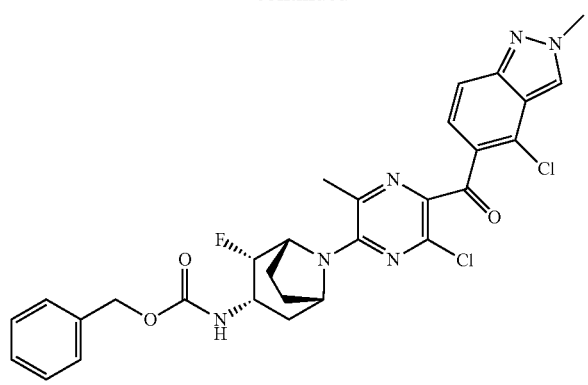

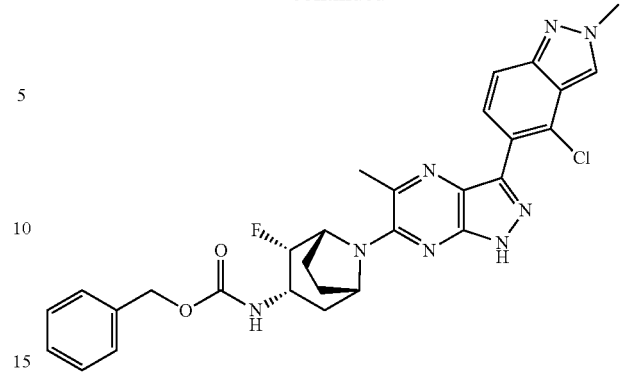

To a stirred solution of 4-chloro-5-(3,5-dichloro-6-methylpyrazine-2-carbonyl)-2-methyl-2H-indazole (0.216 g, 0.607 mmol) and DIPEA (0.212 mL, 1.21 mmol) in NMP (0.607 mL) at 0° C. was added a solution of benzyl N-[(1R,2R,3S,5S)-2-fluoro-8-azabicyclo[3.2.1]octan-3-yl]carbamate (0.229 g, 0.729 mmol) in NMP (0.607 mL). The mixture was stirred at 0° C. for 1 h then allowed to warm to RT and stirred for 24 h. The mixture was diluted with EtOAc/30% brine solution/sat. aq. NH$_4$Cl, the phases were separated, and the organic phase was washed with 30% brine solution/sat. aq. NH$_4$Cl (2×) then with sat. aq. NaHCO$_3$. The organic extract was dried (Na$_2$SO$_4$), filtered and concentrated. The residue was purified by column chromatography on silica gel (gradient elution, 23-50%, acetone/petrol), to give the title compound (0.18 g), MS: [M+H]$^+$=597.

Preparation 126: Benzyl N-[(1R,2S,3S,5S)-8-[3-(4-chloro-2-methyl-2H-indazol-5-yl)-5-methyl-1H-pyrazolo[3,4-b]pyrazin-6-yl]-2-fluoro-8-azabicyclo[3.2.1]octan-3-yl]carbamate

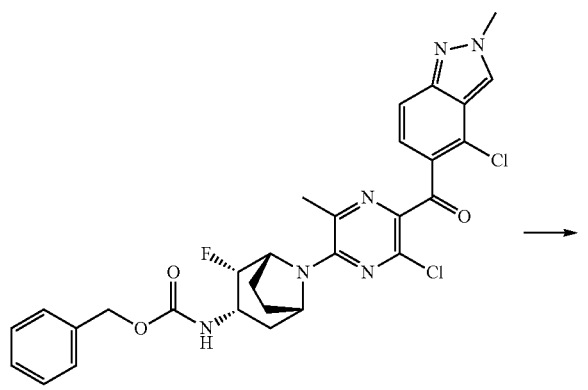

To a stirred solution of benzyl N-[(1R,2S,3S,5S)-8-[6-chloro-5-(4-chloro-2-methyl-2H-indazole-5-carbonyl)-3-methylpyrazin-2-yl]-2-fluoro-8-azabicyclo[3.2.1]octan-3-yl]carbamate (0.18 g, 0.301 mmol) in EtOH (6.03 mL) was added hydrazine monohydrate (0.132 mL, 0.603 mmol) and the mixture was heated to 80° C. for 4 h. The mixture was diluted with 30% brine solution and CHCl$_3$/IPA (3:1) and the phases separated, and the aqueous phase was extracted with CHCl$_3$/IPA (3:1) (2×). The organic extract was dried (Na$_2$SO$_4$), filtered and concentrated. The residue was purified by column chromatography on silica gel (gradient elution, 60-100%, EtOAc/petrol), to give the title compound (0.097 g), MS: [M+H]$^+$=575.

Preparation 127: 2-(5-Bromo-4-chloro-2H-indazol-2-yl)-N,N-dimethylacetamide

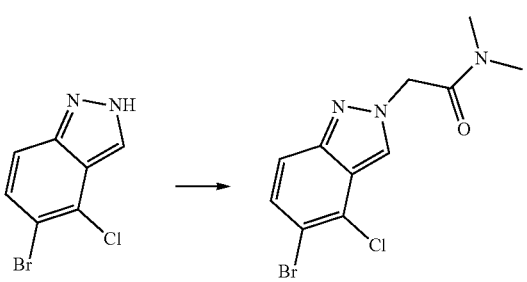 [SMILES: Clc1c(Br)ccc2n[nH]cc12 ; CN(C)C(=O)Cn1cc2c(Cl)c(Br)ccc2n1]

DMF (10.8 mL, 139 mmol) and water (3.6 mL, 14.34 mmol) were added to 5-bromo-4-chloro-1H-indazole (3.32 g, 14.34 mmol), gallium (1.5 g, 21.51 mmol), and aluminium (0.580 g, 21.51 mmol). 2-bromo-N,N-dimethylacetamide (4.64 mL, 43.0 mmol) was then added and the reaction was stirred at 55° C. for 64 h. The reaction was diluted with EtOAc (50 mL) and water (50 mL) and filtered. The organic phase was isolated and the aqueous phase further extracted with EtOAc (2×50 mL). The combined organic phases were washed with 1 M aq. HCl (50 mL) and water (2×50 mL), dried (MgSO$_4$) and concentrated. The residue was purified by column chromatography on silica gel (gradient elution, 50-100%, EtOAc/iso-hexanes), to give the title compound (2.06 g). MS: [M+H]$^+$=316.

Preparation 128: tert-Butyl N-[endo-8-(7-{4-chloro-2-[(dimethylcarbamoyl)methyl]-2H-indazol-5-yl}-5-{[2-(trimethylsilyl)ethoxy]methyl}-5H-pyrrolo[2,3-b]pyrazin-3-yl)-8-azabicyclo[3.2.1]octan-3-yl] carbamate

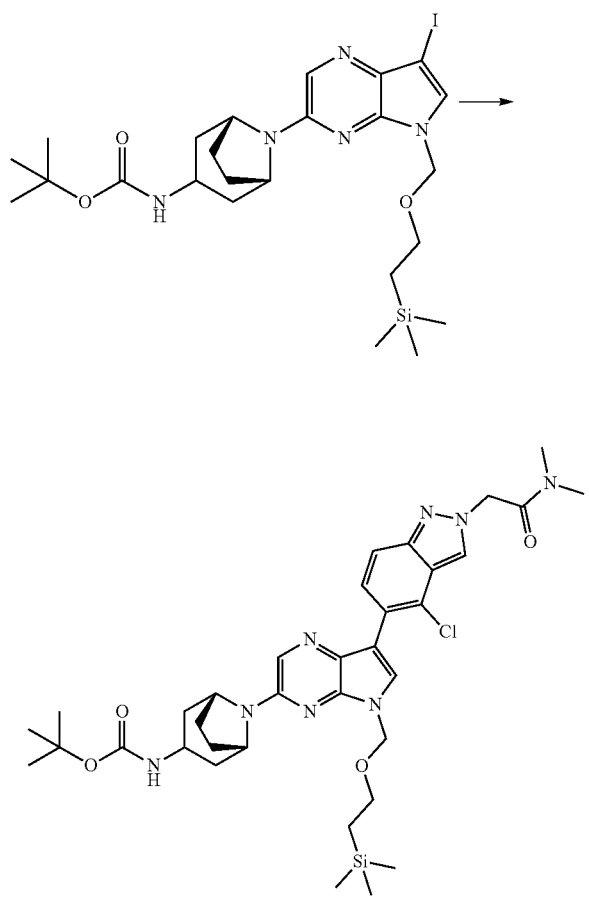

tert-Butyl ((endo-8-(7-iodo-5-((2-(trimethylsilyl)ethoxy)methyl)-5H-pyrrolo[2,3-b]pyrazin-3-yl)-8-azabicyclo[3.2.1]octan-3-yl)carbamate (473 mg, 0.790 mmol) was charged to a 40 mL vial which was sealed and then evacuated and back-filled with nitrogen (3×). THF (3 mL) was added and the resulting solution was cooled to 0° C. before isopropylmagnesium chloride lithium chloride complex solution (1.3 M in THF, 1.336 mL, 1.737 mmol) was added dropwise and the resulting solution stirred at 0° C. for 45 min. Zinc(II) chloride solution (1.9 M in THF, 0.914 mL, 1.737 mmol) was added dropwise and the reaction stirred at 0° C. for 10 min and then at RT for 45 min. 2-(5-bromo-4-chloro-2H-indazol-2-yl)-N,N-dimethylacetamide (250 mg, 0.790 mmol) and SPhos Pd G3 (30.8 mg, 0.039 mmol) were added and the reaction vial evacuated and back-filled with nitrogen (3×) before being stirred at RT for 24 h. The reaction mixture was diluted with EtOAc (25 mL) and sat. aq. NH$_4$Cl (25 mL). The organic phase was isolated and the aqueous further extracted with EtOAc (25 mL). The combined organic phases were dried (MgSO$_4$), filtered, and concentrated. The residue was purified by column chromatography on silica gel (gradient elution, 50-100%, EtOAc/iso-hexanes), to give the title compound (164 mg). MS: [M+H]$^+$=709.

Preparation 129: 1-(5-Bromo-4-chloro-2H-indazol-2-yl)-2-methylpropan-2-ol

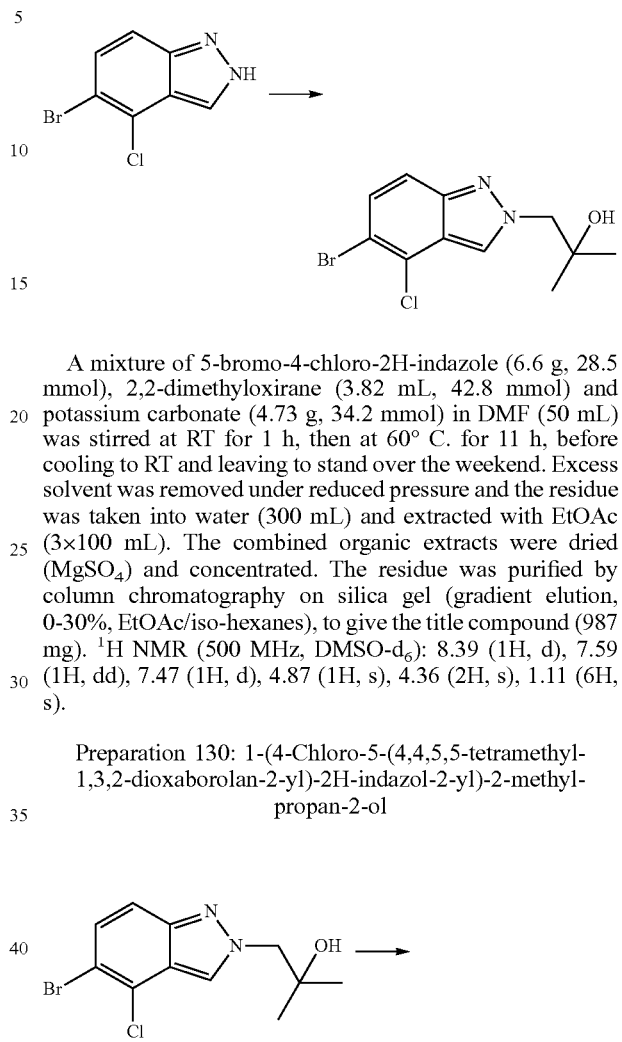

A mixture of 5-bromo-4-chloro-2H-indazole (6.6 g, 28.5 mmol), 2,2-dimethyloxirane (3.82 mL, 42.8 mmol) and potassium carbonate (4.73 g, 34.2 mmol) in DMF (50 mL) was stirred at RT for 1 h, then at 60° C. for 11 h, before cooling to RT and leaving to stand over the weekend. Excess solvent was removed under reduced pressure and the residue was taken into water (300 mL) and extracted with EtOAc (3×100 mL). The combined organic extracts were dried (MgSO$_4$) and concentrated. The residue was purified by column chromatography on silica gel (gradient elution, 0-30%, EtOAc/iso-hexanes), to give the title compound (987 mg). $^1$H NMR (500 MHz, DMSO-d$_6$): 8.39 (1H, d), 7.59 (1H, dd), 7.47 (1H, d), 4.87 (1H, s), 4.36 (2H, s), 1.11 (6H, s).

Preparation 130: 1-(4-Chloro-5-(4,4,5,5-tetramethyl-1,3,2-dioxaborolan-2-yl)-2H-indazol-2-yl)-2-methyl-propan-2-ol

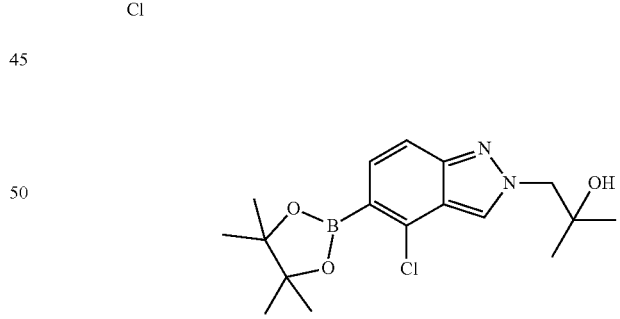

Prepared as preparation 43, except using 1-(5-bromo-4-chloro-2H-indazol-2-yl)-2-methylpropan-2-ol (977 mg, 3.22 mmol). The residue was purified by column chromatography on silica gel (gradient elution, 0-5%, MeOH/DCM), to give the title compound (767 mg). MS: [M+H]$^+$=351.

Preparation 131: tert-Butyl N-[endo-8-{7-[4-chloro-2-(2-hydroxy-2-methylpropyl)-2H-indazol-5-yl]-5-{[2-(trimethylsilyl)ethoxy]methyl}-5H-pyrrolo[2,3-b]pyrazin-3-yl}-8-azabicyclo[3.2.1]octan-3-yl]carbamate

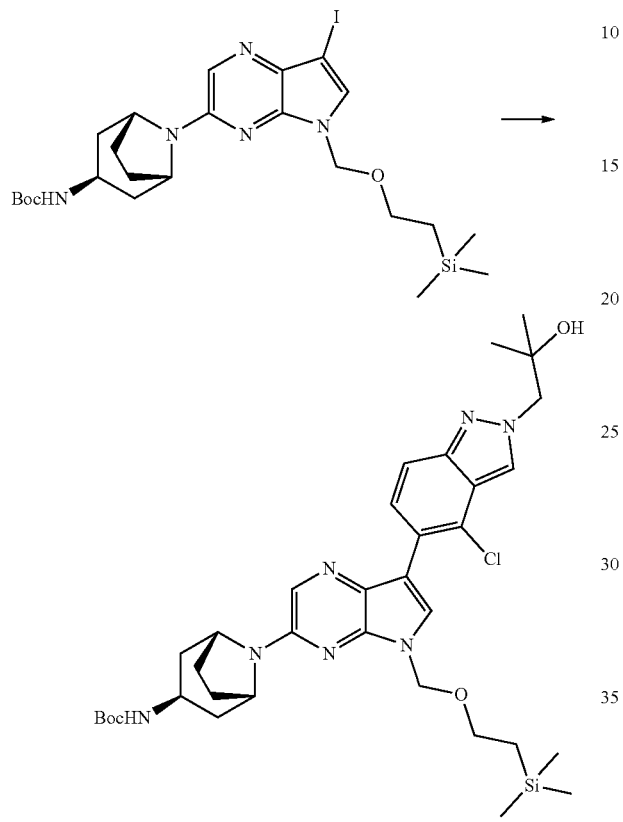

Prepared as general procedure 2, except using 1-(4-chloro-5-(4,4,5,5-tetramethyl-1,3,2-dioxaborolan-2-yl)-2H-indazol-2-yl)-2-methylpropan-2-ol (753 mg, 1.911 mmol) in 1,4-dioxane (12 mL). The crude product was purified by column chromatography on silica gel three times (0-50% EtOAc/iso-hexanes, then 40-70% EtOAc/iso-hexanes, then 0-5% MeOH/DCM), to give the title compound (420 mg). $^1$H NMR (500 MHz, DMSO-$d_6$): 8.36 (1H, d), 8.16 (1H, s), 7.92 (1H, d), 7.89 (1H, s), 7.65 (1H, dd), 6.84 (1H, s), 5.57 (2H, s), 4.58 (2H, s), 4.38 (2H, s), 3.62 (2H, t), 3.43 (1H, s), 2.20-2.07 (4H, m), 2.03-1.91 (2H, m), 1.76 (2H, d), 1.39 (9H, s), 1.14 (6H, s), 0.95-0.82 (2H, m), −0.08 (9H, s).

Preparation 132: 3,4-Dichloro-5-(4,4,5,5-tetramethyl-1,3,2-dioxaborolan-2-yl)-1H-indazole

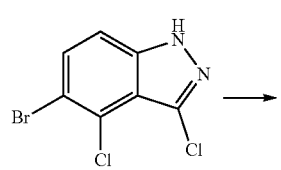

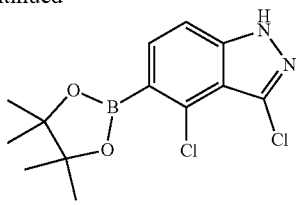

Prepared as preparation 43, except using 5-bromo-3,4-dichloro-1H-indazole (2.45 g, 9.21 mmol). The crude product was purified by column chromatography on silica gel (gradient elution, 0-5%, MeOH/DCM), to give the title compound (1.95 g). MS: [M+H]$^+$=313.

Preparation 133: tert-Butyl N-[endo-8-[7-(3,4-dichloro-2H-indazol-5-yl)-5-{[2-(trimethylsilyl)ethoxy]methyl}-5H-pyrrolo[2,3-b]pyrazin-3-yl]-8-azabicyclo[3.2.1]octan-3-yl]carbamate Prepared as general procedure 2, except using 3,4-dichloro-5-(4,4,5,5-tetramethyl-1,3,2-dioxaborolan-2-yl)-1H-indazole (287 mg, 0.917 mmol) in 1,4-dioxane (12 mL). The crude product was purified by column chromatography on silica gel (gradient elution, 0-50%, EtOAc/iso-hexanes), to give the title compound (274 mg). MS: [M+H]$^+$=658.

Preparation 134: 2-(5-Bromo-4-chloro-2H-indazol-2-yl)acetonitrile

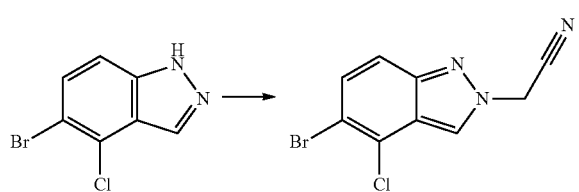 [SMILES: Clc1c(Br)ccc2[nH]ncc12 ; N#CCn1cc2c(Cl)c(Br)ccc2n1]

5-Bromo-4-chloro-1H-indazole (5 g, 21.60 mmol) was dissolved in NMP (2 mL) and bromoacetonitrile (4.51 mL, 64.8 mmol) was added. The solution was stirred at 120° C. for 18 h then, after cooling to RT, EtOAc (200 mL) and water (200 mL) were added. The organic phase was isolated and was washed with water (3×100 mL) before being dried (MgSO$_4$), filtered, and concentrated with silica (ca. 16 g) to dry-load the crude material. The crude product was purified by column chromatography on silica gel (20% EtOAc/iso-hexanes), to give the title compound (2.38 g). MS: [M+H]$^+$=270.

Preparation 135: 2-(4-Chloro-5-(4,4,5,5-tetramethyl-1,3,2-dioxaborolan-2-yl)-2H-indazol-2-yl) acetonitrile

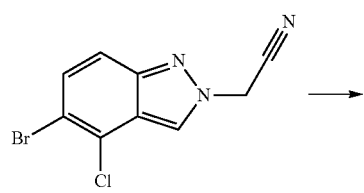

Prepared as preparation 43, except using 2-(5-bromo-4-chloro-2H-indazol-2-yl)acetonitrile (1 g, 3.70 mmol). The crude product was purified by column chromatography on silica gel (gradient elution, 0-50%, EtOAc/iso-hexanes), to give the title compound (1.31 g). MS: [M+H]$^+$=318.

Preparation 136: tert-Butyl N-[endo-8-{7-[4-chloro-2-(cyanomethyl)-2H-indazol-5-yl]-5-{[2-(trimethylsilyl)ethoxy]methyl}-5H-pyrrolo[2,3-b]pyrazin-3-yl}-8-azabicyclo[3.2.1]octan-3-yl]carbamate

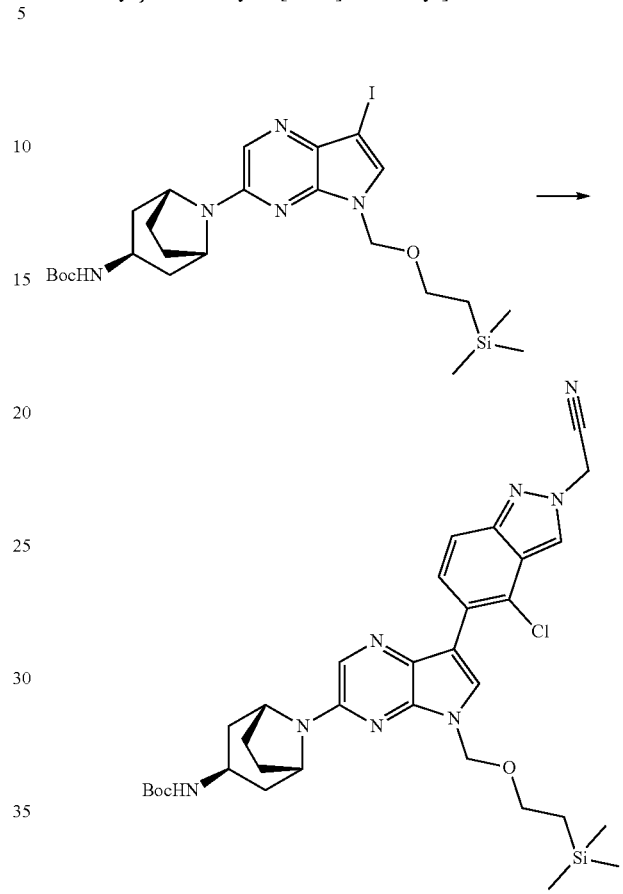

Prepared as general procedure 2, except using 2-(4-chloro-5-(4,4,5,5-tetramethyl-1,3,2-dioxaborolan-2-yl)-2H-indazol-2-yl)acetonitrile (1.059 g, 2.50 mmol). The crude product was dry-loaded on silica (ca. 8 g) and purified by column chromatography on silica gel (gradient elution, 10-50%, EtOAc/iso-hexanes), to give the title compound (286 mg). MS: [M+H]$^+$=663.

Preparation 137: 5-Bromo-4-chloro-3-(chloromethyl)-2-methyl-2H-indazole

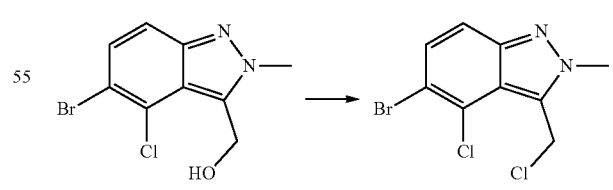

To a solution of (5-bromo-4-chloro-2-methyl-2H-indazol-3-yl)methanol (1.21 g, 4.39 mmol) in CHCl$_3$ (100 mL) was added sulfurous dichloride (0.481 mL, 6.59 mmol). The reaction was heated to 60° C. for 2 h, before addition of SOCl$_2$ (0.2 mL). After a further 1 h at 60° C. the reaction was cooled to RT and the solvent was evaporated. The residue was purified by column chromatography on silica gel (gradient elution, 0-50%, EtOAc/iso-hexanes), to give the title compound (1.1 g). ¹H NMR (500 MHz, DMSO-d₆): 7.60 (1H, d), 7.54 (1H, d), 5.45 (2H, s), 4.22 (3H, s).

Preparation 138: 2-(5-Bromo-4-chloro-2-methyl-2H-indazol-3-yl)acetonitrile

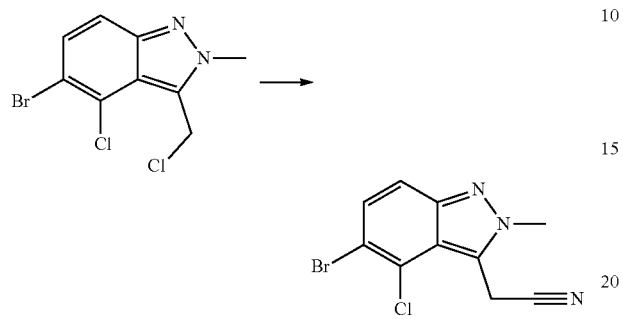

To a solution of 5-bromo-4-chloro-3-(chloromethyl)-2-methyl-2H-indazole (1.054 g, 3.59 mmol) in DMSO (15 mL) was added sodium cyanide (0.193 g, 3.94 mmol) before heating to 60° C. for 1 h. The reaction was cooled to RT, sat. aq. NaHCO₃ (50 mL) was added and extracted with EtOAc (2×100 mL). The combined organic extracts were dried (MgSO₄) and concentrated to give the title compound (957 mg). ¹H NMR (500 MHz, DMSO-d₆): (1H, d), 7.52 (1H, d), 4.73 (2H, s), 4.21 (3H, s).

Preparation 139: 2-[4-Chloro-2-methyl-5-(4,4,5,5-tetramethyl-1,3,2-dioxaborolan-2-yl)-2H-indazol-3-yl]acetonitrile

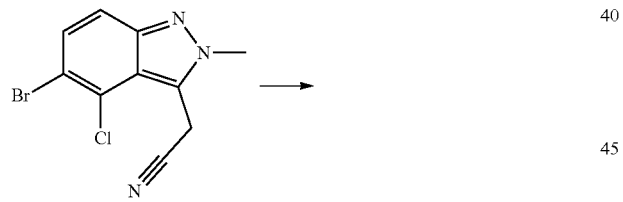

Prepared as preparation 43, except using 2-(5-bromo-4-chloro-2-methyl-2H-indazol-3-yl)acetonitrile (847 mg, 2.98 mmol). The crude product was purified by column chromatography on silica gel (gradient elution, 0-5%, MeOH/DCM), to give the title compound (549 mg). ¹H NMR (500 MHz, DMSO-d₆): 7.55 (1H, d), 7.44 (1H, d), 4.21 (2H, s), 3.18 (3H, s), 1.16 (12H, s).

Preparation 140: tert-Butyl N-[endo-8-{7-[4-chloro-3-(cyanomethyl)-2-methyl-2H-indazol-5-yl]-5-{[2-(trimethylsilyl)ethoxy]methyl}-5H-pyrrolo[2,3-b]pyrazin-3-yl}-8-azabicyclo[3.2.1]octan-3-yl]carbamate Prepared as general procedure 2, except using 2-(4-chloro-2-methyl-5-(4,4,5,5-tetramethyl-1,3,2-dioxaborolan-2-yl)-2H-indazol-3-yl)acetonitrile (434 mg, 0.916 mmol) and potassium carbonate (380 mg, 2.75 mmol) in 1,4-dioxane (10 mL). The crude product was purified by column chromatography on silica gel (gradient elution, 0-90%, EtOAc/iso-hexanes), to give the title compound (244 mg). MS: [M+H]⁺=677.

Preparation 141: 4-Chloro-2-methyl-5-(4,4,5,5-tetramethyl-1,3,2-dioxaborolan-2-yl)-2H-indazole-3-carbaldehyde

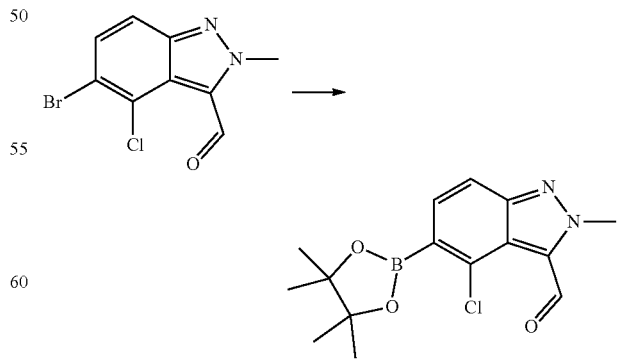

Prepared as preparation 43, except using 5-bromo-4-chloro-2-methyl-2H-indazole-3-carbaldehyde (1.45 g, 5.30 mmol). The crude product was purified by column chromatography on silica gel (gradient elution, 0-10%, MeOH/DCM), to give the title compound (1.69 g). MS: [M+H]⁺=321.

Preparation 142: tert-Butyl N-[endo-8-[7-(4-chloro-3-formyl-2-methyl-2H-indazol-5-yl)-5-{[2-(trimethylsilyl)ethoxy]methyl}-5H-pyrrolo[2,3-b]pyrazin-3-yl]-8-azabicyclo[3.2.1]octan-3-yl]carbamate

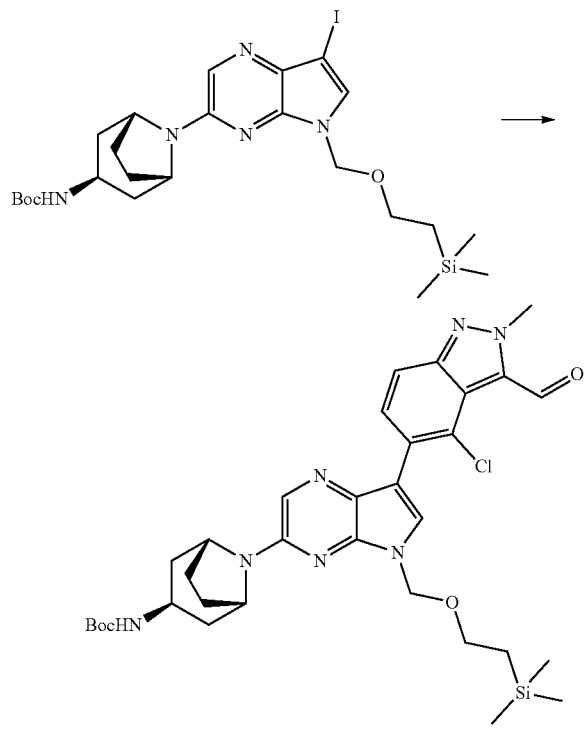

Prepared as general procedure 2, except using 4-chloro-2-methyl-5-(4,4,5,5-tetramethyl-1,3,2-dioxaborolan-2-yl)-2H-indazole-3-carbaldehyde (285 mg, 0.67 mmol) in 1,4-dioxane (8 mL). The crude product was purified by column chromatography on silica gel (gradient elution, 0-50%, EtOAc/iso-hexanes), to give the title compound (253 mg). MS: [M+H]⁺=666.

Preparation 143: tert-Butyl N-(endo-8-(7-(4-chloro-3-((E)-(hydroxyimino)methyl)-2-methyl-2H-indazol-5-yl)-5-((2-(trimethylsilyl)ethoxy)methyl)-5H-pyrrolo[2,3-b]pyrazin-3-yl)-8-azabicyclo[3.2.1]octan-3-yl)carbamate

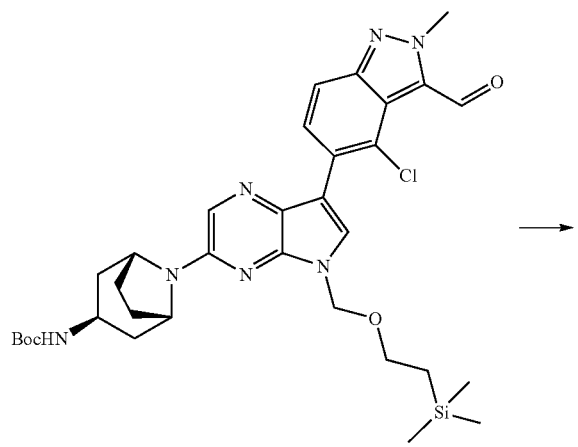

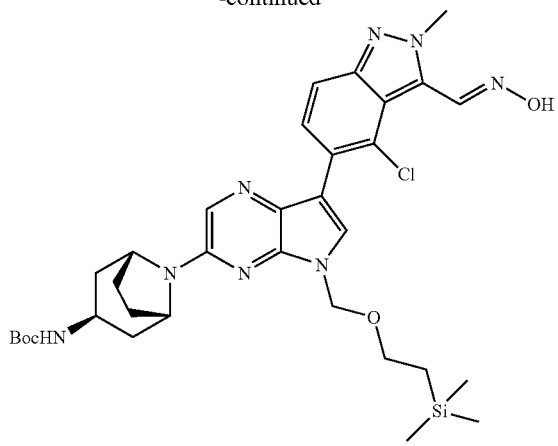

A mixture of tert-butyl N-(endo-8-(7-(4-chloro-3-formyl-2-methyl-2H-indazol-5-yl)-5-((2-(trimethylsilyl)ethoxy)methyl)-5H-pyrrolo[2,3-b]pyrazin-3-yl)-8-azabicyclo[3.2.1]octan-3-yl)carbamate (415 mg, 0.62 mmol), hydroxylamine hydrochloride (87 mg, 1.25 mmol) and sodium carbonate (132 mg, 1.25 mmol) in IPA (3.5 mL) and water (1 mL) was stirred at RT over the weekend. Further hydroxylamine hydrochloride (87 mg, 1.25 mmol) and sodium carbonate (132 mg, 1.25 mmol) were added and stirred for a further 4 h. Water was added and the precipitate collected by filtration. The crude product was purified by column chromatography on silica gel (gradient elution, 0-90%, EtOAc/iso-hexanes) to give title compound and recovered starting material. The recovered starting material was stirred with hydroxylamine hydrochloride (87 mg, 1.25 mmol) and sodium carbonate (132 mg, 1.25 mmol) in MeOH (4 mL) for 18 h. The reaction was diluted in water (5 mL) and the precipitate was collected by filtration, washing with water (5 mL) and the residue was purified by column chromatography on silica gel (gradient elution, 0-70%, EtOAc/iso-hexanes) to afford, when combined with the previous batch, the title compound (265 mg). MS: [M+H]⁺=681.

Preparation 144: tert-Butyl N-(endo-8-(7-(4-chloro-3-cyano-2-methyl-2H-indazol-5-yl)-5-((2-(trimethylsilyl)ethoxy)methyl)-5H-pyrrolo[2,3-b]pyrazin-3-yl)-8-azabicyclo[3.2.1]octan-3-yl)carbamate

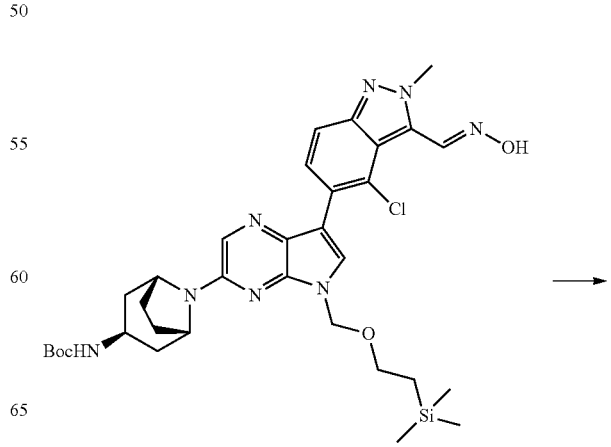

-continued

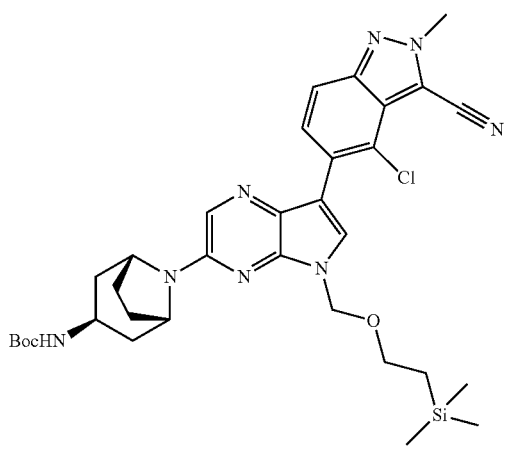

A mixture of tert-butyl N-(endo-8-(7-(4-chloro-3-((E)-(hydroxyimino)methyl)-2-methyl-2H-indazol-5-yl)-5-((2-(trimethylsilyl)ethoxy)methyl)-5H-pyrrolo[2,3-b]pyrazin-3-yl)-8-azabicyclo[3.2.1]octan-3-yl)carbamate (265 mg, 0.389 mmol) and copper(II) acetate (14.13 mg, 0.078 mmol) in MeCN (5 mL) was stirred at 80° C. for 5 h. Further copper(II) acetate (10 mg) was added and the reaction was stirred at 80° C. for a further 2 h before cooling to RT and stirring overnight. The solvent was removed under reduced pressure, and the residue was partitioned between water (10 mL) and DCM (50 mL) and the aq. phase was extracted with DCM (2×50 mL). The combined organic extracts were dried (MgSO4) and concentrated. The residue was purified by column chromatography on silica gel (gradient elution, 0-50%, EtOAc/iso-hexanes), to give the title compound (122 mg). MS: [M+H]+=663.

Preparation 145: 5-Bromo-4-chloro-2-((1-methyl-1H-imidazol-2-yl)methyl)-2H-indazole

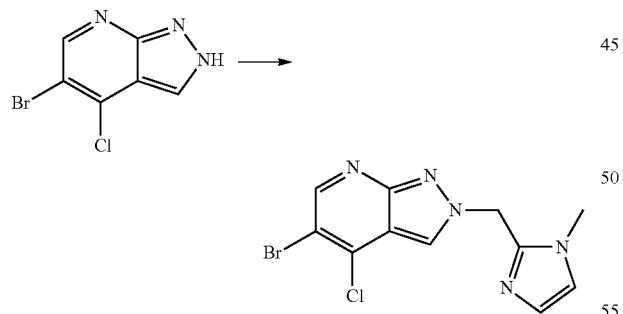

A mixture of 5-bromo-4-chloro-2H-indazole (2.305 g, 9.96 mmol) and 2-(chloromethyl)-1-methyl-1H-imidazole (2.6 g, 19.91 mmol) in NMP (50 mL) was stirred at 140° C. for 24 h before cooling to RT. The organic phase was washed with sat. aq. NaHCO3 (250 mL) and water (2×300 mL), dried (MgSO4) and concentrated. The residue was purified by column chromatography on silica gel (gradient elution, 0-100%, EtOAc/iso-hexanes, then flushed with 100% (0.07% NH3 in MeOH)/DCM), to give the title compound (1.66 g). MS: [M+H]+=325.

Preparation 146: 4-Chloro-2-((1-methyl-1H-imidazol-2-yl)methyl)-5-(4,4,5,5-tetramethyl-1,3,2-dioxaborolan-2-yl)-2H-indazole

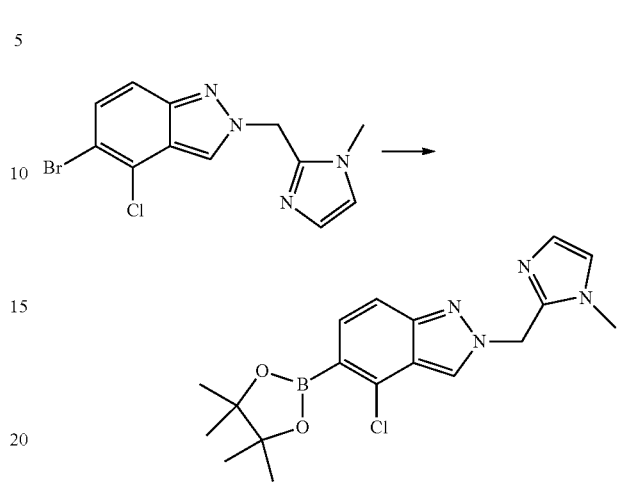

Prepared as preparation 43 using 5-bromo-4-chloro-2-((1-methyl-1H-imidazol-2-yl)methyl)-2H-indazole (1.66 g, 5.10 mmol). The crude product was purified by column chromatography on silica gel twice (0-2% MeOH/DCM, then 70-100% EtOAc/iso-hexanes), to give the title compound (763 mg). MS: [M+H]+=373.

Preparation 147: tert-Butyl N-(endo-8-(7-(4-chloro-2-((1-methyl-1H-imidazol-2-yl)methyl)-2H-indazol-5-yl)-5-((2-(trimethylsilyl)ethoxy)methyl)-5H-pyrrolo[2,3-b]pyrazin-3-yl)-8-azabicyclo[3.2.1]octan-3-yl)carbamate

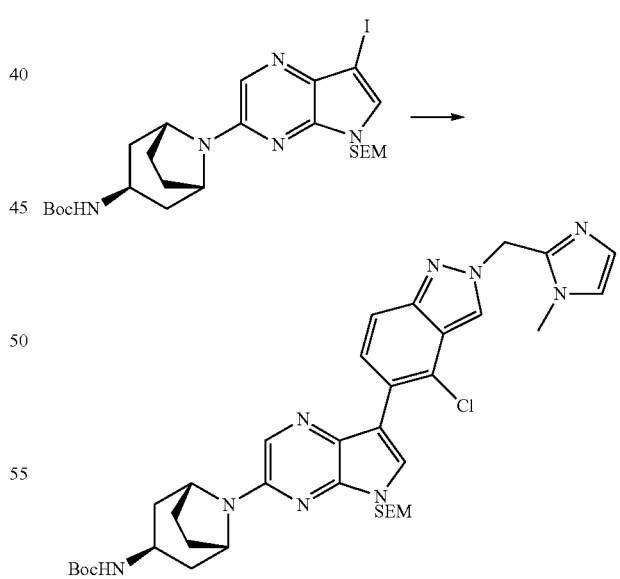

Prepared as general procedure 2, except using 4-chloro-2-((1-methyl-1H-imidazol-2-yl)methyl)-5-(4,4,5,5-tetramethyl-1,3,2-dioxaborolan-2-yl)-2H-indazole (426 mg, 1.14 mmol) in 1,4-dioxane (12 mL). The crude product was purified by column chromatography on silica gel (gradient elution, 0-100%, EtOAc/iso-hexanes), to give the title compound (413 mg). MS: [M+H]+=718.

Preparation 148: 5-((5-Bromo-4-chloro-2H-indazol-2-yl)methyl)-3-methyl-1,2,4-oxadiazole

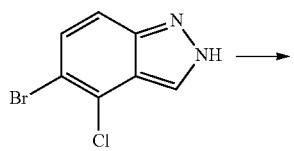

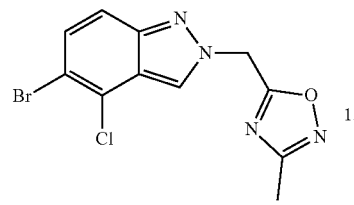

Prepared using the same alkylation procedure as preparation 145 using 5-(chloromethyl)-3-methyl-1,2,4-oxadiazole (5 g, 37.7 mmol), to give the title compound (3 g). MS: [M+H]⁺=327.

Preparation 149: 5-((4-Chloro-5-(4,4,5,5-tetramethyl-1,3,2-dioxaborolan-2-yl)-2H-indazol-2-yl)methyl)-3-methyl-1,2,4-oxadiazole

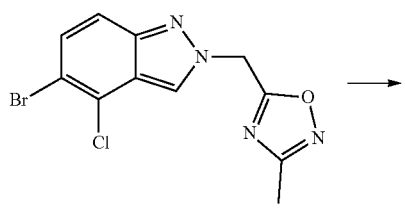

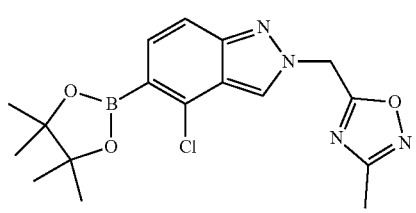

Prepared as preparation 43 using 5-((5-bromo-4-chloro-2H-indazol-2-yl)methyl)-3-methyl-1,2,4-oxadiazole (3 g, 9.16 mmol). The crude product was purified by column chromatography on silica gel (gradient elution, 0-100%, ted-butyl methyl ether/iso-hexanes) to give 3 g of an orange oil. The oil was dissolved in tert-butyl methyl ether (50 mL) then extracted with 1 M aq. NaOH (30 mL, then 10 mL). The aqueous layer was treated with NH₄Cl (2.0 g, 37.4 mmol) then extracted with DCM (3×30 mL). The combined organic phases were concentrated under reduced pressure to yield the title compound (1.4 g). MS: [M+H]⁺=375.

Preparation 150: tert-Butyl N-(endo-8-(7-(4-chloro-2-((3-methyl-1,2,4-oxadiazol-5-yl)methyl)-2H-indazol-5-yl)-5-((2-(trimethylsilyl)ethoxy)methyl)-5H-pyrrolo[2,3-b]pyrazin-3-yl)-8-azabicyclo[3.2.1]octan-3-yl)carbamate

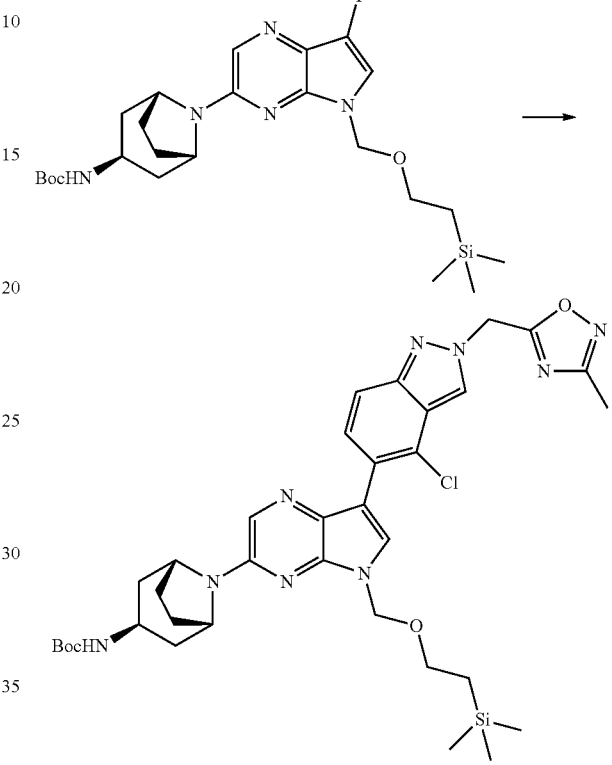

Prepared as general procedure 2, except using 5-((4-chloro-5-(4,4,5,5-tetramethyl-1,3,2-dioxaborolan-2-yl)-2H-indazol-2-yl)methyl)-3-methyl-1,2,4-oxadiazole (660 mg, 1.67 mmol), in 1,4-dioxane (12 mL). The crude product was purified by column chromatography on silica gel (gradient elution, 15-75% tert-butyl methyl ether/iso-hexanes), to give the title compound (460 mg). MS: [M+H]⁺=720.

Preparation 151: 5-Bromo-4-chloro-2-((1-methyl-1H-pyrazol-3-yl)methyl)-2H-indazole

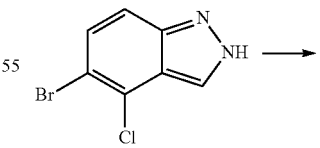

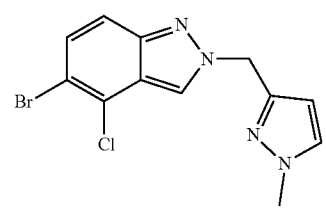

Prepared using the same alkylation procedure as preparation 145 using 3-(chloromethyl)-1-methyl-1H-pyrazole (4.95 g, 37.9 mmol). The crude product was purified by column chromatography on silica gel (gradient elution, 20-100%, EtOAc/iso-hexanes), to give the title compound (2.46 g). MS: [M+H]$^+$=325.

Preparation 152: 4-Chloro-2-((1-methyl-1H-pyrazol-3-yl)methyl)-5-(4,4,5,5-tetramethyl-1,3,2-dioxaborolan-2-yl)-2H-indazole

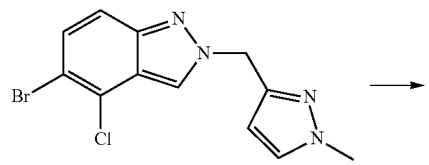

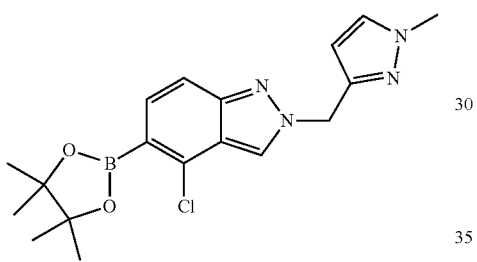

Prepared as preparation 43 using 5-bromo-4-chloro-2-((1-methyl-1H-pyrazol-3-yl)methyl)-2H-indazole (2.44 g, 7.49 mmol). The crude product was purified by column chromatography on silica gel (gradient elution, 0-5%, MeOH/DCM), to give the title compound (2.71 g). $^1$H NMR (500 MHz, DMSO-d$_6$): 8.53 (1H, s), 7.63 (1H, d), 7.52 (1H, d), 7.43 (1H, d), 6.25 (1H, d), 5.59 (2H, s), 3.80 (3H, s), 1.31 (12H, s).

Preparation 153: tert-Butyl N-(endo-8-(7-(4-chloro-2-((1-methyl-1H-pyrazol-3-yl)methyl)-2H-indazol-5-yl)-5-((2-(trimethylsilyl)ethoxy)methyl)-5H-pyrrolo[2,3-b]pyrazin-3-yl)-8-azabicyclo[3.2.1]octan-3-yl)carbamate

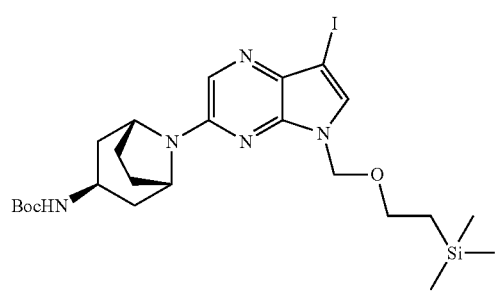

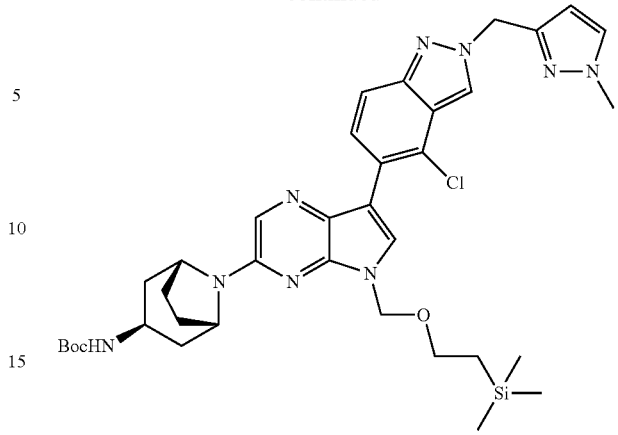

Prepared as general procedure 2, except using 4-chloro-2-((1-methyl-1H-pyrazol-3-yl)methyl)-5-(4,4,5,5-tetramethyl-1,3,2-dioxaborolan-2-yl)-2H-indazole (435 mg, 1.17 mmol) in 1,4-dioxane (12 mL). The crude product was purified by column chromatography on silica gel twice (20-100% EtOAc/iso-hexanes, then 0-3% MeOH/DCM), to give the title compound (205 mg). MS: [M+H]$^+$=718.

Preparation 154: 6-Bromo-5-chloro-2-methylisoquinolin-2-ium iodide

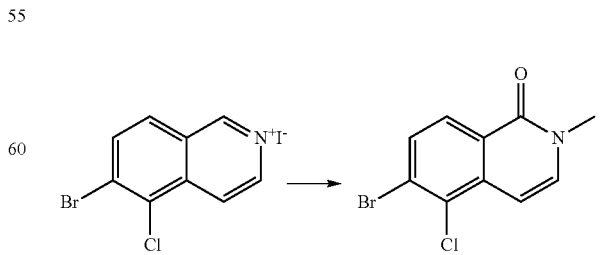

To a solution of 6-bromo-5-chloroisoquinoline (5.3 g, 21.86 mmol) in THF (50 mL) was added iodomethane (1.429 mL, 22.95 mmol). The solution was stirred at RT for 18 h. The precipitate was collected by filtration, washed with THF (50 mL) and the solid was dried in vacuo. The filtrate was stirred for a further 6 h. Iodomethane (1 mL) was added and the reaction was left to stir over the weekend. The precipitate was collected by filtration, washing with THF (40 mL) before combining with the previous batch and drying in vacuo, to give the title compound (4.95 g). $^1$H NMR (500 MHz, DMSO-d$_6$): 10.10 (1H, s), 8.85 (1H, dd), 8.70 (1H, d), 8.41 (1H, ddd), 8.38 (1H, dd), 4.48 (3H, s).

Preparation 155: 6-Bromo-5-chloro-2-methyl-1,2-dihydroisoquinolin-1-one

A mixture of 6-bromo-5-chloro-2-methylisoquinolin-2-ium iodide (4.7 g, 12.23 mmol), cesium carbonate (5.98 g, 18.34 mmol) and Eosin Y (0.423 g, 0.611 mmol) in DMF (300 mL) was stirred under air and irradiated with a 400 W lamp for 10 h. Excess DMF was removed under reduced pressure before addition of water (400 mL) and extraction with EtOAc (3×210 mL). The organic extracts were dried (MgSO$_4$) and concentrated. The residue was purified by column chromatography on silica gel (gradient elution, 0-50%, EtOAc/iso-hexanes), to give the title compound (740 mg). MS: [M+H]$^+$=272.

Preparation 156: 5-Chloro-2-methyl-6-(4,4,5,5-tetramethyl-1,3,2-dioxaborolan-2-yl)-1,2-dihydroisoquinolin-1-one

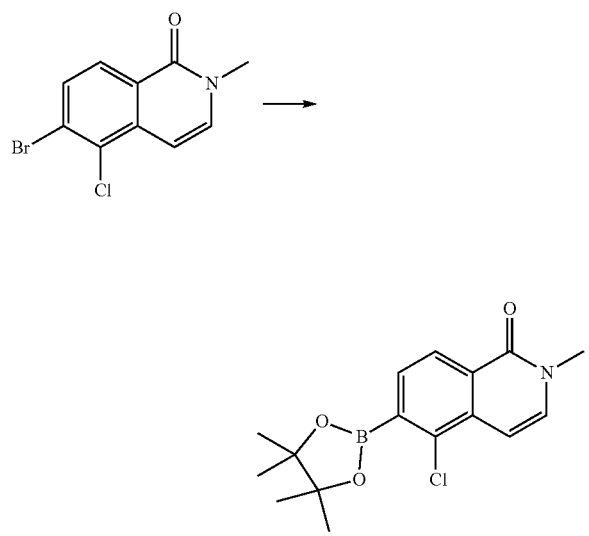

Prepared as preparation 43 using 6-bromo-5-chloro-2-methyl-1,2-dihydroisoquinolin-1-one (1.01 g, 3.71 mmol). The crude product was purified by column chromatography on silica gel (gradient elution, 0-1%, MeOH/DCM), to give the title compound (501 mg). $^1$H NMR (500 MHz, DMSO-d$_6$): 8.18 (1H, d), 7.64 (2H, dd), 6.80 (1H, d), 3.52 (3H, s), 1.34 (12H, s).

Preparation 157: tert-Butyl ((3R,4S)-1-(7-(5-chloro-2-methyl-1-oxo-1,2-dihydroisoquinolin-6-yl)-5-((2-(trimethylsilyl)ethoxy)methyl)-5H-pyrrolo[2,3-b]pyrazin-3-yl)-3-fluoropiperidin-4-yl)carbamate

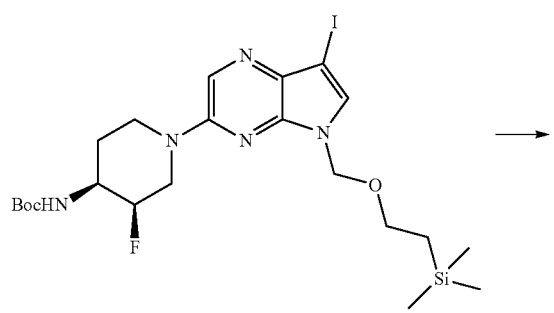

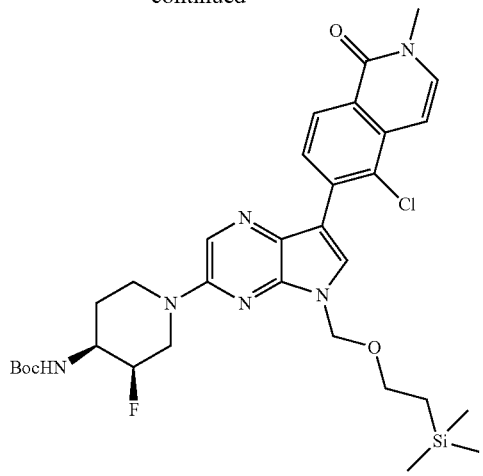

Prepared as general procedure 2, except using 5-chloro-2-methyl-6-(4,4,5,5-tetramethyl-1,3,2-dioxaborolan-2-yl)-1,2-dihydroisoquinolin-1-one (400 mg, 1.16 mmol), tert-butyl N-((3R,4S)-3-fluoro-1-(7-iodo-5-((2-(trimethylsilyl)ethoxy)methyl)-5H-pyrrolo[2,3-b]pyrazin-3-yl)piperidin-4-yl)carbamate (0.575 g, 0.967 mmol) and potassium phosphate, tribasic (741 mg, 3.49 mmol) in 1,4-dioxane (14 mL). The crude product was purified by column chromatography on silica gel twice (0-80% EtOAc/iso-hexanes, then 0-80% EtOAc/iso-hexanes), to give the title compound (509 mg). MS: [M+H]$^+$=657.

Preparation 158: Methyl 4-bromo-2-(bromomethyl)-3-chlorobenzoate

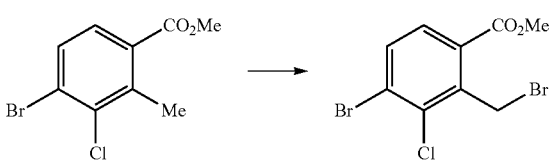 [SMILES: COC(=O)c1ccc(Br)c(Cl)c1C ; COC(=O)c1ccc(Br)c(Cl)c1CBr]

1-bromopyrrolidine-2,5-dione (0.34 g, 1.90 mmol) and (E)-2,2'-(diazene-1,2-diyl)bis(2-methylpropanenitrile) (0.023 g, 0.142 mmol) were added to a solution of methyl 4-bromo-3-chloro-2-methylbenzoate (0.25 g, 0.949 mmol) in chloroform (5 mL, 0.949 mmol), and the mixture was heated to reflux for 2.5 h, then concentrated onto silica. The crude product was purified by column chromatography on silica gel (gradient elution, 0-15%, EtOAc in iso-hexanes), to give the title compound (0.308 g). $^1$H NMR (400 MHz, CDCl$_3$): 7.75 (1H, d), 7.70 (1H, d), 5.19 (2H, s), 3.98 (3H, s).

Preparation 159: 5-Bromo-4-chloro-2-methyl-2,3-dihydro-1H-isoindol-1-one

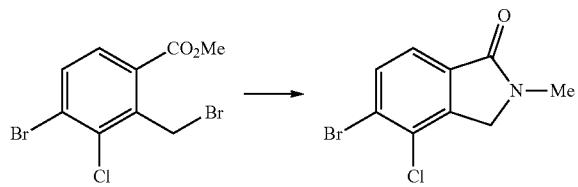 [SMILES: COC(=O)c1ccc(Br)c(Cl)c1CBr ; CN1Cc2c(ccc(Br)c2Cl)C1=O]

Methyl 4-bromo-2-(bromomethyl)-3-chlorobenzoate (0.30 g, 0.88 mmol) was suspended in methylamine (33 wt % in EtOH, 1.96 mL, 15.77 mmol) and stirred at RT for 30 min. THF (2 mL) was added, and the suspension was heated to 50° C. for 16 h. The mixture was cooled to RT, diluted with 1 M aq. HCl (20 mL) and extracted with EtOAc (3×50 mL). The combined organic phases were passed through a phase separator and concentrated, to give the title compound (0.220 g). MS: [M+H]$^+$, 260.

Preparation 160: 4-Chloro-2-methyl-5-(4,4,5,5-tetramethyl-1,3,2-dioxaborolan-2-yl)-2,3-dihydro-1H-isoindol-1-one

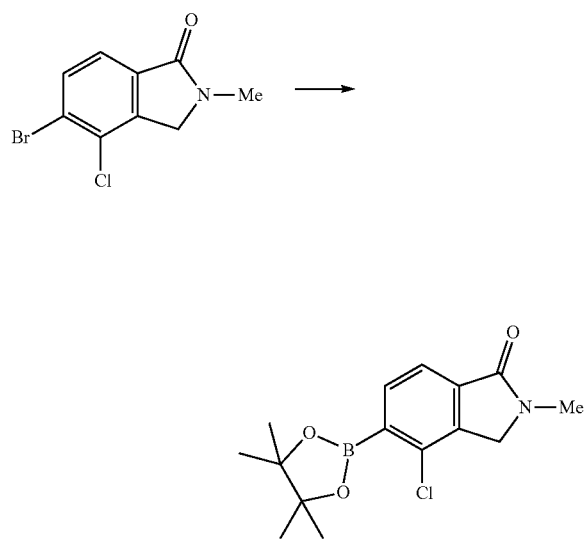

A mixture of 5-bromo-4-chloro-2-methyl-2,3-dihydro-1H-isoindol-1-one (1.0 g, 3.84 mmol), bis(pinacolato)diboron (2.92 g, 11.52 mmol), potassium acetate (1.130 g, 11.52 mmol) and [1,1'-bis(diphenylphosphino)ferrocene]dichloropalladium(II) complex with dichloromethane (0.313 g, 0.38 mmol) in 1,4-dioxane (15 mL) was degassed under a flow of N$_2$ then heated to 100° C. for 18 h, cooled to RT, concentrated and diluted with EtOAc (50 mL). After sonication, the mixture was filtered and concentrated onto silica. The residue was purified by column chromatography on silica gel (gradient elution, 1-4%, MeOH/DCM) to give the title compound (1.02 g). $^1$H NMR (400 MHz, CDCl$_3$): 7.85 (1H, d), 7.74 (1H, d), 4.39 (2H, s), 3.25 (3H, s), 1.41 (12H, s).

Preparation 161: tert-Butyl N-((3R,4S)-1-(7-(4-chloro-2-methyl-1-oxo-2,3-dihydro-1H-isoindol-5-yl)-5-((2-(trimethylsilyl)ethoxy)methyl)-5H-pyrrolo[2,3-b]pyrazin-3-yl)-3-fluoropiperidin-4-yl)carbamate

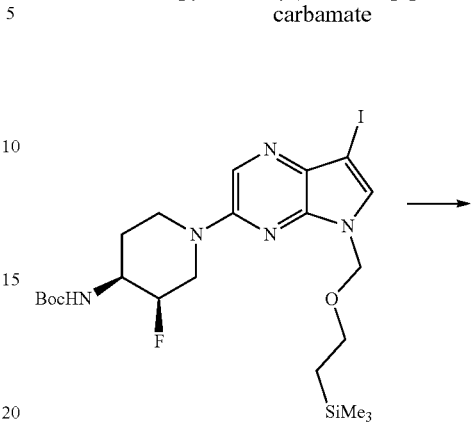

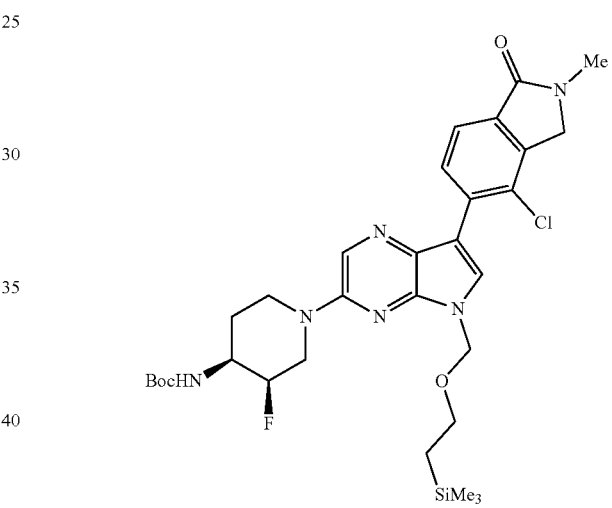

A mixture of tert-butyl N-((3R,4S)-3-fluoro-1-(7-iodo-5-((2-(trimethylsilyl)ethoxy)methyl)-5H-pyrrolo[2,3-b]pyrazin-3-yl)piperidin-4-yl)carbamate (0.5 g, 0.84 mmol), 4-chloro-2-methyl-5-(4,4,5,5-tetramethyl-1,3,2-dioxaborolan-2-yl)-2,3-dihydro-1H-isoindol-1-one (0.42 g, 1.01 mmol), potassium phosphate, tribasic (0.59 g, 2.54 mmol) and [1,1'-bis(diphenylphosphino)ferrocene]dichloropalladium(II) complex with dichloromethane (0.069 g, 0.085 mmol) in 1,4-dioxane (10 mL) and water (2.5 mL) was degassed under a flow of N$_2$ then heated to 70° C. for 1 h, cooled to RT, diluted with DCM (10 mL), passed through a phase separator and concentrated onto silica. The residue was purified by column chromatography on silica gel (gradient elution, 20-100% EtOAc/iso-hexanes), to give the title compound (0.339 g). $^1$H NMR (400 MHz, CDCl$_3$): 8.25-8.19 (2H, m), 7.86-7.84 (2H, m), 5.63 (2H, s), 4.94-4.82 (2H, m), 4.52 (1H, d), 4.45 (2H, s), 3.97-3.90 (1H, m), 3.64 (2H, t), 3.26 (3H, s), 3.23-3.14 (1H, m), 3.10-3.05 (2H, m), 1.99-1.95 (2H, m), 1.49 (9H, s), 0.97 (2H, t), −0.02 (9H, s).

Preparation 162: 6-Bromo-7-chloro-1-methyl-1H-1,3-benzodiazole

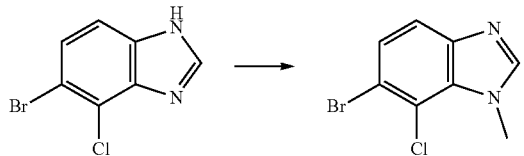

To a solution of 5-bromo-4-chloro-1H-1,3-benzodiazole (5 g, 21.60 mmol) in DMF (50.2 mL, 648 mmol) at 0° C. was added NaH (60 wt % in mineral oil, 1.123 g, 28.1 mmol). The reaction mixture was warmed to RT over 30 min then iodomethane (1.486 mL, 23.76 mmol) was added. The reaction mixture was stirred at RT for 3 h, before addition of sat. aq. NH$_4$Cl (200 mL) and extraction with DCM (3×50 mL). The combined organic phase was washed with sat. aq. NH$_4$Cl (100 mL), water (100 mL), and 1M aq. LiCl (100 mL) then dried (MgSO$_4$) and concentrated. The residue was purified by column chromatography on NH silica gel (gradient elution, 0-30%, EtOAc/iso-hexanes), to give the title compound (746 mg). MS: [M+H]$^+$=245.

Preparation 163: 7-Chloro-1-methyl-6-(4,4,5,5-tetramethyl-1,3,2-dioxaborolan-2-yl)-1H-1,3-benzodiazole

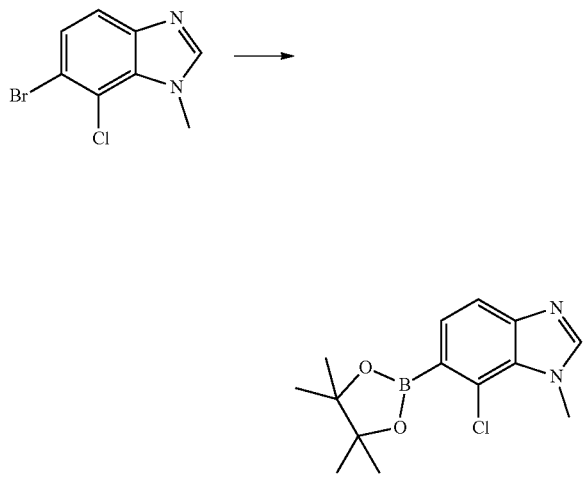

Prepared as preparation 43 using 6-bromo-7-chloro-1-methyl-1H-1,3-benzodiazole (444 mg, 1.81 mmol). The crude product was purified by column chromatography on silica gel (gradient elution, 0-2%, MeOH/DCM), to give the title compound (268 mg). MS: [M+H]$^+$=293.

Preparation 164: tert-Butyl N-((3R,4S)-1-(7-(7-chloro-1-methyl-1H-1,3-benzodiazol-6-yl)-5-((2-(trimethylsilyl)ethoxy)methyl)-5H-pyrrolo[2,3-b]pyrazin-3-yl)-3-fluoropiperidin-4-yl)carbamate

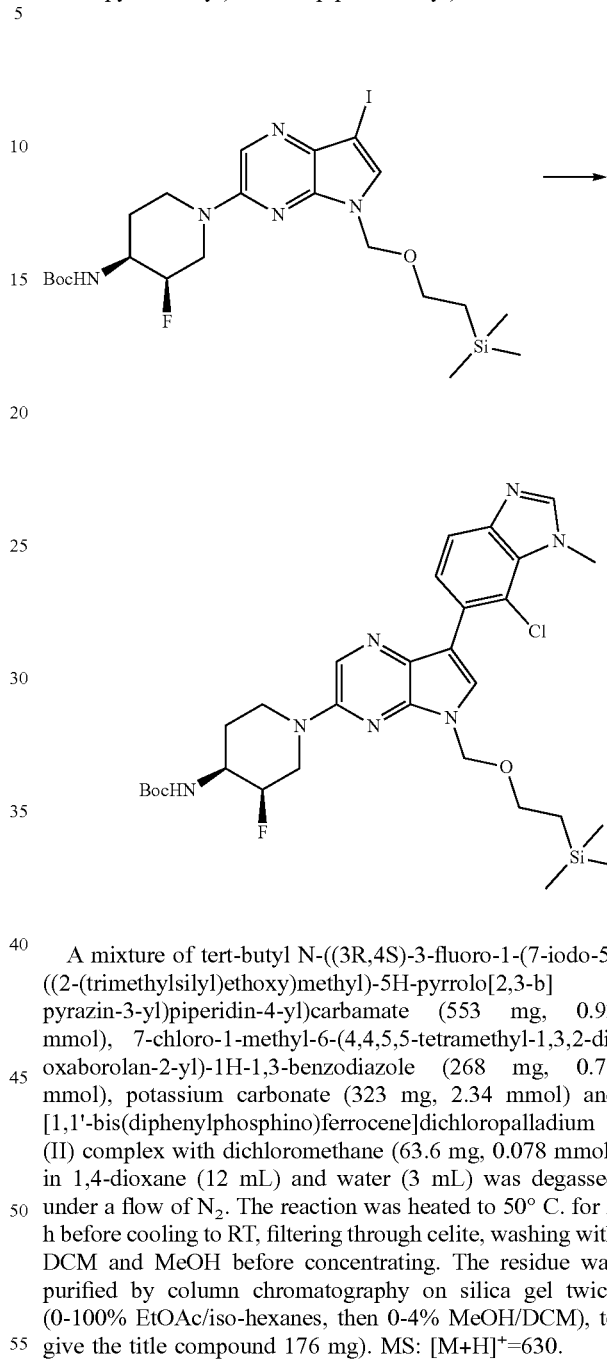

A mixture of tert-butyl N-((3R,4S)-3-fluoro-1-(7-iodo-5-((2-(trimethylsilyl)ethoxy)methyl)-5H-pyrrolo[2,3-b]pyrazin-3-yl)piperidin-4-yl)carbamate (553 mg, 0.93 mmol), 7-chloro-1-methyl-6-(4,4,5,5-tetramethyl-1,3,2-dioxaborolan-2-yl)-1H-1,3-benzodiazole (268 mg, 0.78 mmol), potassium carbonate (323 mg, 2.34 mmol) and [1,1'-bis(diphenylphosphino)ferrocene]dichloropalladium (II) complex with dichloromethane (63.6 mg, 0.078 mmol) in 1,4-dioxane (12 mL) and water (3 mL) was degassed under a flow of N$_2$. The reaction was heated to 50° C. for 2 h before cooling to RT, filtering through celite, washing with DCM and MeOH before concentrating. The residue was purified by column chromatography on silica gel twice (0-100% EtOAc/iso-hexanes, then 0-4% MeOH/DCM), to give the title compound 176 mg). MS: [M+H]$^+$=630.

Preparation 165: 3-Chloro-5-{[2-(trimethylsilyl)ethoxy]methyl}-5H-pyrrolo[2,3-b]pyrazine

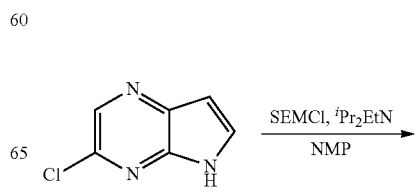

-continued

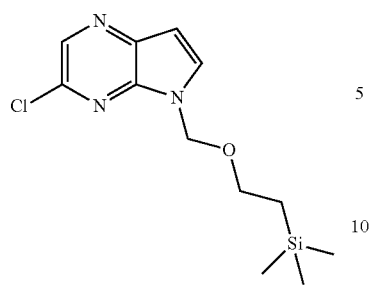

A solution of 3-chloro-5H-pyrrolo[2,3-b]pyrazine (20 g, 131 mmol) and DIPEA (37 mL, 212 mmol) in NMP (100 mL) was stirred with cooling provided by a salt/ice-bath. 2-(Trimethylsilyl)ethoxymethyl chloride (28.3 mL, 160 mmol) in NMP (40 mL) was added over a period of 5-10 min. The cooling bath was removed, and the mixture stirred overnight at RT. A 5% aq. LiCl solution (100 mL) was added. EtOAc (400 mL) was added and the mixture transferred to a 2 L separating funnel. The aqueous layer was removed and the EtOAc layer was washed with further 5% aq. LiCl solution (3×100 mL). The EtOAc layer was then washed successively with 0.5 M aq. KHSO$_4$ (2×100 mL), sat. aq. Na$_2$CO$_3$ (50 mL), 5% aq. LiCl (50 mL) and sat. brine solution (100 mL). The EtOAc layer was dried (MgSO$_4$), filtered and evaporated, to give a dark oil. The residue was purified by column chromatography on silica gel (gradient elution, 0-50%, EtOAc/petrol), to give the title compound (31.8 g), MS: [M+H]$^+$=284.

Preparation 166: 5-{[2-(Trimethylsilyl)ethoxy]methyl}-5H-pyrrolo[2,3-b]pyrazin-3-amine

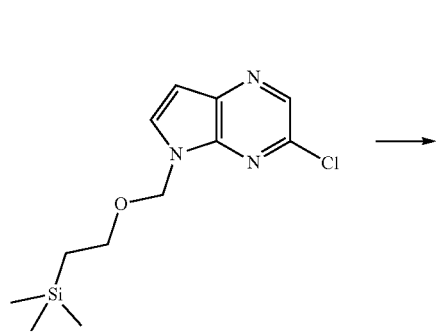

-continued

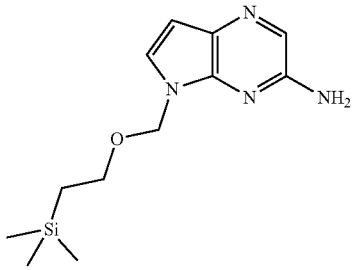

A suspension of 3-chloro-5-{[2-(trimethylsilyl)ethoxy]methyl}-5H-pyrrolo[2,3-b]pyrazine (20.0 g, 70.5 mmol), benzophenone imine (13.6 mL, 81.0 mmol), [(4,5-bis(diphenylphosphino)-9,9-dimethylxanthene)-2-(2'-amino-1,1'-biphenyl)]palladium(II) methanesulfonate (2.67 g, 2.82 mmol) and NaOtBu (10.2 g, 106 mmol) in 1,4-dioxane (140 mL) was evacuated and N$_2$ back-filled (3×) before heating to 100° C. for 3 h. After cooling, 2M aq. HCl (50 mL) was added and the reaction stirred at rt for 30 min. The reaction was diluted with EtOAc and basified with 2M aq. NaOH to pH 10. The separated aq. layer was extracted with EtOAc (2×) and combined organics washed with brine, dried (MgSO$_4$) and evaporated. The residue was purified by column chromatography on silica gel (gradient elution, 20-50%, EtOAc/petrol), to give the title compound (15.5 g), MS: [M+H]$^+$=265.

Preparation 167: 3-Fluoro-5-{[2-(trimethylsilyl)ethoxy]methyl}-5H-pyrrolo[2,3-b]pyrazine

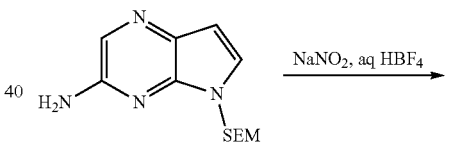

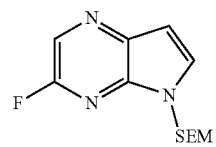

To a stirred mixture of 5-{[2-(trimethylsilyl)ethoxy]methyl}-5H-pyrrolo[2,3-b]pyrazin-3-amine (2.28 g, 8.6 mmol) in 48% aq. HBF$_4$ (11.4 mL) and THF (11.4 mL) at 0° C. was added a solution of NaNO$_2$ (0.655 g, 9.5 mmol, in 2.3 mL water) dropwise over 30 min. After 10 min, the cold mixture was added to a mixture of sat. aq. NaHCO$_3$, sat. aq. Na$_2$SO$_3$ solution and EtOAc. The phases were separated and the EtOAc layer was concentrated. The crude material was dissolved in 10% tert-butyl methyl ether/petrol, passed through a phase separator and purified by column chromatography on silica gel (gradient elution, 10-35%, tert-butyl methyl ether/petrol), to give the title compound (1.16 g), MS: [M+H]$^+$=268.

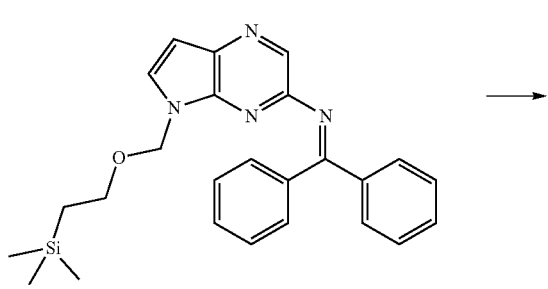

Preparation 168: 3-Fluoro-7-iodo-5-{[2-(trimethylsilyl)ethoxy]methyl}-5H-pyrrolo[2,3-b]pyrazine

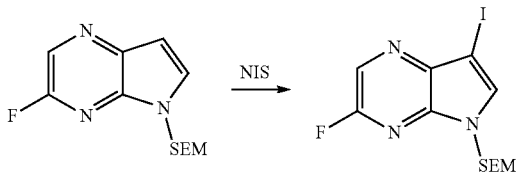

To a stirred solution of 3-fluoro-5-{[2-(trimethylsilyl)ethoxy]methyl}-5H-pyrrolo[2,3-b]pyrazine (1.28 g, 4.79 mmol) in DMF (8.6 mL) at RT was added N-iodosuccinimide (1.51 g, 6.7 mmol) and the mixture stirred for 1.5 h. The mixture was poured into a mixture of sat. aq. Na$_2$S$_2$O$_3$ solution and ice water. The resulting solid was collected by filtration and washed with water (3×) and then dried under vacuum, to give the title compound (1.88 g), MS: [M+H]$^+$=394.

Preparation 169: 3-Fluoro-7-iodo-5H-pyrrolo[2,3-b]pyrazine

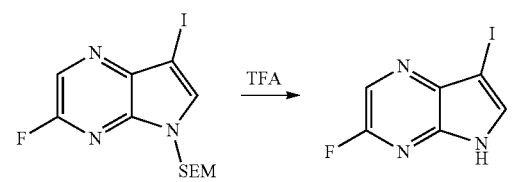 [SMILES: C[Si](C)(C)CCOCn1cc(I)c2ncc(F)nc21 ; Fc1cnc2c(I)c[nH]c2n1 ; "TFA"]

A solution of 3-fluoro-7-iodo-5-{[2-(trimethylsilyl)ethoxy]methyl}-5H-pyrrolo[2,3-b]pyrazine (1.43 g, 3.63 mmol) in DCM (15 mL) and TFA (10 mL) was stirred at RT for 24 h. The mixture was evaporated. The residue was dissolved in MeOH/aq. NH$_3$ and stirred for 1 h. The MeOH was evaporated and the resulting solid was collected by filtration. The solid was washed with water and dried, to give the title compound (0.848 g), MS: [M+H]$^+$=264.

Preparation 170: 3-Fluoro-7-iodo-N,N-dimethyl-5H-pyrrolo[2,3-b]pyrazine-5-sulfonamide

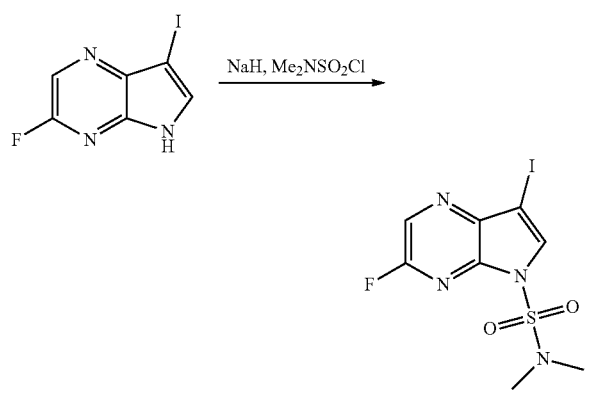

3-Fluoro-7-iodo-5H-pyrrolo[2,3-b]pyrazine (0.848 g, 3.22 mmol) was dissolved in THF/DMF (1:1, 10 mL) and cooled in an ice bath. NaH (60% in mineral oil) (0.17 g, 4.19 mmol) was added and the mixture stirred at RT for 1 h. After re-cooling to 0° C., N,N-dimethylsulfamoyl chloride (0.45 mL, 4.19 mmol) was added and the mixture allowed to warm to RT and stirred overnight. Sat. aq. NH$_4$Cl was added and the mixture extracted with EtOAc. The EtOAc layer was dried (MgSO$_4$) and then evaporated. The residue was purified by column chromatography on silica gel (gradient elution, 0-60%, EtOAc/petrol), to give the title compound (0.72 g), MS: [M+H]$^+$=371.

Preparation 171: rac-tert-Butyl (1R,2S,5S)-2-fluoro-3-oxo-8-azabicyclo[3.2.1]octane-8-carboxylate and rac-tert-butyl (1R,2R,5S)-2-fluoro-3-oxo-8-azabicyclo[3.2.1]octane-8-carboxylate (Unseparated Mixture)

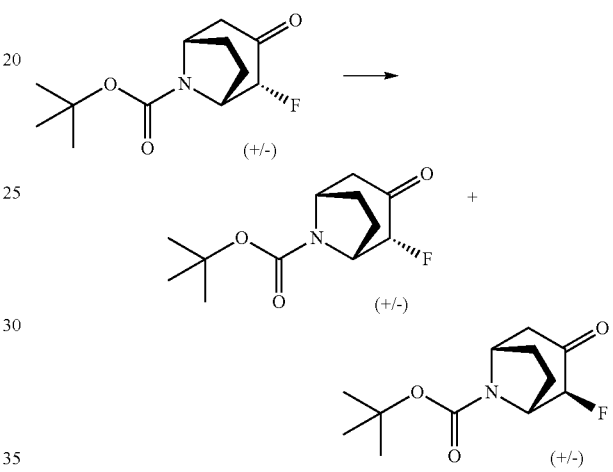

A solution of rac-tert-butyl (1R,2R,5S)-2-fluoro-3-oxo-8-azabicyclo[3.2.1]octane-8-carboxylate (50 g, 195 mmol) in THF (200 mL) was added dropwise to a suspension of NaOtBu (20 g, 208 mmol) in THF (200 mL) then stirred at RT for 2 h. The mixture was quenched with a solution of NH$_4$Cl (20 g, 374 mmol) in water (200 mL) then diluted with saturated brine (800 mL). The mixture was extracted with EtOAc (3×500 mL). The combined organic phases were concentrated under reduced pressure, to give the crude product as a pale yellow oil. The residue was purified by column chromatography on silica gel (gradient elution, 0-10%, acetone/isohexane), to give a 1:1 mixture of the title compounds (32.2 g). Isomer 1: $^1$H NMR (500 MHz, DMSO-d$_6$): 4.69-4.28 (m, 3H), 2.92-2.80 (m, 1H), 2.41-2.31 (m, 1H), 2.16-1.97 (m, 1H), 1.97-1.84 (m, 1H), 1.60-1.31 (m, 11H); Isomer 2: $^1$H NMR (500 MHz, DMSO-d$_6$): 5.05 (dd, J=47.7, 5.0 Hz, 1H), 4.69-4.28 (m, 2H), 2.79-2.68 (m, 1H), 2.42-2.28 (m, 1H), 2.17-1.82 (m, 2H), 1.72-1.25 (m, 11H).

Preparation 172: rac-tert-Butyl (1S,2S,3S,5R)-3-(benzylamino)-2-fluoro-8-azabicyclo[3.2.1]octane-8-carboxylate

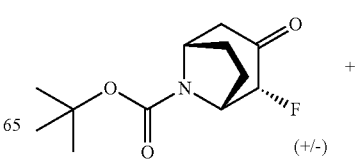

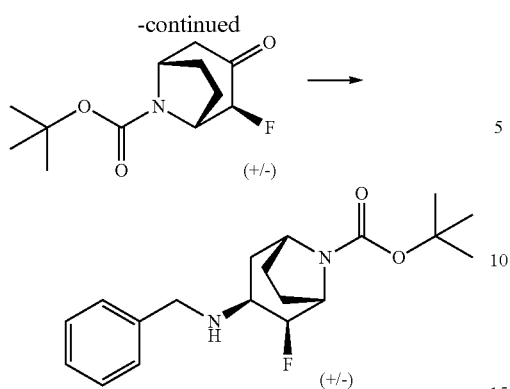

NaBH(OAc)₃ (65 g, 307 mmol) was added to a solution of a rac-tert-butyl (1R,2S,5S)-2-fluoro-3-oxo-8-azabicyclo[3.2.1]octane-8-carboxylate and rac-tert-butyl (1R,2R,5S)-2-fluoro-3-oxo-8-azabicyclo[3.2.1]octane-8-carboxylate (1:1 mixture prepared using the method of Preparation 171, 49.7 g, 184 mmol), benzylamine (24 mL, 216 mmol) and acetic acid (12 mL, 210 mmol) in DCM (500 mL) then stirred at RT for 18 h. A solution of NaHCO₃ (100 g, 1190 mmol) in water (750 mL) was added then the mixture was extracted with DCM (3×500 mL). The combined organic phases were then concentrated under reduced pressure. The residue was purified by column chromatography on silica gel (gradient elution, 0-20%, EtOAc/isohexane), to give the title compound (24.5 g). $^1$H NMR (500 MHz, DMSO-d₆): 7.42-7.28 (m, 4H), 7.29-7.18 (m, 1H), 4.68 (dt, 1H), 4.16-4.04 (m, 1H), 4.05-3.94 (m, 1H), 3.82 (dd, 1H), 3.63 (dd, 1H), 3.29-3.20 (m, 1H), 2.44-2.31 (m, 1H), 2.21-2.04 (m, 2H), 1.97-1.87 (m, 1H), 1.89-1.61 (m, 3H), 1.39 (s, 9H).

Preparation 173: rac-tert-Butyl (1S,2S,3S,5R)-3-amino-2-fluoro-8-azabicyclo[3.2.1]octane-8-carboxylate

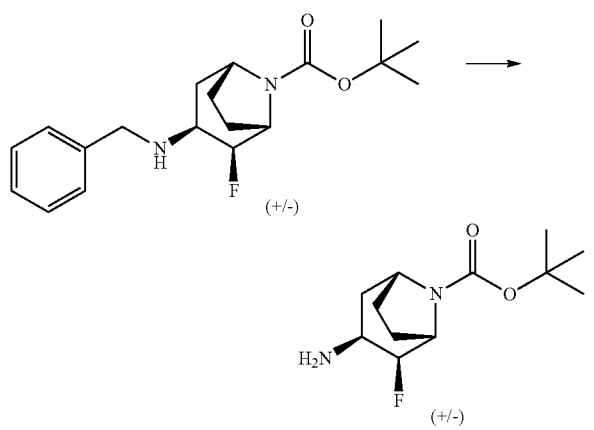

rac-tert-Butyl (1S,2S,3S,5R)-3-(benzylamino)-2-fluoro-8-azabicyclo[3.2.1]octane-8-carboxylate (27.8 g, 79 mmol) and 10% Pd/C (JM Type 39, 57.3% moisture) (6 g, 2.407 mmol) were dissolved in acetic acid/ethanol (1:3, 260 mL) and stirred under hydrogen at 1 bar for 18 h. The catalyst was removed by filtration and the filtrate was concentrated under reduced pressure. The residue was treated with sat. aq. NaHCO₃ solution (500 mL) then extracted with chloroform/IPA (9:1, 3×200 mL). The combined organic phases were concentrated under reduced pressure, to give the title compound (19.6 g). $^1$H NMR (500 MHz, DMSO-d₆): 4.53 (dt, 1H), 4.13-4.03 (m, 1H), 4.03-3.91 (m, 1H), 3.64-3.53 (m, 1H), 2.50-2.40 (m, 1H), 2.22-2.05 (m, 1H), 1.97-1.49 (m, 6H), 1.39 (d, 9H).

Preparation 174: rac-tert-Butyl (1S,2S,3S,5R)-3-{[(benzyloxy)carbonyl]amino}-2-fluoro-8-azabicyclo[3.2.1]octane-8-carboxylate

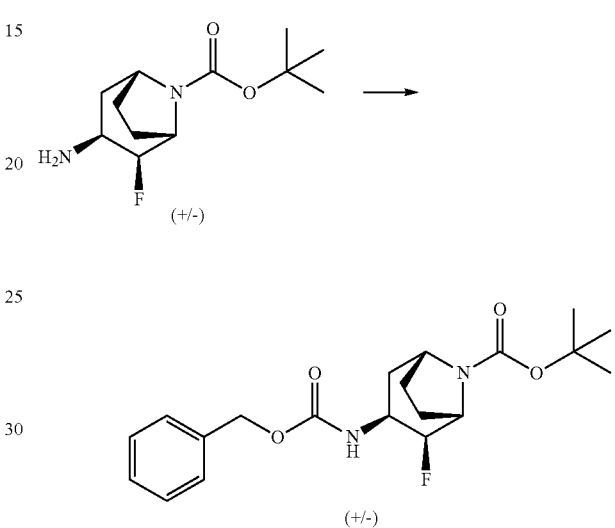

Benzyl chloroformate (12 mL, 84 mmol) was added to an ice bath-cooled solution of rac-tert-butyl (1S,2S,3S,5R)-3-amino-2-fluoro-8-azabicyclo[3.2.1]octane-8-carboxylate (19.6 g, 76 mmol) and DIPEA (30 ml, 172 mmol) in DCM (150 mL) and THF (50 mL) then stirred at RT for 18 h. Water (300 mL) was added then the mixture was extracted with DCM (3×300 mL) and combined organic phases were concentrated under reduced pressure. The residue was purified by column chromatography on silica gel (gradient elution, 0-25%, acetone/isohexane), to give the title compound (28.4 g). $^1$H NMR (500 MHz, DMSO-d₆) δ 7.41-7.35 (m, 4H), 7.35-7.28 (m, 1H), 7.14-6.93 (m, 1H), 5.23-4.89 (m, 2H), 4.85-4.65 (m, 1H), 4.22-4.07 (m, 2H), 4.07-3.97 (m, 1H), 2.29-2.17 (m, 1H), 2.08-2.02 (m, 1H), 1.99-1.79 (m, 2H), 1.80-1.64 (m, 2H), 1.40 (s, 9H).

Preparation 175: rac-Benzyl N-[(1S,2R,3S,5R)-2-fluoro-8-azabicyclo[3.2.1]octan-3-yl]carbamate hydrochloride

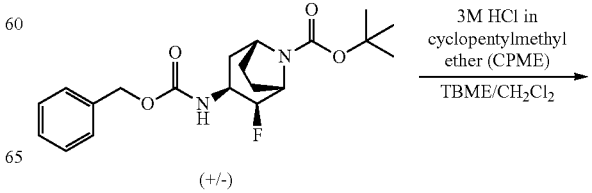

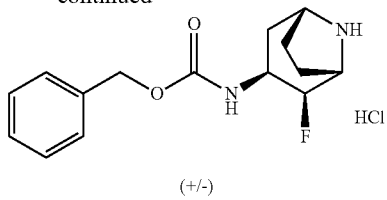

(+/-)

rac-tert-Butyl (1S,2S,3S,5R)-3-{[(benzyloxy)carbonyl]amino}-2-fluoro-8-azabicyclo[3.2.1]octane-8-carboxylate (28.4 g, 71.3 mmol) was dissolved in DCM (100 mL) then added dropwise to a stirred mixture of HCl (3M in cyclopentyl methyl ether, 200 mL, 600 mmol) and DCM (100 mL). The mixture was stirred at RT for 3 h then diluted with tert-butyl methyl ether (500 mL) added dropwise. Acetonitrile (50 mL) was added and the mixture was stirred vigorously for 1 h. The resulting solid was collected by filtration and washed with tert-butyl methyl ether (50 mL) followed by isohexane (50 mL), to give the title compound (21.9 g). $^1$H NMR (500 MHz, DMSO-$d_6$): 10.08-9.28 (m, 2H), 7.46-7.14 (m, 6H), 5.21-5.00 (m, 3H), 4.27-4.15 (m, 1H), 4.13-4.04 (m, 1H), 3.96-3.88 (m, 1H), 2.42 (ddd, 1H), 2.36-2.26 (m, 1H), 2.16 (ddd, 1H), 2.04-1.90 (m, 2H), 1.89-1.78 (m, 1H).

Preparation 176: Benzyl N-[(1S,2R,3S,5R)-2-fluoro-8-azabicyclo[3.2.1]octan-3-yl]carbamate hydrochloride (Fast Eluting Isomer)

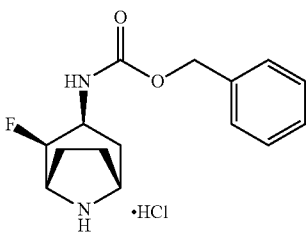 [SMILES: O=C(N[C@H]1C[C@H]2CC[C@H](N2)[C@H]1F)OCc1ccccc1 ; Cl]

rac-Benzyl N-[(1S,2R,3S,5R)-2-fluoro-8-azabicyclo[3.2.1]octan-3-yl]carbamate hydrochloride (21.9 g) was dissolved in methanol (50 mg/mL) then purified by chiral preparative supercritical fluid chromatography (Lux A1 (4.6 mm×250 mm, 5 um); 40° C., Flow Rate 50 mL/min, BPR 125 BarG, Detection at 210 nm, Injection Volume 1000 uL (50 mg), 50:50 MeOH:CO2 (0.7% v/v DEA)). Pure fractions were combined then evaporated. The residue was then dissolved in DCM (5 mL) then added dropwise to a stirred mixture of tert-butyl methyl ether (20 mL), isohexane (20 mL) and HCl (3 M in cyclopentyl methyl ether, 2 mL, 6.00 mmol) to give a solid which was recrystallised in acetonitrile (15 mL), to give the title compound (8.7 g). 1H NMR (500 MHz, DMSO-$d_6$) δ 9.82-9.29 (m, 2H), 7.62-6.86 (m, 6H), 5.25-4.87 (m, 3H), 4.29-4.13 (m, 1H), 4.13-4.00 (m, 1H), 3.98-3.85 (m, 1H), 2.42 (ddd, J=14.1, 9.7, 4.7 Hz, 1H), 2.33-2.23 (m, 1H), 2.22-2.11 (m, 1H), 2.03-1.86 (m, 2H), 1.87-1.73 (m, 1H).

Preparation 177: Benzyl N-[(1R,2S,3R,5S)-2-fluoro-8-azabicyclo[3.2.1]octan-3-yl]carbamate hydrochloride (Slow Eluting Isomer)

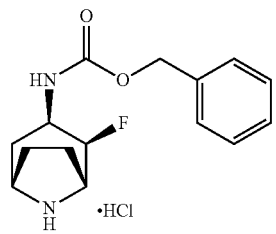 [SMILES: O=C(N[C@@H]1C[C@@H]2CC[C@@H](N2)[C@@H]1F)OCc1ccccc1 ; Cl]

From the same chromatography experiment described in preparation 176, the title compound was obtained as the slow eluting isomer. The residue was then dissolved in DCM (5 mL) then diluted with tert-butyl methyl ether (20 mL) and treated with HCl (3 M in cyclopentyl methyl ether, 2 mL, 6.00 mmol) to give a sticky suspension. The suspension was diluted with isohexane (30 mL) stirred for 18 h and collected by filtration, to give the title compound (7.5 g). 1H NMR (500 MHz, DMSO-$d_6$) δ 9.82-9.29 (m, 2H), 7.62-6.86 (m, 6H), 5.25-4.87 (m, 3H), 4.29-4.13 (m, 1H), 4.13-4.00 (m, 1H), 3.98-3.85 (m, 1H), 2.42 (ddd, J=14.1, 9.7, 4.7 Hz, 1H), 2.33-2.23 (m, 1H), 2.22-2.11 (m, 1H), 2.03-1.86 (m, 2H), 1.87-1.73 (m, 1H).

Compounds of Table 6 below were prepared using procedures analogous to that described in preparation 43, starting from the appropriate substituted aryl halide (synthesised as described by the preparations indicated) with any significant variations indicated.

TABLE 6

| Compound | Compound Name | MS: [M + H]+ m/z | Procedure |
|---|---|---|---|
| | 5-Chloro-3-methyl-6-(4,4,5,5-tetramethyl-1,3,2-dioxaborolan-2-yl)-3,4-dihydroquinazolin-4-one | 321 | Prepared as preparation 43 above using 6-bromo-5-chloro-3-methyl-3,4-dihydroquinazolin-4-one, see preparation 110 |

TABLE 6-continued

| Compound | Compound Name | MS: [M + H]+ m/z | Procedure |
|---|---|---|---|
| 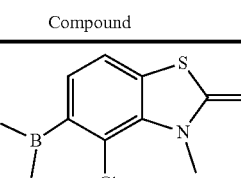 | 4-Chloro-3-methyl-5-(4,4,5,5-tetramethyl-1,3,2-dioxaborolan-2-yl)-2,3-dihydro-1,3-benzothiazol-2-one | | Prepared as preparation 43 above using 5-bromo-4-chloro-3-methyl-2,3-dihydro-1,3-benzothiazol-2-one see preparation 186 |
| 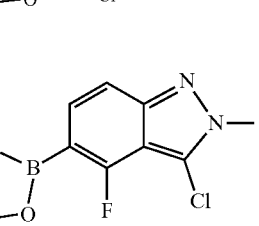 | 3-Chloro-4-fluoro-2-methyl-5-(4,4,5,5-tetramethyl-1,3,2-dioxaborolan-2-yl)-2H-indazole | 311 | Prepared as preparation 43, except using 5-bromo-3-chloro-4-fluoro-2-methyl-2H-indazole (see preparation 202) and purifying by column chromatography on NH silica gel (gradient elution, 0-50%, EtOAc/petrol) |

Preparation 178: 6-Chloro-3-iodo-1-((2-(trimethylsilyl)ethoxy)methyl)-1H-pyrazolo[3,4-b]pyrazine Preparation 179: (6-Chloro-3-iodo-1-{[2-(trimethylsilyl)ethoxy]methyl}-1H-pyrazolo[3,4-b]pyrazin-5-yl)methanol

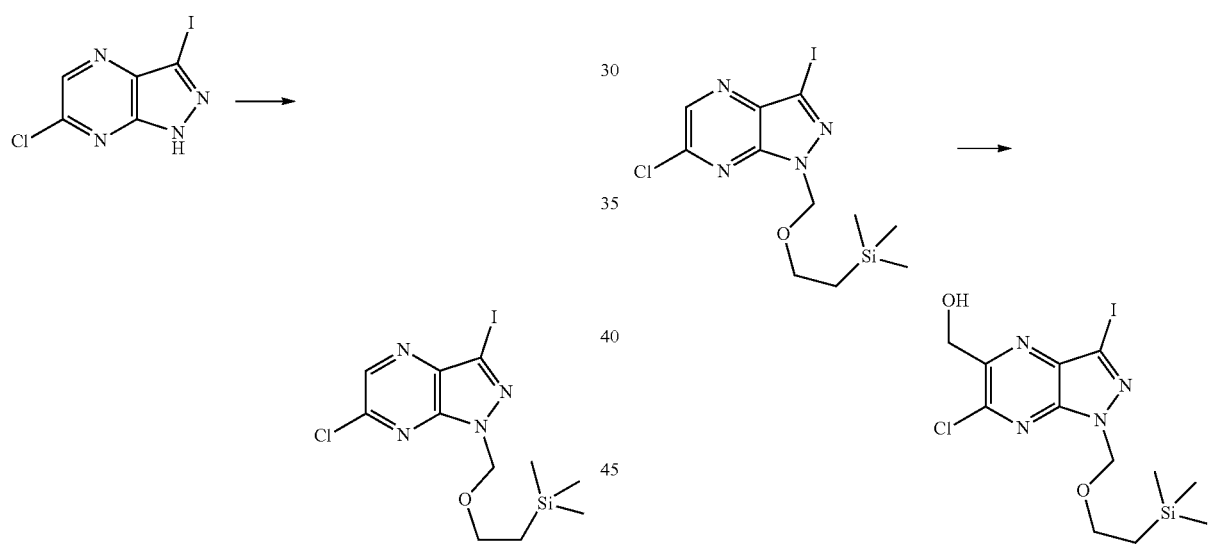

Sodium hydride (60% mineral oil, 3.14 g, 78 mmol) was added over 5 min to a solution of 6-chloro-3-iodo-1H-pyrazolo[3,4-b]pyrazine (20 g, 71.3 mmol) in THF (300 mL) at 0° C. After stirring at 0° C. for 45 min, 2-(trimethylsilyl)ethoxymethyl chloride (15.2 mL, 86 mmol) was added over 2 min. The mixture was stirred at RT for a further 3 h, quenched with sat. aq. NH$_4$Cl (150 mL), diluted with water (200 mL) and extracted with EtOAc (2×150 mL). The combined organic phases were passed through a phase separator and concentrated. The residue was purified by column chromatography on silica gel (gradient elution, 0-25%, EtOAc/isohexane), to give the title compound (24.2 g). MS: [M+H]+=411.

A solution of 6-chloro-3-iodo-1-((2-(trimethylsilyl)ethoxy)methyl)-1H-pyrazolo[3,4-b]pyrazine (11.5 g, 26.2 mmol) in MeOH (91 mL) and DMSO (100 mL) was bubbled with N$_2$ for 15 min, then silver nitrate (1.78 g, 10.5 mmol) and TFA (2.02 mL, 26.2 mmol) were added sequentially. The mixture was heated to 70° C. and a solution of ammonium persulfate (15.0 g, 65.5 mmol) in water (33 mL) was added dropwise over 45 min. The mixture was stirred at 70° C. for a further 2 h, then cooled to RT, diluted with EtOAc (100 mL) and filtered through celite with an EtOAc wash (2×50 mL). The filtrate was diluted with sat. aq. NaHCO$_3$ (75 mL) and water (300 mL) and partitioned. The aqueous phase was extracted with EtOAc (2×150 mL), and the combined organic phases were dried (Na$_2$SO$_4$), filtered and concentrated. The residue was purified by column chromatography on silica gel (gradient elution, 5-40%, EtOAc/isohexane), to give the title compound (5.9 g). 1H NMR (500 MHz, CDCl$_3$): 5.83 (2H, s), 5.02 (2H, s), 3.76-3.66 (2H, m), 1.02-0.88 (2H, m), −0.01 (s, 9H).

Preparation 180: tert-Butyl N-[(1R,2R,3S,5S)-2-fluoro-8-azabicyclo[3.2.1]octan-3-yl]carbamate

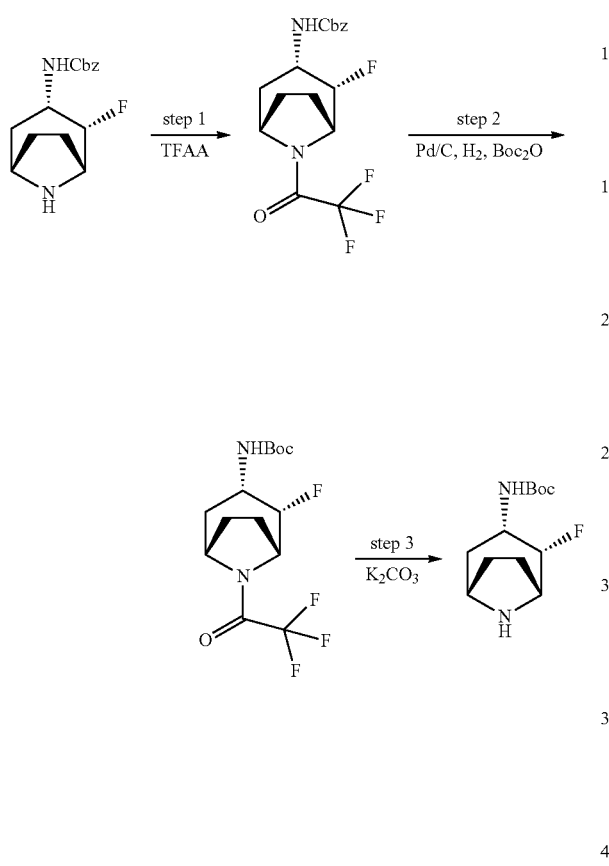

Step 1: Benzyl N-[(1R,2S,3S,5S)-2-fluoro-8-(2,2,2-trifluoroacetyl)-8-azabicyclo[3.2.1]octan-3-yl]carbamate To a solution of benzyl N-[(1R,2R,3S,5S)-2-fluoro-8-azabicyclo[3.2.1]octan-3-yl]carbamate (1.0 g, 3.6 mmol) and Et$_3$N (1.0 mL, 7.2 mmol) in DCM (15 mL) was added trifluoroacetic anhydride (0.53 mL, 3.78 mmol) and the reaction mixture was stirred at RT for 1 h. The reaction was diluted with DCM and sat. aq. NaHCO$_3$ was added. The aqueous layer was extracted with DCM, the organic phase was dried (MgSO$_4$), filtered and concentrated. The crude product was purified by column chromatography on silica gel (gradient elution, 0-60%, EtOAc/petrol), to give the title compound (1.32 g). 1H NMR (400 MHz, DMSO-d$_6$): 7.47 (1H, d), 7.42-7.25 (5H, m), 5.05 (2H, s), 4.88-4.60 (2H, m), 4.59-4.33 (1H, m), 4.01-3.85 (1H, m), 3.35 (1H, s), 2.13-2.01 (1H, m), 1.99-1.68 (5H, m).

Step 2: tert-Butyl N-[(1R,2S,3S,5S)-2-fluoro-8-(2,2,2-trifluoroacetyl)-8-azabicyclo[3.2.1]octan-3-yl]carbamate To a solution of benzyl N-[(1R,2S,3S,5S)-2-fluoro-8-(2,2,2-trifluoroacetyl)-8-azabicyclo[3.2.1]octan-3-yl]carbamate (1.32 g, 3.53 mmol) in ethanol (15 mL) were added di-tert-butyl dicarbonate (1.0 g, 4.58 mmol) and Pd/C (10%, 0.13 g) and the mixture was hydrogenated for 6 h. The reaction was filtered and the filtrate evaporated. The residue was purified by column chromatography on silica gel (gradient elution, 0-40%, EtOAc/petrol), to give the title compound (1.04 g). 1H NMR (400 MHz, DMSO-d$_6$): 6.98 (1H, d), 4.89-4.21 (3H, m), 3.86 (1H, d), 2.19-1.53 (6H, m), 1.39 (9H, s).

Step 3: tert-Butyl N-[(1R,2R,3S,5S)-2-fluoro-8-azabicyclo[3.2.1]octan-3-yl]carbamate To a solution of tert-butyl N-[(1R,2S,3S,5S)-2-fluoro-8-(2,2,2-trifluoroacetyl)-8-azabicyclo[3.2.1]octan-3-yl]carbamate (1.04 g, 3.07 mmol) in MeOH (15 mL) and H$_2$O (3 mL) was added K$_2$CO$_3$ (2.11 g, 15.35 mmol) and the mixture was stirred overnight. The MeOH was evaporated, H$_2$O was added and the product was extracted with DCM. The organic phase was dried (MgSO$_4$), filtered and evaporated, to give the title compound (0.733 g). 1H NMR (400 MHz, DMSO-d$_6$): 6.75 (1H, d), 4.34 (1H, d), 3.72-3.52 (1H, m), 3.46 (1H, s), 3.35 (1H, s), 2.14 (1H, s), 1.69 (2H, d), 1.60-1.25 (13H, m).

Preparation 181: tert-Butyl N-[(1S,2R,3S,5R)-2-fluoro-8-azabicyclo[3.2.1]octan-3-yl]carbamate

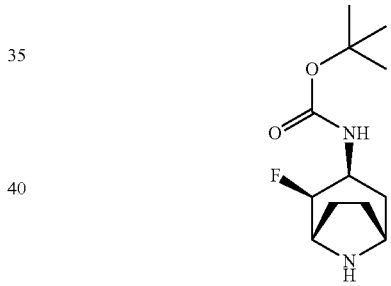

The title compound was prepared using similar method as in preparation 180 using benzyl N-[(1S,2R,3S,5R)-2-fluoro-8-azabicyclo[3.2.1]octan-3-yl]carbamate instead of benzyl N-[(1R,2R,3S,5S)-2-fluoro-8-azabicyclo[3.2.1]octan-3-yl] carbamate, to give the title compound, 1H NMR (400 MHz, DMSO-d$_6$): 6.02 (1H, s), 4.96-4.44 (1H, m), 4.11-3.85 (1H, m), 3.40 (1H, q), 3.27 (1H, d), 2.35 (1H, s), 2.18-1.97 (1H, m), 1.97-1.83 (1H, m), 1.83-1.68 (1H, m), 1.68-1.48 (3H, m), 1.39 (9H, s).

Compounds of Table 7 below were prepared using procedures analogous to that described in general procedure 1, starting from the appropriate substituted protected pyrrolopyrazine or pyrazolopyrazine and varying the amine, with any significant variations indicated below.

TABLE 7

| Compound | Compound Name | NMR or MS: [M + H]+ m/z | Procedure |
|---|---|---|---|
| (structure) | Benzyl N-[(1R,2S,3S,5S)-2-fluoro-8-[5-(hydroxymethyl)-3-iodo-1-(oxan-2-yl)-1H-pyrazolo[3,4-b]pyrazin-6-yl]-8-azabicyclo[3.2.1]octan-3-yl]carbamate | 637 | Prepared as General Procedure 1 using [6-chloro-3-iodo-1-(oxan-2-yl)-1H-pyrazolo[3,4-b]pyrazin-5-yl]methanol and benzyl N-[(1R,2R,3S,5S)-2-fluoro-8-azabicyclo[3.2.1]octan-3-yl]carbamate, heating for 1 h. |
| (structure) (+/−) | rac-Benzyl N-[(1R,2S,3S,5S)-2-fluoro-8-[5-(hydroxymethyl)-3-iodo-1-(oxan-2-yl)-1H-pyrazolo[3,4-b]pyrazin-6-yl]-8-azabicyclo[3.2.1]octan-3-yl]carbamate | 637 | Prepared as General Procedure 1 using [6-chloro-3-iodo-1-(oxan-2-yl)-1H-pyrazolo[3,4-b]pyrazin-5-yl]methanol and rac-benzyl N-[(1S,2S,3R,5R)-2-fluoro-8-azabicyclo[3.2.1]octan-3-yl]carbamate, heating for 1 h |
| (structure) | tert-Butyl N-[(1R,2S,3S,5S)-2-fluoro-8-[5-(hydroxymethyl)-3-iodo-1-{[2-(trimethylsilyl)ethoxy]methyl}-1H-pyrazolo[3,4-b]pyrazin-6-yl]-8-azabicyclo[3.2.1]octan-3-yl]carbamate | 649 | Prepared as General Procedure 1 using (6-chloro-3-iodo-1-{[2-(trimethylsilyl)ethoxy]methyl}-1H-pyrazolo[3,4-b]pyrazin-5-yl)methanol and tert-butyl N-[(1R,2R,3S,5S-2-fluoro-8-azabicyclo[3.2.1]octan-3-yl]carbamate, heating at 130° C. for 1.5 h |
| (structure) | Benzyl N-[(1S,2S,3S,5R)-2-fluoro-8-[5-(hydroxymethyl)-3-iodo-1-(oxan-2-yl)-1H-pyrazolo[3,4-b]pyrazin-6-yl]-8-azabicyclo[3.2.1]octan-3-yl]carbamate | 637 | Prepared as General Procedure 1, except using 6-chloro-3-iodo-1-(oxan-2-yl)-1H-pyrazolo[3,4-b]pyrazin-5-yl]methanol and benzyl N-[(1S,2R,3S,5R)-2-fluoro-8-azabicyclo[3.2.1]octan-3-yl]carbamate heated at 110° C. for 6 h |
| (structure) | tert-Butyl N-[(3R,4S)-1-[5-(dimethylsulfamoyl)-7-iodo-5H-pyrrolo[2,3-b]pyrazin-3-yl]-3-fluoropiperidin-4-yl]carbamate | 569 | Prepared as General Procedure 1, except using 3-chloro-7-iodo-N,N-dimethyl-5H-pyrrolo[2,3-b]pyrazine-5-sulfonamide, tert-butyl N-[(3R,4S)-3-fluoropiperidin-4-yl]carbamate and triethylamine instead of DIPEA at 120° C. for 21 h |
| (structure) | Benzyl N-[(1S,2S,3S,5R)-8-[5-(dimethylsulfamoyl)-7-iodo-5H-pyrrolo[2,3-b]pyrazin-3-yl]-2-fluoro-8-azabicyclo[3.2.1]octan-3-yl]carbamate | 629 | Prepared as General Procedure 1 using 3-fluoro-7-iodo-N,N-dimethyl-5H-pyrrolo[2,3-b]pyrazine-5-sulfonamide and benzyl N-[(1S,2R,3S,5R)-2-fluoro-8-azabicyclo[3.2.1]octan-3-yl]carbamate, heating for 18 h |
| (structure) | tert-Butyl N-[(1S,2S,3S,5R)-2-fluoro-8-[5-(hydroxymethyl)-3-iodo-1-(oxan-2-yl)-1H-pyrazolo[3,4-b]pyrazin-6-yl]-8-azabicyclo[3.2.1]octan-3-yl]carbamate | 603 | Prepared as General Procedure 1 using [6-chloro-3-iodo-1-(oxan-2-yl)-1H-pyrazolo[3,4-b]pyrazin-5-yl]methanol and tert-butyl N-[(1S,2R,3S,5R)-2-fluoro-8-azabicyclo[3.2.1]octan-3-yl]carbamate, heating at 110° C. for 6 h |

TABLE 7-continued

| Compound | Compound Name | NMR or MS: [M + H]+ m/z | Procedure |
|---|---|---|---|
| 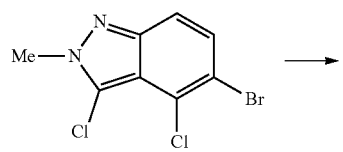 | tert-Butyl 8-[5-(hydroxymethyl)-3-iodo-1-{[2-(trimethylsilyl)ethoxy]methyl}-1H-pyrazolo[3,4-b]pyrazin-6-yl]-3,8-diazabicyclo[3.2.1]octane-3-carboxylate | 617 | Prepared as General Procedure 1 using (6-chloro-3-iodo-1-{[2-(trimethylsilyl)ethoxy]methyl}-1H-pyrazolo[3,4-b]pyrazin-5-yl)methanol and tert-butyl 3,8-diazabicyclo[3.2.1]octane-3-carboxylate, using N,N,N',N'-tetramethylethylenediamine, heating at 125° C. for 2 h |
| 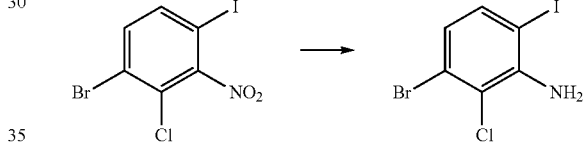 | tert-Butyl N-[endo-8 [5-(hydroxymethyl)-3-iodo-1-{[2-(trimethylsilyl)ethoxy]methyl}-1H-pyrazolo[3,4-b]pyrazin-6-yl]-8-azabicyclo[3.2.1]octan-3-yl]carbamate | 630 | Prepared as General Procedure 1 using (6-chloro-3-iodo-1-{[2-(trimethylsilyl)ethoxy]methyl}-1H-pyrazolo[3,4-b]pyrazin-5-yl)methanol and tert-butyl N-[(1R,3S,5S)-8-azabicyclo[3.2.1]octan-3-yl]carbamate, heating at 100° C. for 1h |

Preparation 182: 3,4-Dichloro-2-methyl-2H-indazol-5-yl)boronic Acid

To a solution of 5-bromo-3,4-dichloro-2-methyl-2H-indazole (30.0 g, 107 mmol) in THF (450 mL) was added isopropylmagnesium chloride lithium chloride complex solution (1.3 M in THF, 200 mL, 260 mmol) at 0° C. and stirred for 1.5 h. The reaction was cooled to −20° C. and triisopropyl borate (125 mL, 544 mmol) was added. After warming to 0° C., the reaction was stirred for 1.5 h. Acetic acid (123 mL, 2.1 mol), water (300 mL) and 2-methyltetrahydrofuran (150 mL) were added to the reaction mixture and stirred for 2 h at RT. 5 M NaOH (500 mL) and water (300 mL) were added at 0° C. and organic layer was extracted with 3 M NaOH (150 mL). The combined aqueous layer was acidified with 6 M HCl (ca. 400 mL, pH 4) at RT, and stirred for 1 h at the same temperature. The precipitate was collected, washed with dil. HCl (pH 3), water and dried at 50° C. overnight under reduced pressure, to give the title compound (19.8 g). MS: [M+H]+=246, 248.

Preparation 183: 3-Bromo-2-chloro-6-iodoaniline

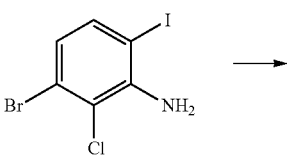

Sodium dithionite (8.65 g, 49.7 mmol) in water (30 mL) was added to an ice bath-cooled solution of 2-chloro-3-bromo-6-iodonitrobenzene (3.00 g, 0.276 mmol) in THF (30 mL) and MeOH (30 mL). The mixture was stirred at RT for 3 h and then partitioned between EtOAc and sat. aq. NaHCO$_3$. The phases were separated, the aqueous phase was extracted with EtOAc and the combined organic phases dried (MgSO$_4$) and concentrated to give the title compound (1.76 g). $^1$H NMR (400 MHz, CDCl$_3$): 7.42 (1H, d), 6.78 (1H, d), 4.73 (2H, br. s).

Preparation 184: 2-Ethylhexyl 3-[(2-amino-4-bromo-3-chlorophenyl)sulfanyl]propanoate

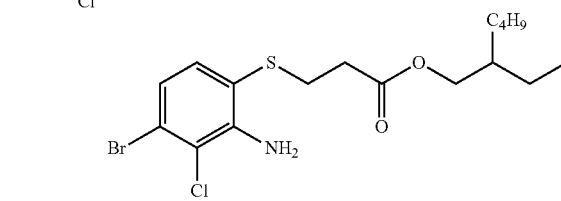

Prepared as preparation 23, except using 3-bromo-2-chloro-6-iodoaniline, to give the title compound. $^1$H NMR (400 MHz, CDCl$_3$): 7.19 (1H, d), 6.96 (1H, d), 5.04 (2H, s), 4.03 (2H, dd), 3.00 (2H, t), 2.57 (2H, t), 1.65-1.53 (1H, m), 1.44-1.25 (9H, m), 0.98-0.85 (6H, m).

Preparation 185: 5-Bromo-4-chloro-2,3-dihydro-1,3-benzothiazol-2-one

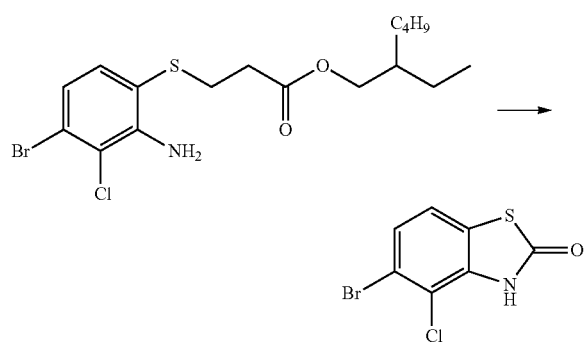

Prepared as preparation 24, except using 2-ethylhexyl 3-[(2-amino-4-bromo-3-chlorophenyl)sulfanyl]propanoate, to give the title compound. $^1$H NMR (400 MHz, CDCl$_3$): 8.61-8.43 (1H, m), 7.47-7.41 (1H, m), 7.20 (1H, d).

Preparation 186: 5-Bromo-4-chloro-3-methyl-2,3-dihydro-1,3-benzothiazol-2-one

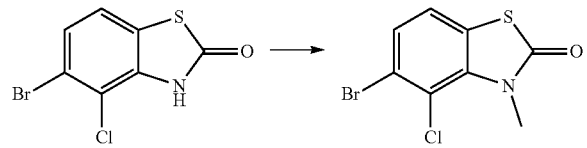

Methyl iodide (0.128 mL, 2.05 mmol) was added to a solution of 5-bromo-4-chloro-2,3-dihydro-1,3-benzothiazol-2-one (291 mg, 1.02 mmol) and K$_2$CO$_3$ (425 mg, 3.07 mmol) in DMSO (3 mL). The mixture was stirred at RT for 3 days and then partitioned between EtOAc and water. The phases were separated, the aqueous phase was extracted with EtOAc and combined organic phases washed with brine, dried (MgSO$_4$) and concentrated. The residue was purified by column chromatography on silica gel (gradient elution, 0-20%, EtOAc/petrol) to give the title compound (208 mg). $^1$H NMR (400 MHz, CDCl$_3$): 7.47 (1H, d), 7.20 (1H, d), 3.90 (3H, s).

Preparation 187: 4-Bromo-3-chloro-2-nitroaniline and 6-bromo-3-chloro-2-nitroaniline

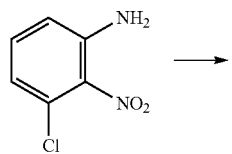

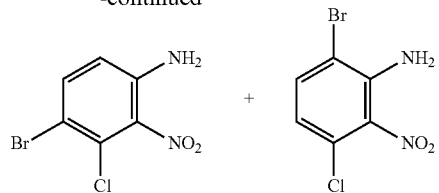

A solution of 3-chloro-2-nitroaniline (25 g, 145 mmol) and N-bromosuccinimide (25.5 g, 143 mmol) in AcOH (600 mL) was refluxed for 45 min. After cooling to RT, the reaction mixture was poured into ice-cold water (2 L). The precipitate was collected by filtration, washed with ice-cold water (2×200 mL) and dried in a vacuum oven overnight, to give the title compounds (36 g) as a mixture of isomers (4-bromo/6-bromo in 9:1 ratio). $^1$H NMR (500 MHz, DMSO-d$_6$): 7.56 (1H, d), 6.84 (1H, d), 6.40 (2H, s).

Preparation 188: Ethyl 2-[(4-bromo-3-chloro-2-nitrophenyl)amino]acetate and ethyl 2-[(6-bromo-3-chloro-2-nitrophenyl)amino]acetate

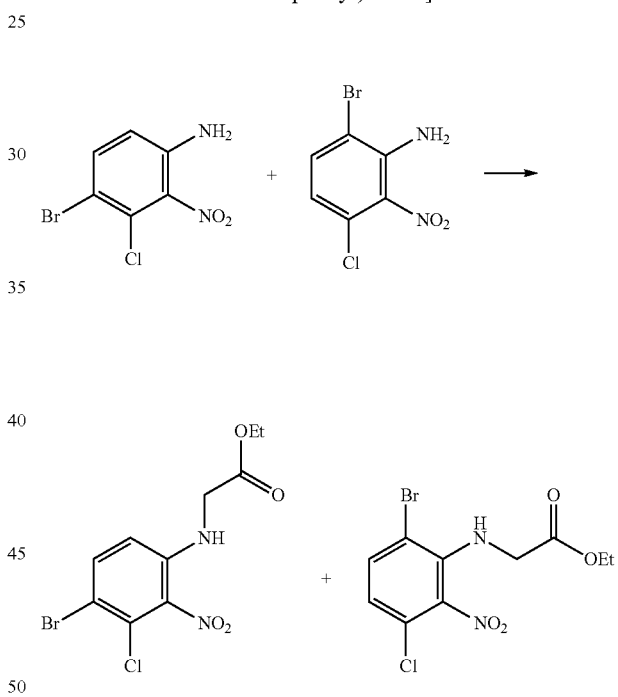

A mixture of 4-bromo-3-chloro-2-nitroaniline and 6-bromo-3-chloro-2-nitroaniline in a 9:1 ratio (30 g, 119 mmol), ethyl bromoacetate (133 mL, 119 mmol) and K$_2$CO$_3$ (26.4 g, 191 mmol) was heated at 140° C. under nitrogen for 30 h. The mixture was cooled to RT, then 1M aq. NaOH solution (250 mL) was added over 10 min. The mixture was stirred for a further 10 min, then extracted with DCM (3×30 mL). The combined organic layers were dried over MgSO$_4$, filtered and concentrated under vacuum. The crude product was purified by column chromatography on silica gel (gradient elution, 5-30%, EtOAc/isohexane). The purified mixture was recrystallised from boiling IPA (70 mL). The solid was filtered, washed with cyclohexane (2×50 mL), and dried in a vacuum oven overnight, to give the title compounds (4 g) as a mixture of isomers (4-bromo/6-bromo in 9:1 ratio). MS: [M+H]$^+$=337.

Preparation 189: 7-Bromo-8-chloro-1,2,3,4-tetrahydroquinoxalin-2-one and 8-bromo-5-chloro-1,2,3,4-tetrahydroquinoxalin-2-one

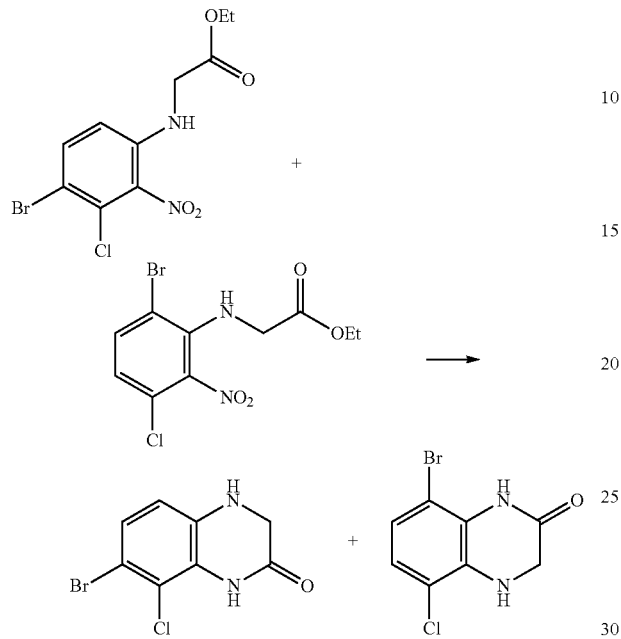

A mixture of ethyl 2-[(4-bromo-3-chloro-2-nitrophenyl)amino]acetate and ethyl 2-[(6-bromo-3-chloro-2-nitrophenyl)amino]acetate in a 9:1 ratio (3.5 g, 10.4 mmol), iron (3.5 g, 62.7 mmol) and NH$_4$Cl (0.555 g, 10.4 mmol) in EtOH (75 mL) was refluxed for 30 min. AcOH (30 mL) was added and heating was continued for 30 min. The reaction mixture was diluted with water (300 mL) and extracted with DCM (3×100 mL). The combined organic layers were dried over MgSO$_4$, filtered and concentrated under vacuum, to give the title compounds (2.8 g) as a mixture of isomers (7-bromo/8-bromo in 9:1 ratio). MS: [M+H]$^+$=261.

Preparation 190: 7-Bromo-8-chloroquinoxalin-2-ol

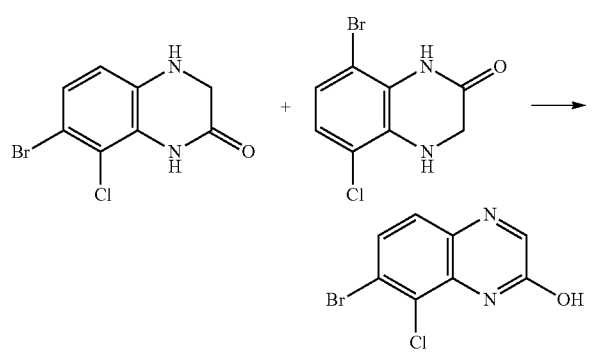

7-Bromo-8-chloro-1,2,3,4-tetrahydroquinoxalin-2-one and 8-bromo-5-chloro-1,2,3,4-tetrahydroquinoxalin-2-one in a 9:1 ratio (3.2 g, 12.2 mmol) were suspended in 50 wt % aq. NaOH (1.5 mL, 29.3 mmol) and 3 wt % aq. H$_2$O$_2$ (32 mL, 28.1 mmol). The reaction mixture was refluxed for 3 h. The mixture was cooled to RT, causing product to precipitate. AcOH (1.6 mL) was added. The precipitate was collected by filtration, washing with water (2×5 mL). The solid was azeotroped with acetonitrile (2×20 mL), to give the title compound (2.8 g). MS: [M+H]$^+$=259.

Preparation 191: 7-Bromo-8-chloro-2-methoxyquinoxaline

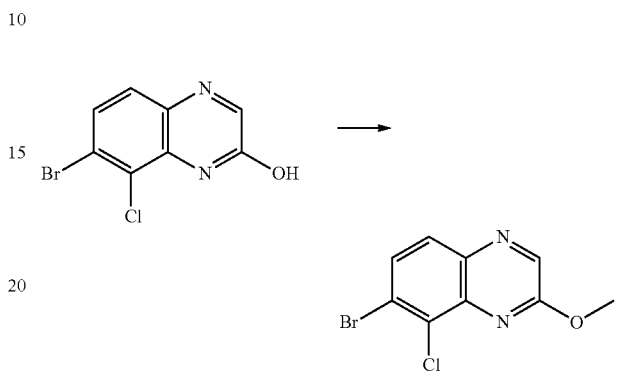

A suspension of 7-bromo-8-chloroquinoxalin-2-ol (2.8 g, 10.8 mmol) and K$_2$CO$_3$ (2.24 g, 16.2 mmol) in DMF (33 mL) was treated with iodomethane (0.74 mL, 11.9 mmol), and stirred for 3 h at RT. Water (300 mL) was added and the precipitate collected by filtration. The crude product was purified by column chromatography on silica gel (gradient elution, 0-100%, EtOAc/isohexane), to give the title compound (1.8 g). MS: [M+H]$^+$=275.

Preparation 192: 7-Bromo-2,8-dichloroquinoxaline

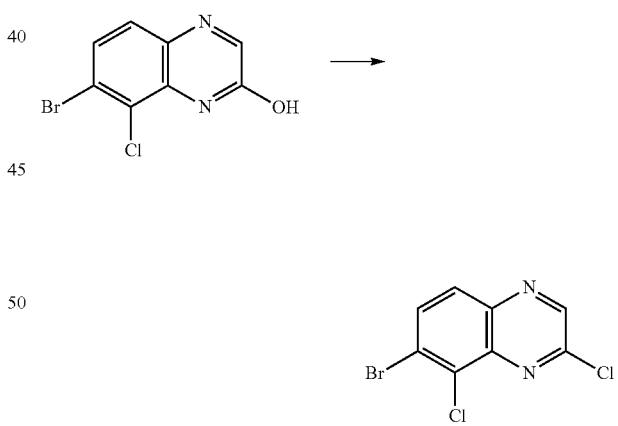

To a solution of 7-bromo-8-chloroquinoxalin-2-ol (3 g, 11.6 mmol) in toluene (23 mL) was added phosphorus(V) oxychloride (4.85 mL, 52.0 mmol) and the reaction mixture was stirred overnight at 70° C. The reaction mixture was quenched by dropwise addition into ice-cold sat. aq. NaHCO$_3$ (200 mL) and stirred for 2 h at RT. The mixture was then extracted with DCM (3×80 mL) and the combined organic layers were dried over MgSO$_4$, filtered and concentrated under reduced pressure, to give the title compound (2.5 g). $^1$H NMR (500 MHz, DMSO-d$_6$): 9.13 (1H, s), 8.22 (1H, d), 8.07 (1H, d).

Preparation 193: 7-Bromo-8-chloro-2-fluoroquinoxaline

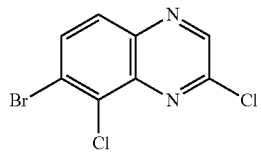
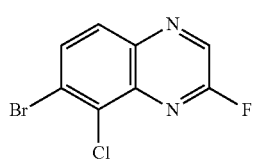

To a solution of 7-bromo-2,8-dichloroquinoxaline (2.5 g, 8.99 mmol) in DMSO (19 mL) was added TBAF (1M in THF) (10.8 mL, 10.8 mmol). The reaction mixture was stirred at 50° C. for 3 h then poured into water (150 mL). The precipitate was collected by filtration, washing with water and air dried. The crude product was purified by column chromatography on silica gel (gradient elution, 0-15%, EtOAc/isohexane), to give the title compound (0.85 g). $^1$H NMR (500 MHz, DMSO-$d_6$): 9.09 (1H, s), 8.19 (1H, d), 8.10 (1H, d). $^{19}$F NMR (471 MHz, DMSO-$d_6$): −71.22.

Preparation 194: 7-Bromo-8-chloro-N,N-dimethylquinoxalin-2-amine

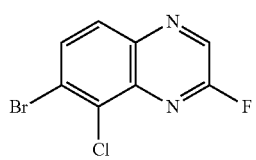
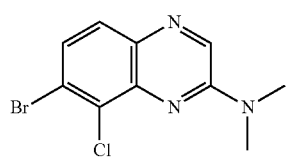

To a solution of 7-bromo-8-chloro-2-fluoroquinoxaline (0.85 g, 3.25 mmol) in DMSO (8.5 mL) was added dimethylamine (2 M in THF) (34 mL, 68 mmol) and the reaction mixture was stirred at RT for 5 h. The mixture was concentrated under vacuum and the DMSO solution was diluted with sat. aq. NaHCO$_3$ (30 mL) and extracted with DCM (2×20 mL). The combined organic layers were passed through a phase separator and concentrated under reduced pressure, to give the title compound (0.84 g). MS: [M+H]$^+$=288.

Preparation 195: tert-Butyl N-[(3R,4S)-1-(6-chloro-5-formyl-3-methylpyrazin-2-yl)-3-fluoropiperidin-4-yl]carbamate

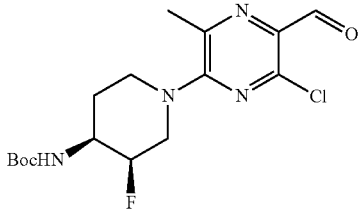 [SMILES: Cc1nc(C=O)c(Cl)nc1N1CC[C@H](NC(=O)OC(C)(C)C)[C@H](F)C1]

3,5-Dichloro-6-methylpyrazine-2-carbaldehyde (0.497 g, 2.6 mmol) was dissolved in NMP (5 mL) and cooled to 0° C. Triethylamine (1.1 mL, 7.8 mmol) was added followed by tert-butyl N-[(3R,4S)-3-fluoropiperidin-4-yl]carbamate (0.68 g, 3.12 mmol). The reaction was allowed to warm to RT and stirred overnight. Sat. aq. NaHCO$_3$ was added and the mixture extracted with EtOAc (3×). The combined organics were passed through a phase separator and concentrated in vacuo. The residue was purified by column chromatography on silica gel (gradient elution, 0-60%, EtOAc/petrol), to give the title compound (0.494 g), MS: [M+H]$^+$=317.

Preparation 196: tert-Butyl N-[(3R,4S)-3-fluoro-1-{5-methyl-1H-pyrazolo[3,4-b]pyrazin-6-yl}piperidin-4-yl]carbamate

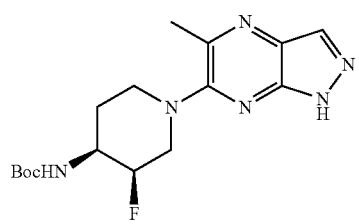 [SMILES: Cc1nc2cn[nH]c2nc1N1CC[C@H](NC(=O)OC(C)(C)C)[C@H](F)C1]

Hydrazine hydrate (50-60%, 1.3 mL, 14.6 mmol) was added to a solution of tert-butyl N-[(3R,4S)-1-(6-chloro-5-formyl-3-methylpyrazin-2-yl)-3-fluoropiperidin-4-yl]carbamate (0.49 g, 1.31 mmol) in NMP (3 mL) and the reaction mixture was heated at 100° C. overnight. The reaction mixture was cooled, water was added the mixture extracted with EtOAc (3×). The combined organics were washed with brine, dried (MgSO$_4$), filtered and evaporated. The residue was purified by column chromatography on silica gel (gradient elution, 0-60%, EtOAc/petrol), to give the title compound (0.212 g), MS: [M+H]$^+$=351.

Preparation 197: tert-Butyl N-[(3R,4S)-3-fluoro-1-{3-iodo-5-methyl-1H-pyrazolo[3,4-b]pyrazin-6-yl}piperidin-4-yl]carbamate

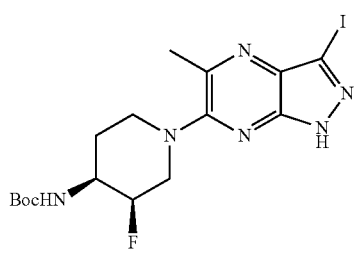 [SMILES: Cc1nc2c(I)n[nH]c2nc1N1CC[C@H](NC(=O)OC(C)(C)C)[C@H](F)C1]

N-Iodosuccinimide (0.2 g, 0.9 mmol) was added to a solution of tert-butyl N-[(3R,4S)-3-fluoro-1-{5-methyl-1H-pyrazolo[3,4-b]pyrazin-6-yl}piperidin-4-yl]carbamate (0.212 g, 0.6 mmol) in DMF (3 mL). The reaction was stirred at RT overnight. Further N-iodosuccinimide (0.1 g, 0.45 mmol) was added and stirred for 3 h. The reaction mixture was diluted with EtOAc, washed with sat. aq. Na$_2$S$_2$O$_3$, sat. aq. NaHCO$_3$, then brine. The organic phase was dried (MgSO$_4$), filtered and concentrated in vacuo to give the title compound (0.25 g), MS: [M+H]$^+$=477.

Preparation 198: tert-Butyl N-[(3R,4S)-3-fluoro-1-[3-iodo-5-methyl-1-(oxan-2-yl)-1H-pyrazolo[3,4-b]pyrazin-6-yl]piperidin-4-yl]carbamate

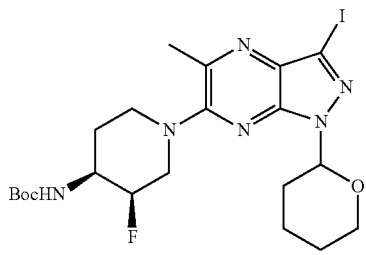 [SMILES: Cc1nc2c(I)nn(C3CCCCO3)c2nc1N1CC[C@H](NC(=O)OC(C)(C)C)[C@H](F)C1]

3,4-Dihydro-2H-pyran (0.14 mL, 1.57 mmol) was added to a solution of tert-butyl N-[(3R,4S)-3-fluoro-1-{3-iodo-5-methyl-1H-pyrazolo[3,4-b]pyrazin-6-yl}piperidin-4-yl]carbamate (0.25 g, 0.52 mmol) and para-toluenesulfonic acid (0.01 g, 0.05 mmol) in DCM (5 mL) at 0° C. The reaction was allowed to warm to RT and stirred overnight then diluted with DCM and washed with sat. aq. NaHCO$_3$ and brine. The organic layer was dried by passing through a phase separator then concentrated. The residue was purified by column chromatography on silica gel (gradient elution, 0-50%, EtOAc/petrol), to give the title compound (0.183 g), MS: [M+H]$^+$=561.

Preparation 199: 6-Chloro-3-iodo-1-(oxan-2-yl)-1H-pyrazolo[3,4-b]pyrazine

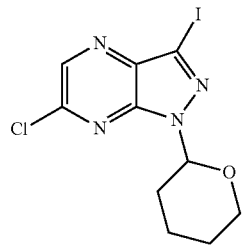 [SMILES: Clc1cnc2c(I)nn(C3CCCCO3)c2n1]

3,4-Dihydro-2H-pyran (9.76 mL, 107 mmol) was added to a solution of 6-chloro-3-iodo-1H-pyrazolo[3,4-b]pyrazine (10 g, 35.7 mmol) and para-toluenesulfonic acid (0.614 g, 3.57 mmol) in DCM (100 mL) at 0° C. The reaction was allowed to warm to RT and stirred overnight then diluted with DCM and washed with sat. aq. NaHCO$_3$ then brine. The organic layer was dried by passing through a phase separator then concentrated. The crude product was purified by column chromatography on silica gel (gradient elution, 0-20%, ethyl acetate/petrol), to give the title compound (7 g). 1H NMR (400 MHz, DMSO-d$_6$): 8.79 (1H, s), 5.92 (1H, dd), 3.94 (1H, d), 3.80-3.67 (1H, m), 2.45-2.17 (1H, m), 2.15-1.91 (2H, m), 1.91-1.68 (1H, m), 1.59 (1H, s), 1.54-1.41 (1H, m).

Preparation 200: [6-Chloro-3-iodo-1-(oxan-2-yl)-1H-pyrazolo[3,4-b]pyrazin-5-yl]methanol

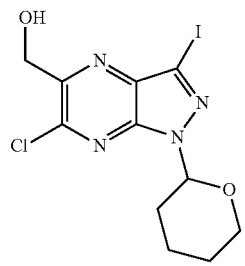 [SMILES: OCc1nc2c(I)nn(C3CCCCO3)c2nc1Cl]

6-Chloro-3-iodo-1-(oxan-2-yl)-1H-pyrazolo[3,4-b]pyrazine (0.191 g, 0.525 mmol) and tetrakis(9H-carbazol-9-yl)benzene-1,3-dicarbonitrile (0.004 g, 0.00525 mmol) were weighed into a microwave vial. Methanol (4 mL) and DMSO (2 mL) which had been de-oxygenated by bubbling nitrogen through for 20 min, were added followed by tert-butyl peracetate (50 wt % in min. spirits, 0.75 ml, 2.36 mmol) and TFA (0.4 ml, 5.25 mmol). The reaction vessel was purged with nitrogen, sealed with a crimp cap and irradiated with a blue LED light overnight. The reaction was concentrated then diluted with EtOAc and washed with sat. aq. Na$_2$CO$_3$ then brine. The organic phase was dried by passing through a phase separator and concentrated in vacuo. The crude product was purified by column chromatography on silica gel (gradient elution, 0-30%, ethyl acetate/petrol), to give the title compound (0.082 g), MS: [M−H]$^+$=394.

Preparation 201: 4-Chloro-2-ethyl-5-(4,4,5,5-tetramethyl-1,3,2-dioxaborolan-2-yl)-2H-indazole

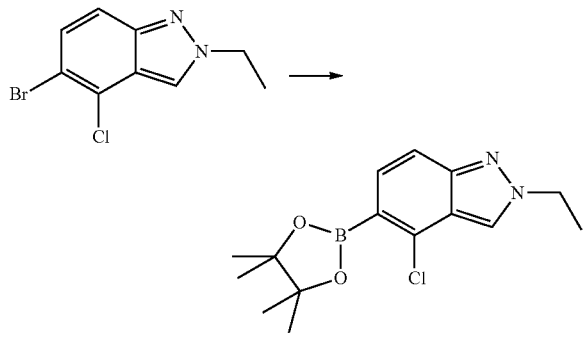

Isopropylmagnesium chloride lithium chloride complex solution (1.3 M in THF) (5.93 mL, 7.71 mmol) was added to a solution of 5-bromo-4-chloro-2-ethyl-2H-indazole (1.00 g, 3.85 mmol) in THF (10 mL) at 0° C. and the reaction stirred for 4 h. After cooling to −10° C. using an acetone-ice bath, 2-isopropoxy-4,4,5,5-tetramethyl-1,3,2-dioxaborolane (2.36 mL, 11.6 mmol) was added and stirring continued for 30 min at −10° C. The reaction was quenched with sat. aq. NH$_4$Cl and H$_2$O and extracted with EtOAc (3×). Combined organics were washed with brine, dried (MgSO$_4$) and evaporated. The residue was suspended in IPA and evaporated, then re-suspended in minimal IPA (3 mL) and cooled to 0° C. H$_2$O (25 mL) was added dropwise with stirring and the resulting suspension stirred at 0° C. for 1 h. The solid was collected by filtration, washing initially with a minimal volume of 8:1 H$_2$O:IPA (5 mL), and then with petrol (3×). The solid was dried in vacuo to give the title compound. MS: [M+H]$^+$=307.

Compounds of Table 8 set out below were prepared in an analogous manner to general procedure 2, using the corresponding aryl halide and boronate or boronic acid with any significant variations indicated).

TABLE 8

| Compound | Compound Name | NMR or MS: [M + H]$^+$ m/z | Procedure |
|---|---|---|---|
|  | Benzyl N-[(1R,2S,3S,5S)-8-[3-(4-chloro-2-ethyl-2H-indazol-5-yl)-5-(hydroxymethyl)-1-(oxan-2-yl)-1H-pyrazolo[3,4-b]pyrazin-6-yl]-2-fluoro-8-azabicyclo[3.2.1]octan-3-yl]carbamate | 689 | Prepared as general procedure 2, except using benzyl N-[(1R,2S,3S,5S)-2-fluoro-8-[5-(hydroxymethyl)-3-iodo-1-(oxan-2-yl)-1H-pyrazolo[3,4-b]pyrazin-6-yl]-8-azabicyclo[3.2.1]octan-3-yl]carbamate and 4-Chloro-2-ethyl-5-(4,4,5,5-tetramethyl-1,3,2-dioxaborolan-2-yl)-2H-indazole, heating to 60° C. for 2 h |
|  | Benzyl N-[(1R,2S,3S,5S)-8-[3-(3-chloro-4-fluoro-2-methyl-2H-indazol-5-yl)-5-(hydroxymethyl)-1-(oxan-2-yl)-1H-pyrazolo[3,4-b]pyrazin-6-yl]-2-fluoro-8-azabicyclo[3.2.1]octan-3-yl]carbamate | 693 | Prepared as General Procedure 2, except using benzyl N-[(1R,2S,3S,5S)-2-fluoro-8-[5-(hydroxymethyl)-3-iodo-1-(oxan-2-yl)-1H-pyrazolo[3,4-b]pyrazin-6-yl]-8-azabicyclo[3.2.1]octan-3-yl]carbamate and 3-chloro-4-fluoro-2-methyl-5-(4,4,5,5-tetramethyl-1,3,2-dioxaborolan-2-yl)-2H-indazole, heating to 60° C. for 2 h |
|  | Benzyl N-[(1S,2S,3S,5R)-8-[7-(5-chloro-3-methyl-4-oxo-3,4-dihydroquinazolin-6-yl)-5-(dimethylsulfamoyl)-5H-pyrrolo[2,3-b]pyrazin-3-yl]-2-fluoro-8-azabicyclo[3.2.1]octan-3-yl]carbamate | 695 | Prepared as General Procedure 2 using benzyl N-[(1S,2S,3S,5R)-8-[5-(dimethylsulfamoyl)-7-iodo-5H-pyrrolo[2,3-b]pyrazin-3-yl]-2-fluoro-8-azabicyclo[3.2.1]octan-3-yl]carbamate and 5-chloro-3-methyl-6-(4,4,5,5-tetramethyl-1,3,2-dioxaborolan-2-yl)-3,4-dihydroquinazolin-4-one and 1,4-dioxane as solvent |

TABLE 8-continued

| Compound | Compound Name | NMR or MS: [M + H]+ m/z | Procedure |
| --- | --- | --- | --- |
| | Benzyl N-[(1R,2S,3S,5S)-8-[3-(4-chloro-2-methyl-2H-indazol-5-yl)-5-(hydroxymethyl)-1-(oxan-2-yl)-1H-pyrazolo[3,4-b]pyrazin-6-yl]-2-fluoro-8-azabicyclo[3.2.1]octan-3-yl]carbamate | 675 | Prepared as General Procedure 2 using benzyl N-[(1R,2S,3S,5S)-2-fluoro-8-[5-(hydroxymethyl)-3-iodo-1-(oxan-2-yl)-1H-pyrazolo[3,4-b]pyrazin-6-yl]-8-azabicyclo[3.2.1]octan-3-yl]carbamate and 1,4-dioxane as solvent |
| (+/−) | rac-Benzyl N-[(1R,2S,3S,5S)-8-[3-(4-chloro-2-methyl-2H-indazol-5-yl)-5-(hydroxymethyl)-1-(oxan-2-yl)-1H-pyrazolo[3,4-b]pyrazin-6-yl]-2-fluoro-8-azabicyclo[3.2.1]octan-3-yl]carbamate | 675 | Prepared as General Procedure 2 using rac-benzyl N-[(1R,2S,3S,5S)-2-fluoro-8-[5-(hydroxymethyl)-3-iodo-1-(oxan-2-yl)-1H-pyrazolo[3,4-b]pyrazin-6-yl]-8-azabicyclo[3.2.1]octan-3-yl]carbamate and 1,4-dioxane as solvent |
| | tert-Butyl N-[(1R,2S,3S,5S)-8-[3-(3,4-dichloro-2-methyl-2H-indazol-5-yl)-5-(hydroxymethyl)-1-{[2-(trimethylsilyl)ethoxy]methyl}-1H-pyrazolo[3,4-b]pyrazin-6-yl]-2-fluoro-8-azabicyclo[3.2.1]octan-3-yl]carbamate | 721 | Prepared as General Procedure 2 using tert-butyl N-[(1R,2S,3S,5S)-2-fluoro-8-[5-(hydroxymethyl)-3-iodo-1-{[2-(trimethylsilyl)ethoxy]methyl}-1H-pyrazolo[3,4-b]pyrazin-6-yl]-8-azabicyclo[3.2.1]octan-3-yl]carbamate, (3,4-dichloro-2-methyl-2H-indazol-5-yl)boronic acid and 1,4-dioxane as solvent at 50° C. for 2 h, purified by KP-NH silica (gradient elution, 20-50% EtOAc/Petrol), |
| | tert-Butyl N-[(3R,4S)-1-[3-(4-chloro-2-methyl-2H-indazol-5-yl)-5-methyl-1-(oxan-2-yl)-1H-pyrazolo[3,4-b]pyrazin-6-yl]-3-fluoropiperidin-4-yl]carbamate | 599 | Prepared according to General Procedure 2, using tert-butyl N-[(3R,4S)-3-fluoro-1-[3-iodo-5-methyl-1-(oxan-2-yl)-1H-pyrazolo[3,4-b]pyrazin-6-yl]piperidin-4-yl]carbamate, heating at 70° C. for 2 h |

TABLE 8-continued

| Compound | Compound Name | NMR or MS: [M + H]+ m/z | Procedure |
|---|---|---|---|
| | Benzyl N-[(1S,2S,3S,5R)-8-[3-(4-chloro-2-methyl-2H-indazol-5-yl)-5-(hydroxymethyl)-1-(oxan-2-yl)-1H-pyrazolo[3,4-b]pyrazin-6-yl]-2-fluoro-8-azabicyclo[3.2.1]octan-3-yl]carbamate | 675 | Prepared as General Procedure 2, using benzyl N-[(1S,2S,3S,5R)-2-fluoro-8-[5-(hydroxymethyl)-3-iodo-1-(oxan-2-yl)-1H-pyrazolo[3,4-b]pyrazin-6-yl]-8-azabicyclo[3.2.1]octan-3-yl]carbamate |
| | tert-Butyl N-[(3R,4S)-1-[7-(4-chloro-3-methyl-2-oxo-2,3-dihydro-1,3-benzothiazol-5-yl)-5-(dimethylsulfamoyl)-5H-pyrrolo[2,3-b]pyrazin-3-yl]-3-fluoropiperidin-4-yl]carbamate | 640 | Prepared as General Procedure 2, using tert-butyl N-[(3R,4S)-1-[5-(dimethylsulfamoyl)-7-iodo-5H-pyrrolo[2,3-b]pyrazin-3-yl]-3-fluoropiperidin-4-yl]carbamate and 4-chloro-3-methyl-5-(4,4,5,5-tetramethyl-1,3,2-dioxaborolan-2-yl)-2,3-dihydro-1,3-benzothiazol-2-one |
| | tert-Butyl N-[(1S,2S,3S,5R)-8-[3-(3,4-dichloro-2-methyl-2H-indazol-5-yl)-5-(hydroxymethyl)-1-{[2-(trimethylsilyl)ethoxy]methyl}-1H-pyrazolo[3,4-b]pyrazin-6-yl]-2-fluoro-8-azabicyclo[3.2.1]octan-3-yl]carbamate | 721 | Prepared as General Procedure 2 using tert-butyl N-[(1S,2S,3S,5R)-2-fluoro-8-[5-(hydroxymethyl)-3-iodo-1-{[2-(trimethylsilyl)ethoxy]methyl}-1H-pyrazolo[3,4-b]pyrazin-6-yl]-8-azabicyclo[3.2.1]octan-3-yl]carbamate, (3,4-dichloro-2-methyl-2H-indazol-5-yl)boronic acid and 1,4-dioxane as solvent at 50° C. for 5 h, purified by Biotage KP-NH column chromatography (eluting 15% EtOAc/petrol to 50% EtOAc/petrol). |
| | tert-Butyl 8-[3-(3,4-dichloro-2-methyl-2H-indazol-5-yl)-5-(hydroxymethyl)-1-{[2-(trimethylsilyl)ethoxy]methyl}-1H-pyrazolo[3,4-b]pyrazin-6-yl]-3,8-diazabicyclo[3.2.1]octane-3-carboxylate | 689/691 | Prepared as General Procedure 2 using tert-butyl 8-[5-(hydroxymethyl)-3-iodo-1-{[2-(trimethylsilyl)ethoxy]methyl}-1H-pyrazolo[3,4-b]pyrazin-6-yl]-3,8-diazabicyclo[3.2.1]octane-3-carboxylate, 3,4-dichloro-2-methyl-5-(4,4,5,5-tetramethyl-1,3,2-dioxaborolan-2-yl)-2H-indazole, K3PO4 and 1,4-dioxane as solvent at 40° C. for 4 h. |

TABLE 8-continued

| Compound | Compound Name | NMR or MS: [M + H]+ m/z | Procedure |
|---|---|---|---|
| | tert-butyl N-[(1S,2S,3S,5R)-8-[3-(3-chloro-4-fluoro-2-methyl-2H-indazol-5-yl)-5-(hydroxymethyl)-1-{[2-(trimethylsilyl)ethoxy]methyl}-1H-pyrazolo[3,4-b]pyrazin-6-yl]-2-fluoro-8-azabicyclo[3.2.1]octan-3-yl]carbamate | 705 | Prepared as General Procedure 2 using tert-butyl N-[(1S,2S,3S,5R)-2-fluoro-8-[5-(hydroxymethyl)-3-iodo-1-{[2-(trimethylsilyl)ethoxy]methyl}-1H-pyrazolo[3,4-b]pyrazin-6-yl]-8-azabicyclo[3.2.1]octan-3-yl]carbamate, 3-chloro-4-fluoro-2-methyl-5-(4,4,5,5-tetramethyl-1,3,2-dioxaborolan-2-yl)-2H-indazole and 1,4-dioxane as solvent at 50° C. for 7 h, purified by Biotage KP-NH column chromatography eluting 15% EtOAc/petrol to 50% EtOAc/petrol. |
| | tert-Butyl N-[(1R,2S,3S,5S)-8-[3-(3-chloro-2-ethyl-4-fluoro-2H-indazol-5-yl)-5-(hydroxymethyl)-1-{[2-(trimethylsilyl)ethoxy]methyl}-1H-pyrazolo[3,4-b]pyrazin-6-yl]-2-fluoro-8-azabicyclo[3.2.1]octan-3-yl]carbamate | 719 | Prepared as general procedure 2 from 3-chloro-2-ethyl-4-fluoro-5-(4,4,5,5-tetramethyl-1,3,2-dioxaborolan-2-yl)-2H-indazole and tert-butyl N-[(1R,2S,3S,5S)-2-fluoro-8-[5-(hydroxymethyl)-3-iodo-1-{[2-(trimethylsilyl)ethoxy]methyl}-1H-pyrazolo[3,4-b]pyrazin-6-yl]-8-azabicyclo[3.2.1]octan-3-yl]carbamate using K$_3$PO$_4$ and bis(di-tert-butyl(4-dimethylaminophenyl)phosphine)dichloropalladium(II), heating at 50° C. for 3 h. |
| | tert-Butyl N-[endo-8-[3-(3,4-dichloro-2-methyl-2H-indazol-5-yl)-5-(hydroxymethyl)-1-{[2-(trimethylsilyl)ethoxy]methyl}-1H-pyrazolo[3,4-b]pyrazin-6-yl]-8-azabicyclo[3.2.1]octan-3-yl]carbamate | 703 | Prepared as general procedure 2 from (3,4-dichloro-2-methyl-2H-indazol-5-yl)boronic acid and tert-butyl N-[(1R,3S,5S)-8-[5-(hydroxymethyl)-3-iodo-1-{[2-(trimethylsilyl)ethoxy]methyl}-1H-pyrazolo[3,4-b]pyrazin-6-yl]-8-azabicyclo[3.2.1]octan-3-yl]carbamate using K$_3$PO$_4$ and bis(di-tert-butyl(4-dimethylaminophenyl)phosphine)dichloropalladium(II), heating at 50° C. for 3 h. |

Compounds of Table 9 set out below were prepared in an analogous manner to general procedure 3, using the corresponding aryl halides, with any significant variations indicated.

TABLE 9

| Compound | Compound Name | NMR or MS: [M + H]+ m/z | Procedure |
|---|---|---|---|
| | tert-Butyl N-[(1R,2S,3S,5S)-8-[3-(5-chloro-3-methoxyquinoxalin-6-yl)-5-(hydroxymethyl)-1-{[2-(trimethylsilyl)ethoxy]methyl}-1H-pyrazolo[3,4-b]pyrazin-6-yl]-2-fluoro-8-azabicyclo[3.2.1]octan-3-yl]carbamate | 715 | Prepared as general procedure 3, using 7-bromo-8-chloro-2-methoxyquinoxaline and tert-butyl N-[(1R,2S,3S,5S)-2-fluoro-8-[5-(hydroxymethyl)-3-iodo-1-{[2-(trimethylsilyl)ethoxy]methyl}-1H-pyrazolo[3,4-b]pyrazin-6-yl]-8-azabicyclo[3.2.1]octan-3-yl]carbamate |

Preparation 202:
5-Bromo-3-chloro-4-fluoro-2-methyl-2H-indazole

Method 1: endo-8-[7-(4-Chloro-2-methyl-2H-indazol-5-yl)-5H-pyrrolo[2,3-b]pyrazin-3-yl]-8-azabicyclo[3.2.1]octan-3-amine

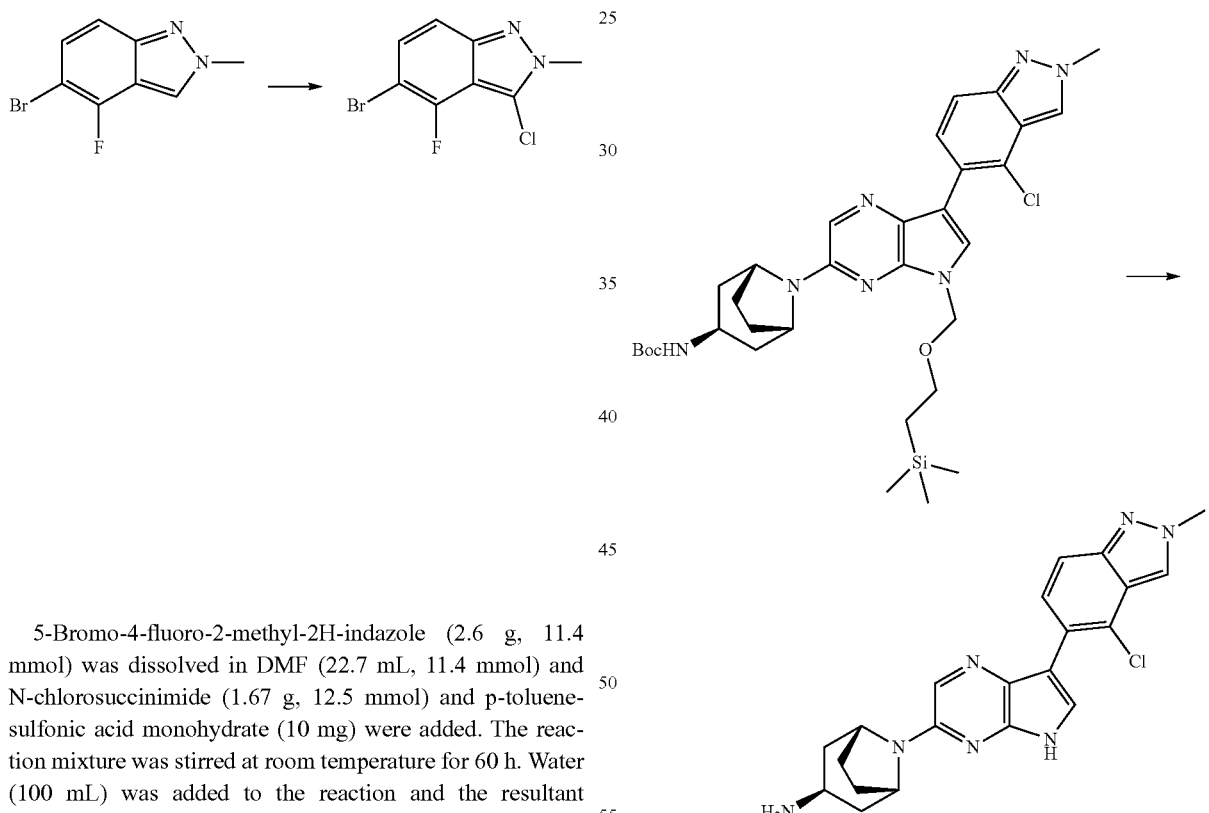

5-Bromo-4-fluoro-2-methyl-2H-indazole (2.6 g, 11.4 mmol) was dissolved in DMF (22.7 mL, 11.4 mmol) and N-chlorosuccinimide (1.67 g, 12.5 mmol) and p-toluenesulfonic acid monohydrate (10 mg) were added. The reaction mixture was stirred at room temperature for 60 h. Water (100 mL) was added to the reaction and the resultant precipitate was filtered. The crude solid was dry loaded onto silica gel and purified by chromatography on silica gel (gradient elution, 0-20% Hexane/EtOAc), to give the title compound (0.972 g). MS: [M+H]+=263.

General Procedures for Preparations of Compounds of Formula (I)

The following procedures are illustrative for general methods used in the preparation of Examples 1-44 and Examples 45-150 listed in Table 10 and Tables 11-17 below.

Trifluoroacetic acid (2.5 mL) was added to tert-butyl N-[endo-8-[7-(4-chloro-2-methyl-2H-indazol-5-yl)-5-{[2-(trimethylsilyl)ethoxy]methyl}-5H-pyrrolo[2,3-b]pyrazin-3-yl]-8-azabicyclo[3.2.1]octan-3-yl]carbamate (261 mg, 0.45 mmol) dissolved in DCM (2.5 mL) and the mixture was stirred for 1.0 h. Additional trifluoroacetic acid (1.0 mL) was added and the reaction stirred for 30 min. The reaction was concentrated in vacuo and to the residue dissolved in methanol (2.0 mL), ethylenediamine was added (2.0 mL). The reaction was stirred for 18 h, and the solid which formed was filtered, washed with methanol twice and dried in a vacuum oven, to give the title compound (0.09 g).

317

Method 2: endo-8-[7-(4-Chloro-2-methyl-2H-indazol-5-yl)-2-methyl-5H-pyrrolo[2,3-b]pyrazin-3-yl]-8-azabicyclo[3.2.1]octan-3-amine

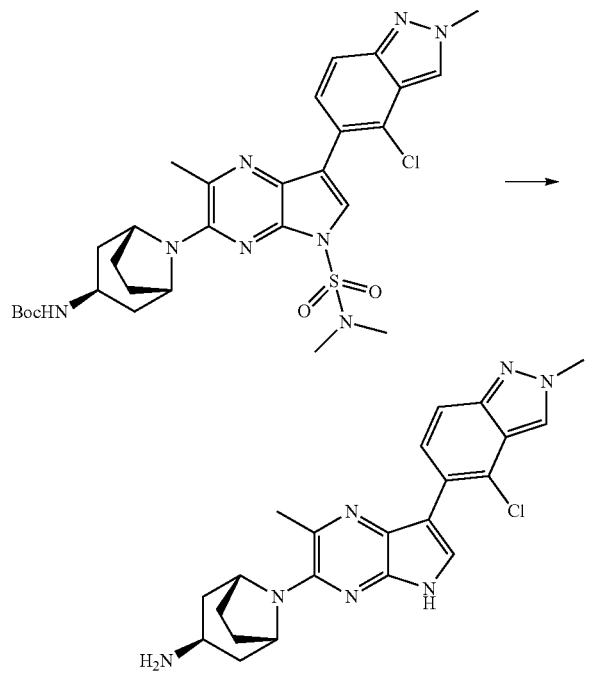

tert-Butyl N-[endo-8-[7-(4-chloro-2-methyl-2H-indazol-5-yl)-5-(dimethylsulfamoyl)-2-methyl-5H-pyrrolo[2,3-b]pyrazin-3-yl]-8-azabicyclo[3.2.1]octan-3-yl]carbamate was carefully dissolved in TFA (2 mL) containing water (0.1 mL). Trifluoromethanesulfonic acid (2 mL) was carefully added to the reaction mixture which was then heated to 90° C. for 2 h in a microwave. The reaction was diluted with EtOAc (50 mL), washed with sat. aq. sodium carbonate to remove the acids. The organic layer was dried by passing through a phase separator cartridge then concentrated under reduced pressure. The residue was purified by column chromatography on KP-NH column (gradient elution, 0-10%, EtOAc/methanol), to give the title compound (0.02 g).

Method 3: 7-[7-(4-Chloro-2-methyl-2H-indazol-5-yl)-5H-pyrrolo[2,3-b]pyrazin-3-yl]-1,7-diazaspiro[3.5]nonane

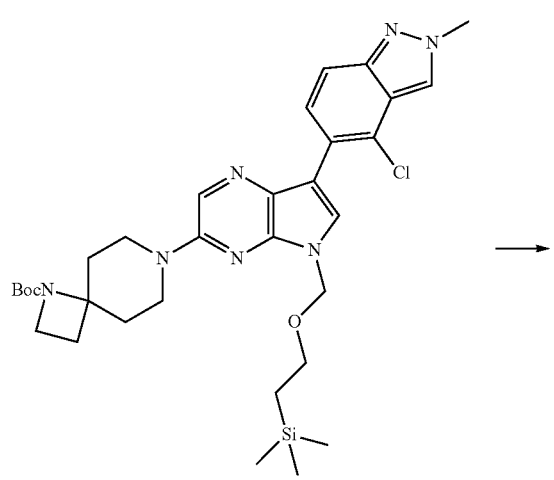

318

-continued

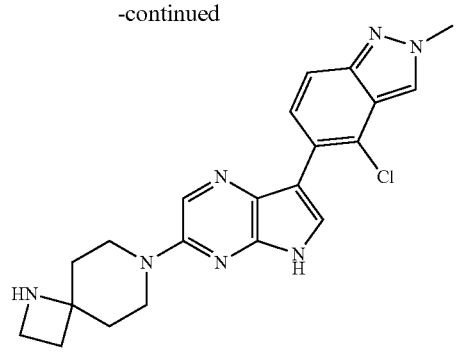

To the mixture of tert-butyl 7-[7-(4-chloro-2-methyl-2H-indazol-5-yl)-5H-pyrrolo[2,3-b]pyrazin-3-yl]-1,7-diazaspiro[3.5]nonane-1-carboxylate (130 mg, 0.26 mmol), 2,6-lutidine (0.089 mL, 0.77 mmol), and DCM (2.6 mL) was added TMSOTf (0.091 mL, 0.51 mmol) at 0° C. for 1.5 h. To the reaction mixture was additional added 2,6-lutidine (0.089 mL, 0.77 mmol) and TMSOTf (0.091 mL, 0.51 mmol) at 0° C. The mixture was stirred at 0° C. for 1.5 h. To the reaction mixture was additional added 2,6-lutidine (0.089 mL, 0.77 mmol) and TMSOTf (0.091 mL, 0.51 mmol) at 0° C. The mixture was stirred at 0° C. for 1.5 h. The reaction mixture was quenched with sat. NaHCO₃ aq. and filtered. The solid was purified by KP-NH column (EtOAc-MeOH=1:0 to 4:1) and triturated with DCM to give the title compound (64 mg).

Method 4: rac-(1S,2R,3R,5R)-8-[7-(4-Chloro-2-methyl-2H-indazol-5-yl)-5H-pyrrolo[2,3-b]pyrazin-3-yl]-2-fluoro-8-azabicyclo[3.2.1]octan-3-amine

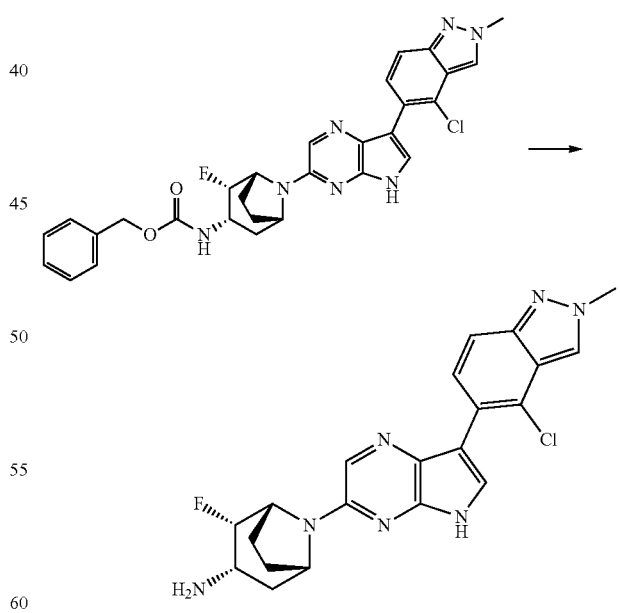

To a stirred suspension of Pd(OAc)₂ (7 mg, 0.03 mmol) in anhydrous DCM (0.66 mL) was added triethylamine (37 uL, 0.26 mmol) and Et₃SiH (0.211 mL, 1.32 mmol) at RT under N₂. After stirring at RT for 5 min, rac-benzyl N-[(1S,2R,3R,5R)-8-[7-(4-chloro-2-methyl-2H-indazol-5-yl)-5H-pyrrolo[2,3-b]pyrazin-3-yl]-2-fluoro-8-azabicyclo[3.2.1]octan- 3-yl]carbamate (37 mg, 0.07 mmol) in DCM (0.4 mL) was added at RT under N₂. The reaction mixture was stirred at RT for 1 h. The mixture was filtered and the filtrate was concentrated in vacuo. The residue was purified by column chromatography on KP-NH column (gradient elution, 0-5%, Methanol/EtOAc), to give the title compound (15 mg).

Method 5: 5-{3-[endo-3-Amino-8-azabicyclo[3.2.1]octan-8-yl]-5H-pyrrolo[2,3-b]pyrazin-7-yl}-4-chloro-2-methyl-2H-indazol-3-yl)methanol, methane sulfonic Acid Salt Method 6: (6-{3-[endo-3-Amino-8-azabicyclo[3.2.1]octan-8-yl]-5H-pyrrolo[2,3-b]pyrazin-7-yl}-7-chloro-1,3-benzothiazol-2-yl)methanol, hydrochloride Salt

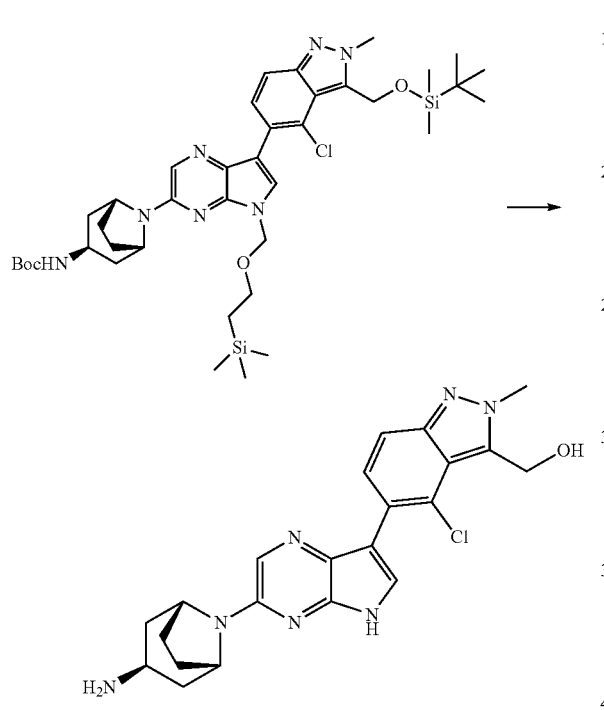

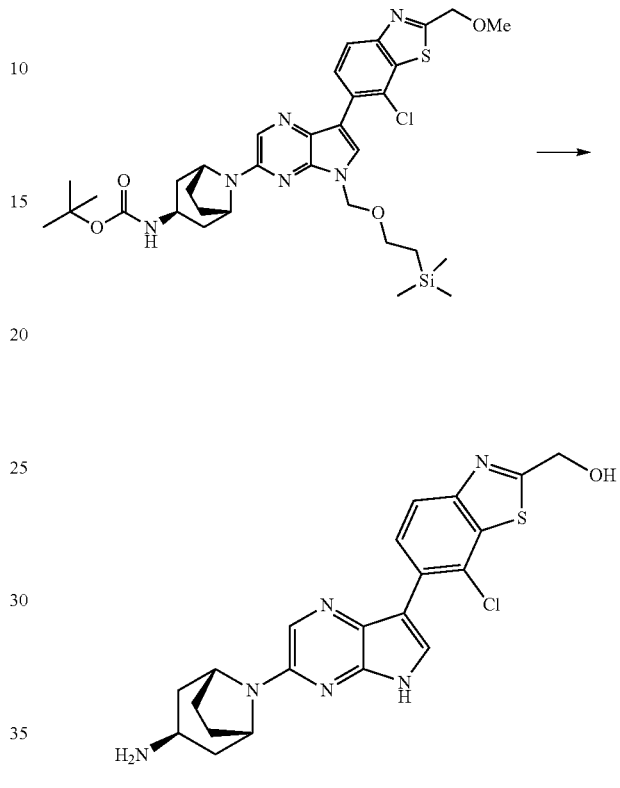

tert-Butyl N-[endo-8-[7-(3-{[(tert-butyldimethylsilyl)oxy]methyl}-4-chloro-2-methyl-2H-indazol-5-yl)-5-{[2-(trimethylsilyl)ethoxy]methyl}-5H-pyrrolo[2,3-b]pyrazin-3-yl]-8-azabicyclo[3.2.1]octan-3-yl]carbamate was dissolved in TFA/DCM (1:1, 3.89 mL) and was stirred for 2 h. The reaction was concentrated in vacuo and the residue was dissolved in methanol (1.0 mL). Ethylene diamine (1.0 mL) was added at 0° C. (ice bath). After stirring for 1 h, water was added dropwise and the solid which formed was filtered washing with water and a small amount of methanol. The solid was dried in a vacuum oven for 18 h. The solid (83 mg) was dissolved in THF (0.75 mL) and tetrabutylammonium fluoride in THF (1M, 0.20 mL) was added at RT. After stirring for 1 h additional tetrabutylammonium fluoride in THF (1M, 0.3 mL) added. After stirring for 30 min, the reaction was poured onto ice water and extracted with EtOAc (3×). The combined organic layers were washed with sat. brine solution (2×) and concentrated in vacuo. The residue was slurried in THF and filtered. The solid was dried in a vacuum oven, to give 5-{3-[endo-3-amino-8-azabicyclo[3.2.1]octan-8-yl]-5H-pyrrolo[2,3-b]pyrazin-7-yl}-4-chloro-2-methyl-2H-indazol-3-yl)methanol (16 mg). The solid was slurried in methanol (0.37 mL) and methanesulfonic acid in methanol (1M, 37 μL) was added, stirred for 5 min and concentrated in vacuo, to give the title compound (20 mg).

tert-Butyl N-[endo-8-{7-[7-chloro-2-(methoxymethyl)-1,3-benzothiazol-6-yl]-5-{[2-(trimethylsilyl)ethoxy]methyl}-5H-pyrrolo[2,3-b]pyrazin-3-yl}-8-azabicyclo[3.2.1]octan-3-yl]carbamate (40 mg, 0.06 mmol) was dissolved in DCM (2 mL), TFA (1 mL) was added and the reaction stirred at room temperature under nitrogen for 16 h. The solvents were evaporated and the reaction azeotroped with toluene (3×) to remove all TFA. The residue was re-dissolved in MeOH (2 mL) and ethylenediamine (1 mL) was added dropwise at 0° C. and the reaction stirred for 3 h. The reaction was evaporated and the residue partitioned between EtOAc and H₂O. The separated aq. layer was extracted with EtOAc (2×), and combined organics were washed with brine, dried (MgSO₄) and evaporated. The residue was re-dissolved in DCM (2 mL) and BBr₃ solution (1M in DCM, 0.26 mL, 0.26 mmol) was added dropwise and portionwise at 0° C. over a period of 2 h, and the reaction stirred at room temperature for 16 h. The reaction was quenched with H₂O and then evaporated. The residue was purified by column chromatography on reverse phase C18 silica gel (gradient elution, 5-95%, MeCN/H₂O+0.1% formic acid). Product fractions were treated with excess 2M aq. HCl and evaporated to give the title compound (4 mg).

321

Method 7: (1R,2S,3R,5S)-8-[7-(4-Chloro-2-methyl-2H-indazol-5-yl)-5H-pyrrolo[2,3-b]pyrazin-3-yl]-2-fluoro-8-azabicyclo[3.2.1]octan-3-amine

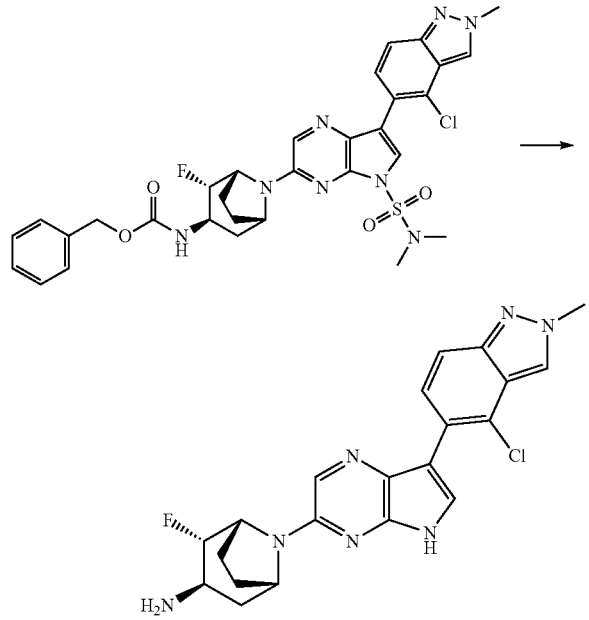 [SMILES: CN(C)S(=O)(=O)n1cc(-c2ccc3nn(C)cc3c2Cl)c2ncc(N3[C@H]4CC[C@@H]3[C@@H](F)[C@H](NC(=O)OCc3ccccc3)C4)nc21 ; Cn1cc2c(Cl)c(-c3c[nH]c4nc(N5[C@H]6CC[C@@H]5[C@@H](F)[C@H](N)C6)cnc34)ccc2n1]

Benzyl N-[(1R,2S,3R,5S)-8-[7-(4-chloro-2-methyl-2H-indazol-5-yl)-5-(dimethylsulfamoyl)-5H-pyrrolo[2,3-b]pyrazin-3-yl]-2-fluoro-8-azabicyclo[3.2.1]octan-3-yl]carbamate (141 mg, 0.21 mmol) in TFA/trifluoromethanesulfonic acid (1:1, 1.06 mL) was heated to 90-100° C. for 1 h. The reaction was cooled to RT and was poured into ice, then basified to pH 10 with solid $K_2CO_3$. The suspension was extracted with EtOAc (2×), filtered and concentrated in vacuo. The residue was purified by reverse phase column chromatography on C18 silica gel (gradient elution, 5-95%, (0.1%, TFA/MeCN)/(0.1%, TFA/water), to give the title compound (19 mg).

Method 8

(1R,2S,3S,5S)-8-[3-(4-Chloro-2-methyl-2H-indazol-5-yl)-5-methyl-1H-pyrazolo[3,4-b]pyrazin-6-yl]-2-fluoro-8-azabicyclo[3.2.1]octan-3-amine

322

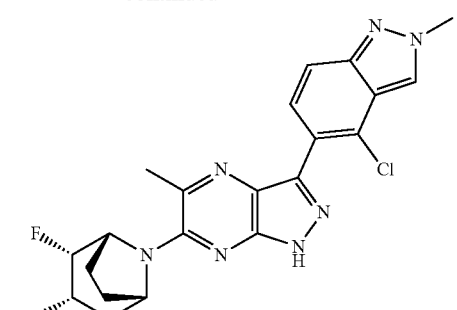

A mixture of benzyl N-[(1R,2S,3S,5S)-8-[3-(4-chloro-2-methyl-2H-indazol-5-yl)-5-methyl-1H-pyrazolo[3,4-b]pyrazin-6-yl]-2-fluoro-8-azabicyclo[3.2.1]octan-3-yl]carbamate (0.097 g, 0.18 mmol) in methanesulfonic acid (0.776 mL) was stirred at RT for 2 h. The mixture was added carefully to a rapidly stirred mixture of sat. aq. $Na_2CO_3$, water and $CHCl_3$/IPA (3:1) and the phases separated, and the aqueous phase was extracted with $CHCl_3$/IPA (3:1) (2×). The organic extract was washed with water, dried ($Na_2SO_4$), filtered and concentrated. The crude material was triturated with a 1:1 mixture of ted-butyl methyl ether and petrol, then dissolved in EtOH before an excess of HCl (2M in $Et_2O$) was added and the mixture was concentrated to give the title compound as the HCl salt (0.0681 g).

Method 9 endo-8-[7-(4-Chloro-2-methyl-2H-1,2,3-benzotriazol-5-yl)-5H-pyrrolo[2,3-b]pyrazin-3-yl]-8-azabicyclo[3.2.1]octan-3-amine

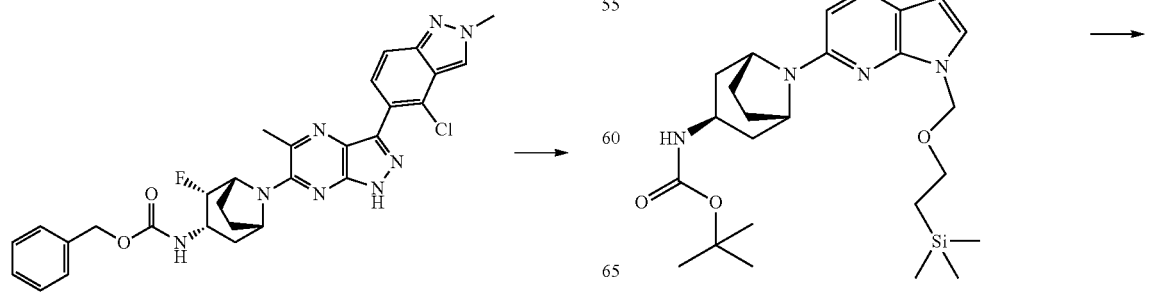

-continued

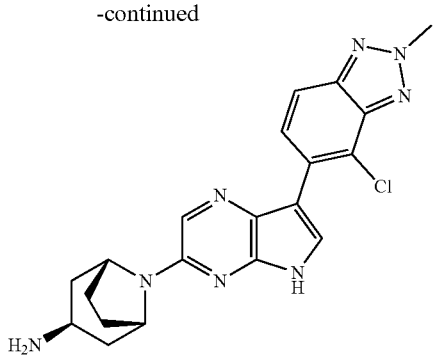

To a solution of tert-butyl N-[endo-8-[7-(4-chloro-2-methyl-2H-1,2,3-benzotriazol-5-yl)-5-{[2-(trimethylsilyl)ethoxy]methyl}-5H-pyrrolo[2,3-b]pyrazin-3-yl]-8-azabicyclo[3.2.1]octan-3-yl]carbamate (38.0 mg, 0.0594 mmol) in CHCl$_3$ (1.00 mL) was added TFA (0.500 mL, 6 mmol) at RT. The mixture was stirred at 60° C. for 1 h. The reaction was concentrated in vacuo and to the residue dissolved in MeOH (1.00 mL), ethylenediamine (0.200 mL, 3 mmol) was added. The reaction was stirred at RT for 18 h, and the solid which formed was filtered, washed with MeOH twice and dried in a vacuum oven, to give the title compound (22 mg).

Method 10

{6-[(1R,2S,3S,5S)-3-Amino-2-fluoro-8-azabicyclo[3.2.1]octan-8-yl]-3-(3,4-dichloro-2-methyl-2H-indazol-5-yl)-1H-pyrazolo[3,4-b]pyrazin-5-yl}methanol (Example 80)

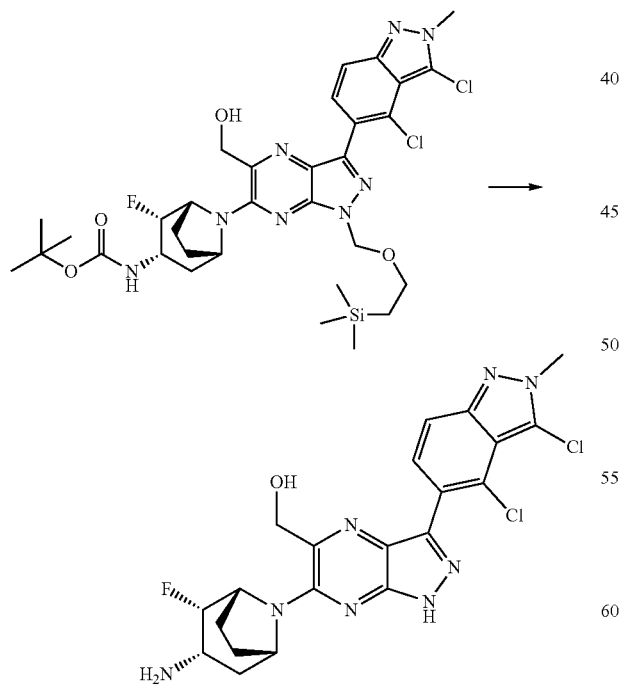

tert-Butyl N-[(1R,2S,3S,5S)-8-[3-(3,4-dichloro-2-methyl-2H-indazol-5-yl)-5-(hydroxymethyl)-1-{[2-(trimethylsilyl)ethoxy]methyl}-1H-pyrazolo[3,4-b]pyrazin-6-yl]-2-fluoro-8-azabicyclo[3.2.1]octan-3-yl]carbamate (0.184 g, 0.26 mmol) was dissolved in DCM (1.28 mL) and TFA (1.28 mL) was added dropwise. The reaction was stirred for 1.5 h at RT. Sat. aq. NaHCO$_3$ was added slowly until the aqueous solution reached a basic pH. The aqueous phase was diluted with DCM and EtOAc. Both the aqueous and organic layers were separated from a gum that had formed. The gum was dissolved in IPA and aq. ammonia (2.0 mL) was added. The solution was stirred for 10 min and then concentrated until a precipitate formed. The precipitate was filtered, washing with water, and dried in a vacuum oven at 40° C., to give the title compound (0.095 g).

Method 11

(3R,4S)-1-[3-(4-Chloro-2-methyl-2H-indazol-5-yl)-5-methyl-1H-pyrazolo[3,4-b]pyrazin-6-yl]-3-fluoropiperidin-4-amine

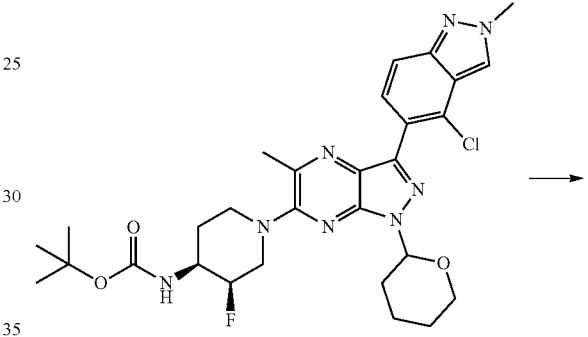

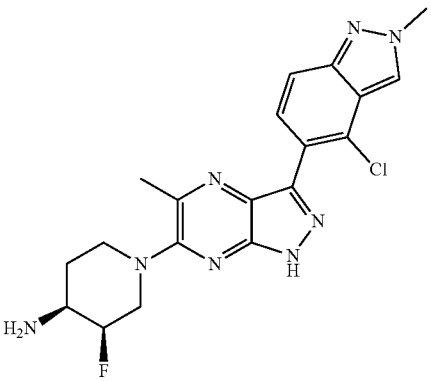

A solution of tert-butyl N-[(3R,4S)-1-[3-(4-chloro-2-methyl-2H-indazol-5-yl)-5-methyl-1-(oxan-2-yl)-1H-pyrazolo[3,4-b]pyrazin-6-yl]-3-fluoropiperidin-4-yl]carbamate (0.066 g, 0.11 mmol) in MeOH (3 mL) and HCl (4 M in 1,4-dioxane, 3 mL) was stirred for 2 h. The solvent was evaporated and the residue was triturated with Et$_2$O, to give the title compound (0.037 g).

Method 12

{6-[(1S,2S,3S,5R)-3-Amino-2-fluoro-8-azabicyclo[3.2.1]octan-8-yl]-3-(3,4-dichloro-2-methyl-2H-indazol-5-yl)-1H-pyrazolo[3,4-b]pyrazin-5-yl}methanol

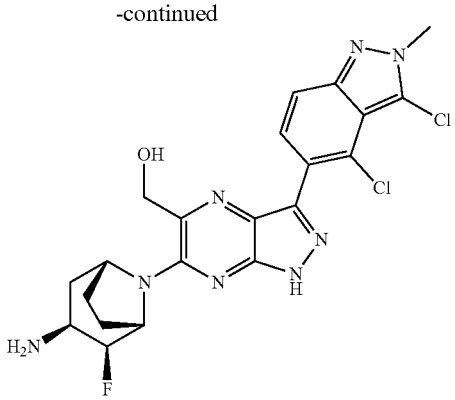

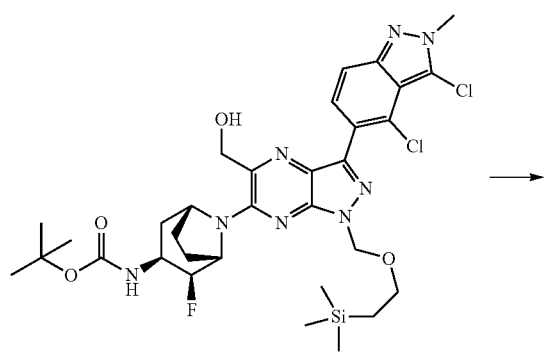

→

To a solution of tert-butyl N-[(1S,2S,3S,5R)-8-[3-(3,4-dichloro-2-methyl-2H-indazol-5-yl)-5-(hydroxymethyl)-1-{[2-(trimethylsilyl)ethoxy]methyl}-1H-pyrazolo[3,4-b]pyrazin-6-yl]-2-fluoro-8-azabicyclo[3.2.1]octan-3-yl] carbamate (0.4 g, 0.554 mmol) in DCM (6 mL) and water (0.24 mL) at RT was added methanesulfonic acid (0.72 mL, 11.1 mmol). The mixture was stirred rapidly for 30 minutes. The reaction mixture was added carefully to a rapidly stirred mixture of sat. aq. $Na_2CO_3$ solution and $CHCl_3$/IPA (3:1). The phases were separated, and the aqueous phase was further extracted into $CHCl_3$/IPA (3:1) (2×). The $CHCl_3$/IPA solution was stirred with 5 mL aq. ammonia solution for 1.5 h then 30% brine solution was added. The phases were separated, and the organic extract was dried ($Na_2SO_4$), filtered and concentrated. tert-Butyl methyl ether (10 mL) was added and rotated on the evaporator (no vac) for 30 minutes at 53° C. before the cooled solvent was removed by pipette; the process was repeated (1×). The solid was suspended in n-PrOH (15 vol) and heated at 100° C. for 1 h then cooled and the solid product was collected by filtration, washing with n-PrOH (10 vol). The solid was dried at 50° C. under vacuum, to give the title compound (198 mg).

TABLE 10

Examples 1-44

| Example | Structure | Name | NMR Data | MS Data | Method |
|---|---|---|---|---|---|
| 1 | 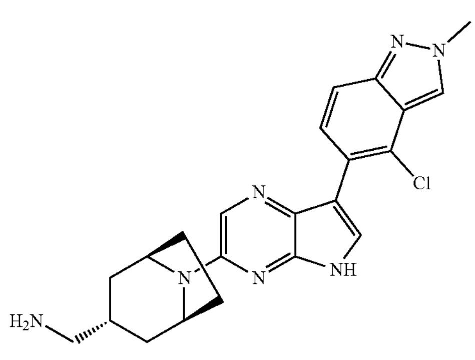 [SMILES: Cn1cc2c(Cl)c(-c3c[nH]c4nc(N5[C@@H]6CC[C@H]5C[C@H](CN)C6)cnc34)ccc2n1] | 1-[exo-8-[7-(4-chloro-2-methyl-2-indazol-5-yl)-5H-pyrrolo[2,3-b]pyrazin-3-yl]-8-azabicyclo[3.2.1]octan-3-yl]methanamine | $^1$H NMR (400 MHz, DMSO-$d_6$): 11.65 (1H, s), 8.44 (1H, s), 8.10 (1H, s), 7.95 (1H, d), 7.70 (1H, s), 7.61 (1H, d), 4.62 (2H, s), 4.21 (3H, s), 2.29 (2H, d), 2.07-1.91 (3H, m), 1.81 (2H, d), 1.57 (2H, d), 1.40 (2H, t). | 422 | 1, purified by preparative HPLC (TFA method) |

TABLE 10-continued

Examples 1-44

| Example | Structure | Name | NMR Data | MS Data | Method |
|---|---|---|---|---|---|
| 2 | 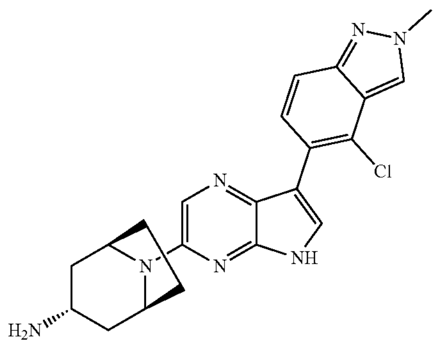 [SMILES: Cn1cc2c(Cl)c(-c3c[nH]c4nc(N5[C@@H]6CC[C@H]5C[C@H](N)C6)cnc34)ccc2n1] | exo-8-[7-(4-chloro-2-methyl-2H-indazol-5-yl)-5H-pyrrolo[2,3-b]pyrazin-3-yl]-8-azabicyclo[3.2.1]octan-3-amine | $^1$H NMR (400 MHz, DMSO-$d_6$): 11.70 (1H, s), 8.44 (1H, s), 8.13 (1H, s), 7.94 (1H, d), 7.71 (1H, s), 7.64-7.59 (1H, m), 4.59 (2H, s), 4.21 (3H, s), 3.23-3.15 (1H, m), 2.10-1.92 (2H, m), 1.90-1.75 (2H, m), 1.75-1.61 (2H, m), 1.49 (2H, t). | 408 | 1 |
| 3 | 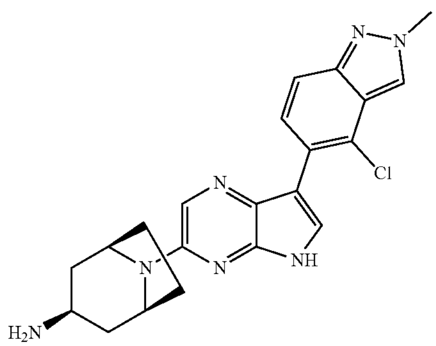 [SMILES: Cn1cc2c(Cl)c(-c3c[nH]c4nc(N5[C@@H]6CC[C@H]5C[C@@H](N)C6)cnc34)ccc2n1] | endo-8-[7-(4-chloro-2-methyl-2H-indazol-5-yl)-5H-pyrrolo[2,3-b]pyrazin-3-yl]-8-azabicyclo[3.2.1]octan-3-amine | $^1$H NMR (400 MHz, DMSO-$d_6$): 11.64 (1H, s), 8.44 (1H, s), 8.09 (1H, s), 7.94 (1H, d), 7.68 (1H, s), 7.61 (1H, d), 4.53 (2H, s), 4.21 (3H, s), 3.23-3.14 (1H, m), 2.41-2.36 (2H, m), 2.15-2.06 (2H, m), 1.96 (2H, s), 1.78-1.53 (2H, m), 1.44 (2H, d). | 408 | 1 |
| 4 | 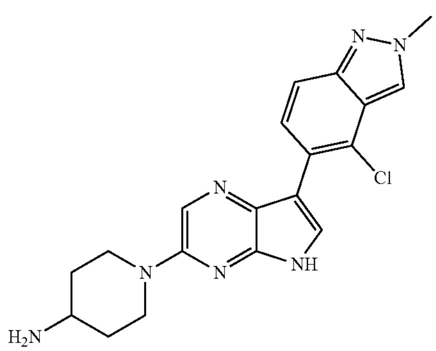 [SMILES: Cn1cc2c(Cl)c(-c3c[nH]c4nc(N5CCC(N)CC5)cnc34)ccc2n1] | 1-[7-(4-chloro-2-methyl-2H-indazol-5-yl)-5H-pyrrolo[2,3-b]pyrazin-3-yl]piperidin-4-amine | $^1$H NMR (400 MHz, DMSO-$d_6$): 11.63 (1H, s), 8.44 (1H, s), 8.25 (1H, s), 7.94 (1H, d), 7.73 (1H, s), 7.61 (1H, dd), 4.27-4.14 (5H, m), 3.05-2.95 (2H, m), 2.87-2.78 (1H, m), 1.80 (2H, d), 1.36-1.21 (2H, m). | 382 | 1 |
| 5 | 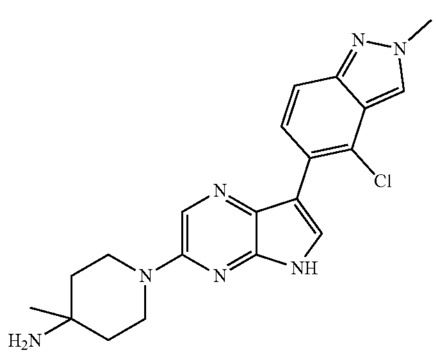 | 1-[7-(4-chloro-2-methyl-2H-indazol-5-yl)-5H-pyrrolo[2,3-b]pyrazin-3-yl]-4-methylpiperidin-4-amine | $^1$H NMR (400 MHz, DMSO-$d_6$): 11.63 (1H, s), 8.44 (1H, s), 8.25 (1H, s), 7.94 (1H, d), 7.72 (1H, s), 7.61 (1H, dd), 4.20 (3H, s), 3.78-3.68 (2H, m), 3.62-3.51 (2H, m), 1.57-1.41 (5H, m), 1.09 (3H, s). | 396 | 1 |

TABLE 10-continued

Examples 1-44

| Example | Structure | Name | NMR Data | MS Data | Method |
|---|---|---|---|---|---|
| 6 | 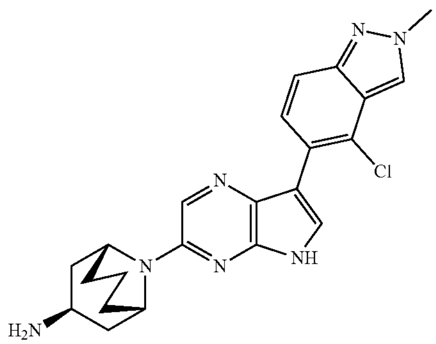 [SMILES: Cn1cc2c(Cl)c(-c3c[nH]c4nc(N5[C@@H]6CCC[C@H]5C[C@@H](N)C6)cnc34)ccc2n1] | endo-9-[7-(4-chloro-2-methyl-2H-indazol-5-yl)-5H-pyrrolo[2,3-b]pyrazin-3-yl]-9-azabicyclo[3.3.1]nonan-3-amine | $^1$H NMR (400 MHz, DMSO-d$_6$): 11.64-11.45 (1H, m), 8.44 (1H, s), 8.22 (1H, s), 7.97-7.91 (1H, m), 7.71-7.66 (1H, m), 7.60 (1H, dd), 4.80 (2H, d), 4.21 (3H, s), 2.48-2.37 (1H, m), 2.32-2.18 (2H, m), 2.18-2.03 (1H, m), 1.70-1.56 (2H, m), 1.56-1.38 (3H, m), 1.31-1.16 (2H, m). | 422 | 1 |
| 7 | 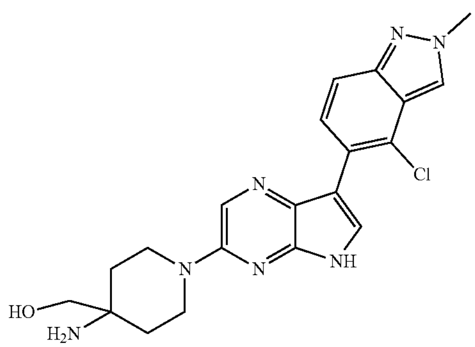 [SMILES: Cn1cc2c(Cl)c(-c3c[nH]c4nc(N5CCC(N)(CO)CC5)cnc34)ccc2n1] | {4-amino-1-[7-(4-chloro-2-methyl-2H-indazol-5-yl)-5H-pyrrolo[2,3-b]pyrazin-3-yl]piperidin-4-yl}methanol | $^1$H NMR (400 MHz, Me-d$_3$-OD): 8.32 (1H, s), 8.16 (1H, s), 7.76 (1H, d), 7.66 (1H, s), 7.60 (1H, d), 4.27 (3H, s), 4.04-3.95 (2H, m), 3.75 (2H, s), 3.63-3.53 (2H, m), 2.08-1.96 (2H, m), 1.92-1.81 (2H, m). | 412 | 1, purified by preparative HPLC (TFA method) |
| 8 | 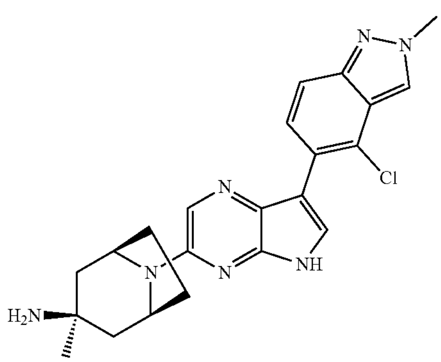 [SMILES: Cn1cc2c(Cl)c(-c3c[nH]c4nc(N5[C@@H]6CC[C@H]5C[C@@](C)(N)C6)cnc34)ccc2n1] | endo-8-[7-(4-chloro-2-methyl-2H-indazol-5-yl)-5H-pyrrolo[2,3-b]pyrazin-3-yl]-3-methyl-8-azabicyclo[3.2.1]octan-3-amine, methanesulfonic acid salt | $^1$H NMR (400 MHz, DMSO-d$_6$): 11.70 (1H, d), 8.45 (1H, s), 8.16 (1H, s), 7.94 (1H, d), 7.84-7.53 (5H, m), 4.72-4.60 (2H, m), 4.21 (3H, s), 2.31 (3H, s), 2.21-2.11 (2H, m), 2.09-2.02 (2H, m), 2.02-1.94 (2H, m), 1.94-1.83 (2H, m), 1.08 (3H, s). | 422 | 1 |
| 9 | 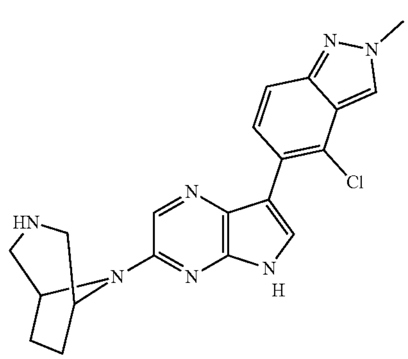 | 4-chloro-5-(3-{3,8-diazabicyclo[3.2.1]octan-8-yl}-5H-pyrrolo[2,3-b]pyrazin-7-yl)-2-methyl-2H-indazole | $^1$H NMR (400 MHz, Me-d$_3$-OD): 8.31 (1H, s), 8.02 (1H, s), 7.77 (1H, d), 7.62-7.57 (2H, m), 4.59 (2H, s), 4.26 (3H, s), 3.16 (2H, d), 2.70 (2H, d), 2.18-1.98 (4H, m). | 394 | 1, purified by preparative HPLC (Basic method) |

TABLE 10-continued

Examples 1-44

| Example | Structure | Name | NMR Data | MS Data | Method |
|---|---|---|---|---|---|
| 10 | 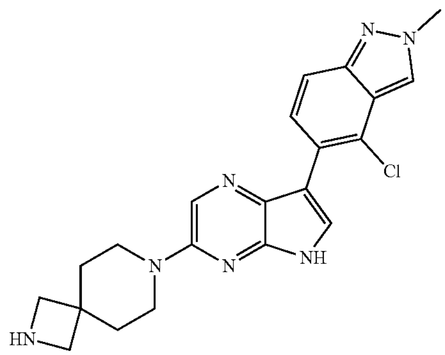 [SMILES: Cn1cc2c(Cl)c(-c3c[nH]c4nc(N5CCC6(CC5)CNC6)cnc34)ccc2n1] | 7-[7-(4-chloro-2-methyl-2H-indazol-5-yl)-5H-pyrrolo[2,3-b]pyrazin-3-yl]-2,7-diazaspiro[3.5]nonane | ¹H NMR (400 MHz, DMSO-d₆): 12.02-11.22 (1H, brs), 8.44 (1H, s), 8.26 (1H, s), 7.93 (1H, d), 7.74 (1H, s), 7.61 (1H, dd), 4.21 (3H, s), 3.57-3.46 (4H, m), 3.27 (4H, s), 1.86-1.75 (4H, m). | 408 | 1 |
| 11 | 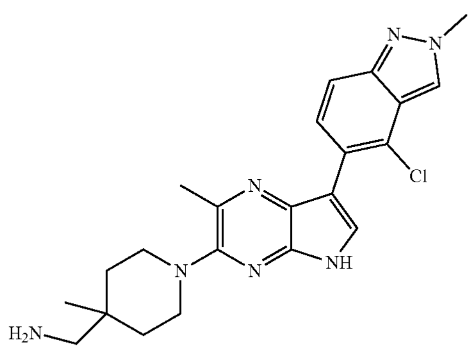 [SMILES: Cc1nc2c(-c3ccc4nn(C)cc4c3Cl)c[nH]c2nc1N1CCC(C)(CN)CC1] | 1-{1-[7-(4-chloro-2-methyl-2H-indazol-5-yl)-2-methyl-5H-pyrrolo[2,3-b]pyrazin-3-yl]-4-methylpiperidin-4-yl}methanamine, dihydrochloride salt | ¹H NMR (400 MHz, DMSO-d₆): 12.06 (1H, d), 8.47 (1H, s), 8.08 (3H, s), 7.92 (1H, t), 7.82 (1H, dd), 7.64 (1H, d), 4.22 (3H, s), 3.68-3.54 (2H, m), 3.54-3.39 (2H, m), 2.85-2.76 (2H, m), 2.56 (3H, s), 1.78-1.67 (2H, m), 1.59 (2H, d), 1.11 (3H, s). | 424 | 1, purified by preparative HPLC (TFA method) |
| 12 | 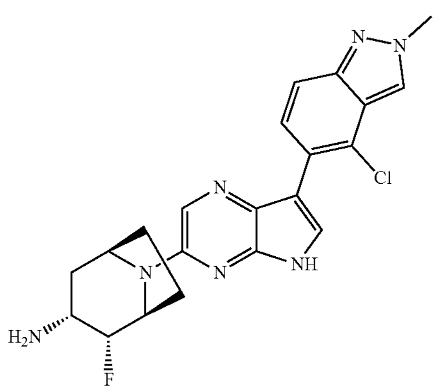 [SMILES: Cn1cc2c(Cl)c(-c3c[nH]c4nc(N5[C@@H]6CC[C@H]5[C@H](F)[C@H](N)C6)cnc34)ccc2n1] | rac-(1S,2R,3R,5R)-8-[7-(4-chloro-2-methyl-2H-indazol-5-yl)-5H-pyrrolo[2,3-b]pyrazin-3-yl]-2-fluoro-8-azabicyclo[3.2.1]octan-3-amine | ¹H NMR (400 MHz, DMSO-d₆): 11.62 (1H, s), 8.43 (1H, s), 8.17 (1H, s), 7.92 (1H, d), 7.66 (1H, d), 7.61 (1H, dd), 4.98 (1H, s), 4.66-4.47 (2H, m), 4.21 (3H, s), 3.11-3.00 (1H, m), 1.94 (2H, d), 1.86-1.57 (4H, m). | 426 | 4 |
| 13 | 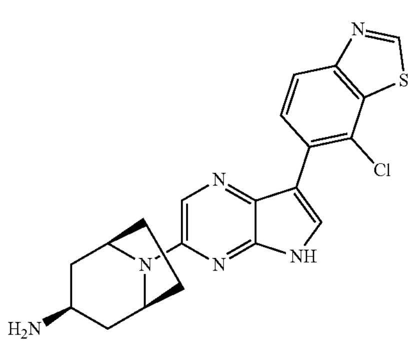 [SMILES: N[C@H]1C[C@H]2CC[C@@H](C1)N2c1cnc2c(-c3ccc4ncsc4c3Cl)c[nH]c2n1] | endo-8-[7-(7-chloro-1,3-benzothiazol-6-yl)-5H-pyrrolo[2,3-b]pyrazin-3-yl]-8-azabicyclo[3.2.1]octan-3-amine, methanesulfonic acid salt | ¹H NMR (400 MHz, DMSO-d₆): 11.88 (1H, d), 9.45 (1H, s), 8.28 (1H, d), 8.22 (1H, s), 8.14 (1H, d), 7.87 (1H, d), 7.68 (3H, s), 4.64 (2H, s), 3.22-3.14 (1H, m), 2.48-2.38 (2H, m), 2.30 (3H, s), 2.19-2.10 (2H, m), 1.99-1.89 (2H, m), 1.62 (2H, d). | 411 | 1 |

TABLE 10-continued

Examples 1-44

| Example | Structure | Name | NMR Data | MS Data | Method |
|---|---|---|---|---|---|
| 14 | 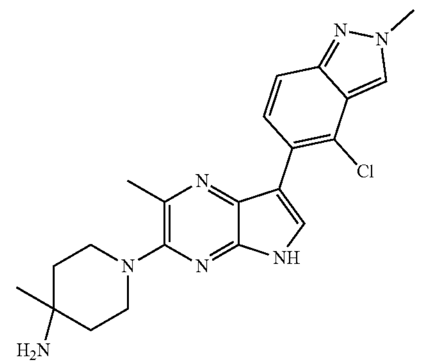 | 1-[7-(4-chloro-2-methyl-2H-indazol-5-yl)-2-methyl-5H-pyrrolo[2,3-b]pyrazin-3-yl]-4-methylpiperidin-4-amine | $^1$H NMR (400 MHz, Me-d$_3$-OD): 8.32 (1H, s), 7.82-7.72 (2H, m), 7.65-7.57 (1H, m), 4.27 (3H, s), 3.47-3.37 (2H, m), 3.26-3.13 (2H, m), 2.61 (3H, s), 1.95-1.85 (4H, m), 1.38 (3H, s). | 410 | 2 |
| 15 | 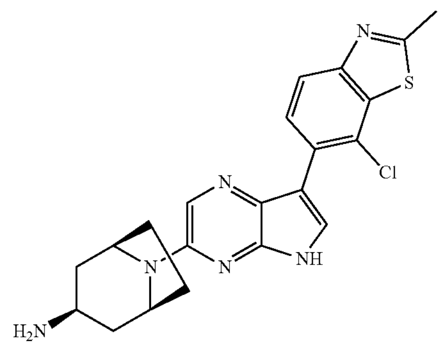 [SMILES: Cc1nc2ccc(-c3c[nH]c4nc(N5[C@@H]6CC[C@H]5C[C@@H](N)C6)cnc34)c(Cl)c2s1] | endo-8-[7-(7-chloro-2-methyl-1,3-benzothiazol-6-yl)-5H-pyrrolo[2,3-b]pyrazin-3-yl]-8-azabicyclo[3.2.1]octan-3-amine, methanesulfonic acid salt | $^1$H NMR (400 MHz, DMSO-d$_6$): 11.84 (1H, d), 8.23-8.16 (2H, m), 7.95 (1H, d), 7.83 (1H, d), 7.69 (3H, s), 4.64 (2H, s), 3.22-3.14 (1H, m), 2.85 (3H, s), 2.46-2.40 (2H, m), 2.30 (3H, s), 2.24-2.10 (2H, m), 2.04-1.88 (2H, m), 1.67-1.57 (2H, m). | 425 | 1 |
| 16 | 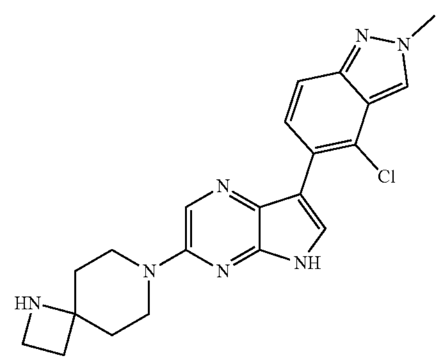 [SMILES: Cn1cc2c(Cl)c(-c3c[nH]c4nc(N5CCC6(CCN6)CC5)cnc34)ccc2n1] | 7-[7-(4-chloro-2-methyl-2H-indazol-5-yl)-5H-pyrrolo[2,3-b]pyrazin-3-yl]-1,7-diazaspiro[3.5]nonane | $^1$H NMR (400 MHz, DMSO-d$_6$): 11.66 (1H, s), 8.44 (1H, s), 8.27 (1H, s), 7.94 (1H, d), 7.74 (1H, s), 7.61 (1H, dd), 4.20 (3H, s), 3.74-3.63 (2H, m), 3.50-3.39 (2H, m), 3.36 (2H, t), 2.05 (2H, t), 1.86-1.74 (2H, m), 1.74-1.62 (2H, m). | 408 | 3 |
| 17 | 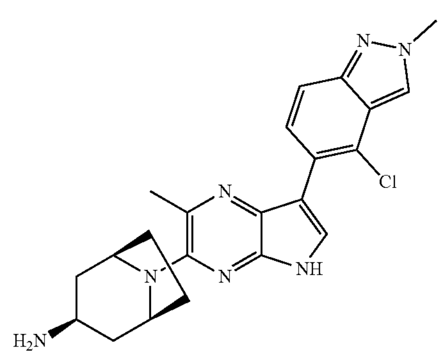 [SMILES: Cc1nc2c(-c3ccc4nn(C)cc4c3Cl)c[nH]c2nc1N1[C@@H]2CC[C@H]1C[C@@H](N)C2] | endo-8-[7-(4-chloro-2-methyl-2H-indazol-5-yl)-2-methyl-5H-pyrrolo[2,3-b]pyrazin-3-yl]-8-azabicyclo[3.2.1]octan-3-amine | $^1$H NMR (400 MHz, DMSO-d$_6$): 11.71 (1H, s), 8.44 (1H, s), 7.91 (1H, d), 7.76 (1H, s), 7.62 (1H, dd), 4.21 (3H, s), 4.17 (2H, s), 3.36-3.32 (1H, m), 2.56 (3H, s), 2.27-2.15 (4H, m), 1.94-1.88 (2H, m), 1.58 (2H, d). | 422 | 2 |

TABLE 10-continued

Examples 1-44

| Example | Structure | Name | NMR Data | MS Data | Method |
|---|---|---|---|---|---|
| 18 | 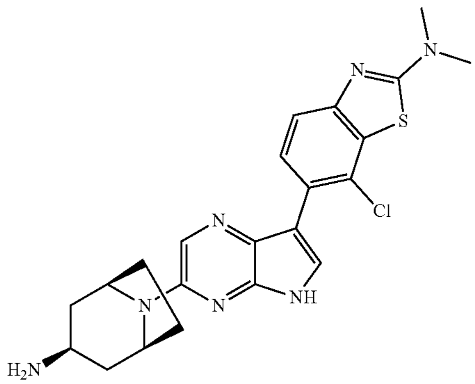 [SMILES: CN(C)c1nc2ccc(-c3c[nH]c4nc(N5[C@@H]6CC[C@H]5C[C@@H](N)C6)cnc34)c(Cl)c2s1] | 6-{3-[endo-3-amino-8-azabicyclo[3.2.1]octan-8-yl]-5H-pyrrolo[2,3-b]pyrazin-7-yl}-7-chloro-N,N-dimethyl-1,3-benzothiazol-2-amine, hydrochloride salt | $^1$H NMR (400 MHz, DMSO-d$_6$): 11.74 (1H, d), 8.17 (1H, s), 8.06-7.85 (4H, m), 7.70 (1H, d), 7.48 (1H, d), 4.64-4.62 (2H, m), 3.20 (6H, s), 3.17-3.11 (1H, m), 2.43-2.39 (2H, m), 2.18-2.08 (2H, m), 2.01-1.93 (2H, m), 1.71-1.61 (2H, m). | 454 | 1, purified by preparative HPLC (TFA method) |
| 19 | 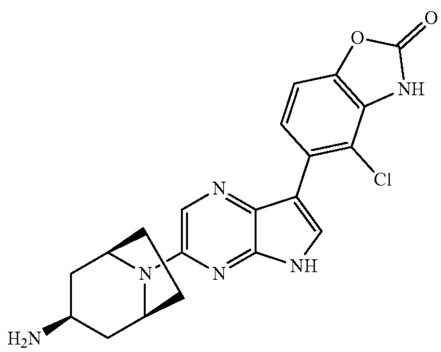 [SMILES: N[C@H]1C[C@H]2CC[C@@H](C1)N2c1cnc2c(-c3ccc4oc(=O)[nH]c4c3Cl)c[nH]c2n1] | 5-{3-[endo-3-amino-8-azabicyclo[3.2.1]octan-8-yl]-5H-pyrrolo[2,3-b]pyrazin-7-yl}-4-chloro-2,3-dihydro-1,3-benzoxazol-2-one, hydrochloride salt | $^1$H NMR (400 MHz, DMSO-d$_6$): 12.20 (1H, s), 11.75 (1H, d), 8.17 (1H, s), 7.84 (3H, d), 7.75-7.68 (2H, m), 7.35 (1H, d), 4.66-4.58 (2H, m), 3.22-3.13 (1H, m), 2.43-2.39 (2H, m), 2.16-2.10 (2H, m), 1.99-1.94 (2H, m), 1.67-1.61 (2H, m). | 411 | 1, purified by preparative HPLC (TFA method) |
| 20 | 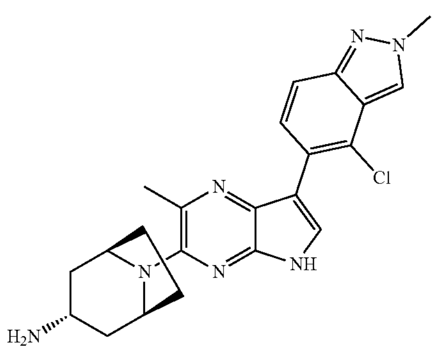 [SMILES: Cc1nc2c(-c3ccc4nn(C)cc4c3Cl)c[nH]c2nc1N1[C@@H]2CC[C@H]1C[C@H](N)C2] | exo-8-[7-(4-chloro-2-methyl-2H-indazol-5-yl)-2-methyl-5H-pyrrolo[2,3-b]pyrazin-3-yl]-8-azabicyclo[3.2.1]octan-3-amine | $^1$H NMR (400 MHz, DMSO-d$_6$): 11.72 (1H, s), 8.44 (1H, s), 7.91 (1H, d), 1.79-7.74 (1H, m), 7.63 (1H, dd), 4.24-4.19 (5H, m), 3.12-2.98 (1H, m), 2.57 (3H, s), 2.00-1.90 (2H, m), 1.86-1.78 (2H, m), 1.77-1.65 (2H, m), 1.58 (2H, t). | 422 | 2 |
| 21 | 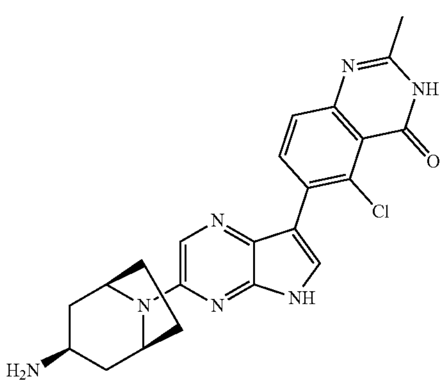 [SMILES: Cc1nc2ccc(-c3c[nH]c4nc(N5[C@@H]6CC[C@H]5C[C@@H](N)C6)cnc34)c(Cl)c2c(=O)[nH]1] | 6-{3-[endo-3-amino-8-azabicyclo[3.2.1]octan-8-yl]-5H-pyrrolo[2,3-b]pyrazin-7-yl}-5-chloro-2-methyl-3,4-dihydroquinazolin-4-one | $^1$H NMR (400 MHz, DMSO-d$_6$): 11.71 (1H, s), 8.25 (1H, d), 8.08 (1H, s), 7.73 (1H, s), 7.56 (1H, d), 4.53 (2H, s), 3.20-3.12 (1H, m), 2.40-2.33 (6H, m), 2.17-2.06 (2H, m), 2.00-1.94 (2H, m), 1.44 (2H, d). | 436 | 1, using DMF instead of DCM, purified by preparative HPLC (TFA method |

TABLE 10-continued

Examples 1-44

| Example | Structure | Name | NMR Data | MS Data | Method |
|---|---|---|---|---|---|
| 22 | 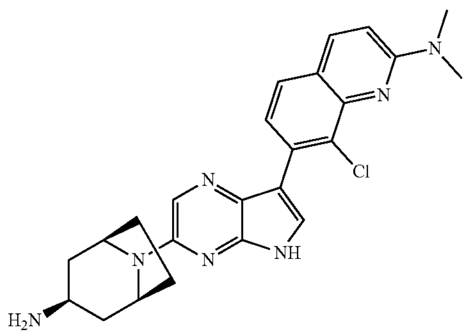 [SMILES: CN(C)c1ccc2ccc(-c3c[nH]c4nc(N5[C@@H]6CC[C@H]5C[C@@H](N)C6)cnc34)c(Cl)c2n1] | 7-{3-[endo-3-amino-8-azabicyclo[3.2.1]octan-8-yl]-5H-pyrrolo[2,3-b]pyrazin-7-yl}-8-chloro-N,N-dimethylquinolin-2-amine, hydrochloride salt | $^1$H NMR (400 MHz, DMSO-d$_6$): 8.23-8.10 (2H, m), 7.97 (1H, d), 7.95-7.87 (1H, m), 7.79 (1H, d), 7.24 (1H, d), 4.63 (2H, s), 3.31 (6H, s), 3.14 (1H, d), 2.44-2.38 (2H, m), 2.18-2.06 (2H, m), 1.98-1.86 (2H, m), 1.63 (2H, d). | 448 | 1, purified by column chromatography on KP-NH silica gel (gradient elution 0-10% methanol in EtOAc) |
| 23 | 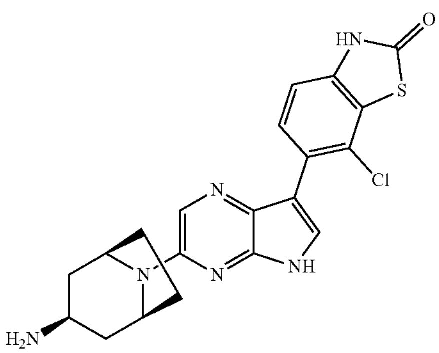 [SMILES: N[C@H]1C[C@H]2CC[C@@H](C1)N2c1cnc2c(-c3ccc4[nH]c(=O)sc4c3Cl)c[nH]c2n1] | 6-{3-[endo-3-amino-8-azabicyclo[3.2.1]octan-8-yl]-5H-pyrrolo[2,3-b]pyrazin-7-yl}-7-chloro-2,3-dihydro-1,3-benzothiazol-2-one, hydrochloride salt | $^1$H NMR (400 MHz, DMSO-d$_6$): 12.20 (1H, s), 11.76 (1H, d), 8.17 (1H, s), 7.93 (1H, d), 7.80 (3H, d), 7.71 (1H, d), 7.19 (1H, d), 4.63 (2H, s), 3.18 (1H, s), 2.46-2.38 (2H, m), 2.17-2.10 (2H, m), 1.98-1.92 (2H, m), 1.63 (2H, d). | 427 | 1 |
| 24 | 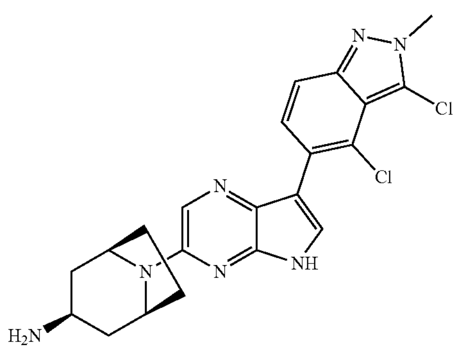 [SMILES: Cn1nc2ccc(-c3c[nH]c4nc(N5[C@@H]6CC[C@H]5C[C@@H](N)C6)cnc34)c(Cl)c2c1Cl] | endo-8-[7-(3,4-dichloro-2-methyl-2H-indazol-5-yl)-5H-pyrrolo[2,3-b]pyrazin-3-yl]-8-azabicyclo[3.2.1]octan-3-amine, methanesulfonic acid salt | $^1$H NMR (400 MHz, DMSO-d$_6$): 11.77 (1H, s), 8.18 (1H, s), 7.90 (1H, d), 7.77 (1H, d), 7.64 (1H, d), 7.46 (3H, s), 4.63 (2H, s), 4.15 (3H, s), 3.22-3.14 (1H, m), 2.44-2.38 (2H, m), 2.30 (3H, s), 2.18-2.09 (2H, m), 1.99-1.92 (2H, m), 1.61 (2H, d). | 442 | 1 |
| 25 | 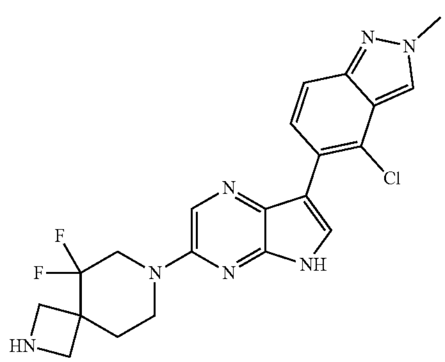 [SMILES: Cn1cc2c(Cl)c(-c3c[nH]c4nc(N5CCC6(CNC6)C(F)(F)C5)cnc34)ccc2n1] | 7-[7-(4-chloro-2-methyl-2H-indazol-5-yl)-5H-pyrrolo[2,3-b]pyrazin-3-yl]-5,5-difluoro-2,7-diazaspiro[3.5]nonane, hydrochloride salt | $^1$H NMR (400 MHz, Me-d$_3$-OD): 8.40 (1H, s), 8.29 (1H, s), 7.93 (1H, s), 7.66 (1H, dd), 7.60 (1H, d), 4.37 (2H, d), 4.29 (3H, s), 4.17 (2H, t), 4.09 (2H, d), 3.87-3.77 (2H, m), 2.37-2.30 (2H, m). | 444 | 2 |

TABLE 10-continued

Examples 1-44

| Example | Structure | Name | NMR Data | MS Data | Method |
|---|---|---|---|---|---|
| 26 | 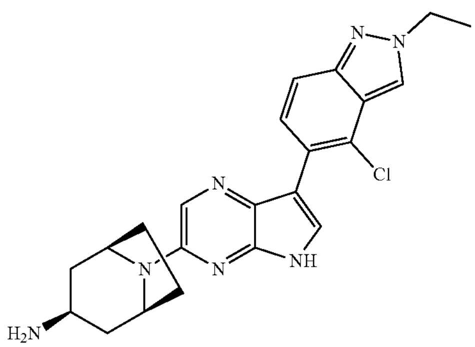 [SMILES: CCn1cc2c(Cl)c(-c3c[nH]c4nc(N5[C@@H]6CC[C@H]5C[C@@H](N)C6)cnc34)ccc2n1] | endo-8-[7-(4-chloro-2-ethyl-2H-indazol-5-yl)-5H-pyrrolo[2,3-b]pyrazin-3-yl]-8-azabicyclo[3.2.1]octan-3-amine, hydrochloride salt | $^1$H NMR (400 MHz, DMSO-d$_6$): 11.76 (1H, d), 8.49 (1H, s), 8.19 (1H, s), 8.04-7.85 (4H, m), 7.75 (1H, d), 7.63 (1H, dd), 4.63 (2H, s), 4.50 (2H, q), 3.17 (1H, s), 2.45-2.38 (2H, m), 2.16-2.10 (2H, m), 1.98 (2H, t), 1.73-1.62 (2H, m), 1.54 (3H, t). | 422 | 1 |
| 27 | 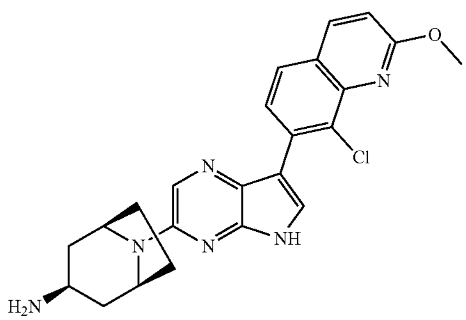 [SMILES: COc1ccc2ccc(-c3c[nH]c4nc(N5[C@@H]6CC[C@H]5C[C@@H](N)C6)cnc34)c(Cl)c2n1] | endo-8-[7-(8-chloro-2-methoxyquinolin-7-yl)-5H-pyrrolo[2,3-b]pyrazin-3-yl]-8-azabicyclo[3.2.1]octan-3-amine, hydrochloride salt | $^1$H NMR (400 MHz, DMSO-d$_6$): 11.91 (1H, s), 8.30 (1H, d), 8.26-8.12 (2H, m), 8.10-7.93 (4H, m), 7.90 (1H, d), 7.08 (1H, d), 4.64 (2H, s), 4.08 (3H, s), 3.18 (1H, s), 2.47-2.37 (2H, m), 2.22-2.07 (2H, m), 2.05-1.81 (2H, m), 1.69 (2H, d). | 435 | 1 |
| 28 | 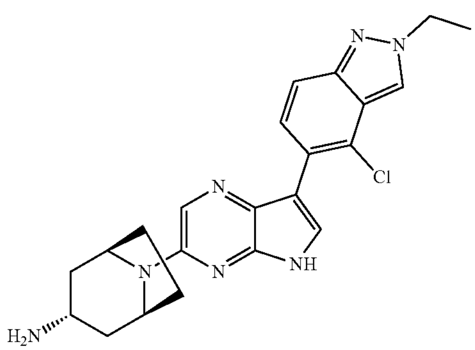 [SMILES: CCn1cc2c(Cl)c(-c3c[nH]c4nc(N5[C@@H]6CC[C@H]5C[C@H](N)C6)cnc34)ccc2n1] | exo-8-[7-(4-chloro-2-ethyl-2H-indazol-5-yl)-5H-pyrrolo[2,3-b]pyrazin-3-yl]-8-azabicyclo[3.2.1]octan-3-amine, hydrochloride salt | $^1$H NMR (400 MHz, Me-d$_3$-OD): 8.37 (1H, s), 8.07 (1H, s), 7.74 (1H, d), 7.65 (1H, s), 7.62 (1H, dd), 4.80 (2H, s), 4.55 (2H, q), 3.83-3.73 (1H, m), 2.29-2.19 (2H, m), 2.03-1.88 (6H, m), 1.65 (3H, t). | 422 | 1, purified by column chromatography on KP-NH silica gel (gradient elution 0-15% methanol in EtOAc) |
| 29 | 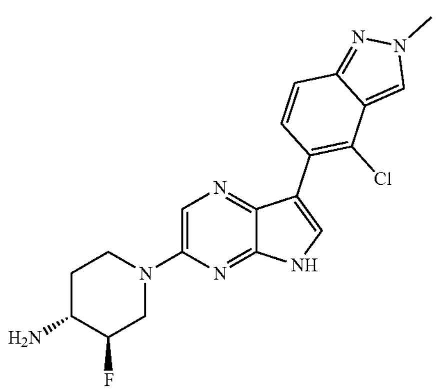 [SMILES: Cn1cc2c(Cl)c(-c3c[nH]c4nc(N5CC[C@@H](N)[C@H](F)C5)cnc34)ccc2n1] | (3R,4R)-1-[7-(4-chloro-2-methyl-2H-indazol-5-yl)-5H-pyrrolo[2,3-b]pyrazin-3-yl]-3-fluoropiperidin-4-amine, hydrochloride salt | $^1$H NMR (400 MHz, Me-d$_3$-OD): 8.48 (1H, s), 8.36 (1H, s), 8.06 (1H, s), 7.71 (1H, d), 7.51 (1H, d), 5.03-4.93 (1H, m), 4.71 (1H, s), 4.55 (1H, d), 4.31 (3H, s), 3.74-3.64 (1H, m), 3.28-3.20 (2H, m), 2.39-2.24 (1H, m), 1.90 (1H, d). | 400 | 1, purified by column chromatography on reverse phase C18 silica gel (gradient elution, 5-95%, MeCN/H$_2$O + 0.1% formic acid) |

TABLE 10-continued

Examples 1-44

| Example | Structure | Name | NMR Data | MS Data | Method |
|---|---|---|---|---|---|
| 30 | 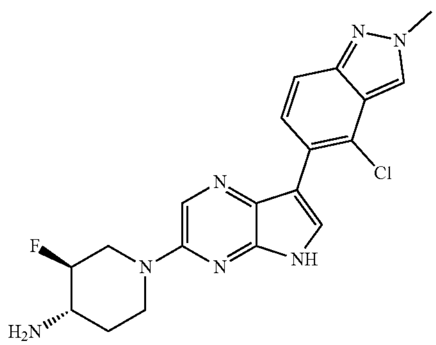 [SMILES: Cn1cc2c(Cl)c(-c3c[nH]c4nc(N5CC[C@H](N)[C@@H](F)C5)cnc34)ccc2n1] | (3S,4S)-1-[7-(4-chloro-2-methyl-2H-indazol-5-yl)-5H-pyrrolo[2,3-b]pyrazin-3-yl]-3-fluoropiperidin-4-amine, hydrochloride salt | $^1$H NMR (400 MHz, DMSO-d$_6$): 11.82 (1H, s), 8.45 (1H, s), 8.36 (1H, s), 7.96-7.78 (5H, m), 7.62 (1H, d), 4.90-4.47 (2H, m), 4.29 (1H, d), 4.21 (3H, s), 3.57-3.47 (1H, m), 3.16-3.04 (2H, m), 2.20-2.06 (1H, m), 1.74-1.60 (1H, m). | 400 | 1 |
| 31 | 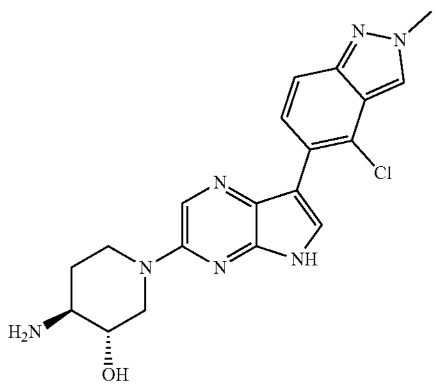 [SMILES: Cn1cc2c(Cl)c(-c3c[nH]c4nc(N5CC[C@H](N)[C@@H](O)C5)cnc34)ccc2n1] | (3S,4S)-4-amino-1-[7-(4-chloro-2-methyl-2H-indazol-5-yl)-5H-pyrrolo[2,3-b]pyrazin-3-yl]piperidin-3-ol, hydrochloride salt | $^1$H NMR (400 MHz, DMSO-d$_6$): 11.73 (1H, s), 8.45 (1H, s), 8.28 (1H, s), 8.03-7.66 (5H, m), 7.62 (1H, d), 5.78 (1H, s), 4.48 (1H, dd), 4.34 (1H, d), 4.21 (3H, s), 3.52 (1H, s), 3.12-2.92 (2H, m), 2.80-2.66 (1H, m), 2.13-1.90 (1H, m), 1.69-1.49 (1H, m). | 398 | 1, purified by column chromatography on KP-NH silica gel (gradient elution 0-20% methanol in EtOAc) |
| 32 | 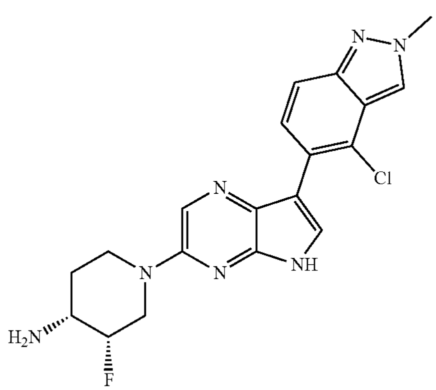 [SMILES: Cn1cc2c(Cl)c(-c3c[nH]c4nc(N5CC[C@@H](N)[C@@H](F)C5)cnc34)ccc2n1] | (3S,4R)-1-[7-(4-chloro-2-methyl-2H-indazol-5-yl)-5H-pyrrolo[2,3-b]pyrazin-3-yl]-3-fluoropiperidin-4-amine, hydrochloride salt | $^1$H NMR (400 MHz, Me-d$_3$-OD): 8.45 (1H, s), 8.31 (1H, s), 8.00 (1H, s), 7.70 (1H, dd), 7.50 (1H, d), 5.15 (1H, d), 5.06-4.94 (1H, m), 4.72 (1H, dd), 4.30 (3H, s), 3.86-3.70 (1H, m), 3.49 (1H, dd), 3.30-3.23 (1H, m), 2.19-2.06 (2H, m). | 400 | 1, purified by column chromatography on reverse phase C18 silica gel (gradient elution, 5-95%, MeCN/H$_2$O + 0.1% formic acid) |
| 33 | 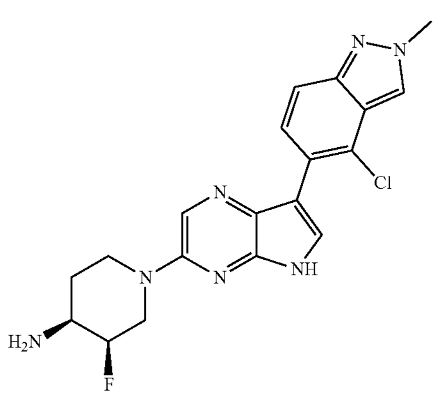 [SMILES: Cn1cc2c(Cl)c(-c3c[nH]c4nc(N5CC[C@H](N)[C@H](F)C5)cnc34)ccc2n1] | (3R,4S)-1-[7-(4-chloro-2-methyl-2H-indazol-5-yl)-5H-pyrrolo[2,3-b]pyrazin-3-yl]-3-fluoropiperidin-4-amine, hydrochloride salt | $^1$H NMR (400 MHz, DMSO-d$_6$): 11.81 (1H, d), 8.54 (3H, s), 8.46 (1H, s), 8.31 (1H, s), 7.89 (1H, d), 7.79 (1H, d), 7.62 (1H, dd), 5.12 (1H, d), 4.76 (1H, t), 4.46 (1H, d), 4.21 (3H, s), 3.73-3.54 (1H, m), 3.33 (1H, dd), 3.13-3.02 (1H, m), 2.01-1.82 (2H, m). | 400 | 1, purified by column chromatography on reverse phase C18 silica gel (gradient elution, 5-95%, MeCN/H$_2$O + 0.1% formic acid) |

TABLE 10-continued

Examples 1-44

| Example | Structure | Name | NMR Data | MS Data | Method |
|---|---|---|---|---|---|
| 34 | 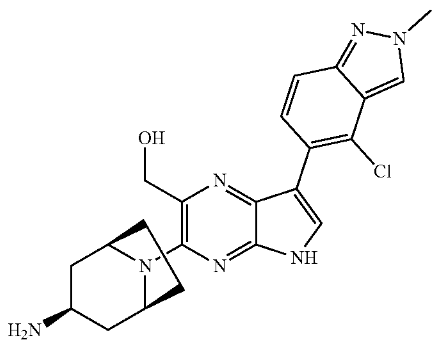 [SMILES: Cn1cc2c(Cl)c(-c3c[nH]c4nc(N5[C@@H]6CC[C@H]5C[C@@H](N)C6)c(CO)nc34)ccc2n1] | {3-[endo-3-amino-8-azabicyclo[3.2.1]octan-8-yl]-7-(4-chloro-2-methyl-2H-indazol-5-yl)-5H-pyrrolo[2,3-b]pyrazin-2-yl}methanol, hydrochloride salt | $^1$H NMR (400 MHz, Me-d$_3$-OD): 8.44 (1H, s), 8.13-8.07 (1H, m), 7.68 (1H, d), 7.57 (1H, d), 5.00 (2H, s), 4.59-4.47 (2H, m), 4.30 (3H, s), 3.66-3.56 (1H, m), 2.85-2.71 (2H, m), 2.39-2.26 (2H, m), 2.00-1.90 (2H, m), 1.84-1.75 (2H, m). | 438 | 1, purified by column chromatography on reverse phase C18 silica gel (gradient elution, 5-95%, MeCN/H$_2$O + 0.1% formic acid) |
| 35 | 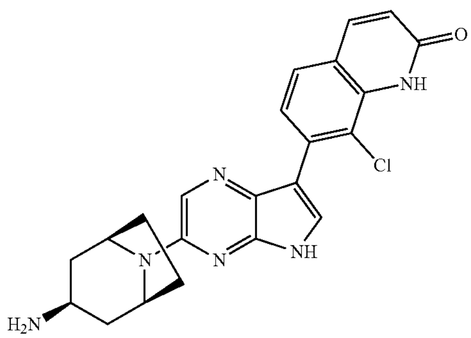 [SMILES: N[C@H]1C[C@H]2CC[C@@H](C1)N2c1cnc2c(-c3ccc4ccc(=O)[nH]c4c3Cl)c[nH]c2n1] | 7-{3-[endo-3-amino-8-azabicyclo[3.2.1]octan-8-yl]-5H-pyrrolo[2,3-b]pyrazin-7-yl}-8-chloro-1,2-dihydroquinolin-2-one, hydrochloride salt | $^1$H NMR (400 MHz, DMSO-d$_6$): 11.92 (1H, d), 10.80 (1H, s), 8.21 (1H, s), 8.04-7.83 (6H, m), 7.71 (1H, d), 6.57 (1H, d), 4.69-4.56 (2H, m), 3.22-3.12 (1H, m), 2.45-2.39 (2H, m), 2.20-2.08 (2H, m), 2.03-1.93 (2H, m), 1.67 (2H, d). | 421 | 1, purified by column chromatography on KP-NH silica gel (gradient elution 0-100% EtOAc/petrol) |
| 36 | 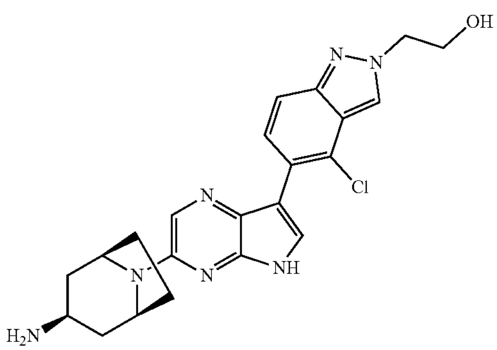 [SMILES: N[C@H]1C[C@H]2CC[C@@H](C1)N2c1cnc2c(-c3ccc4nn(CCO)cc4c3Cl)c[nH]c2n1] | 2-(5-{3-[endo-3-amino-8-azabicyclo[3.2.1]octan-8-yl]-5H-pyrrolo[2,3-b]pyrazin-7-yl}-3,4-dichloro-2H-indazol-2-yl)ethan-1-ol | $^1$H NMR (400 MHz, DMSO-d$_6$): 12.51-10.68 (1H, m), 8.10 (1H, s), 7.94 (1H, d), 7.71 (1H, s), 7.64 (1H, d), 5.13-4.87 (1H, m), 4.64-4.46 (4H, m), 3.91 (2H, t), 3.18-3.14 (1H, m), 2.42-2.32 (2H, m), 2.16-2.05 (2H, m), 2.05-1.92 (2H, m), 1.44 (2H, d). | 472 | 1 |
| 37 | 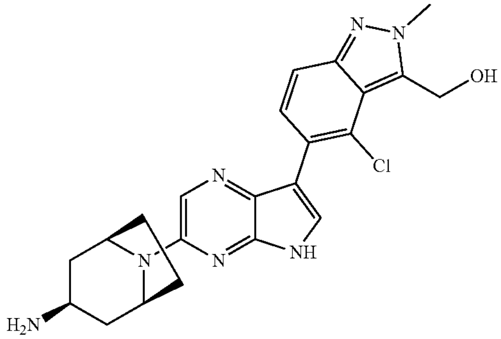 [SMILES: Cn1nc2ccc(-c3c[nH]c4nc(N5[C@@H]6CC[C@H]5C[C@@H](N)C6)cnc34)c(Cl)c2c1CO] | (5-{3-[endo-3-amino-8-azabicyclo[3.2.1]octan-8-yl]-5H-pyrrolo[2,3-b]pyrazin-7-yl}-4-chloro-2-methyl-2H-indazol-3-yl)methanol, methanesulfonic acid salt | $^1$H NMR (400 MHz, DMSO-d$_6$): 11.70 (1H, d), 8.17 (1H, s), 7.76 (1H, d), 7.69 (1H, d), 7.66-7.43 (4H, m), 5.39 (1H, t), 5.14 (2H, d), 4.66-4.59 (2H, m), 4.20 (3H, s), 3.21-3.16 (1H, m), 2.45-2.40 (2H, m), 2.30 (3H, s), 2.18-2.10 (2H, m), 2.02-1.92 (2H, m), 1.61 (2H, d). | 438 | 5 |

TABLE 10-continued

Examples 1-44

| Example | Structure | Name | NMR Data | MS Data | Method |
|---|---|---|---|---|---|
| 38 | 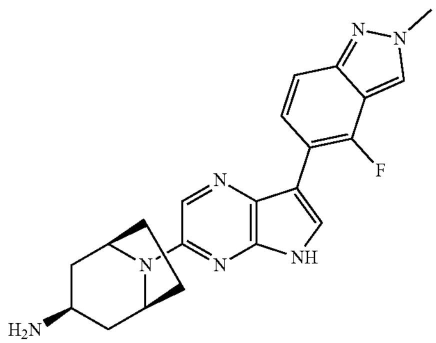 [SMILES: Cn1cc2c(F)c(-c3c[nH]c4nc(N5[C@@H]6CC[C@H]5C[C@@H](N)C6)cnc34)ccc2n1] | endo-8-[7-(4-fluoro-2-methyl-2H-indazol-5-yl)-5H-pyrrolo[2,3-b]pyrazin-3-yl]-8-azabicyclo[3.2.1]octan-3-amine | $^1$H NMR (400 MHz, DMSO-d$_6$): 11.70-11.60 (1H, m), 8.48 (1H, t), 8.31 (1H, s), 8.15 (1H, s), 7.91 (1H, d), 7.66 (1H, d), 7.52-7.41 (2H, m), 4.60-4.53 (2H, m), 4.17 (3H, s), 3.18-3.12 (1H, m), 2.28-2.14 (4H, m), 2.06-1.99 (2H, m), 1.53 (2H, d). | 392 | 1, purified by column chromatography on SNAP Isolute NH$_2$ (gradient elution, 0-8%, MeOH/CHCl$_3$) then preparative HPLC (Formic acid method) |
| 39 | 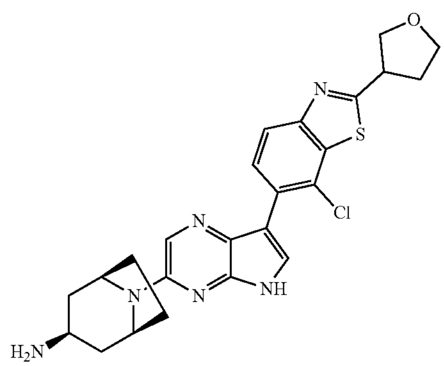 [SMILES: N[C@H]1C[C@H]2CC[C@@H](C1)N2c1cnc2c(-c3ccc4nc(C5CCOC5)sc4c3Cl)c[nH]c2n1] | endo-8-{7-[7-chloro-2-(oxolan-3-yl)-1,3-benzothiazol-6-yl]-5H-pyrrolo[2,3-b]pyrazin-3-yl}-8-azabicyclo[3.2.1]octan-3-amine, dihydrochloride salt | $^1$H NMR (400 MHz, DMSO-d$_6$): 11.91 (1H, d), 8.39 (1H, s), 8.32-8.18 (2H, m), 8.10 (3H, d), 7.99 (1H, d), 7.84 (1H, d), 4.72-4.58 (2H, m), 4.12 (1H, dd), 4.07-3.93 (3H, m), 3.90-3.80 (1H, m), 3.24-3.13 (1H, m), 2.49-2.36 (3H, m), 2.35-2.21 (1H, m), 2.20-1.94 (4H, m), 1.79-1.65 (2H, m). | 481 | 1 |
| 40 | 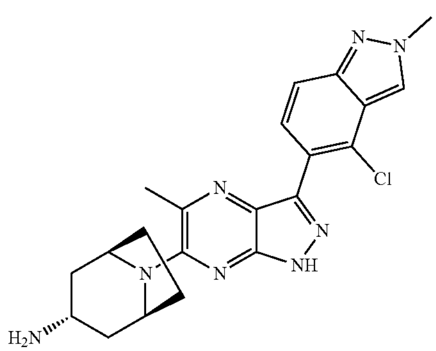 [SMILES: Cc1nc2c(-c3ccc4nn(C)cc4c3Cl)n[nH]c2nc1N1[C@@H]2CC[C@H]1C[C@H](N)C2] | exo-8-[3-(4-chloro-2-methyl-2H-indazol-5-yl)-5-methyl-1H-pyrazolo[3,4-b]pyrazin-6-yl]-8-azabicyclo[3.2.1]octan-3-amine, dihydrochloride salt | $^1$H NMR (400 MHz, Me-d$_3$-OD): 8.46 (1H, s), 7.68 (1H, dd), 7.61 (1H, d), 4.69 (2H, s), 4.31 (3H, s), 3.80-3.70 (1H, m), 2.70 (3H, s), 2.31-2.19 (2H, m), 2.14-2.01 (4H, m), 1.96-1.90 (2H, m). | 423 | 1, using DMF instead of DCM |
| 41 | 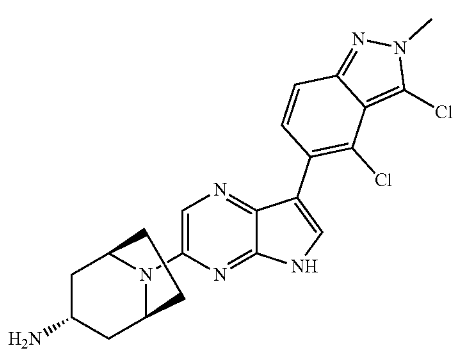 [SMILES: Cn1nc2ccc(-c3c[nH]c4nc(N5[C@@H]6CC[C@H]5C[C@H](N)C6)cnc34)c(Cl)c2c1Cl] | exo-8-[7-(3,4-dichloro-2-methyl-2H-indazol-5-yl)-5H-pyrrolo[2,3-b]pyrazin-3-yl]-8-azabicyclo[3.2.1]octan-3-amine, hydrochloride salt | $^1$H NMR (400 MHz, Me-d$_3$-OD): 8.21 (1H, s), 7.96 (1H, s), 7.67 (1H, d), 7.50 (1H, d), 4.91-4.86 (2H, m), 4.23 (3H, s), 3.91-3.78 (1H, m), 2.32-2.20 (2H, m), 2.13-2.05 (2H, m), 2.05-1.98 (2H, m), 1.98-1.89 (2H, m). | 442 | 1, purified by column chromatography on KP-NH silica gel (gradient elution 0-15% methanol in EtOAc) |

TABLE 10-continued

Examples 1-44

| Example | Structure | Name | NMR Data | MS Data | Method |
|---|---|---|---|---|---|
| 42 | 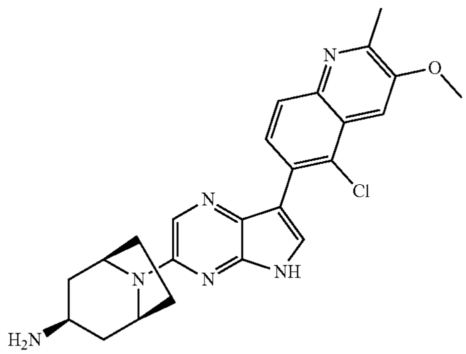 [SMILES: COc1cc2c(Cl)c(-c3c[nH]c4nc(N5[C@@H]6CC[C@H]5C[C@@H](N)C6)cnc34)ccc2nc1C] | endo-8-[7-(5-chloro-3-methoxy-2-methylquinolin-6-yl)-5H-pyrrolo[2,3-b]pyrazin-3-yl]-8-azabicyclo[3.2.1]octan-3-amine | $^1$H NMR (400 MHz, DMSO-$d_6$): 8.25 (1H, d), 8.12 (1H, s), 7.91 (1H, d), 7.84 (1H, s), 7.80 (1H, s), 4.54 (2H, s), 4.03 (3H, s), 3.20-3.15 (1H, m), 2.60 (3H, s), 2.42-2.35 (2H, m), 2.16-2.03 (2H, m), 2.03-1.88 (2H, m), 1.60 (2H, s), 1.45 (2H, d). | 449 | 1 |
| 43 | 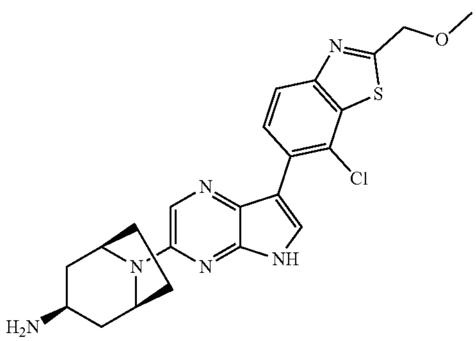 [SMILES: COCc1nc2ccc(-c3c[nH]c4nc(N5[C@@H]6CC[C@H]5C[C@@H](N)C6)cnc34)c(Cl)c2s1] | endo-8-{7-[7-chloro-2-(methoxymethyl)-1,3-benzothiazol-6-yl]-5H-pyrrolo[2,3-b]pyrazin-3-yl}-8-azabicyclo[3.2.1]octan-3-amine, hydrochloride salt | $^1$H NMR (400 MHz, DMSO-$d_6$): 11.89 (1H, d), 8.27-8.16 (2H, m), 8.09-7.88 (4H, m), 7.84 (1H, d), 4.89 (2H, s), 4.67-4.60 (2H, m), 3.50 (3H, s), 3.23-3.12 (1H, m), 2.46-2.38 (2H, m), 2.18-2.08 (2H, m), 2.03-1.94 (2H, m), 1.73-1.58 (2H, m). | 455 | 1, purified by column chromatography on reverse phase C18 silica gel (gradient elution 5-95% water methanol + 0.1% formic acid) |
| 44 | 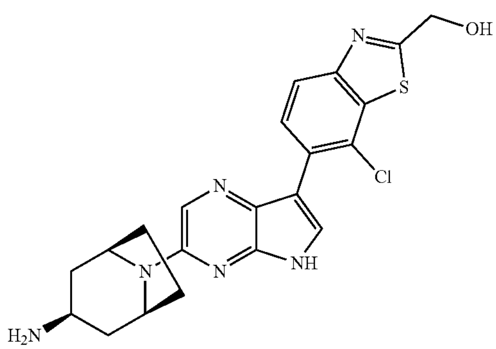 [SMILES: N[C@H]1C[C@H]2CC[C@@H](C1)N2c1cnc2c(-c3ccc4nc(CO)sc4c3Cl)c[nH]c2n1] | (6-{3-[endo-3-amino-8-azabicyclo[3.2.1]octan-8-yl]-5H-pyrrolo[2,3-b]pyrazin-7-yl}-7-chloro-1,3-benzothiazol-2-yl)methanol, hydrochloride salt | $^1$H NMR (400 MHz, DMSO-$d_6$): 11.89 (1H, d), 8.22-8.17 (2H, m), 8.07-7.98 (3H, m), 7.96 (1H, d), 7.83 (1H, d), 7.80-7.39 (1H, m), 4.89 (2H, s), 4.67-4.59 (2H, m), 3.22-3.13 (1H, m), 2.45-2.39 (2H, m), 2.18-2.07 (2H, m), 2.03-1.95 (2H, m), 1.74-1.64 (2H, m). | 441 | 6 |

By following methods similar and/or analogous to those described for general procedures for preparations of compounds of Formula (I) (e.g. methods 1-12), the compounds set out in Table 10 were prepared from the corresponding N-Boc, N-CBz, N—SO$_2$NMe$_2$, SEM or 2-oxanyl protected derivatives, with any significant variations indicated. The title compounds were either isolated directly as the free base or as the appropriate salt without further purification, or purified for example using mass-directed preparative HPLC, chromatography, crystallization or trituration and converted to the appropriate salt.

Example 45. endo-8-{7-[4-Chloro-2-(2-methoxyethyl)-2H-indazol-5-yl]-5H-pyrrolo[2,3-b]pyrazin-3-yl}-8-azabicyclo[3.2.1]octan-3-amine

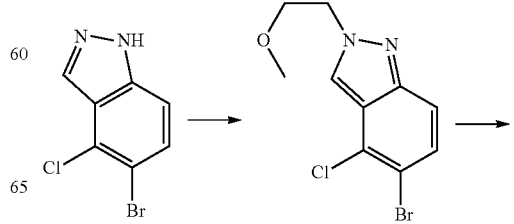

349
-continued

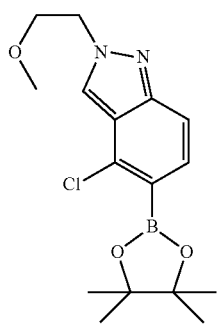

5-Bromo-4-chloro-2-(2-methoxyethyl)-2H-indazole

To a suspension of 5-bromo-4-chloro-1H-indazole (1.0 g, 4.7 mmol) and potassium carbonate (1.79 g, 13 mmol) in DMSO (5 ml) was added 1-bromo-2-methoxy-ethane (0.83 ml, 8.6401 mmol) at room temperature. After stirring at the same temperature over weekend, the mixture was diluted with EtOAc and washed with water. The organic phase was washed with brine, dried over $Na_2SO_4$, filtered, and concentrated in vacuo. Column chromatography (SNAP Ultra 50 g, gradient elution, 0-100% EtOAc in hexane) gave the title compound (0.45 g, 1.5 mmol, 36%) as a brown solid. MS: [M+H]+=289, 291, 293

4-Chloro-2-(2-methoxyethyl)-5-(4,4,5,5-tetramethyl-1,3,2-dioxaborolan-2-yl)-2H-indazole To a suspension of 5-bromo-4-chloro-2-(2-methoxyethyl)-2H-indazole (0.45 g, 1.5 mmol) in 1,4-dioxane (10 mL) was added Potassium acetate (0.30 g, 3.13 mmol), 4,4,4',4',5,5,5',5'-octamethyl-2,2'-bi(1,3,2-dioxaborolane) (0.59 g, 2.3 mmol) and 1,1'-Bis(diphenylphosphino)ferrocene-palladium(II)dichloride dichloromethane complex (0.12 g, 0.15 mmol) at room temperature. After stirring at 120° C. for 4 h, the mixture was diluted with EtOAc and filtered through a pad of Hyflo Super-Cel. The filtrate was concentrated in vacuo. Column chromatography (SNAP Ultra 25 g, gradient elution, 0-100% EtOAc in hexane) gave the title compound (0.68 g) as a pale brown oil. The material was not pure but was used without further purification. MS: [M+H]+=337, 339.

350 tert-Butyl (endo-8-(7-(4-chloro-2-(2-methoxyethyl)-2H-indazol-5-yl)-5-((2-(trimethylsilyl)ethoxy)methyl)-5H-pyrrolo[2,3-b]pyrazin-3-yl)-8-azabicyclo[3.2.1]octan-3-yl)carbamate

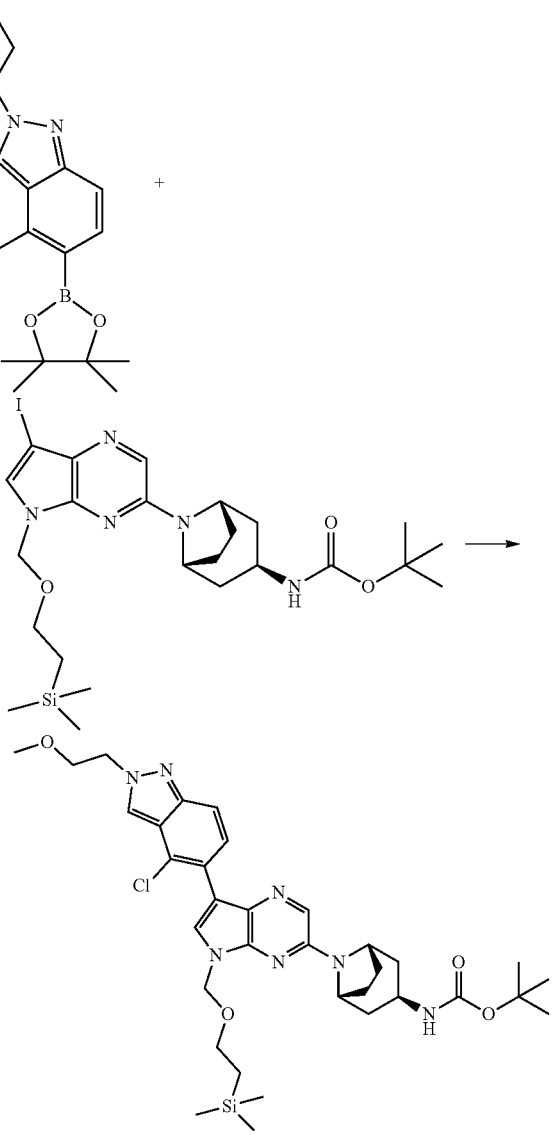

To a suspension of tert-butyl (endo-8-(7-iodo-5-((2-(trimethylsilyl)ethoxy)methyl)-5H-pyrrolo[2,3-b]pyrazin-3-yl)-8-azabicyclo[3.2.1]octan-3-yl)carbamate (500 mg, 0.83 mmol) and 4-fluoro-2-methyl-5-(4,4,5,5-tetramethyl-1,3,2-dioxaborolan-2-yl)-2H-indazole (680 mg) in 1,4-dioxane (8.0 mL) and water (2.0 mL) was added potassium carbonate (340 mg, 2.5 mmol), 1,1'-Bis(diphenylphosphino)ferrocene-palladium(II) dichloromethane complex (68 mg, 0.083 mmol) at room temperature. After stirring at 70° C. for 8 h, the mixture was diluted with water and EtOAc, and extracted with EtOAc. The organic phase was washed with brine, dried over $Na_2SO_4$, filtered, and concentrated in vacuo. Column chromatography (SNAP Ultra 50 g, gradient elution, 0-100% EtOAc in hexane) gave a crude material.

351

Then, the crude material was re-purified by SANP Isolute-Flash-NH2 55 g (0-100% EtOAc in Hex). Concentration of the fractions gave the title compound as a pale yellow amorphous (530 mg, 0.77 mmol, 93%). MS: [M+H]⁺=682, 684.

endo-8-(7-(4-Chloro-2-(2-methoxyethyl)-2H-indazol-5-yl)-5H-pyrrolo[2,3-b]pyrazin-3-yl)-8-azabicyclo[3.2.1]octan-3-amine

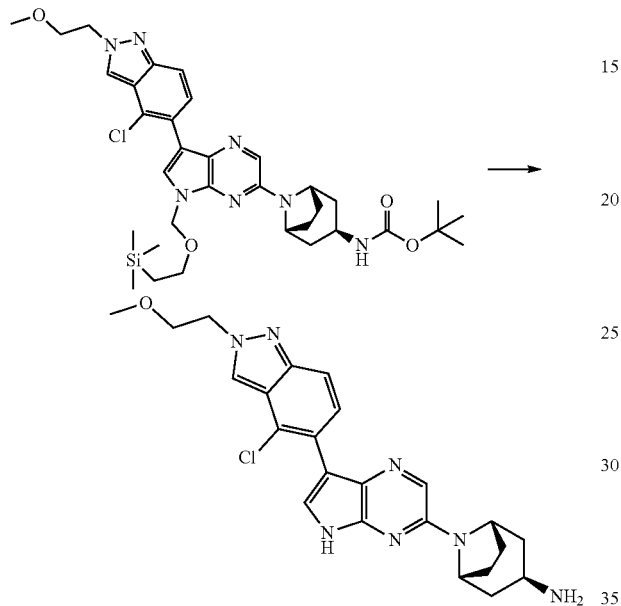

To a solution of tert-butyl tert-butyl (endo-8-(7-(4-chloro-2-(2-methoxyethyl)-2H-indazol-5-yl)-5-((2-(trimethylsilyl)ethoxy)methyl)-5H-pyrrolo[2,3-b]pyrazin-3-yl)-8-azabicyclo[3.2.1]octan-3-yl)carbamate (530 mg, 0.77 mmol) in chloroform (2.0 mL) was added TFA (2 mL) at room temperature. After stirring at room temperature over night, the mixture was concentrated in vacuo. The residue was diluted in EtOAc-MeOH, washed with sat. NaHCO₃ aq. The separated organic phase was washed with brine, dried over Na₂SO₄, filtered, and concentrated in vacuo. The residue was dissolved in MeOH (4.0 ml). Then, ethylenediamine (0.4 mL) was added to the mixture at room temperature. After stirring at 80° C. for 2 h, the mixture was concentrated in vacuo. The residue was purified by RP-HPLC (SHISEIDO C18AQ, 0-50% MeCN in H₂O with 0.1% formic acid). The fractions were basified with sat. NaHCO₃ aq., and then extracted with CHCl₃-MeOH, dried over Na₂SO₄, filtered, and concentrated in vacuo. The residue was suspended in Hexane-EtOAc. The precipitate was collected by filtration, rinsed with Hexane, and dried at 60° C. in vacuo to give the title compound (98 mg, 0.21 mmol, 27%) as a yellow solid. MS: [M+H]⁺=452, 454. ¹H-NMR (DMSO-D₆) δ: 11.64 (1H, brs), 8.41 (1H, s), 8.06 (1H, s), 7.92 (1H, d), 7.65 (1H, s), 7.59 (1H, d), 4.59 (2H, t), 4.50-4.48 (2H, brm), 3.82 (2H, t), 3.22 (3H, s), 3.15-3.10 (1H, m), 2.38-2.31 (2H, m), 2.09-2.02 (2H, m), 1.96-1.92 (2H, m), 1.71-1.57 (2H, brm), 1.40 (2H, d).

352

Example 46. endo-8-{7-[4-Chloro-2-(oxetan-3-yl)-2H-indazol-5-yl]-5H-pyrrolo[2,3-b]pyrazin-3-yl}-8-azabicyclo[3.2.1]octan-3-amine

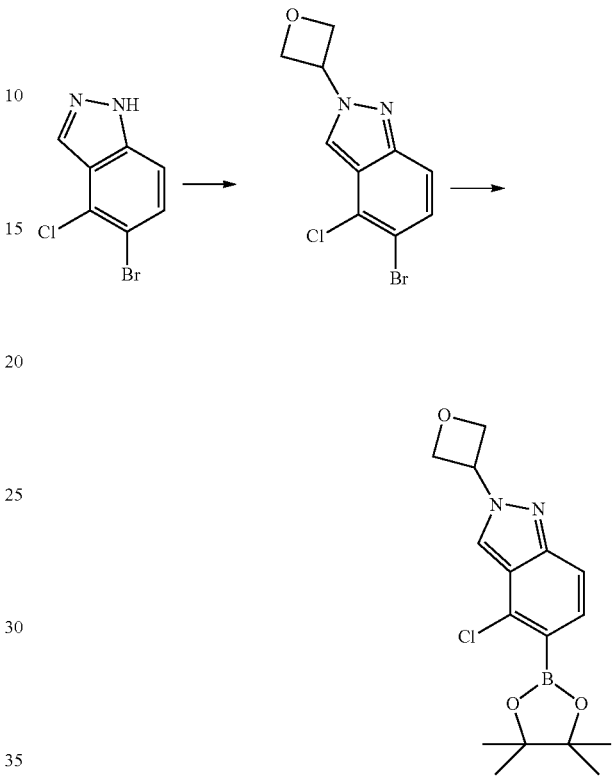

5-Bromo-4-chloro-2-(oxetan-3-yl)-2H-indazole

To a suspension of 5-bromo-4-chloro-1H-indazole (1.0 g, 4.3 mmol) and Potassium carbonate (1.79 g, 13 mmol) in DMSO (5 ml) was added 3-iodooxetane (0.74 ml, 8.6 mmol) at room temperature. After stirring at 80° C. for 12 h, the mixture was diluted with EtOAc and washed with water. The separated organic phase was washed with brine, dried over Na₂SO₄, filtered, and concentrated in vacuo. Column chromatography (SNAP Ultra 50 g, gradient elution, 0-100% EtOAc in hexane) gave the title compound (0.43 g, 1.5 mmol, 34%) as a brown solid. MS: [M+H]+=287, 289, 291

4-Chloro-2-(oxetan-3-yl)-5-(4,4,5,5-tetramethyl-1,3,2-dioxaborolan-2-yl)-2H-indazole To a suspension of 5-bromo-4-chloro-2-(oxetan-3-yl)-2H-indazole (0.43 g, 1.5 mmol) in 1,4-dioxane (10 mL) was added Potassium acetate (0.29 g, 3.0 mmol), 4,4,4',4',5,5,5',5'-octamethyl-2,2'-bi(1,3,2-dioxaborolane) (0.57 g, 2.2 mmol) and 1,1'-Bis(diphenylphosphino)ferrocene-palladium(II)dichloride dichloromethane complex (0.12 g, 0.15 mmol) at room temperature. After stirring at 120° C. for 2 h, the mixture was diluted with EtOAc and filtered through a pad of Hyflo Super-Cel. The filtrate was concentrated in vacuo. Column chromatography (SNAP Ultra 50 g, gradient elution, 0-100% EtOAc in hexane) gave the title compound (0.36 g) as a colourless solid. The material was not pure but used without further purification. MS: [M+H]+=335, 337.

353 tert-Butyl (endo-8-(7-(4-chloro-2-(oxetan-3-yl)-2H-indazol-5-yl)-5-((2-(trimethylsilyl)ethoxy)methyl)-5H-pyrrolo[2,3-b]pyrazin-3-yl)-8-azabicyclo[3.2.1]octan-3-yl)carbamate

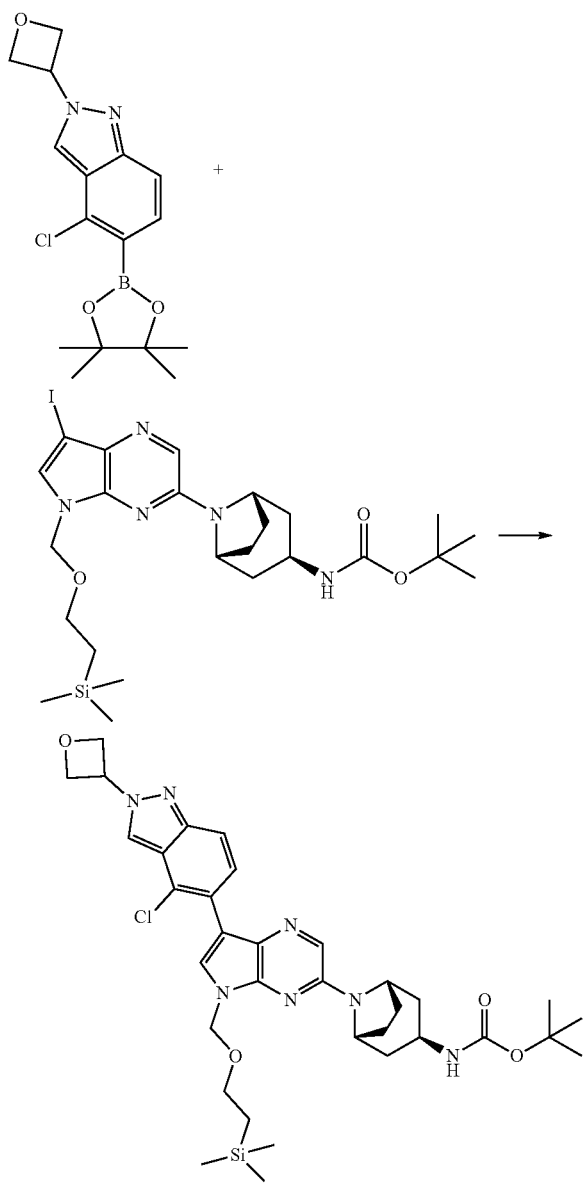

To a suspension of tert-butyl (endo-8-(7-iodo-5-((2-(trimethylsilyl)ethoxy)methyl)-5H-pyrrolo[2,3-b]pyrazin-3-yl)-8-azabicyclo[3.2.1]octan-3-yl)carbamate (400 mg, 0.66 mmol) and 4-fluoro-2-methyl-5-(4,4,5,5-tetramethyl-1,3,2-dioxaborolan-2-yl)-2H-indazole (360 mg) in 1,4-dioxane (8.0 mL) and water (2.0 mL) was added potassium carbonate (270 mg, 2.0 mmol), 1,1'-Bis(diphenylphosphino)ferrocene-palladium(II) dichloride dichloromethane complex (54 mg, 0.066 mmol) at room temperature. After stirring at 70° C. for 8 h, the mixture was diluted with water and EtOAc, and extracted with EtOAc. The organic phase was washed with brine, dried over Na₂SO₄, filtered, and concentrated in vacuo. Column chromatography (SNAP Ultra 50 g, gradient elution, 0-100% EtOAc in hexane) gave the title compound as a pale yellow amorphous (380 mg, 0.56 mmol, 83%). MS: [M+H]⁺=680, 682.

endo-8-(7-(4-Chloro-2-(oxetan-3-yl)-2H-indazol-5-yl)-5H-pyrrolo[2,3-b]pyrazin-3-yl)-8-azabicyclo[3.2.1]octan-3-amine

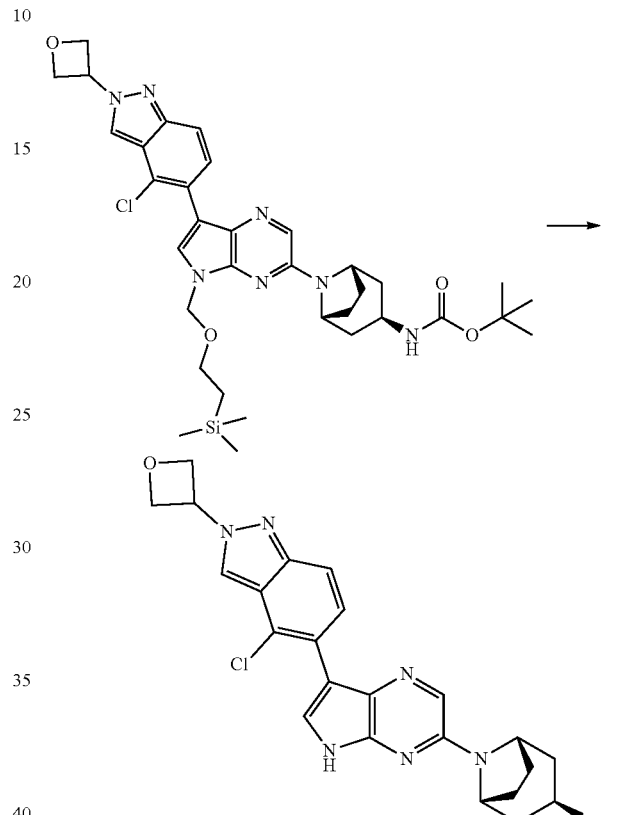

To a tert-butyl (endo-8-(7-(4-chloro-2-(oxetan-3-yl)-2H-indazol-5-yl)-5-((2-(trimethylsilyl)ethoxy)methyl)-5H-pyrrolo[2,3-b]pyrazin-3-yl)-8-azabicyclo[3.2.1]octan-3-yl)carbamate (380 mg, 0.55 mmol) in chloroform (3.0 mL) was added TFA (3 mL) at room temperature. After stirring at room temperature overnight, TFA (3 ml) was added to the mixture at room temperature. After stirring at 60° C. for 1 h, the mixture was concentrated in vacuo. The residue was dissolved in MeOH (4 ml) and ethylenediamine (0.6 mL) was added to the mixture at room temperature. After stirring at 60° C. for 1 h, the mixture was concentrated in vacuo. The residue was purified by RP-HPLC (SHISEIDO C18AQ, 0-50% MeCN in H₂O with 0.1% formic acid). The fractions were basified with sat. NaHCO₃ aq., and then extracted with CHCl₃-MeOH, dried over Na₂SO₄, filtered, and concentrated in vacuo. The residue was suspended in Hexane-EtOAc. The precipitate was collected by filtration, rinsed with Hexane, and dried at 60° C. in vacuo to give the title compound (78 mg, 0.17 mmol, 31%) as a yellow solid. MS: [M+H]⁺=450, 452. ¹H-NMR (DMSO-D₆) δ: 11.67 (1H, s), 8.58 (1H, s), 8.07 (1H, s), 7.99 (1H, d), 7.68 (1H, s), 7.67 (1H, d), 5.94-5.87 (1H, m), 5.06-4.97 (4H, m), 4.50-4.48 (2H, br m), 3.13-3.12 (1H, m), 2.39-2.31 (2H, m), 2.10-2.03 (2H, m), 1.98-1.88 (2H, m), 1.76-1.56 (2H, br m), 1.40 (2H, d).

Example 47: 6-{3-[endo-3-Amino-8-azabicyclo[3.2.1]octan-8-yl]-5H-pyrrolo[2,3-b]pyrazin-7-yl}-5-chloro-2-methyl-1,2-dihydroisoquinolin-1-one, dihydrochloride salt tert-Butyl N-[endo-8-[7-(5-chloro-2-methyl-1-oxo-1,2-dihydroisoquinolin-6-yl)-5-{[2-(trimethylsilyl)ethoxy]methyl}-5H-pyrrolo[2,3-b]pyrazin-3-yl]-8-azabicyclo[3.2.1]octan-3-yl]carbamate

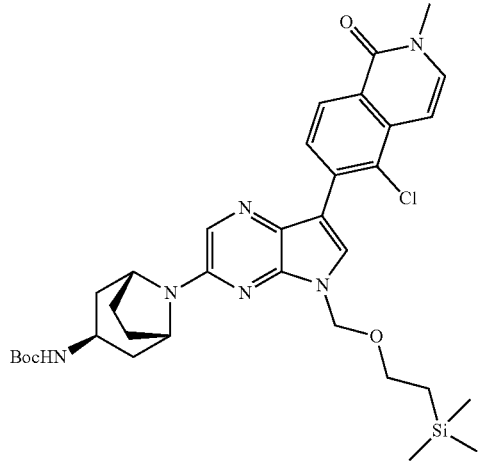 [SMILES: Cn1ccc2c(Cl)c(-c3cn(COCC[Si](C)(C)C)c4nc(N5[C@@H]6CC[C@H]5C[C@@H](NC(=O)OC(C)(C)C)C6)cnc34)ccc2c1=O]

A mixture of tert-butyl N-[endo-8-(7-iodo-5-{[2-(trimethylsilyl)ethoxy]methyl}-5H-pyrrolo[2,3-b]pyrazin-3-yl)-8-azabicyclo[3.2.1]octan-3-yl]carbamate (0.500 g, 0.83 mmol), 5-chloro-2-methyl-6-(4,4,5,5-tetramethyl-1,3,2-dioxaborolan-2-yl)-1,2-dihydroisoquinolin-1-one (157 mg, 0.491 mmol), [1,1-bis(diphenylphosphino)ferrocene]dichloropalladium(II), complex with dichloromethane (33.9 mg, 0.042 mmol) and Na$_2$CO$_3$ (132 mg, 1.246 mmol) in 1,4-dioxane (6 mL) and water (1 mL) was degassed under a flow of N$_2$. The reaction was heated to 100° C. for 1 h. The reaction was cooled to RT, filtered through celite, washing with DCM (10 mL) and MeOH (10 mL) and concentrated under reduced pressure. The crude product was purified by column chromatography on silica gel (gradient elution, 0-100% EtOAc/isohexane), to give the title compound (193 mg), MS: [M+H]$^+$=665.

tert-Butyl N-[endo-8-[7-(5-chloro-2-methyl-1-oxo-1,2-dihydroisoquinolin-6-yl)-5-(hydroxymethyl)-5H-pyrrolo[2,3-b]pyrazin-3-yl]-8-azabicyclo[3.2.1]octan-3-yl]carbamate and tert-butyl N-[endo-8-[7-(5-chloro-2-methyl-1-oxo-1,2-dihydroisoquinolin-6-yl)-5H-pyrrolo[2,3-b]pyrazin-3-yl]-8-azabicyclo[3.2.1]octan-3-yl]carbamate

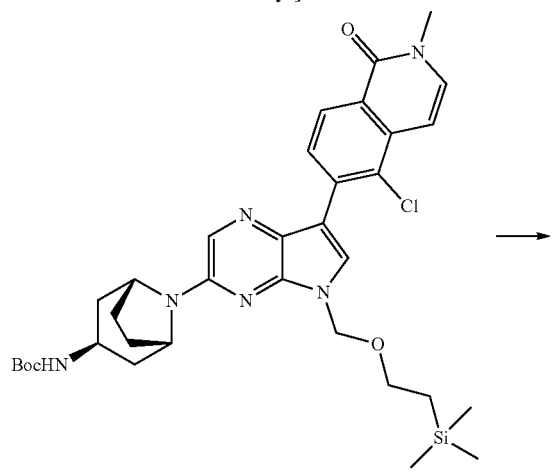

→

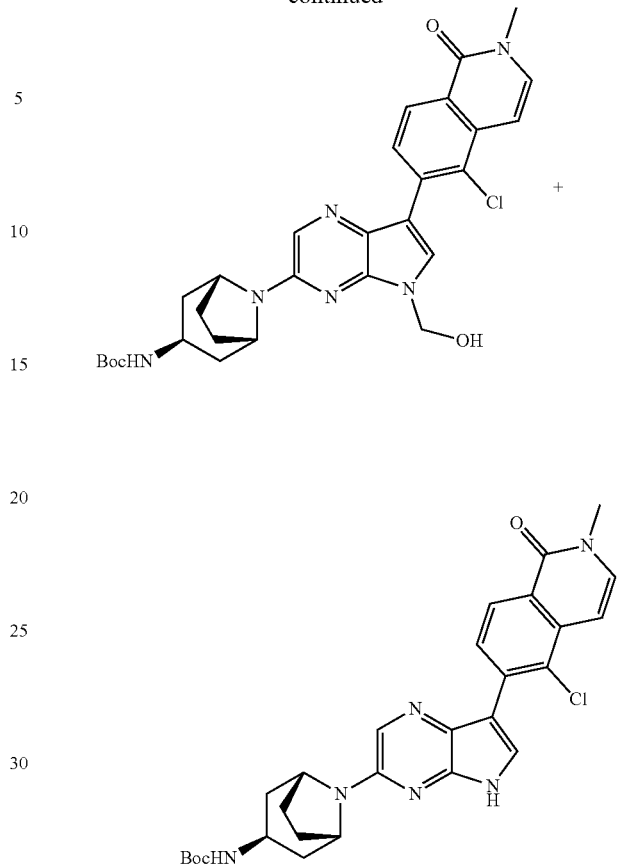

To a solution of tert-butyl N-[endo-8-[7-(5-chloro-2-methyl-1-oxo-1,2-dihydroisoquinolin-6-yl)-5-{[2-(trimethylsilyl)ethoxy]methyl}-5H-pyrrolo[2,3-b]pyrazin-3-yl]-8-azabicyclo[3.2.1]octan-3-yl]carbamate (177 mg, 0.266 mmol) in THF (3 mL) was added TBAF (1 M in THF) (0.8 mL, 0.800 mmol). The solution was stirred at 50° C. for 1 h. The reaction was stirred for a further 1 h at this temperature. TBAF (1 M in THF) (0.8 mL, 0.800 mmol) was added and the reaction was stirred at 50° C. for 1 h, before addition of TBAF (1 M in THF) (0.8 mL, 0.800 mmol) and stirring at 50° C. for a further 1 h. The reaction was cooled to 45° C. and stirred over night. The reaction was cooled to RT, diluted in DCM (40 mL) and washed with water (2×30 mL). The aq. phases were extracted with DCM (40 mL) and the combined organic extracts were dried (MgSO$_4$) and concentrated under reduced pressure. The crude product was purified by column chromatography on silica gel (gradient elution, 0-5% MeOH/DCM) to afford a 1:1 mixture of the title compounds (70 mg). The reaction mixture was taken forward without any further purification.

6-{3-[endo-3-Amino-8-azabicyclo[3.2.1]octan-8-yl]-5H-pyrrolo[2,3-b]pyrazin-7-yl}-5-chloro-2-methyl-1,2-dihydroisoquinolin-1-one, dihydrochloride Salt

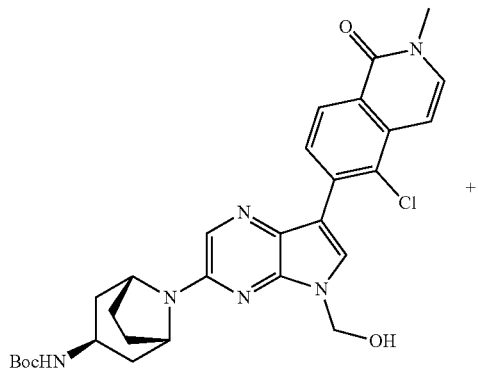

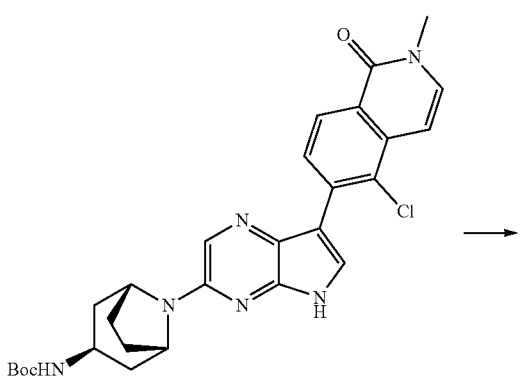

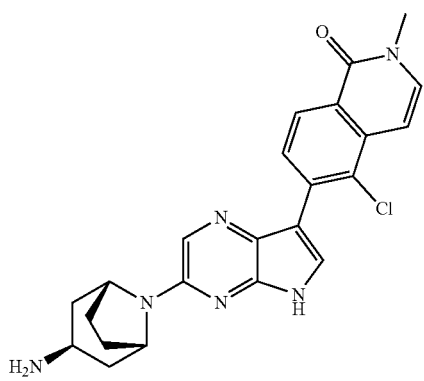

To a solution of tert-butyl N-[endo-8-[7-(5-chloro-2-methyl-1-oxo-1,2-dihydroisoquinolin-6-yl)-5-(hydroxymethyl)-5H-pyrrolo[2,3-b]pyrazin-3-yl]-8-azabicyclo[3.2.1]octan-3-yl]carbamate and tert-butyl N-[endo-8-[7-(5-chloro-2-methyl-1-oxo-1,2-dhydroisoquinolin-6-yl)-5H-pyrrolo[2,3-b]pyrazin-3-yl]-8-azabicyclo[3.2.1]octan-3-yl]carbamate (1:1 mixture, 70 mg, 0.13 mmol) in THF (1.5 mL) was added NaOH (2 M, 0.1 mL). After 30 mins, HCl (4 M in dioxane, 1 mL) was added and the reaction was stirred at RT for 2 h. The reaction was passed through an SCX ion exchange column, washing with MeOH and eluting with NH$_3$/MeOH (0.7 M). The material was stirred in THF (1 mL) with NaOH (2 M, 0.05 mL) for 30 mins, before diluting in MeOH and passed through an SCX ion exchange column, washing with MeOH and eluting with NH$_3$/MeOH (0.7 M) and concentrated under reduced pressure. The material was triturated with MeCN (5 mL) and collected by filtration. The residue was taken into 1,4-dioxane (1 mL) and HCl (4 N in dioxane, 1 mL) was added before stirring for 30 min. The precipitate was collected by filtration and concentrated under reduced pressure, to give the title compound (23 mg), MS: [M+H]+=435. 1H NMR (500 MHz, DMSO-d$_6$) δ 11.98 (1H, d), 8.26-8.20 (2H, m), 8.19 (1H, d), 7.99 (2H, d), 7.95 (1H, d), 7.64 (1H, d), 6.88 (1H, d), 4.67-4.58 (2H, m), 3.54 (3H, s), 3.24-3.11 (1H, m), 2.46-2.35 (2H, m), 2.15-2.09 (2H, m), 2.02-1.94 (2H, m), 1.67 (2H, dd).

The compound of Example 47 is also disclosed herein as the hydrochloride salt i.e. 6-{3-[endo-3-amino-8-azabicyclo[3.2.1]octan-8-yl]-5H-pyrrolo[2,3-b]pyrazin-7-yl}-5-chloro-2-methyl-1,2-dihydroisoquinolin-1-one, hydrochloride salt.

Example 48. endo-8-[3-(4-Chloro-2-methyl-2H-indazol-5-yl)-5-methyl-1H-pyrazolo[3,4-b]pyrazin-6-yl]-8-azabicyclo[3.2.1]octan-3-amine, hydrochloride salt tert-Butyl N-[endo-8-[3-(4-chloro-2-methyl-2H-indazol-5-yl)-5-methyl-1-{[2-(trimethylsilyl)ethoxy]methyl}-1H-pyrazolo[3,4-b]pyrazin-6-yl]-8-azabicyclo[3.2.1]octan-3-yl]carbamate

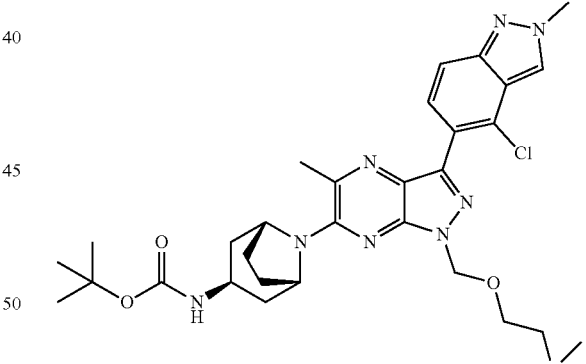

Prepare using analogous procedures as tert-butyl N-[exo-8-[3-(4-chloro-2-methyl-2H-indazol-5-yl)-5-methyl-1-{[2-(trimethylsilyl)ethoxy]methyl}-1H-pyrazolo[3,4-b]pyrazin-6-yl]-8-azabicyclo[3.2.1]octan-3-yl]carbamate, except using tert-butyl N-(endo-8-azabicyclo[3.2.1]octan-3-yl)carbamate.

TABLE 11

(Example 48)

| Example | Structure | Name | NMR Data | MS Data |
|---|---|---|---|---|
| 48 | 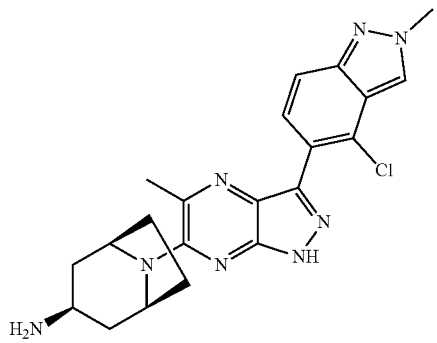 [SMILES: Cc1nc2c(-c3ccc4nn(C)cc4c3Cl)n[nH]c2nc1N1[C@@H]2CC[C@H]1C[C@@H](N)C2] | endo-8-[3-(4-chloro-2-methyl-2H-indazol-5-yl)-5-methyl-1H-pyrazolo[3,4-b]pyrazin-6-yl]-8-azabicyclo[3.2.1]octan-3-amine, hydrochloride salt | ¹H NMR (400 MHz, Me-d₃-OD): 8.50 (1H, s), 7.70 (1H, dd), 7.63 (1H, d), 4.67 (2H, s), 4.31 (3H, s), 3.68 (3H, s), 3.61-3.48 (1H, m), 2.84-2.65 (5H, m), 2.42-2.23 (2H, m), 2.10-1.87 (2H, m), 1.76 (2H, dd). | 423 |

Example 48 was obtained by following the general procedures for preparations of compounds of Formula (I) using deprotection method 1.

TABLE 12

Examples 49-57

| Example | Structure | Name | NMR Data | MS Data | Method |
|---|---|---|---|---|---|
| 49 | 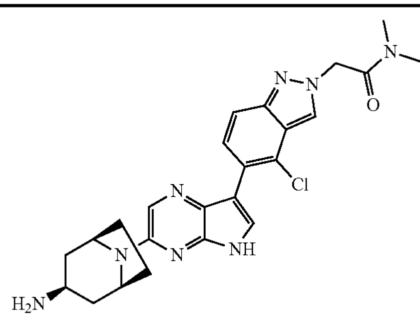 | 2-(5-{3-[endo-3-amino-8-azabicyclo[3.2.1]octan-8-yl]-5H-pyrrolo[2,3-b]pyrazin-7-yl}-4-chloro-2H-indazol-2-yl)-N,N-dimethylacetamide | 1H NMR (500 MHz, DMSO-d₆) 8.36 (1H, d), 8.10 (1H, s), 7.96 (1H, d), 7.69 (1H, s), 7.60 (1H, dd), 5.48 (2H, s), 4.52 (2H, s), 3.15 (1H, app. t), 3.10 (3H, s), 2.89 (3H, s), 2.40-2.34 (2H, m), 2.14-2.05 (2H, m), 2.00-1.91 (2H, m), 1.43 (2H, app. d) | 479 | 1 |
| 50 | 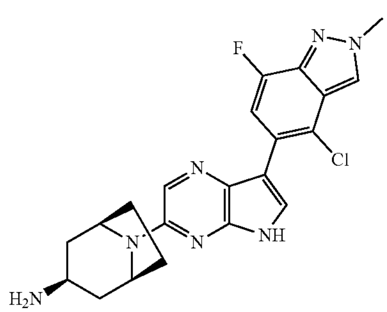 | endo-8-[7-(4-chloro-7-fluoro-2-methyl-2H-indazol-5-yl)-5H-pyrrolo[2,3-b]pyrazin-3-yl]-8-azabicyclo[3.2.1]octan-3-amine | 1H NMR (400 MHz, CDCl3): 8.49 (1H, br s), 8.07 (1H, s), 8.02 (1H, d), 7.80 (1H, d), 7.66 (1H, d), 4.57 (2H, br s), 4.27 (3H, s), 3.25 (1H, t), 2.37-2.22 (4H, m), 2.16-2.08 (2H, m), 1.49 (2H, br d). | 426 | 1, purified by column chromatography on KP-NH silica gel (gradient elution 0-10% methanol in chloroform |
| 51 | 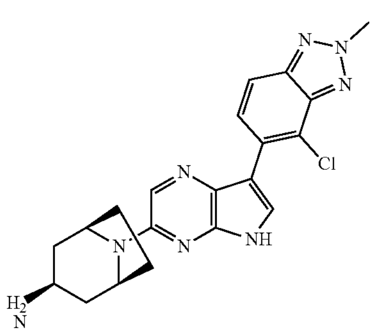 [SMILES: Cn1nc2ccc(-c3c[nH]c4nc(N5[C@@H]6CC[C@H]5C[C@@H](N)C6)cnc34)c(Cl)c2n1] | endo-8-[7-(4-chloro-2-methyl-2H-1,2,3-benzotriazol-5-yl)-5H-pyrrolo[2,3-b]pyrazin-3-yl]-8-azabicyclo[3.2.1]octan-3-amine | 1H-NMR (DMSO-d₆) 11.82 (1H, br s), 8.22 (1H, d), 8.12 (1H, s), 7.91 (1H, d), 7.85 (1H, s), 4.56-4.51 (5H, m), 3.18-3.13 (1H, m), 2.36-2.32 (2H, m), 2.14-2.06 (2H, m), 2.00-1.93 (2H, m), 1.45 (2H, d). | 409 | 9 |

TABLE 12-continued

Examples 49-57

| Example | Structure | Name | NMR Data | MS Data | Method |
|---|---|---|---|---|---|
| 52 | 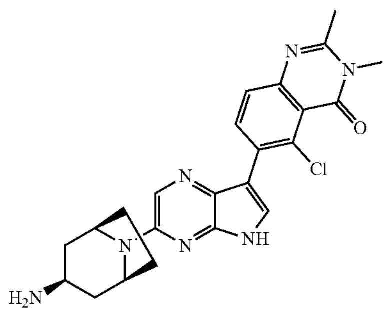 [SMILES: Cc1nc2ccc(-c3c[nH]c4nc(N5[C@@H]6CC[C@H]5C[C@@H](N)C6)cnc34)c(Cl)c2c(=O)n1C] | 6-{3-[endo-3-amino-8-azabicyclo[3.2.1]octan-8-yl]-5H-pyrrolo[2,3-b]pyrazin-7-yl}-5-chloro-2,3-dimethyl-3,4-dihydroquinazolin-4-one, methanesulfonic acid salt | 1H NMR (400 MHz, DMSO-$d_6$): 11.78 (1H, s), 8.22 (1H, d), 8.17 (1H, s), 7.79 (1H, s), 7.57 (1H, d), 7.51-6.98 (3H, m), 4.62 (2H, s), 3.51 (3H, s), 3.20-3.15 (1H, m), 2.58 (3H, s), 2.46-2.38 (2H, m), 2.31 (3H, s), 2.18-2.02 (2H, m), 2.02-1.88 (2H, m), 1.61 (2H, d). | 450 | 1 |
| 53 | 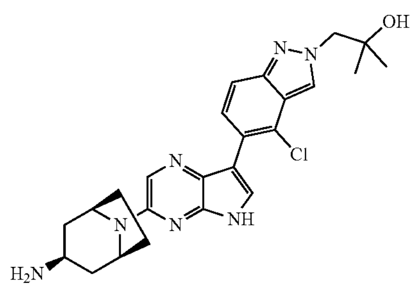 [SMILES: CC(C)(O)Cn1cc2c(Cl)c(-c3c[nH]c4nc(N5[C@@H]6CC[C@H]5C[C@@H](N)C6)cnc34)ccc2n1] | 1-(5-{3-[endo-3-amino-8-azabicyclo[3.2.1]octan-8-yl]-5H-pyrrolo[2,3-b]pyrazin-7-yl}-4-chloro-2H-indazol-2-yl)-2-methylpropan-2-ol | 1H NMR (500 MHz, DMSO-$d_6$) 8.34 (1H, d), 8.09 (1H, s), 7.94 (1H, d), 7.68 (1H, s), 7.63 (1H, dd,), 4.88 (1H, s), 4.56-4.50 (2H, m), 4.38 (2H, s), 3.16 (1H, t), 2.41-2.35 (2H, m), 2.10 (2H, dt), 1.99-1.94 (2H, m), 1.78-1.49 (2H, bs), 1.44 (2H, d), 1.14 (6H, s). | 466 | 1 |
| 54 | 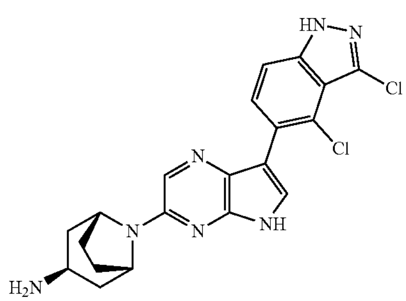 [SMILES: N[C@H]1C[C@H]2CC[C@@H](C1)N2c1cnc2c(-c3ccc4[nH]nc(Cl)c4c3Cl)c[nH]c2n1] | endo-8-[7-(3,4-dichloro-1H-indazol-5-yl)-5H-pyrrolo[2,3-b]pyrazin-3-yl]-8-azabicyclo[3.2.1]octan-3-amine | 1H NMR (500 MHz, DMSO-$d_6$) 11.68 (1H, bs), 8.08 (1H, s), 7.99 (1H, d), 7.67 (1H, s), 7.58 (1H, d), 4.52 (2H, s), 3.15 (1H, t), 2.37-2.31 (2H, m), 2.14-2.07 (2H, m), 2.01-1.92 (2H, m), 1.44 (2H, d). | 428 | 1, purified by chromatography on silica (12 g cartridge, 0-10% (MeOH with 0.7M $NH_3$)/DCM), then by chiral preparative HPLC (Gilson, 15CHdcb2 method, IC column, 15% EtOH/17% $CHCl_3$/68% heptane (0.28% $HNEt_3$)) |
| 55 | 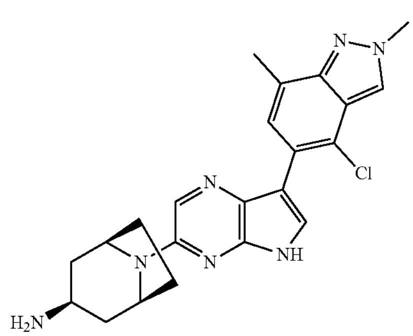 [SMILES: Cc1cc(-c2c[nH]c3nc(N4[C@@H]5CC[C@H]4C[C@@H](N)C5)cnc23)c(Cl)c2cn(C)nc12] | endo-8-[7-(4-chloro-2,7-dimethyl-2H-indazol-5-yl)-5H-pyrrolo[2,3-b]pyrazin-3-yl]-8-azabicyclo[3.2.1]octan-3-amine | $^1$H NMR (400 MHz, $CDCl_3$): 8.51 (1H, br s), 8.07 (1H, s), 7.97 (1H, s), 7.65 (1H, d), 7.56 (1H, d), 4.57 (2H, br s), 4.25 (3H, s), 3.25 (1H, t), 2.64 (3H, d), 2.37-2.26 (4H, m), 2.23-2.07 (2H, m), 1.49 (2H, br d). | 422 | 1, purified by column chromatography on KP-NH silica gel (gradient elution 0-10% methanol in chloroform |

TABLE 12-continued

Examples 49-57

| Example | Structure | Name | NMR Data | MS | Data Method |
|---|---|---|---|---|---|
| 56 | 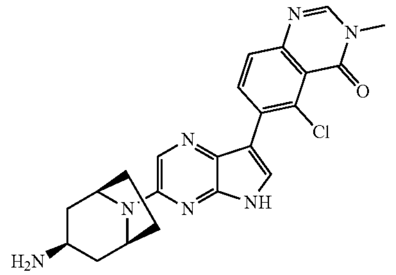 [SMILES: Cn1cnc2ccc(-c3c[nH]c4nc(N5[C@@H]6CC[C@H]5C[C@@H](N)C6)cnc34)c(Cl)c2c1=O] | 6-{3-[endo-3-amino-8-azabicyclo[3.2.1]octan-8-yl]-5H-pyrrolo[2,3-b]pyrazin-7-yl}-5-chloro-3-methyl-3,4-dihydroquinazolin-4-one, hydrochloride salt | 1H NMR (400 MHz, DMSO-d<sub>6</sub>): 11.95 (1H, d), 8.58 (1H, s), 8.29 (1H, d), 8.19 (1H, s), 8.15 (3H, d), 7.84 (1H, d), 7.70 (1H, d), 4.69-4.56 (2H, m), 3.49 (3H, s), 3.20-3.14 (1H, m), 2.45-2.37 (2H, m), 2.16-2.06 (2H, m), 2.06-1.97 (2H, m), 1.80-1.61 (2H, m). | 436 | 1 |
| 57 | 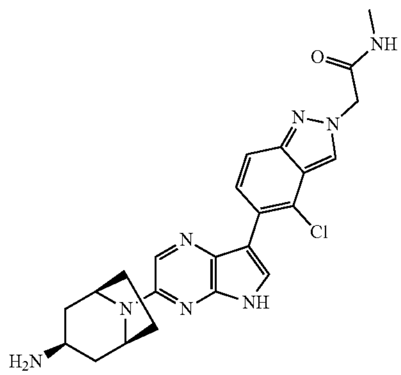 [SMILES: CNC(=O)Cn1cc2c(Cl)c(-c3c[nH]c4nc(N5[C@@H]6CC[C@H]5C[C@@H](N)C6)cnc34)ccc2n1] | 2-(5-{3-[endo-3-amino-8-azabicyclo[3.2.1]octan-8-yl]-5H-pyrrolo[2,3-b]pyrazin-7-yl}-4-chloro-2H-indazol-2-yl)-N-methylacetamide | $^1$H-NMR (DMSO-d$_6$): 11.69 (1H, br s), 8.44 (1H, d), 8.11 (1H, s), 7.96 (1H, d), 7.70 (1H, d), 7.60 (1H, dd), 5.13 (2H, s), 4.56-4.51 (2H, m), 3.18-3.13 (1H, m), 2.66-2.62 (3H, m), 2.31 (2H, d), 2.17-2.10 (2H, m), 2.02-1.95 (2H, m), 1.46 (2H, d). | 465 | 9, The reaction solution was then vacuum-concentrated, and the residue was purified by RP-HPLC (SHISEIDO C18AQ, 0-50% MeCN in H$_2$O with 0.1% formic acid). The fractions were basified with sat. NaHCO$_3$ aq., and then extracted with CHCl$_3$—MeOH, dried over Na$_2$SO$_4$, filtered, and concentrated in vacuo |

By following methods similar and/or analogous to those described for general procedures for preparations of compounds of Formula (I) (e.g. methods 1-12), the compounds set out in Table 12 were prepared from the corresponding N-Boc, N-Cbz, N—SO$_2$NMe$_2$, 2-oxanyl or SEM protected derivatives, with any significant variations indicated. The title compounds were either isolated directly as the free base or as the appropriate salt without further purification, or purified for example using mass-directed preparative HPLC, chromatography, crystallization or trituration and converted to the appropriate salt.

Example 58: 3-(5-{3-[endo-3-Amino-8-azabicyclo[3.2.1]octan-8-yl]-5H-pyrrolo[2,3-b]pyrazin-7-yl}-4-chloro-2H-indazol-2-yl)-N,N-dimethylpropanamide

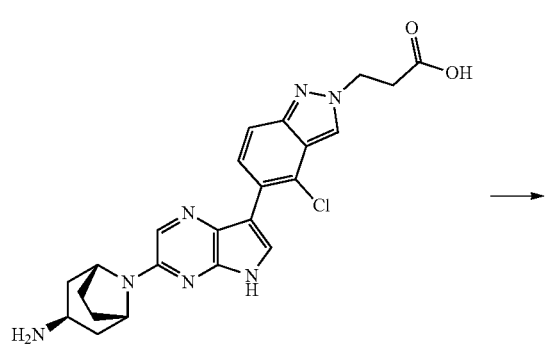

→

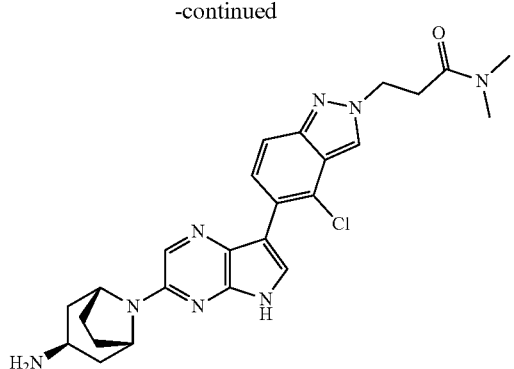

To a solution of 3-(5-{3-[endo-3-amino-8-azabicyclo[3.2.1]octan-8-yl]-5H-pyrrolo[2,3-b]pyrazin-7-yl}-4-chloro-2H-indazol-2-yl)propanoic acid (10 mg, 0.0215 mmol) in DMSO (1.00 mL) was added Et$_3$N (0.0299 mL, 0.215 mmol), 2,4,6-tripropyl-1,3,5,2,4,6-trioxatriphosphorinane-2,4,6-trioxide (1.6 M in THF, 0.0270 mL, 0.0429 mmol), and dimethylamine (2.0 M in THF, 0.210 mL, 0.429 mmol) at RT. The mixture was stirred at RT for 3 days. The reaction solution was then vacuum-concentrated, and the residue was purified by RP-HPLC (SHISEIDO C18AQ, 0-50% MeCN in H$_2$O with 0.1% formic acid). The fractions were basified with sat. aq. NaHCO$_3$, and then extracted with CHCl$_3$-MeOH, dried over Na$_2$SO$_4$, filtered, and concentrated in vacuo, to give the title compound (1.32 mg). MS: [M+H]$^+$=493.

TABLE 13

Examples 59-74

| Example | Structure | Name | NMR Data | MS Data | Method |
|---|---|---|---|---|---|
| 59 | 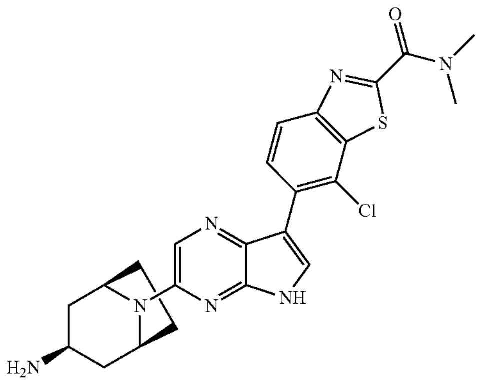 [SMILES: CN(C)C(=O)c1nc2ccc(-c3c[nH]c4nc(N5[C@@H]6CC[C@H]5C[C@@H](N)C6)cnc34)c(Cl)c2s1] | 6-{3-[endo-3-amino-8-azabicyclo[3.2.1]octan-8-yl]-5H-pyrrolo[2,3-b]pyrazin-7-yl}-7-chloro-N,N-dimethyl-1,3-benzothiazole-2-carboxamide, hydrochloride salt | 1H NMR (400 MHz, DMSO-$d_6$): 11.99 (1H, d), 8.42 (1H, d), 8.23 (1H, s), 8.18 (1H, d), 8.07 (3H, d), 7.93 (1H, d), 4.71-4.57 (2H, m), 3.59 (3H, s), 3.20-3.15 (1H, m), 3.12 (3H, s), 2.46-2.37 (2H, m), 2.16-2.05 (2H, m), 2.05-1.92 (2H, m), 1.75-1.65 (2H, m). | 482 | Prepared as method 1 (Table 5), purified by column chromatography on reverse phase C18 silica gel (gradient elution, 5-95%, MeCN/$H_2O$ + 0.1% formic acid) |
| 60 | 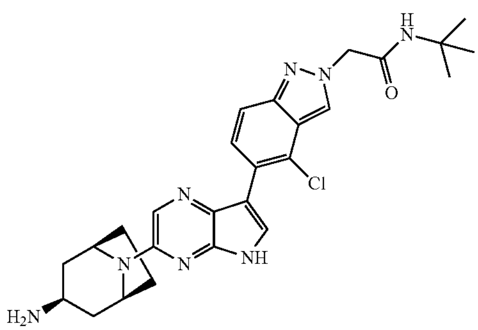 [SMILES: CC(C)(C)NC(=O)Cn1cc2c(Cl)c(-c3c[nH]c4nc(N5[C@@H]6CC[C@H]5C[C@@H](N)C6)cnc34)ccc2n1] | 2-(5-{3-[endo-3-amino-8-azabicyclo[3.2.1]octan-8-yl]-5H-pyrrolo[2,3-b]pyrazin-7-yl}-4-chloro-2H-indazol-2-yl)-N-tert-butylacetamide | 1H NMR (500 MHz, DMSO-$d_6$): 11.66 (1H, br. s), 8.40 (1H, d), 8.09 (1H, s), 8.00 (1H, s), 7.97 (1H, d), 7.69 (1H, s), 7.60 (1H, dd), 5.08 (2H, s), 4.55-4.49 (2H, s), 3.15 (1H, app. t), 2.41-2.34 (2H, m), 2.13-2.05 (2H, m), 2.00-1.90 (2H, m), 1.59 (2H, br. s), 1.43 (2H, app. d), 1.29 (9H, s). | 507 | 1, purified by preparative HPLC (Basic) |
| 61 | 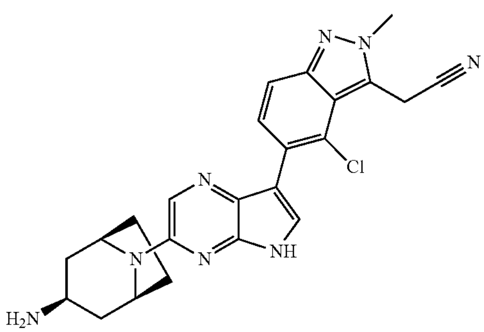 [SMILES: Cn1nc2ccc(-c3c[nH]c4nc(N5[C@@H]6CC[C@H]5C[C@@H](N)C6)cnc34)c(Cl)c2c1CC#N] | 2-(5-{3-[endo-3-amino-8-azabicyclo[3.2.1]octan-8-yl]-5H-pyrrolo[2,3-b]pyrazin-7-yl}-4-chloro-2-methyl-2H-indazol-3-yl)acetonitrile | 1H NMR (500 MHz, DMSO-$d_6$): 8.09 (1H, s), 7.86 (1H, d), 7.67 (1H, s), 7.62 (1H, d), 4.80 (2H, s), 4.57-4.49 (2H, m), 4.23 (3H, s), 3.16 (1H, t), 2.38 (2H, q), 2.09 (2H, ddd), 1.99-1.93 (2H, m), 1.61 (2H, bs), 1.44 (2H, d). NH not observed. | 447 | 1 |
| 62 | 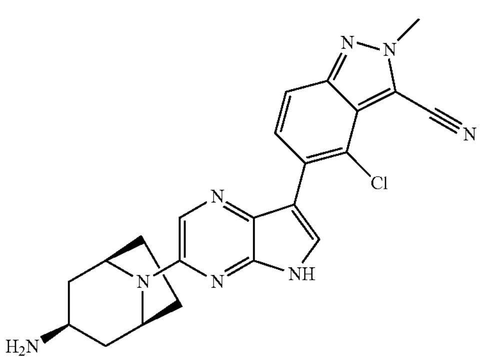 [SMILES: Cn1nc2ccc(-c3c[nH]c4nc(N5[C@@H]6CC[C@H]5C[C@@H](N)C6)cnc34)c(Cl)c2c1C#N] | 5-{3-[endo-3-amino-8-azabicyclo[3.2.1]octan-8-yl]-5H-pyrrolo[2,3-b]pyrazin-7-yl}-4-chloro-2-methyl-2H-indazole-3-carbonitrile | 8.23 (d, 1H), 8.12 (s, 1H), 7.89 (d, 1H), 7.85 (s, 1H), 4.56-4.51 (m, 2H), 4.37 (s, 3H), 3.16 (t, 1H), 2.39 (q, 2H), 2.09 (dt, 2H), 2.00-1.92 (m, 2H), 1.44 (d, 2H), exchangeable protons not observed. | 433 | 1 |

TABLE 13-continued

Examples 59-74

| Example | Structure | Name | NMR Data | MS Data | Method |
|---|---|---|---|---|---|
| 63 | 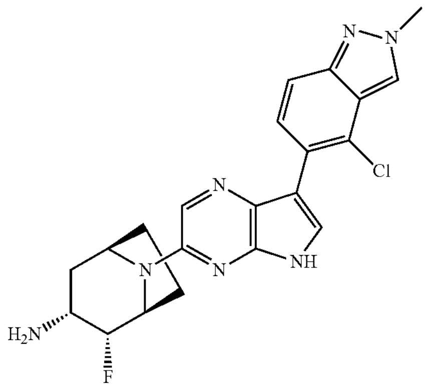 [SMILES: Cn1cc2c(Cl)c(-c3c[nH]c4nc(N5[C@@H]6CC[C@H]5[C@H](F)[C@H](N)C6)cnc34)ccc2n1] | (1S,2R,3R,5R)-8-[7-(4-chloro-2-methyl-2H-indazol-5-yl)-5H-pyrrolo[2,3-b]pyrazin-3-yl]-2-fluoro-8-azabicyclo[3.2.1]octan-3-amine | 1H NMR (400 MHz, DMSO-d$_6$): 11.62 (1H, s), 8.43 (1H, s), 8.17 (1H, s), 7.92 (1H, d), 7.66 (1H, d), 7.61 (1H, d), 4.98 (1H, s), 4.71-4.43 (2H, m), 4.20 (3H, s), 3.05 (1H, s), 2.04-1.88 (2H, m), 1.81-1.62 (4H, m), 1.40 (2H, s). | 426 | 7 |
| 64 | 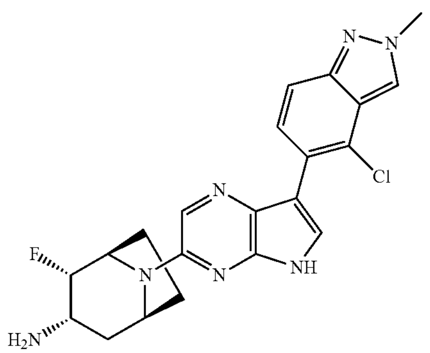 [SMILES: Cn1cc2c(Cl)c(-c3c[nH]c4nc(N5[C@H]6CC[C@@H]5[C@@H](F)[C@@H](N)C6)cnc34)ccc2n1] | (1R,2S,3S,5S)-8-[7-(4-chloro-2-methyl-2H-indazol-5-yl)-5H-pyrrolo[2,3-b]pyrazin-3-yl]-2-fluoro-8-azabicyclo[3.2.1]octan-3-amine | 1H NMR (400 MHz, DMSO-d6): 11.62 (1H, s), 8.43 (1H, s), 8.17 (1H, s), 7.92 (1H, d), 7.68-7.57 (2H, m), 4.97 (1H, s), 4.68-4.44 (2H, m), 4.20 (3H, s), 3.05 (1H, s), 1.94 (3H, d), 1.82-1.59 (5H, m). | 426 | 7 |
| 65 | 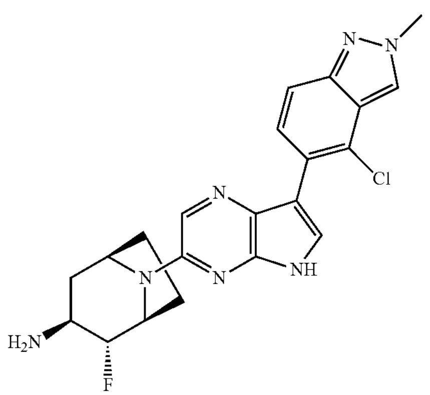 [SMILES: Cn1cc2c(Cl)c(-c3c[nH]c4nc(N5[C@@H]6CC[C@H]5[C@H](F)[C@@H](N)C6)cnc34)ccc2n1] | (1S,2R,3S,5R)-8-[7-(4-chloro-2-methyl-2H-indazol-5-yl)-5H-pyrrolo[2,3-b]pyrazin-3-yl]-2-fluoro-8-azabicyclo[3.2.1]octan-3-amine | 1H NMR (400 MHz, DMSO-d$_6$): 11.61 (1H, s), 8.43 (1H, s), 8.15 (1H, s), 7.92 (1H, d), 7.69-7.57 (2H, m), 4.91 (1H, t), 4.63 (1H, s), 4.45 (1H, d), 4.20 (3H, s), 3.17-3.08 (1H, m), 2.32-2.16 (2H, m), 2.09 (1H, t), 2.03-1.71 (4H, m), 1.42 (1H, d). | 426 | 7 |
| 66 | 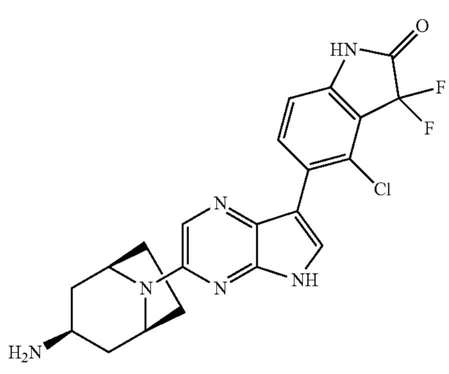 [SMILES: N[C@H]1C[C@H]2CC[C@@H](C1)N2c1cnc2c(-c3ccc4c(c3Cl)C(F)(F)C(=O)N4)c[nH]c2n1] | 5-{3-[endo-3-amino-8-azabicyclo[3.2.1]octan-8-yl]-5H-pyrrolo[2,3-b]pyrazin-7-yl}-4-chloro-3,3-difluoro-2,3-dihydro-1H-indol-2-one, dihydrochloride salt | 1H NMR (400 MHz, Me-d$_3$-OD): 8.17 (1H, s), 7.84 (1H, s), 7.77 (1H, d), 7.06 (1H, d), 4.82 (2H, s), 3.78-3.71 (1H, m), 2.73-2.59 (2H, m), 2.40-2.25 (2H, m), 2.12-1.96 (2H, m), 1.84-1.65 (2H, m). | 445 | General Method 1, purified by preparative HPLC (TFA method |

TABLE 13-continued

Examples 59-74

| Example | Structure | Name | NMR Data | MS Data | Method |
|---|---|---|---|---|---|
| 67 | 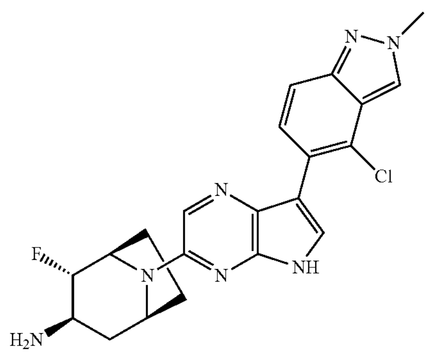 [SMILES: Cn1cc2c(Cl)c(-c3c[nH]c4nc(N5[C@H]6CC[C@@H]5[C@@H](F)[C@H](N)C6)cnc34)ccc2n1] | (1R,2S,3R,5S)-8-[7-(4-chloro-2-methyl-2H-indazol-5-yl)-5H-pyrrolo[2,3-b]pyrazin-3-yl]-2-fluoro-8-azabicyclo[3.2.1]octan-3-amine | 1H NMR (400 MHz, DMSO-d₆): 11.61 (1H, s), 8.43 (1H, s), 8.15 (1H, s), 7.92 (1H, dd), 7.69-7.57 (2H, m), 4.91 (1H, s), 4.63 (1H, d), 4.45 (1H, d), 4.20 (3H, s), 3.17-3.07 (1H, m), 2.31-2.18 (2H, m), 2.10 (1H, d), 1.97-1.75 (4H, m), 1.42 (1H, d). | 426 | 7 |
| 68 | 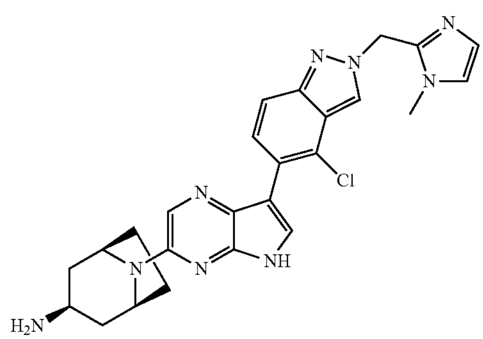 [SMILES: Cn1ccnc1Cn1cc2c(Cl)c(-c3c[nH]c4nc(N5[C@@H]6CC[C@H]5C[C@@H](N)C6)cnc34)ccc2n1] | endo-8-(7-{4-chloro-2-[(1-methyl-1H-imidazol-2-yl)methyl]-2H-indazol-5-yl}-5H-pyrrolo[2,3-b]pyrazin-3-yl)-8-azabicyclo[3.2.1]octan-3-amine, trihydrochloride salt | 1H NMR (500 MHz, DMSO-d₆): 11.85 (1H, d), 8.82 (1H, s), 8.38 (1H, s), 8.18-8.10 (4H, m), 8.00 (1H, d), 7.79-7.75 (2H, m), 7.73 (1H, d), 7.63 (1H, d), 6.19 (2H, s), 4.61 (2H, s), 3.92 (3H, s), 3.16 (1H, s), 3.11-3.05 (1H, m), 2.42-2.35 (2H, m), 2.14-2.07 (2H, m), 2.04-1.97 (2H, m), 1.76-1.63 (2H, m). | 488 | 1 |
| 69 | 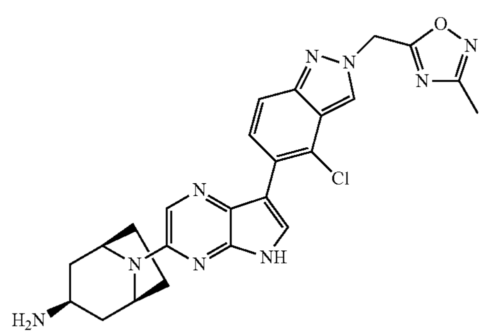 [SMILES: Cc1noc(Cn2cc3c(Cl)c(-c4c[nH]c5nc(N6[C@@H]7CC[C@H]6C[C@@H](N)C7)cnc45)ccc3n2)n1] | endo-8-(7-{4-chloro-2-[(3-methyl-1,2,4-oxadiazol-5-yl)methyl]-2H-indazol-5-yl}-5H-pyrrolo[2,3-b]pyrazin-3-yl)-8-azabicyclo[3.2.1]octan-3-amine, hydrochloride salt | 1H NMR (500 MHz, DMSO-d₆): 11.78 (1H, br s), 8.70 (1H, d), 8.17 (1H, s), 8.00 (1H, d), 7.76 (1H, s), 7.64 (1H, dd), 7.06 (3H, br s), 6.15 (2H, s), 4.60 (2H, d), 3.21-3.13 (1H, m), 2.40-2.28 (2H, m), 2.33 (3H, s), 2.14-2.00 (4H, m), 1.68-1.56 (2H, m). | 490 | 1, purified by chromatography on silica gel (24 g cartridge, 0-10% (0.7 M Ammonia/MeOH)/DCM) |
| 70 | 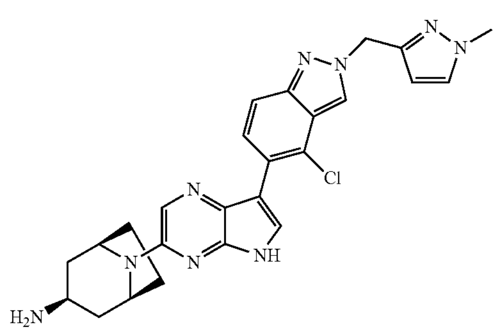 [SMILES: Cn1ccc(Cn2cc3c(Cl)c(-c4c[nH]c5nc(N6[C@@H]7CC[C@H]6C[C@@H](N)C7)cnc45)ccc3n2)n1] | endo-8-(7-{4-chloro-2-[(1-methyl-1H-pyrazol-3-yl)methyl]-2H-indazol-5-yl}-5H-pyrrolo[2,3-b]pyrazin-3-yl)-8-azabicyclo[3.2.1]octan-3-amine, trihydrochloride salt | 1H NMR (500 MHz, DMSO-d₆): 11.82 (d, 1H), 8.47 (s, 1H), 8.18 (s, 1H), 8.05 (d, 3H), 7.89 (d, 1H), 7.75 (d, 1H), 7.65 (d, 1H), 7.61 (d, 1H), 6.25 (d, 1H), 5.60 (s, 2H), 4.62 (s, 2H), 3.81 (s, 3H), 3.20-3.05 (m, 2H), 2.40 (dt, 2H), 2.11 (d, 3H), 1.99 (t, 2H), 1.75-1.51 (m, 2H). | 488 | 1 |

TABLE 13-continued

Examples 59-74

| Example | Structure | Name | NMR Data | MS Data | Method |
|---|---|---|---|---|---|
| 71 | 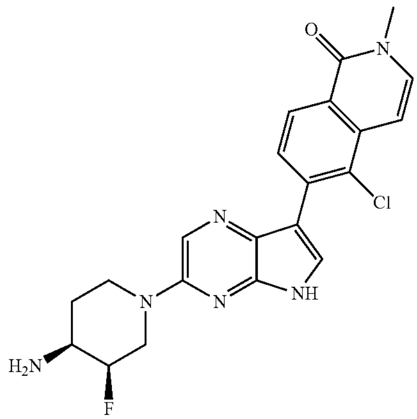 [SMILES: Cn1ccc2c(Cl)c(-c3c[nH]c4nc(N5CC[C@H](N)[C@H](F)C5)cnc34)ccc2c1=O] | 6-{3-[(3R,4S)-4-amino-3-fluoro-piperidin-1-yl]-5H-pyrrolo[2,3-b]pyrazin-7-yl}-5-chloro-2-methyl-1,2-dihydroisoquinolin-1-one, hydrochloride salt | 1H NMR (500 MHz, DMSO-$d_6$): 11.95 (1H, d), 8.45 (3H, d), 8.35 (1H, s), 8.23 (1H, d), 8.18 (1H, d), 7.97 (1H, d), 7.64 (1H, d), 6.88 (1H, d), 5.10 (1H, d), 4.82-4.72 (1H, m), 4.52-4.42 (1H, m), 3.64 (1H, dd), 3.54 (3H, s), 3.32 (1H, dd), 3.11-3.02 (1H, m), 1.97-1.83 (2H, m). | 427 | 1, preparative HPLC (Gilson, Basic (0.1% Ammonium Bicarbonate), Basic, Waters X-Bridge Prep-C18, 5 μm, 19 × 50 mm column, 15-20 MeCN in Water), |
| 72 | 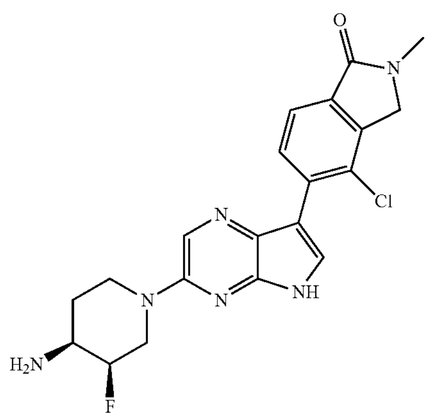 [SMILES: CN1Cc2c(ccc(-c3c[nH]c4nc(N5CC[C@H](N)[C@H](F)C5)cnc34)c2Cl)C1=O] | 5-{3-[(3R,4S)-4-amino-3-fluoro-piperidin-1-yl]-5H-pyrrolo[2,3-b]pyrazin-7-yl}-4-chloro-2-methyl-2,3-dihydro-1H-isoindol-1-one, hydrochloride salt | 1H NMR (500 MHz, DMSO-$d_6$): 11.90 (s, 1H), 8.34 (s, 1H), 8.30 (d, 1H), 7.93 (s, 1H), 7.70 (d, 1H), 6.92 (br s, 3H), 4.98 (d, 1H), 4.72-4.67 (m, 1H), 4.51 (s, 2H), 4.40 (d, 1H), 3.50-3.30 (m, 2H), 3.11 (s, 3H), 3.09-3.03 (m, 1H), 1.88-1.77 (m, 2H). | 415 | 1 |
| 73 | 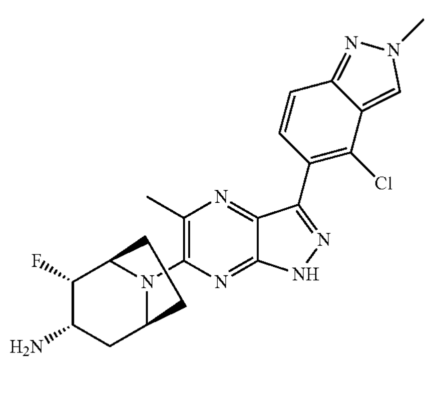 [SMILES: Cc1nc2c(-c3ccc4nn(C)cc4c3Cl)n[nH]c2nc1N1[C@H]2CC[C@@H]1[C@@H](F)[C@@H](N)C2] | (1R,2S,3S,5S)-8-[3-(4-chloro-2-methyl-2H-indazol-5-yl)-5-methyl-1H-pyrazolo[3,4-b]pyrazin-6-yl]-2-fluoro-8-azabicyclo[3.2.1]octan-3-amine, hydrochloride salt | $^1$H NMR (400 MHz, Me-$d_3$-OD): 8.45 (1H, s), 7.68 (1H, dd), 7.61 (1H, d), 5.05-4.99 (1H, m), 4.83-4.68 (3H, m), 4.30 (3H, s), 3.91-3.76 (1H, m), 2.70 (3H, s), 2.67-2.57 (1H, m), 2.35-2.15 (2H, m), 2.09-2.01 (1H, m), 1.94-1.82 (2H, m). | 441 | 8 |

TABLE 13-continued

Examples 59-74

| Example | Structure | Name | NMR Data | MS Data | Method |
|---|---|---|---|---|---|
| 74 | 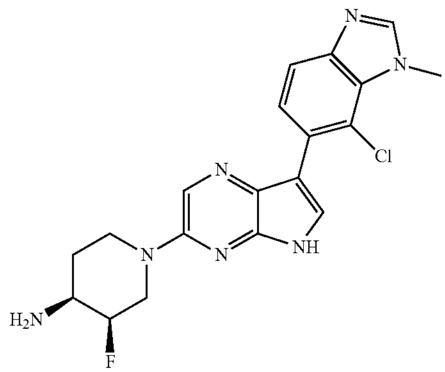 [SMILES: Cn1cnc2ccc(-c3c[nH]c4nc(N5CC[C@H](N)[C@H](F)C5)cnc34)c(Cl)c21] | (3R,4S)-1-[7-(7-chloro-1-methyl-1H-1,3-benzodiazol-6-yl)-5H-pyrrolo[2,3-b]pyrazin-3-yl]-3-fluoropiperidin-4-amine | $^1$H NMR (500 MHz, DMSO-$d_6$): 11.73 (1H, d), 8.48 (3H, d), 8.41 (1H, s), 8.29 (1H, s), 7.73-7.64 (3H, m), 5.10 (1H, d), 4.81-4.70 (1H, m), 4.45 (1H, d), 4.15 (3H, s), 3.69-3.56 (1H, ), 3.31 (1H, dd), 3.10-3.00 (1H, m), 1.97-1.84 (2H, m). | 400 | 1, except using ammonium instead of ethylene diamine |

By following methods similar and/or analogous to those described for general procedures for preparations of compounds of Formula (I) (e.g. methods 1-12), the compounds set out in Table 13 were prepared from the corresponding N-Boc, N-Cbz, N—SO$_2$NMe$_2$, 2-oxanyl or SEM protected derivatives, with any significant variations indicated. The title compounds were either isolated directly as the free base or as the appropriate salt without further purification, or purified for example using mass-directed preparative HPLC, chromatography, crystallization or trituration and converted to the appropriate salt.

TABLE 14

Examples 75-89

| Example | Structure | Name | NMR Data | Data | Method |
|---|---|---|---|---|---|
| 75 | 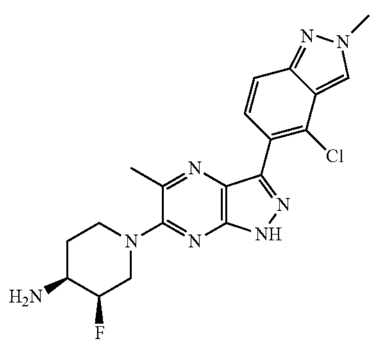 [SMILES: Cc1nc2c(-c3ccc4nn(C)cc4c3Cl)n[nH]c2nc1N1CC[C@H](N)[C@H](F)C1] | (3R,4S)-1-[3-(4-chloro-2-methyl-2H-indazol-5-yl)-5-methyl-1H-pyrazolo[3,4-b]pyrazin-6-yl]-3-fluoropiperidin-4-amine, hydrochloride | $^1$H NMR (400 MHz, DMSO-$d_6$/D$_2$O): 8.54 (1H, s), 7.68 (1H, d), 7.60 (1H, d), 5.06 (1H, d), 4.22 (3H, s), 4.15-3.98 (1H, m), 3.84 (1H, d), 3.70-3.60 (1H, m), 3.29 (1H, dd), 3.01 (1H, t), 2.57 (3H, s), 2.21-2.07 (1H, m), 2.04-1.90 (1H, m). | 415 | 11 |
| 76 | 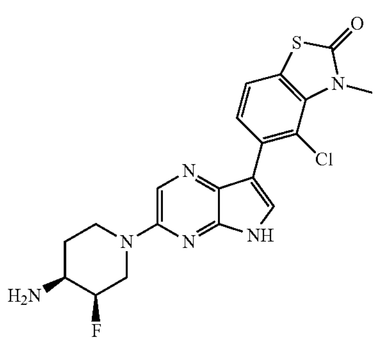 [SMILES: Cn1c(=O)sc2ccc(-c3c[nH]c4nc(N5CC[C@H](N)[C@H](F)C5)cnc34)c(Cl)c21] | 5-{3-[(3R,4S)-4-amino-3-fluoropiperidin-1-yl]-5H-pyrrolo[2,3-b]pyrazin-7-yl}-4-chloro-3-methyl-2,3-dihydro-1,3-benzothiazol-2-one, hydrochloride | $^1$H NMR (400 MHz, Me-$d_3$ OD): 8.26 (1H, s), 7.78 (1H, s), 7.60 (1H, d), 7.41 (1H, d), 5.20-5.03 (1H, m), 5.00-4.90 (1H, m), 4.73-4.65 (1H, m), 3.94 (3H, s), 3.82-3.67 (1H, m), 3.49-3.36 (1H, m), 3.27-3.17 (1H, m), 2.17-2.04 (2H, m). | 433 | 8 heating to 90° C. for 2 h, purified by chromatography on reverse phase C18 silica gel (gradient elution, 5-50% MeCN/H$_2$O + 0.1% TFA). |

TABLE 14-continued

Examples 75-89

| Example | Structure | Name | NMR Data | Data | Method |
|---|---|---|---|---|---|
| 77 | 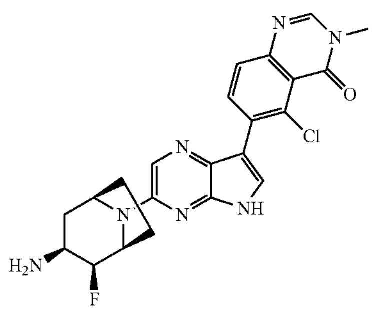 [SMILES: Cn1cnc2ccc(-c3c[nH]c4nc(N5[C@@H]6CC[C@H]5[C@@H](F)[C@@H](N)C6)cnc34)c(Cl)c2c1=O] | 6-{3-[(1S,2S,3S,5R)-3-amino-2-fluoro-8-azabicyclo[3.2.1]octan-8-yl]-5H-pyrrolo[2,3-b]pyrazin-7-yl}-5-chloro-3-methyl-3,4-dihydroquinazolin-4-one | $^1$H NMR (400 MHz, DMSO-d$_6$): 11.83 (1H, s), 8.40 (1H, s), 8.31-8.25 (1H, m), 8.16 (1H, s), 7.80 (1H, d), 7.66 (1H, d), 4.82-4.64 (2H, m), 4.54 (1H, s), 3.56 (1H, t), 3.48 (3H, s), 2.67-2.59 (1H, m), 2.33-2.28 (1H, m), 2.13-2.06 (1H, m), 1.98-1.91 (1H, m), 1.91-.77 (2H, m), 1.77-1.59 (2H, m). | 454 | 8, heating 80° for 3.5 h, purified by column chromatography on NH silica gel (gradient elution, 0-10%, MeOH/EtOAc). |
| 78 | 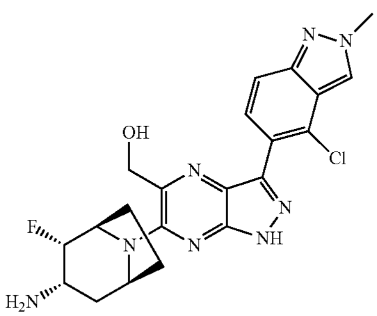 [SMILES: Cn1cc2c(Cl)c(-c3n[nH]c4nc(N5[C@H]6CC[C@@H]5[C@@H](F)[C@@H](N)C6)c(CO)nc34)ccc2n1] | rac-{6-[(1R,2S,3S,5S)-3-amino-2-fluoro-8-azabicyclo[3.2.1]octan-8-yl]-3-(4-chloro-2-methyl-2H-indazol-5-yl)-1H-pyrazolo[3,4-b]pyrazin-5-yl}methanol | 1H NMR (400 MHz, DMSO-d$_6$): 13.62-13.29 (1H, m), 8.56 (1H, s), 7.68 (1H, d), 7.66 (1H, d), 5.40-5.22 (1H, m), 5.04-4.92 (1H, m), 4.73 (1H, dd), 4.67-4.59 (2H, m), 4.52-4.44 (1H, m), 4.24 (3H, s), 3.13-3.03 (1H, m), 1.97-1.88 (3H, m), 1.77-1.70 (3H, m). | 457 | Prepared using analogous method to 8, purified by column chromatography on NH silica gel (gradient elution, 0-10%, MeOH/EtOAc). |
| 79 | 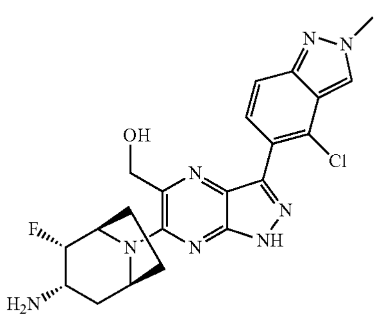 [SMILES: Cn1cc2c(Cl)c(-c3n[nH]c4nc(N5[C@H]6CC[C@@H]5[C@@H](F)[C@@H](N)C6)c(CO)nc34)ccc2n1] | {6-[(1R,2S,3S,5S)-3-amino-2-fluoro-8-azabicyclo[3.2.1]octan-8-yl]-3-(4-chloro-2-methyl-2H-indazol-5-yl)-1H-pyrazolo[3,4-b]pyrazin-5-yl}methanol | $^1$H NMR (400 MHz, DMSO-d$_6$): 13.46 (1H, s), 8.56 (1H, s), 7.71-7.67 (1H, m), 7.66 (1H, d), 5.28 (1H, t), 5.01-4.94 (1H, m), 4.73 (1H, dd), 4.69-4.44 (3H, m), 4.24 (3H, s), 3.05 (1H, s), 1.98-1.87 (3H, m), 1.77-1.66 (3H, m), 1.56-1.29 (2H, m). | 457 | Prepared using analogous method to 8, purified by column chromatography on NH silica gel (gradient elution, 0-10%, MeOH/EtOAc). |
| 80 | 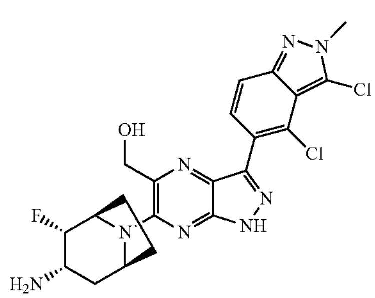 [SMILES: Cn1nc2ccc(-c3n[nH]c4nc(N5[C@H]6CC[C@@H]5[C@@H](F)[C@@H](N)C6)c(CO)nc34)c(Cl)c2c1Cl] | {6-[(1R,2S,3S,5S)-3-amino-2-fluoro-8-azabicyclo[3.2.1]octan-8-yl]-3-(3,4-dichloro-2-methyl-2H-indazol-5-yl)-1H-pyrazolo[3,4-b]pyrazin-5-yl}methanol | 1H NMR (400 MHz, DMSO-d$_6$): 13.64-13.36 (1H, m), 7.70 (1H, d), 7.63 (1H, d), 5.30 (1H, t), 5.03-4.94 (1H, m), 4.73 (1H, dd), 4.69-4.45 (3H, m), 4.19 (3H, s), 3.16-3.00 (1H, m), 2.04-1.80 (4H, m), 1.80-1.48 (4H, m). | 491 | 10 |

TABLE 14-continued

Examples 75-89

| Example | Structure | Name | NMR Data | Data | Method |
|---|---|---|---|---|---|
| 81 | 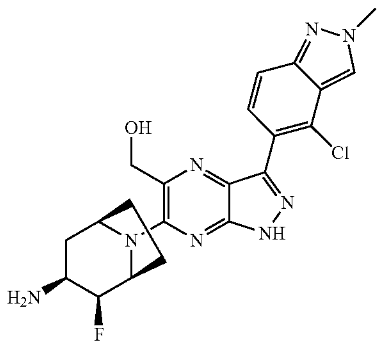 [SMILES: Cn1cc2c(Cl)c(-c3n[nH]c4nc(N5[C@@H]6CC[C@H]5[C@@H](F)[C@@H](N)C6)c(CO)nc34)ccc2n1] | {6-[(1S,2S,3S,5R)-3-amino-2-fluoro-8-azabicyclo[3.2.1]octan-8-yl]-3-(4-chloro-2-methyl-2H-indazol-5-yl)-1H-pyrazolo[3,4-b]pyrazin-5-yl}methanol | $^1$H NMR (400 MHz, DMSO-$d_6$): 13.54 (1H, s), 8.57 (1H, s), 7.69 (1H, d), 7.66 (1H, d), 5.39 (1H, t), 4.97-4.79 (1H, m), 4.78-4.70 (1H, m), 4.65-4.57 (3H, m), 4.24 (3H, s), 3.64 (1H, t), 2.64-2.55 (1H, m), 2.32-2.20 (1H, m), 2.20-2.10 (1H, m), 1.99-1.88 (1H, m), 1.88-1.80 (1H, m), 1.80-1.71 (1H, m), 1.61 (2H, s), | 457 | 8, triturated with diethyl ester |
| 82 | 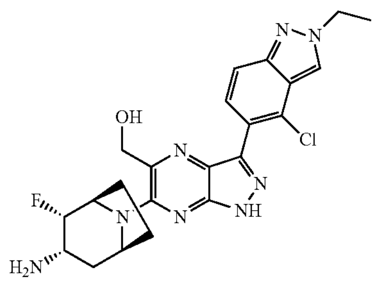 [SMILES: CCn1cc2c(Cl)c(-c3n[nH]c4nc(N5[C@H]6CC[C@@H]5[C@@H](F)[C@@H](N)C6)c(CO)nc34)ccc2n1] | {6-[(1R,2S,3S,5S)-3-amino-2-fluoro-8-azabicyclo[3.2.1]octan-8-yl]-3-(4-chloro-2-ethyl-2H-indazol-5-yl)-1H-pyrazolo[3,4-b]pyrazin-5-yl}methanol | $^1$H NMR (400 MHz, DMSO-$d_6$): 14.08-12.77 (1H, m), 8.61 (1H, s), 7.70 (1H, dd), 7.66 (1H, d), 5.34-5.23 (1H, m), 5.05-4.87 (1H, m), 4.73 (1H, dd), 4.69-4.46 (5H, m), 3.16-2.99 (1H, m), 2.01-1.87 (3H, m), 1.78-1.69 (3H, m), 1.56 (3H, t). | 471 | 8, purified by column chromatography on NH silica gel (gradient elution, 0-15%, MeOH/EtOAc) |
| 83 | 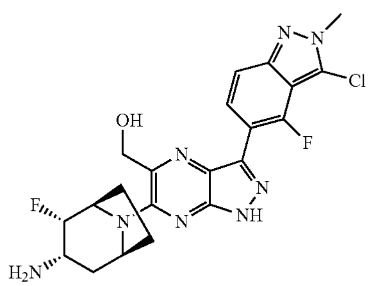 | {6-[(1R,2S,3S,5S)-3-amino-2-fluoro-8-azabicyclo[3.2.1]octan-8-yl]-3-(3-chloro-4-fluoro-2-methyl-2H-indazol-5-yl)-1H-pyrazolo[3,4-b]pyrazin-5-yl}methanol | $^1$H NMR (400 MHz, DMSO-$d_6$): 14.23-12.93 (1H, m), 8.06 (1H, dd), 7.57 (1H, d), 5.36 (1H, t), 5.06-4.95 (1H, m), 4.78 (1H, dd), 4.72-4.51 (3H, m), 4.17 (3H, s), 3.18-3.10 (1H, m), 2.02-1.86 (3H, m), 1.80-1.71 (3H, m). | 475 | 8, purified by column chromatography on NH silica gel (gradient elution, 0-15%, MeOH/EtOAc). |
| 84 | 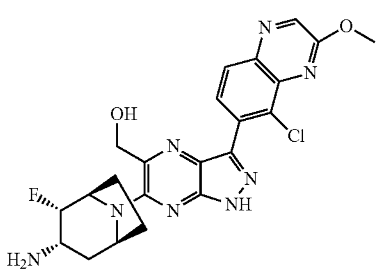 [SMILES: COc1cnc2ccc(-c3n[nH]c4nc(N5[C@H]6CC[C@@H]5[C@@H](F)[C@@H](N)C6)c(CO)nc34)c(Cl)c2n1] | {6-[(1R,2S,3S,5S)-3-amino-2-fluoro-8-azabicyclo[3.2.1]octan-8-yl]-3-(5-chloro-3-methoxyquinoxalin-6-yl)-1H-pyrazolo[3,4-b]pyrazin-5-yl}methanol | $^1$H NMR (400 MHz, Me-$d_3$-OD): 8.69-8.60 (1H, m), 8.16-8.05 (1H, m), 8.05-7.95 (1H, m), 4.99 (1H, s), 4.93-4.90 (2H, m), 4.84-4.76 (1H, m), 4.74-4.55 (1H, m), 4.28-4.24 (3H, m), 3.32-3.15 (1H, m), 2.29-2.06 (3H, m), 1.98-1.80 (3H, m). | 485 | 10 |
| 85 | 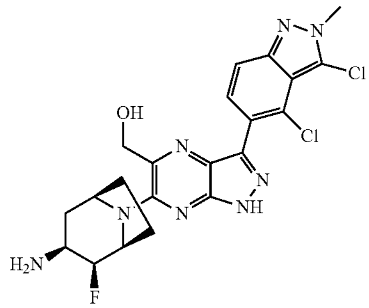 | {6-[(1S,2S,3S,5R)-3-amino-2-fluoro-8-azabicyclo[3.2.1]octan-8-yl]-3-(3,4-dichloro-2-methyl-2H-indazol-5-yl)-1H-pyrazolo[3,4-b]pyrazin-5-yl}methanol | $^1$H NMR (400 MHz, DMSO-$d_6$): 13.75-13.45 (1H, m), 7.74-7.66 (1H, m), 7.65-7.59 (1H, m), 5.41 (1H, t), 4.09 (1H, dt), 4.79-4.71 (1H, m), 4.67-4.57 (3H, m), 4.18 (3H, s), 3.64 (1H, t), 2.64-2.55 (1H, m), 2.30-2.11 (3H, m), 2.01-1.69 (4H, m). | 491 | 12 |

TABLE 14-continued

Examples 75-89

| Example | Structure | Name | NMR Data | Data | Method |
|---|---|---|---|---|---|
| 86 | 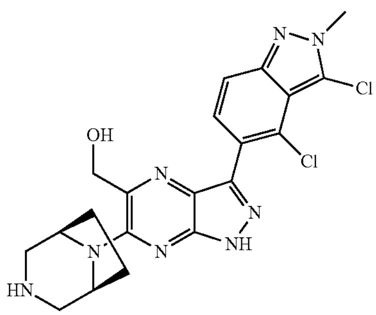 [SMILES: Cn1nc2ccc(-c3n[nH]c4nc(N5[C@@H]6CC[C@H]5CNC6)c(CO)nc34)c(Cl)c2c1Cl] | {6-[3,8-diazabicyclo[3.2.1]octan-8-yl]-3-(3,4-dichloro-2-methyl-2H-indazol-5-yl)-1H-pyrazolo[3,4-b]pyrazin-5-yl}methanol | $^1$H NMR (500 MHz, DMSO-d$_6$): 13.53 (1H, s), 7.71 (1H, d), 7.64 (1H, d), 5.35 (1H, t), 4.62 (2H, d), 4.51 (2H, s), 4.19 (3H, s), 3.02 (2H, d), 2.66 (2H, dd), 1.97-1.82 (4H, m). | 459 | 1, purified by chromatography on silica gel (gradient elution, 7-15% MeOH/DCM) |
| 87 | 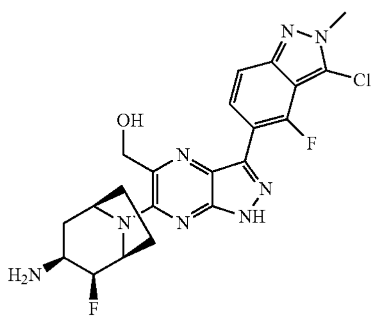 [SMILES: Cn1nc2ccc(-c3n[nH]c4nc(N5[C@@H]6CC[C@H]5[C@@H](F)[C@@H](N)C6)c(CO)nc34)c(F)c2c1Cl] | {6-[(1S,2S,3S,5R)-3-amino-2-fluoro-8-azabicyclo[3.2.1]octan-8-yl]-3-(3-chloro-4-fluoro-2-methyl-2H-indazol-5-yl)-1H-pyrazolo[3,4-b]pyrazin-5-yl}methanol | $^1$H NMR (400 MHz, DMSO-d$_6$): 13.66-13.51 (1H, m), 8.06 (1H, dd), 7.57 (1H, d), 5.45 (1H, t), 4.88 (1H, dt), 4.78-4.71 (1H, m), 4.67 (2H, d), 4.62 (1H, d), 4.17 (3H, s), 3.64 (1H, t), 2.64-2.56 (1H, m), 2.30-2.22 (1H, m), 2.15 (1H, d), 1.99-1.71 (3H, m). | 475 | 12, further purified by chromatography on reverse phase C18 silica gel (gradient elution, 5-50% MeCN/H2O + 0.1% TFA). |
| 88 | 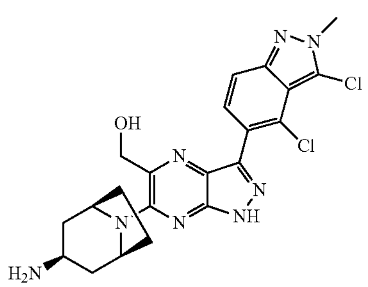 [SMILES: Cn1nc2ccc(-c3n[nH]c4nc(N5[C@@H]6CC[C@H]5C[C@@H](N)C6)c(CO)nc34)c(Cl)c2c1Cl] | {6-[endo-3-amino-8-azabicyclo[3.2.1]octan-8-yl]-3-(3,4-dichloro-2-methyl-2H-indazol-5-yl)-1H-pyrazolo[3,4-b]pyrazin-5-yl}methanol | $^1$H NMR (400 MHz, DMSO-d$_6$): 7.74-7.67 (1H, m), 7.67-7.61 (1H, m), 5.35-5.26 (1H, m), 4.76-4.53 (4H, m), 4.18 (3H, s), 3.29-3.26 (1H, m), 2.32-2.17 (4H, m), 1.97-1.88 (2H, m), 1.62-1.53 (2H, m) | 473 | 12 |
| 97 | 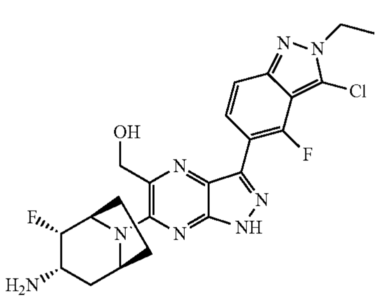 [SMILES: CCn1nc2ccc(-c3n[nH]c4nc(N5[C@H]6CC[C@@H]5[C@@H](F)[C@@H](N)C6)c(CO)nc34)c(F)c2c1Cl] | {6-[(1R,2S,3S,5S)-3-amino-2-fluoro-8-azabicyclo[3.2.1]octan-8-yl]-3-(3-chloro-2-ethyl-4-fluoro-2H-indazol-5-yl)-1H-pyrazolo[3,4-b]pyrazin-5-yl}methanol | $^1$H NMR (400 MHz, DMSO_cap): 8.08 (1H, dd), 7.59 (1H, d), 5.35 (1H, d), 5.04-4.97 (1H, m), 4.78 (1H, d), 4.74-4.45 (5H, m), 2.06-1.86 (3H, m), 1.75 (3H, d), 1.51 (3H, t). | 489 | 10, triturated with MeOH |

By following methods similar and/or analogous to those described for general procedures for preparations of compounds of Formula (I) (e.g. methods 1-12), the compounds set out in Table 14 were prepared from the corresponding N-Boc, N-CBz, N—SO₂NMe₂, 2-oxanyl or SEM protected derivatives, with any significant variations indicated. The title compounds were either isolated directly as the free base or as the appropriate salt without further purification, or purified for example using mass-directed preparative HPLC, chromatography, crystallization or trituration and converted to the appropriate salt.

Example 90: rac-(1S,2S,3S,5R)-3-Amino-8-[3-(3,4-dichloro-2-methyl-2H-indazol-5-yl)-5-methyl-1H-pyrazolo[3,4-b]pyrazin-6-yl]-8-azabicyclo[3.2.1]octan-2-ol 3,4-Dichloro-2-methyl-2H-indazole-5-carbaldehyde

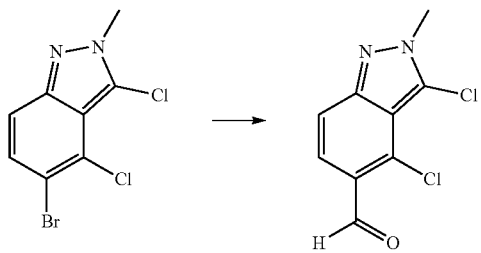

A solution of isopropylmagnesium chloride lithium chloride complex (1.3 M in THF) (5.50 mL, 7.14 mmol) was added dropwise to a solution of 5-bromo-3,4-dichloro-2-methyl-2H-indazole (1.0 g, 3.57 mmol, azeotropically dried from toluene 3×) in dry THF (8.78 mL) at 0° C. and stirred for 3 h. DMF (1.11 mL, 14.3 mmol) was added dropwise and the reaction warmed to RT and stirred for 1 h. The reaction was quenched with sat. aq. NH₄Cl (20 mL) and extracted with EtOAc (3×20 mL). The combined organics were washed with brine (20 mL), dried (MgSO₄) and evaporated. The resulting solid (0.83 g) was triturated with petrol (2×50 mL) and azeotropically dried with THF (3×20 mL), to give the title compound (0.71 g). MS: [M+H]⁺=229/231.

rac-(3,4-Dichloro-2-methyl-2H-indazol-5-yl)(3,5-dichloro-6-methylpyrazin-2-yl)methanol

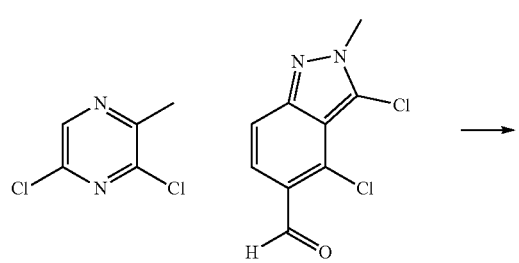

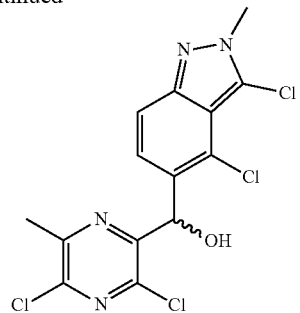

A solution of 2,2,6,6-tetramethylpiperidinylmagnesium chloride lithium chloride complex (1 M in THF/toluene, 3.10 mL, 3.10 mmol) was added dropwise to a solution of 3,5-dichloro-2-methylpyrazine (0.421 g, 2.58 mmol) in dry THF (5.02 mL) at −78° C. and the deep red mixture was stirred for 2.5 h. A solution of 3,4-dichloro-2-methyl-2H-indazole-5-carbaldehyde (0.71 g, 3.10 mmol) in dry THF (6 mL) was added in one portion and the reaction allowed to warm to RT, stirring for 30 min. The reaction was stirred overnight at RT then quenched with sat. aq. NH₄Cl (20 mL) and extracted with EtOAc (3×20 mL). The combined organics were dried (MgSO₄) and concentrated. The residue was purified by column chromatography on silica gel (gradient elution, 0-100%, EtOAc/ioshexane), to give the title compound (330 mg). MS: [M+H]⁺=391/393/395.

3,4-Dichloro-5-(3,5-dichloro-6-methylpyrazine-2-carbonyl)-2-methyl-2H-indazole

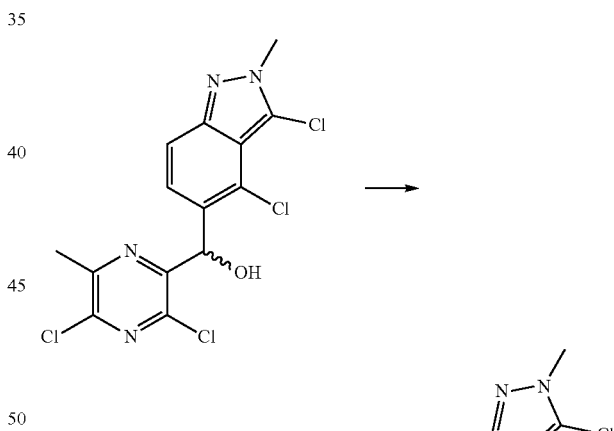

Manganese dioxide (1.46 g, 16.8 mmol) was added to a solution of rac-(3,4-dichloro-2-methyl-2H-indazol-5-yl)(3,5-dichloro-6-methylpyrazin-2-yl)methanol (330 mg, 0.842 mmol) in DCM (8.23 mL) and the reaction stirred at RT for 18 h. The reaction was filtered through Celite, washing with DCM, and the filtrate evaporated, to give the title compound (0.28 g). MS: [M+H]⁺=389/391.

383 rac-tert-Butyl (1S,2R,5R)-2-hydroxy-3,3-dimethoxy-8-azabicyclo[3.2.1]octane-8-carboxylate

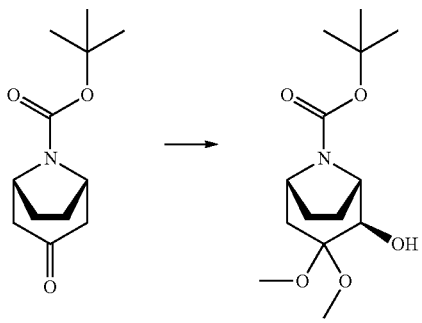

To an ice bath-cooled solution of potassium hydroxide (43 g, 766 mmol) in anhydrous MeOH (300 mL) was added N-Boc-nortropinone (38 g, 169 mmol) in MeOH (200 mL) dropwise over 25 minutes maintaining the internal temperature in the range 0-3° C. The mixture was stirred for 20 minutes. Iodobenzene diacetate (83 g, 258 mmol) was added portionwise then the mixture was allowed to warm to RT and stir for 2 h. The mixture was diluted with water (1 L) then extracted with isohexane (3×500 mL). The combined organic phases were dried (MgSO$_4$), filtered and concentrated to give the title compound (85 g) containing 61 wt % iodobenzene. 1H NMR (500 MHz, DMSO-d$_6$): 4.89 (1H, d), 3.96 (1H, br. s), 3.79 (1H, br. s), 3.61 (1H, br. s), 3.20 (3H, s), 3.19 (3H, s), 2.18-1.94 (2H, m), 1.80-1.51 (3H, m), 1.39 (10H, m).

rac-tert-Butyl (1S,2R,5R)-2-(benzyloxy)-3,3-dimethoxy-8-azabicyclo[3.2.1]octane-8-carboxylate

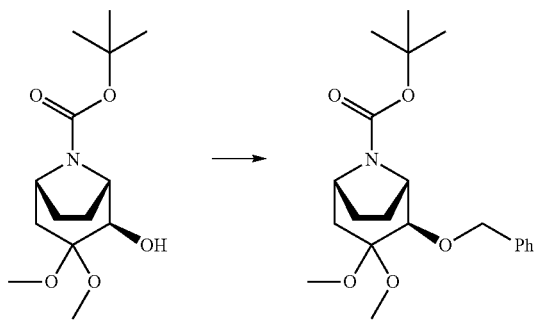

A solution of rac-tert-butyl (1S,2R,5R)-2-hydroxy-3,3-dimethoxy-8-azabicyclo[3.2.1]octane-8-carboxylate (85 g, 115 mmol) in THF (100 mL) was added dropwise to an ice bath-cooled suspension of sodium hydride (60% in mineral oil, 5 g, 125 mmol) in THF (200 mL) then stirred at 0° C. for 20 min. Benzyl bromide (17.4 mL, 146 mmol) was added dropwise and the mixture was stirred at RT for 18 h. The mixture was diluted with water (1 L) then extracted with isohexane (3×500 mL). The organic phases were loaded onto silica gel (1 kg) and purified by column chromatography (gradient elution, 0-50%, EtOAc/isohexane), to give the title compound (47 g). MS: [M+Na]$^+$=400.

384 rac-tert-Butyl (1S,2R,5R)-2-(benzyloxy)-3-oxo-8-azabicyclo[3.2.1]octane-8-carboxylate

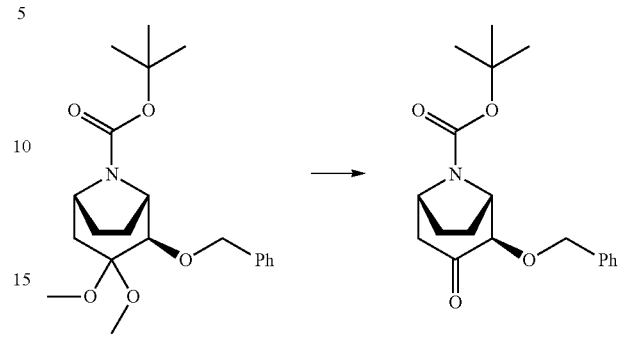

p-Toluenesulfonic acid monohydrate (1 g, 5.26 mmol) was added to a stirred solution of rac-tert-butyl (1S,2R,5R)-2-(benzyloxy)-3,3-dimethoxy-8-azabicyclo[3.2.1]octane-8-carboxylate (47 g, 100 mmol) in acetone (400 mL) and water (3 mL, 167 mmol) then the mixture was stirred at RT for 1 h. The mixture was concentrated then diluted with sat. aq. NaHCO$_3$ (220 mL) and extracted with DCM (2×300 mL). The combined organic phases were concentrated. Overnight, the product crystallised and the yellow oil was decanted away, to give the title compound (31.5 g). 1H NMR (500 MHz, 90° C./363K, DMSO-d$_6$): 7.38-7.25 (5H, m), 4.80 (1H, d), 4.60 (1H, d), 4.38-4.29 (2H, m), 4.02 (1H, d), 2.69 (1H, ddt), 2.27 (1H, dd), 2.03-1.84 (2H, m), 1.81-1.72 (1H, m), 1.56-1.47 (1H, m), 1.42 (9H, s).

rac-tert-Butyl (1S,2S,3S,5R)-3-(benzylamino)-2-(benzyloxy)-8-azabicyclo[3.2.1]octane-8-carboxylate

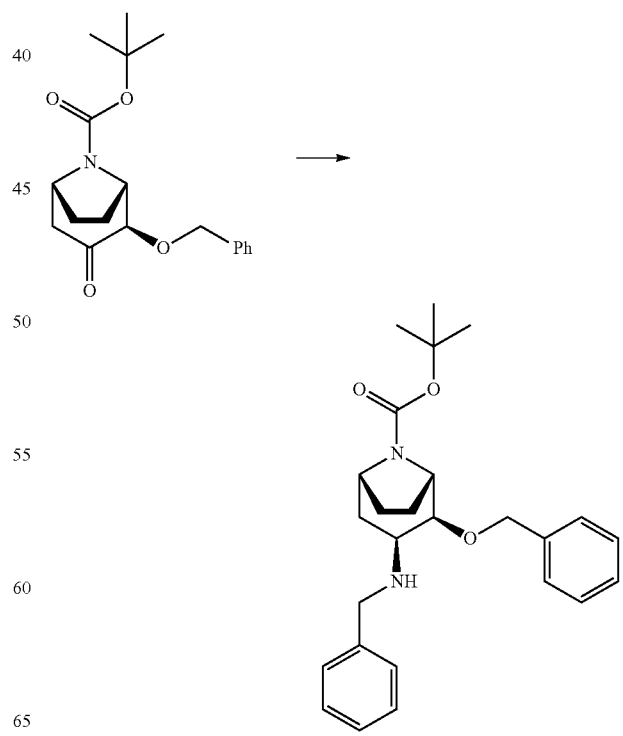

Sodium triacetoxyborohydride (30 g, 142 mmol) was added to an ice bath-cooled solution of rac-tert-butyl (1S,2R,5R)-2-(benzyloxy)-3-oxo-8-azabicyclo[3.2.1]octane-8-carboxylate (30.5 g, 92 mmol) and benzylamine (13 mL, 119 mmol) in DCM (300 mL) then allowed to warm to RT and stir for 2 days. The mixture was diluted with sat. aq. NaHCO$_3$ (25 g) and water (250 mL) then extracted with DCM (3×200 mL). The combined organic phases were concentrated then purified by column chromatography on silica gel (gradient elution, 5-50%, acetone/isohexane), to give the title compound (30.5 g). 1H NMR (500 MHz, 90° C./363K, DMSO-d6): 7.42-7.20 (10H, m), 4.58-4.48 (2H, m), 4.11-3.98 (2H, m), 3.83 (1H, d), 3.63 (1H, t), 3.55 (1H, d), 3.16 (1H, t), 2.24 (2H, td), 2.13 (1H, s), 1.91-1.58 (4H, m), 1.38 (9H, s).

rac-tert-butyl (1S,2S,3S,5R)-3-amino-2-hydroxy-8-azabicyclo[3.2.1]octane-8-carboxylate A solution of rac-tert-butyl (1S,2S,3S,5R)-3-(benzylamino)-2-(benzyloxy)-8-azabicyclo[3.2.1]octane-8-carboxylate (7 g, 15.7 mmol) in ethanol (150 mL) and cyclohexene (50 mL, 494 mmol) was treated with 5% Pd/C (4 g, 0.801 mmol) then heated to 75° C. overnight. Ammonium formate (10 g, 159 mmol) was added portionwise then heating was continued for 1 h. The mixture was filtered then concentrated. The residue was heated with ammonium formate (10 g, 159 mmol) and 5% Pd/C (4 g, 0.801 mmol) in IPA (150 mL) at 65° C. for 1 h. A further four portions of ammonium formate (10 g, 159 mmol) were added over the next 5 h. The mixture was cooled, filtered through Celite then concentrated. The residue was loaded onto an MCI Gel CHP20P column (100 g). The product was eluted with MeCN/H$_2$O (10-50%), to give the title compound (2.25 g). 1H NMR (500 MHz, 90° C./363K, DMSO-d$_6$): 4.03-3.96 (1H, m), 3.88 (1H, dd), 3.61 (1H, dd), 3.26 (1H, t), 2.32 (1H, ddd), 2.08 (1H, ddd), 1.98-1.87 (1H, m), 1.77 (1H, tddd), 1.66-1.57 (2H, m), 1.42 (9H, s), 1.14 (1H, s). Two exchangeable protons not observed.

rac-(1S,2S,3S,5R)-3-Amino-8-[6-chloro-5-(3,4-dichloro-2-methyl-2H-indazole-5-carbonyl)-3-methylpyrazin-2-yl]-8-azabicyclo[3.2.1]octan-2-ol

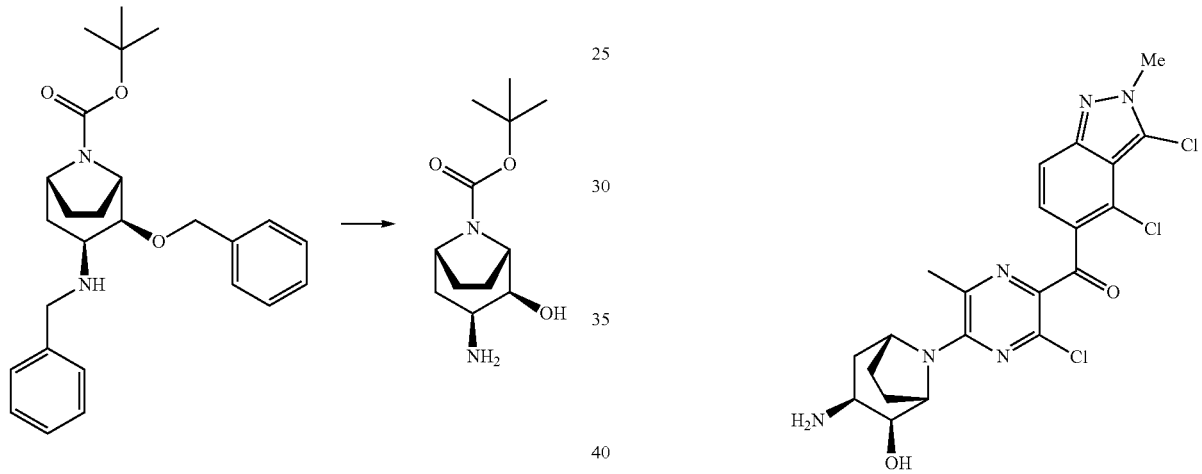

HCl (3 M in cyclopentyl methyl ether, 657 µL, 1.970 mmol) was added slowly to a solution of rac-tert-butyl (1S,2S,3S,5R)-3-amino-2-hydroxy-8-azabicyclo[3.2.1]octane-8-carboxylate (75 mg, 0.310 mmol) in DCM (199 µL) then stirred for 3 h. The reaction mixture was concentrated in vacuo, to give rac-(1S,2S,3S,5R)-3-amino-8-azabicyclo[3.2.1]octan-2-ol dihydrochloride. This compound was added to a solution of 3,4-dichloro-5-(3,5-dichloro-6-methylpyrazine-2-carbonyl)-2-methyl-2H-indazole (110 mg, 0.281 mmol) and DIPEA (197 µL, 1.126 mmol) in NMP (1.33 mL) at 0° C. and the mixture was stirred overnight at RT. The mixture was diluted with EtOAc (10 mL) then washed sequentially with sat. aq. NH$_4$Cl (3×5 mL) and water (3×5 mL). The organic phase was dried (MgSO$_4$) and concentrated. The residue was purified by column chromatography on silica gel (gradient elution, 0-10%, 0.7% NH$_3$ in MeOH/DCM), to give the title compound (33 mg). MS: [M+H]$^+$=495/497/499.

387 rac-(1S,2S,3S,5R)-3-Amino-8-[3-(3,4-dichloro-2-methyl-2H-indazol-5-yl)-5-methyl-1H-pyrazolo[3,4-b]pyrazin-6-yl]-8-azabicyclo[3.2.1]octan-2-ol

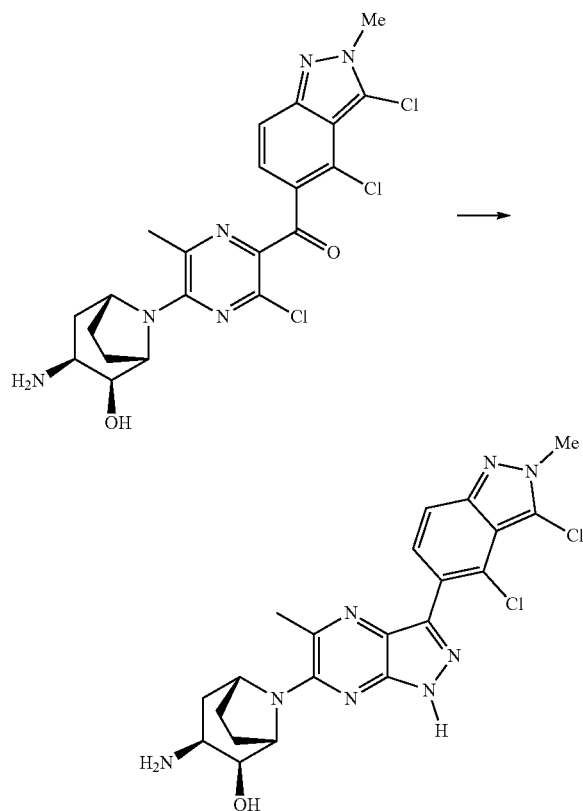

Hydrazine monohydrate (6.68 µL, 0.211 mmol) was added to a solution of rac-(1S,2S,3S,5R)-3-amino-8-[6-chloro-5-(3,4-dichloro-2-methyl-2H-indazole-5-carbonyl)-3-methylpyrazin-2-yl]-8-azabicyclo[3.2.1]octan-2-ol (20.9 mg, 0.042 mmol) in EtOH (0.829 mL) and the mixture was heated to 80° C. for 5 h then concentrated in vacuo. The residue was purified by column chromatography on silica gel (gradient elution, 0-10%, 0.7% NH$_3$ in MeOH/DCM), to give the title compound (5.5 mg). MS: [M+H]$^+$=473/475. 1H NMR (500 MHz, methanol-d$_4$): 7.62 (1H, d), 7.53 (1H, d), 4.46-4.41 (1H, m), 4.36 (1H, dd), 4.20 (3H, s), 4.05 (1H, dd), 3.35-3.32 (1H, m), 2.64 (3H, s), 2.47-2.35 (2H, m2H), 2.13-1.95 (3H, m), 1.90-1.85 (1H, m).

Examples 91-96

4-Chloro-2-ethyl-2H-indazole-5-carbaldehyde

388

Prepared similarly to 3,4-dichloro-2-methyl-2H-indazole-5-carbaldehyde, to give the title compound.

rac-(4-Chloro-2-ethyl-2H-indazol-5-yl)(3,5-dichloro-6-methylpyrazin-2-yl)methanol

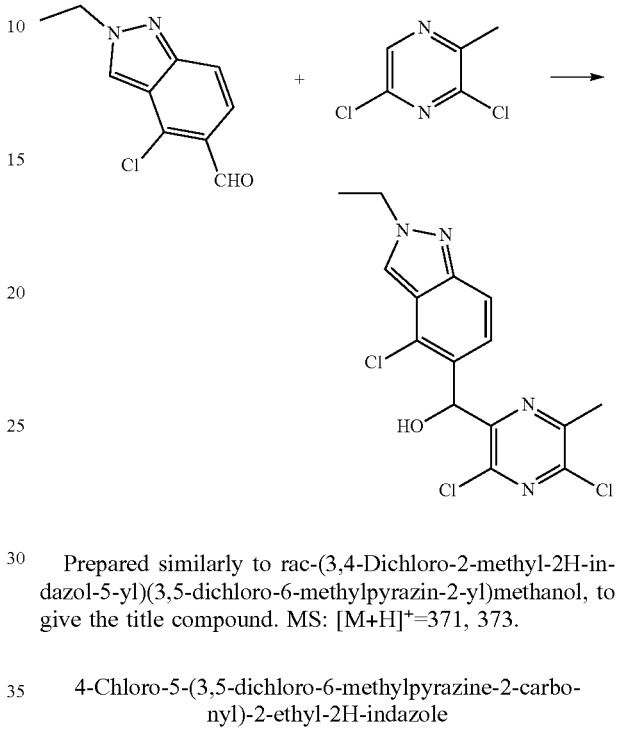

Prepared similarly to rac-(3,4-Dichloro-2-methyl-2H-indazol-5-yl)(3,5-dichloro-6-methylpyrazin-2-yl)methanol, to give the title compound. MS: [M+H]$^+$=371, 373.

4-Chloro-5-(3,5-dichloro-6-methylpyrazine-2-carbonyl)-2-ethyl-2H-indazole

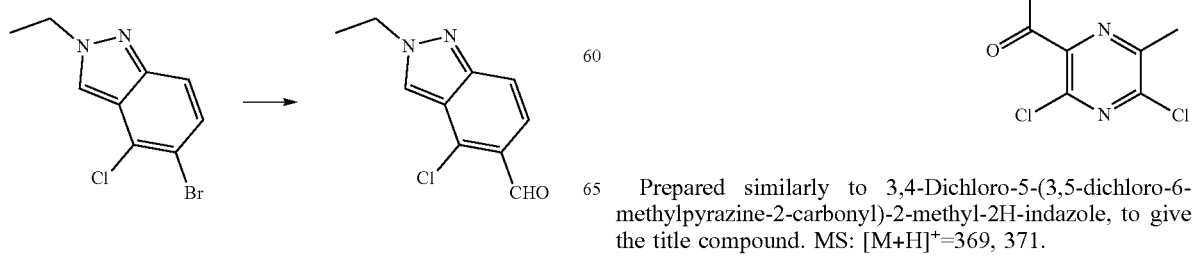

Prepared similarly to 3,4-Dichloro-5-(3,5-dichloro-6-methylpyrazine-2-carbonyl)-2-methyl-2H-indazole, to give the title compound. MS: [M+H]$^+$=369, 371.

389

Benzyl N-[(1R,2S,3S,5S)-8-[6-chloro-5-(4-chloro-2-ethyl-2H-indazole-5-carbonyl)-3-methylpyrazin-2-yl]-2-fluoro-8-azabicyclo[3.2.1]octan-3-yl]carbamate

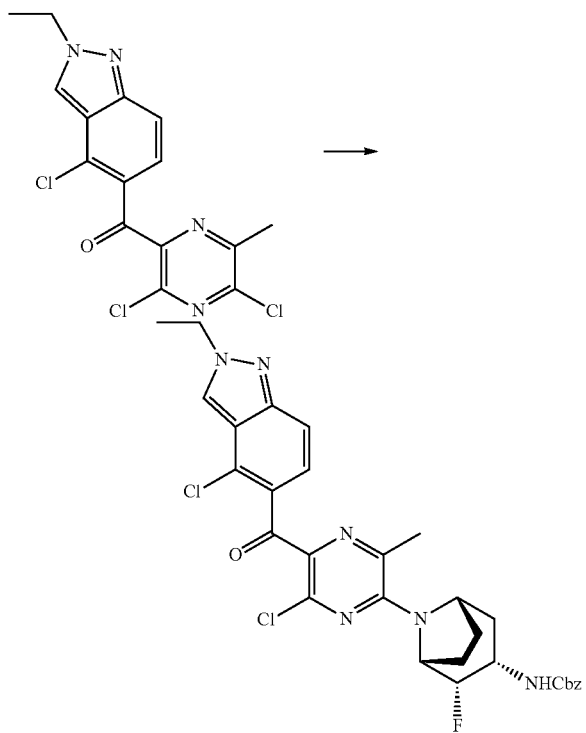

Prepared similarly to preparation 125: benzyl N-[(1R,2S,3S,5S)-8-[6-chloro-5-(4-chloro-2-methyl-2H-indazole-5-carbonyl)-3-methylpyrazin-2-yl]-2-fluoro-8-azabicyclo[3.2.1]octan-3-yl]carbamate, to give the title compound, to give the title compound (253 mg). MS: [M+H]$^+$=611, 613.

tert-Butyl 9-[6-chloro-5-(4-chloro-2-methyl-2H-indazole-5-carbonyl)-3-methylpyrazin-2-yl]-3,9-diazabicyclo[3.3.1]nonane-3-carboxylate

390

-continued

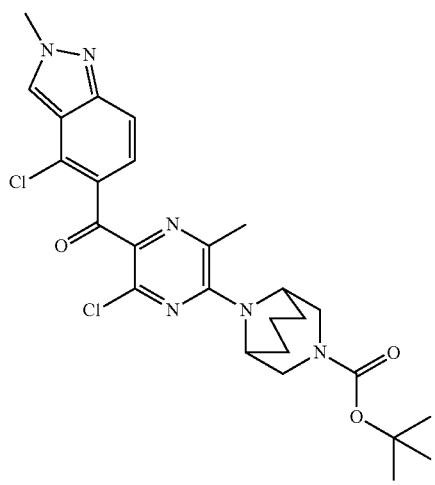

Prepared similarly to preparation 125: benzyl N-[(1R,2S,3S,5S)-8-[6-chloro-5-(4-chloro-2-methyl-2H-indazole-5-carbonyl)-3-methylpyrazin-2-yl]-2-fluoro-8-azabicyclo[3.2.1]octan-3-yl]carbamate, except stirring at RT for 2 h. Then, the mixture was stirred at 60° C. overnight. The mixture was stirred additionally at 80° C. for 2 h, to give the title compound. MS: [M+H]$^+$=545, 547

Benzyl N-[(1R,2S,3S,5S)-8-[6-chloro-5-(3,4-dichloro-2-methyl-2H-indazole-5-carbonyl)-3-methylpyrazin-2-yl]-2-fluoro-8-azabicyclo[3.2.1]octan-3-yl]carbamate

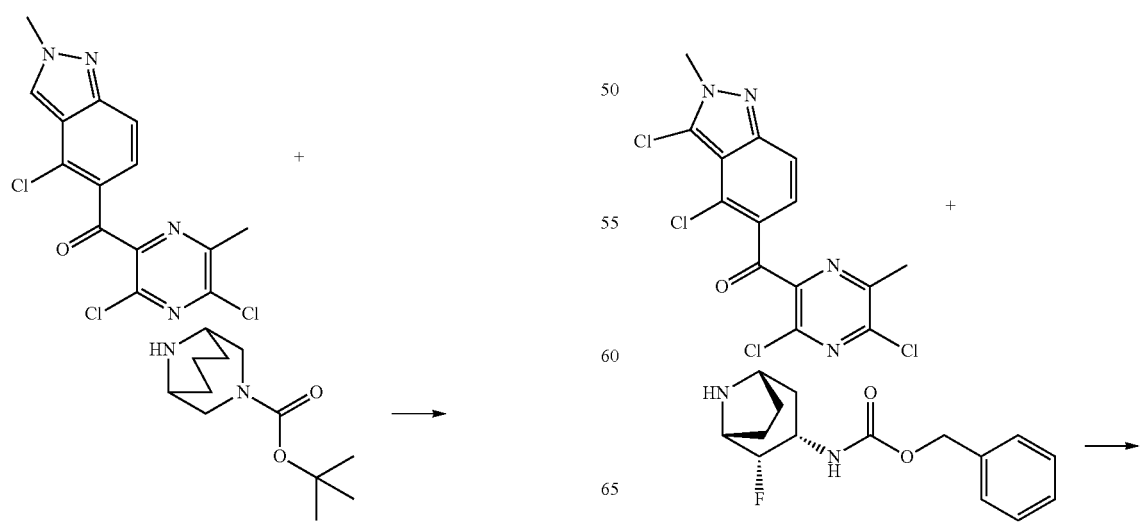

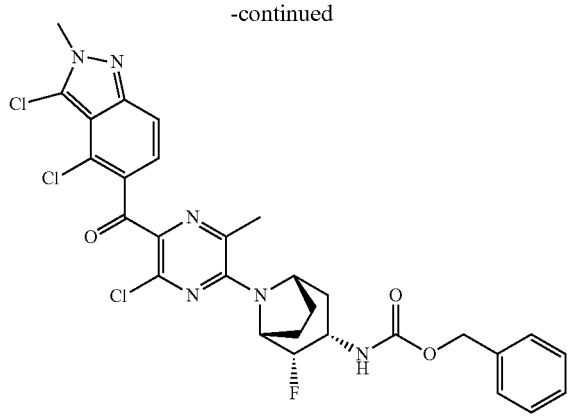

Prepared similarly to preparation 125: benzyl N-[(1R,2S,3S,5S)-8-[6-chloro-5-(4-chloro-2-methyl-2H-indazole-5-carbonyl)-3-methylpyrazin-2-yl]-2-fluoro-8-azabicyclo[3.2.1]octan-3-yl]carbamate, except stirring at RT for 3 days, to give the title compound. MS: [M+H]⁺=631, 633.

Benzyl N-[(1R,2S,3S,5S)-8-[3-(3,4-dichloro-2-methyl-2H-indazol-5-yl)-5-methyl-1H-pyrazolo[3,4-b]pyrazin-6-yl]-2-fluoro-8-azabicyclo[3.2.1]octan-3-yl]carbamate

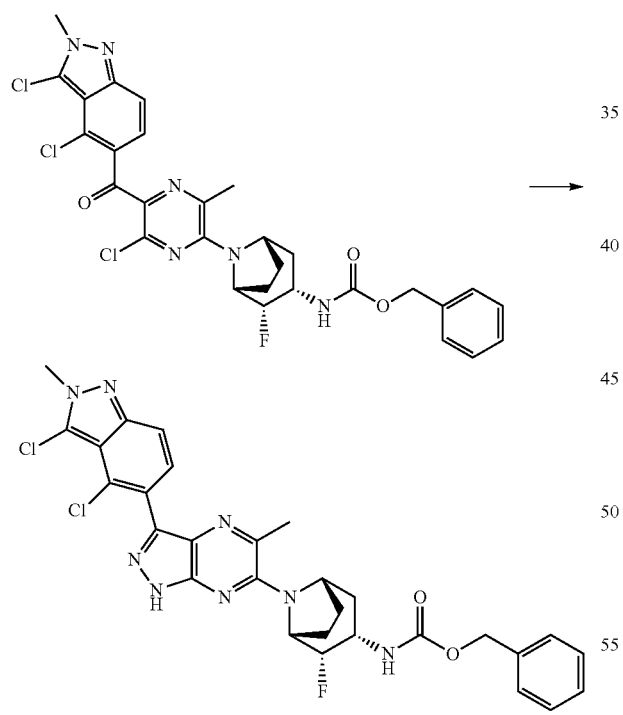

To a solution of benzyl N-[(1R,2S,3S,5S)-8-[6-chloro-5-(3,4-dichloro-2-methyl-2H-indazole-5-carbonyl)-3-methylpyrazin-2-yl]-2-fluoro-8-azabicyclo[3.2.1]octan-3-yl]carbamate (154 mg, 0.24 mmol) in THF (2.0 mL), hydrazine hydrate (0.059 mL, 1.22 mmol) was added at RT. The mixture was stirred at 70° C. for 2 h. The reaction solution was then concentrated under vacuum, and the residue was purified by column chromatography on silica gel (gradient elution, 20-100%, EtOAc/hexane). The crude mixture was dissolved in 1,2-dimethoxyethane (2.0 mL). To the solution, HCl solution (4 M in dioxane, 1.0 mL) was added at RT. The solution was stirred at 80° C. for 1 h. The reaction solution was then concentrated under vacuum, and the residue was purified by column chromatography on silica gel (gradient elution, 20-100%, EtOAc/hexane), to give the title compound (40 mg). MS: [M+H]⁺=609, 611.

tert-Butyl 9-[3-(4-chloro-2-methyl-2H-indazol-5-yl)-5-methyl-1H-pyrazolo[3,4-b]pyrazin-6-yl]-3,9-diazabicyclo[3.3.1]nonane-3-carboxylate

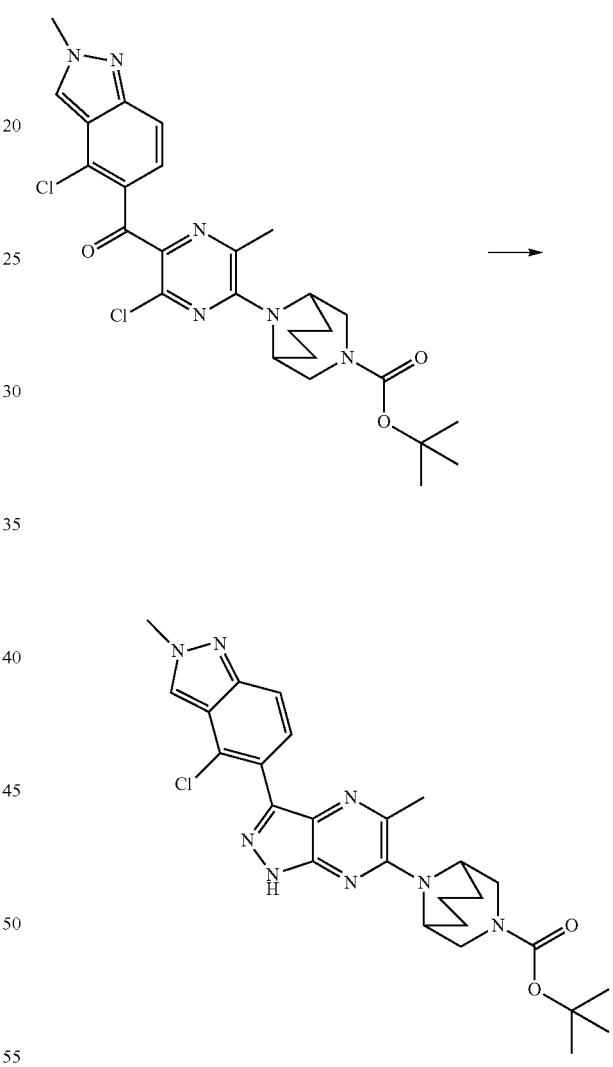

Prepared similarly to benzyl N-[(1R,2S,3S,5S)-8-[3-(3,4-dichloro-2-methyl-2H-indazol-5-yl)-5-methyl-1H-pyrazolo[3,4-b]pyrazin-6-yl]-2-fluoro-8-azabicyclo[3.2.1]octan-3-yl]carbamate, except the the mixture was stirred at 80° C. for 8 h. Then, the mixture was stirred at RT for 4 days, to give the title compound. MS: [M+H]⁺=523.

393

Benzyl N-[(1R,2S,3S,5S)-8-[3-(4-chloro-2-ethyl-2H-indazol-5-yl)-5-methyl-1H-pyrazolo[3,4-b]pyrazin-6-yl]-2-fluoro-8-azabicyclo[3.2.1]octan-3-yl]carbamate

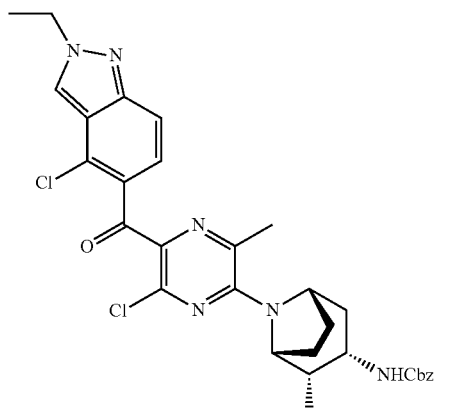

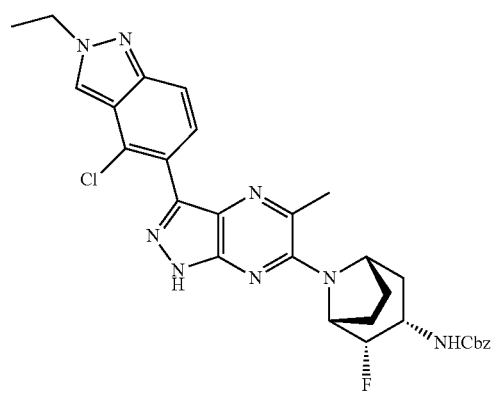

Prepared similarly to benzyl N-[(1R,2S,3S,5S)-8-[3-(3,4-dichloro-2-methyl-2H-indazol-5-yl)-5-methyl-1H-pyrazolo[3,4-b]pyrazin-6-yl]-2-fluoro-8-azabicyclo[3.2.1]octan-3-yl]carbamate except the mixture was stirred at 90° C. for 2 h and concentrated in vacuo to give the title compound. MS: [M+H]⁺=589, 591.

tert-Butyl 7-[3-(4-chloro-2-methyl-2H-indazol-5-yl)-5-methyl-1H-pyrazolo[3,4-b]pyrazin-6-yl]-2,7-diazaspiro[3.5]nonane-2-carboxylate

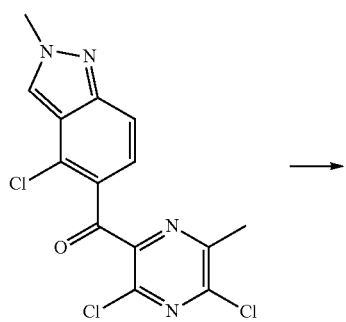

394

-continued

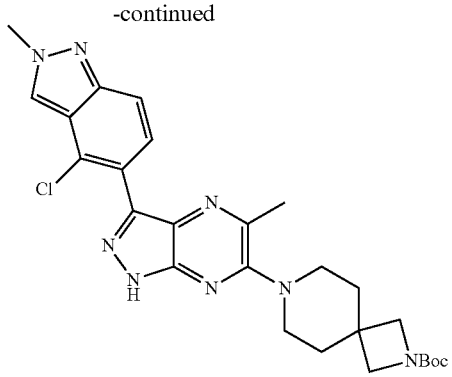

Prepared similarly to benzyl N-[(1R,2S,3S,5S)-8-[6-chloro-5-(4-chloro-2-methyl-2H-indazole-5-carbonyl)-3-methylpyrazin-2-yl]-2-fluoro-8-azabicyclo[3.2.1]octan-3-yl]carbamate and benzyl N-[(1R,2S,3S,5S)-8-[3-(3,4-dichloro-2-methyl-2H-indazol-5-yl)-5-methyl-1H-pyrazolo[3,4-b]pyrazin-6-yl]-2-fluoro-8-azabicyclo[3.2.1]octan-3-yl]carbamate, to give the title compound. MS: [M+H]⁺=523, 525.

6-Chloro-1H-4λ⁵-pyrazolo[3,4-b]pyrazin-4-one

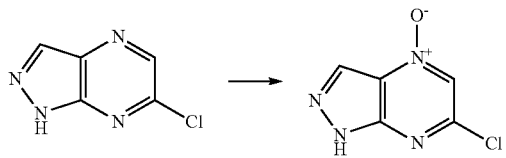 [SMILES: Clc1cnc2cn[nH]c2n1 ; [O-][n+]1cc(Cl)nc2[nH]ncc21]

To a suspension of 6-chloro-1H-pyrazolo[3,4-b]pyrazine (17.4 g) in acetonitrile (174 mL), urea hydrogen peroxide (22.2 g, 236 mmol) and trifluoroacetic anhydride (31.3 mL, 225 mmol) were added at 0° C., and then the mixture was stirred at RT for 1.5 h. The mixture was diluted with water (200 mL) and the precipitate was collected by filtration and dried under vacuum at 60° C., to give the title compound (10.4 g), MS: [M+H]⁺=171, 173.

6-Chloro-1-(oxan-2-yl)-1H-4λ⁵-pyrazolo[3,4-b]pyrazin-4-one

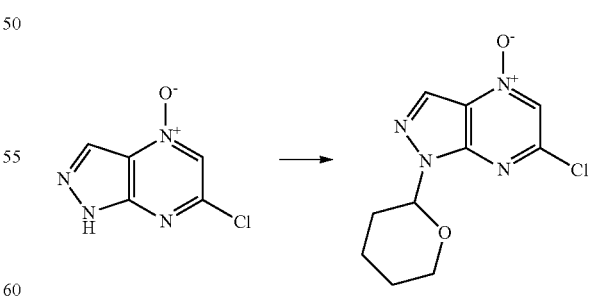

To a suspension of 6-chloro-1H-4λ⁵-pyrazolo[3,4-b]pyrazin-4-one (10.4 g, 61.4 mmol) in THF (200 ml), 3,4-dihydro-2H-pyran (16.7 mL, 184 mmol), and p-toluenesulfonic acid monohydrate (0.58 g, 3.06 mmol) were added, and then the mixture was stirred at RT overnight. The reaction was concentrated in vacuo and the residue was purified by column chromatography on silica gel (gradient elution, 0-30%, EtOAc/CHCl₃), to give the title compound (12.9 g), MS: [M+H]⁺=255, 257.

6-Chloro-5-methyl-1-(oxan-2-yl)-1H-pyrazolo[3,4-b]pyrazine

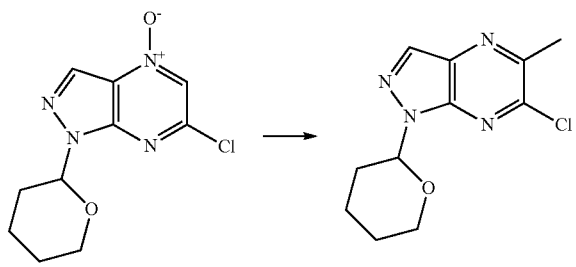 [SMILES: [O-][n+]1cc(Cl)nc2c1cnn2C1CCCCO1 ; Cc1nc2cnn(C3CCCCO3)c2nc1Cl]

To a solution of 6-chloro-1-(oxan-2-yl)-1H-4λ⁵-pyrazolo[3,4-b]pyrazin-4-one (12.9 g, 50.5 mmol) in toluene (260 mL), methylmagnesium chloride (3 M in THF, 50.5 mL) was added at 0° C. After stirring for 10 min at the same temperature, the mixture was quenched with sat. aq. NH₄Cl and water, the separated organic layer was washed with brine, dried over Na₂SO₄, filtered and then concentrated in vacuo. The crude material was purified by column chromatography on silica gel (gradient elution, 0-40%, EtOAc/hexane), to give the title compound (5.20 g), MS: [M+H]⁺=253, 255.

6-Chloro-5-methyl-1H-pyrazolo[3,4-b]pyrazine

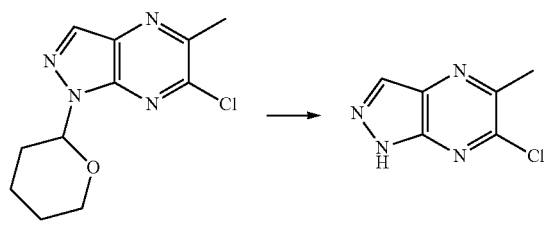 [SMILES: Cc1nc2cnn(C3CCCCO3)c2nc1Cl ; Cc1nc2cn[nH]c2nc1Cl]

To a suspension of 6-chloro-5-methyl-1-(oxan-2-yl)-1H-pyrazolo[3,4-b]pyrazine (5.20 g) in MeOH (100 mL), HCl (4M in dioxane, 20 mL) was added and then the mixture was stirred at RT overnight. After concentration of the mixture, the residue was dissolved in MeOH—CHCl₃, and then basified with sat. aq. NaHCO₃. The separated organic layer was dried over Na₂SO₄, filtered and then concentrated in vacuo. The material was suspended in hexane, collected by filtration and dried under vacuum at 60° C., to give the title compound (3.26 g), MS: [M+H]⁺=169, 171.

6-Chloro-3-iodo-5-methyl-1H-pyrazolo[3,4-b]pyrazine

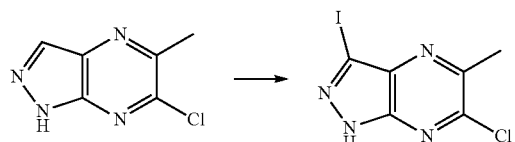

To a solution of 6-chloro-5-methyl-1H-pyrazolo[3,4-b]pyrazine (3.26 g) in DMF (65 mL), N-iodosuccinimide (8.70 g, 38.7 mmol) was added, and then the mixture was stirred at 50° C. for 8 h. Then, the mixture was diluted with EtOAc and water. The separated organic layer was washed with water (2×), sat. aq. Na₂S₂O₃, then brine, then dried over Na₂SO₄, filtered and then concentrated. The crude material was suspended in hexane-CHCl₃, collected by filtration and dried under vacuum at 60° C., to give the title compound (5.35 g), MS: [M+H]⁺=295, 297.

6-Chloro-3-iodo-5-methyl-1-(oxan-2-yl)-1H-pyrazolo[3,4-b]pyrazine

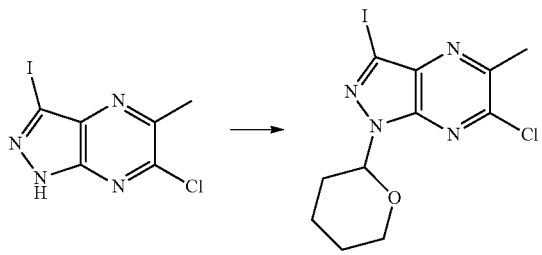 [SMILES: Cc1nc2c(I)n[nH]c2nc1Cl ; Cc1nc2c(I)nn(C3CCCCO3)c2nc1Cl]

To a solution of 6-chloro-3-iodo-5-methyl-1H-pyrazolo[3,4-b]pyrazine (4.90 g) in THF (98 mL), 3,4-dihydro-2H-pyran (7.55 mL, 83.2 mmol) and p-toluenesulfonic acid monohydrate (0.317 g, 1.66 mmol) were added, and the mixture was stirred at RT over the weekend. After concentration of the mixture in vacuo, the residue was purified by column chromatography on silica gel (gradient elution, 0-25%, EtOAc/hexane), to give crude material which was suspended in hexane, collected by filtration and dried under vacuum at 60° C., to give the title compound (3.6 g), MS: [M+H]⁺=379, 381.

tert-Butyl N-[(1R,2S,3S,5S)-2-fluoro-8-[3-iodo-5-methyl-1-(oxan-2-yl)-1H-pyrazolo[3,4-b]pyrazin-6-yl]-8-azabicyclo[3.2.1]octan-3-yl]carbamate

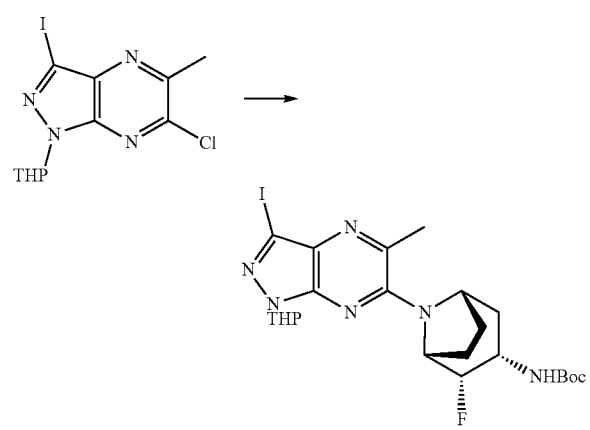

A mixture of 6-chloro-3-iodo-5-methyl-1-(oxan-2-yl)-1H-pyrazolo[3,4-b]pyrazine (400 mg, 1.98 mmol), tert-butyl [(1R,2R,3S,5S)-2-fluoro-8-azabicyclo[3.2.1]octan-3-yl]carbamate (387 mg, 1.59 mmol), DIPEA (0.552 mL, 3.17 mmol) and NMP (4.0 mL) was stirred at 120° C. for 6 h. The tert-Butyl N-[(1R,2S,3S,5S)-8-[3-(5-chloro-3-methoxyquinoxalin-6-yl)-5-methyl-1-(oxan-2-yl)-1H-pyrazolo[3,4-b]pyrazin-6-yl]-2-fluoro-8-azabicyclo[3.2.1]octan-3-yl]carbamate tert-Butyl N-[(1R,2S,3S,5S)-8-{3-[5-chloro-3-(dimethylamino)quinoxalin-6-yl]-5-methyl-1-(oxan-2-yl)-1H-pyrazolo[3,4-b]pyrazin-6-yl}-2-fluoro-8-azabicyclo[3.2.1]octan-3-yl]carbamate

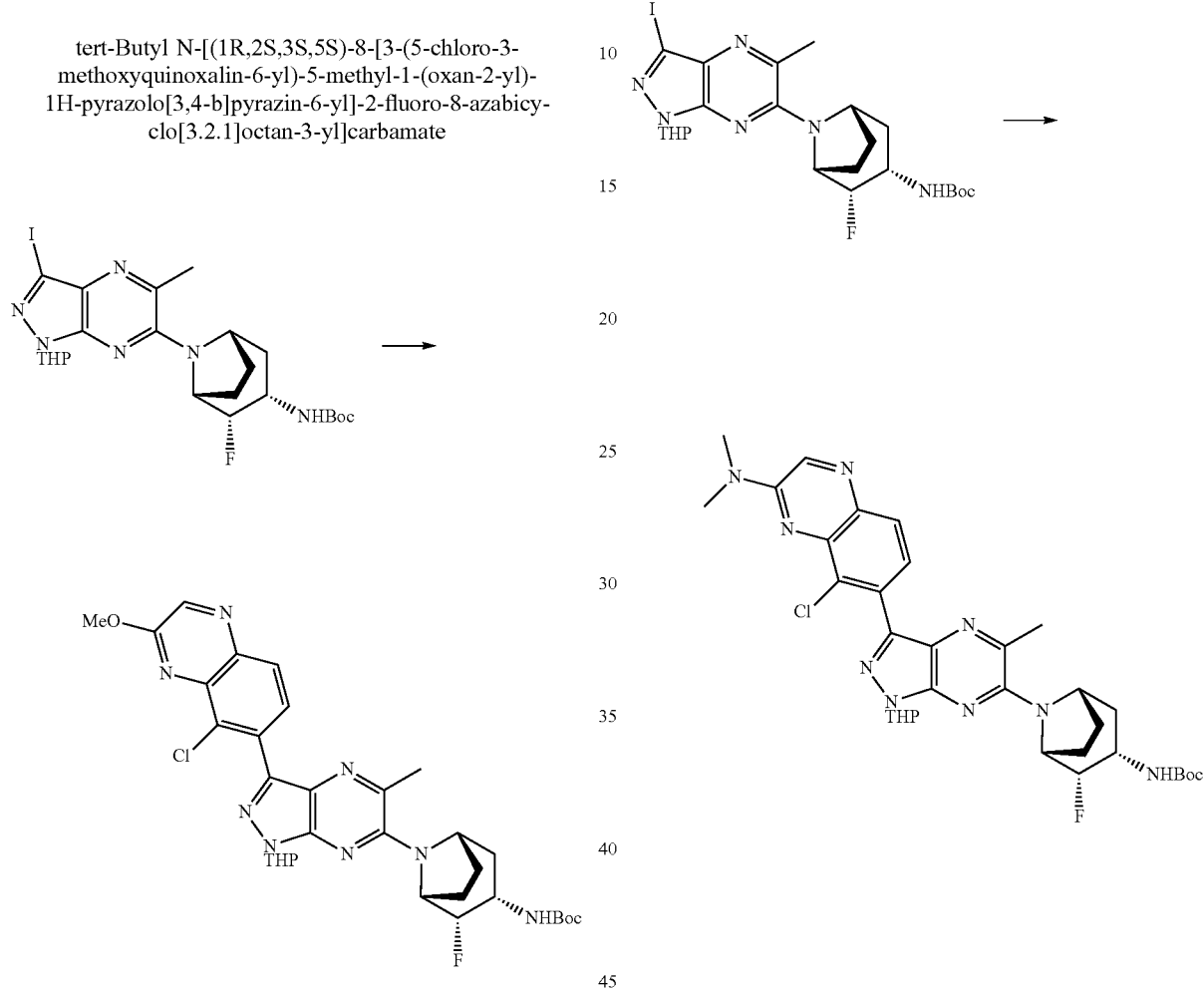

A mixture of tert-butyl N-[(1R,2S,3S,5S)-2-fluoro-8-[3-iodo-5-methyl-1-(oxan-2-yl)-1H-pyrazolo[3,4-b]pyrazin-6-yl]-8-azabicyclo[3.2.1]octan-3-yl]carbamate (75.0 mg, 0.13 mmol), 8-chloro-2-methoxy-7-(4,4,5,5-tetramethyl-1,3,2-dioxaborolan-2-yl)quinoxaline (49.2 mg, 0.15 mmol), K$_3$PO$_4$ (40.7 mg, 0.19 mmol), bis(di-tert-butyl(4-dimethylaminophenyl)phosphine)dichloropalladium(II) (9.06 mg, 0.01 mmol), 1,4-dioxane (0.75 mL) and water (0.075 mL) was stirred at 80° C. for 2 h, cooled to RT, poured into water, and extracted with EtOAc. The organic layer was washed with brine, dried over anhydrous Na$_2$SO$_4$, filtered, and concentrated in vacuo. The residue was purified by column chromatography on silica gel (gradient elution, 0-100% Hexane/EtOAc), to give the title compound (100 mg). MS: [M+H]$^+$=653, 655.

A mixture of tert-butyl N-[(1R,2S,3S,5S)-2-fluoro-8-[3-iodo-5-methyl-1-(oxan-2-yl)-1H-pyrazolo[3,4-b]pyrazin-6-yl]-8-azabicyclo[3.2.1]octan-3-yl]carbamate (75.0 mg, 0.13 mmol), 8-chloro-N,N-dimethyl-7-(4,4,5,5-tetramethyl-1,3,2-dioxaborolan-2-yl)quinoxalin-2-amine (51.1 mg, 0.15 mmol), K$_3$PO$_4$ (40.7 mg, 0.19 mmol), bis(di-tert-butyl(4-dimethylaminophenyl)phosphine)dichloropalladium(II) (9.06 mg, 0.01 mmol), 1,4-dioxane (0.75 mL) and water (0.08 mL) was stirred at 80° C. for 2 h, cooled to RT, poured into water, and extracted with EtOAc. The organic layer was washed with brine, dried over anhydrous Na$_2$SO$_4$, filtered, and concentrated in vacuo. The residue was purified by column chromatography on silica gel (gradient elution, 0-100% Hexane/EtOAc), to give the title compound (160 mg). MS: [M+H]$^+$=666, 668.

reaction mixture was cooled to RT, poured into water, and extracted with EtOAc. The organic layer was washed with water and brine, dried over anhydrous Na$_2$SO$_4$, filtered, and concentrated in vacuo. The residue was purified by column chromatography on silica gel (gradient elution, 50-100%, EtOAc/hexane), to give the title compound (330 mg). MS: [M+H]$^+$=587.

TABLE 15

Examples 91-96

| Example | Structure | Name | NMR Data | MS Data | Method |
|---|---|---|---|---|---|
| 91 | 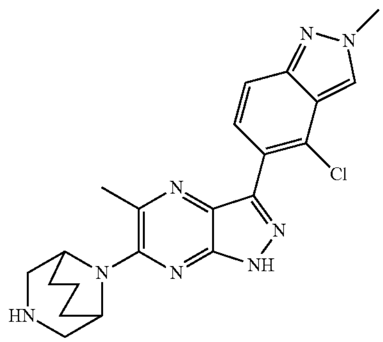 [SMILES: Cc1nc2c(-c3ccc4nn(C)cc4c3Cl)n[nH]c2nc1N1C2CCCC1CNC2] | 4-Chloro-5-(6-{3,9-diaza-bicyclo[3.3.1]nonan-9-yl}-5-methyl-1H-pyrazolo[3,4-b]pyrazin-3-yl)-2-methyl-2H-indazole, hydrochloride salt | $^1$H-NMR (400 MHz, DMSO-d$_6$): 13.60 (1H, br s), 9.82-9.46 (1H, m), 8.53 (1H, s), 8.28-8.07 (1H, m), 7.67 (1H, d), 7.60 (1H, d), 4.21 (3H, s), 4.20-4.16 (2H, m), 3.46-3.37 (2H, m), 2.51 (3H, s), 2.24-2.04 (3H, m), 1.86-1.80 (2H, m), 1.74-1.65 (1H, m). | 423, 425 | 11 |
| 92 | 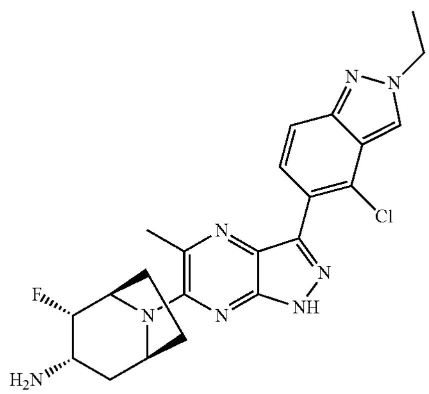 [SMILES: CCn1cc2c(Cl)c(-c3n[nH]c4nc(N5[C@H]6CC[C@@H]5[C@@H](F)[C@@H](N)C6)c(C)nc34)ccc2n1] | (1R,2S,3S,5S)-8-[3-(4-Chloro-2-ethyl-2H-indazol-5-yl)-5-methyl-1H-pyrazolo[3,4-b]pyrazin-6-yl]-2-fluoro-8-aza-bicyclo[3.2.1]octan-3-amine | $^1$H-NMR: (500 MHz, DMSO-d$_6$): 13.45 (1H, br s), 8.61 (1H, d), 7.70 (1H, dd), 7.63 (1H, d), 4.82-4.79 (1H, m), 4.56-4.51 (3H, m), 4.47-4.44 (1H, m), 3.09-2.98 (1H, m), 2.59 (3H, s), 2.04-1.87 (3H, m), 1.76-1.69 (3H, m), 1.31-1.21 (3H, m), 0.88-0.84 (1H, m). | 455, 457 | 8, The residue was purified by column chromatography on NH silica gel (gradient elution, 0-20%, MeOH/CHCl$_3$), to give a first crop of crude product. The crude product was purified by preparative HPLC |
| 93 | 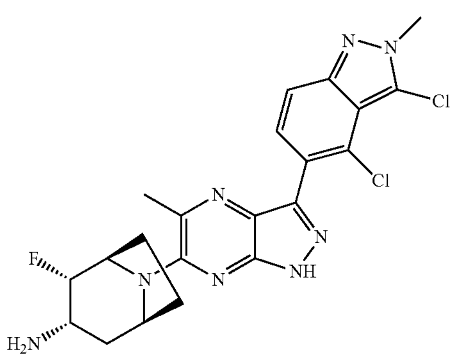 [SMILES: Cc1nc2c(-c3ccc4nn(C)c(Cl)c4c3Cl)n[nH]c2nc1N1[C@H]2CC[C@@H]1[C@@H](F)[C@@H](N)C2] | (1R,2S,3S,5S)-8-[3-(3,4-Dichloro-2-methyl-2H-indazol-5-yl)-5-methyl-1H-pyrazolo[3,4-b]pyrazin-6-yl]-2-fluoro-8-aza-bicyclo[3.2.1]octan-3-amine | $^1$H-NMR: (500 MHz, DMSO-d$_6$): 13.50 (1H, br s), 7.69 (1H, d), 7.59 (1H, d), 4.81 (1H, s), 4.59-4.44 (2H, m), 4.18 (3H, s), 3.17 (1H, d), 3.13-3.02 (1H, m), 2.59 (3H, s), 2.06-2.01 (1H, m), 1.95-1.88 (1H, m), 1.76-1.69 (3H, m) | 475, 477 | 8 |
| 94 | 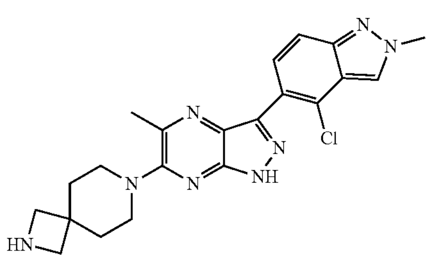 [SMILES: Cc1nc2c(-c3ccc4nn(C)cc4c3Cl)n[nH]c2nc1N1CCC2(CC1)CNC2] | 7-[3-(4-Chloro-2-methyl-2H-indazol-5-yl)-5-methyl-1H-pyrazolo[3,4-b]pyrazin-6-yl]-2,7-diazaspiro[3.5]nonane | $^1$H-NMR: (500 MHz, DMSO-d$_6$): 8.56 (1H, s), 7.68 (1H, dd), 7.62 (1H, d), 4.23 (3H, s), 3.28 (4H, s), 3.19-3.13 (4H, m), 2.55 (3H, s), 1.91-1.85 (4H, m) | 423, 425 | Prepared using analogous methods to method 1 without dissolving the crude in methanol and treating with ethylene diamine |

TABLE 15-continued

Examples 91-96

| Example | Structure | Name | NMR Data | MS Data | Method |
|---|---|---|---|---|---|
| 95 | 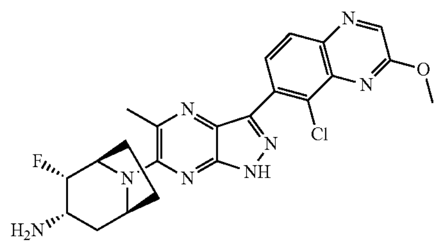 [SMILES: COc1cnc2ccc(-c3n[nH]c4nc(N5[C@H]6CC[C@@H]5[C@@H](F)[C@@H](N)C6)c(C)nc34)c(Cl)c2n1] | (1R,2S,3S,5S)-8-[3-(5-chloro-3-methoxy-quinoxalin-6-yl)-5-methyl-1H-pyrazolo[3,4-b]pyrazin-6-yl]-2-fluoro-8-azabicyclo[3.2.1]octan-3-amine | $^1$H-NMR: (400 MHz, DMSO-$d_6$): 8.73 (1H, s), 8.10 (1H, d), 7.98 (1H, d), 4.85-4.81 (1H, m), 4.60-4.47 (1H, m), 4.13 (3H, s), 3.14-3.01 (1H, m), 2.60 (3H, s), 2.09-1.86 (3H, m), 1.77-1.69 (3H, m), 1.29-1.20 (1H, m), 0.87-0.83 (1H, m). | 469, 471 | 11 |
| 96 | 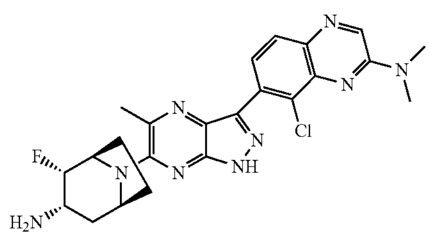 [SMILES: Cc1nc2c(-c3ccc4ncc(N(C)C)nc4c3Cl)n[nH]c2nc1N1[C@H]2CC[C@@H]1[C@@H](F)[C@@H](N)C2] | 7-{6-[(1R,2S,3S,5S)-3-amino-2-fluoro-8-azabicyclo[3.2.1]octan-8-yl]-5-methyl-1H-pyrazolo[3,4-b]pyrazin-3-yl}-8-chloro-N,N-dimethylquinoxalin-2-amine | $^1$H-NMR: (400 MHz, DMSO-$d_6$): 8.78 (1H, s), 7.87 (1H, d), 7.63 (1H, d), 4.84-4.79 (1H, m), 4.59-4.46 (2H, m), 3.30 (3H, s), 3.13-2.99 (1H, m), 2.58 (3H, s), 2.05-1.88 (3H, m), 1.76-1.68 (3H, m), 1.29-1.21 (1H, m), 0.88-0.83 (1H, m). | 482, 484 | 11. The residue was purified by column chromatography on NH silica gel (gradient elution, 0-20%, MeOH/CHCl$_3$) |

By following methods similar and/or analogous to those described for general procedures for preparations of compounds of Formula (I) (e.g. methods 1-12), the compounds set out in Table 15 were prepared from the corresponding N-Boc, N-CBz, N—SO$_2$NMe$_2$, 2-oxanyl or SEM protected derivatives, with any significant variations indicated. The title compounds were either isolated directly as the free base or as the appropriate salt without further purification, or purified for example using mass-directed preparative HPLC, chromatography, crystallization or trituration and converted to the appropriate salt.

Examples 97-123

5-Bromo-2-ethyl-4-fluoro-2H-indazole

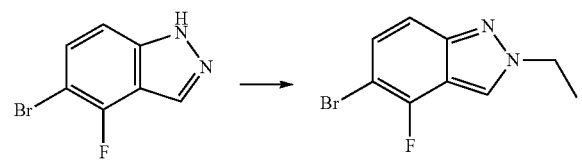

Triethyloxonium tetrafluoroborate (6.23 g, 32.8 mmol) was added to a solution of 5-bromo-4-fluoro-1H-indazole (4.75 g, 21.9 mmol) in EtOAc (300 mL) then stirred at RT for 18 h. Additional triethyloxonium tetrafluoroborate (2 g, 10.5 mmol) was added and stirring continued for 2 h. The mixture was washed with sat. aq. NaHCO$_3$ (150 mL) and the aqueous layer was extracted with a further portion of EtOAc (125 mL). The combined organic phases were concentrated onto loose silica gel. The silicate was purified by column chromatography on silica gel (gradient elution, 5-50% EtOAc/isohexane), to give the title compound (3.17 g). MS: [M+H]$^+$=243/245.

5-Bromo-3-chloro-2-ethyl-4-fluoro-2H-indazole

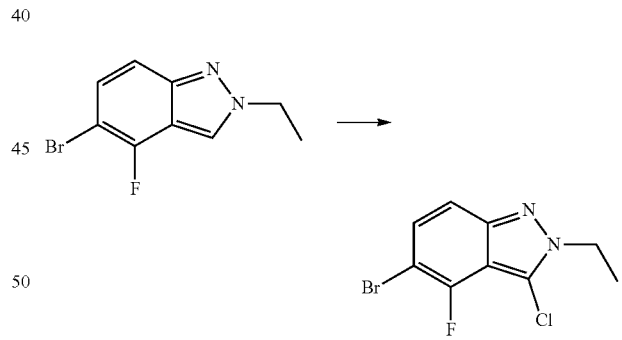

N-Chlorosuccinimide (1.09 g, 8.15 mmol) was added portionwise to 5-bromo-2-ethyl-4-fluoro-2H-indazole (1.5 g, 5.43 mmol) in DMF (20 mL) at 10° C. The mixture was then stirred at RT for 1 h, which showed no conversion. p-Toluenesulfonic acid monohydrate (10 mg) was added and stirring continued for 3 h, then quenched with water (90 mL) and sodium thiosulfate (5 g). The resulting mixture was stirred for 30 min, left to stand for 30 min, then filtered off and dried. The crude product was purified by column chromatography on silica gel (gradient elution, 5-25% EtOAc/isohexane), to give the title compound (1.5 g). MS: [M+H]$^+$=279/281.

403

5-Bromo-4-chloro-2,3-dimethyl-2H-indazole

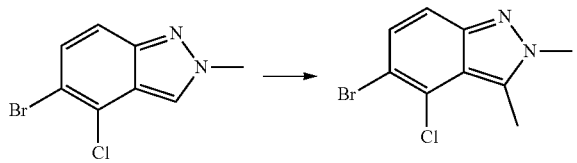

N-Butyllithium (2.5M in hexanes, 4 mL, 10.0 mmol) was added to a cooled (−10° C.) solution of diisopropylamine (1.5 mL, 10.5 mmol) in THF (10 mL). The mixture was stirred for 10 min before cooling to −78° C. To this solution was added a solution of 5-bromo-4-chloro-2-methyl-2H-indazole (2.0 g, 8.15 mmol) in THF (10 mL). The mixture was warmed to 0° C. for 10 min, then re-cooled to −78° C. Iodomethane (0.66 mL, 10.6 mmol) was added and the mixture was stirred at −78° C. for 1 h. The mixture was quenched with sat. aq. NH₄Cl (30 mL) and extracted with EtOAc (3×30 mL). The combined organic phases were dried (Na₂SO₄), filtered and concentrated. The crude product was purified by column chromatography on silica gel (gradient elution, 15-75% EtOAc/isohexane), to give the title compound (1.7 g). MS: [M+H]⁺=259/261/263.

5-Bromo-3,4-dichloro-2-ethyl-2H-indazole

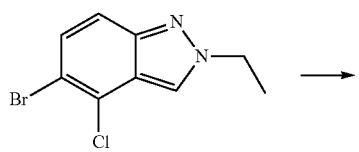

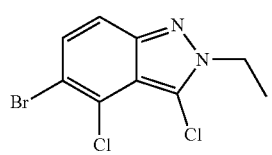

Prepared using analogous methods to preparation 35, 5-bromo-3,4-dichloro-2-methyl-2H-indazole, to give the title compound, MS: [M+H]⁺=293.

5-Bromo-2,4-dimethyl-2H-indazole

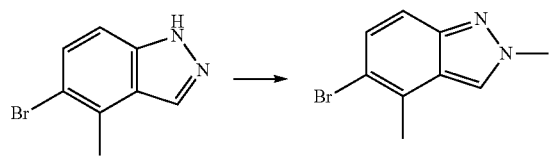

Prepared using analogous methods to preparation 33 5-bromo-4-fluoro-2-methyl-2H-indazole, to give the title compound, MS: [M+H]⁺=225.

404

5-Bromo-3-chloro-2,4-dimethyl-2H-indazole

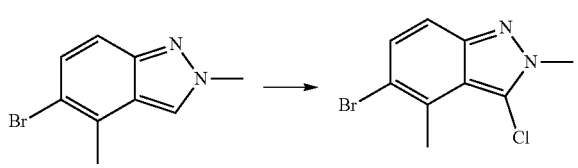

Prepared using analogous methods to the preparation of 5-bromo-3-chloro-2-ethyl-4-fluoro-2H-indazole, to give the title compound, MS: [M+H]⁺=259.

3-Chloro-2,4-dimethyl-5-(4,4,5,5-tetramethyl-1,3,2-dioxaborolan-2-yl)-2H-indazole

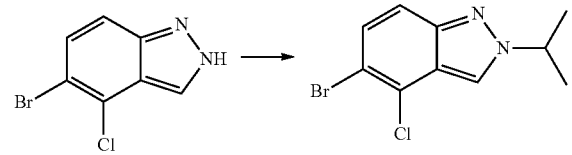

Prepared using analogous methods to preparation 43: 4-chloro-2-methyl-5-(4,4,5,5-tetramethyl-1,3,2-dioxaborolan-2-yl)-2H-indazole, to give the title compound, MS: [M+H]⁺=307.

5-Bromo-4-chloro-2-(propan-2-yl)-2H-indazole

Potassium tert-butoxide (3.64 g, 32.4 mmol) was added to 5-bromo-4-chloro-2H-indazole (7.5 g, 32.4 mmol) and 2-bromopropane (3.05 mL, 32.4 mmol) at RT in DMF (20 mL). The resulting mixture was then stirred overnight for 16 h, diluted with tert-butyl methyl ether/EtOAc (300 mL, 5:1) then water (400 mL) was added. The layers were separated, and the aqueous further extracted with ted-butyl methyl ether (100 mL). The combined organics were washed with water (3×100 mL), dried by passing through a phase separator and concentrated onto loose silica gel. The silicate was purified by column chromatography on silica gel (gradient elution, 0-50% EtOAc/isohexane), to give the title compound (2.17 g). MS: [M+H]⁺=273.

405

4-Chloro-2-(propan-2-yl)-5-(4,4,5,5-tetramethyl-1,3,2-dioxaborolan-2-yl)-2H-indazole

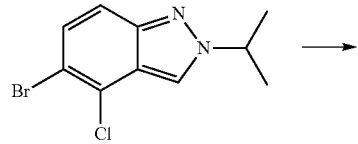

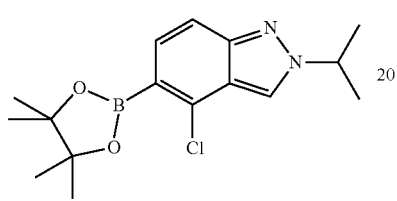

Prepared using analogous methods to preparation 43: 4-chloro-2-methyl-5-(4,4,5,5-tetramethyl-1,3,2-dioxaborolan-2-yl)-2H-indazole, to give the title compound, MS: [M+H]$^+$=321.

tert-Butyl N-[(1R,2S,3S,5S)-2-fluoro-8-[3-(4-fluoro-2-methyl-2H-indazol-5-yl)-5-(hydroxymethyl)-1-{[2-(trimethylsilyl)ethoxy]methyl}-1H-pyrazolo[3,4-b]pyrazin-6-yl]-8-azabicyclo[3.2.1]octan-3-yl]carbamate

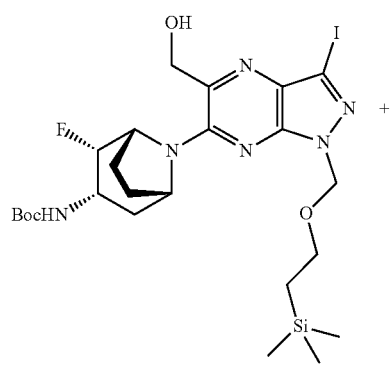

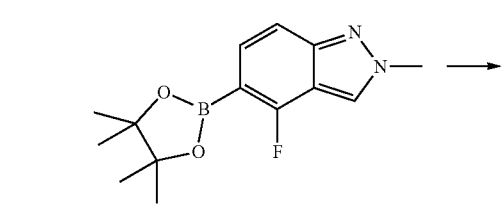

406

-continued

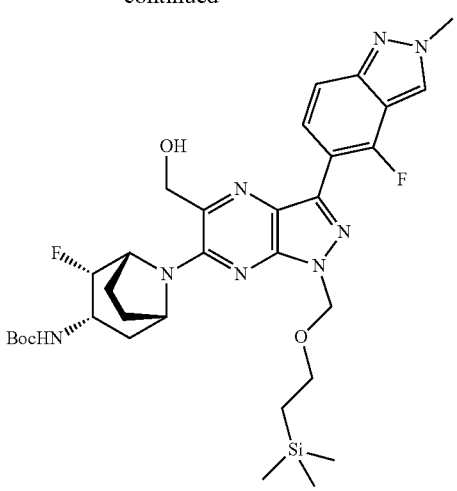

Prepared as General Procedure 2, except using tert-butyl N-[(1R,2S,3S,5S)-2-fluoro-8-[5-(hydroxymethyl)-3-iodo-1-{[2-(trimethylsilyl)ethoxy]methyl}-1H-pyrazolo[3,4-b]pyrazin-6-yl]-8-azabicyclo[3.2.1]octan-3-yl]carbamate and 4-fluoro-2-methyl-5-(4,4,5,5-tetramethyl-1,3,2-dioxaborolan-2-yl)-2H-indazole, heating to 60° C. for 2 h and purifying by column chromatography on NH silica gel (gradient elution, 0-50%, acetone/petrol), to give the title compound, MS: [M+H]$^+$=671.

tert-Butyl N-[(1R,2S,3S,5S)-8-[3-(3-bromo-4-fluoro-2-methyl-2H-indazol-5-yl)-5-(hydroxymethyl)-1-{[2-(trimethylsilyl)ethoxy]methyl}-1H-pyrazolo[3,4-b]pyrazin-6-yl]-2-fluoro-8-azabicyclo[3.2.1]octan-3-yl]carbamate

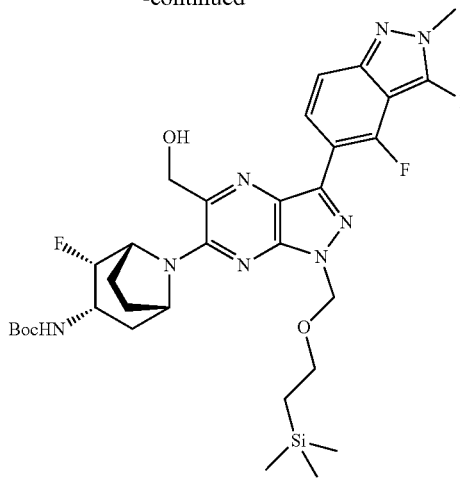

N-Bromosuccinimide (73 mg, 0.41 mmol) was added to a solution of tert-butyl N-[(1R,2S,3S,5S)-2-fluoro-8-[3-(4-fluoro-2-methyl-2H-indazol-5-yl)-5-(hydroxymethyl)-1-{[2-(trimethylsilyl)ethoxy]methyl}-1H-pyrazolo[3,4-b]pyrazin-6-yl]-8-azabicyclo[3.2.1]octan-3-yl]carbamate (250 mg, 0.37 mmol) in DMF (6 mL) and the reaction stirred at RT for 1 h. Further N-bromosuccinimide (13 mg, 0.074 mmol) was added and stirring continued for 30 min. Again, further N-bromosuccinimide (13 mg, 0.074 mmol) was added and stirring continued for a further 1 h. H$_2$O was added and the resultant precipitate collected by filtration, washing with H$_2$O. This solid was purified by column chromatography on silica gel (gradient elution, 5-30%, acetone/petrol) to give the title compound, MS: [M+H]$^+$=749.

2-Bromo-3-chloro-5-{[2-(trimethylsilyl)ethoxy]methyl}-5H-pyrrolo[2,3-b]pyrazine

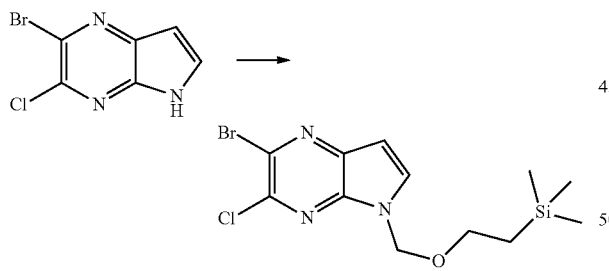

To a mixture of 2-bromo-3-chloro-5H-pyrrolo[2,3-b]pyrazine (3.7 g, 15.9 mmol) in DMF (111 mL) at 0° C. was added NaH (0.76 g, 19.1 mmol) portionwise over 20 min. The reaction was stirred at 0° C. for 30 min. At the same temperature, 2-(trimethylsilyl)ethoxymethyl chloride (3.39 mL, 19.1 mmol) was added dropwise. The reaction was allowed to slowly warm to RT in the ice bath before stirring overnight. The reaction mixture was carefully quenched at 0° C. with sat. aq. NH$_4$Cl (200 mL) and extracted with DCM (3×70 mL). The combined organic extracts were concentrated under reduced pressure. The oily residue was diluted with DCM (50 mL) and washed with 1M aq. lithium chloride (100 mL) then brine (50 mL), dried over MgSO$_4$, filtered and concentrated under reduced pressure. The residue was purified by column chromatography on silica gel (gradient elution, 0-50% DCM/isohexane), to give the title compound (3.8 g). $^1$H NMR (500 MHz, DMSO-d$_6$): 8.19 (1H, d), 6.80 (1H, d), 5.60 (2H, s), 3.61-3.49 (2H, m), 0.91-0.80 (2H, m), −0.09 (9H, s).

Methyl 3-chloro-5-{[2-(trimethylsilyl)ethoxy]methyl}-5H-pyrrolo[2,3-b]pyrazine-2-carboxylate

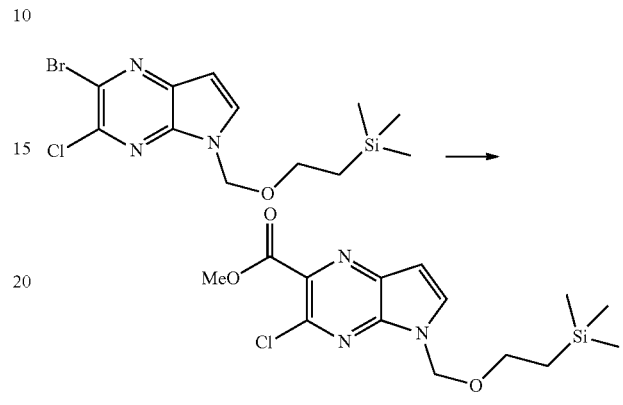

To a solution of 2-bromo-3-chloro-5-{[2-(trimethylsilyl)ethoxy]methyl}-5H-pyrrolo[2,3-b]pyrazine (3.40 g, 9.37 mmol) in toluene (40 mL) and methanol (10 mL), bis(triphenylphosphine)palladium(II) dichloride (0.077 g, 0.11 mmol) and triethylamine (1 mL, 7.17 mmol) were added. The mixture was transferred into a pressure bomb, purged with nitrogen three times then put under a carbon monoxide atmosphere (5 bar) and heated at 80° C. for 48 h. The reaction mixture was filtered, concentrated under reduced pressure to remove MeOH, washed with 0.5M HCl (20 mL), dried over MgSO$_4$ and concentrated under reduced pressure. The residue was purified by column chromatography on silica gel (gradient elution, 0-50% EtOAc/isohexane), to give the title compound (1.5 g). MS: [M+H]+=342.

Methyl 3-chloro-7-iodo-5-{[2-(trimethylsilyl)ethoxy]methyl}-5H-pyrrolo[2,3-b]pyrazine-2-carboxylate

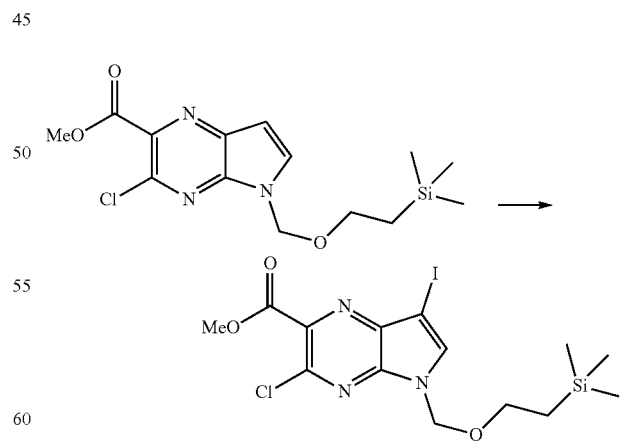

A mixture of methyl 3-chloro-5-{[2-(trimethylsilyl)ethoxy]methyl}-5H-pyrrolo[2,3-b]pyrazine-2-carboxylate (1.80 g, 5.27 mmol) and 1-iodopyrrolidine-2,5-dione (2.50 g, 11.1 mmol) in DMF (14.3 mL, 184 mmol) was stirred at RT for 22 h. The reaction mixture was heated at 50° C. for an additional 5 h, cooled to RT, then quenched by dropwise addition into a mixture of aq. NH₄Cl (5 g in 150 mL) and 10% aq. Na₂S₂O₃ (20 mL). The mixture was extracted with DCM (3×20 mL). The combined organics were washed with water (2×30 mL), passed through a phase separator and concentrated under reduced pressure. The residue was purified by column chromatography on silica gel (gradient elution, 0-50% EtOAc/isohexane), to give the title compound (1.2 g). MS: [M+H]⁺=468.

Methyl 3-[(1R,2S,3S,5S)-3-{[(tert-butoxy)carbonyl]amino}-2-fluoro-8-azabicyclo[3.2.1]octan-8-yl]-7-(3,4-dichloro-2-methyl-2H-indazol-5-yl)-5-{[2-(trimethylsilyl)ethoxy]methyl}-5H-pyrrolo[2,3-b]pyrazine-2-carboxylate

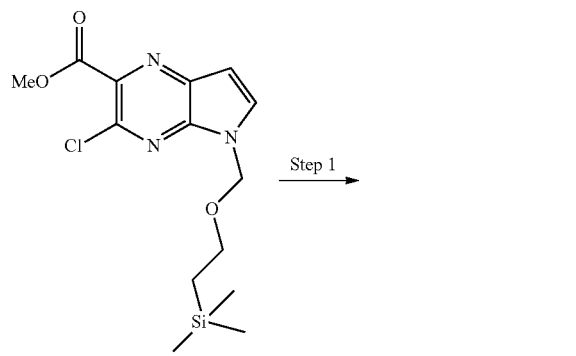

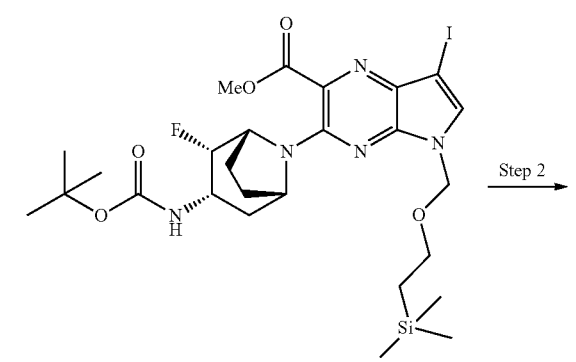

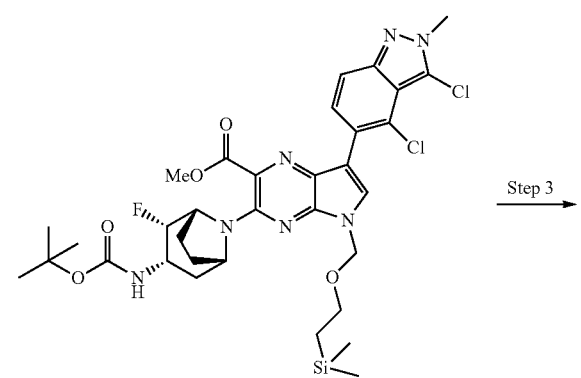

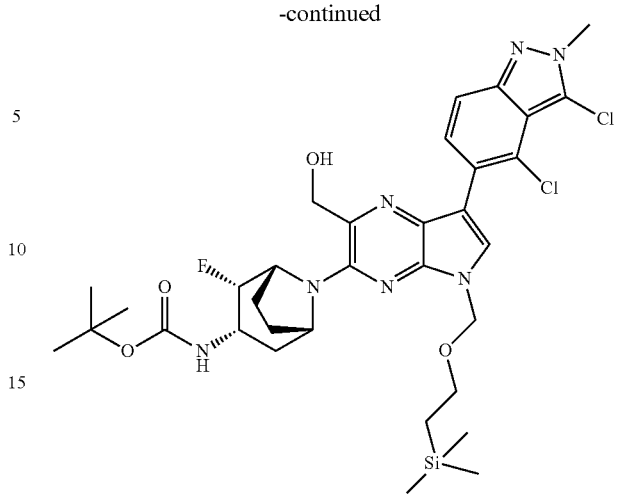

Step 1: Using tert-butyl N-[(1R,2R,3S,5S)-2-fluoro-8-azabicyclo[3.2.1]octan-3-yl]carbamate, and heating at 120° C. for 5 h, Step 1 was performed using methods similar to those described in General procedure 1. MS: [M+H]⁺=676

Step 2: Using (3,4-dichloro-2-methyl-2H-indazol-5-yl)boronic acid, the title compound was prepared using methods similar to those described in General Procedure 2, but using K₃PO₄ and 1,4-dioxane at 50° C. instead of K₂CO₃ and 1,2-dimethoxyethane respectively. MS: [M+H]⁺=748.

Step 3: To a solution of methyl 3-[(1R,2S,3S,5S)-3-{[(tert-butoxy)carbonyl]amino}-2-fluoro-8-azabicyclo[3.2.1]octan-8-yl]-7-(3,4-dichloro-2-methyl-2H-indazol-5-yl)-5-{[2-(trimethylsilyl)ethoxy]methyl}-5H-pyrrolo[2,3-b]pyrazine-2-carboxylate (0.25 g, 0.334 mmol) in THF (2.67 mL) at 0° C. was added lithium aluminium hydride solution (1.0 M in THF) (0.668 mL, 0.668 mmol) dropwise. The reaction was stirred at 0° C. for 10 minutes. The reaction was quenched by the addition of 10% Rochelle's salt solution followed by EtOAc. The phases were separated, and the aqueous phase was extracted into EtOAc (×2). The combined organic extracts were dried (Na₂SO₄), filtered and concentrated. Biotage column (25 g) eluting with 15% acetone/petrol to 50% acetone/petrol provided tert-butyl N-[(1R,2S,3S,5S)-8-[7-(3,4-dichloro-2-methyl-2H-indazol-5-yl)-2-(hydroxymethyl)-5-{[2-(trimethylsilyl)ethoxy]methyl}-5H-pyrrolo[2,3-b]pyrazin-3-yl]-2-fluoro-8-azabicyclo[3.2.1]octan-3-yl]carbamate (220 mg). MS: [M+H]⁺=720.

TABLE 16

Examples 97-123

| Example | Structure | Name | NMR Data | MS Data | Method |
|---|---|---|---|---|---|
| 97 | 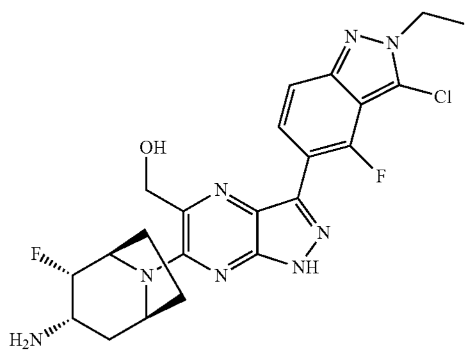 [SMILES: CCn1nc2ccc(-c3n[nH]c4nc(N5[C@H]6CC[C@@H]5[C@@H](F)[C@@H](N)C6)c(CO)nc34)c(F)c2c1Cl] | {6-[(1R,2S,3S,5S)-3-amino-2-fluoro-8-azabicyclo[3.2.1]octan-8-yl]-3-(3-chloro-2-ethyl-4-fluoro-2H-indazol-5-yl)-1H-pyrazolo[3,4-b]pyrazin-5-yl}methanol | ¹H NMR (400 MHz, DMSO_cap): 8.08 (1H, dd), 7.59 (1H, d), 5.35 (1H, d), 5.04-4.97 (1H, m), 4.78 (1H, d), 4.74-4.45 (5H, m), 2.06-1.86 (3H, m), 1.75 (3H, d), 1.51 (3H, t). | 489 | Prepared using analogous methods to example 80 except using dichlorobis{[4-(N,N-dimethylamino)phenyl]di-t-butylphosphino}palladium(II) and K₃PO₄ in general procedure 2 |
| 98 | 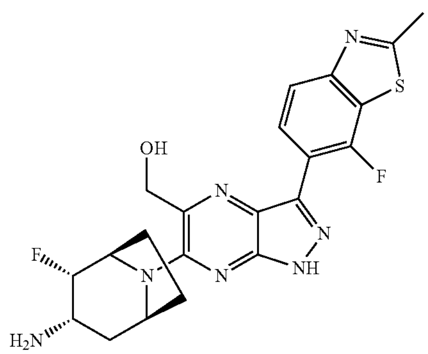 [SMILES: Cc1nc2ccc(-c3n[nH]c4nc(N5[C@H]6CC[C@@H]5[C@@H](F)[C@@H](N)C6)c(CO)nc34)c(F)c2s1] | {6-[(1R,2S,3S,5S)-3-amino-2-fluoro-8-azabicyclo[3.2.1]octan-8-yl]-3-(7-chloro-2-methyl-1,3-benzothiazol-6-yl)-1H-pyrazolo[3,4-b]pyrazin-5-yl}methanol | ¹H NMR (500 MHz, DMSO-d₆) δ 8.02 (d, J = 8.4 Hz, 1H), 8.00 (d, J = 8.4 Hz, 1H), 5.31 (s, 1H), 5.00-4.92 (m, 1H), 4.77-4.69 (m, 1H), 4.67-4.60 (m, 2H), 4.52 (dt, J = 49.3, 3.6 Hz, 1H), 3.11-2.96 (m, 1H), 2.87 (s, 3H), 2.04-1.82 (m, 3H), 1.80-1.66 (m, 3H), 19F NMR (471 MHz, DMSO-d₆) δ −196.25 (s) | 474 | Prepared using analogous methods to example 80, except using an analogous deprotection to method 12 |
| 99 | 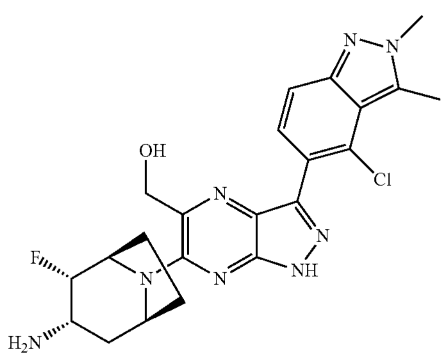 [SMILES: Cc1c2c(Cl)c(-c3n[nH]c4nc(N5[C@H]6CC[C@@H]5[C@@H](F)[C@@H](N)C6)c(CO)nc34)ccc2nn1C] | {6-[(1R,2S,3S,5S)-3-amino-2-fluoro-8-azabicyclo[3.2.1]octan-8-yl]-3-(4-chloro-2,3-dimethyl-2H-indazol-5-yl)-1H-pyrazolo[3,4-b]pyrazin-5-yl}methanol | ¹H NMR (400 MHz, DMSO-d₆): 13.43 (1H, br. s), 7.58 (1H, d), 7.48 (1H, d), 5.28 (1H, br. s), 5.07-4.93 (1H, m), 4.86-4.47 (4H, m), 4.12 (3H, s), 3.20-3.04 (1H, m), 2.87 (3H, s), 2.05-1.84 (3H, m), 1.84-1.68 (3H, m). | 471 | Prepared using analogous methods to example 80 except using dichlorobis{[4-(N,N-dimethylamino)phenyl]di-t-butylphosphino}palladium(II) and K₃PO₄ in general procedure 2 and using an analogous deprotection to method 12 |
| 100 | 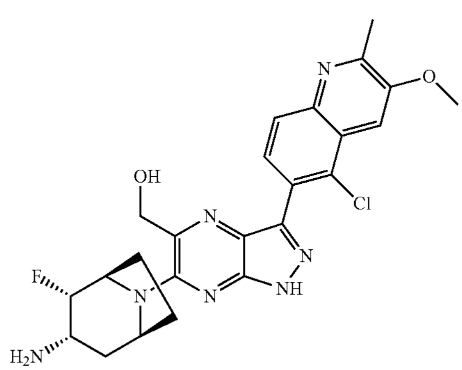 [SMILES: COc1cc2c(Cl)c(-c3n[nH]c4nc(N5[C@H]6CC[C@@H]5[C@@H](F)[C@@H](N)C6)c(CO)nc34)ccc2nc1C] | {6-[(1R,2S,3S,5S)-3-amino-2-fluoro-8-azabicyclo[3.2.1]octan-8-yl]-3-(5-chloro-3-methoxy-2-methylquinolin-6-yl)-1H-pyrazolo[3,4-b]pyrazin-5-yl}methanol | ¹H NMR (400 MHz, DMSO-d₆): 8.02-7.96 (1H, m), 7.91 (1H, d), 7.84 (1H, s), 5.30 (1H, t), 4.99 (1H, s), 4.83-4.70 (1H, m), 4.70-4.52 (3H, m), 4.51-4.42 (1H, m), 4.05 (3H, s), 3.13-2.97 (1H, m), 2.63 (3H, s), 1.99-1.89 (3H, m), 1.74 (3H, d). | 498 | Prepared using analogous methods to example 80 |

TABLE 16-continued

Examples 97-123

| Example | Structure | Name | NMR Data | MS Data | Method |
|---|---|---|---|---|---|
| 101 | 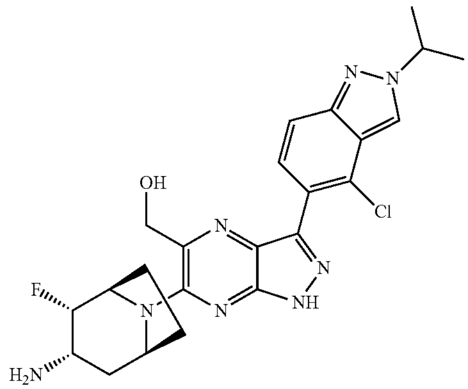 [SMILES: CC(C)n1cc2c(Cl)c(-c3n[nH]c4nc(N5[C@H]6CC[C@@H]5[C@@H](F)[C@@H](N)C6)c(CO)nc34)ccc2n1] | {6-[(1R,2S,3S,5S)-3-amino-2-fluoro-8-azabicyclo[3.2.1]octan-8-yl]-3-[4-chloro-2-(propan-2-yl)-2H-indazol-5-yl]-1H-pyrazolo[3,4-b]pyrazin-5-yl}methanol | $^1$H NMR (500 MHz, DMSO-$d_6$) δ 13.49 (1H, s), 8.61 (1H, s), 7.70 (1H, d), 7.64 (1H, d), 5.30 (1H, t), 5.01 (1H, m), 4.97-4.81 (1H, m), 4.77-4.59 (5H, m), 4.33 (1H, s), 3.77 (1H, t), 2.14-1.83 (4H, m), 1.75 (2H, d), 1.60 (6H, d). 19F NMR (471 MHz, DMSO-$d_6$) δ −196.4. | 485 | Prepared using analogous methods to example 80 except using an analogous deprotection to method 12 |
| 102 | 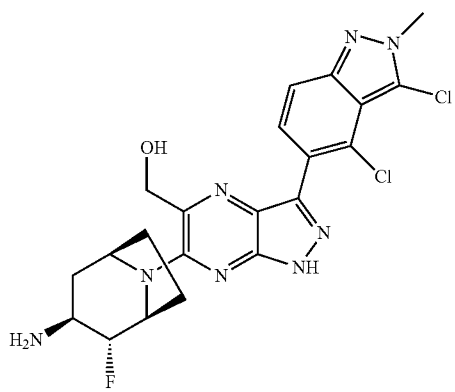 [SMILES: Cn1nc2ccc(-c3n[nH]c4nc(N5[C@@H]6CC[C@H]5[C@H](F)[C@@H](N)C6)c(CO)nc34)c(Cl)c2c1Cl] | {6-[(1S,2R,3S,5R)-3-amino-2-fluoro-8-azabicyclo[3.2.1]octan-8-yl]-3-(3,4-dichloro-2-methyl-2H-indazol-5-yl)-1H-pyrazolo[3,4-b]pyrazin-5-yl}methanol | $^1$H NMR (500 MHz, DMSO-$d_6$) δ 13.43 (br s, 1H), 7.70 (d, J = 8.9 Hz, 1H), 7.63 (d, J = 8.8 Hz, 1H), 5.28 (s, 1H), 4.88 (t, J = 9.2 Hz, 1H), 4.71 (d, J = 12.8 Hz, 1H), 4.61 (d, J = 12.3 Hz, 2H), 4.44 (d, J = 45.8 Hz, 1H), 4.17 (s, 3H), 3.20 (dd, J = 20.6, 6.5 Hz, 1H), 2.47 (d, J = 17.4 Hz, 1H), 2.39-1.61 (m, 6H), 1.53-1.38 (m, 1H). 19F NMR (471 MHz, DMSO-d6) δ −168.42 | 491 | Prepared using analogous methods to example 80 except using an analogous deprotection to method 12 |
| 103 | 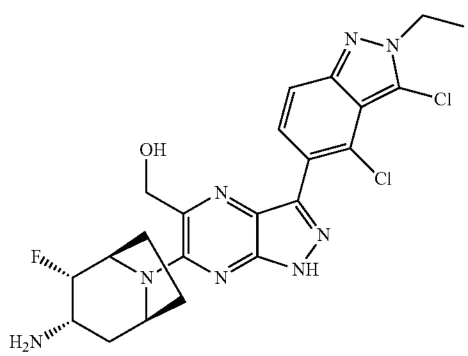 [SMILES: CCn1nc2ccc(-c3n[nH]c4nc(N5[C@H]6CC[C@@H]5[C@@H](F)[C@@H](N)C6)c(CO)nc34)c(Cl)c2c1Cl] | {6-[(1R,2S,3S,5S)-3-amino-2-fluoro-8-azabicyclo[3.2.1]octan-8-yl]-3-(3,4-dichloro-2-ethyl-2H-indazol-5-yl)-1H-pyrazolo[3,4-b]pyrazin-5-yl}methanol | $^1$H NMR (400 MHz, DMSO-$d_6$): 14.25-12.87 (1H, m), 7.72 (1H, d), 7.63 (1H, d), 5.37-5.28 (1H, m), 5.07-4.99 (1H, m), 4.77-4.60 (2H, m), 4.54 (2H, q), 3.43-3.36 (1H, m), 2.14-1.88 (3H, m), 1.84-1.71 (3H, m), 1.51 (3H, t). | 505 | Prepared using analogous methods to example 80 |
| 104 | 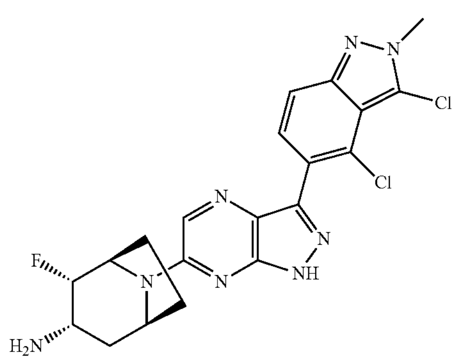 [SMILES: Cn1nc2ccc(-c3n[nH]c4nc(N5[C@H]6CC[C@@H]5[C@@H](F)[C@@H](N)C6)cnc34)c(Cl)c2c1Cl] | (1R,2S,3S,5S)-8-[7-(3,4-dichloro-2-methyl-2H-indazol-5-yl)-5H-pyrrolo[2,3-b]pyrazin-3-yl]-2-fluoro-8-azabicyclo[3.2.1]octan-3-amine, hydrochloride | $^1$H NMR (400 MHz, DMSO-$d_6$): 11.81 (1H, d), 8.48-8.27 (3H, m), 8.24 (1H, s), 7.87 (1H, d), 7.73 (1H, d), 7.63 (1H, d), 5.16-5.07 (1H, m), 5.03-4.88 (1H, m), 4.74-4.71 (1H, m), 4.15 (3H, s), 3.85-3.67 (1H, m), 2.14-1.97 (3H, m), 1.92-1.76 (3H, m). | 460 | Prepared using analogous methods to example 77 |

TABLE 16-continued

Examples 97-123

| Example | Structure | Name | NMR Data | MS Data | Method |
|---|---|---|---|---|---|
| 105 | 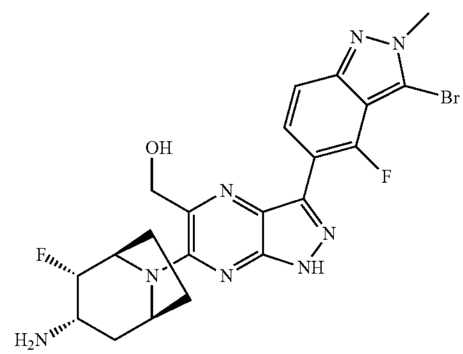 [SMILES: Cn1nc2ccc(-c3n[nH]c4nc(N5[C@H]6CC[C@@H]5[C@@H](F)[C@@H](N)C6)c(CO)nc34)c(F)c2c1Br] | {6-[(1R,2S,3S,5S)-3-amino-2-fluoro-8-azabicyclo[3.2.1]octan-8-yl]-3-(3-bromo-4-fluoro-2-methyl-2H-indazol-5-yl)-1H-pyrazolo[3,4-b]pyrazin-5-yl}methanol | $^1$H NMR (400 MHz, DMSO-$d_6$): 14.11-12.99 (1H, m), 8.05 (1H, dd), 7.59 (1H, d), 5.43-5.33 (1H, m), 5.10-4.97 (1H, m), 4.83-4.74 (1H, m), 4.71-4.56 (3H, m), 4.19 (3H, s), 3.27-3.17 (1H, m), 2.08-1.89 (3H, m), 1.84-1.70 (3H, m). | 519 | Prepared using method 1 except using NH$_3$ (4M in MeOH), from tert-butyl N-[(1R,2S,3S,5S)-8-[3-(3-bromo-4-fluoro-2-methyl-2H-indazol-5-yl)-5-(hydroxymethyl)-1-{[2-(trimethylsilyl)ethoxy]methyl}-1H-pyrazolo[3,4-b]pyrazin-6-yl]-2-fluoro-8-azabicyclo[3.2.1]octan-3-yl]carbamate |
| 106 | 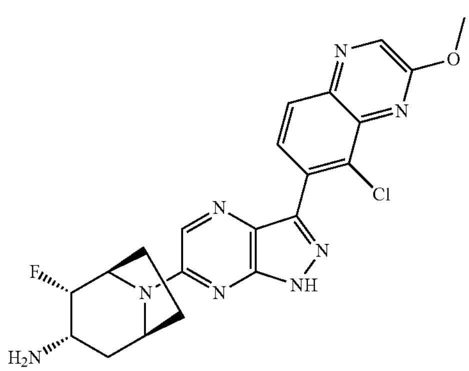 [SMILES: COc1cnc2ccc(-c3n[nH]c4nc(N5[C@H]6CC[C@@H]5[C@@H](F)[C@@H](N)C6)cnc34)c(Cl)c2n1] | (1R,2S,3S,5S)-8-[7-(5-chloro-3-methoxyquinoxalin-6-yl)-5H-pyrrolo[2,3-b]pyrazin-3-yl]-2-fluoro-8-azabicyclo[3.2.1]octan-3-amine, hydrochloride | $^1$H NMR (400 MHz, DMSO-$d_6$): 11.99 (1H, d), 8.63 (1H, s), 8.45 (1H, d), 8.31 (1H, s), 8.30-8.20 (3H, m), 8.06-7.99 (2H, m), 5.19-5.10 (1H, m), 4.95 (1H, dt), 4.78-4.70 (1H, m), 4.13 (3H, s), 3.80-3.70 (1H, m), 2.14-2.00 (3H, m), 1.91-1.79 (3H, m). | 454 | Prepared using analogous methods to example 77 except using General Procedure 3 |
| 107 | 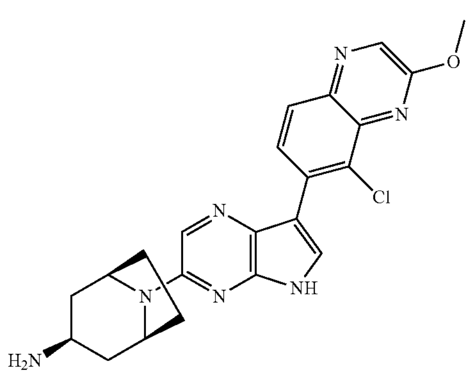 [SMILES: COc1cnc2ccc(-c3c[nH]c4nc(N5[C@@H]6CC[C@H]5C[C@@H](N)C6)cnc34)c(Cl)c2n1] | endo-8-[7-(5-chloro-3-methoxyquinoxalin-6-yl)-5H-pyrrolo[2,3-b]pyrazin-3-yl]-8-azabicyclo[3.2.1]octan-3-amine, hydrochloride | $^1$H NMR (400 MHz, DMSO-$d_6$): 12.00 (1H, d), 8.64 (1H, s), 8.48 (1H, d), 8.24 (1H, s), 8.07-8.02 (2H, m), 7.96 (3H, d), 4.68-4.62 (2H, m), 4.13 (3H, s), 3.22-3.15 (1H, m), 2.45-2.40 (2H, m), 2.17-2.11 (2H, m), 2.02-1.96 (2H, m), 1.72-1.65 (2H, m). | 436 | Prepared using analogous methods to example 77, except using General Procedure 3 |
| 108 | 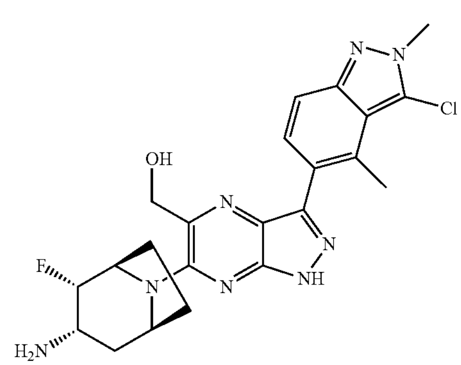 | {6-[(1R,2S,3S,5S)-3-amino-2-fluoro-8-azabicyclo[3.2.1]octan-8-yl]-3-(3-chloro-2,4-dimethyl-2H-indazol-5-yl)-1H-pyrazolo[3,4-b]pyrazin-5-yl}methanol | $^1$H NMR (500 MHz, DMSO-$d_6$) δ $^1$H NMR (500 MHz, DMSO-$d_6$) δ 7.62 (1H, d), 7.51 (1H, d), 5.30 (1H, s), 4.96 (1H, s), 4.81-4.41 (5H, m), 4.15 (3H, s), 2.80-2.68 (3H, m), 2.63 (d, 1H), 2.02-1.65 (6H, m). 19F NMR (471 MHz, DMSO-d6) δ −196.5. | 471 | Prepared using analogous methods to example 80 except using an analogous deprotection to method 12 |

TABLE 16-continued

Examples 97-123

| Example | Structure | Name | NMR Data | MS Data | Method |
|---|---|---|---|---|---|
| 109 | 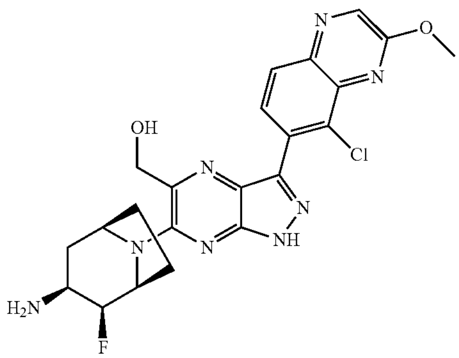 [SMILES: COc1cnc2ccc(-c3n[nH]c4nc(N5[C@@H]6CC[C@H]5[C@@H](F)[C@@H](N)C6)c(CO)nc34)c(Cl)c2n1] | {6-[(1S,2S,3S,5R)-3-amino-2-fluoro-8-azabicyclo[3.2.1]octan-8-yl]-3-(5-chloro-3-methoxyquinoxalin-6-yl)-1H-pyrazolo[3,4-b]pyrazin-5-yl}methanol | 1H NMR (400 MHz, DMSO-d₆): 14.03-13.37 (1H, m), 8.74 (1H, s), 8.15-8.07 (1H, m), 8.05-7.92 (1H, m), 5.52-5.36 (1H, m), 5.00-4.81 (1H, m), 4.77 (1H, d), 4.63 (3H, d), 4.14 (3H, d), 3.64 (1H, d), 2.66-2.57 (1H, m), 2.31-1.69 (7H, m). | 485 | Prepared using analogous methods to example 80 |
| 110 | 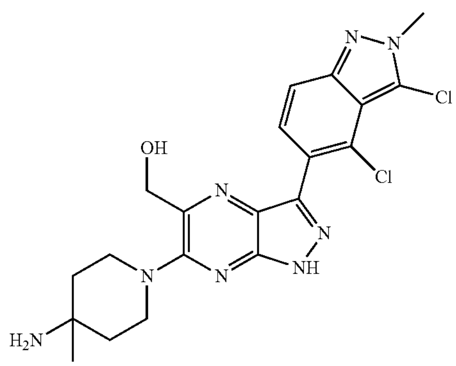 [SMILES: Cn1nc2ccc(-c3n[nH]c4nc(N5CCC(C)(N)CC5)c(CO)nc34)c(Cl)c2c1Cl] | [6-(4-amino-4-methylpiperidin-1-yl)-3-(3,4-dichloro-2-methyl-2H-indazol-5-yl)-1H-pyrazolo[3,4-b]pyrazin-5-yl]methanol | 1H NMR (400 MHz, DMSO-d6): 7.71 (1H, d), 7.65 (1H, d), 5.30 (1H, t), 4.58 (2H, d), 4.19 (3H, s), 3.44 (4H, d), 1.69-1.57 (2H, m), 1.57-1.49 (2H, m), 1.13 (3H, s). | 461 | Prepared using analogous methods to example 80 |
| 111 | 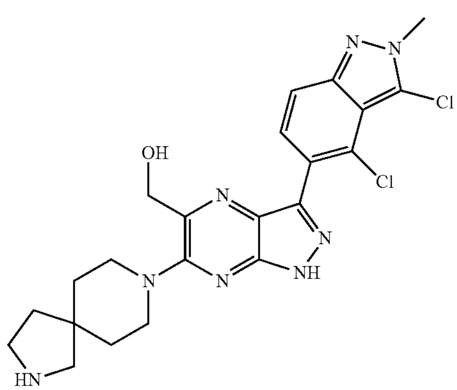 [SMILES: Cn1nc2ccc(-c3n[nH]c4nc(N5CCC6(CCNC6)CC5)c(CO)nc34)c(Cl)c2c1Cl] | (6-{2,8-diazaspiro[4.5]decan-8-yl}-3-(3,4-dichloro-2-methyl-2H-indazol-5-yl)-1H-pyrazolo[3,4-b]pyrazin-5-yl)methanol | ¹H NMR (400 MHz, DMSO-d₆): 7.73-7.67 (1H, m), 7.67-7.63 (1H, m), 5.49-5.19 (1H, m), 4.60 (2H, s), 4.19 (3H, s), 2.89-2.82 (2H, m), 1.74-1.62 (4H, m), 1.61-1.52 (2H, m). | 487 | Prepared using analogous methods to example 80 |
| 112 | 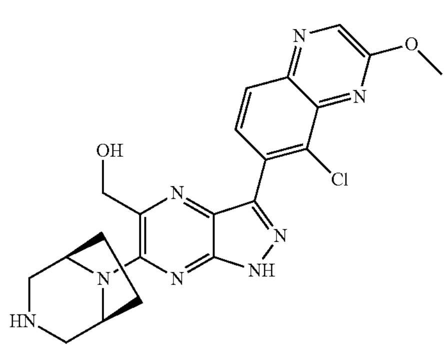 [SMILES: COc1cnc2ccc(-c3n[nH]c4nc(N5[C@@H]6CC[C@H]5CNC6)c(CO)nc34)c(Cl)c2n1] | [3-(5-Chloro-3-methoxyquinoxalin-6-yl)-6-{3,8-diazabicyclo[3.2.1]octan-8-yl}-1H-pyrazolo[3,4-b]pyrazin-5-yl]methanol | ¹H NMR (400 MHz, DMSO-d₆): 13.67 (1H, s), 8.74 (1H, s), 8.11 (1H, d), 8.03 (1H, d), 5.34 (1H, t), 4.77-4.57 (3H, m), 4.53 (2H, bs), 4.15 (3H, s), 3.02 (2H, d), 2.71-2.62 (3H, m), 1.97-1.85 (4H, m). | 453 | Prepared using analogous methods to example 80 |

TABLE 16-continued

Examples 97-123

| Example | Structure | Name | NMR Data | MS Data | Method |
|---|---|---|---|---|---|
| 113 | 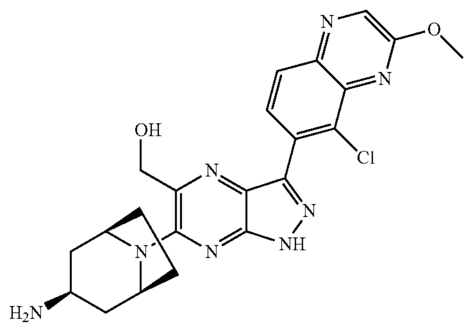 [SMILES: COc1cnc2ccc(-c3n[nH]c4nc(N5[C@@H]6CC[C@H]5C[C@@H](N)C6)c(CO)nc34)c(Cl)c2n1] | {6-[endo-3-amino-8-aza-bicyclo[3.2.1]octan-8-yl]-3-(5-chloro-3-methoxyquinoxalin-6-yl)-1H-pyrazolo[3,4-b]pyrazin-5-yl}methanol | $^1$H NMR (400 MHz, DMSO-d$_6$): 8.73 (1H, s), 8.10 (1H, d), 8.03 (1H, d), 5.38-5.26 (1H, m), 4.68-4.58 (4H, m), 4.14 (3H, s), 3.29-3.27 (1H, m), 2.32-2.26 (2H, m), 2.25-2.17 (2H, m), 1.98-1.90 (2H, m), 1.58 (2H, d). | 467 | Prepared using analogous methods to example 80, except using General Procedure 3 |
| 114 | 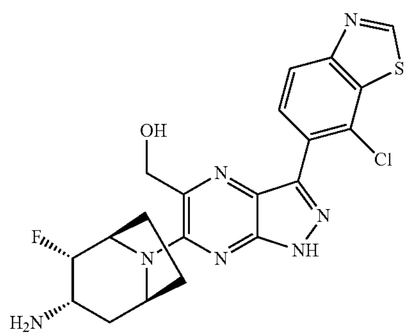 [SMILES: N[C@H]1C[C@@H]2CC[C@H]([C@H]1F)N2c1nc2[nH]nc(-c3ccc4ncsc4c3Cl)c2nc1CO] | {6-[(1R,2S,3S,5S)-3-amino-2-fluoro-8-azabicyclo[3.2.1]octan-8-yl]-3-(7-chloro-1,3-benzothiazol-6-yl)-1H-pyrazolo[3,4-b]pyrazin-5-yl}methanol | $^1$H NMR (400 MHz, DMSO-d$_6$): 14.19-13.07 (1H, m), 9.55 (1H, s), 8.21 (1H, d), 8.09 (1H, d), 5.37-5.28 (1H, m), 5.03-4.96 (1H, m), 4.75 (1H, dd), 4.70-4.48 (3H, m), 3.16-3.03 (1H, m), 2.04-1.88 (3H, m), 1.79-1.70 (3H, m). | 460 | Prepared using analogous methods to example 80 except using General Procedure 3 |
| 115 | 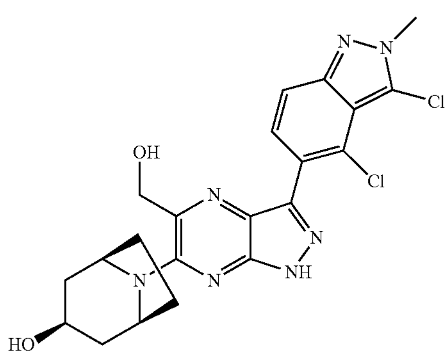 [SMILES: Cn1nc2ccc(-c3n[nH]c4nc(N5[C@@H]6CC[C@H]5C[C@@H](O)C6)c(CO)nc34)c(Cl)c2c1Cl] | endo-8-[3-(3,4-dichloro-2-methyl-2H-indazol-5-yl)-5-(hydroxymethyl)-1H-pyrazolo[3,4-b]pyrazin-6-yl]-8-azabicyclo[3.2.1]octan-3-ol | $^1$H NMR (400 MHz, DMSO-d$_6$): 13.47 (1H, s), 7.70 (1H, d), 7.64 (1H, d), 5.39-5.25 (1H, m), 4.69-4.41 (6H, m), 4.19 (3H, s), 3.95 (1H, s), 2.37-2.23 (2H, m), 2.19-2.10 (2H, m), 1.92 (2H, s), 1.78 (2H, d). | 473 | Prepared using analogous methods to example 80 |
| 116 | 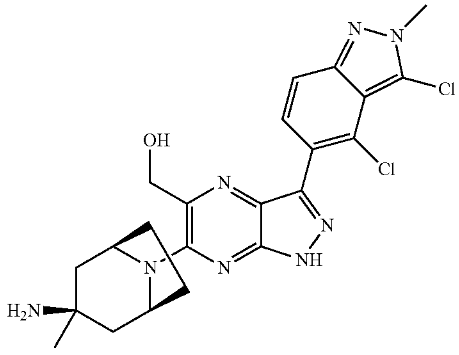 [SMILES: Cn1nc2ccc(-c3n[nH]c4nc(N5[C@@H]6CC[C@H]5C[C@@](C)(N)C6)c(CO)nc34)c(Cl)c2c1Cl] | {6-[endo-3-amino-3-methyl-8-azabicyclo[3.2.1]octan-8-yl]-3-(3,4-dichloro-2-methyl-2H-indazol-5-yl)-1H-pyrazolo[3,4-b]pyrazin-5-yl}methanol | 1H-NMR (DMSO-D$_6$) δ: 7.70 (1H, d, J = 8.9 Hz), 7.64 (1H, d, J = 8.9 Hz), 5.38-5.26 (1H, m), 4.66-4.57 (1H, m), 4.18 (3H, s), 2.41-2.32 (2H, m), 1.96-1.80 (4H, m), 1.66-1.56 (2H, m), 1.03 (3H, s). | 487 | Prepared using analogous methods to example 80, except using an analogous deprotection to method 1 |

TABLE 16-continued

Examples 97-123

| Example | Structure | Name | NMR Data | MS Data | Method |
|---|---|---|---|---|---|
| 117 | 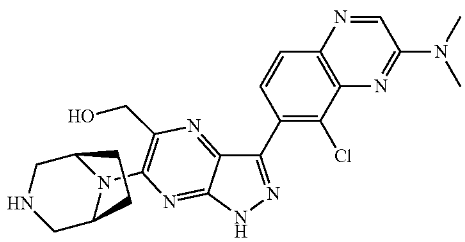 [SMILES: CN(C)c1cnc2ccc(-c3n[nH]c4nc(N5[C@@H]6CC[C@H]5CNC6)c(CO)nc34)c(Cl)c2n1] | {3-[Chloro-3-(dimethylamino)quinoxalin-6-yl]-6-{3,8-diazabicyclo[3.2.1]octan-8-yl}-1H-pyrazolo[3,4-b]pyrazin-5-yl}methanol | $^1$H-NMR (DMSO-D$_6$) δ: 8.78 (1H, s), 7.87 (1H, d, J = 8.4 Hz), 7.67 (1H, d, J = 8.4 Hz), 5.32 (1H, br s), 4.69-4.44 (4H, m), 3.31 (6H, s), 3.01 (2H, d, J = 12.0 Hz), 2.65 (2H, dd, J = 12.0, 2.0 Hz), 1.98-1.80 (4H, m). | 466 | Prepared using analogous methods to example 80, except using an analogous deprotection to method 1 |
| 118 | 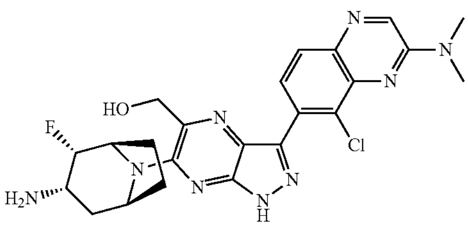 [SMILES: CN(C)c1cnc2ccc(-c3n[nH]c4nc(N5[C@H]6CC[C@@H]5[C@@H](F)[C@@H](N)C6)c(CO)nc34)c(Cl)c2n1] | {6-[(1R,2S,3S,5S)-3-amino-2-fluoro-8-azabicyclo[3.2.1]octan-8-yl]-3-[5-chloro-3-(dimethylamino)quinoxalin-6-yl]-1H-pyrazolo[3,4-b]pyrazin-5-yl}methanol | 1H-NMR (400 MHz, DMSO-d6) δ: 13.54 (1H, br s), 8.79 (1H, s), 7.87 (1H, d, J = 8.4 Hz), 7.66 (1H, d, J = 8.5 Hz), 5.30 (1H, t, J = 5.7 Hz), 5.00-4.95 (1H, m), 4.75-4.45 (4H, m), 3.31 (6H, s), 3.13-2.98 (1H, m), 2.01-1.47 (8H, m). | 498 | Prepared using analogous methods to example 80, except using an analogous deprotection to method 1 |
| 119 | 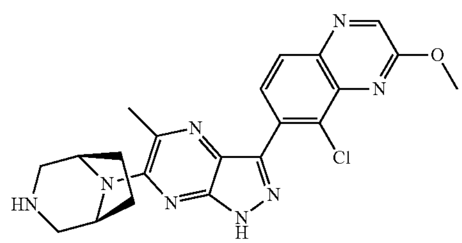 [SMILES: COc1cnc2ccc(-c3n[nH]c4nc(N5[C@@H]6CC[C@H]5CNC6)c(C)nc34)c(Cl)c2n1] | 8-Chloro-7-(6-{3,8-diazabicyclo[3.2.1]octan-8-yl}-5-methyl-1H-pyrazolo[3,4-b]pyrazin-3-yl)-2-methoxyquinoxaline | $^1$H-NMR (DMSO-D$_6$) δ: 8.73 (1H, s), 8.10 (1H, d, J = 8.6 Hz), 7.99 (1H, d, J = 8.6 Hz), 4.28 (2H, br s), 4.13 (3H, s), 3.02 (2H, d, J = 12.1 Hz), 2.67 (2H, dd, J = 12.1, 2.8 Hz), 2.59 (3H, s), 1.94-1.85 (4H, m). | 437 | Prepared using analogous methods to example 96 |
| 120 | 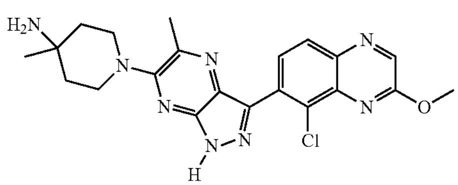 | 1-[3-(5-chloro-3-methoxyquinoxalin-6-yl)-5-methyl-1H-pyrazolo[3,4-b]pyrazin-6-yl]-4-methylpiperidin-4-amine | 1H-NM0R (400 MHz, DMSO-d6) δ: 13.73 (1H, s), 8.74 (1H, s), 8.11 (1H, d, J = 8.5 Hz), 7.99 (1H, d, J = 8.5 Hz), 4.14 (3H, s), 3.52-3.35 (4H, m), 2.55 (3H, s), 1.70-1.56 (4H, m), 1.23 (2H, br s), 1.17 (3H, s). | 439 | Prepared using analogous methods to example 96 |
| 121 | 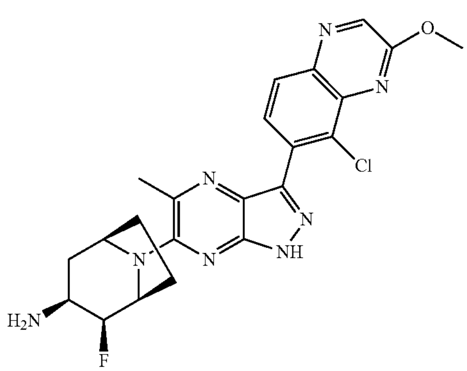 [SMILES: COc1cnc2ccc(-c3n[nH]c4nc(N5[C@@H]6CC[C@H]5[C@@H](F)[C@@H](N)C6)c(C)nc34)c(Cl)c2n1] | (1S,2S,3S,5R)-8-[3-(5-chloro-3-methoxyquinoxalin-6-yl)-5-methyl-1H-pyrazolo[3,4-b]pyrazin-6-yl]-2-fluoro-8-azabicyclo[3.2.1]octan-3-amine | 1H NMR (400 MHz, DMSO-d6): 13.72 (1H, br. s), 8.74 (1H, s), 8.11 (1H, d), 7.99 (1H, d), 5.00-4.82 (1H, m), 4.56-4.48 (1H, m), 4.42-4.33 (1H, m), 4.14 (3H, s), 3.67 (1H, t), 2.64-2.55 (4H, m), 2.31-2.21 (1H, m), 2.20-2.10 (1H, m), 2.00-1.82 (2H, m), 1.82-1.70 (1H, m). | 469 | Prepared using analogous methods to example 96 |

TABLE 16-continued

Examples 97-123

| Example | Structure | Name | NMR Data | MS Data | Method |
|---|---|---|---|---|---|
| 122 | 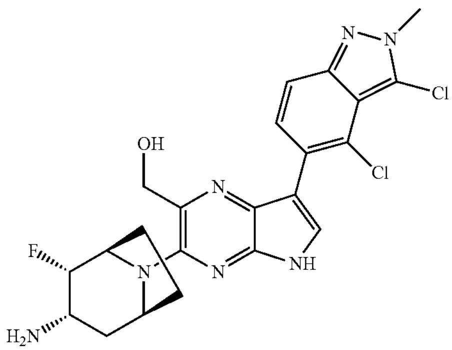 [SMILES: Cn1nc2ccc(-c3c[nH]c4nc(N5[C@H]6CC[C@@H]5[C@@H](F)[C@@H](N)C6)c(CO)nc34)c(Cl)c2c1Cl] | {3-[(1R,2S,3S,5S)-3-amino-2-fluoro-8-azabicyclo[3.2.1]octan-8-yl]-7-(3,4-dichloro-2-methyl-2H-indazol-5-yl)-5H-pyrrolo[2,3-b]pyrazin-2-yl}methanol | $^1$H NMR (400 MHz, DMSO-d$_6$): 11.88 (1H, s), 7.91 (1H, d), 7.85 (1H, s), 7.64 (1H, d), 5.09 (1H, t), 4.79-4.62 (3H, m), 4.57-4.37 (2H, m), 4.16 (3H, s), 3.07-2.88 (1H, m), 1.99-1.61 (6H, m), 1.48 (2H, s). | 490 | Prepared from methyl 3-[(1R,2S,3S,5S)-3-{[(tert-butoxy)carbonyl]amino}-2-fluoro-8-azabicyclo[3.2.1]octan-8-yl]-7-(3,4-dichloro-2-methyl-2H-indazol-5-yl)-5-{[2-(trimethylsilyl)ethoxy]methyl}-5H-pyrrolo[2,3-b]pyrazine-2-carboxylate using an analogous deprotection procedure to method 10 |
| 123 | 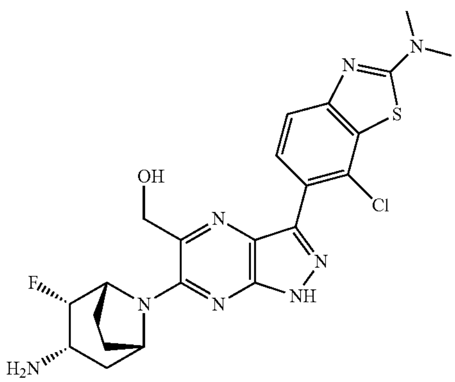 [SMILES: CN(C)c1nc2ccc(-c3n[nH]c4nc(N5[C@H]6CC[C@@H]5[C@@H](F)[C@@H](N)C6)c(CO)nc34)c(Cl)c2s1] | {6-[(1S,2S,3S,5R)-3-amino-2-fluoro-8-azabicyclo[3.2.1]octan-8-yl]-3-[7-chloro-2-(dimethylamino)-1,3-benzothiazol-6-yl]-1H-pyrazolo[3,4-b]pyrazin-5-yl}methanol | $^1$H NMR (400 MHz, DMSO-d$_6$): 13.43 (1H, bs), 7.78 (1H, d), 7.52 (1H, d), 5.30 (1H, t), 5.01-4.93 (1H, m), 4.73 (1H, dd), 4.68-4.60 (2H, m), 4.53 (1H, dt), 3.21 (6H, s), 3.13-2.96 (1H, m), 2.02-1.68 (6H, m), 1.51 (2H, s). | 503 | Prepared using analogous methods to example 80 except using analogous method to General Procedure 3 followed by an analogous deprotection procedure to method 12 |

By following methods similar and/or analogous to those described for general procedures for preparations of compounds of Formula (I) (e.g. methods 1-12), the compounds set out in Table 16 were prepared, with any significant variations indicated. The title compounds were either isolated directly as the free base or as the appropriate salt without further purification, or purified for example using mass-directed preparative HPLC, chromatography, crystallization or trituration and converted to the appropriate salt.

Examples 124-150

5-Bromo-4-chloro-2-ethyl-2H-indazole-3-carbaldehyde

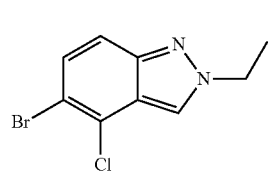

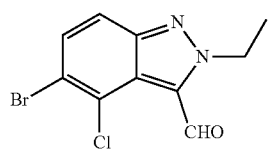

Prepared using analogous methods to the preparation of 5-bromo-4-chloro-2-methyl-2H-indazole-3-carbaldehyde (preparation 40). $^1$H NMR (400 MHz, DMSO-d$_6$): 10.66 (1H, s), 7.83 (1H, d), 7.72 (1H, d), 4.84 (2H, q), 1.47 (3H, t).

4-Bromo-5-chloro-2-ethyl-2H-indazole-3-carbonitrile

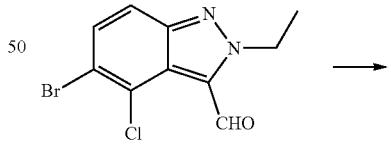

Hydroxylamine hydrochloride (943 mg, 13.6 mmol) and Na$_2$CO$_3$ (1.44 g, 13.6 mmol) were added to a suspension of 5-bromo-4-chloro-2-ethyl-2H-indazole-3-carbaldehyde (2.60 g, 9.04 mmol) in a mixture of IPA (40 mL), MeOH (40 mL) and H$_2$O (10 mL) and the reaction stirred at 50° C. overnight. After cooling, most of the solvent was evaporated and further H$_2$O was added to the remaining aqueous suspension. The solid precipitate was collected under suction and washed on the filter with H₂O, then dried in vacuo to provide intermediate oxime as a pale yellow solid (2.52 g). To a solution of this material in MeCN (80 mL) was added copper(II) acetate (753 mg, 4.15 mmol) and the reaction stirred at 85° C. for 2 h. After cooling, the solvent was evaporated and the residue purified by column chromatography on silica gel (gradient elution, 0-20%, EtOAc/petrol) to give the title compound (2.30 g). ¹H NMR (400 MHz, DMSO-d₆): 7.86 (1H, d), 7.72 (1H, d), 4.68 (2H, q), 1.58 (3H, t).

4-Bromo-5-chloro-2-methyl-2H-indazole-3-carbonitrile

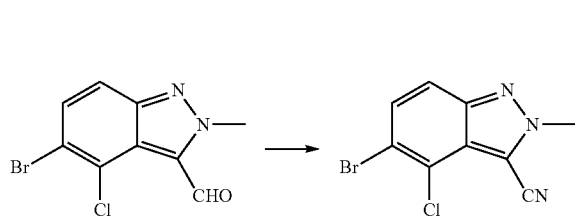

Prepared using analogous methods to preparation of 4-bromo-5-chloro-2-ethyl-2H-indazole-3-carbonitrile. MS: [M+H]⁺=270.

4-Chloro-2-methyl-5-(4,4,5,5-tetramethyl-1,3,2-dioxaborolan-2-yl)-2H-indazole-3-carbonitrile

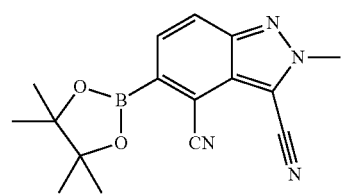

Prepared using analogous methods to preparation of 4-chloro-2-methyl-5-(4,4,5,5-tetramethyl-1,3,2-dioxaborolan-2-yl)-2H-indazole MS: [M+H]⁺=318.

7-Bromo-8-chloro-2-ethoxyquinoxaline

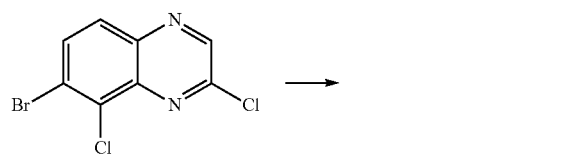

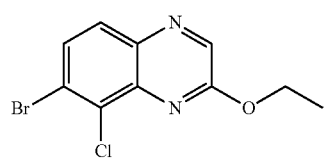

A suspension of 7-bromo-2,8-dichloroquinoxaline (650 mg, 2.34 mmol) and K₂CO₃ (1.29 g, 9.36 mmol) in EtOH (6 mL) was heated at reflux for 3 h and then cooled to RT and partitioned between EtOAc and water. The phases separated, the aqueous phase was extracted with EtOAc and the combined organic phases washed with brine, dried (MgSO₄+hydrophobic frit) and concentrated, to give the title compound (598 mg). ¹H NMR (400 MHz, DMSO-d₆): 8.66 (1H, s), 7.94 (1H, d), 7.91 (1H, d), 4.57 (2H, q), 1.45 (3H, t).

7-Bromo-8-chloro-2-(propan-2-yloxy)quinoxaline

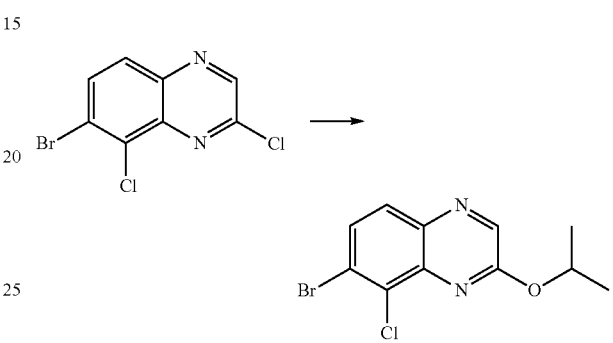

Prepared using analogous methods to preparation of 7-bromo-8-chloro-2-ethoxyquinoxaline, MS: [M+H]⁺=301

2-(Azetidin-1-yl)-7-bromo-8-chloroquinoxaline

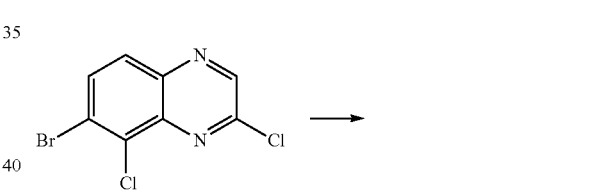

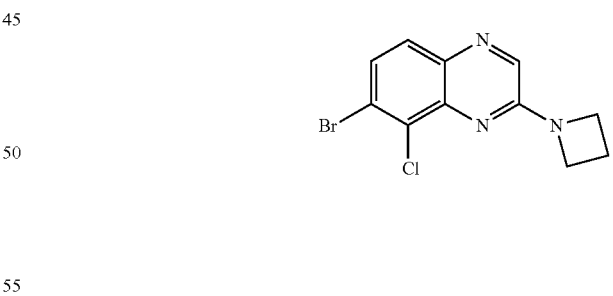

Azetidine (0.49 mL, 7.20 mmol) was added to a solution of 7-bromo-2,8-dichloroquinoxaline (1.00 g, 3.60 mmol) and triethylamine (1.00 mL, 7.20 mmol) in THF (5 mL) and the mixture immediately became yellow. Stirred at RT for 80 h and then partitioned between EtOAc and saturated aqueous NaHCO₃. Phases separated, aqueous phase extracted with EtOAc and combined organic phases washed with brine, dried (MgSO₄+hydrophobic frit) and concentrated, to give the title compound (1.05 g). ¹H NMR (400 MHz, DMSO-d₆): 8.36 (1H, s), 7.71 (1H, d), 7.64 (1H, d), 4.28 (4H, t), 2.49-2.41 (2H, m).

TABLE 17

Table 17: Examples 124-150

| Example | Structure | Name | NMR Data | MS Data | Method |
|---|---|---|---|---|---|
| 124 | 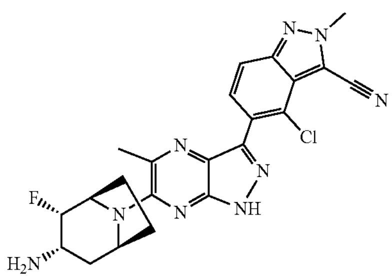 [SMILES: Cc1nc2c(-c3ccc4nn(C)c(C#N)c4c3Cl)n[nH]c2nc1N1[C@H]2CC[C@@H]1[C@@H](F)[C@@H](N)C2] | 5-{6-[(1R,2S,3S,5S)-3-amino-2-fluoro-8-azabicyclo[3.2.1]octan-8-yl]-5-methyl-1H-pyrazolo[3,4-b]pyrazin-3-yl}-4-chloro-2-methyl-2H-indazole-3-carbonitrile | $^1$H NMR (400 MHz, DMSO-$d_6$): 7.98 (1H, d), 7.88 (1H, d), 4.88-4.78 (1H, m), 4.60-4.43 (2H, m), 4.41 (3H, s), 3.13-2.96 (1H, m), 2.61 (3H, s), 2.10-1.67 (6H, m). | 466 | Prepared using analogous methods to example 96 |
| 125 | 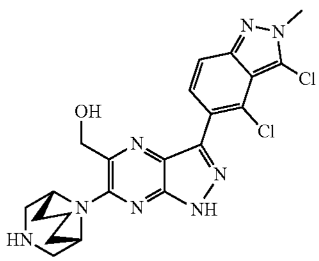 [SMILES: Cn1nc2ccc(-c3n[nH]c4nc(N5[C@@H]6CCC[C@H]5CNC6)c(CO)nc34)c(Cl)c2c1Cl] | 6-[3,9-diazabicyclo[3.3.1]nonan-9-yl]-3-(3,4-dichloro-2-methyl-2H-indazol-5-yl)-1H-pyrazolo[3,4-b]pyrazin-5-yl}methanol | $^1$H NMR (500 MHz, DMSO-$d_6$): 13.81-13.54 (1H, s), 7.70 (1H, d), 7.63 (1H, d), 5.38 (1H, t), 4.66 (2H, d), 4.18 (3H, s), 3.88 (2H, d), 3.23 (2H, d), 3.06 (2H, s), 1.94-1.83 (2H, m), 1.80 (2H, dd), 1.63-1.53 (1H, m). | 473 | Prepared using analogous methods to example 80 except using an analogous deprotection to method 12 |
| 126 | 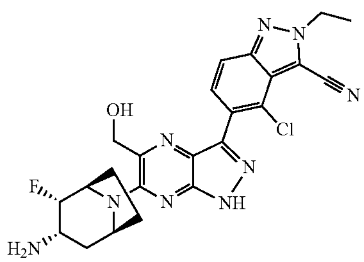 [SMILES: CCn1nc2ccc(-c3n[nH]c4nc(N5[C@H]6CC[C@@H]5[C@@H](F)[C@@H](N)C6)c(CO)nc34)c(Cl)c2c1C#N] | 5-{6-[(1R,2S,3S,5S)-3-amino-2-fluoro-8-azabicyclo[3.2.1]octan-8-yl]-5-(hydroxymethyl)-1H-pyrazolo[3,4-b]pyrazin-3-yl}-4-chloro-2-ethyl-2H-indazole-3-carbonitrile | $^1$H NMR (400 MHz, DMSO-$d_6$): 14.19-12.66 (1H, m), 8.00 (1H, d), 7.92 (1H, d), 5.31 (1H, t), 5.04-4.96 (1H, m), 4.78-4.49 (6H, m), 3.17-3.03 (1H, m), 2.02-1.88 (3H, m), 1.79-1.70 (3H, m), 1.62 (3H, t). | 496 | Prepared using analogous methods to example 80 except using General Procedure 3 |
| 127 | 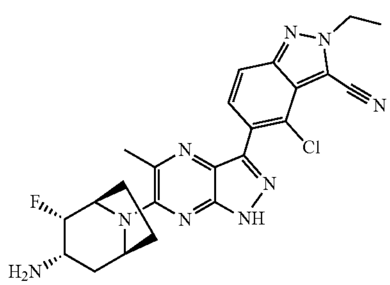 [SMILES: CCn1nc2ccc(-c3n[nH]c4nc(N5[C@H]6CC[C@@H]5[C@@H](F)[C@@H](N)C6)c(C)nc34)c(Cl)c2c1C#N] | 5-{6-[(1R,2S,3S,5S)-3-amino-2-fluoro-8-azabicyclo[3.2.1]octan-8-yl]-5-methyl-1H-pyrazolo[3,4-b]pyrazin-3-yl}-4-chloro-2-ethyl-2H-indazole-3-carbonitrile, hydrochloride salt | $^1$H NMR (400 MHz, DMSO-$d_6$): 13.70 (1H, s), 8.26 (3H, s), 8 01 (1H, d), 7.87 (1H, d), 5.00-4.81 (2H, m), 4.73 (2H, q), 4.62-4.52 (1H, m), 3.84-3.67 (1H, m), 2.62 (3H, s), 2.43-2.35 (1H, m), 2.16-1.89 (3H, m), 1.86-1.74 (2H, m), 1.62 (3H, t). | 480 | Prepared using analogous methods to example 80 except using General Procedure 3 and using an analogous deprotection to method 11 |
| 128 | 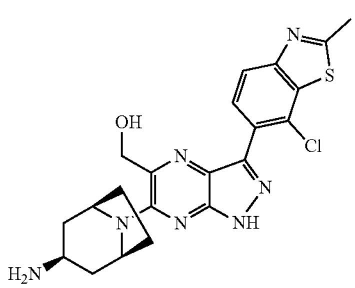 [SMILES: Cc1nc2ccc(-c3n[nH]c4nc(N5[C@@H]6CC[C@H]5C[C@@H](N)C6)c(CO)nc34)c(Cl)c2s1] | {6-[endo-3-amino-8-azabicyclo[3.2.1]octan-8-yl]-3-(7-chloro-2-methyl-1,3-benzothiazol-6-yl)-1H-pyrazolo[3,4-b]pyrazin-5-yl}methanol | $^1$H NMR (400 MHz, DMSO-$d_6$): 8.03 (1H, d), 8.01 (1H, d), 5.40-5.25 (1H, m), 4.67-4.58 (4H, m), 3.28-3.26 (1H, m), 2.88 (3H, s), 2.31-2.18 (4H, m), 1.97-1.90 (2H, m), 1.61-1.55 (2H, m). | 456 | Prepared using analogous methods to example 80 except using General Procedure 3 |

TABLE 17-continued

Table 17: Examples 124-150

| Example | Structure | Name | NMR Data | MS Data | Method |
|---|---|---|---|---|---|
| 129 | 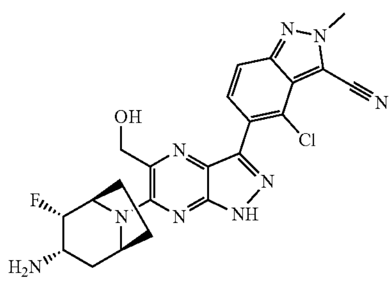 [SMILES: Cn1nc2ccc(-c3n[nH]c4nc(N5[C@H]6CC[C@@H]5[C@@H](F)[C@@H](N)C6)c(CO)nc34)c(Cl)c2c1C#N] | 5-{6-[(1R,2S,3S,5S)-3-amino-2-fluoro-8-azabicyclo[3.2.1]octan-8-yl]-5-(hydroxymethyl)-1H-pyrazolo[3,4-b]pyrazin-3-yl}-4-chloro-2-methyl-2H-indazole-3-carbonitrile | $^1$H NMR (400 MHz, DMSO-d$_6$): 7.97 (1H, d), 7.90 (1H, d), 5.32 (1H, t), 5.04-4.95 (1H, m), 4.78-4.46 (4H, m), 4.40 (3H, s), 3.12-2.99 (1H, m), 2.04-1.83 (3H, m), 1.78-1.68 (3H, m). | 482 | Prepared using analogous methods to example 80, except using an analogous deprotection to method 1 |
| 130 | 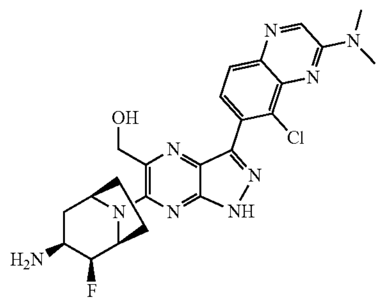 [SMILES: CN(C)c1cnc2ccc(-c3n[nH]c4nc(N5[C@@H]6CC[C@H]5[C@@H](F)[C@@H](N)C6)c(CO)nc34)c(Cl)c2n1] | {6-[(1S,2S,3S,5R)-3-amino-2-fluoro-8-azabicyclo[3.2.1]octan-8-yl]-3-[5-chloro-3-(dimethylamino)quinoxalin-6-yl]-1H-pyrazolo[3,4-b]pyrazin-5-yl}methanol | $^1$H NMR (400 MHz, DMSO-d$_6$): 13.64 (1H, br s), 8.79 (1H, s), 7.88 (1H, d), 7.65 (1H, d), 5.41 (1H, t, J = 5.5 Hz), 4.88 (1H, dt), 4.78-4.71 (1H, m), 4.56 (1H, t), 3.67-3.60 (1H, m), 3.30 (6H, s), 2.30-2.09 (2H, m), 2.00-1.70 (4H, m). | 498 | Prepared using analogous methods to Prepared using 80, except using an analogous deprotection to method 1 |
| 131 | 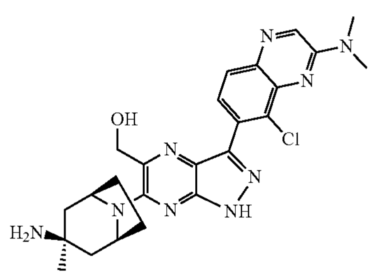 [SMILES: CN(C)c1cnc2ccc(-c3n[nH]c4nc(N5[C@@H]6CC[C@H]5C[C@@](C)(N)C6)c(CO)nc34)c(Cl)c2n1] | {6-[endo-3-amino-3-methyl-8-azabicyclo[3.2.1]octan-8-yl]-3-[5-chloro-3-(dimethylamino)quinoxalin-6-yl]-1H-pyrazolo[3,4-b]pyrazin-5-yl}methanol | $^1$H NMR (400 MHz, DMSO-d$_6$): 13.50 (1H, br s), 8.79 (1H, s), 7.87 (1H, d), 7.67 (1H, d), 5.30 (1H, t), 4.68-4.55 (4H, m), 3.31 (6H, s), 2.41-2.32 (2H, m), 1.99-1.79 (4H, m), 1.61 (2H, d), 1.02 (3H, s). | 494 | Prepared using analogous methods to example 80, except using an analogous deprotection to method 1 |
| 132 | 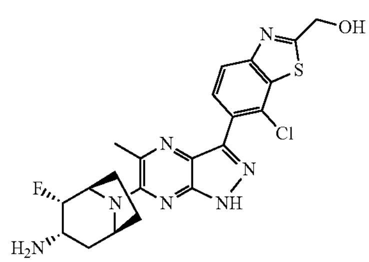 [SMILES: Cc1nc2c(-c3ccc4nc(CO)sc4c3Cl)n[nH]c2nc1N1[C@H]2CC[C@@H]1[C@@H](F)[C@@H](N)C2] | (6-{6-[(1R,2S,3S,5S)-3-amino-2-fluoro-8-azabicyclo[3.2.1]octan-8-yl]-5-methyl-1H-pyrazolo[3,4-b]pyrazin-3-yl}-7-chloro-1,3-benzothiazol-2-yl)methanol, hydrochloride | $^1$H NMR (400 MHz, DMSO-d$_6$): 8.29 (3H, d), 8.04 (1H, d), 7.97 (1H, d), 5.00-4.79 (4H, m), 4.57 (1H, d), 3.75 (1H, d), 2.62 (3H, s), 2.45-2.35 (1H, m), 2.02 (3H, m), 1.85-1.74 (2H, m). | 474 | Prepared using analogous methods to example 80, and using an analogous deprotection to method 11 |
| 133 | 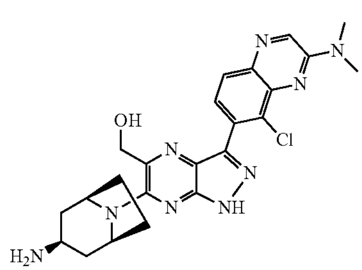 [SMILES: CN(C)c1cnc2ccc(-c3n[nH]c4nc(N5[C@@H]6CC[C@H]5C[C@@H](N)C6)c(CO)nc34)c(Cl)c2n1] | {6-[endo-3-amino-8-azabicyclo[3.2.1]octan-8-yl]-3-[5-chloro-3-(dimethylamino)quinoxalin-6-yl]-1H-pyrazolo[3,4-b]pyrazin-5-yl}methanol | $^1$H NMR (400 MHz, DMSO-d$_6$): 13.52 (1H, s), 8.79 (1H, s), 7.87 (1H, d), 7.66 (1H, d), 5.29 (1H, t), 4.64-4.58 (4H, m), 3.39-3.34 (1H, m), 2.31 (2H, d), 2.19-2.16 (2H, m), 1.92-1.90 (2H, m), 1.56 (2H, d), 1.24-1.03 (2H, m). | 480 | Prepared using analogous methods to example 97, except using an analogous deprotection to method 1 |

TABLE 17-continued

Table 17: Examples 124-150

| Example | Structure | Name | NMR Data | MS Data | Method |
|---|---|---|---|---|---|
| 134 | 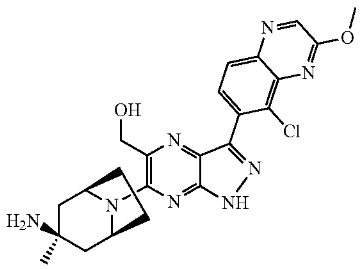 [SMILES: COc1cnc2ccc(-c3n[nH]c4nc(N5[C@@H]6CC[C@H]5C[C@@](C)(N)C6)c(CO)nc34)c(Cl)c2n1] | {6-[endo-3-amino-3-methyl-8-azabicyclo[3.2.1]octan-8-yl]-3-(5-chloro-3-methoxyquinoxalin-6-yl)-1H-pyrazolo[3,4-b]pyrazin-5-yl}methanol | 1H NMR (400 MHz, DMSO-$d_6$): 8.73 (1H, s), 8.10 (1H, d), 8.02 (1H, d), 5.38 (1H, t), 4.68 (2H, br s), 4.62 (2H, d), 4.13 (3H, s), 2.15-1.80 (6H, m), 1.18 (3H, s). | 481 | Prepared using analogous methods to example 80, except using an analogous deprotection to method 1 |
| 135 | 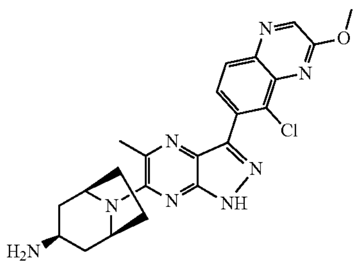 [SMILES: COc1cnc2ccc(-c3n[nH]c4nc(N5[C@@H]6CC[C@H]5C[C@@H](N)C6)c(C)nc34)c(Cl)c2n1] | endo-8-[3-(5-chloro-3-methoxyquinoxalin-6-yl)-5-methyl-1H-pyrazolo[3,4-b]pyrazin-6-yl]-8-azabicyclo[3.2.1]octan-3-amine | $^1$H NMR (400 MHz, DMSO-$d_6$): 13.59 (1H, br s), 8.73 (1H, s), 8.10 (1H, d), 7.99 (1H, d), 4.47-4.40 (2H, m), 4.14 (3H, s), 3.41-3.35 (1H, m), 2.57 (3H, s), 2.31-2.24 (2H, m), 2.22-2.16 (2H, m), 1.98-1.89 (2H, m), 1.59 (2H, d, J = 14.2 Hz), 1.27-1.12 (2H, m). | 451 | Prepared using analogous methods to example 96 |
| 136 | 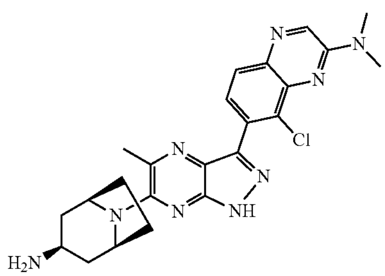 [SMILES: Cc1nc2c(-c3ccc4ncc(N(C)C)nc4c3Cl)n[nH]c2nc1N1[C@@H]2CC[C@H]1C[C@@H](N)C2] | 7-{6-[endo-3-amino-8-azabicyclo[3.2.1]octan-8-yl]-5-methyl-1H-pyrazolo[3,4-b]pyrazin-3-yl}-8-chloro-N,N-dimethylquinoxalin-2-amine | $^1$H NMR (400 MHz, DMSO-$d_6$): 13.51 (1H, s), 8.79 (1H, s), 7.87 (1H, d), 7.64 (1H, d), 4.44-4.38 (2H, m), 3.41-3.37 (1H, m), 2.56 (3H, s), 2.30 (2H, d), 2.22-2.14 (2H, m), 1.96-1.89 (2H, m), 1.58 (2H, d), 1.24 (2H, br s). | 464 | Prepared using analogous methods to example 96 |
| 137 | 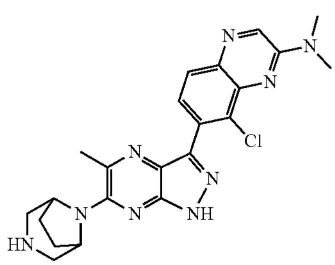 [SMILES: Cc1nc2c(-c3ccc4ncc(N(C)C)nc4c3Cl)n[nH]c2nc1N1C2CCC1CNC2] | 8-Chloro-7-(6-{3,8-diazabicyclo[3.2.1]octan-8-yl}-5-methyl-1H-pyrazolo[3,4-b]pyrazin-3-yl)-N,N-dimethylquinoxalin-2-amine | $^1$H NMR (400 MHz, DMSO-$d_6$): 8.79 (1H, s), 7.88 (1H, d), 7.64 (1H, d), 4.36 (2H, br s), 3.15 (2H, d), 2.87 (2H, d), 2.59 (3H, s), 2.02-1.91 (4H, m). | 450 | Prepared using analogous methods to example 96 |
| 138 | 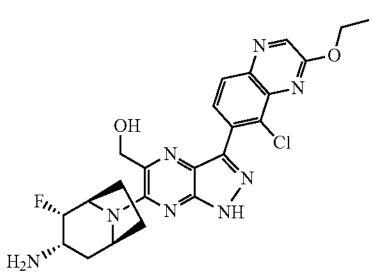 [SMILES: CCOc1cnc2ccc(-c3n[nH]c4nc(N5[C@H]6CC[C@@H]5[C@@H](F)[C@@H](N)C6)c(CO)nc34)c(Cl)c2n1] | {6-[(1R,2S,3S,5S)-3-amino-2-fluoro-8-azabicyclo[3.2.1]octan-8-yl]-3-(5-chloro-3-ethoxyquinoxalin-6-yl)-1H-pyrazolo[3,4-b]pyrazin-5-yl}methanol | $^1$H NMR (400 MHz, DMSO-$d_6$): 8.71 (1H, s), 8.09 (1H, d), 8.01 (1H, d), 5.31 (1H, t), 5.04-4.95 (1H, m), 4.78-4.46 (6H, m), 3.20-2.98 (1H, m), 2.07-1.84 (3H, m), 1.80-1.68 (3H, m), 1.48 (3H, t). | 499 | Prepared using analogous methods to example 80 except using an analogous deprotection to method 10 |

TABLE 17-continued

Table 17: Examples 124-150

| Example | Structure | Name | NMR Data | MS Data | Method |
|---|---|---|---|---|---|
| 139 | 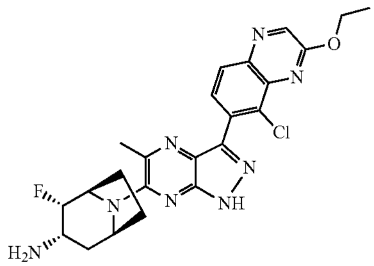 [SMILES: CCOc1cnc2ccc(-c3n[nH]c4nc(N5[C@H]6CC[C@@H]5[C@@H](F)[C@@H](N)C6)c(C)nc34)c(Cl)c2n1] | (1R,2S,3S,5S)-8-[3-(5-chloro-3-ethoxyquinoxalin-6-yl)-5-methyl-1H-pyrazolo[3,4-b]pyrazin-6-yl]-2-fluoro-8-azabicyclo[3.2.1]octan-3-amine | $^1$H NMR (400 MHz, DMSO-d$_6$): 13.60 (1H, br. s), 8.70 (1H, s), 8.09 (1H, d), 7.98 (1H, d), 4.87-4.77 (1H, m), 4.66-4.40 (4H, m), 3.13-2.96 (1H, m), 2.60 (3H, s), 2.11-1.84 (3H, m), 1.84-1.67 (3H, m), 1.48 (3H, t). | 483 | Prepared using analogous methods to example 96 using deprotection method 11 |
| 140 | 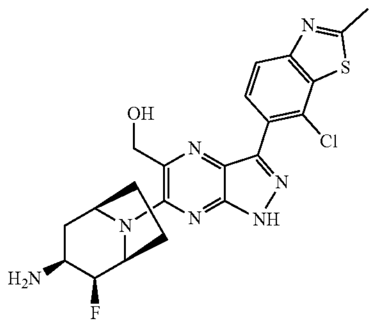 [SMILES: Cc1nc2ccc(-c3n[nH]c4nc(N5[C@@H]6CC[C@H]5[C@@H](F)[C@@H](N)C6)c(CO)nc34)c(Cl)c2s1] | {6-[(1S,2S,3S,5R)-3-amino-2-fluoro-8-azabicyclo[3.2.1]octan-8-yl]-3-(7-chloro-2-methyl-1,3-benzothiazol-6-yl)-1H-pyrazolo[3,4-b]pyrazin-5-yl}methanol | $^1$H NMR (400 MHz, DMSO-d$_6$): 13.93-13.41 (1H, m), 8.03 (1H, d), 8.01 (1H, d), 5.42 (1H, t), 4.98-4.82 (1H, m), 4.79-4.70 (1H, m), 4.66-4.58 (3H, m), 3.68-3.60 (1H, m), 2.88 (3H, s), 2.62-2.55 (1H, m), 2.26-2.15 (2H, m), 1.96-1.74 (3H, m). | 474 | Prepared using analogous methods to example 80 except using General Procedure 3 |
| 141 | 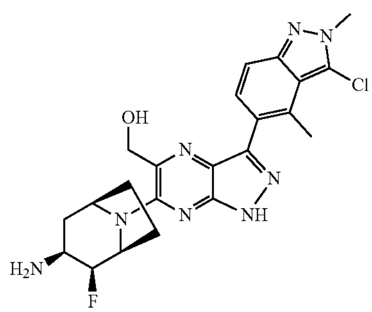 [SMILES: Cc1c(-c2n[nH]c3nc(N4[C@@H]5CC[C@H]4[C@@H](F)[C@@H](N)C5)c(CO)nc23)ccc2nn(C)c(Cl)c12] | {6-[(1S,2S,3S,5R)-3-amino-2-fluoro-8-azabicyclo[3.2.1]octan-8-yl]-3-(3-chloro-2,4-dimethyl-2H-indazol-5-yl)-1H-pyrazolo[3,4-b]pyrazin-5-yl}methanol | $^1$H NMR (400 MHz, DMSO-d$_6$): 13.46 (1H, s), 7.62 (1H, d), 7.53 (1H, d), 5.40 (1H, t), 4.89 (1H, dt), 4.77-4.70 (1H, m), 4.65-4.57 (3H, m), 4.15 (3H, s), 3.67-3.61 (1H, m), 2.76 (3H, s), 2.62-2.55 (1H, m), 2.28-2.13 (2H, m), 1.93-1.75 (3H, m). | | Prepared using analogous methods to example 80 |
| 142 | 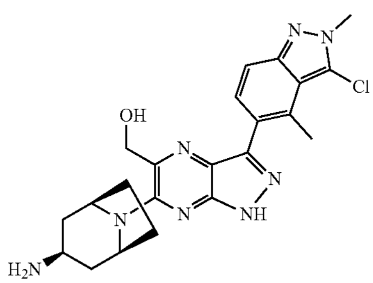 [SMILES: Cc1c(-c2n[nH]c3nc(N4[C@@H]5CC[C@H]4C[C@@H](N)C5)c(CO)nc23)ccc2nn(C)c(Cl)c12] | {6-[endo-3-amino-8-azabicyclo[3.2.1]octan-8-yl]-3-(3-chloro-2,4-dimethyl-2H-indazol-5-yl)-1H-pyrazolo[3,4-b]pyrazin-5-yl}methanol | $^1$H NMR (400 MHz, DMSO-d$_6$): 7.63 (1H, d), 7.52 (1H, d), 5.39-5.22 (1H, m), 4.67-4.55 (4H, m), 4.15 (3H, s), 3.29-3.27 (1H, m), 2.76 (3H, s), 2.31-2.25 (2H, m), 2.25-2.16 (2H, m), 1.97-1.88 (2H, m), 1.57 (2H, d). | 453 | Prepared using analogous methods to example 80 |
| 143 | 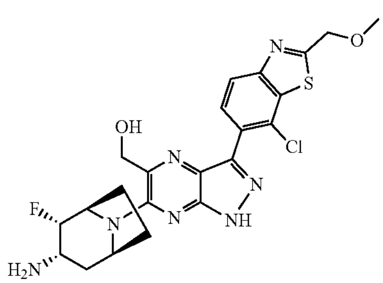 [SMILES: COCc1nc2ccc(-c3n[nH]c4nc(N5[C@H]6CC[C@@H]5[C@@H](F)[C@@H](N)C6)c(CO)nc34)c(Cl)c2s1] | {6-[(1R,2S,3S,5S)-3-amino-2-fluoro-8-azabicyclo[3.2.1]octan-8-yl]-3-[7-chloro-2-(methoxymethyl)-1,3-benzothiazol-6-yl]-1H-pyrazolo[3,4-b]pyrazin-5-yl}methanol | $^1$H NMR (400 MHz, DMSO-d$_6$): 14.19-12.96 (1H, m), 8.09 (1H, d), 8.06 (1H, d), 5.42-5.22 (1H, m), 5.04-4.97 (1H, m), 4.93 (2H, s), 4.78-4.72 (1H, m), 4.70-4.50 (3H, m), 3.52 (3H, s) 3.19-3.09 (1H, m), 2.05-1.85 (3H, m), 1.80-1.70 (3H, m). | 504 | Prepared using analogous methods to example 80 except using General Procedure 3 |

TABLE 17-continued

Table 17: Examples 124-150

| Example | Structure | Name | NMR Data | MS Data | Method |
|---|---|---|---|---|---|
| 144 | 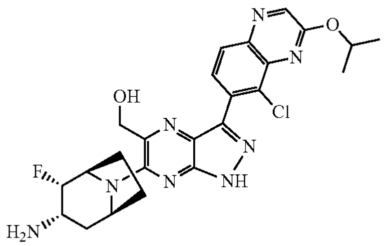 [SMILES: CC(C)Oc1cnc2ccc(-c3n[nH]c4nc(N5[C@H]6CC[C@@H]5[C@@H](F)[C@@H](N)C6)c(CO)nc34)c(Cl)c2n1] | {6-[(1R,2S,3S,5S)-3-amino-2-fluoro-8-azabicyclo[3.2.1]octan-8-yl]-3-[5-chloro-3-(propan-2-yloxy)quinoxalin-6-yl]-1H-pyrazolo[3,4-b]pyrazin-5-yl}methanol | 1H NMR (400 MHz, DMSO-d$_6$): 14.07-13.12 (1H, m), 8.65 (1H, s), 8.07 (1H, d), 8.00 (1H, d), 5.60-5.50 (1H, m), 5.37-5.26 (1H, m,) 4.99 (1H, s), 4.74 (1H, dd), 4.70-4.44 (3H, m), 3.20-2.93 (1H, m), 2.05-1.82 (4H, m), 1.82-1.60 (4H, m), 1.47 (6H, d). | 513 | Prepared using analogous methods to example 80 except using General Procedure 3, and deprotection method 12 |
| 145 | 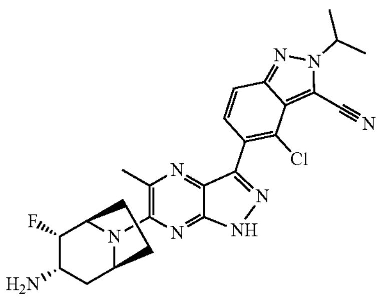 [SMILES: Cc1nc2c(-c3ccc4nn(C(C)C)c(C#N)c4c3Cl)n[nH]c2nc1N1[C@H]2CC[C@@H]1[C@@H](F)[C@@H](N)C2] | 5-{6-[(1R,2S,3S,5S)-3-amino-2-fluoro-8-azabicyclo[3.2.1]octan-8-yl]-5-methyl-1H-pyrazolo[3,4-b]pyrazin-3-yl}-4-chloro-2-(propan-2-yl)-2H-indazole-3-carbonitrile, hydrochloride | $^1$H NMR (400 MHz, DMSO-d$_6$): 8.31 (3H, s), 8.02 (1H, d), 7.86 (1H, d), 5.19 (1H, m), 4.84-4.95 (2H, m), 4.58 (1H, s), 3.68 – 3.84 (1H, m), 2.62 (3H, s), 2.39 (1H, t), 2.20-1.87 (3H, m), 1.87-1.71 (2H, m), 1.67 (6H, d) | 494 | Prepared in a similar fashion to Example 127. Final deprotection using TFA followed by CH$_2$Cl$_2$/aqueous work up and HCl salt formation |
| 146 | 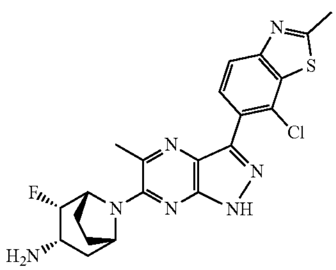 [SMILES: Cc1nc2ccc(-c3n[nH]c4nc(N5[C@H]6CC[C@@H]5[C@@H](F)[C@@H](N)C6)c(C)nc34)c(Cl)c2s1] | (1S,2S,3S,5R)-8-[3-(7-chloro-2-methyl-1,3-benzothiazol-6-yl)-5-methyl-1H-pyrazolo[3,4-b]pyrazin-6-yl]-2-fluoro-8-azabicyclo[3.2.1]octan-3-amine | $^1$H NMR (400 MHz, DMSO-d$_6$): 13.84-13.28 (1H, m), 8.02 (1H, d), 7.97 (1H, d), 4.85 (1H, s), 4.62 (1H, dt), 4.50 (1H, d), 3.23 (1H, d), 2.88 (3H, s), 2.61 (3H, s), 2.27-1.56 (8H, m) | 458 | Prepared using analogous methods to example 80 except using General Procedure 3, and deprotection method 12 |
| 147 | 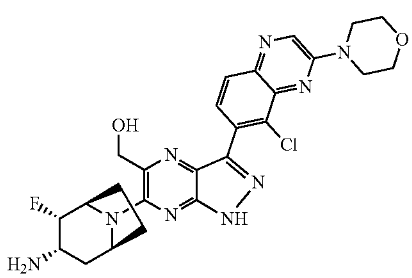 [SMILES: N[C@H]1C[C@@H]2CC[C@H]([C@H]1F)N2c1nc2[nH]nc(-c3ccc4ncc(N5CCOCC5)nc4c3Cl)c2nc1CO] | {6-[(1R,2S,3S,5S)-3-amino-2-fluoro-8-azabicyclo[3.2.1]octan-8-yl]-3-[5-chloro-3-(morpholin-4-yl)quinoxalin-6-yl]1H-pyrazolo[3,4-b]pyrazin-5-yl}methanol | $^1$H NMR (500 MHz, DMSO-d$_6$) δ 14.0 – 13.0 (br s, 1H), 8.92 (s, 1H), 7.90 (d, J = 8.4 Hz, 1H), 7.73 (d, J = 8.5 Hz, 1H), 5.39 – 5.32 (m, 1H), 5.29 (t, J = 5.7 Hz, 1H), 5.01 – 4.95 (m, 1H), 4.73 (dd, J = 12.9, 5.9 Hz, 1H), 4.68-4.64 (m, 1H), 4.63 (d, J = 4.6 Hz, 0.5H), 4.60 – 4.55 (m, 1H), 4.48 (t, J = 3.6 Hz, 0.5H), 3.90-3.82 (m, 4H), 3.81 – 3.76 (m, 4H), 3.14 – 2.98 (m, 1H), 2.03 – 1.82 (m, 4H), 1.79 – 1.67 (m, 3H). | 540 | Prepared using analogous methods to example 80 |
| 148 | 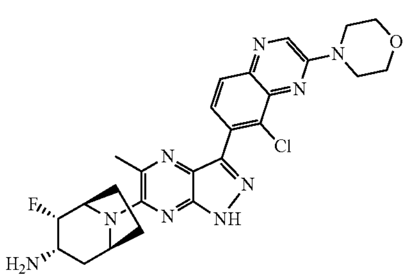 [SMILES: Cc1nc2c(-c3ccc4ncc(N5CCOCC5)nc4c3Cl)n[nH]c2nc1N1[C@H]2CC[C@@H]1[C@@H](F)[C@@H](N)C2] | (1R,2S,3S,5S)-8-{3-[5-chloro-3-(morpholin-4-yl)quinoxalin-6-yl]5-methyl-1H-pyrazolo[3,4-b]pyrazin-6-yl}-2-fluoro-8-azabicyclo[3.2.1]octan-3-amine | $^1$H NMR (400 MHz, DMSO-d$_6$): 13.55 (1H, br. s), 8.92 (1H, s), 7.91 (1H, d), 7.72 (1H, d), 4.85-4.78 (1H, m), 4.61-4.42 (2H, m), 3.90-3.83 (4H, m), 3.83-3.74 (4H, m), 3.13-2.97 (1H, m), 2.59 (3H, s), 2.10-1.87 (3H, m), 1.79-1.66 (3H, m). | 524 | Prepared using analogous methods to example 96 except using an analogous deprotection to method 1 without using ethylene diamine. |

TABLE 17-continued

Table 17: Examples 124-150

| Example | Structure | Name | NMR Data | MS Data | Method |
|---|---|---|---|---|---|
| 149 | 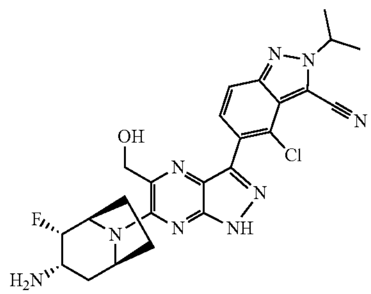 [SMILES: CC(C)n1nc2ccc(-c3n[nH]c4nc(N5[C@H]6CC[C@@H]5[C@@H](F)[C@@H](N)C6)c(CO)nc34)c(Cl)c2c1C#N] | 5-{6-[(1R,2S,3S,5S)-3-amino-2-fluoro-8-azabicyclo[3.2.1]octan-8-yl]-5-(hydroxymethyl)-1H-pyrazolo[3,4-b]pyrazin-3-yl}-4-chloro-2-(propan-2-yl)-2H-indazole-3-carbonitrile | $^1$H NMR (400 MHz, DMSO-$d_6$): 8.01 (1H, d), 7.92 (1H, d), 5.30 (1H, t), 5.23-5.14 (1H, m), 5.03-4.96 (1H, m), 4.74 (1H, dd), 4.71-4.42 (3H, m), 3.14-2.99 (1H, m), 1.99-1.86 (3H, m), 1.86-1.69 (4H, m), 1.67 (6H, d). | 510 | Prepared using analogous methods to example 80 |
| 150 | 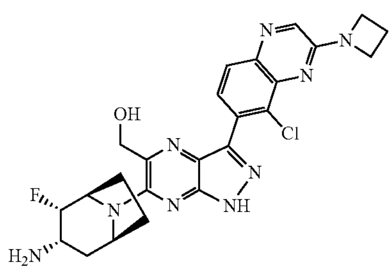 [SMILES: N[C@H]1C[C@@H]2CC[C@H]([C@H]1F)N2c1nc2[nH]nc(-c3ccc4ncc(N5CCC5)nc4c3Cl)c2nc1CO] | {6-[(1R,2S,3S,5S)-3-amino-2-fluoro-8-azabicyclo[3.2.1]octan-8-yl]-3-(azetidin-1-yl)-5-chloroquinoxalin-6-yl]-1H-pyrazolo[3,4-b]pyrazin-5-yl}methanol | $^1$H NMR (400 MHz, DMSO-$d_6$): 13.55 (1H, s), 8.40 (1H, s), 7.88 (1H, d), 7.68 (1H, d), 5.28 (1H, t), 5.01-4.94 (1H, m), 4.76-4.45 (4H, m), 4.30 (4H, t), 3.15-2.97 (1H, m), 2.49-2.43 (4H, m, overlapped), 2.05-1.84 (3H, m), 1.81-1.69 (3H, m). | 510 | Prepared using analogous methods to example 80 except using an analogous deprotection to method 10 |

By following methods similar and/or analogous to those described for general procedures for preparations of compounds of Formula (I) (e.g. methods 1-12), the compounds set out in Table 17 were prepared, with any significant variations indicated. The title compounds were either isolated directly as the free base or as the appropriate salt without further purification, or purified for example using mass-directed preparative HPLC, chromatography, crystallization or trituration and converted to the appropriate salt.

Biological Assays

SHP2 Biochemical Assay

SHP2 activity was monitored by measuring the conversion of the surrogate substrate 6,8-difluoromethylumbelliferyl phosphate (DiFMUP) to the fluorescent product, 6,8-difluoromethylumbelliferone (DiFMU).

SHP2 was pre-incubated with test compounds and the activating peptide pIRS1 (H$_2$N-LN(pY)IDLDLV-(PEG)$_8$-LST(pY)ASINFQK-amide) for 30 min, prior to addition of the 6,8-difluoromethylumbelliferyl phosphate (DiFMUP), (Thermo Fisher D6567). Final assay concentrations were 10 µM SHP2, 0.25 µM pIRS1 peptide, 50 µM DiFMUP, 25 mM Bis-Tris propane, pH 7.0, 150 mM NaCl, 0.05% (v/v) Tween-20, 0.5 mM TCEP and 5% (v/v) DMSO. Rates of reaction were then measured over 30 min by monitoring fluorescence on a BMG Pherastar reader at excitation 360 nm/emission 450 nm. IC$_{50}$ values were calculated from the normalized dose-response plots using four parameter logistic curve fit.

Cellular pERK Inhibition Assay

HCC827 cells (ATCC, Manassas, USA) were seeded into 96-well plates at a density of 1×10$^5$ cells/well in RPMI medium supplemented with 10% FBS and incubated 24 h. Compounds were diluted first in DMSO and then into serum-free medium, before being added to cells in triplicate to give a final concentration of 0.1% DMSO. Plates were incubated at 37° C. for 0.5 hours in a humidified atmosphere of 5% CO2 in air.

Following compound treatment, medium was removed and cells were lysed by adding 50 µL of lysis buffer (Cell Signalling Technology, Beverly, USA) to each well. Plates were then incubated at room temperature for 25 minutes with shaking. pERK levels were measured in lysates using the PathScan® phospho-p44/42 MAPK (Thr202/Tyr204) sandwich ELISA (Cell Signalling Technology, Beverly, USA) as per kit instructions. Briefly, 50 µL of cell lysate was added to 50 µL of ELISA sample diluent in a 96-well ELISA plate and incubated overnight at 4° C. Following washing, 100 µL of detection antibody was added per well and the plates incubated for 1 hour at 37° C. Plates were washed again and incubated at 37° C. for 30 minutes with 100 µl of HRP-linked secondary antibody per well. After final washing, 100 µL per well of TMB substrate was added and plates incubated at 37° C. to develop colour. Colour development was stopped by the addition of 100 µL per well of stop solution. Plates were read at 450 nm on a SpectraMax Gemini reader (Molecular Devices, Uckfield, UK).

The average signal from blank wells (no cells added) was subtracted from the signals from each sample well. Levels of pERK were then expressed as "percent of control", using DMSO treated samples as control. Dose response curves were generated using GraphPad Prism Version 6 (GraphPad Software, La Jolla, USA) and fitted using the four parameter logistic curve fit.

Results

TABLE 18 biological data obtained from assays as described herein

| Example | SHP2 (IC50) | Cellular pERK assay (% of control) |
|---|---|---|
| 1 | 0.013 | |
| 2 | 0.0081 | 0.025 |
| 3 | 0.01 | 0.11 |

TABLE 18-continued biological data obtained from assays as described herein

| Example | SHP2 (IC50) | Cellular pERK assay (% of control) |
|---|---|---|
| 4 | 0.016 | 0.13 |
| 5 | 0.018 | 0.08 |
| 6 | 0.009 | 0.22 |
| 7 | 0.023 | 0.29 |
| 8 | 0.017 | 0.1 |
| 9 | 0.026 | 0.23 |
| 10 | 0.014 | 0.15 |
| 11 | 0.043 | |
| 12 | 0.015 | 0.12 |
| 13 | 0.0062 | 1.6 |
| 14 | 0.089 | |
| 15 | 0.0059 | 0.89 |
| 16 | 0.024 | 0.17 |
| 17 | 0.02 | 0.48 |
| 18 | 0.013 | 2.2 |
| 19 | 0.047 | |
| 20 | 0.01 | 0.024 |
| 21 | 0.011 | 0.26 |
| 22 | 0.026 | 0.3 |
| 23 | 0.0052 | 0.16 |
| 24 | 0.0043 | 0.24 |
| 25 | 0.052 | 1.4 |
| 26 | 0.014 | 0.67 |
| 27 | 0.017 | 53% at 10 uM |
| 28 | 0.0096 | 0.066 |
| 29 | 0.041 | 0.53 |
| 30 | 0.15 | |
| 31 | 0.022 | 2.3 |
| 32 | 0.056 | |
| 33 | 0.033 | 0.53 |
| 34 | 0.013 | 0.25 |
| 35 | 0.19 | |
| 36 | 0.006 | 0.11 |
| 37 | 0.051 | 1.2 |
| 38 | 0.053 | 0.76 |
| 39 | 0.0069 | 1.2 |
| 40 | 0.01 | 0.1 |
| 41 | 0.0036 | 0.091 |
| 42 | 0.017 | 24% at 1 μM |
| 43 | 0.0058 | 1.2 |
| 44 | 0.0068 | 0.19 |
| 45 | 0.017 | 0.27 |
| 46 | 0.020 | 0.26 |
| 47 | 0.015 | 0.21 |
| 48 | 0.017 | 0.14 |
| 49 | 0.015 | 0.26 |
| 50 | 0.031 | |
| 51 | 0.029 | |
| 52 | 0.013 | 0.19 |
| 53 | 0.029 | 0.25 |
| 54 | 0.010 | 0.17 |
| 55 | 0.022 | |
| 56 | 0.021 | 0.17 |
| 57 | 0.023 | |
| 58 | 0.17 | |
| 59 | 0.018 | 0.81 |
| 60 | 0.012 | 0.16 |
| 61 | 0.13 | |
| 62 | 0.0071 | 0.28 |
| 63 | | 1.0 |
| 64 | 0.0077 | 0.040 |
| 65 | 0.037 | 0.53 |
| 66 | 0.0044 | 0.20 |
| 67 | 0.057 | 1.1 |
| 68 | 0.021 | 1.1 |
| 69 | 0.0068 | 0.076 |
| 70 | 0.0088 | 0.14 |
| 71 | 0.055 | 1.2 |
| 72 | 50%@0.30 uM | |
| 73 | 0.0098 | 0.025 |
| 74 | 0.089 | 1.4 |
| 75 | 0.13 | |
| 76 | 0.44 | |
| 77 | 0.018 | 0.12 |
| 78 | 0.015 | 0.045 |
| 79 | 0.0091 | 0.018 |
| 80 | 0.0052 | 0.0048 |
| 81 | 0.015 | 0.043 |
| 82 | 0.012 | 0.014 |
| 83 | 0.0086 | 0.013 |
| 84 | 0.0074 | 0.0090 |
| 85 | 0.0075 | 0.032 |
| 86 | 0.0072 | 0.025 |
| 87 | 0.0080 | 0.057 |
| 88 | 0.0071 | 0.019 |
| 90 | | 0.56 |
| 91 | 0.022 | |
| 92 | 0.0083 | |
| 93 | 0.0036 | |
| 94 | 0.070 | |
| 95 | 0.0030 | |
| 96 | 0.0047 | |
| 97 | | 0.012 |
| 98 | 0.0040 | 0.0052 |
| 99 | 45%@0.010 uM | 0.026 |
| 100 | 0.012 | 0.017 |
| 101 | 0.021 | 0.014 |
| 102 | 0.015 | 0.16 |
| 103 | 0.0089 | 0.0087 |
| 104 | 0.0095 | 0.078 |
| 105 | 0.0089 | 0.019 |
| 106 | 0.022 | 0.27 |
| 107 | 0.022 | 1.0 |
| 108 | 0.0066 | 0.0099 |
| 109 | 0.011 | 0.12 |
| 110 | 0.0070 | 0.026 |
| 112 | 0.012 | 0.11 |
| 113 | 0.0074 | 0.042 |
| 114 | 0.0030 | 0.017 |
| 115 | 50%@0.30 uM | 2.7 |
| 116 | 0.0075 | |
| 117 | 0.0088 | |
| 118 | 0.0053 | 0.010 |
| 119 | 0.014 | |
| 120 | 0.025 | |
| 121 | 0.014 | 0.65 |
| 122 | 0.0052 | 0.031 |
| 123 | 0.0097 | 0.013 |
| 124 | 0.0081 | |
| 125 | 0.0071 | 0.12 |
| 126 | 0.0097 | 0.011 |
| 127 | 0.014 | 0.058 |
| 128 | 0.0073 | 0.037 |
| 129 | 0.0050 | |
| 130 | 0.0095 | |
| 131 | 0.0088 | |
| 132 | 0.011 | 0.021 |
| 133 | 0.0060 | |
| 134 | 0.010 | |
| 135 | 0.016 | |
| 136 | 0.0090 | |
| 137 | 0.021 | |
| 138 | 0.013 | 0.015 |
| 139 | 0.022 | 0.17 |
| 150 | 0.015 | 0.014 |
| 142 | 0.013 | 0.080 |
| 141 | 0.013 | 0.081 |
| 140 | 0.0077 | 0.055 |
| 143 | 0.0061 | |
| 144 | 0.028 | |
| 147 | 0.014 | |
| 145 | 0.036 | |
| 148 | 0.025 | |
| 146 | 0.0074 | |
| 149 | 0.014 | |

Where more than one data point has been obtained, the table above shows an average (e.g. geometric or arithmetic mean) of these data points.

It is of course to be understood that the invention is not intended to be restricted to the details of the above embodiments which are described by way of example only.

Pharmaceutical Formulations Examples (i) Tablet Formulation

A tablet composition containing a compound of the formula (I) is prepared by mixing an appropriate amount of the compound (for example 50-250 mg) with an appropriate diluent, disintegrant, compression agent and/or glidant. One possible tablet comprises 50 mg of the compound with 197 mg of lactose (BP) as diluent, and 3 mg magnesium stearate as a lubricant and compressing to form a tablet in known manner. The compressed tablet may be optionally film coated.

(ii) Capsule Formulation

A capsule formulation is prepared by mixing 100-250 mg of a compound of the formula (I) with an equivalent amount of lactose and filling the resulting mixture into standard hard gelatin capsules. An appropriate disintegrant and/or glidant can be included in appropriate amounts as required.

(iii) Injectable Formulation I

A parenteral composition for administration by injection can be prepared by dissolving a compound of the formula (I) (e.g. in a salt form) in water containing 10% propylene glycol to give a concentration of active compound of 1.5% by weight. The solution is then made isotonic, sterilised by filtration or by terminal sterilisation, filled into an ampoule or vial or pre-filled syringe, and sealed.

(iv) Injectable Formulation II

A parenteral composition for injection is prepared by dissolving in water a compound of the formula (I) (e.g. in salt form) (2 mg/ml) and mannitol (50 mg/ml), sterile filtering the solution or by terminal sterilisation, and filling into sealable 1 ml vials or ampoules or pre-filled syringe.

(v) Injectable formulation III

A formulation for i.v. delivery by injection or infusion can be prepared by dissolving the compound of formula (I) (e.g. in a salt form) in water at 20 mg/ml and then adjusted for isotonicity. The vial is then sealed and sterilised by autoclaving or filled into an ampoule or vial or pre-filled syringe, sterilised by filtration and sealed.

(vi) Injectable formulation IV

A formulation for i.v. delivery by injection or infusion can be prepared by dissolving the compound of formula (I) (e.g. in a salt form) in water containing a buffer (e.g. 0.2 M acetate pH 4.6) at 20 mg/ml. The vial, ampoule or pre-filled syringe is then sealed and sterilised by autoclaving or sterilized by filtration and sealed.

(vii) Subcutaneous or Intramuscular Injection Formulation

A composition for sub-cutaneous or intramuscular administration is prepared by mixing a compound of the formula (I) with pharmaceutical grade corn oil to give a concentration of 5-50 mg/ml. The composition is sterilised and filled into a suitable container.

(viii) Lyophilised formulation I

Aliquots of formulated compound of formula (I) are put into 50 ml vials and lyophilized. During lyophilisation, the compositions are frozen using a one-step freezing protocol at (−45° C.). The temperature is raised to −10° C. for annealing, then lowered to freezing at −45° C., followed by primary drying at +25° C. for approximately 3400 minutes, followed by a secondary drying with increased steps if temperature to 50° C. The pressure during primary and secondary drying is set at 80 millitor.

(ix) Lyophilised Formulation II

Aliquots of formulated compound of formula (I) or a salt thereof as defined herein are put into 50 mL vials and lyophilized. During lyophilisation, the compositions are frozen using a one-step freezing protocol at (−45° C.). The temperature is raised to −10° C. for annealing, then lowered to freezing at −45° C., followed by primary drying at +25° C. for approximately 3400 minutes, followed by a secondary drying with increased steps if temperature to 50° C. The pressure during primary and secondary drying is set at 80 millitor.

(x) Lyophilised Formulation for Use in i.v. Administration III

An aqueous buffered solution is prepared by dissolving a compound of formula I in a buffer. The buffered solution is filled, with filtration to remove particulate matter, into a container (such as a Type 1 glass vial) which is then partially sealed (e.g. by means of a Fluorotec stopper). If the compound and formulation are sufficiently stable, the formulation is sterilised by autoclaving at 121° C. for a suitable period of time. If the formulation is not stable to autoclaving, it can be sterilised using a suitable filter and filled under sterile conditions into sterile vials. The solution is freeze dried using a suitable cycle. On completion of the freeze drying cycle the vials are back filled with nitrogen to atmospheric pressure, stoppered and secured (e.g. with an aluminium crimp). For intravenous administration, the freeze dried solid can be reconstituted with a pharmaceutically acceptable diluent, such as 0.9% saline or 5% dextrose. The solution can be dosed as is, or can be diluted further into an infusion bag (containing a pharmaceutically acceptable diluent, such as 0.9% saline or 5% dextrose), before administration.

(xii) Powder in a Bottle

A composition for oral administration is prepared by filling a bottle or vial with a compound of the formula (I). The composition is then reconstituted with a suitable diluent for example water, fruit juice, or commercially available vehicle such as OraSweet or Syrspend. The reconstituted solution may be dispensed into dosing cups or oral syringes for administration.

The invention claimed is:

1. A compound of formula (I):

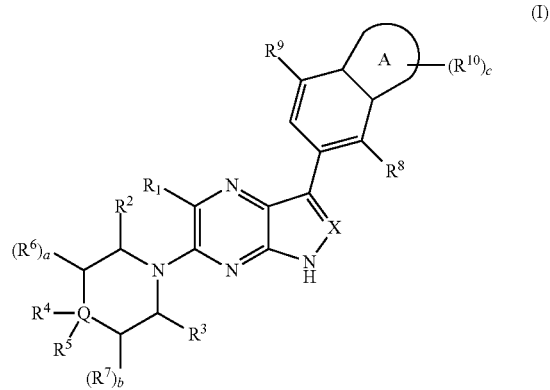

or a tautomer or a solvate or a pharmaceutically acceptable salt thereof, wherein:

X is CH or N;

$R^1$ is hydrogen, —$CH_3$ or —$CH_2OH$ but when X is N then $R^1$ is selected from —$CH_3$ and —$CH_2OH$;

$R^2$ and $R^3$ are either:

(i) independently selected from hydrogen and $C_{1-4}$alkyl; or (ii) together form a one- to three-membered bridge group selected from $C_{1-3}$alkylene, $C_{2-3}$alkenylene, methylene-NR$^q$-methylene and methylene-O-methylene, wherein the bridge group is optionally substituted by a group selected from $C_{1-4}$alkyl, hydroxyl and halogen and R$^q$ is selected from hydrogen, $C_{1-4}$alkyl, hydroxyl and halogen;

Q is C or N;

wherein when Q is C then either:

(i) R$^4$ is hydrogen or $C_{1-4}$alkyl optionally substituted by amino;

R$^5$ is hydrogen, amino, hydroxyl or $C_{1-4}$alkyl optionally substituted by 1 or 2 groups selected from halogen, hydroxyl and amino;

provided that R$^4$ and R$^5$ must not both be selected from amino and $C_{1-4}$alkyl substituted by amino; or (ii) R$^4$ and R$^5$ together with Q form a four- to six-membered nitrogen-containing heterocyclic ring; and wherein when Q is N then:

R$^4$ is absent;

R$^5$ is hydrogen; and

R$^2$ and R$^3$ together form the one- to three-membered bridge group;

R$^6$ and R$^7$ are independently selected from halogen, $C_{1-4}$alkyl and hydroxyl provided that when Q is N then R$^6$ or R$^7$ are not halogen or hydroxyl;

a is selected from 0, 1 and 2;

b is selected from 0, 1 and 2;

Ring A is either:

(i) a five-membered nitrogen-containing heterocyclic ring wherein the heterocyclic ring optionally contains one or two additional heteroatoms selected from N, O and S, or (ii) a six-membered aromatic nitrogen-containing heterocyclic ring, wherein the heterocyclic ring optionally contains one or two additional heteroatoms selected from N, O and S; or (iii) a six-membered non-aromatic nitrogen-containing heterocyclic ring, wherein the heterocyclic ring optionally contains one or two additional heteroatoms selected from N and S;

R$^8$ is selected from halo$C_{1-4}$alkyl, —CH$_3$ and halogen;

R$^9$ is selected from hydrogen, $C_{1-4}$alkyl, halo$C_{1-4}$alkyl and halogen;

R$^{10}$ is independently selected from halogen, cyano, cyano$C_{1-4}$alkyl, hydroxyl, =O (oxo), $C_{1-4}$alkyl, halo$C_{1-4}$alkyl, $C_{1-4}$alkoxy, hydroxyl$C_{1-4}$alkyl, $C_{1-4}$alkoxy$C_{1-4}$alkylene, amino, mono$C_{1-4}$alkylamino, di$C_{1-4}$alkylamino, amino$C_{1-4}$alkylene, —$C_{1-4}$alkylene-C(=O)NH$_{(2-q)}$($C_{1-6}$ alkyl)$_q$), —$C_{0-4}$alkylene-NHC(=O)$C_{1-6}$ alkyl, sulfonamide$C_{0-4}$alkylene, 3 to 6 membered cycloalkyl, optionally substituted five- or six-membered unsaturated heterocyclic group containing 1, 2, 3 or 4 heteroatoms selected from O, N, and S where the optional substituent is selected from $C_{1-4}$alkyl, $C_{1-4}$alkyl substituted with 3 to 6 membered cycloalkyl, $C_{1-4}$alkyl substituted with optionally substituted five- or six-membered unsaturated heterocyclic group containing 1, 2, 3 or 4 heteroatoms selected from O, N, and S where the optional substituent is selected from $C_{1-4}$alkyl, $C_{1-4}$alkyl substituted with optionally substituted four- to six-membered saturated heterocyclic group containing 1 or 2 heteroatoms selected from O, N, and S where the optional substituent is selected from $C_{1-4}$alkyl and optionally substituted four- to six-membered saturated heterocyclic group containing 1 or 2 heteroatoms selected from O, N, and S where the optional substituent is selected from $C_{1-4}$alkyl;

q is selected from 0, 1 and 2; and c is selected from 0, 1, 2 and 3.

2. A compound according to claim 1, or a tautomer, pharmaceutically acceptable salt or solvate thereof, wherein:

X is CH or N;

R$^1$ is hydrogen, —CH$_3$ or —CH$_2$OH but when X is N then R$^1$ is selected from —CH$_3$ and —CH$_2$OH;

R$^2$ and R$^3$ are either:

(i) independently selected from hydrogen and $C_{1-4}$alkyl; or (ii) together form a one- to three-membered bridge group selected from $C_{1-3}$ alkylene, $C_{2-3}$ alkenylene, methylene-NR$^q$-methylene and methylene-O-methylene, wherein the bridge group is optionally substituted by a group selected from $C_{1-4}$alkyl, hydroxyl and halogen and R$^q$ is selected from hydrogen, $C_{1-4}$alkyl, hydroxyl and halogen;

Q is C or N;

wherein when Q is C then either:

(i) R$^4$ is hydrogen or $C_{1-4}$alkyl optionally substituted by amino;

R$^5$ is hydrogen, amino, or $C_{1-4}$alkyl optionally substituted by 1 or 2 groups selected from halogen, hydroxyl and amino;

provided that R$^4$ and R$^5$ must not both be selected from amino and $C_{1-4}$alkyl substituted by amino; or (ii) R$^4$ and R$^5$ together with Q form a four- to six-membered nitrogen-containing heterocyclic ring; and wherein when Q is N then:

R$^4$ is absent;

R$^5$ is hydrogen; and

R$^2$ and R$^3$ together form the one- to three-membered bridge group;

R$^6$ and R$^7$ are independently selected from halogen, $C_{1-4}$alkyl and hydroxyl provided that when Q is N then R$^6$ or R$^7$ are not halogen or hydroxyl;

a is selected from 0, 1 and 2;

b is selected from 0, 1 and 2;

Ring A is either:

(i) a five-membered nitrogen-containing heterocyclic ring wherein the heterocyclic ring optionally contains one or two additional heteroatoms selected from N, O and S, or (ii) a six-membered aromatic nitrogen-containing heterocyclic ring, wherein the heterocyclic ring optionally contains one or two additional heteroatoms selected from N, O and S; or (iii) a six-membered non-aromatic nitrogen-containing heterocyclic ring, wherein the heterocyclic ring optionally contains one or two additional heteroatoms selected from N and S;

R$^8$ is selected from halo$C_{1-4}$alkyl, —CH$_3$ and halogen;

R$^9$ is selected from hydrogen, $C_{1-4}$alkyl, halo$C_{1-4}$alkyl and halogen;

R$^{10}$ is independently selected from halogen, cyano, cyano$C_{1-4}$alkyl, hydroxyl, =O (oxo), $C_{1-4}$alkyl, halo$C_{1-4}$alkyl, $C_{1-4}$alkoxy, hydroxyl$C_{1-4}$alkyl, $C_{1-4}$alkoxy$C_{1-4}$alkylene, $C_{1-4}$alkylsulfone, amino, mono$C_{1-4}$alkylamino, di$C_{1-4}$alkylamino, amino$C_{1-4}$alkylene, —$C_{1-4}$alkylene-C(=O)NH$_{(2-q)}$($C_{1-6}$ alkyl)$_q$), —$C_{1-4}$alkylene-NHC(=O)$C_{1-6}$ alkyl, sulfonamide $C_{0-4}$alkylene, and optionally substituted four- to six-membered saturated heterocyclic group containing 1 or 2 heteroatoms selected from O, N, and S where the optional substituent is selected from $C_{1-4}$alkyl;
q is selected from 0, 1 and 2; and
c is selected from 0, 1 and 2.

3. A compound according to claim 1, or a tautomer, pharmaceutically acceptable salt or solvate thereof, wherein X is CH.

4. A compound according to claim 1, or a tautomer, pharmaceutically acceptable salt or solvate thereof, wherein X is N.

5. A compound according claim 1, or a tautomer, pharmaceutically acceptable salt or solvate thereof, wherein $R^1$ is H.

6. A compound according to claim 1, or a tautomer, N oxide, pharmaceutically acceptable salt or solvate thereof, wherein $R^2$ and $R^3$ together form:
   a one- to three-membered bridge group selected from $C_{1-3}$ alkylene, $C_{2-3}$ alkenylene, methylene-$NR^q$-methylene and methylene-O-methylene, wherein the bridge group is optionally substituted by a group selected from $C_{1-4}$alkyl, hydroxyl and halogen and $R^q$ is selected from hydrogen and $C_{1-4}$alkyl; or
   a one- to three-membered bridge group which is $C_{1-3}$ alkylene.

7. A compound according to claim 1, or a tautomer, pharmaceutically acceptable salt or solvate thereof, wherein Q is C.

8. A compound according to claim 1, or a tautomer, pharmaceutically acceptable salt or solvate thereof, wherein:
   $R^4$ is hydrogen or $C_{1-4}$alkyl; and/or
   $R^5$ is hydrogen, amino, or $C_{1-4}$alkyl optionally substituted by 1 or 2 groups selected from halogen, hydroxyl and amino.

9. A compound according to claim 1, or a tautomer, pharmaceutically acceptable salt or solvate thereof, wherein:
   a is 0 or 1; and/or
   b is 0 or 1.

10. A compound according to claim 1, or a tautomer, pharmaceutically acceptable salt or solvate thereof, wherein a is 1 and $R^6$ is halogen or hydroxyl.

11. A compound according to claim 1, or a tautomer, pharmaceutically acceptable salt or solvate thereof, wherein ring A is a:
   five-membered nitrogen-containing heterocyclic ring, or a six-membered aromatic nitrogen-containing heterocyclic ring, wherein the heterocyclic ring optionally contains one or two additional heteroatoms selected from N, O and S; or
   five-membered nitrogen-containing heterocyclic ring, wherein the heterocyclic ring optionally contains one or two additional heteroatoms selected from N, O and S; or
   five-membered aromatic nitrogen-containing heterocyclic ring, wherein the heterocyclic ring optionally contains one or two additional heteroatoms selected from N and S; or
   a six-membered aromatic nitrogen-containing heterocyclic ring, wherein the heterocyclic ring optionally contains one or two additional heteroatoms selected from N, O and S; or
   a six-membered non-aromatic nitrogen-containing heterocyclic ring, wherein the heterocyclic ring optionally contains one or two additional heteroatoms selected from N and S.

12. A compound according to claim 1, or a tautomer, pharmaceutically acceptable salt or solvate thereof, wherein the moiety

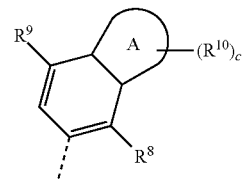

is selected from Table I or Table II below:

TABLE I

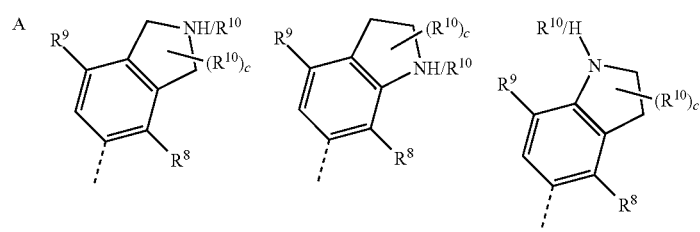

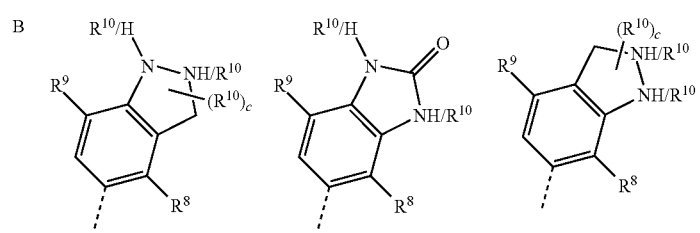

TABLE I-continued
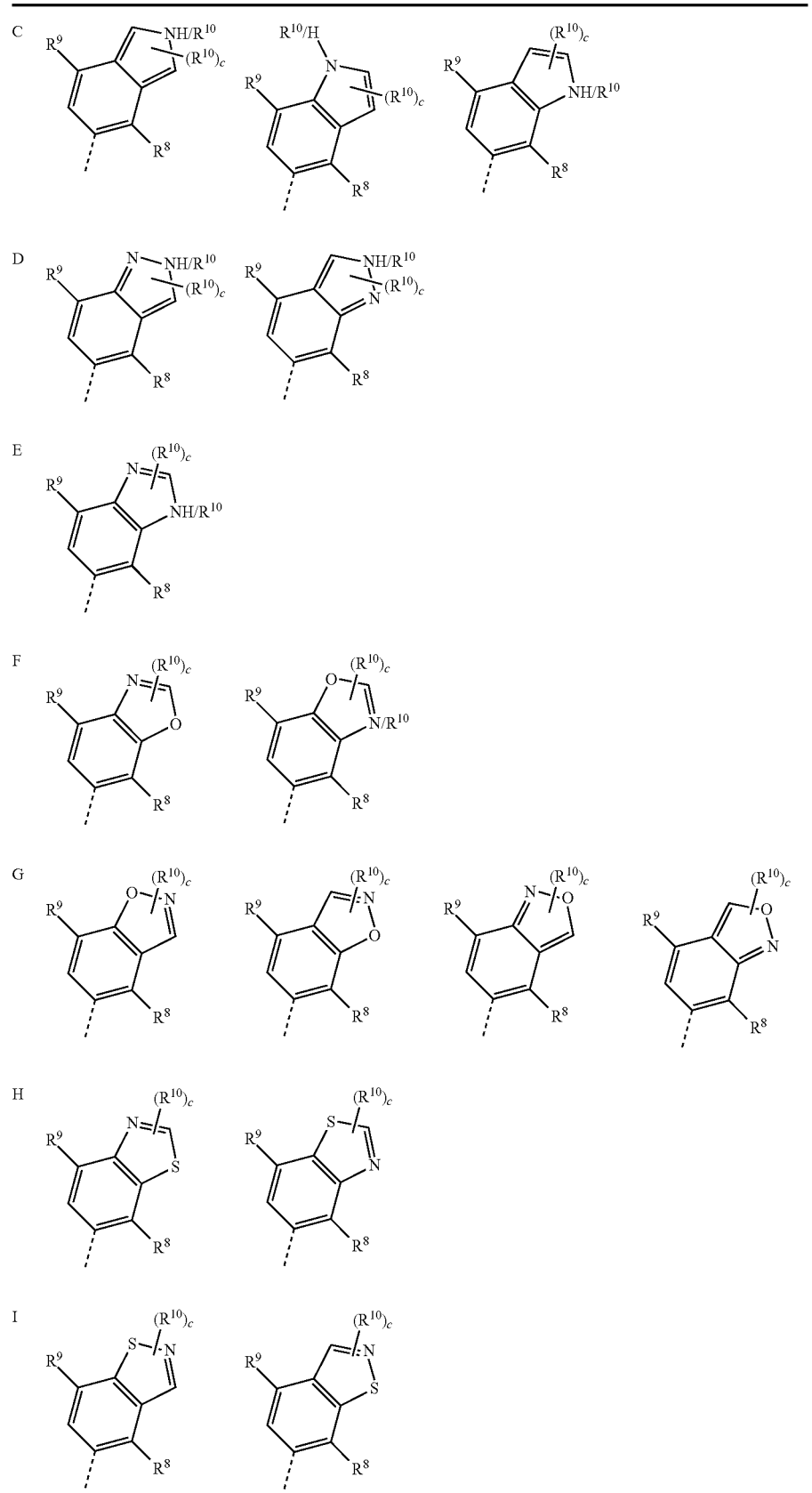

TABLE I-continued
J 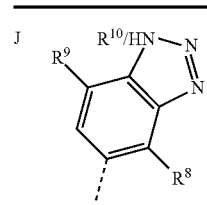 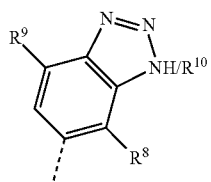
K 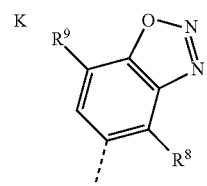 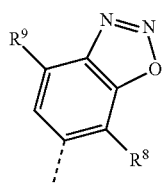
L 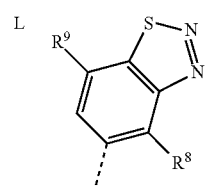 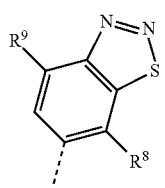
M 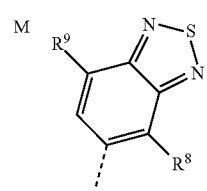
N 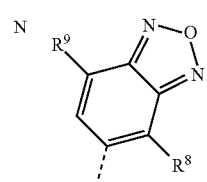
O 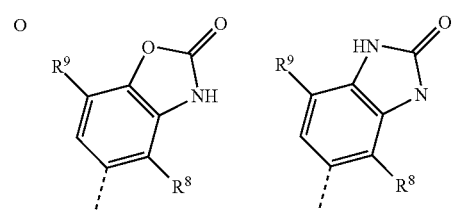
P 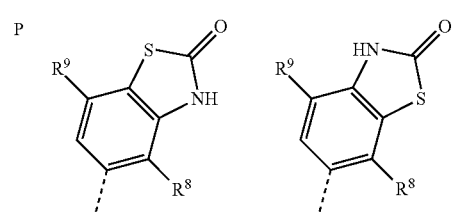

TABLE II
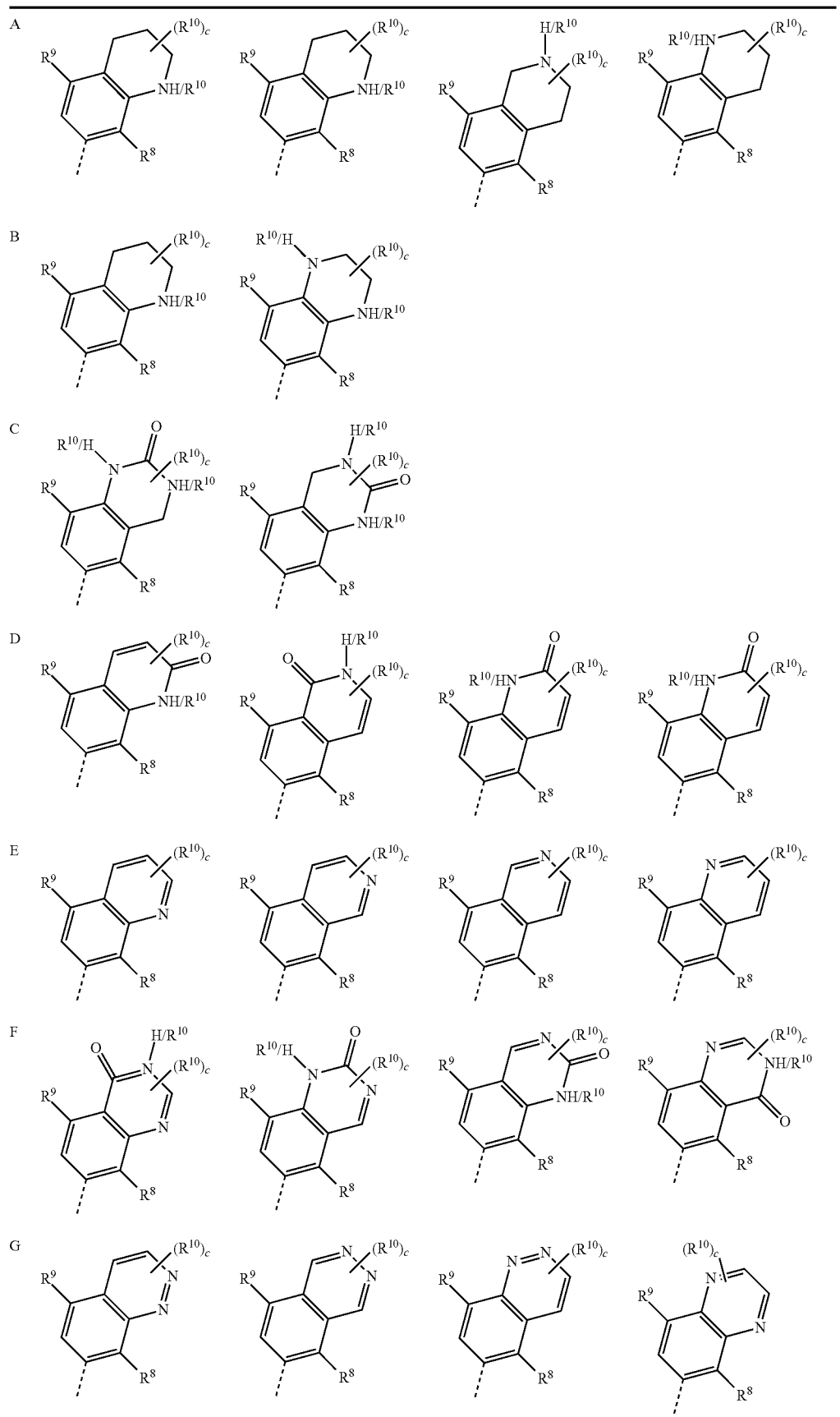

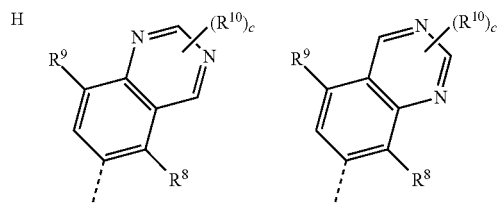

13. A compound according to claim 12, or a tautomer, pharmaceutically acceptable salt or solvate thereof, wherein the moiety

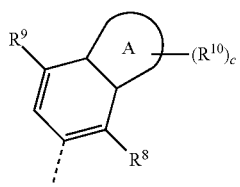

is selected from:

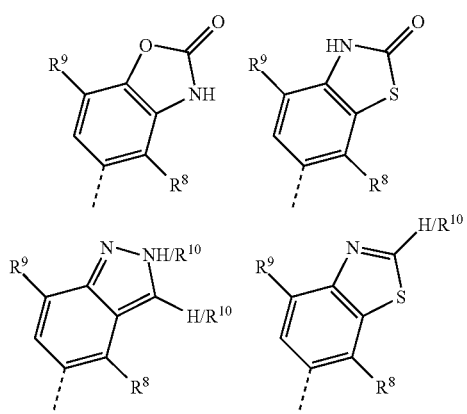

or is selected from:

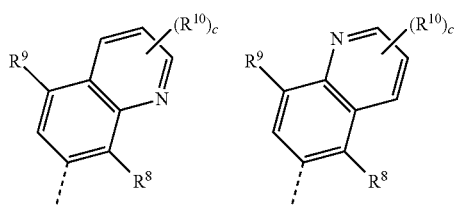

14. A compound according to claim 1, or a tautomer, pharmaceutically acceptable salt or solvate thereof, wherein:
$R^8$ is selected from —$CF_3$, —$CH_3$ and halogen; and/or
$R^9$ is hydrogen; and/or
$R^{10}$ is independently selected from halogen, cyano, cyano$C_{1-4}$alkyl, hydroxyl, =O (oxo), $C_{1-4}$alkyl, halo$C_{1-4}$alkyl, $C_{1-4}$alkoxy, hydroxyl$C_{1-4}$alkyl di$C_{1-4}$alkylamino, and $C_{1-4}$alkoxy$C_{1-4}$alkylene; or $R^{10}$ are independently selected from halogen, cyano, hydroxyl, =O (oxo), $C_{1-4}$alkoxy, di$C_{1-4}$alkylamino, and $C_{1-4}$alkyl.

15. A compound according to claim 1, or a tautomer, pharmaceutically acceptable salt or solvate thereof, wherein the compound is selected from:
1-[exo-8-[7-(4-chloro-2-methyl-2H-indazol-5-yl)-5H-pyrrolo[2,3-b]pyrazin-3-yl]-8-azabicyclo[3.2.1]octan-3-yl]methanamine;
exo-8-[7-(4-chloro-2-methyl-2H-indazol-5-yl)-5H-pyrrolo[2,3-b]pyrazin-3-yl]-8-azabicyclo[3.2.1]octan-3-amine;
endo-8-[7-(4-chloro-2-methyl-2H-indazol-5-yl)-5H-pyrrolo[2,3-b]pyrazin-3-yl]-8-azabicyclo[3.2.1]octan-3-amine;
1-[7-(4-chloro-2-methyl-2H-indazol-5-yl)-5H-pyrrolo[2,3-b]pyrazin-3-yl]piperidin-4-amine;
1-[7-(4-chloro-2-methyl-2H-indazol-5-yl)-5H-pyrrolo[2,3-b]pyrazin-3-yl]-4-methylpiperidin-4-amine;
endo-9-[7-(4-chloro-2-methyl-2H-indazol-5-yl)-5H-pyrrolo[2,3-b]pyrazin-3-yl]-9-azabicyclo[3.3.1]nonan-3-amine;
{4-amino-1-[7-(4-chloro-2-methyl-2H-indazol-5-yl)-5H-pyrrolo[2,3-b]pyrazin-3-yl]piperidin-4-yl}methanol;
endo-8-[7-(4-chloro-2-methyl-2H-indazol-5-yl)-5H-pyrrolo[2,3-b]pyrazin-3-yl]-3-methyl-8-azabicyclo[3.2.1]octan-3-amine;
4-chloro-5-(3-{3,8-diazabicyclo[3.2.1]octan-8-yl}-5H-pyrrolo[2,3-b]pyrazin-7-yl)-2-methyl-2H-indazole;
7-[7-(4-chloro-2-methyl-2H-indazol-5-yl)-5H-pyrrolo[2,3-b]pyrazin-3-yl]-2,7-diazaspiro[3.5]nonane;
1-{1-[7-(4-chloro-2-methyl-2H-indazol-5-yl)-2-methyl-5H-pyrrolo[2,3-b]pyrazin-3-yl]-4-methylpiperidin-4-yl}methanamine;
rac-(1S,2R,3R,5R)-8-[7-(4-chloro-2-methyl-2H-indazol-5-yl)-5H-pyrrolo[2,3-b]pyrazin-3-yl]-2-fluoro-8-azabicyclo[3.2.1]octan-3-amine;
endo-8-[7-(7-chloro-1,3-benzothiazol-6-yl)-5H-pyrrolo[2,3-b]pyrazin-3-yl]-8-azabicyclo[3.2.1]octan-3-amine;
1-[7-(4-chloro-2-methyl-2H-indazol-5-yl)-2-methyl-5H-pyrrolo[2,3-b]pyrazin-3-yl]-4-methylpiperidin-4-amine;
endo-8-[7-(7-chloro-2-methyl-1,3-benzothiazol-6-yl)-5H-pyrrolo[2,3-b]pyrazin-3-yl]-8-azabicyclo[3.2.1]octan-3-amine;
7-[7-(4-chloro-2-methyl-2H-indazol-5-yl)-5H-pyrrolo[2,3-b]pyrazin-3-yl]-1,7-diazaspiro[3.5]nonane;
endo-8-[7-(4-chloro-2-methyl-2H-indazol-5-yl)-2-methyl-5H-pyrrolo[2,3-b]pyrazin-3-yl]-8-azabicyclo[3.2.1]octan-3-amine;
6-{3-[endo-3-amino-8-azabicyclo[3.2.1]octan-8-yl]-5H-pyrrolo[2,3-b]pyrazin-7-yl}-7-chloro-N,N-dimethyl-1,3-benzothiazol-2-amine;

5-{3-[endo-3-amino-8-azabicyclo[3.2.1]octan-8-yl]-5H-pyrrolo[2,3-b]pyrazin-7-yl}-4-chloro-2,3-dihydro-1,3-benzoxazol-2-one;
exo-8-[7-(4-chloro-2-methyl-2H-indazol-5-yl)-2-methyl-5H-pyrrolo[2,3-b]pyrazin-3-yl]-8-azabicyclo[3.2.1]octan-3-amine;
6-{3-[endo-3-amino-8-azabicyclo[3.2.1]octan-8-yl]-5H-pyrrolo[2,3-b]pyrazin-7-yl}-5-chloro-2-methyl-3,4-dihydroquinazolin-4-one;
7-{3-[endo-3-amino-8-azabicyclo[3.2.1]octan-8-yl]-5H-pyrrolo[2,3-b]pyrazin-7-yl}-8-chloro-N,N-dimethylquinolin-2-amine;
6-{3-[endo-3-amino-8-azabicyclo[3.2.1]octan-8-yl]-5H-pyrrolo[2,3-b]pyrazin-7-yl}-7-chloro-2,3-dihydro-1,3-benzothiazol-2-one;
endo-8-[7-(3,4-dichloro-2-methyl-2H-indazol-5-yl)-5H-pyrrolo[2,3-b]pyrazin-3-yl]-8-azabicyclo[3.2.1]octan-3-amine;
7-[7-(4-chloro-2-methyl-2H-indazol-5-yl)-5H-pyrrolo[2,3-b]pyrazin-3-yl]-5,5-difluoro-2,7-diazaspiro[3.5]nonane;
endo-8-[7-(4-chloro-2-ethyl-2H-indazol-5-yl)-5H-pyrrolo[2,3-b]pyrazin-3-yl]-8-azabicyclo[3.2.1]octan-3-amine;
endo-8-[7-(8-chloro-2-methoxyquinolin-7-yl)-5H-pyrrolo[2,3-b]pyrazin-3-yl]-8-azabicyclo[3.2.1]octan-3-amine;
exo-8-[7-(4-chloro-2-ethyl-2H-indazol-5-yl)-5H-pyrrolo[2,3-b]pyrazin-3-yl]-8-azabicyclo[3.2.1]octan-3-amine;
(3R,4R)-1-[7-(4-chloro-2-methyl-2H-indazol-5-yl)-5H-pyrrolo[2,3-b]pyrazin-3-yl]-3-fluoropiperidin-4-amine;
(3S,4S)-1-[7-(4-chloro-2-methyl-2H-indazol-5-yl)-5H-pyrrolo[2,3-b]pyrazin-3-yl]-3-fluoropiperidin-4-amine;
(3S,4S)-4-amino-1-[7-(4-chloro-2-methyl-2H-indazol-5-yl)-5H-pyrrolo[2,3-b]pyrazin-3-yl]piperidin-3-ol;
(3S,4R)-1-[7-(4-chloro-2-methyl-2H-indazol-5-yl)-5H-pyrrolo[2,3-b]pyrazin-3-yl]-3-fluoropiperidin-4-amine;
(3R,4S)-1-[7-(4-chloro-2-methyl-2H-indazol-5-yl)-5H-pyrrolo[2,3-b]pyrazin-3-yl]-3-fluoropiperidin-4-amine;
{3-[endo-3-amino-8-azabicyclo[3.2.1]octan-8-yl]-7-(4-chloro-2-methyl-2H-indazol-5-yl)-5H-pyrrolo[2,3-b]pyrazin-2-yl}methanol;
7-{3-[endo-3-amino-8-azabicyclo[3.2.1]octan-8-yl]-5H-pyrrolo[2,3-b]pyrazin-7-yl}-8-chloro-1,2-dihydroquinolin-2-one;
2-(5-{3-[endo-3-amino-8-azabicyclo[3.2.1]octan-8-yl]-5H-pyrrolo[2,3-b]pyrazin-7-yl}-3,4-dichloro-2H-indazol-2-yl)ethan-1-ol;
(5-{3-[endo-3-amino-8-azabicyclo[3.2.1]octan-8-yl]-5H-pyrrolo[2,3-b]pyrazin-7-yl}-4-chloro-2-methyl-2H-indazol-3-yl)methanol;
endo-8-[7-(4-fluoro-2-methyl-2H-indazol-5-yl)-5H-pyrrolo[2,3-b]pyrazin-3-yl]-8-azabicyclo[3.2.1]octan-3-amine;
endo-8-{7-[7-chloro-2-(oxetan-3-yl)-1,3-benzothiazol-6-yl]-5H-pyrrolo[2,3-b]pyrazin-3-yl}-8-azabicyclo[3.2.1]octan-3-amine;
exo-8-[3-(4-chloro-2-methyl-2H-indazol-5-yl)-5-methyl-1H-pyrazolo[3,4-b]pyrazin-6-yl]-8-azabicyclo[3.2.1]octan-3-amine;
exo-8-[7-(3,4-dichloro-2-methyl-2H-indazol-5-yl)-5H-pyrrolo[2,3-b]pyrazin-3-yl]-8-azabicyclo[3.2.1]octan-3-amine;
endo-8-[7-(5-chloro-3-methoxy-2-methylquinolin-6-yl)-5H-pyrrolo[2,3-b]pyrazin-3-yl]-8-azabicyclo[3.2.1]octan-3-amine;
endo-8-{7-[7-chloro-2-(methoxymethyl)-1,3-benzothiazol-6-yl]-5H-pyrrolo[2,3-b]pyrazin-3-yl}-8-azabicyclo[3.2.1]octan-3-amine;
(6-{3-[endo-3-amino-8-azabicyclo[3.2.1]octan-8-yl]-5H-pyrrolo[2,3-b]pyrazin-7-yl}-7-chloro-1,3-benzothiazol-2-yl)methanol;
endo-8-{7-(4-chloro-2-(2-methoxyethyl)-2H-indazol-5-yl)-5H-pyrrolo[2,3-b]pyrazin-3-yl}-8-azabicyclo[3.2.1]octan-3-amine;
endo-8-{7-(4-chloro-2-(oxetan-3-yl)-2H-indazol-5-yl)-5H-pyrrolo[2,3-b]pyrazin-3-yl}-8-azabicyclo[3.2.1]octan-3-amine;
6-{3-[endo-3-amino-8-azabicyclo[3.2.1]octan-8-yl]-5H-pyrrolo[2,3-b]pyrazin-7-yl}-5-chloro-2-methyl-1,2-dihydroisoquinolin-1-one; and
endo-8-[3-(4-chloro-2-methyl-2H-indazol-5-yl)-5-methyl-1H-pyrazolo[3,4-b]pyrazin-6-yl]-8-azabicyclo[3.2.1]octan-3-amine;
2-(5-{3-[endo-3-amino-8-azabicyclo[3.2.1]octan-8-yl]-5H-pyrrolo[2,3-b]pyrazin-7-yl}-4-chloro-2H-indazol-2-yl)-N,N-dimethylacetamide;
endo-8-[7-(4-chloro-7-fluoro-2-methyl-2H-indazol-5-yl)-5H-pyrrolo[2,3-b]pyrazin-3-yl]-8-azabicyclo[3.2.1]octan-3-amine;
endo-8-[7-(4-chloro-2-methyl-2H-1,2,3-benzotriazol-5-yl)-5H-pyrrolo[2,3-b]pyrazin-3-yl]-8-azabicyclo[3.2.1]octan-3-amine;
6-{3-[endo-3-amino-8-azabicyclo[3.2.1]octan-8-yl]-5H-pyrrolo[2,3-b]pyrazin-7-yl}-5-chloro-2,3-dimethyl-3,4-dihydroquinazolin-4-one;
1-(5-{3-[endo-3-amino-8-azabicyclo[3.2.1]octan-8-yl]-5H-pyrrolo[2,3-b]pyrazin-7-yl}-4-chloro-2H-indazol-2-yl)-2-methylpropan-2-ol;
endo-8-[7-(3,4-dichloro-1H-indazol-5-yl)-5H-pyrrolo[2,3-b]pyrazin-3-yl]-8-azabicyclo[3.2.1]octan-3-amine;
endo-8-[7-(4-chloro-2,7-dimethyl-2H-indazol-5-yl)-5H-pyrrolo[2,3-b]pyrazin-3-yl]-8-azabicyclo[3.2.1]octan-3-amine;
6-{3-[endo-3-amino-8-azabicyclo[3.2.1]octan-8-yl]-5H-pyrrolo[2,3-b]pyrazin-7-yl}-5-chloro-3-methyl-3,4-dihydroquinazolin-4-one;
2-(5-{3-[endo-3-amino-8-azabicyclo[3.2.1]octan-8-yl]-5H-pyrrolo[2,3-b]pyrazin-7-yl}-4-chloro-2H-indazol-2-yl)-N-methylacetamide;
3-(5-{3-[endo-3-amino-8-azabicyclo[3.2.1]octan-8-yl]-5H-pyrrolo[2,3-b]pyrazin-7-yl}-4-chloro-2H-indazol-2-yl)-N,N-dimethylpropanamide;
6-{3-[endo-3-amino-8-azabicyclo[3.2.1]octan-8-yl]-5H-pyrrolo[2,3-b]pyrazin-7-yl}-7-chloro-N,N-dimethyl-1,3-benzothiazole-2-carboxamide;
2-(5-{3-[endo-3-amino-8-azabicyclo[3.2.1]octan-8-yl]-5H-pyrrolo[2,3-b]pyrazin-7-yl}-4-chloro-2H-indazol-2-yl)-N-tert-butylacetamide;
2-(5-{3-[endo-3-amino-8-azabicyclo[3.2.1]octan-8-yl]-5H-pyrrolo[2,3-b]pyrazin-7-yl}-4-chloro-2-methyl-2H-indazol-3-yl)acetonitrile;
5-{3-[endo-3-amino-8-azabicyclo[3.2.1]octan-8-yl]-5H-pyrrolo[2,3-b]pyrazin-7-yl}-4-chloro-2-methyl-2H-indazole-3-carbonitrile;

(1S,2R,3R,5R)-8-[7-(4-chloro-2-methyl-2H-indazol-5-yl)-5H-pyrrolo[2,3-b]pyrazin-3-yl]-2-fluoro-8-azabicyclo[3.2.1]octan-3-amine;

(1R,2S,3S,5S)-8-[7-(4-chloro-2-methyl-2H-indazol-5-yl)-5H-pyrrolo[2,3-b]pyrazin-3-yl]-2-fluoro-8-azabicyclo[3.2.1]octan-3-amine;

(1S,2R,3S,5R)-8-[7-(4-chloro-2-methyl-2H-indazol-5-yl)-5H-pyrrolo[2,3-b]pyrazin-3-yl]-2-fluoro-8-azabicyclo[3.2.1]octan-3-amine;

5-{3-[endo-3-amino-8-azabicyclo[3.2.1]octan-8-yl]-5H-pyrrolo[2,3-b]pyrazin-7-yl}-4-chloro-3,3-difluoro-2,3-dihydro-1H-indol-2-one;

(1R,2S,3R,5S)-8-[7-(4-chloro-2-methyl-2H-indazol-5-yl)-5H-pyrrolo[2,3-b]pyrazin-3-yl]-2-fluoro-8-azabicyclo[3.2.1]octan-3-amine;

endo-8-(7-{4-chloro-2-[(1-methyl-1H-imidazol-2-yl)methyl]-2H-indazol-5-yl}-5H-pyrrolo[2,3-b]pyrazin-3-yl)-8-azabicyclo[3.2.1]octan-3-amine;

endo-8-(7-{4-chloro-2-[(3-methyl-1,2,4-oxadiazol-5-yl)methyl]-2H-indazol-5-yl}-5H-pyrrolo[2,3-b]pyrazin-3-yl)-8-azabicyclo[3.2.1]octan-3-amine;

endo-8-(7-{4-chloro-2-[(1-methyl-1H-pyrazol-3-yl)methyl]-2H-indazol-5-yl}-5H-pyrrolo[2,3-b]pyrazin-3-yl)-8-azabicyclo[3.2.1]octan-3-amine;

6-{3-[(3R,4S)-4-amino-3-fluoropiperidin-1-yl]-5H-pyrrolo[2,3-b]pyrazin-7-yl}-5-chloro-2-methyl-1,2-dihydroisoquinolin-1-one;

5-{3-[(3R,4S)-4-amino-3-fluoropiperidin-1-yl]-5H-pyrrolo[2,3-b]pyrazin-7-yl}-4-chloro-2-methyl-2,3-dihydro-1H-isoindol-1-one;

(1R,2S,3S,5S)-8-[3-(4-chloro-2-methyl-2H-indazol-5-yl)-5-methyl-1H-pyrazolo[3,4-b]pyrazin-6-yl]-2-fluoro-8-azabicyclo[3.2.1]octan-3-amine;

(3R,4S)-1-[7-(7-chloro-1-methyl-1H-1,3-benzodiazol-6-yl)-5H-pyrrolo[2,3-b]pyrazin-3-yl]-3-fluoropiperidin-4-amine;

(3R,4S)-1-[3-(4-chloro-2-methyl-2H-indazol-5-yl)-5-methyl-1H-pyrazolo[3,4-b]pyrazin-6-yl]-3-fluoropiperidin-4-amine;

5-{3-[(3R,4S)-4-amino-3-fluoropiperidin-1-yl]-5H-pyrrolo[2,3-b]pyrazin-7-yl}-4-chloro-3-methyl-2,3-dihydro-1,3-benzothiazol-2-one;

6-{3-[(1S,2S,3S,5R)-3-amino-2-fluoro-8-azabicyclo[3.2.1]octan-8-yl]-5H-pyrrolo[2,3-b]pyrazin-7-yl}-5-chloro-3-methyl-3,4-dihydroquinazolin-4-one;

rac-{6-[(1R,2S,3S,5S)-3-amino-2-fluoro-8-azabicyclo[3.2.1]octan-8-yl]-3-(4-chloro-2-methyl-2H-indazol-5-yl)-1H-pyrazolo[3,4-b]pyrazin-5-yl}methanol;

{6-[(1R,2S,3S,5S)-3-amino-2-fluoro-8-azabicyclo[3.2.1]octan-8-yl]-3-(4-chloro-2-methyl-2H-indazol-5-yl)-1H-pyrazolo[3,4-b]pyrazin-5-yl}methanol;

{6-[(1R,2S,3S,5S)-3-amino-2-fluoro-8-azabicyclo[3.2.1]octan-8-yl]-3-(3,4-dichloro-2-methyl-2H-indazol-5-yl)-1H-pyrazolo[3,4-b]pyrazin-5-yl}methanol;

{6-[(1S,2S,3S,5R)-3-amino-2-fluoro-8-azabicyclo[3.2.1]octan-8-yl]-3-(4-chloro-2-methyl-2H-indazol-5-yl)-1H-pyrazolo[3,4-b]pyrazin-5-yl}methanol;

{6-[(1R,2S,3S,5S)-3-amino-2-fluoro-8-azabicyclo[3.2.1]octan-8-yl]-3-(4-chloro-2-ethyl-2H-indazol-5-yl)-1H-pyrazolo[3,4-b]pyrazin-5-yl}methanol;

{6-[(1R,2S,3S,5S)-3-amino-2-fluoro-8-azabicyclo[3.2.1]octan-8-yl]-3-(3-chloro-4-fluoro-2-methyl-2H-indazol-5-yl)-1H-pyrazolo[3,4-b]pyrazin-5-yl}methanol;

{6-[(1R,2S,3S,5S)-3-amino-2-fluoro-8-azabicyclo[3.2.1]octan-8-yl]-3-(5-chloro-3-methoxyquinoxalin-6-yl)-1H-pyrazolo[3,4-b]pyrazin-5-yl}methanol;

{6-[(1S,2S,3S,5R)-3-amino-2-fluoro-8-azabicyclo[3.2.1]octan-8-yl]-3-(3,4-dichloro-2-methyl-2H-indazol-5-yl)-1H-pyrazolo[3,4-b]pyrazin-5-yl}methanol;

{6-[3,8-diazabicyclo[3.2.1]octan-8-yl]-3-(3,4-dichloro-2-methyl-2H-indazol-5-yl)-1H-pyrazolo[3,4-b]pyrazin-5-yl}methanol;

{6-[(1S,2S,3S,5R)-3-amino-2-fluoro-8-azabicyclo[3.2.1]octan-8-yl]-3-(3-chloro-4-fluoro-2-methyl-2H-indazol-5-yl)-1H-pyrazolo[3,4-b]pyrazin-5-yl}methanol;

{6-[endo-3-amino-8-azabicyclo[3.2.1]octan-8-yl]-3-(3,4-dichloro-2-methyl-2H-indazol-5-yl)-1H-pyrazolo[3,4-b]pyrazin-5-yl}methanol;

rac-(1S,2S,3S,5R)-3-Amino-8-[3-(3,4-dichloro-2-methyl-2H-indazol-5-yl)-5-methyl-1H-pyrazolo[3,4-b]pyrazin-6-yl]-8-azabicyclo[3.2.1]octan-2-ol;

4-Chloro-5-(6-{3,9-diazabicyclo[3.3.1]nonan-9-yl)-5-methyl-1H-pyrazolo[3,4-b]pyrazin-3-yl)-2-methyl-2H-indazole;

(1R,2S,3S,5S)-8-[3-(4-Chloro-2-ethyl-2H-indazol-5-yl)-5-methyl-1H-pyrazolo[3,4-b]pyrazin-6-yl]-2-fluoro-8-azabicyclo[3.2.1]octan-3-amine;

(1R,2S,3S,5S)-8-[3-(3,4-Dichloro-2-methyl-2H-indazol-5-yl)-5-methyl-1H-pyrazolo[3,4-b]pyrazin-6-yl]-2-fluoro-8-azabicyclo[3.2.1]octan-3-amine;

7-[3-(4-Chloro-2-methyl-2H-indazol-5-yl)-5-methyl-1H-pyrazolo[3,4-b]pyrazin-6-yl]-2,7-diazaspiro[3.5]nonane;

(1R,2S,3S,5S)-8-[3-(5-chloro-3-methoxyquinoxalin-6-yl)-5-methyl-1H-pyrazolo[3,4-b]pyrazin-6-yl]-2-fluoro-8-azabicyclo[3.2.1]octan-3-amine;

7-{6-[(1R,2S,3S,5S)-3-amino-2-fluoro-8-azabicyclo[3.2.1]octan-8-yl]-5-methyl-1H-pyrazolo[3,4-b]pyrazin-3-yl}-8-chloro-N,N-dimethylquinoxalin-2-amine;

{6-[(1R,2S,3S,5S)-3-amino-2-fluoro-8-azabicyclo[3.2.1]octan-8-yl]-3-(3-chloro-2-ethyl-4-fluoro-2H-indazol-5-yl)-1H-pyrazolo[3,4-b]pyrazin-5-yl}methanol;

{6-[(1R,2S,3S,5S)-3-amino-2-fluoro-8-azabicyclo[3.2.1]octan-8-yl]-3-(7-chloro-2-methyl-1,3-benzothiazol-6-yl)-1H-pyrazolo[3,4-b]pyrazin-5-yl}methanol;

{6-[(1R,2S,3S,5S)-3-amino-2-fluoro-8-azabicyclo[3.2.1]octan-8-yl]-3-(4-chloro-2,3-dimethyl-2H-indazol-5-yl)-1H-pyrazolo[3,4-b]pyrazin-5-yl}methanol;

{6-[(1R,2S,3S,5S)-3-amino-2-fluoro-8-azabicyclo[3.2.1]octan-8-yl]-3-(5-chloro-3-methoxy-2-methylquinolin-6-yl)-1H-pyrazolo[3,4-b]pyrazin-5-yl}methanol;

{6-[(1R,2S,3S,5S)-3-amino-2-fluoro-8-azabicyclo[3.2.1]octan-8-yl]-3-[4-chloro-2-(propan-2-yl)-2H-indazol-5-yl]-1H-pyrazolo[3,4-b]pyrazin-5-yl}methanol;

{6-[(1S,2R,3S,5R)-3-amino-2-fluoro-8-azabicyclo[3.2.1]octan-8-yl]-3-(3,4-dichloro-2-methyl-2H-indazol-5-yl)-1H-pyrazolo[3,4-b]pyrazin-5-yl}methanol;

{6-[(1R,2S,3S,5S)-3-amino-2-fluoro-8-azabicyclo[3.2.1]octan-8-yl]-3-(3,4-dichloro-2-ethyl-2H-indazol-5-yl)-1H-pyrazolo[3,4-b]pyrazin-5-yl}methanol;

(1R,2S,3S,5S)-8-[7-(3,4-dichloro-2-methyl-2H-indazol-5-yl)-5H-pyrrolo[2,3-b]pyrazin-3-yl]-2-fluoro-8-azabicyclo[3.2.1]octan-3-amine;

{6-[(1R,2S,3S,5S)-3-amino-2-fluoro-8-azabicyclo[3.2.1]octan-8-yl]-3-(3-bromo-4-fluoro-2-methyl-2H-indazol-5-yl)-1H-pyrazolo[3,4-b]pyrazin-5-yl}methanol;

(1R,2S,3S,5S)-8-[7-(5-chloro-3-methoxyquinoxalin-6-yl)-5H-pyrrolo[2,3-b]pyrazin-3-yl]-2-fluoro-8-azabicyclo[3.2.1]octan-3-amine;

endo-8-[7-(5-chloro-3-methoxyquinoxalin-6-yl)-5H-pyrrolo[2,3-b]pyrazin-3-yl]-8-azabicyclo[3.2.1]octan-3-amine;

{6-[(1R,2S,3S,5S)-3-amino-2-fluoro-8-azabicyclo[3.2.1]
octan-8-yl]-3-(3-chloro-2,4-dimethyl-2H-indazol-5-
yl)-1H-pyrazolo[3,4-b]pyrazin-5-yl}methanol;
{6-[(1S,2S,3S,5R)-3-amino-2-fluoro-8-azabicyclo[3.2.1]
octan-8-yl]-3-(5-chloro-3-methoxyquinoxalin-6-yl)-
1H-pyrazolo[3,4-b]pyrazin-5-yl}methanol;
[6-(4-amino-4-methylpiperidin-1-yl)-3-(3,4-dichloro-2-
methyl-2H-indazol-5-yl)-1H-pyrazolo[3,4-b]pyrazin-
5-yl]methanol;
(6-{2,8-diazaspiro[4.5]decan-8-yl}-3-(3,4-dichloro-2-
methyl-2H-indazol-5-yl)-1H-pyrazolo[3,4-b]pyrazin-
5-yl)methanol;
[3-(5-Chloro-3-methonquinoxalin-6-yl)-6-{3,8-diazabi-
cyclo[3.2.1]octan-8-yl}-1H-pyrazolo[3,4-b]pyrazin-5-
yl]methanol;
{6-[endo-3-amino-8-azabicyclo[3.2.1]octan-8-yl]-3-(5-
chloro-3-methoxyquinoxalin-6-yl)-1H-pyrazolo[3,4-b]
pyrazin-5-yl}methanol;
{6-[(1R,2S,3S,5S)-3-amino-2-fluoro-8-azabicyclo[3.2.1]
octan-8-yl]-3-(7-chloro-1,3-benzothiazol-6-yl)-1H-
pyrazolo[3,4-b]pyrazin-5-yl}methanol;
endo-8-[3-(3,4-dichloro-2-methyl-2H-indazol-5-yl)-5-
(hydroxymethyl)-1H-pyrazolo[3,4-b]pyrazin-6-yl]-8-
azabicyclo[3.2.1]octan-3-ol;
{6-[endo-3-amino-3-methyl-8-azabicyclo[3.2.1]octan-8-
yl]-3-(3,4-dichloro-2-methyl-2H-indazol-5-yl)-1H-
pyrazolo[3,4-b]pyrazin-5-yl}methanol;
{3-[5-Chloro-3-(dimethylamino)quinoxalin-6-yl]-6-{3,8-
diazabicyclo[3.2.1]octan-8-yl}-1H-pyrazolo[3,4-b]
pyrazin-5-yl}methanol;
{6-[(1R,2S,3S,5S)-3-amino-2-fluoro-8-azabicyclo[3.2.1]
octan-8-yl]-3-[5-chloro-3-(dimethylamino)quinoxalin-
6-yl]-1H-pyrazolo[3,4-b]pyrazin-5-yl}methanol;
8-Chloro-7-(6-{3,8-diazabicyclo[3.2.1]octan-8-yl}-5-
methyl-1H-pyrazolo[3,4-b]pyrazin-3-yl)-2-methoxyqui-
noxaline;
1-[3-(5-chloro-3-methoxyquinoxalin-6-yl)-5-methyl-1H-
pyrazolo[3,4-b]pyrazin-6-yl]-4-methylpiperidin-4-
amine;
(1S,2S,3S,5R)-8-[3-(5-chloro-3-methoxyquinoxalin-6-
yl)-5-methyl-1H-pyrazolo[3,4-b]pyrazin-6-yl]-2-
fluoro-8-azabicyclo[3.2.1]octan-3-amine;
{3-[(1R,2S,3S,5S)-3-amino-2-fluoro-8-azabicyclo[3.2.1]
octan-8-yl]-7-(3,4-dichloro-2-methyl-2H-indazol-5-
yl)-5H-pyrrolo[2,3-b]pyrazin-2-yl}methanol;
{6-[(1S,2S,3S,5R)-3-amino-2-fluoro-8-azabicyclo[3.2.1]
octan-8-yl]-3-[7-chloro-2-(dimethylamino)-1,3-benzo-
thiazol-6-yl]-1H-pyrazolo[3,4-b]pyrazin-5-
yl}methanol;
5-{6-[(1R,2S,3S,5S)-3-amino-2-fluoro-8-azabicyclo
[3.2.1]octan-8-yl]-5-methyl-1H-pyrazolo[3,4-b]
pyrazin-3-yl}-4-chloro-2-methyl-2H-indazole-3-car-
bonitrile;
6-[3,9-diazabicyclo[3.3.1]nonan-9-yl]-3-(3,4-dichloro-2-
methyl-2H-indazol-5-yl)-1H-pyrazolo[3,4-b]pyrazin-
5-yl]methanol;
5-{6-[(1R,2S,3S,5S)-3-amino-2-fluoro-8-azabicyclo
[3.2.1]octan-8-yl]-5-(hydroxymethyl)-1H-pyrazolo[3,
4-b]pyrazin-3-yl}-4-chloro-2-ethyl-2H-indazole-3-car-
bonitrile;
5-{6-[(1R,2S,3S,5S)-3-amino-2-fluoro-8-azabicyclo
[3.2.1]octan-8-yl]-5-methyl-1H-pyrazolo[3,4-b]
pyrazin-3-yl}-4-chloro-2-ethyl-2H-indazole-3-carbo-
nitrile;
{6-[endo-3-amino-8-azabicyclo[3.2.1]octan-8-yl]-3-(7-
chloro-2-methyl-1,3-benzothiazol-6-yl)-1H-pyrazolo
[3,4-b]pyrazin-5-yl}methanol;
5-{6-[(1R,2S,3S,5S)-3-amino-2-fluoro-8-azabicyclo
[3.2.1]octan-8-yl]-5-(hydroxymethyl)-1H-pyrazolo[3,
4-b]pyrazin-3-yl}-4-chloro-2-methyl-2H-indazole-3-
carbonitrile;
{6-[(1S,2S,3S,5R)-3-amino-2-fluoro-8-azabicyclo[3.2.1]
octan-8-yl]-3-[5-chloro-3-(dimethylamino)quinoxalin-
6-yl]-1H-pyrazolo[3,4-b]pyrazin-5-yl}methanol;
{6-[endo-3-amino-3-methyl-8-azabicyclo[3.2.1]octan-8-
yl]-3[5-chloro-3-(dimethylamino)quinoxalin-6-yl]-1H-
pyrazolo[3,4-b]pyrazin-5-yl}methanol;
(6-{6-[(1R,2S,3S,5S)-3-amino-2-fluoro-8-azabicyclo
[3.2.1]octan-8-yl]-5-methyl-1H-pyrazolo[3,4-b]
pyrazin-3-yl}-7-chloro-1,3-benzothiazol-2-yl)metha-
nol;
{6-[endo-3-amino-8-azabicyclo[3.2.1]octan-8-yl]-3[5-
chloro-3-(dimethylamino)quinoxalin-6-yl]-1H-pyra-
zolo[3,4-b]pyrazin-5-yl}methanol;
{6-[endo-3-amino-3-methyl-8-azabicyclo[3.2.1]octan-8-
yl]-3-(5-chloro-3-methoxyquinoxalin-6-yl)-1H-pyra-
zolo[3,4-b]pyrazin-5-yl}methanol;
endo-8[3-(5-chloro-3-methoxyquinoxalin-6-yl)-5-
methyl-1H-pyrazolo[3,4-b]pyrazin-6-yl]-8-azabicyclo
[3.2.1]octan-3-amine;
7-{6-[endo-3-amino-8-azabicyclo[3.2.1]octan-8-yl]-5-
methyl-1H-pyrazolo[3,4-b]pyrazin-3-yl}-8-chloro-N,
N-dimethylquinoxalin-2-amine;
8-Chloro-7-(6-{3,8-diazabicyclo[3.2.1]octan-8-yl}-5-
methyl-1H-pyrazolo[3,4-b]pyrazin-3-yl)-N,N-dimeth-
ylquinoxalin-2-amine;
{6-[(1R,2S,3S,5S)-3-amino-2-fluoro-8-azabicyclo[3.2.1]
octan-8-yl]-3-(5-chloro-3-ethoxyquinoxalin-6-yl)-1H-
pyrazolo[3,4-b]pyrazin-5-yl}methanol;
(1R,2S,3S,5S)-8-[3-(5-chloro-3-ethoxyquinoxalin-6-yl)-
5-methyl-1H-pyrazolo[3,4-b]pyrazin-6-yl]-2-fluoro-8-
azabicyclo[3.2.1]octan-3-amine;
{6-[(1S,2S,3S,5R)-3-amino-2-fluoro-8-azabicyclo[3.2.1]
octan-8-yl]-3-(7-chloro-2-methyl-1,3-benzothiazol-6-
yl)-1H-pyrazolo[3,4-b]pyrazin-5-yl}methanol;
{6-[(1S,2S,3S,5R)-3-amino-2-fluoro-8-azabicyclo[3.2.1]
octan-8-yl]-3-(3-chloro-2,4-dimethyl-2H-indazol-5-
yl)-1H-pyrazolo[3,4-b]pyrazin-5-yl}methanol;
{6-[endo-3-amino-8-azabicyclo[3.2.1]octan-8-yl]-3-(3-
chloro-2,4-dimethyl-2H-indazol-5-yl)-1H-pyrazolo[3,
4-b]pyrazin-5-yl}methanol;
{6-[(1R,2S,3S,5S)-3-amino-2-fluoro-8-azabicyclo[3.2.1]
octan-8-yl]-3-[7-chloro-2-(methoxymethyl)-1,3-ben-
zothiazol-6-yl]-1H-pyrazolo[3,4-b]pyrazin-5-
yl}methanol;
{6-[(1R,2S,3S,5S)-3-amino-2-fluoro-8-azabicyclo[3.2.1]
octan-8-yl]-3-[5-chloro-3-(propan-2-yloxy)quinoxalin-
6-yl]-1H-pyrazolo[3,4-b]pyrazin-5-yl}methanol;
5-{6-[(1R,2S,3S,5S)-3-amino-2-fluoro-8-azabicyclo
[3.2.1]octan-8-yl]-5-methyl-1H-pyrazolo[3,4-b]
pyrazin-3-yl}-4-chloro-2-(propan-2-yl)-2H-indazole-
3-carbonitrile;
(1S,2S,3S,5R)-8-[3-(7-chloro-2-methyl-1,3-benzothi-
azol-6-yl)-5-methyl-1H-pyrazolo[3,4-b]pyrazin-6-yl]-
2-fluoro-8-azabicyclo[3.2.1]octan-3-amine;
{6-[(1R,2S,3S,5S)-3-amino-2-fluoro-8-azabicyclo[3.2.1]
octan-8-yl]-3-[5-chloro-3-(morpholin-4-yl)quinoxalin-
6-yl]-1H-pyrazolo[3,4-b]pyrazin-5-yl}methanol;
(1R,2S,3S,5S)-8-{3-[5-chloro-3-(morpholin-4-yl)qui-
noxalin-6-yl]-5-methyl-1H-pyrazolo[3,4-b]pyrazin-6-
yl}-2-fluoro-8-azabicyclo[3.2.1]octan-3-amine;

5-{6-[(1R,2S,3S,5S)-3-amino-2-fluoro-8-azabicyclo[3.2.1]octan-8-yl]-5-(hydroxymethyl)-1H-pyrazolo[3,4-b]pyrazin-3-yl}-4-chloro-2-(propan-2-yl)-2H-indazole-3-carbonitrile; and {6-[(1R,2S,3S,5S)-3-amino-2-fluoro-8-azabicyclo[3.2.1]octan-8-yl]-3-[3-(azetidin-1-yl)-5-chloroquinoxalin-6-yl]-1H-pyrazolo[3,4-b]pyrazin-5-yl}methanol.

16. A combination comprising a compound of formula (I) as defined in claim 1, or a tautomer or a solvate or a pharmaceutically acceptable salt thereof, with one or more other therapeutic agents.

17. A pharmaceutical composition comprising a compound of formula (I) as defined in claim 1, or a tautomer or a solvate or a pharmaceutically acceptable salt thereof.

18. A pharmaceutical composition comprising a combination according to claim 16.

19. A method for:
   inhibiting the activity of SHP2; or
   the treatment of a disease state or condition mediated by SHP2; or
   the treatment of cancer; or
   the treatment of cancer, wherein the compound is used in combination with one or more other therapeutic agents or therapies; or
   the treatment of hepatocellular carcinoma, melanoma, oesophageal, renal, colon, colorectal, lung, mesothelioma or lung adenocarcinoma, breast, bladder, gastrointestinal, ovarian or prostate cancers,
comprising administering to a patient a compound of formula (I) as defined in claim 1, or a tautomer or a solvate or a pharmaceutically acceptable salt thereof.

20. A process for the preparation of a compound of formula (I) as defined in claim 1, or a tautomer, pharmaceutically acceptable salt, or solvate thereof which comprises:
   (a) coupling a compound of formula (A) or a protected derivative thereof:

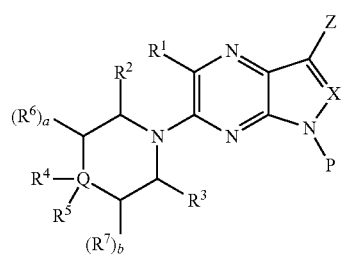

(A)

wherein $R^1$, $R^2$, $R^3$, $R^4$, $R^5$, $R^6$, $R^7$, Q, X, a, b, are as defined hereinbefore for the compounds of formula (I), and P represents a protecting group or is hydrogen, and Z is a metal residue or a leaving group with a compound of the formula (B) or a protected version thereof:

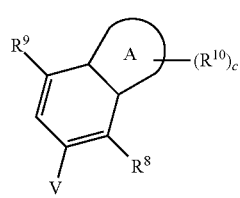

(B)

wherein $R^8$, $R^9$, $R^{10}$, A, c, are as defined hereinbefore for the compounds of formula (I) and V represents a metal or metaloid residue or a leaving group, followed by a deprotection reaction suitable to remove the protecting groups to give a compound of formula (I); or (b) coupling a compound of formula (C) or a protected derivative thereof:

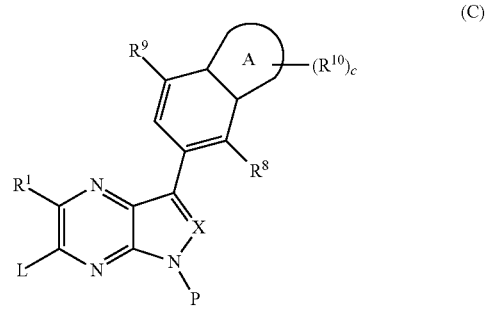

(C)

wherein $R^8$, $R^9$, $R^{10}$, A, c, are as defined hereinbefore for the compounds of formula (I), X is CH, P represents protecting group or is hydrogen, L is leaving group, with a compound of formula (D) or a protected derivative thereof, wherein $R^2$, $R^3$, $R^4$, $R^5$, $R^6$, $R^7$, Q, a, b, are as defined hereinbefore for the compounds of formula (I);

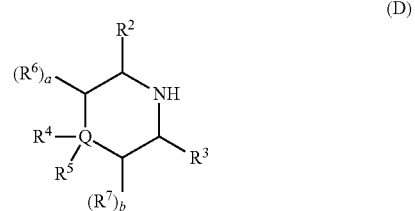

(D)

to give a compound of formula (I); or (c) reacting a compound of formula (K) or a protected derivative thereof,

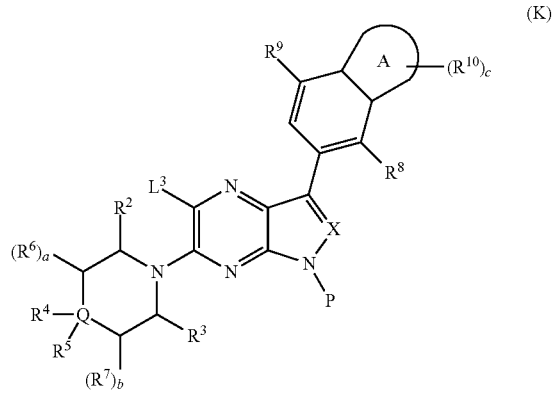

(K)

wherein $R^2$, $R^3$, $R^4$, $R^5$, $R^6$, $R^7$, $R^8$, $R^9$, $R^{10}$, Q, a, b and c are as defined herein for the compound of formula (I), P represents an amine protecting group, N,N-dimethylsulfamoyl or hydrogen, $L^3$ is leaving group either:

(i) with a organometallic species of the formula CH₃M, where M is a metal in the presence of a metal catalyst to give a compound of formula (I) wherein R¹ is —CH₃; or (ii) with an alkyl boronate in the presence of a photoredox catalyst, a metal catalyst, a ligand, a base, and a source of light, to give a compound of formula (I) wherein R¹ is —CH₂OH; or (d) cyclisation of a compound of formula (R), or a protected derivatives thereof;

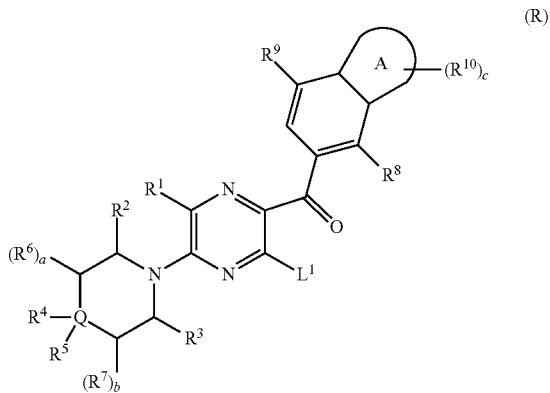

(R)

wherein R¹, R², R³, R⁴, R⁵, R⁶, R⁷, R⁸, R⁹, R¹⁰, Q, a, b, c, A, are as defined hereinbefore for the compounds of formula (I) and L¹ represents a suitable leaving group, using hydrazine or a protected hydrazine derivative;

in each case optionally followed by a deprotection step to give a compound of formula (I); or (e) deprotection of a protected derivative of a compound of formula (I); or (f) interconversion of a compound of formula (I) or protected derivative thereof to a further compound of formula (I) or protected derivative thereof; or (g) optionally formation of a pharmaceutically acceptable salt of a compound of formula (I).

21. A process according to claim 20, wherein in process (a):
P represents 2-(trimethylsilyl)ethoxymethyl; and/or
Z is zinc halide or a halogen; and/or
V is boronic acid, pinacol boronate, magnesium halide, zinc halide or halogen; and/or in process (b):
P is 2-(trimethylsilyl)ethoxymethyl; and/or
L is chloride; and/or in process (c):
P is 2-(trimethylsilyl)ethoxymethyl; and/or
L³ is halogen; and/or
M is CH₃—Zn-Hal, where Hal is halogen; and/or
the metal catalyst is 1,3-diisopropylimidazol-2-ylidene)(3-chloropyridyl)palladium(II) dichloride; and/or
the alkyl boronate is potassium (2-trimethylsilyl)-ethoxymethyl trifluoroborate; and/or
the photoredox catalyst is [Ir{dFCF₃ppy}₂(bpy)]PF₆); and/or
the metal catalyst is nickel(II) chloride ethylene glycol dimethyl ether complex; and/or
the ligand is 4,4'-di-tert-butyl-2,2'-dipyridyl; and/or
the base is dipotassium phosphate; and/or the source of light is a blue LED; and/or
in process (d):
L¹ is halogen.

22. A compound according to claim 1, or a tautomer, pharmaceutically acceptable salt or solvate thereof, wherein:
R⁴ is methyl; and/or
R⁴ is substituted by —CH₂NH₂; and/or
R⁵ is methyl; and/or
R⁵ is substituted by 1 hydroxyl group; and/or
R⁶ and R⁷ are independently selected form fluorine or —CH₃; and/or
Ring A is a five-membered nitrogen-containing heterocyclic aromatic or non-aromatic ring wherein the heterocyclic ring optionally contains one or two additional heteroatoms selected from N, O and S; and/or
R⁸ is —CF₃, chlorine or fluorine; and/or
R⁹ is —CH₃, —CF₃ or chlorine; and/or
R¹⁰ is independently selected from —CH₂—CN, —CH₃, —CH(CH₃)₂, —CH₂CH₃, —CHF₂, —OCH₃, —OCH₂CH₃, —OCH(CH₃)₂, —CH₂C(CH₃)₂OH, —CH(CH₃)CH₂OH, —CH(CH₃)OH, —CH₂CH₂OH, —CH₂OH, —CH₂—O—CH₃, —CH₂—CH₂—O—CH₃, —SO₂CH₃, —N(CH₃)₂, —CH₂NH₂, —SO₂NRˣ₂, and —CH₂SO₂NRˣ₂, wherein Rˣ is independently selected from H and C₁₋₆alkyl.

23. A compound according to claim 8, or a tautomer, pharmaceutically acceptable salt or solvate thereof, wherein:
R⁴ is hydrogen; and/or
R⁵ is amino or methyl, optionally substituted by 1 or 2 groups selected from halogen, —CH₂OH, and amino.

24. A compound according to claim 10, or a tautomer, pharmaceutically acceptable salt or solvate thereof, wherein a is 1 and R⁶ is fluorine.

25. A compound according to claim 1, or a tautomer, pharmaceutically acceptable salt or solvate thereof, wherein the moiety

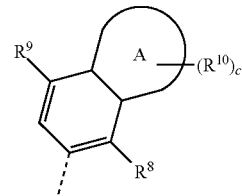

is selected from:

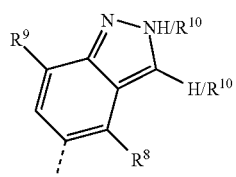

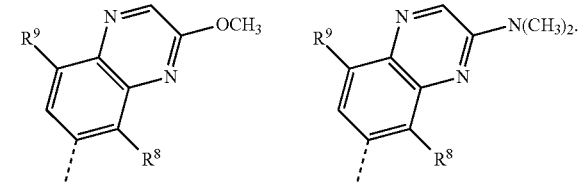

26. A compound according to claim 14, or a tautomer, pharmaceutically acceptable salt or solvate thereof, wherein:

$R^8$ is chlorine or fluorine and/or $R^{10}$ is independently selected from —CH$_2$—CN, —CH$_3$, —CH(CH$_3$)$_2$, —CH$_2$CH$_3$, —CHF$_2$, —OCH$_3$, —CH(CH$_3$)CH$_2$OH, —CH(CH$_3$)OH, —CH$_2$CH$_2$OH, —CH$_2$OH, —CH$_2$—O—CHs and —N(CH$_3$)$_2$; and/or c is 0, 1 or 2.

27. A combination according to claim 16 wherein the other therapeutic agents are anticancer agents.

* * * * *

UNITED STATES PATENT AND TRADEMARK OFFICE
CERTIFICATE OF CORRECTION

PATENT NO. : 11,466,016 B2
APPLICATION NO. : 16/976631
DATED : October 11, 2022
INVENTOR(S) : Johnson et al.

It is certified that error appears in the above-identified patent and that said Letters Patent is hereby corrected as shown below:

In the Claims

Column 443, Line 51: Claim 1, Delete "($C_{1-6}$ alkyl)$_q$)," and insert -- ($C_{1-6}$alkyl)$_q$), --

Column 444, Line 15: Claim 2, Delete "$C_{2-3}$ alkenylene," and insert -- $C_{2-3}$alkenylene, --

Column 444, Line 64: Claim 2, Delete "($C_{1-6}$ alkyl)$_q$)," and insert -- ($C_{1-6}$alkyl)$_q$), --

Column 444, Line 65: Claim 2, Delete "-$C_{1-4}$alkylene-NHC(=O)$C_{1-6}$ alkyl," and insert -- -$C_{1-4}$alkylene-NHC(=O)$C_{1-6}$alkyl, --

Column 445, Line 11: Claim 5, Delete "A compound according claim 1" and insert -- A compound according to claim 1 --

Column 445, Lines 14-15: Claim 6, Delete "or a tautomer, N-oxido, pharmaceutically" and insert -- or a tautomer, pharmaceutically --

Column 445, Line 18: Claim 6, Delete "$C_{2-3}$ alkenylene," and insert -- $C_{2-3}$alkenylene, --

Column 449, Claim 12, Delete " 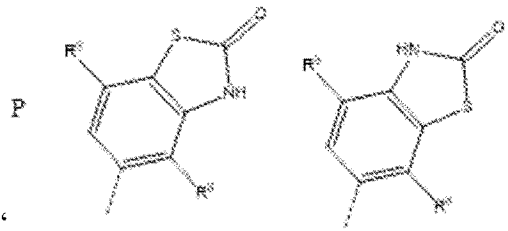 " and insert

Signed and Sealed this
Twenty-eighth Day of March, 2023

Katherine Kelly Vidal
*Director of the United States Patent and Trademark Office*

CERTIFICATE OF CORRECTION (continued)
U.S. Pat. No. 11,466,016 B2

Page 2 of 2

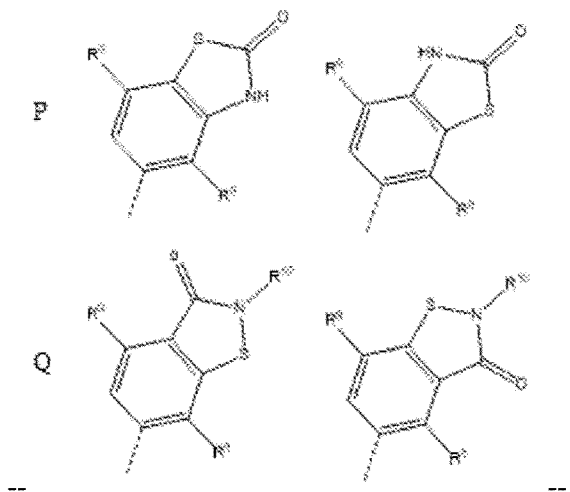

--                                           --

Column 453, Line 64: Claim 14, Delete "hydroxy1C$_{1-4}$alkyl" and insert -- hydroxylC$_{1-4}$alkyl, --